US012492210B2

(12) United States Patent
Su et al.

(10) Patent No.: US 12,492,210 B2
(45) Date of Patent: Dec. 9, 2025

(54) TRICYCLIC COMPOUNDS AND THEIR USE

(71) Applicant: HUTCHISON MEDIPHARMA LIMITED, Shanghai (CN)

(72) Inventors: Wei-Guo Su, Shanghai (CN); Weihan Zhang, Shanghai (CN); Jinshui Li, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 939 days.

(21) Appl. No.: 17/616,904

(22) PCT Filed: Jun. 5, 2020

(86) PCT No.: PCT/CN2020/094692
§ 371 (c)(1),
(2) Date: Dec. 6, 2021

(87) PCT Pub. No.: WO2020/244637
PCT Pub. Date: Dec. 10, 2020

(65) Prior Publication Data

US 2022/0315597 A1 Oct. 6, 2022

(30) Foreign Application Priority Data

Jun. 6, 2019 (CN) ......................... 201910489162.9
May 26, 2020 (CN) ......................... 202010455709.6

(51) Int. Cl.

| | |
|---|---|
| ***C07D 487/14*** | (2006.01) |
| ***A61K 31/4985*** | (2006.01) |
| ***A61K 31/506*** | (2006.01) |
| ***A61K 31/55*** | (2006.01) |
| ***A61K 31/551*** | (2006.01) |
| ***C07D 491/22*** | (2006.01) |
| ***C07D 498/14*** | (2006.01) |
| ***C07D 513/14*** | (2006.01) |

(52) U.S. Cl.
CPC ........ *C07D 487/14* (2013.01); *A61K 31/4985* (2013.01); *A61K 31/506* (2013.01); *A61K 31/55* (2013.01); *A61K 31/551* (2013.01); *C07D 491/22* (2013.01); *C07D 498/14* (2013.01); *C07D 513/14* (2013.01)

(58) Field of Classification Search
CPC .. C07D 487/14; C07D 491/22; C07D 498/14; C07D 513/14; A61K 31/4985; A61K 31/506; A61K 31/55; A61K 31/551
See application file for complete search history.

(56) References Cited

FOREIGN PATENT DOCUMENTS

| | | | | | |
|---|---|---|---|---|---|
| WO | WO 2006/023750 | A2 | | 3/2006 | |
| WO | WO 2007/127138 | A1 | | 11/2007 | |
| WO | WO 2009/071890 | A1 | | 6/2009 | |
| WO | WO 2012/051410 | A2 | | 4/2012 | |
| WO | WO 2012/172093 | A1 | | 12/2012 | |
| WO | WO 2013/130660 | A1 | | 9/2013 | |
| WO | WO-2015085007 | A1 | * | 6/2015 | ........... A61K 31/519 |
| WO | 2015/103137 | A1 | | 7/2015 | |
| WO | WO 2016/162325 | A1 | | 10/2016 | |
| WO | WO 2016/192063 | A1 | | 12/2016 | |
| WO | WO 2017/028314 | A1 | | 2/2017 | |
| WO | 2017/080979 | A1 | | 5/2017 | |
| WO | 2018/213302 | A1 | | 11/2018 | |
| WO | WO 2019/081691 | A1 | | 5/2019 | |
| WO | 2020/244968 | A1 | | 12/2020 | |
| WO | 2021/086833 | A1 | | 5/2021 | |

OTHER PUBLICATIONS

Boga et al., "MK-8353, Discovery of and orally bioavailable Dual Mechanism ERK inhibitor for Oncology", *ACS Medicinal Chemistry Letters*, 9(7), pp. 761-767, (2018).
Khisamutdinov, G. et al., "Synthesis and properties of 1,2,4-triaazolo[4,3-d]-1,2,4-triazolo-[3,4-f]furazano[3,4-b] pyrazines," Russian Chemical Bulletin, vol. 42, No. 10, 3 pages, (1993).
Bagdanoff et al., "Tetrahydropyrrolo-diazepenones as inhibitors of ERK2 kinase", *Bioorganic & Medicinal Chemistry Letters*, 25(18), pp. 3788-3792, (2015).
Ward et al., "Structure-Guided Discovery of Potent and Selective Inhibitors of ERK1/2 from a Modestly Active and Promiscuous Chemical Start Point", *Journal of Medicinal Chemistry*, 60(8), pp. 3438-3450, (2017).

* cited by examiner

*Primary Examiner* — John S Kenyon
*Assistant Examiner* — Sara Elizabeth Bell
(74) *Attorney, Agent, or Firm* — Hoxie & Associates LLC

(57) ABSTRACT

Tricyclic compounds and their use are provided. More specifically, tricyclic compounds, pharmaceutical compositions containing them, methods for preparing them, and their use in therapy are also provided.

40 Claims, 1 Drawing Sheet

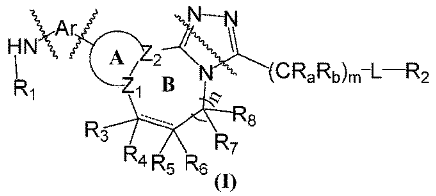
(I)
1
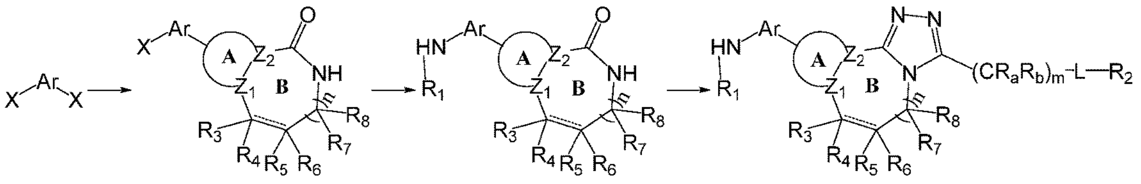
2
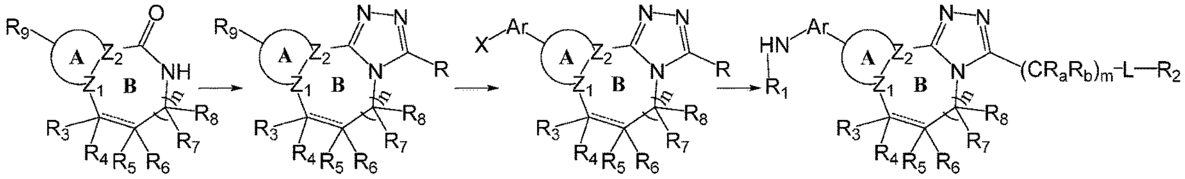
3
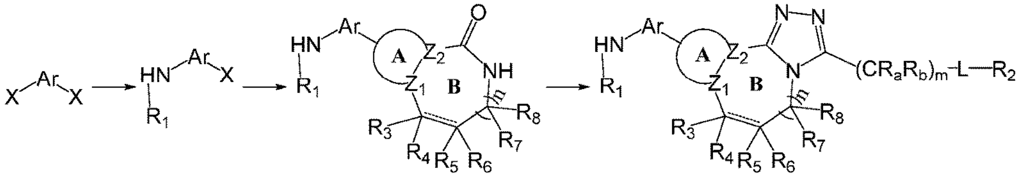
4
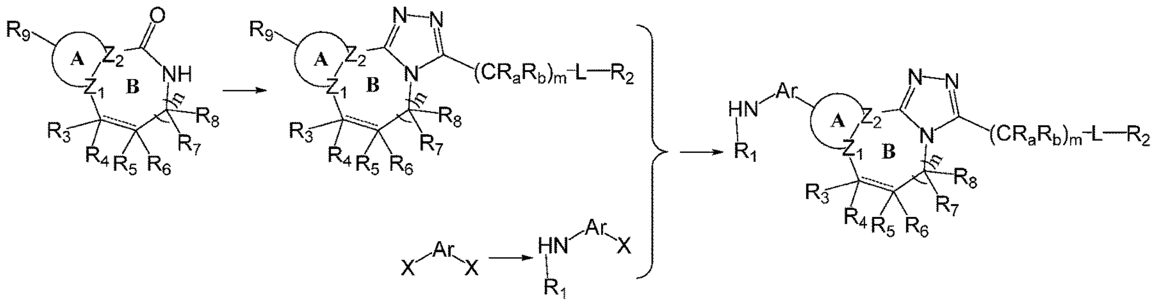

TRICYCLIC COMPOUNDS AND THEIR USE

CROSS REFERENCE TO RELATED APPLICATIONS

This application is a United States Application under 35 U.S.C. 371 claiming benefit of International Application No. PCT/CN2020/094692, filed on Jun. 5, 2020, which claims the benefit of Chinese Patent Application Nos. 201910489162.9 filed on Jun. 6, 2019, and 202010455709.6 filed on May 26, 2020, the contents of each of which are incorporated herein by reference.

FIELD OF THE INVENTION

The present invention relates to tricyclic compounds, a pharmaceutical composition comprising them, a process for preparing them, and their medical use.

BACKGROUND OF THE INVENTION

The RAS/RAF/MEK/ERK pathway is an evolutionary conserved signaling cascade that regulates a large variety of processes including cell adhesion, cell cycle progression, cell migration, cell survival, differentiation, metabolism and proliferation. It has been widely appreciated that aberrant activation of this pathway is closely linked to various kinds of cancers. The ERK signaling pathway is hyperactivated in a high percentage of tumors, most frequently owing to activating mutations of the KRAS, NRAS and BRAF genes. About 30% of all human cancers were found having RAS mutations with 90% in pancreatic cancer, 50% in colon cancer, 50% in papillary thyroid cancer, 30% in non-small cell lung cancer (NSCLC) and 25% in melanoma respectively. BRAF mutations have been widely identified in tumors, with a significant percentage (7%) of all human cancers. This mutation is highly prevalent in hairy cell leukemia (100%), melanoma (50%-60%), papillary thyroid cancer (40%-60%), colorectal cancers (CRC, 5%-10%), pilocytic astrocytoma (10%-15%) and non-small cell lung cancer (NSCLC) (3%-5%). MEK mutations have been mainly identified in melanoma, and also in ovarian cancer cell lines and gliomas. Generally, all of the upstream mutations can lead to ERK protein hyperactivation, which is responsible for a series of ERK-signaling-regulated substrate activation and consequently related to a wide range of tumors.

Targeting the MAPK/ERK pathway has attracted significant interest in cancer therapy. Clinical benefits achieved by BRAF and MEK inhibitors have shown that targeting these downstream RAS effectors is a very promising approach for therapies of cancers harboring BRAF mutations. But now evidence indicates that inhibition of BRAF or MEK alone is not sufficient for clinical benefit of RAS-mutant cancers. Both intrinsic and acquired resistance to BRAF and MEK inhibitors are frequently associated with the persistence of ERK signaling in the presence of the drug, implying the need to target the ERK. The primary efficacy of ERK inhibitors was already observed in clinical trial. In the phase I study of BVD-523, clinical responses were found in patients with BRAF and NRAS mutations, even among patients who had progressed on prior BRAF and/or MEK inhibitors. The combination approaches with ERK inhibitors were investigated and the pre-clinical data support the combo strategy with other target inhibitors, such as CDK4/6 inhibitor, VEGFR2 inhibitor, PARP inhibitor, multi-ERBB inhibitor and autophagy inhibitor in KRAS mutant cancer cells. So ERK inhibitors may have a chance to benefit a broader patient population in clinic.

Accordingly, new compounds and methods for modulating ERK activity and treating related disorders, including cancer, are needed. The present invention, addresses these needs.

SUMMARY OF THE INVENTION

The present invention provides a compound of formula (I):

(I)

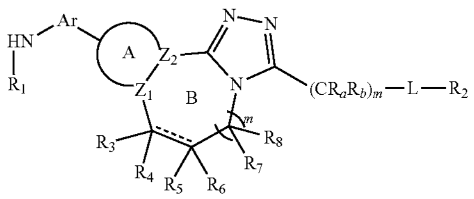

or a pharmaceutically acceptable salt thereof, or solvates, racemic mixtures, enantiomers, diasteromers, or tautomers of the compound of formula (I) or a pharmaceutically acceptable salt thereof, wherein $Z_1$ and $Z_2$ are independently N or C, and

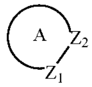

is 5 membered heteroaryl containing 1, 2, 3, or 4 ring heteroatoms selected from N, O or S; said 5 membered heteroaryl is optionally substituted with one or more substituents independently selected from deuterium, halo, hydroxy, amino, —NH($C_{1-6}$ alkyl), —N($C_{1-6}$ alkyl)$_2$, —CN, mercapto, $C_{1-6}$ alkyl, $C_{2-6}$ alkenyl, $C_{2-6}$ alkynyl, $C_{1-6}$ alkoxyl, $C_{1-6}$ haloalkyl, —($C_{1-6}$ alkyl)-OH, and —($C_{1-6}$ alkyl)-O—($C_{1-6}$ alkyl), wherein each of said $C_{1-6}$ alkyl, $C_{1-6}$ alkoxyl, and $C_{1-6}$ haloalkyl is optionally substituted with one or more deuterium;

L is absent, or L is —$NR_c$, O, or S;

$R_c$ is hydrogen or $C_{1-6}$ alkyl;

Ar is heteroaryl optionally substituted with one or more substituents independently selected from deuterium, halo, hydroxy, amino, —NH($C_{1-6}$ alkyl), —N($C_{1-6}$ alkyl)$_2$, —CN, mercapto, $C_{1-6}$ alkyl, $C_{2-6}$ alkenyl, $C_{2-6}$ alkynyl, $C_{1-6}$ alkoxyl, $C_{1-6}$ haloalkyl, —($C_{1-6}$ alkyl)-OH, —($C_{1-6}$ alkyl)-O—($C_{1-6}$ alkyl), $C_{3-8}$ cycloalkyl, 3-8 membered heterocyclyl, phenyl, and heteroaryl, wherein each of said $C_{1-6}$ alkyl, $C_{1-6}$ alkoxyl, $C_{1-6}$ haloalkyl, $C_{3-8}$ cycloalkyl, 3-8 membered heterocyclyl, phenyl, and heteroaryl is optionally substituted with one or more deuterium;

$R_1$ is selected from hydrogen, $C_{1-6}$ alkyl optionally substituted with one or more deuterium, $C_{2-6}$ alkenyl, $C_{2-6}$ alkynyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-($C_{3-8}$ cycloalkyl), —($C_{1-6}$ alkyl)-(3-8 membered heterocyclyl), —($C_{1-6}$ alkyl)-phenyl, —($C_{1-6}$ alkyl)-heteroaryl, $C_{3-8}$ cycloalkyl, 3-8 membered heterocyclyl, phenyl, and heteroaryl, wherein each of said $C_{2-6}$ alkenyl, $C_{2-6}$ alkynyl, $C_{3-8}$ cycloalkyl, 3-8 membered heterocyclyl, phenyl, and heteroaryl is optionally substituted with one or more substituents independently selected from deuterium, halo, —CN, hydroxy, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{3-8}$ cycloalkyl, 3-8 membered heterocyclyl, phenyl, heteroaryl, $C_{1-6}$ alkyl optionally substituted with one or more deuterium, $C_{1-6}$ alkoxyl, and $C_{1-6}$ haloalkyl;

$R_2$ is selected from hydrogen, deuterium, halo, hydroxy, amino, —NH($C_{1-6}$ alkyl), —N($C_{1-6}$ alkyl)$_2$, —CN, mercapto, $C_{1-6}$ alkyl optionally substituted with one or more deuterium, $C_{2-6}$ alkenyl, $C_{2-6}$ alkynyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-($C_{3-8}$ cycloalkyl), —($C_{1-6}$ alkyl)-(3-8 membered heterocyclyl), —($C_{1-6}$ alkyl)-phenyl, —($C_{1-6}$ alkyl)-heteroaryl, $C_{3-8}$ cycloalkyl, 3-8 membered heterocyclyl, phenyl, and heteroaryl, wherein each of said $C_{2-6}$ alkenyl, $C_{2-6}$ alkynyl, $C_{3-8}$ cycloalkyl, 3-8 membered heterocyclyl, phenyl, and heteroaryl is optionally substituted with one or more substituents independently selected from deuterium, halo, —CN, hydroxy, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{1-6}$ alkyl, $C_{1-6}$ alkoxyl, $C_{1-6}$ haloalkyl, and oxo;

$R_a$ and $R_b$ are independently selected from hydrogen, deuterium, halo, hydroxy, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), —CN, mercapto, $C_{1-6}$ alkyl, $C_{1-6}$ alkoxyl, and $C_{1-6}$ haloalkyl; or $R_a$ and $R_b$ together with the carbon atom they are attached to form $C_{3-6}$ cycloalkyl or 4-6 membered heterocyclyl, wherein each of said $C_{3-6}$ cycloalkyl or 4-6 membered heterocyclyl is optionally substituted with one or more substituents independently selected from deuterium, halo, —CN, hydroxy, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{1-6}$ alkyl, $C_{1-6}$ alkoxyl, and $C_{1-6}$ haloalkyl;

------ is double bond or single bond, and when ------ is double bond, $R_3$ and $R_5$ are absent;

$R_3$, $R_4$, $R_5$, $R_6$, $R_7$, and $R_8$ are independently selected from hydrogen, deuterium, halo, hydroxy, —CN, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{1-6}$ alkyl, —($C_{1-6}$ alkyl)-phenyl, $C_{1-6}$ alkoxyl, and $C_{1-6}$ haloalkyl; or any two of $R_3$, $R_4$, $R_5$, $R_6$, $R_7$, and $R_8$ together with the carbon atom they are attached to and the B ring form a 8-13 membered spirocyclic, fused, or bridged ring optionally containing 1-3 ring heteroatoms independently selected from N, O, or S; wherein said spirocyclic, fused, or bridged ring is optionally substituted with one or more substituents independently selected from deuterium, halo, —CN, hydroxy, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{1-6}$ alkyl, $C_{1-6}$ alkoxyl, and $C_{1-6}$ haloalkyl; or $R_3$ and $R_4$ together, $R_5$ and $R_6$ together, or $R_7$ and $R_8$ together are oxo;

n is 0, 1, or 2;

m is 0, 1, 2, 3, 4, or 5.

The compounds above as well as the active compounds disclosed in the context of the present invention and covered by the scope of the compounds above are collectively called "the compound of the present invention" or "a compound of the present invention".

Also provided is a compound of the present invention used for in vivo or in vitro inhibiting the activity of ERK.

Also provided is a compound of the present invention used as a medicament, especially a compound of the present invention used for treating or preventing a disease responsive to inhibition of ERK.

Also provided is a pharmaceutical composition, comprising the compound of the present invention, and optionally a pharmaceutically acceptable carrier.

Also provided is a method of in vivo or in vitro inhibiting the activity of ERK, comprising contacting an effective amount of the compound of the present invention with ERK.

Also provided is a method for treating or preventing a disease responsive to inhibition of ERK, comprising administering to the subject in need thereof an effective amount of the compound of the present invention.

Also provided is use of the compound of the present invention for treating or preventing a disease responsive to inhibition of ERK.

Also provided is use of the compound of the present invention in the manufacture of a medicament for treating or preventing a disease responsive to inhibition of ERK.

BRIEF DESCRIPTION OF THE DRAWINGS

FIG. 1 shows the synthetic routes for preparing the compound of the present invention, wherein X is halo; $Z_1$, $Z_2$,

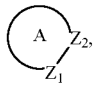

L, $R_1$, $R_2$, $R_3$, $R_4$, $R_5$, $R_6$, $R_7$, $R_8$, $R_a$, $R_b$, m, and n are defined as in the compound of formula (I) and sub-formula (I-1), (I-2) or (I-3) thereof; $R_9$ is defined as in the compound of formula (II) or (III).

DETAILED DESCRIPTION OF THE INVENTION

Definitions

As used in the present application, the following words, phrases and symbols have the meanings as set forth below, unless specified otherwise in the context.

A dash ("-") that is not between two letters or symbols is used to indicate a point of attachment for a substituent. For example, —O($C_{1-6}$ alkyl) is attached to the rest of the molecule through the oxygen.

The dotted line intersected with the chemical bond is used to indicate a site of attachment for a group to the rest of the molecule. For example, Ar may be (Ib-1)

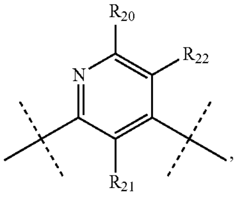

wherein the left and right two dotted lines indicate the attachments to $R_1$—NH— and A ring, respectively.

The term "alkyl" as used herein refers to a straight or branched saturated hydrocarbon radical having 1-18 carbon atoms ($C_{1-18}$), preferably 1-10 carbon atoms ($C_{1-10}$), and more preferably 1-6 carbon atoms ($C_{1-6}$). For example, "$C_{1-6}$ alkyl" refers to the alkyl having 1-6 carbon atoms. Examples of the alkyl include, but are not limited to, methyl, ethyl, n-propyl, i-propyl, n-butyl, i-butyl, s-butyl and t-butyl.

The term "alkenyl" as used herein refers to a straight or branched unsaturated hydrocarbon radical containing one or more, for example 1, 2, or 3 carbon-carbon double bonds (C═C) and having 2-10 carbon atoms ($C_{2-10}$), preferably 2-6 carbon atoms ($C_{2-6}$), more preferably 2-4 carbon atoms ($C_{2-4}$). For example, "$C_{2-6}$ alkenyl" refers to the alkenyl having 2-6 carbon atoms, which preferably contains 1 or 2 carbon-carbon double bonds; "$C_{2-4}$ alkenyl" refers to the alkenyl having 2-4 carbon atoms, which preferably contains 1 carbon-carbon double bond. Examples of the alkenyl include, but are not limited to, vinyl, 2-propenyl, and 2-butenyl. The point of attachment for the alkenyl may or may not be on the double bond.

The term "alkynyl" as used herein refers to a straight or branched unsaturated hydrocarbon radical containing one or more, for example 1, 2, or 3, carbon-carbon triple bonds (C≡C) and having 2-10 carbon atoms ($C_{2-10}$), preferably 2-6 carbon atoms ($C_{2-6}$), more preferably 2-4 carbon atoms ($C_{2-4}$). For example, "$C_{2-6}$ alkynyl" refers to the alkynyl having 2-6 carbon atoms, which preferably contains 1 or 2 carbon-carbon triple bonds; "$C_{2-4}$ alkynyl" refers to the alkynyl having 2-4 carbon atoms, which preferably contains 1 carbon-carbon triple bond. Examples of the alkynyl include, but are not limited to, ethynyl, 2-propynyl, and 2-butynyl. The point of attachment for the alkynyl may or may not be on the triple bond.

The term "halogen" or "halo" as used herein refers to fluoro, chloro, bromo, and iodo, preferably fluoro, chloro and bromo, more preferably fluoro and chloro.

The term "haloalkyl" as used herein refers to the alkyl as defined herein, in which one or more, for example 1, 2, 3, 4, or 5 hydrogen atoms are replaced with halogen atom, and when more than one hydrogen atoms are replaced with halogen atoms, the halogen atoms may be the same or different from each other. In one embodiment, the term "haloalkyl" as used herein refers to the alkyl as defined herein, in which two or more, such as 2, 3, 4, or 5 hydrogen atoms are replaced with halogen atoms, wherein the halogen atoms are the same as each other. In another embodiment, the term "haloalkyl" as used herein refers to the alkyl as defined herein, in which two or more hydrogen atoms, for example 2, 3, 4, or 5 hydrogen atoms are replaced with halogen atoms, wherein the halogen atoms are different from each other. Examples of the haloalkyl include, but are not limited to, $-CF_3$, $-CHF_2$, $-CH_2F$, $-CH_2CF_3$, $-CF_2CF_3$, $-CF_2CH_3$, and the like.

The term "alkoxyl" as used herein refers to the group —O-alkyl, wherein the alkyl is as defined above. Examples of the alkoxyl include, but are not limited to, $C_{1-6}$ alkoxyl, such as methoxy, ethoxy, n-propoxy, i-propoxy, n-butoxy, i-butoxy, t-butoxy, pentoxy, and hexyloxy, including their isomers.

The term "cycloalkyl" as used herein refers to saturated or partially unsaturated cyclic hydrocarbon radical having 3-12 ring carbon atoms ($C_{3-12}$), such as 3-8 ring carbon atoms ($C_{3-8}$), 3-7 ring carbon atoms ($C_{3-7}$), or 3-6 ring carbon atoms ($C_{3-6}$), which may have 1 or 2 rings. "Cycloalkyl" may include a fused ring, a bridged ring, or a spirocyclic ring. The ring(s) of the cycloalkyl may be saturated or may have one or more, for example, one or two double bonds in the ring(s) (i.e. partially unsaturated), but is(are) not fully conjugated, and not the aryl as defined herein. In one embodiment, said cycloalkyl is monocyclic cycloalkyl, preferably monocyclic $C_{3-8}$ cycloalkyl, more preferably monocyclic $C_{3-6}$ cycloalkyl. In another embodiment, said cycloalkyl is saturated monocyclic cycloalkyl, preferably saturated monocyclic $C_{3-8}$ cycloalkyl, more preferably saturated monocyclic $C_{3-6}$ cycloalkyl. Examples of the monocyclic cycloalkyl include, but are not limited to, cyclopropyl, cyclobutyl, cyclopentyl, cyclohexyl, cycloheptyl, cyclooctyl, cyclononyl, cyclodecyl, cycloundecyl, cyclododecyl, cyclopropenyl, cyclobutenyl, cyclopentenyl (such as 1-cyclopenta-1-enyl, 1-cyclopenta-2-enyl, 1-cyclopenta-3-enyl), cyclohexenyl (such as 1-cyclohexa-1-enyl, 1-cyclohexa-2-enyl, 1-cyclohexa-3-enyl), cyclohexadienyl. In another embodiment, said cycloalkyl is bicyclic cycloalkyl, preferably bicyclic $C_5$-$C_{12}$ cycloalkyl, more preferably bicyclic $C_7$-$C_{12}$ cycloalkyl. Examples of the bicyclic cycloalkyl include, but are not limited to, bicyclo[4.1.0]heptyl, bicyclo[3.1.1]heptyl, bicyclo[2.2.1]heptyl, bicyclo[2.2.2]octyl, bicyclo[3.2.2]nonyl, spiro[3.3]heptyl, spiro[2.2]pentyl, spiro[2.3]hexyl, spiro[2.4]heptyl, spiro[2.5]octyl, spiro[4.5]decyl, and bicyclo[3.1.1]hepta-2-enyl. Most preferably, the cycloalkyl is saturated monocyclic $C_{3-6}$ cycloalkyl, such as cyclopropyl, cyclobutyl, cyclopentyl, cyclohexyl.

The term "heterocycle", "heterocyclyl" or "heterocyclic" as used herein refers to a saturated or partially unsaturated ring having 3-12 ring atoms (3-12 membered), such as 3-8 ring atoms (3-8 membered), 5-7 ring atoms (5-7 membered), 3-6 ring atoms (3-6 membered), or 4-6 ring atoms (4-6 membered), with 1, 2 or 3, preferably 1 or 2 of the ring atoms being heteroatoms independently selected from N, O and S, and the remaining ring atoms being carbon, and having one or more, for example 1, 2 or 3, preferably 1 or 2 rings, wherein the N or S heteroatom is optionally oxidized to various oxidation states. The point of attachment of heterocyclyl may be on N heteroatom or carbon atom. The ring(s) of the heterocyclyl also include(s) a fused ring, a bridged ring, or a spirocyclic ring. The ring(s) of the heterocyclyl may be saturated or contain(s) one or more, for example, one or two double bonds (i.e. partially unsaturated), but is(are) not fully conjugated, and not the heteroaryl as defined herein. For example, "3-8 membered heterocyclyl" refers to the heterocyclyl having 3-8 ring atoms and containing 1, 2 or 3, preferably 1 or 2 ring heteroatoms independently selected from N, O and S, preferably is saturated monocyclic 3-8 membered heterocyclyl. Also for example, "3-6 membered heterocyclyl" refers to the heterocyclyl having 3-6 ring atoms and containing 1 or 2 ring heteroatoms independently selected from N, O and S, preferably is saturated monocyclic 3-6 membered heterocyclyl, such as saturated monocyclic 3, 4, 5, or 6 membered heterocyclyl. Examples of the heterocyclyl include, but are not limited to, oxiranyl, aziridinyl, oxetanyl, azetidinyl, pyrrolidinyl, tetrahydrofuryl, dioxolaneyl, morpholinyl, thiomorpholinyl, piperidinyl, piperazinyl, and tetrahydropyranyl.

The term "aryl" as used herein refers to carbocyclic hydrocarbon radical having 6-14 carbon atoms ($C_{6-14}$), preferably 6-10 carbon atoms ($C_{6-10}$) and consisting of one ring or more fused rings, wherein at least one ring is aromatic. Examples of the aryl include, but are not limited to, phenyl, naphthalenyl, 1,2,3,4-tetrahydronaphthalenyl, phenanthryl, indenyl, indanyl, azulenyl, preferably phenyl and naphthalenyl.

The term "heteroaryl" as used herein refers to:

monocyclic heteroaryl, i.e. monocyclic aromatic hydrocarbon radical having 5, 6 or 7 ring atoms (5, 6 or 7 membered), with one or more, for example 1, 2 or 3, preferably 1 or 2 of the ring atoms being ring heteroatoms independently selected from N, O, and S (preferably N), and the remaining ring atoms being carbon; preferably, monocyclic aromatic hydrocarbon radical having 5 or 6 ring atoms (5 or 6 membered), with 1, 2 or 3, preferably 1 or 2 of the ring atoms being heteroatoms independently selected from N, O, and S, preferably N;

and bicyclic heteroaryl, i.e. bicyclic aromatic hydrocarbon radical having 8-12 ring atoms (8-12 membered), such as having 8, 9 or 10 ring atoms (8, 9 or 10 membered), with one or more, for example, 1, 2, 3 or 4, preferably 2, 3 or 4 of the ring atoms are ring heteroatoms independently selected from N, O, and S (preferably N), and the remaining ring atoms being carbon, wherein at least one of the rings is aromatic. When the total number of S and O atoms in the heteroaryl group exceeds 1, said S and O heteroatoms are not adjacent to one another. For example, the bicyclic heteroaryl includes 5 or 6 membered heteroaryl ring fused to 5 or 6 membered cycloalkyl ring.

Examples of the heteroaryl groups include, but are not limited to, pyridyl, pyridyl N-oxide, pyrazinyl, pyrimidinyl, pyrazolyl, imidazolyl, oxazolyl, isoxazolyl, 1,2,5-oxadiazolyl, thiazolyl, isothiazolyl, thiadiazolyl (such as 1,3,4-thiadiazolyl), tetrazolyl, triazolyl (such as 1,2,4-triazolyl), triazinyl (such as 1,3,5-triazinyl), thienyl, furyl, pyranyl, pyrrolyl, pyridazinyl, benzodioxolyl, benzooxazolyl, benzoisoxazolyl, benzothienyl, benzothiazolyl, benzoisothiazolyl, imidazopyridyl, triazolopyridyl, indazolyl, pyrrolopyridyl, pyrrolopyrimidinyl, pyrazolopyridyl, pyrazolopyrimidinyl, tetrazolopyridyl, tetrahydropyrazolopyridyl, benzofuryl, benzoimidazolinyl, indolyl, 3,4-dihydro-2H-benzo[b][1,4]oxazinyl, indolinyl, purinyl, quinolinyl, tetrahydroquinolinyl, isoquinolinyl, 2,4,5,6-tetrahydrocyclopentadieno[c]pyrazolyl, and 5,6,7,8-tetrahydro[1,2,4]triazolo[1,5-a]pyridyl.

The term “combined ring”, “fused ring” or “condensed ring” as used herein may be used interchangeably in the present invention, and refers to saturated, partially unsaturated, or aromatic ring system in which two rings share a single ring edge. In one embodiment, said “combined ring”, “fused ring” or “condensed ring” has 8-13 ring atoms (8-13 membered), such as 9-12 ring atoms (9-12 membered), 8-11 ring atoms (8-11 membered), or 8, 9 or 10 ring atoms (8, 9 or 10 membered), with 1, 2 or 3, preferably 1 or 2 of the ring atoms being optionally ring heteroatoms independently selected from N, O and S and the remaining ring atoms being carbon.

The term “spirocyclic ring” as used herein refers to saturated or partially unsaturated, preferably saturated ring system in which two rings share a single carbon atom (called “spiro union”), with 1, 2 or 3, preferably 1 or 2 of the ring atoms optionally being ring heteroatoms independently selected from N, O and S, and the remaining ring atoms being carbon. In one embodiment, said “spirocyclic ring” has 8-13 ring atoms (8-13 membered), such as 9-12 ring atoms (9-12 membered), 8-11 ring atoms (8-11 membered), or 8, 9 or 10 ring atoms (8, 9 or 10 membered), with 1, 2 or 3, preferably 1 or 2 of the ring atoms optionally being ring heteroatoms independently selected from N, O and S, and the remaining ring atoms being carbon.

The term “bridge ring” or “bridged ring” as used herein may be used interchangeably in the present invention, and refers to saturated or partially unsaturated, preferably saturated ring system in which two rings share two atoms not connected directly (called “bridgehead atom”), with 1, 2 or 3, preferably 1 or 2 of the ring atoms optionally being heteroatoms independently selected from N, O and S, and the remaining ring atoms being carbon. In one embodiment, said “bridge ring” or “bridged ring” has 8-13 ring atoms (8-13 membered), such as 9-12 ring atoms (9-12 membered), 8-11 ring atoms (8-11 membered), or 8, 9 or 10 ring atoms (8, 9 or 10 membered), with 1, 2 or 3, preferably 1 or 2 of the ring atoms optionally being ring heteroatoms independently selected from N, O and S, and the remaining ring atoms being carbon.

The term “hydroxy” as used herein refers to the group —OH.

The term “mercapto” as used herein refers to the group —SH.

The term “oxo” as used herein refers to the group =O.

The term “amino” as used herein refers to the group $-NH_2$.

The term “cyano” as used herein refers to the group —CN.

When a structure herein contains an asterisk “*”, it means that the chiral center of the compound marked by “*” is a single configuration in either R-configuration or S-configuration, and the content of the single configuration of the compound marked by “*” is at least 90% (e.g., 90%, 91%, 92%, 93%, 94%, 95%, 96%, 97%, 98%, 99%, 99.5%, 99.9%, 100%, or any value between those enumerated values).

When a structure herein contains “(RS)”, it means that the chiral center of the compound marked by “(RS)” contains both R-configuration and S-configuration.

The term “optional” or “optionally” as used herein means that the subsequently described event or circumstance may or may not occur, and the description includes instances wherein the event or circumstance occur and instances in which it does not occur. For example, “optionally substituted alkyl” or “alkyl optionally substituted with . . . ” encompasses both “unsubstituted alkyl” and “substituted alkyl” as defined herein. It will be understood by those skilled in the art, with respect to any group containing one or more substituents, that such groups are not intended to introduce any substitution or substitution patterns that are sterically impractical, chemically incorrect, synthetically non-feasible and/or inherently unstable.

The term “substituted” or “substituted with . . . ” as used herein, means that one or more hydrogens on the designated atom or group are replaced with one or more substituents selected from the indicated group of substituents, provided that the designated atom’s normal valence is not exceeded. When a substituent is oxo (i.e., =O), then 2 hydrogens on a single atom are replaced by the oxo. Combinations of substituents and/or variables are permissible only if such combinations result in a chemically correct and stable compound. A chemically correct and stable compound is meant to imply a compound that is sufficiently robust to survive sufficient isolation from a reaction mixture.

Unless otherwise specified, substituents are named into the core structure. For example, it is to be understood that when (cycloalkyl)alkyl is listed as a possible substituent, the point of attachment of this substituent to the core structure is in the alkyl portion.

The term “substituted with one or more substituents” as used herein means that one or more hydrogens on the designated atom or group are independently replaced with one or more substituents selected from the indicated group of substituents. In some embodiments, “substituted with one or more substituents" means that the designated atom or group is substituted with 1, 2, 3, or 4, preferably 1, 2 or 3, more preferably 1 or 2 substituents independently selected from the indicated group of substituents.

The term "leaving group" refers to the atoms or functional groups that are replaced in the process of a reaction. Examples of the leaving group include, but are not limited to, halo, alkoxyl, and sulfonyloxy. Examples of sulfonyloxy include, but are not limited to, alkylsulfonyloxy (such as methanesulfonyloxy (also known as methanesulfonate group) and trifluoromethanesulfonyloxy (also known as trifluoromethanesulfonate group)) and arylsulfonyloxy (such as p-toluenesulfonyloxy (also known as p-tosylate group) and p-nitrophenylsulfonyloxy (also known as p-nitrophenylsulfonate group)).

It will be appreciated by a person skilled in the art that some of the compounds of formula (I) may contain one or more chiral centers and therefore exist in two or more stereoisomers. The racemates of these isomers, the individual isomers and mixtures enriched in one enantiomer, as well as diastereomers and mixtures partially enriched with specific diastereomers when there are two chiral centers are within the scope of the present invention. It will be further appreciated by a person skilled in the art that the present invention includes all the individual stereoisomers (e.g. enantiomers), racemic mixtures or partially resolved mixtures of the compounds of formula (I) and, where appropriate, the individual tautomeric forms thereof.

In other words, in some embodiments, the present invention provides the compounds of various stereoisomeric purities, i.e., diastereomeric or enantiomeric purity represented by various "ee" or "de" values. In some embodiments, the compounds of formula (I) or subformula (I-1), (I-2), (I-3) thereof as described herein have an enantiomeric purity of at least 60% ee (e.g., 60%, 65%, 70%, 75%, 80%, 85%, 90%, 91%, 92%, 93%, 94%, 95%, 96%, 97%, 98%, 99%, 99.5%, 99.9% ee, or any values between those enumerated values). In some embodiments, the compounds of formula (I) or subformula (I-1), (I-2), (I-3) thereof as described herein have an enantiomeric purity of greater than 99.9% ee. In some embodiments, the compounds of formula (I) or subformula (I-1), (I-2), (I-3) thereof as described herein have a diastereomeric purity of at least 60% de (e.g., 60%, 65%, 70%, 75%, 80%, 85%, 90%, 91%, 92%, 93%, 94%, 95%, 96%, 97%, 98%, 99%, 99.5%, 99.9% de, or any values between those enumerated values). In some embodiments, the compounds of formula (I) or subformula (I-1), (I-2), (I-3) thereof as described herein have a diastereomeric purity of greater than 99.9% de.

The term "enantiomeric excess" or "ee" designates how much one enantiomer is present as compared to the other. For a mixture of R and S enantiomers, the percent enantiomeric excess is defined as $|R-S|*100$, where R and S are the respective mole or weight fractions of enantiomers in a mixture, and $R+S=1$. With knowledge of the optical rotation of a chiral substance, the percent enantiomeric excess is defined as ([a]obs/[a]max)*100, where [a]obs is the optical rotation of the mixture of enantiomers and [a]max is the optical rotation of the pure enantiomer.

The term "diastereomeric excess" or "de" designates how much one diastereomer is present as compared to the other, and is defined by analogy to enantiomeric excess. Thus, for a mixture of diastereomers, D1 and D2, the percent diastereomeric excess is defined as $|D1|D2|*100$, wherein D1 and D2 are the respective mole or weight fractions of diastereomers in the mixture, and $D1+D2=1$.

The diastereomeric and/or enantiomeric excess may be determined using a variety of analytical techniques, including NMR spectroscopy, chiral column chromatography and/or optical polarimetry according to routine protocols familiar to a person skilled in the art.

The racemate can be used as such or can be resolved into their individual isomers. The resolution can afford stereochemically pure compounds or mixtures enriched in one or more isomers. Methods for separation of isomers are well known (cf. Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively, individual isomers can be separated chemically from a mixture by forming diastereomeric salts with a chiral acid (such as the individual enantiomers of 10-camphorsulfonic acid, camphoric acid, alpha-bromocamphoric acid, tartaric acid, diacetyltartaric acid, malic acid, pyrrolidone-5-carboxylic acid, and the like), fractionally crystallizing the salts, and then freeing one or both of the resolved bases, optionally repeating the process, so as to obtain either or both isomers substantially free of the other; i.e., in an isomer having an optical purity of >95%. Alternatively, the racemate can be covalently linked to a chiral compound (auxiliary) to produce diastereomers which can be separated by chromatography or by fractional crystallization, and subsequently the chiral auxiliary is chemically removed to afford the pure enantiomers, as is known to a person skilled in the art.

The term "pharmaceutically acceptable salt" includes, but is not limited to, acid addition salts formed by the compounds of formula (I) or subformula (I-1), (I-2), (I-3) thereof with an inorganic acid, such as hydrochloride, hydrobromide, carbonate, bicarbonate, phosphate, sulfate, sulfite, nitrate and the like; as well as with an organic acid, such as formate, acetate, malate, maleate, fumarate, tartrate, succinate, citrate, lactate, methanesulfonate, p-toluenesulfonate, 2-hydroxyethylsulfonate, benzoate, salicylate, stearate, and salts with alkane-dicarboxylic acid of formula $HOOC-(CH_2)_n-COOH$ wherein n is 0-4, and the like. Also, "pharmaceutically acceptable salt" includes base addition salts formed by the compounds of formula (I) or subformula (I-1), (I-2), (I-3) thereof carrying an acidic moiety with pharmaceutically acceptable cations, for example, sodium, potassium, calcium, aluminum, lithium, and ammonium.

In addition, if the compound described herein is obtained as an acid addition salt, the free base can be obtained by basifying a solution of the acid addition salt. Conversely, if the product is a free base, an acid addition salt, particularly a pharmaceutically acceptable acid addition salt, may be produced from a base compound by dissolving the free base in a suitable solvent and treating the solution with an acid, in accordance with conventional procedures for preparing acid addition salts. A person skilled in the art will recognize various synthetic methodologies that may be used without undue experimentation to prepare non-toxic pharmaceutically acceptable acid addition salts or base addition salts.

The term "solvates" means solvent addition forms that contain either stoichiometric or non-stoichiometric amounts of solvent. Some compounds have a tendency to trap a fixed molar ratio of solvent molecules in the solid state, thus forming a solvate. If the solvent is water, the solvate formed is a hydrate, when the solvent is alcohol, the solvate formed is an alcoholate. Hydrates are formed by the combination of one or more molecules of water with one molecule of the substance, in which the water retains its molecular state $H_2O$. Such combination is able to form one or more hydrates, for example, hemihydrate, monohydrate, and dihydrate.

The term "deuterated compounds" means compounds, in which one or more, for example 1, 2 or 3 hydrogen atoms are replaced with its isotope deuterium. Wherein, the content of deuterium isotope of the deuterium element at its replaced position (deuteration degree) should be at least greater than the content of natural deuterium isotope. In some embodiments, the deuterated compound of formula (I) or subformula (I-1), (I-2), (I-3) thereof has a deuteration degree of at least 50% (e.g., 50%, 60%, 65%, 70%, 75%, 80%, 85%, 90%, 91%, 92%, 93%, 94%, 95%, 96%, 97%, 98%, 99%, 99.5%, 99.9%, or any value between those enumerated values). In some embodiments, the compound of formula (I) or subformula (I-1), (I-2), (I-3) thereof has a deuteration degree of greater than 99.9% up to 100%.

As used herein, the terms "group", "radical" and "moiety" are synonymous and are intended to indicate functional groups or fragments of molecules attachable to other fragments of molecules.

The term "treating", "treat" or "treatment" in connection with a disease or disorder refers to administering one or more pharmaceutical substances, especially a compound of formula (I) or a pharmaceutically acceptable salt thereof described herein to a subject that has the disease or disorder, or has a symptom of a disease or disorder, with the purpose to cure, heal, alleviate, relieve, alter, remedy, ameliorate, improve, or affect the disease or disorder, the symptoms of the disease or disorder. In some embodiments, the disease or disorder is a disease responsive to inhibition of ERK, preferably cancer.

The term "prevent" or "preventing" in connection with a disease or disorder refer to administering one or more pharmaceutical substances, especially a compound of formula (I) or a pharmaceutically acceptable salt thereof described herein to a subject that has a predisposition toward a disease or disorder, or has a risk of suffering from a disease or disorder, with the purpose to prevent or slow down the occurrence of the disease or disorder in the subject. In some embodiments, the disease or disorder is a disease responsive to inhibition of ERK, preferably cancer.

The terms "treating", "contacting" and "reacting" in the context of a chemical reaction, mean adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately lead to the formation of the indicated and/or the desired product.

The term "effective amount" as used herein refers to an amount of a compound of formula (I) or a pharmaceutically acceptable salt thereof described herein effective to "treat" or "prevent", as defined above, a disease or disorder responsive to inhibition of ERK in a subject. The effective amount may cause any changes observable or measurable in a subject as described in the definition of "treating", "treat", "treatment", "preventing", or "prevent" above. For example, in the case of cancer, the effective amount can reduce the number of cancer or tumor cells; reduce the tumor size; inhibit or stop tumor cell infiltration into peripheral organs including, for example, the spread of tumor into soft tissue and bone; inhibit and stop tumor metastasis; inhibit and stop tumor growth; relieve to some extent one or more of the symptoms associated with the cancer; reduce morbidity and mortality; improve quality of life; or a combination of such effects. An effective amount may be an amount sufficient to reduce the symptoms of a disease responsive to inhibition of ERK. The term "effective amount" may also refer to an amount of a compound of formula (I) or a pharmaceutically acceptable salt thereof described herein effective to inhibit the activity of ERK in a subject.

The term "inhibition" or "inhibiting" indicates a decrease in the baseline activity of a biological activity or process. "Inhibition of ERK" refers to a decrease in the activity of ERK as a direct or indirect response to the presence of a compound of formula (I) or a pharmaceutically acceptable salt thereof described herein, relative to the activity of ERK in the absence of a compound of formula (I) or a pharmaceutically acceptable salt thereof. The decrease in activity may be due to the direct interaction of a compound of formula (I) or a pharmaceutically acceptable salt thereof described herein with ERK, or due to the interaction of a compound of formula (I) or a pharmaceutically acceptable salt thereof described herein with one or more other factors that in turn affect the ERK activity. For example, the presence of a compound of formula (I) or a pharmaceutically acceptable salt thereof described herein may decrease the ERK activity by directly binding to the ERK, by directly or indirectly causing another factor to decrease the ERK activity, or by directly or indirectly decreasing the amount of ERK present in the cell or organism.

The term "subject" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The term "pharmaceutically acceptable" means that the substance following this term is useful in preparing a pharmaceutical composition and is generally safe, non-toxic, and neither biologically nor otherwise undesirable, especially for human pharmaceutical use.

The term "about" is used herein to mean approximately, in the region of, roughly, or around. When the term "about" is used in conjunction with a numerical range, it modifies that range by extending the boundaries above or below the numerical values set forth. In general, the term "about" is used herein to modify a numerical value above or below the stated value by a variance of 20%.

Technical and scientific terms used herein and not specifically defined have the meaning commonly understood by a person skilled in the art, to which the present disclosure pertains.

EMBODIMENTS OF THE INVENTION

Embodiment 1. A compound of formula (I):

(I)

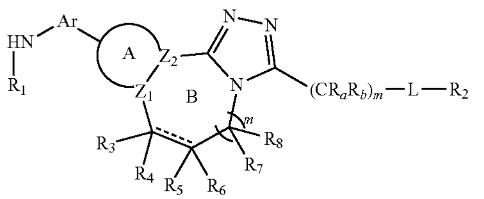

or a pharmaceutically acceptable salt thereof, or solvates, racemic mixtures, enantiomers, diasteromers, or tautomers of the compound of formula (I) or a pharmaceutically acceptable salt thereof, wherein $Z_1$ and $Z_2$ are independently N or C, and

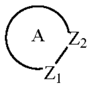

is 5 membered heteroaryl containing 1, 2, 3, or 4 ring heteroatoms selected from N, O or S; said 5 membered heteroaryl is optionally substituted with one or more substituents independently selected from deuterium, halo, hydroxy, amino, —NH($C_{1-6}$ alkyl), —N($C_{1-6}$ alkyl)$_2$, —CN, mercapto, $C_{1-6}$ alkyl, $C_{2-6}$ alkenyl, $C_{2-6}$ alkynyl, $C_{1-6}$ alkoxyl, $C_{1-6}$ haloalkyl, —($C_{1-6}$ alkyl)-OH, and —($C_{1-6}$ alkyl)-O—($C_{1-6}$ alkyl), wherein each of said $C_{1-6}$ alkyl, $C_{1-6}$ alkoxyl, and $C_{1-6}$ haloalkyl is optionally substituted with one or more deuterium;

L is absent, or L is —N$R_c$, O, or S;

$R_c$ is hydrogen or $C_{1-6}$ alkyl;

Ar is heteroaryl optionally substituted with one or more substituents independently selected from deuterium, halo, hydroxy, amino, —NH($C_{1-6}$ alkyl), —N($C_{1-6}$ alkyl)$_2$, —CN, mercapto, $C_{1-6}$ alkyl, $C_{2-6}$ alkenyl, $C_{2-6}$ alkynyl, $C_{1-6}$ alkoxyl, $C_{1-6}$ haloalkyl, —($C_{1-6}$ alkyl)-OH, —($C_{1-6}$ alkyl)-O—($C_{1-6}$ alkyl), $C_{3-8}$ cycloalkyl, 3-8 membered heterocyclyl, phenyl, and heteroaryl, wherein each of said $C_{1-6}$ alkyl, $C_{1-6}$ alkoxyl, $C_{1-6}$ haloalkyl, $C_{3-8}$ cycloalkyl, 3-8 membered heterocyclyl, phenyl, and heteroaryl is optionally substituted with one or more deuterium;

$R_1$ is selected from hydrogen, $C_{1-6}$ alkyl optionally substituted with one or more deuterium, $C_{2-6}$ alkenyl, $C_{2-6}$ alkynyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-($C_{3-8}$ cycloalkyl), —($C_{1-6}$ alkyl)-(3-8 membered heterocyclyl), —($C_{1-6}$ alkyl)-phenyl, —($C_{1-6}$ alkyl)-heteroaryl, $C_{3-8}$ cycloalkyl, 3-8 membered heterocyclyl, phenyl, and heteroaryl, wherein each of said $C_{2-6}$ alkenyl, $C_{2-6}$ alkynyl, $C_{3-8}$ cycloalkyl, 3-8 membered heterocyclyl, phenyl, and heteroaryl is optionally substituted with one or more substituents independently selected from deuterium, halo, —CN, hydroxy, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{3-8}$ cycloalkyl, 3-8 membered heterocyclyl, phenyl, heteroaryl, $C_{1-6}$ alkyl optionally substituted with one or more deuterium, $C_{1-6}$ alkoxyl, and $C_{1-6}$ haloalkyl;

$R_2$ is selected from hydrogen, deuterium, halo, hydroxy, amino, —NH($C_{1-6}$ alkyl), —N($C_{1-6}$ alkyl)$_2$, —CN, mercapto, $C_{1-6}$ alkyl optionally substituted with one or more deuterium, $C_{2-6}$ alkenyl, $C_{2-6}$ alkynyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-($C_{3-8}$ cycloalkyl), —($C_{1-6}$ alkyl)-(3-8 membered heterocyclyl), —($C_{1-6}$ alkyl)-phenyl, —($C_{1-6}$ alkyl)-heteroaryl, $C_{3-8}$ cycloalkyl, 3-8 membered heterocyclyl, phenyl, and heteroaryl, wherein each of said $C_{2-6}$ alkenyl, $C_{2-6}$ alkynyl, $C_{3-8}$ cycloalkyl, 3-8 membered heterocyclyl, phenyl, and heteroaryl is optionally substituted with one or more substituents independently selected from deuterium, halo, —CN, hydroxy, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{1-6}$ alkyl, $C_{1-6}$ alkoxyl, $C_{1-6}$ haloalkyl, and oxo;

$R_a$ and $R_b$ are independently selected from hydrogen, deuterium, halo, hydroxy, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), —CN, mercapto, $C_{1-6}$ alkyl, $C_{1-6}$ alkoxyl, and $C_{1-6}$ haloalkyl; or $R_a$ and $R_b$ together with the carbon atom they are attached to form $C_{3-6}$ cycloalkyl or 4-6 membered heterocyclyl, wherein each of said $C_{3-6}$ cycloalkyl or 4-6 membered heterocyclyl is optionally substituted with one or more substituents independently selected from deuterium, halo, —CN, hydroxy, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{1-6}$ alkyl, $C_{1-6}$ alkoxyl, and $C_{1-6}$ haloalkyl;

is double bond or single bond, and when  is double bond, $R_3$ and $R_5$ are absent;

$R_3$, $R_4$, $R_5$, $R_6$, $R_7$, and $R_8$ are independently selected from hydrogen deuterium, halo, hydroxy, —CN, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{1-6}$ alkyl, —($C_{1-6}$ alkyl)-phenyl, $C_{1-6}$ alkoxyl, and $C_{1-6}$ haloalkyl; or any two of $R_3$, $R_4$, $R_5$, $R_6$, $R_7$, and $R_8$ together with the carbon atom they are attached to and the B ring form a 8-13 membered spirocyclic, fused, or bridged ring optionally containing 1-3 ring heteroatoms independently selected from N, O, or S; wherein said spirocyclic, fused, or bridged ring is optionally substituted with one or more substituents independently selected from deuterium, halo, —CN, hydroxy, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{1-6}$ alkyl, $C_{1-6}$ alkoxyl, and $C_{1-6}$ haloalkyl; or $R_3$ and $R_4$ together, $R_5$ and $R_6$ together, or $R_7$ and $R_8$ together are oxo;

n is 0, 1, or 2;

m is 0, 1, 2, 3, 4, or 5.

Embodiment 2. The compound of formula (I) according to embodiment 1, or a pharmaceutically acceptable salt thereof, or solvates, racemic mixtures, enantiomers, diasteromers, or tautomers of the compound of formula (I) or a pharmaceutically acceptable salt thereof, wherein

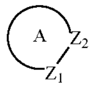

is selected from:

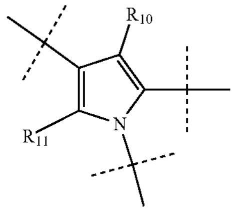
(Ia-1)

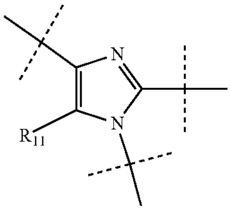
(Ia-2)

-continued

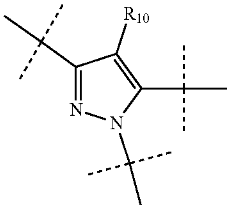

(Ia-3)

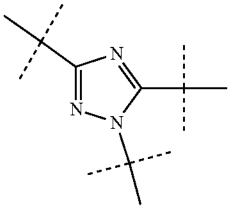

(Ia-4)

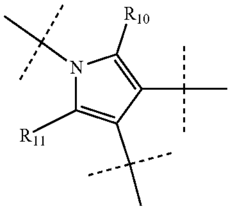

(Ia-5)

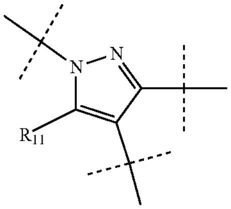

(Ia-6)

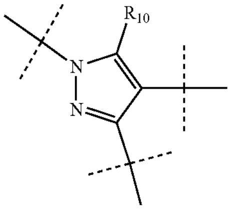

(Ia-7)

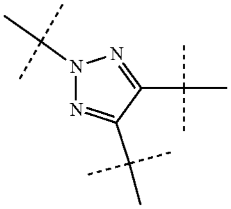

(Ia-8)

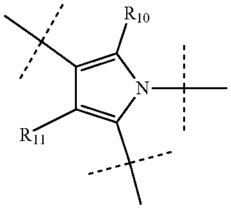

(Ia-9)

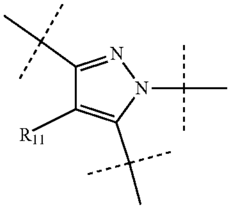

(Ia-10)

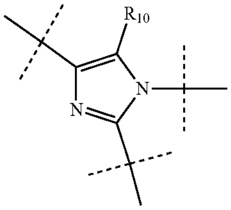

(Ia-11)

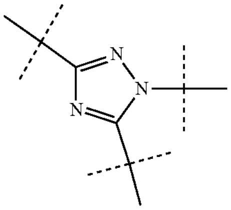

(Ia-12)

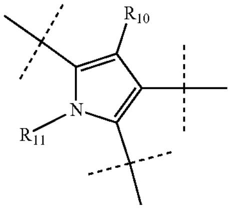

(Ia-13)

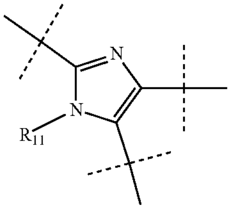

(Ia-14)

-continued

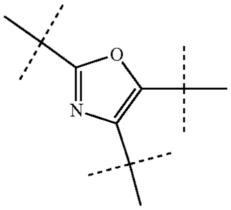

(Ia-15)

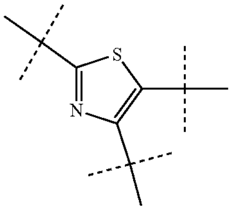

(Ia-16)

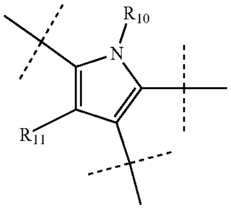

(Ia-17)

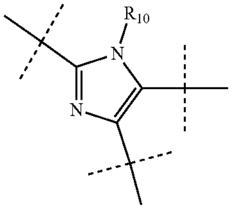

(Ia-18)

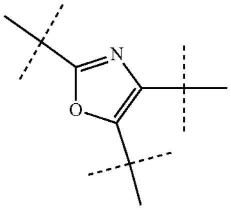

(Ia-19)

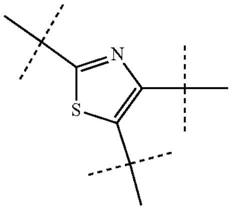

(Ia-20)

wherein $R_{10}$ and $R_{11}$ are independently selected from hydrogen, deuterium, halo, hydroxy, amino, —CN, mercapto, $C_{1-6}$ alkyl, $C_{1-6}$ alkoxyl, $C_{1-6}$ haloalkyl, —($C_{1-6}$ alkyl)-OH, and —($C_{1-6}$ alkyl)-O—($C_{1-6}$ alkyl), wherein each of said $C_{1-6}$ alkyl, $C_{1-6}$ alkoxyl, and $C_{1-6}$ haloalkyl is optionally substituted with one or more deuterium.

Embodiment 3. The compound of formula (I) according to embodiment 1, or a pharmaceutically acceptable salt thereof, or solvates, racemic mixtures, enantiomers, diasteromers, or tautomers of the compound of formula (I) or a pharmaceutically acceptable salt thereof, wherein

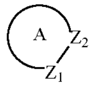

is selected from:

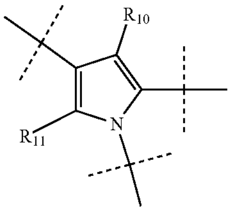

(Ia-1)

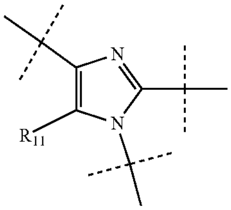

(Ia-2)

-continued

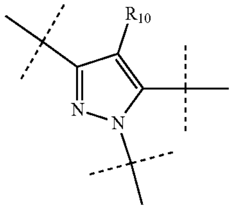

(Ia-3)

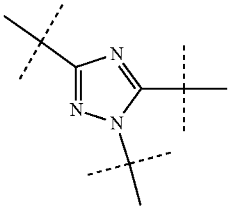

(Ia-4)

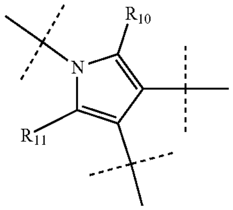

(Ia-5)

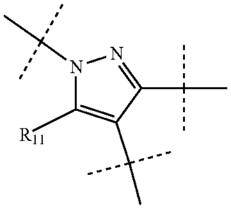

(Ia-6)

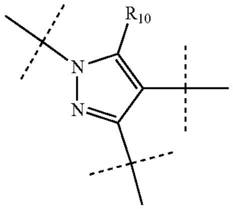

(Ia-7)

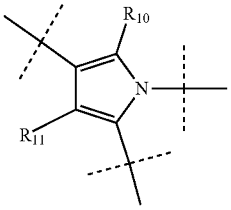

(Ia-9)

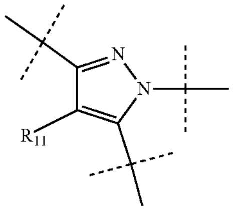

(Ia-10)

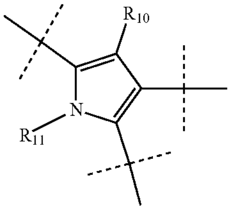

(Ia-13)

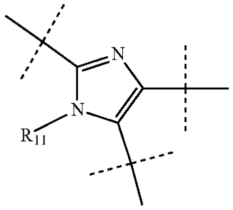

(Ia-14)

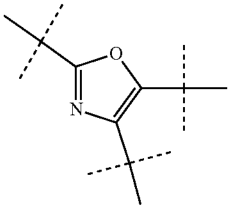

(Ia-15)

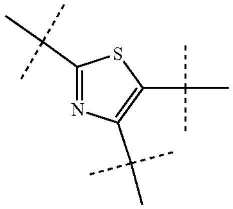

(Ia-16)

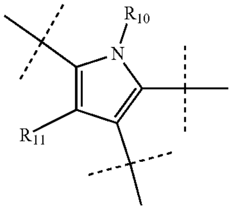

(Ia-17)

-continued

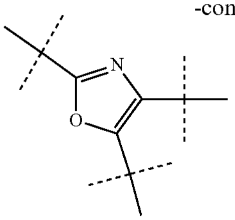

(Ia-19)

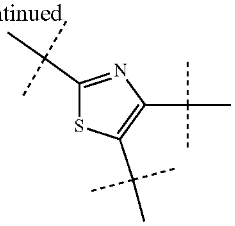

(Ia-20)

wherein $R_{10}$ and $R_{11}$ are independently selected from hydrogen, halo, —CN, $C_{1-6}$ alkyl, $C_{1-6}$ alkoxyl, and $C_{1-6}$ haloalkyl.

Embodiment 4. The compound of formula (I) according to embodiment 3, or a pharmaceutically acceptable salt thereof, or solvates, racemic mixtures, enantiomers, diasteromers, or tautomers of the compound of formula (I) or a pharmaceutically acceptable salt thereof, wherein (Ia-1)

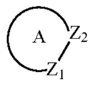

is

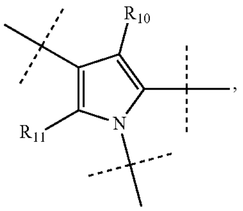

, and $R_{10}$ and $R_{11}$ are independently selected from hydrogen, halo, and $C_{1-6}$ alkyl.

Embodiment 5. The compound of formula (I) according to any one of embodiments 1-4, or a pharmaceutically acceptable salt thereof, or solvates, racemic mixtures, enantiomers, diasteromers, or tautomers of the compound of formula (I) or a pharmaceutically acceptable salt thereof, wherein Ar is monocyclic heteroaryl having 5 or 6 ring atoms with 1, 2 or 3 of the ring atoms being ring heteroatoms independently selected from N, O, and S, and the remaining ring atoms being carbon; each of which is optionally substituted with one or more substituents independently selected from deuterium, halo, hydroxy, amino, —CN, mercapto, $C_{1-6}$ alkyl, $C_{1-6}$ alkoxyl, $C_{1-6}$ haloalkyl, —($C_{1-6}$ alkyl)-OH, —($C_{1-6}$ alkyl)-O—($C_{1-6}$ alkyl), $C_{3-8}$ cycloalkyl, 3-8 membered heterocyclyl, phenyl, and heteroaryl, wherein each of said $C_{1-6}$ alkyl, $C_{1-6}$ alkoxyl, $C_{1-6}$ haloalkyl, $C_{3-8}$ cycloalkyl, 3-8 membered heterocyclyl, phenyl, and heteroaryl is optionally substituted with one or more deuterium.

Embodiment 6. The compound of formula (I) according to embodiment 5, or a pharmaceutically acceptable salt thereof, or solvates, racemic mixtures, enantiomers, diasteromers, or tautomers of the compound of formula (I) or a pharmaceutically acceptable salt thereof, wherein Ar is selected from pyridyl, pyrimidinyl, pyridazinyl, pyrazinyl, 1,3,5-triazinyl, 1,2,4-triazolyl, and thiazolyl (more preferably, Ar is selected from pyridyl, pyrimidinyl, and 1,3,5-triazinyl), each of which is optionally substituted with one or more substituents independently selected from halo, —CN, $C_{1-6}$ alkyl optionally substituted with one or more deuterium, $C_{1-6}$ alkoxyl, and $C_{1-6}$ haloalkyl.

Embodiment 7. The compound of formula (I) according to embodiment 6, or a pharmaceutically acceptable salt thereof, or solvates, racemic mixtures, enantiomers, diasteromers, or tautomers of the compound of formula (I) or a pharmaceutically acceptable salt thereof, wherein Ar is (Ib-1)

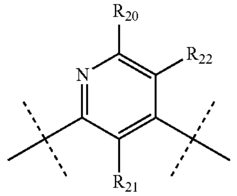

or (Ib-2)

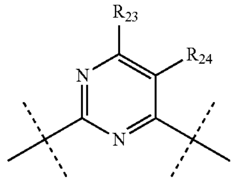

, wherein $R_{20}$, $R_{21}$, $R_{22}$, $R_{23}$, and $R_{24}$ are independently selected from hydrogen, halo, —CN, $C_{1-6}$ alkyl optionally substituted with one or more deuterium, $C_{1-6}$ alkoxyl, and $C_{1-6}$ haloalkyl.

Embodiment 8. The compound of formula (I) according to any one of embodiments 1-7, or a pharmaceutically acceptable salt thereof, or solvates, racemic mixtures, enantiomers, diasteromers, or tautomers of the compound of formula (I) or a pharmaceutically acceptable salt thereof, wherein $R_1$ is selected from $C_{1-6}$ alkyl, —($C_{1-6}$ alkyl)-OH, saturated monocyclic $C_{3-8}$ cycloalkyl, saturated monocyclic 3-8 membered heterocyclyl containing 1 or 2 ring heteroatoms independently selected from N, O and S, and heteroaryl, wherein said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another, and wherein each of said $C_{3-8}$ cycloalkyl, 3-8 membered heterocyclyl, and heteroaryl is optionally substituted with one or more substituents independently selected from halo, —($C_{1-6}$ alkyl)-OH, —($C_{1-6}$ alkyl)-O—($C_{1-6}$ alkyl), 3-6 membered heterocyclyl, $C_{1-6}$ alkyl optionally substituted with one or more deuterium, $C_{1-6}$ alkoxyl, or $C_{1-6}$ haloalkyl.

Embodiment 9. The compound of formula (I) according to embodiment 8, or a pharmaceutically acceptable salt thereof, or solvates, racemic mixtures, enantiomers, diasteromers, or tautomers of the compound of formula (I) or a pharmaceutically acceptable salt thereof, wherein $R_1$ is heteroaryl selected from pyrazolyl, pyridyl, isoxazolyl, 1,2,4-triazolyl, 1,3,4-thiadiazolyl, 2,4,5,6-tetrahydrocyclopentadieno[c]pyrazolyl, and 5,6,7,8-tetrahydro[1,2,4]triazolo[1,5-a]pyridyl, wherein said heteroaryl is each optionally substituted with one or more substituents independently selected from $C_{1-6}$ alkyl optionally substituted with one or more deuterium, $C_{1-6}$ haloalkyl, $C_{1-6}$ alkoxyl, halo, —($C_{1-6}$ alkyl)-OH, —($C_{1-6}$ alkyl)-O—($C_{1-6}$ alkyl), and 3-6 membered heterocyclyl.

Embodiment 10. The compound of formula (I) according to embodiment 9, or a pharmaceutically acceptable salt thereof, or solvates, racemic mixtures, enantiomers, diasteromers, or tautomers of the compound of formula (I) or a pharmaceutically acceptable salt thereof, wherein $R_1$ is pyrazolyl, which is optionally substituted with one or more substituents independently selected from $C_{1-6}$ alkyl optionally substituted with one or more deuterium, $C_{1-6}$ haloalkyl, $C_{1-6}$ alkoxyl, halo, —($C_{1-6}$ alkyl)-OH, —($C_{1-6}$ alkyl)-O—($C_{1-6}$ alkyl), and oxetanyl.

Embodiment 11. The compound of formula (I) according to any one of embodiments 1-10, or a pharmaceutically acceptable salt thereof, or solvates, racemic mixtures, enantiomers, diasteromers, or tautomers of the compound of formula (I) or a pharmaceutically acceptable salt thereof, wherein $R_2$ is selected from halo, —CN, $C_{1-6}$ alkyl, $C_{1-6}$ haloalkyl, saturated monocyclic $C_{3-8}$ cycloalkyl, phenyl, and heteroaryl, wherein said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another, and wherein each of said $C_{3-8}$ cycloalkyl, phenyl, and heteroaryl is optionally substituted with one or more substituents independently selected from halo, —CN, $C_{1-6}$ alkyl, $C_{1-6}$ alkoxyl, $C_{1-6}$ haloalkyl, and oxo.

Embodiment 12. The compound of formula (I) according to embodiment 11, or a pharmaceutically acceptable salt thereof, or solvates, racemic mixtures, enantiomers, diasteromers, or tautomers of the compound of formula (I) or a pharmaceutically acceptable salt thereof, wherein $R_2$ is phenyl, wherein said phenyl is optionally substituted with one or more substituents independently selected from halo, —CN, and $C_{1-6}$ alkoxyl.

Embodiment 13. The compound of formula (I) according to embodiment 11, or a pharmaceutically acceptable salt thereof, or solvates, racemic mixtures, enantiomers, diasteromers, or tautomers of the compound of formula (I) or a pharmaceutically acceptable salt thereof, wherein $R_2$ is heteroaryl selected from 1,2,5-oxadiazolyl, indolyl, indolinyl, quinolinyl, isoquinolinyl, tetrahydroquinolinyl, tetrahydroisoquinolinyl, pyrazolyl, oxazolyl, isoxazolyl, pyridyl, thiazolyl, isothiazolyl, benzo[d]isoxazolyl, thienyl, indazolyl, and pyrrolyl, each of which is optionally substituted with one or more substituents independently selected from $C_{1-6}$ alkyl, halo, oxo, and —CN.

Embodiment 14. The compound of formula (I) according to embodiment 11, or a pharmaceutically acceptable salt thereof, or solvates, racemic mixtures, enantiomers, diasteromers, or tautomers of the compound of formula (I) or a pharmaceutically acceptable salt thereof, wherein $R_2$ is saturated monocyclic $C_{3-8}$ cycloalkyl optionally substituted with one or more substituents independently selected from $C_{1-6}$ haloalkyl.

Embodiment 15. The compound of formula (I) according to any one of embodiments 1-14, or a pharmaceutically acceptable salt thereof, or solvates, racemic mixtures, enantiomers, diasteromers, or tautomers of the compound of formula (I) or a pharmaceutically acceptable salt thereof, wherein m is 0, 1, or 2.

Embodiment 16. The compound of formula (I) according to any one of embodiments 1-15, or a pharmaceutically acceptable salt thereof, or solvates, racemic mixtures, enantiomers, diasteromers, or tautomers of the compound of formula (I) or a pharmaceutically acceptable salt thereof, wherein $R_a$ and $R_b$ are independently selected from hydrogen, halo, hydroxy, and $C_{1-6}$ alkyl; or $R_a$ and $R_b$ together with the carbon atom they are attached to form a saturated monocyclic $C_{3-6}$ cycloalkyl or a 3-6 membered heterocyclyl, wherein said 3-6 membered heterocyclyl is a saturated monocyclic ring having 3-6 ring atoms with 1 or 2 of the ring atoms being ring heteroatoms independently selected from N, O and S, and the remaining ring atoms being carbon; wherein each of said saturated monocyclic $C_{3-6}$ cycloalkyl or 3-6 membered heterocyclyl is optionally substituted with one or more substituents selected from halo.

Embodiment 17. The compound of formula (I) according to any one of embodiments 1-16, or a pharmaceutically acceptable salt thereof, or solvates, racemic mixtures, enantiomers, diasteromers, or tautomers of the compound of formula (I) or a pharmaceutically acceptable salt thereof, wherein L is absent, or L is NH, O or S.

Embodiment 18. The compound of formula (I) according to embodiment 1, or a pharmaceutically acceptable salt thereof, wherein the compound of formula (I) is selected from Compounds 1-322.

Embodiment 19. The compound of formula (I) according to embodiment 1, or a pharmaceutically acceptable salt thereof, or solvates, racemic mixtures, enantiomers, diagnosis or tautomers of the compound of formula (I) or a pharmaceutically acceptable salt thereof, wherein n is 0, ------ is double bond, $R_3$ and $R_5$ are absent, $R_4$ and $R_6$ are independently selected from hydrogen and $C_{1-6}$ alkyl.

Embodiment 20. The compound of formula (I) according to embodiment 19, or a pharmaceutically acceptable salt thereof, or solvates, racemic mixtures, enantiomers, diastereomers, or tautomers of the compound of formula (I) or a pharmaceutically acceptable salt thereof, wherein the compound of formula (I) is the compound of formula (I-1), (I-1)

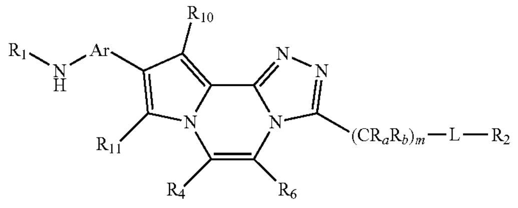

wherein,

- $R_1$ is heteroaryl optionally substituted with one or more substituents independently selected from $C_{1-6}$ alkyl optionally substituted with one or more deuterium, $C_{1-6}$ haloalkyl, $C_{1-6}$ alkoxyl, halo, —($C_{1-6}$ alkyl)-OH, —($C_{1-6}$ alkyl)-O—($C_{1-6}$ alkyl), and 3-6 membered heterocyclyl;
- Ar is heteroaryl optionally substituted with one or more substituents independently selected from halo, —CN, $C_{1-6}$ alkyl optionally substituted with one or more deuterium, $C_{1-6}$ alkoxyl, and $C_{1-6}$ haloalkyl;
- $R_2$ is selected from halo, —CN, $C_{1-6}$ alkyl, $C_{1-6}$ haloalkyl, saturated monocyclic $C_{3-8}$ cycloalkyl, phenyl, and heteroaryl, wherein each of said saturated monocyclic $C_{3-8}$ cycloalkyl, phenyl, or heteroaryl is optionally substituted with one or more substituents independently selected from halo, —CN, $C_{1-6}$ alkyl, $C_{1-6}$ alkoxyl, $C_{1-6}$ haloalkyl, and oxo;
- $R_4$ and $R_6$ are independently selected from hydrogen and $C_{1-6}$ alkyl;
- $R_{10}$ and $R_{11}$ are independently selected from hydrogen, halo, $C_{1-6}$ alkyl, $C_{1-6}$ alkoxyl, $C_{1-6}$ haloalkyl, and —($C_{1-6}$ alkyl)-OH;
- m is 0, 1, or 2;
- $R_a$ and $R_b$ are independently selected from hydrogen, halo, hydrogen, or $C_{1-6}$ alkyl; or $R_a$ and $R_b$ together with the carbon atom they are attached to form a saturated monocyclic $C_{3-6}$ cycloalkyl or a 3-6 membered heterocyclyl, wherein said 3-6 membered heterocyclyl is a saturated monocyclic ring having 3-6 ring atoms with 1 or 2 of the ring atoms being ring heteroatoms independently selected from N, O and S, and the remaining ring atoms being carbon; wherein each of said saturated monocyclic $C_{3-6}$ cycloalkyl or 3-6 membered heterocyclyl is optionally substituted with one or more substituents selected from halo;
- L is absent, or L is NH, O or S;
- said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another.

Embodiment 21. The compound of formula (I) according to embodiment 20, or a pharmaceutically acceptable salt thereof, or solvates, racemic mixtures, enantiomers, diastereomers, or tautomers of the compound of formula (I) or a pharmaceutically acceptable salt thereof, wherein,

- $R_1$ is pyrazolyl, which is optionally substituted with one or more substituents independently selected from $C_{1-6}$ alkyl;
- Ar is pyrimidinyl, which is optionally substituted with one or more substituents independently selected from $C_{1-6}$ alkyl optionally substituted with one or more deuterium, and halo;
- $R_2$ is selected from $C_{1-6}$ haloalkyl or phenyl, wherein said phenyl is optionally substituted with one or more substituents independently selected from halo;
- $R_{10}$ and $R_{11}$ are hydrogen;
- m is 0 or 1;
- $R_a$ and $R_b$ are independently selected from hydrogen or $C_{1-6}$ alkyl; or $R_a$ and $R_b$ together with the carbon atom they are attached to form a saturated monocyclic $C_{3-6}$ cycloalkyl; and
- L is absent, or L is NH or O.

Embodiment 22. The compound of formula (I) according to embodiment 20, or a pharmaceutically acceptable salt thereof, wherein, the compound of formula (I) is selected from the group consisting of:

| Compound | Structure |
|---|---|
| 2 | 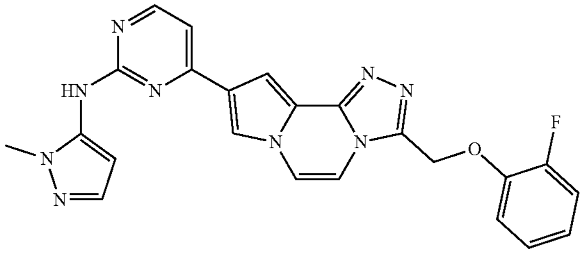 [SMILES: Cn1nccc1Nc1nccc(-c2cc3c4nnc(COc5ccccc5F)n4ccn3c2)n1] |
| 39 | 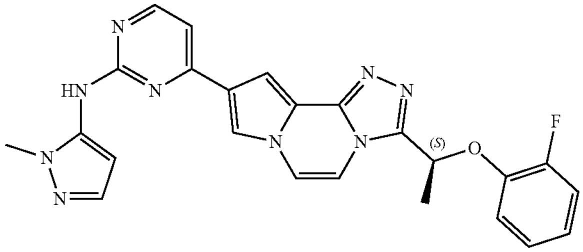 |
| 40 | 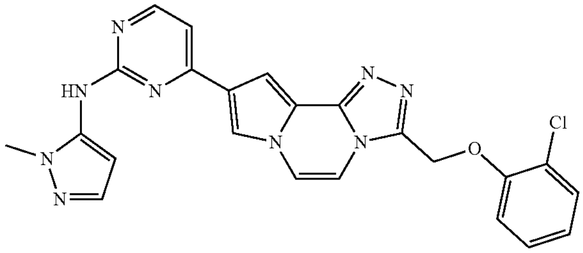 [SMILES: Cn1nccc1Nc1nccc(-c2cc3c4nnc(COc5ccccc5Cl)n4ccn3c2)n1] |
| 41 | 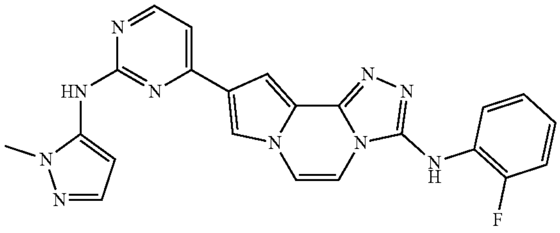 [SMILES: Cn1nccc1Nc1nccc(-c2cc3c4nnc(Nc5ccccc5F)n4ccn3c2)n1] |
| 45 | 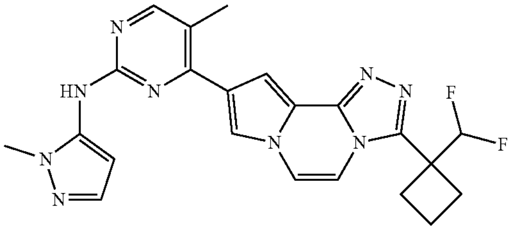 [SMILES: Cc1cnc(Nc2ccnn2C)nc1-c1cc2c3nnc(C4(C(F)F)CCC4)n3ccn2c1] |
| 212 | 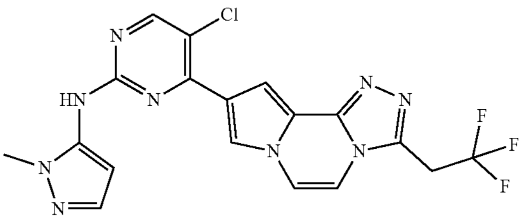 [SMILES: Cn1nccc1Nc1ncc(Cl)c(-c2cc3c4nnc(CC(F)(F)F)n4ccn3c2)n1] |

-continued

| Compound | Structure |
|---|---|
| 231 | 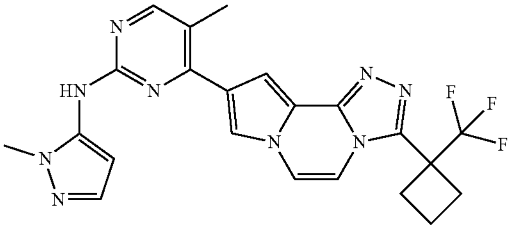 [SMILES: Cc1cnc(Nc2ccnn2C)nc1-c1cc2c3nnc(C4(C(F)(F)F)CCC4)n3ccn2c1] |
| 232 | 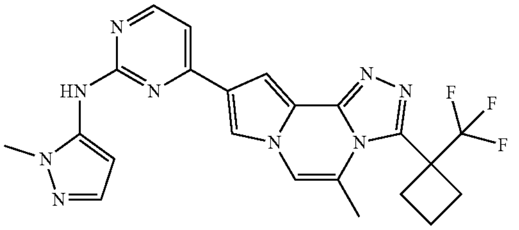 [SMILES: Cc1cn2cc(-c3ccnc(Nc4ccnn4C)n3)cc2c2nnc(C3(C(F)(F)F)CCC3)n12] |
| 236 | 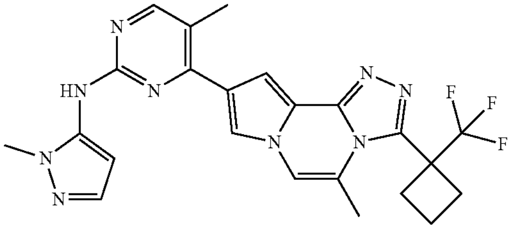 [SMILES: Cc1cnc(Nc2ccnn2C)nc1-c1cc2c3nnc(C4(C(F)(F)F)CCC4)n3c(C)cn2c1] |
| 282 | 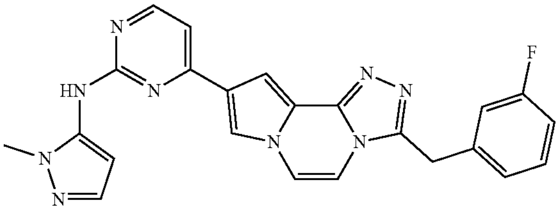 [SMILES: Cn1nccc1Nc1nccc(-c2cc3c4nnc(Cc5cccc(F)c5)n4ccn3c2)n1] |
| 283 | 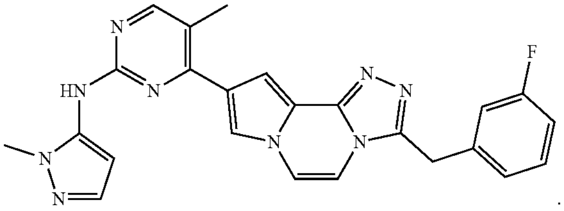 [SMILES: Cc1cnc(Nc2ccnn2C)nc1-c1cc2c3nnc(Cc4cccc(F)c4)n3ccn2c1] |

Embodiment 23. The compound of formula (I) according to embodiment 1, or a pharmaceutically acceptable salt thereof, or solvates, racemic mixtures, enantiomers, diastereomers, or tautomers of the compound of formula (I) or a pharmaceutically acceptable salt thereof, wherein n is 0, ------ is single bond, $R_3$, $R_4$, $R_5$, and $R_6$ are independently selected from hydrogen, $C_{1-6}$ alkyl, $C_{1-6}$ haloalkyl, —($C_{1-6}$ alkyl)-O—($C_{1-6}$ alkyl), and —($C_{1-6}$ alkyl)-phenyl; or any pair of $R_3$ and $R_4$, or $R_5$ and $R_6$, together with the carbon atom they are attached to form a saturated monocyclic $C_{3-6}$ cycloalkyl or a saturated monocyclic 3-6 membered heterocyclyl having 1 or 2 ring heteroatoms selected from N, O and S, thereby together with the B ring forming a spirocyclic ring.

Embodiment 24. The compound of formula (I) according to embodiment 23, or a pharmaceutically acceptable salt thereof, or solvates, racemic mixtures, enantiomers, diastereomers, or tautomers of the compound of formula (I) or a pharmaceutically acceptable salt thereof, wherein the compound of formula (I) is the compound of formula (I-2), (I-2)

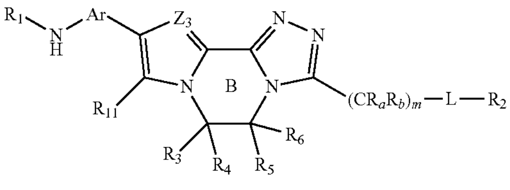

wherein, $R_1$ is selected from $C_{1-6}$ alkyl, —($C_{1-6}$ alkyl)-OH, saturated monocyclic $C_{3-8}$ cycloalkyl, saturated 3-8 membered heterocyclyl containing 1 or 2 ring heteroatoms independently selected from N, O and S, and heteroaryl, wherein each of said $C_{3-8}$ cycloalkyl, 3-8 membered heterocyclyl, and heteroaryl is optionally substituted with one or more substituents independently selected from halo, —($C_{1-6}$ alkyl)-OH, —($C_{1-6}$ alkyl)-O—($C_{1-6}$ alkyl), saturated 3-6 membered heterocyclyl containing 1 or 2 ring heteroatoms independently selected from N, O and S, $C_{1-6}$ alkyl optionally substituted with one or more deuterium, $C_{1-6}$ alkoxyl, and $C_{1-6}$ haloalkyl;

Ar is heteroaryl optionally substituted with one or more substituents independently selected from halo, —CN, $C_{1-6}$ alkyl optionally substituted with one or more deuterium, $C_{1-6}$ alkoxyl, and $C_{1-6}$ haloalkyl;

$R_2$ is selected from halo, —CN, $C_{1-6}$ alkyl, $C_{1-6}$ haloalkyl, saturated monocyclic $C_{3-8}$ cycloalkyl, phenyl, or heteroaryl, wherein each of said $C_{3-8}$ cycloalkyl, phenyl, or heteroaryl is optionally substituted with one or more substituents independently selected from halo, —CN, $C_{1-6}$ alkyl, $C_{1-6}$ alkoxyl, $C_{1-6}$ haloalkyl, and oxo;

$Z_3$ is $CR_{10}$ or N;

$R_3$, $R_4$, $R_5$, and $R_6$ are independently selected from hydrogen, $C_{1-6}$ alkyl, $C_{1-6}$ haloalkyl, —($C_{1-6}$ alkyl)-O—($C_{1-6}$ alkyl), and —($C_{1-6}$ alkyl)-phenyl; or any pair of $R_3$ and $R_4$, or $R_5$ and $R_6$, together with the carbon atom they are attached to form a saturated monocyclic $C_{3-6}$ cycloalkyl or a saturated monocyclic 3-6 membered heterocyclyl having 1 or 2 ring heteroatoms selected from N, O and S, thereby together with the B ring forming a spirocyclic ring;

$R_{10}$ and $R_{11}$ are independently selected from hydrogen, halo, $C_{1-6}$ alkyl, $C_{1-6}$ alkoxyl, $C_{1-6}$ haloalkyl, and —($C_{1-6}$ alkyl)-OH;

m is 0, 1, or 2;

$R_a$ and $R_b$ are independently selected from hydrogen, halo, hydroxy, or $C_{1-6}$ alkyl; or $R_a$ and $R_b$ together with the carbon atom they are attached to form a saturated monocyclic $C_{3-6}$ cycloalkyl or a 3-6 membered heterocyclyl, wherein said 3-6 membered heterocyclyl is a saturated monocyclic ring having 3-6 ring atoms with 1 or 2 of the ring atoms being ring heteroatoms independently selected from N, O and S, and the remaining ring atoms being carbon; wherein each of said saturated monocyclic $C_{3-6}$ cycloalkyl or 3-6 membered heterocyclyl is optionally substituted with one or more substituents selected from halo;

L is absent, or L is NH, O or S;

said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another.

Embodiment 25. The compound of formula (I) according to embodiment 24, or a pharmaceutically acceptable salt thereof, or solvates, racemic mixtures, enantiomers, diastereomers, or tautomers of the compound of formula (I) or a pharmaceutically acceptable salt thereof, wherein, $R_1$ is selected from saturated monocyclic 3-8 membered heterocyclyl containing 1 or 2 ring heteroatoms independently selected from N, O and S, and heteroaryl, wherein said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another, and wherein each of said 3-8 membered heterocyclyl and heteroaryl is optionally substituted with one or more substituents independently selected from $C_{1-6}$ alkyl, $C_{1-6}$ haloalkyl, halo, —($C_{1-6}$ alkyl)-OH, $C_{1-6}$ alkoxyl, —($C_{1-6}$ alkyl)-O—($C_{1-6}$ alkyl), and saturated monocyclic 3-6 membered heterocyclyl containing 1 or 2 ring heteroatoms independently selected from N, O and S;

Ar is heteroaryl, wherein said heteroaryl is monocyclic aromatic hydrocarbon radical having 5 or 6 ring atoms with 1, 2 or 3 of the ring atoms being heteroatoms independently selected from N, O, and S, and the remaining ring atoms being carbon, and when the total number of S and O atoms in the heteroaryl group exceeds 1, said S and O heteroatoms are not adjacent to one another, and wherein said heteroaryl is optionally substituted with one or more substituents independently selected from $C_{1-6}$ alkyl optionally substituted with one or more deuterium, and halo;

$R_2$ is selected from halo, $C_{1-6}$ alkyl, $C_{1-6}$ haloalkyl, phenyl, and heteroaryl, wherein said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another, and wherein each of said phenyl and heteroaryl is optionally substituted with one or more substituents independently selected from halo, $C_{1-6}$ alkyl, $C_{1-6}$ alkoxyl, and oxo;

$Z_3$ is $CR_{10}$ or N;

$R_3$, $R_4$, $R_5$, and $R_6$ are independently selected from hydrogen, $C_{1-6}$ alkyl, $C_{1-6}$ haloalkyl, —($C_{1-6}$ alkyl)-O—($C_{1-6}$ alkyl), and —($C_{1-6}$ alkyl)-phenyl; or any pair of $R_3$ and $R_4$, or $R_5$ and $R_6$, together with the carbon atom they are attached to form a saturated monocyclic $C_{3-6}$ cycloalkyl or a saturated monocyclic 3-6 membered heterocyclyl having 1 or 2 ring heteroatoms selected from N, O and S, thereby together with the B ring forming a spirocyclic ring;

m is 1 or 2;

$R_a$ and $R_b$ are independently selected from hydrogen and halo; or $R_a$ and $R_b$ together with the carbon atom they are attached to form a saturated monocyclic $C_{3-6}$ cycloalkyl;

$R_{10}$ and $R_{11}$ are hydrogen;

L is absent, or L is O.

Embodiment 26. The compound of formula (I) according to embodiment 25, or a pharmaceutically acceptable salt thereof, or solvates, racemic mixtures, enantiomers, diastereomers, or tautomers of the compound of formula (I) or a pharmaceutically acceptable salt thereof, wherein $R_1$ is selected from morpholinyl, thiomorpholinyl, and heteroaryl, wherein said heteroaryl is selected from pyrazolyl, 2,4,5,6-tetrahydrocyclopentadieno[c]pyrazolyl, 1,2,4-triazolyl, 5,6,7,8-tetrahydro[1,2,4]triazolo[1,5-a]pyridyl, 1,3,4-thiadiazolyl, and pyridyl, and said heteroaryl is each optionally substituted with one or more substituents independently selected from $C_{1-6}$ alkyl, $C_{1-6}$ haloalkyl, halo, —($C_{1-6}$ alkyl)-OH, $C_{1-6}$ alkoxyl, —($C_{1-6}$ alkyl)-O—($C_{1-6}$ alkyl), and oxetanyl.

Embodiment 27. The compound of formula (I) according to embodiment 24, or a pharmaceutically acceptable salt thereof, or solvates, racemic mixtures, enantiomers, diastereomers, or tautomers of the compound of formula (I) or a pharmaceutically acceptable salt thereof, wherein Ar is heteroaryl selected from pyridyl, pyrimidinyl, and 1,3,5-triazinyl; wherein said heteroaryl is each optionally substituted with one or more substituents selected from $C_{1-6}$ alkyl optionally substituted with one or more deuterium, and halo.

Embodiment 28. The compound of formula (I) according to embodiment 27, or a pharmaceutically acceptable salt thereof, or solvates, racemic mixtures, enantiomers, diastereomers, or tautomers of the compound of formula (I) or a pharmaceutically acceptable salt thereof, wherein Ar is (Ib-1)

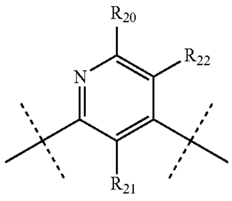

or

-continued (Ib-2)

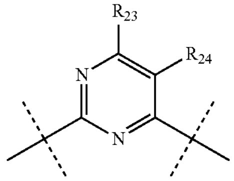

, wherein $R_{20}$, $R_{21}$, $R_{22}$, $R_{23}$, and $R_{24}$ are independently selected from hydrogen, halo, and $C_{1-6}$ alkyl optionally substituted with one or more deuterium.

Embodiment 29. The compound of formula (I) according to embodiment 24, or a pharmaceutically acceptable salt thereof, or solvates, racemic mixtures, enantiomers, diastereomers, or tautomers of the compound of formula (I) or a pharmaceutically acceptable salt thereof, wherein $R_2$ is selected from halo, $C_{1-6}$ alkyl, $C_{1-6}$ haloalkyl, phenyl, and heteroaryl, wherein said heteroaryl is selected from isoxazolyl, 1,2,5-oxadiazolyl, pyrazolyl, oxazolyl, pyridyl, thiazolyl, isothiazolyl, thienyl, and benzo[d]isoxazolyl; wherein each of said phenyl and heteroaryl is optionally substituted with one or more substituents independently selected from halo, $C_{1-6}$ alkyl, $C_{1-6}$ alkoxyl, and oxo.

Embodiment 30. The compound of formula (I) according to embodiment 24, or a pharmaceutically acceptable salt thereof, wherein the compound of formula (I) is selected from:

| Compound | Structure |
|---|---|
| 3 | 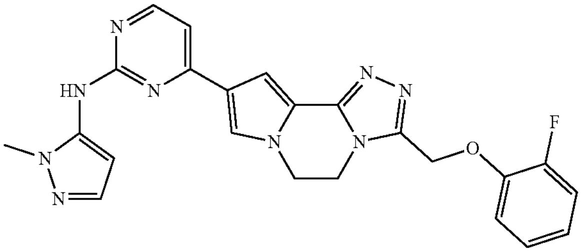 [SMILES: Cn1nccc1Nc1nccc(-c2cc3n(c2)CCn2c(COc4ccccc4F)nnc2-3)n1] |
| 5 | 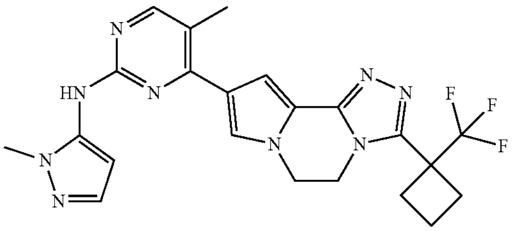 [SMILES: Cc1cnc(Nc2ccnn2C)nc1-c1cc2n(c1)CCn1c-2nnc1C1(C(F)(F)F)CCC1] |

-continued
| Compound | Structure |
| --- | --- |
| 7 | 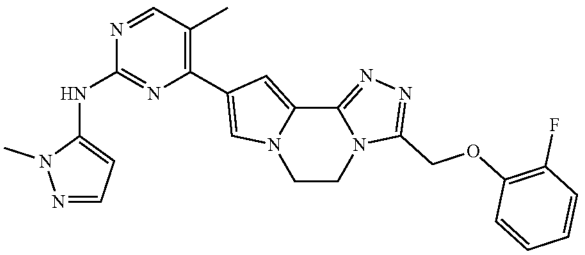 [SMILES: Cc1cnc(Nc2ccnn2C)nc1-c1cc2n(c1)CCn1c(COc3ccccc3F)nnc1-2] |
| 9 | 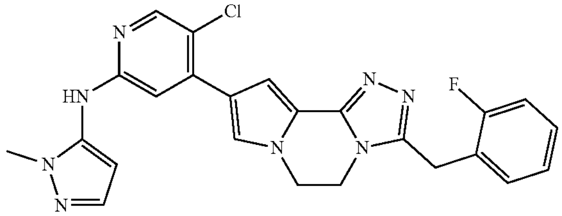 [SMILES: Cn1nccc1Nc1cc(-c2cc3n(c2)CCn2c(Cc4ccccc4F)nnc2-3)c(Cl)cn1] |
| 20 | 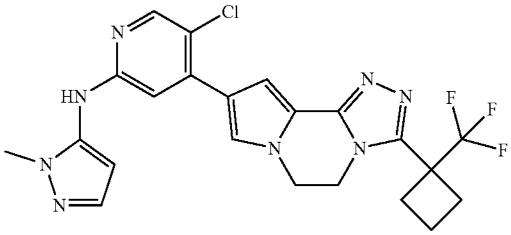 [SMILES: Cn1nccc1Nc1cc(-c2cc3n(c2)CCn2c-3nnc2C2(C(F)(F)F)CCC2)c(Cl)cn1] |
| 23 | 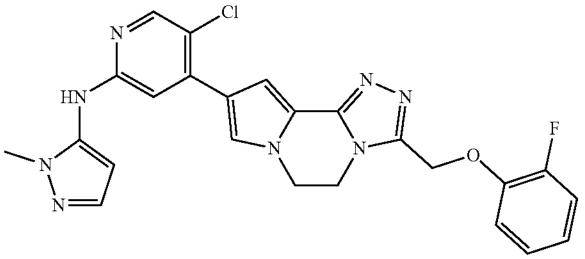 [SMILES: Cn1nccc1Nc1cc(-c2cc3n(c2)CCn2c(COc4ccccc4F)nnc2-3)c(Cl)cn1] |
| 46 | 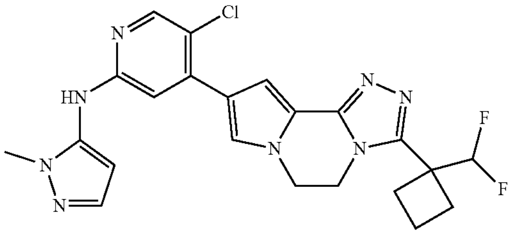 [SMILES: Cn1nccc1Nc1cc(-c2cc3n(c2)CCn2c-3nnc2C2(C(F)F)CCC2)c(Cl)cn1] |
| 47 | 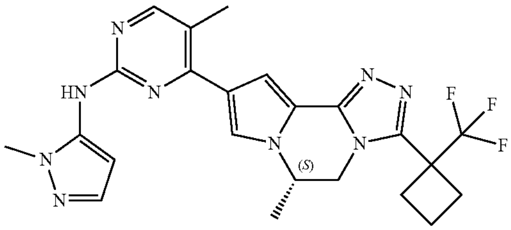 |

-continued
| Compound | Structure |
| --- | --- |
| 48 | 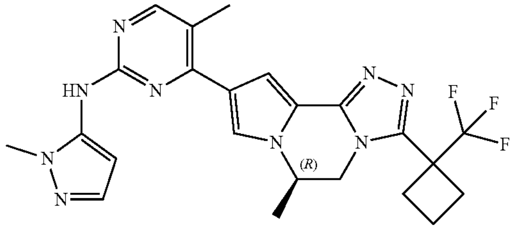 |
| 50 | 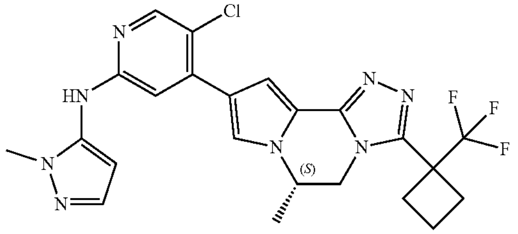 |
| 56 | 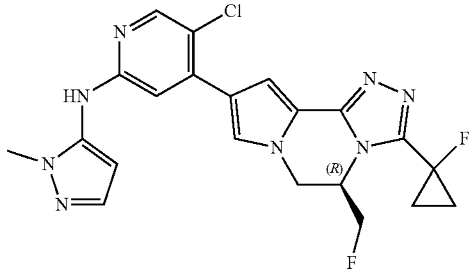 |
| 57 | 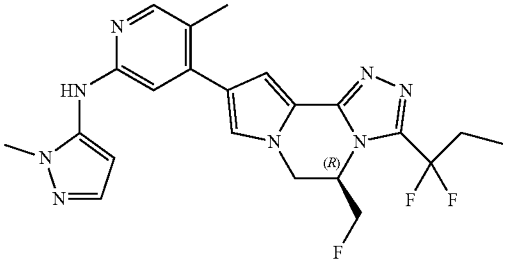 |
| 58 | 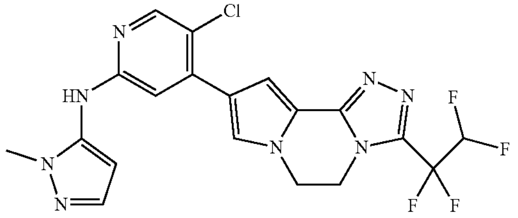 [SMILES: Cn1nccc1Nc1cc(-c2cc3n(c2)CCn2c-3nnc2C(F)(F)C(F)F)c(Cl)cn1] |
| 61 | 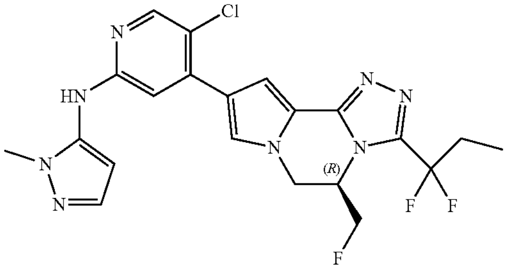 |

-continued
| Compound | Structure |
| --- | --- |
| 62 | 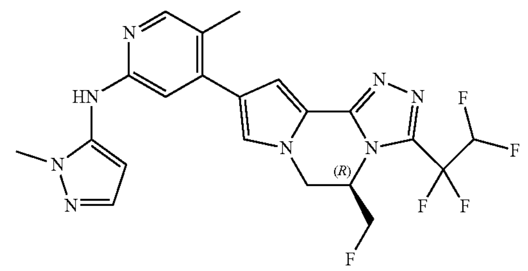 |
| 63 | 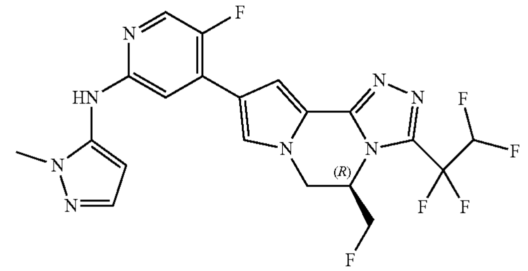 |
| 64 | 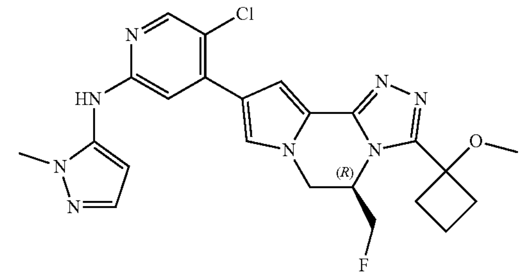 |
| 68 | 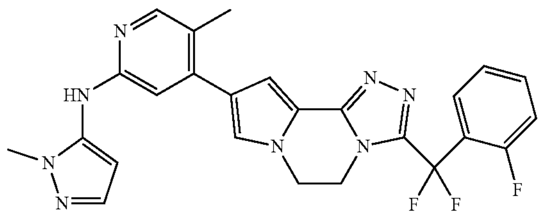 [SMILES: Cc1cnc(Nc2ccnn2C)cc1-c1cc2n(c1)CCn1c-2nnc1C(F)(F)c1ccccc1F] |
| 69 | 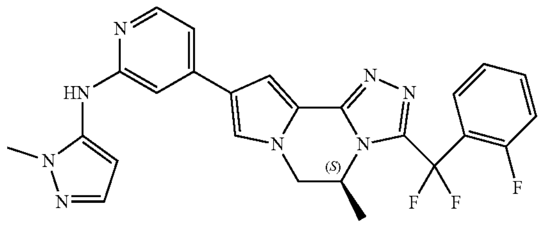 |
| 70 | 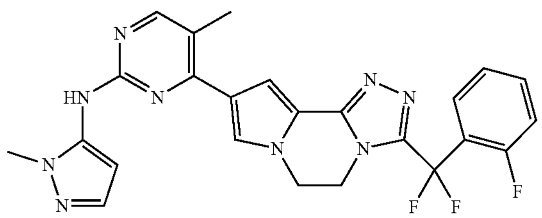 [SMILES: Cc1cnc(Nc2ccnn2C)nc1-c1cc2n(c1)CCn1c-2nnc1C(F)(F)c1ccccc1F] |

-continued
| Compound | Structure |
| --- | --- |
| 71 | 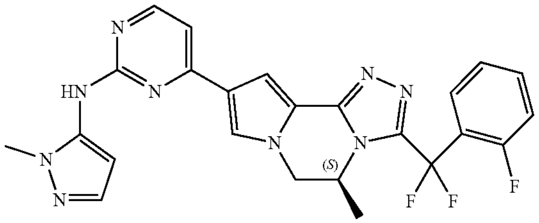 |
| 76 | 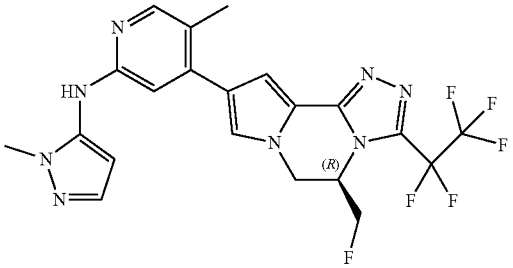 |
| 79 | 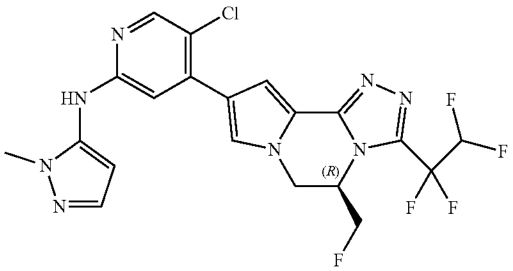 |
| 82 | 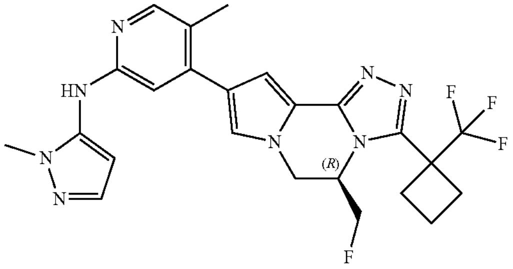 |
| 83 | 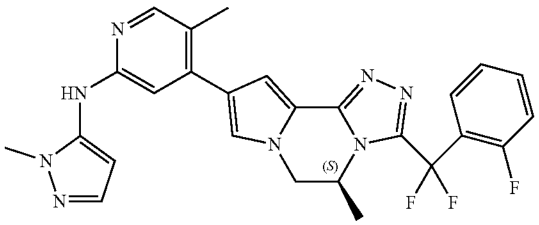 |
| 86 | 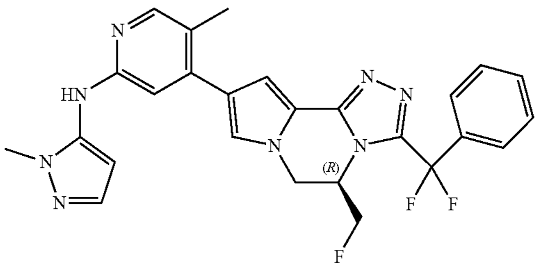 |

-continued
| Compound | Structure |
|---|---|
| 88 | 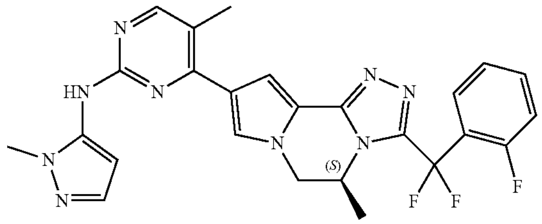 |
| 89 | 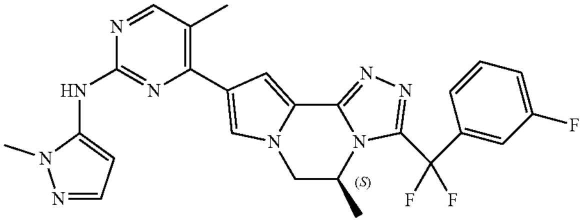 |
| 90 | 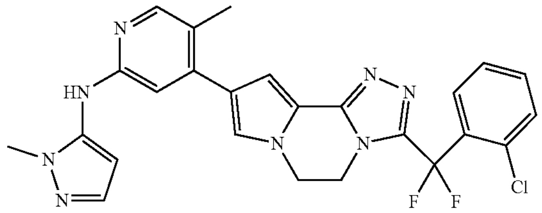 [SMILES: Cc1cnc(Nc2ccnn2C)cc1-c1cc2n(c1)CCn1c-2nnc1C(F)(F)c1ccccc1Cl] |
| 91 | 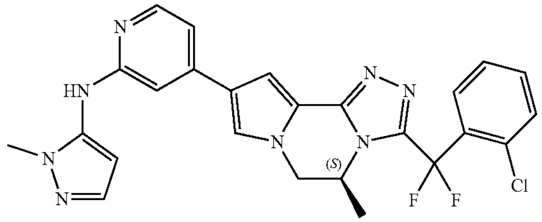 |
| 92 | 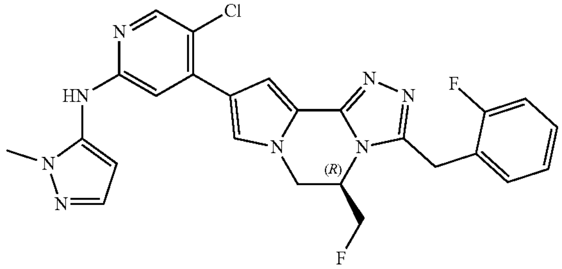 |
| 94 | 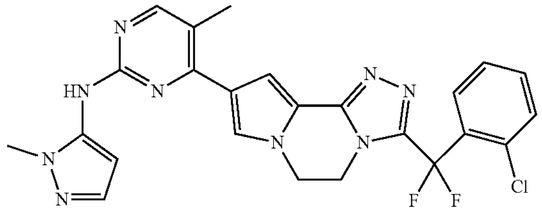 |

-continued
| Compound | Structure |
|---|---|
| 95 | 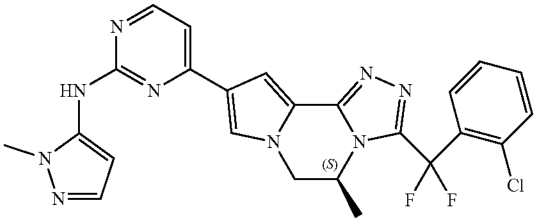 |
| 96 | 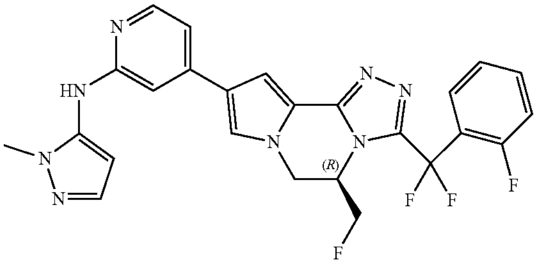 |
| 97 | 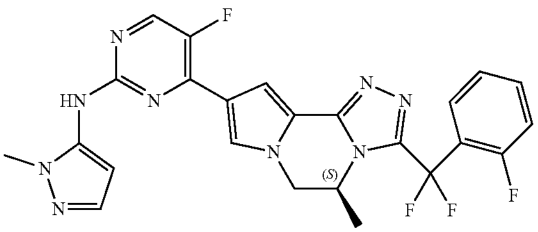 |
| 98 | 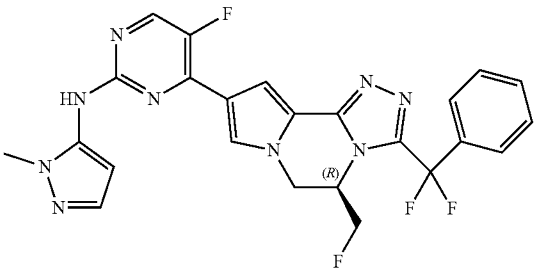 |
| 99 | 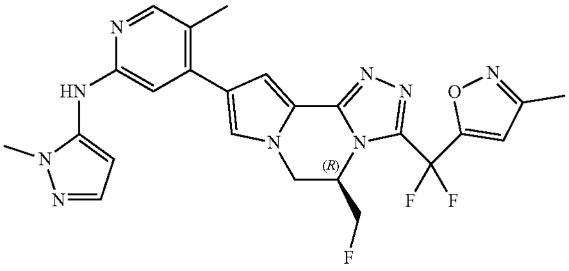 |
| 100 | 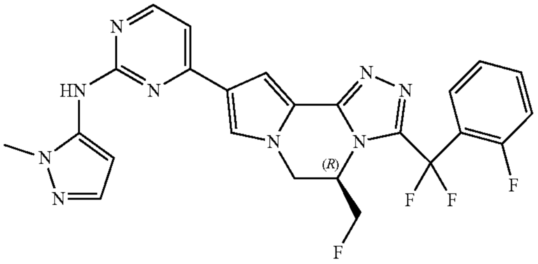 |

-continued
| Compound | Structure |
|---|---|
| 101 | 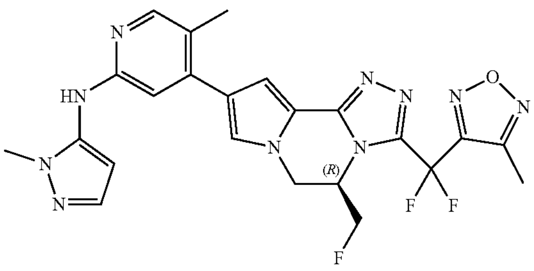 |
| 102 | 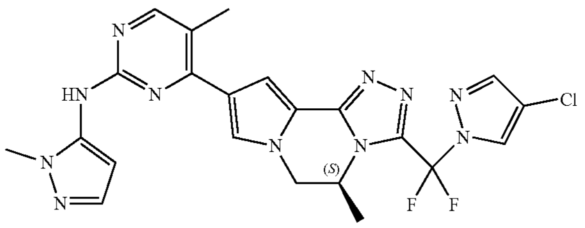 |
| 103 | 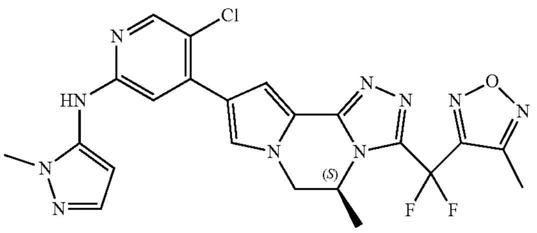 |
| 104 | 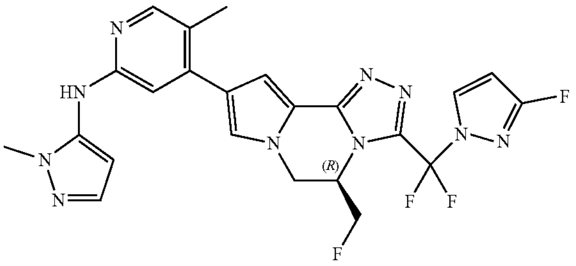 |
| 108 | 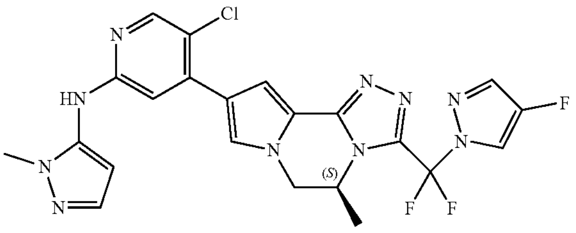 |
| 109 | 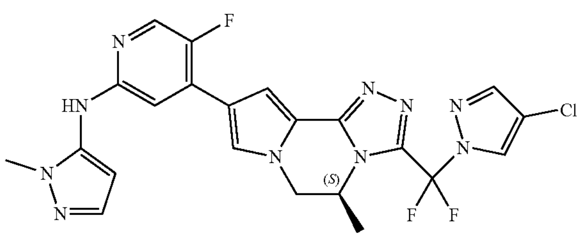 |

-continued
| Compound | Structure |
| --- | --- |
| 110 | 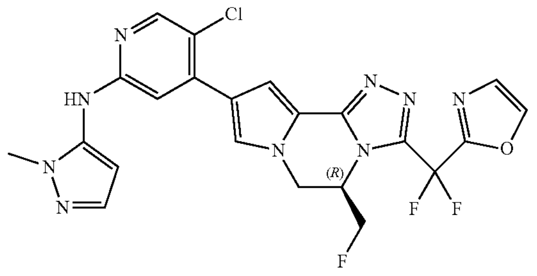 |
| 111 | 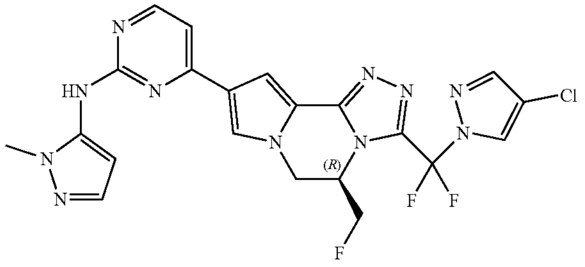 |
| 112 | 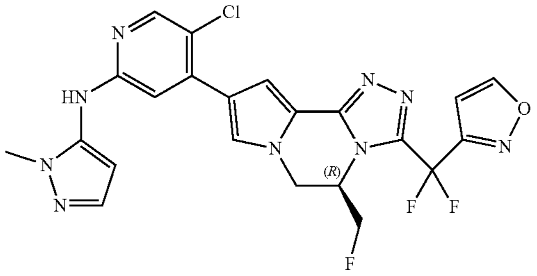 |
| 114 | 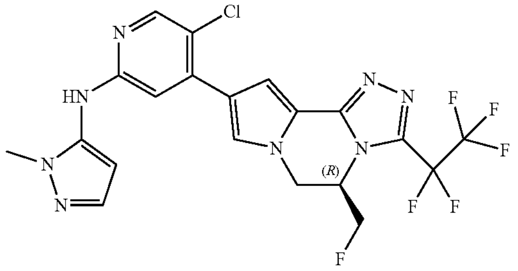 |
| 116 | 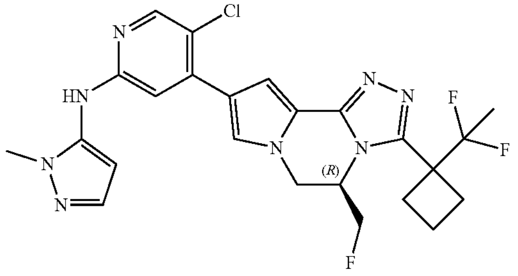 |

-continued
| Compound | Structure |
| --- | --- |
| 118 | 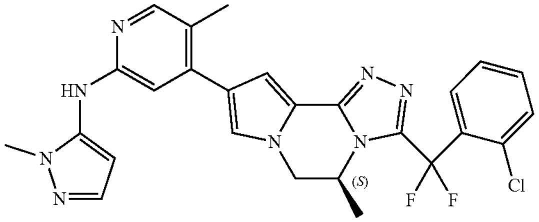 |
| 121 | 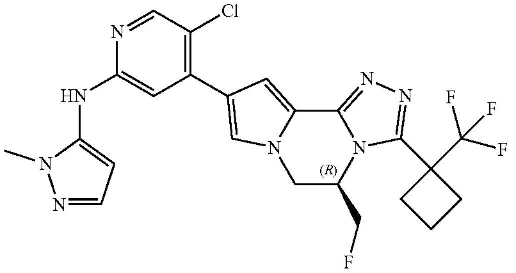 |
| 124 | 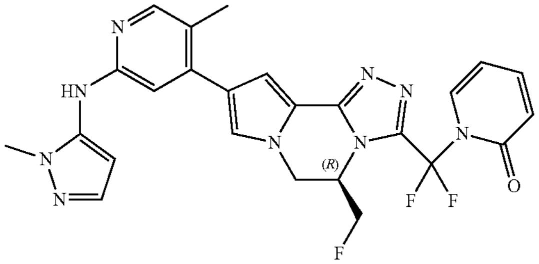 |
| 125 | 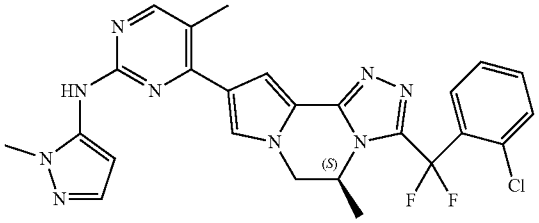 |
| 126 | 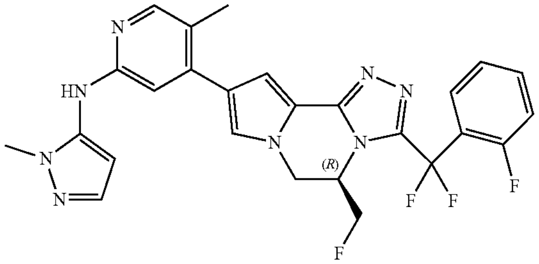 |
| 127 | 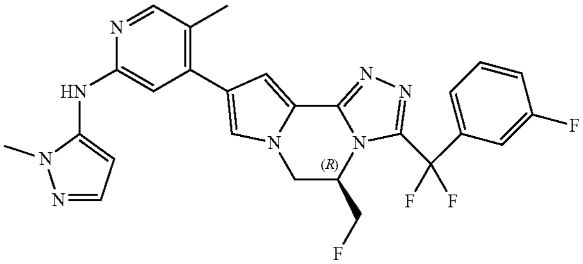 |

-continued
| Compound | Structure |
| --- | --- |
| 128 | 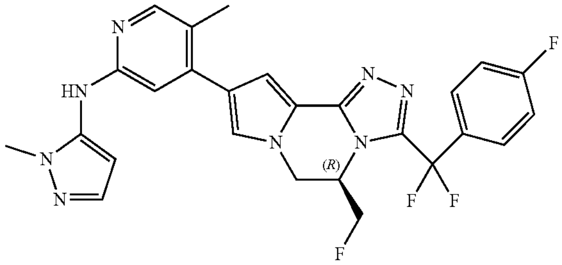 |
| 130 | 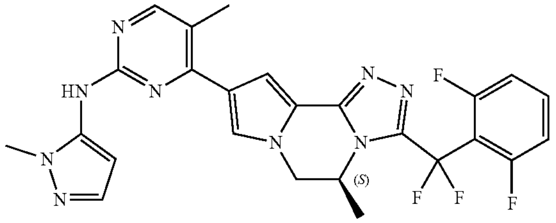 |
| 131 | 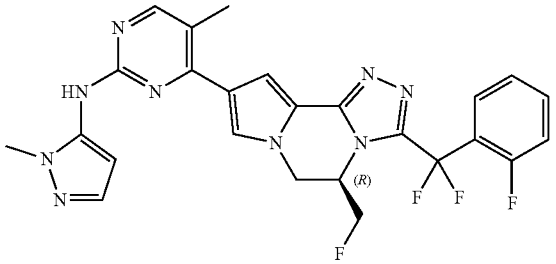 |
| 133 | 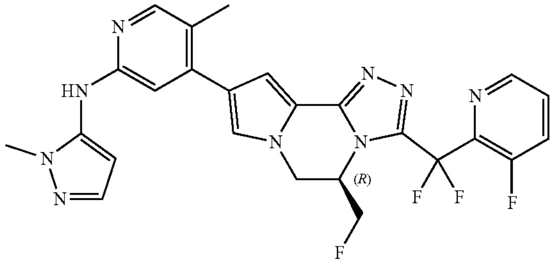 |
| 134 | 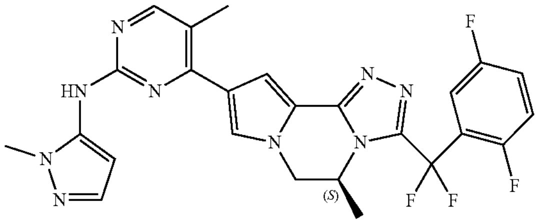 |
| 135 | 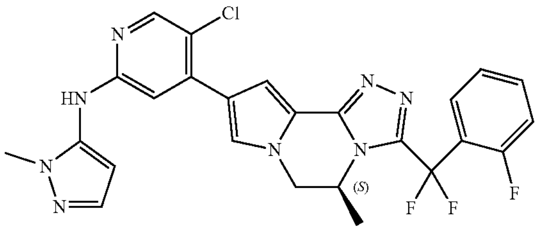 |

-continued
| Compound | Structure |
|---|---|
| 137 | 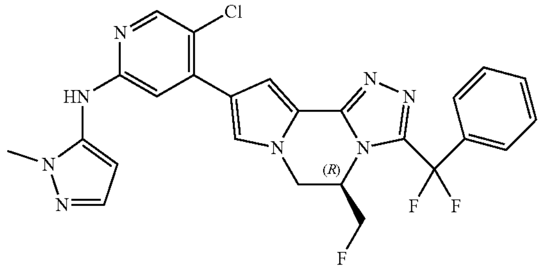 |
| 138 | 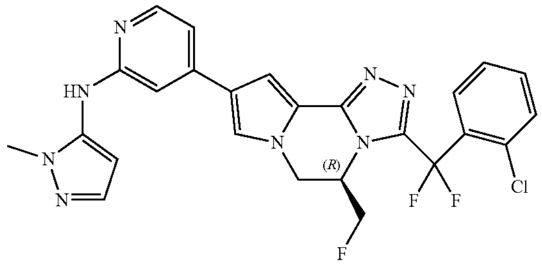 |
| 139 | 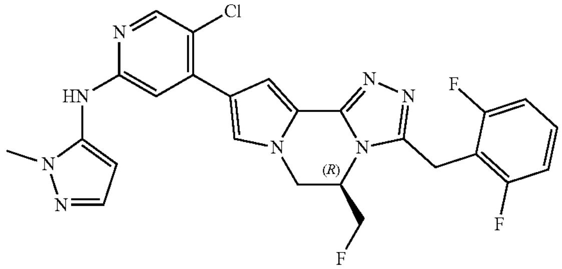 |
| 141 | 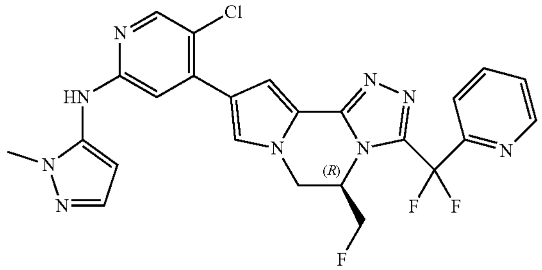 |
| 142 | 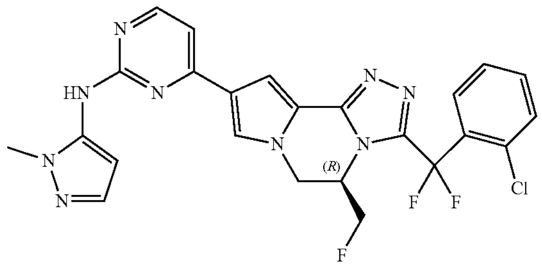 |
| 143 | 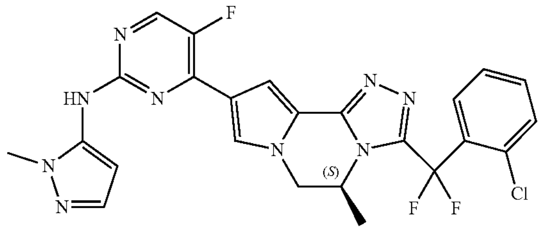 |

-continued
| Compound | Structure |
| --- | --- |
| 144 | 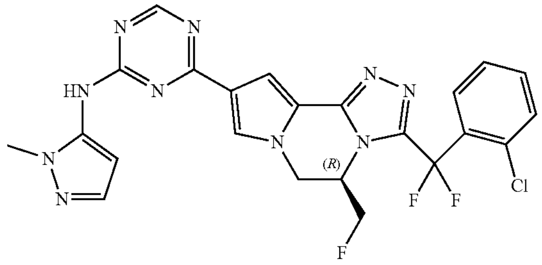 |
| 145 | 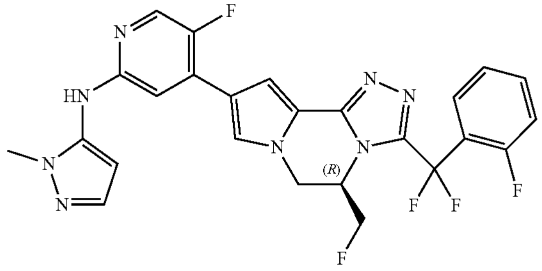 |
| 148 | 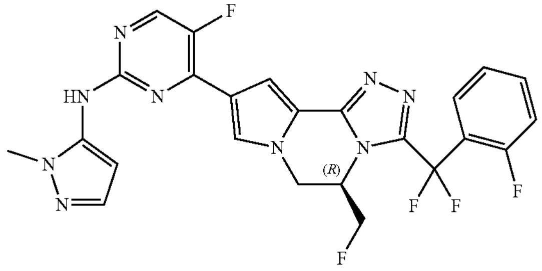 |
| 149 | 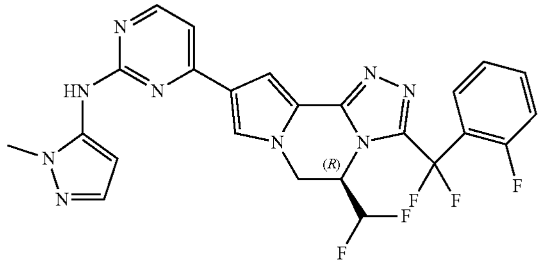 |
| 150 | 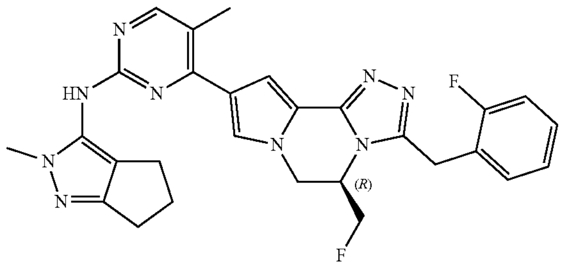 |

-continued
| Compound | Structure |
| --- | --- |
| 151 | 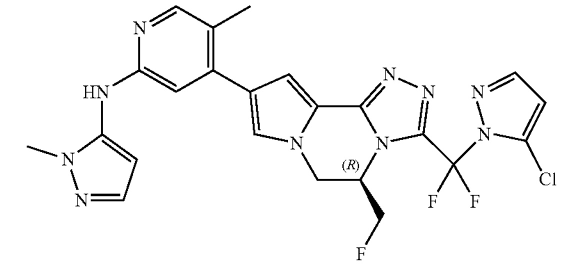 |
| 152 | 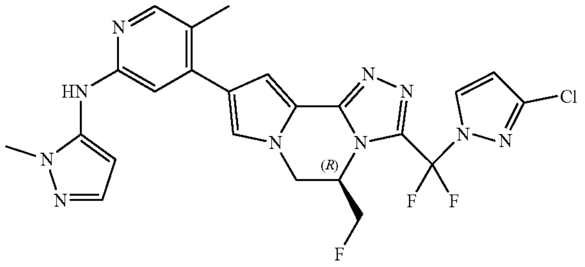 |
| 153 | 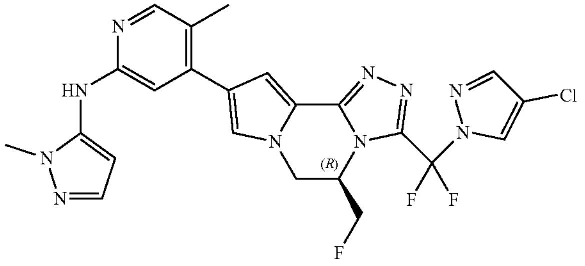 |
| 154 | 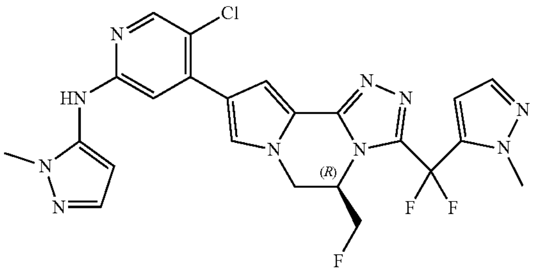 |
| 156 | 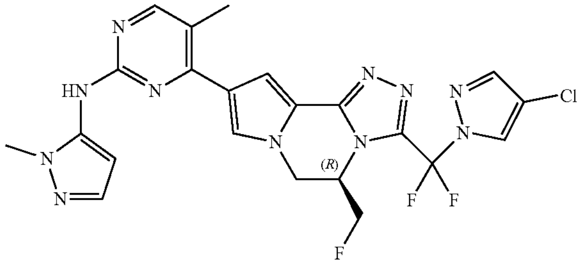 |
| 157 | 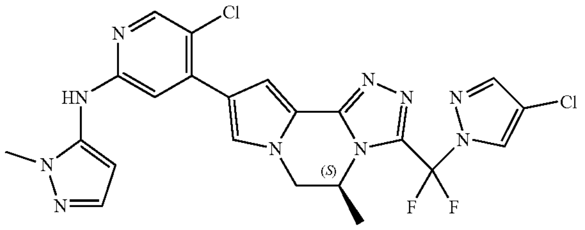 |

-continued
| Compound | Structure |
|---|---|
| 158 | 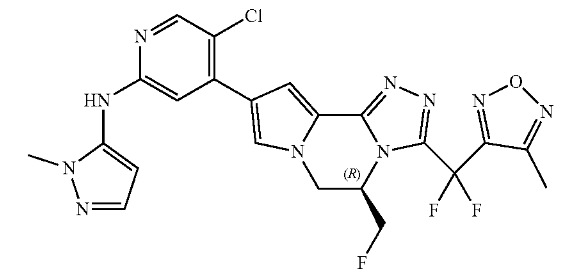 |
| 161 | 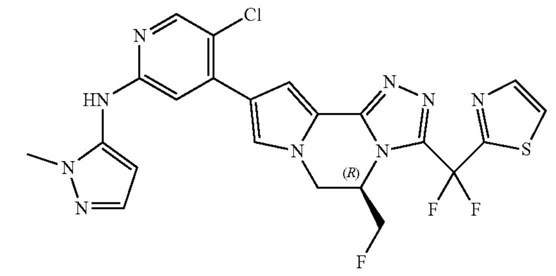 |
| 163 | 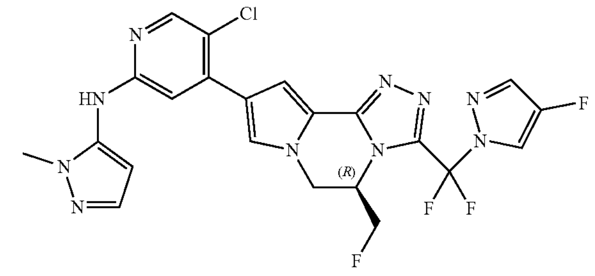 |
| 164 | 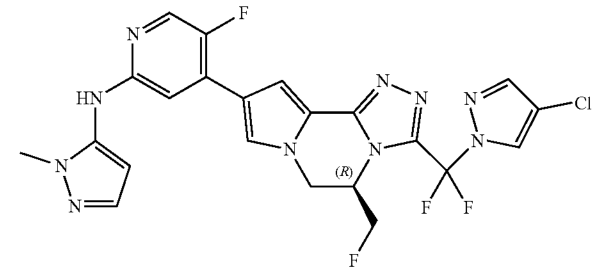 |
| 166 | 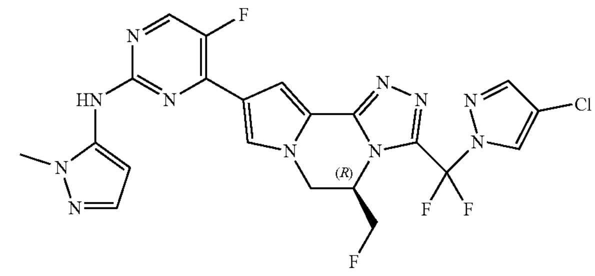 |

-continued
| Compound | Structure |
|---|---|
| 167 | 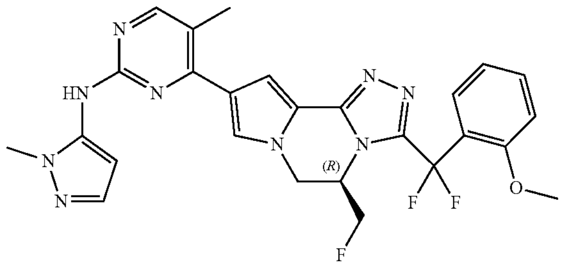 |
| 170 | 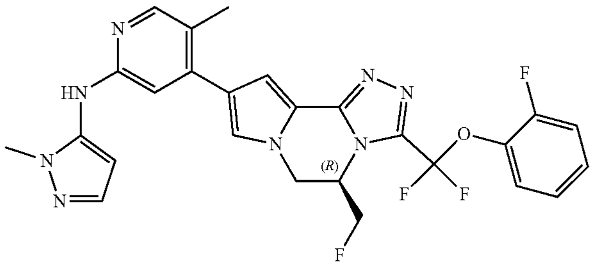 |
| 172 | 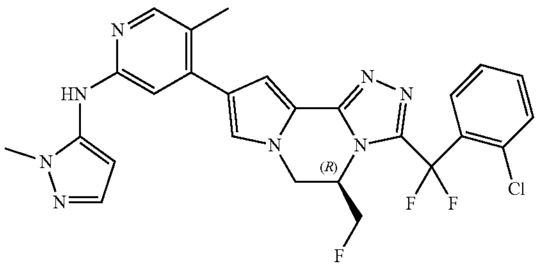 |
| 173 | 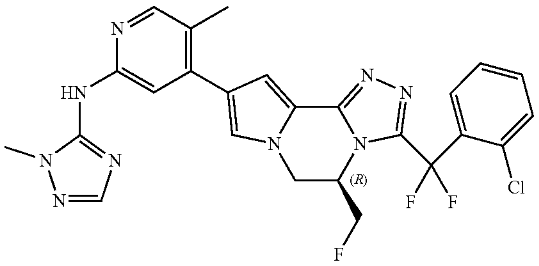 |
| 174 | 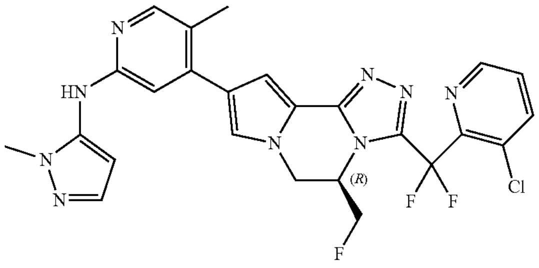 |

-continued
| Compound | Structure |
|---|---|
| 175 | 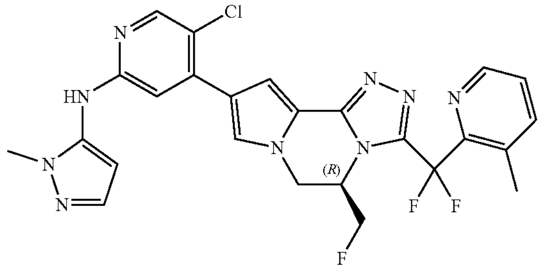 |
| 176 | 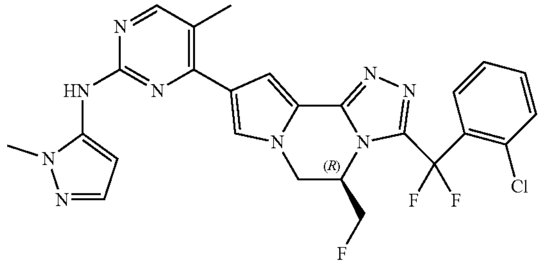 |
| 177 | 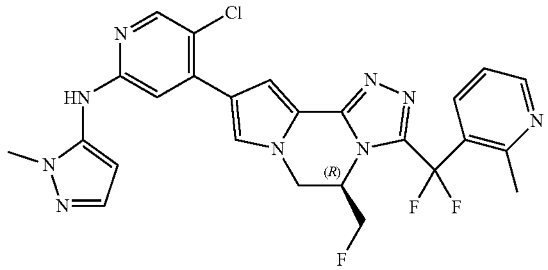 |
| 178 | 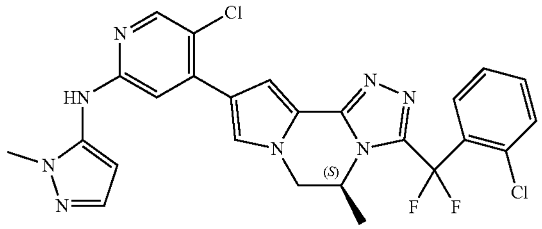 |
| 179 | 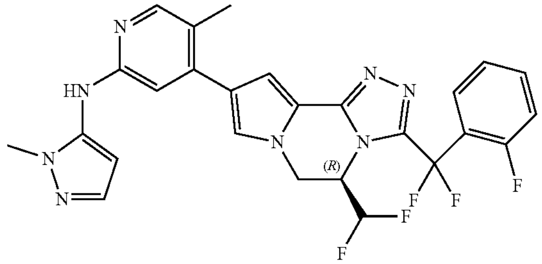 |
| 180 | 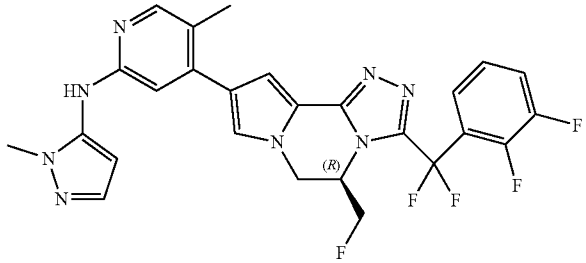 |

-continued
| Compound | Structure |
|---|---|
| 181 | 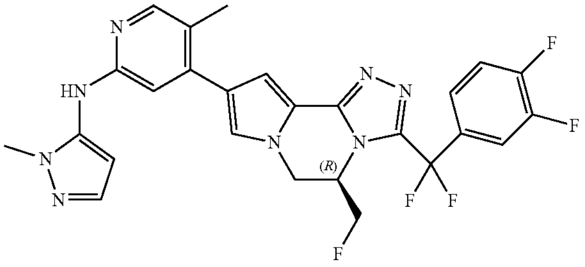 |
| 182 | 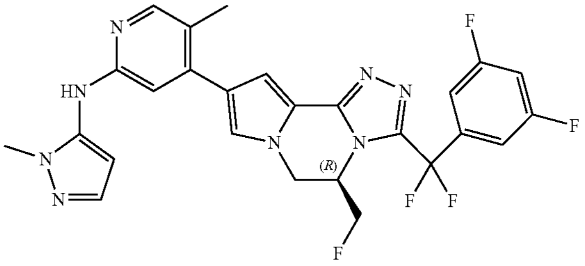 |
| 183 | 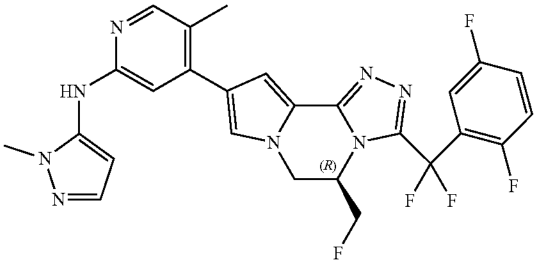 |
| 184 | 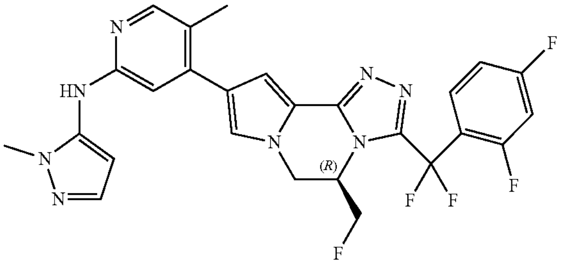 |
| 185 | 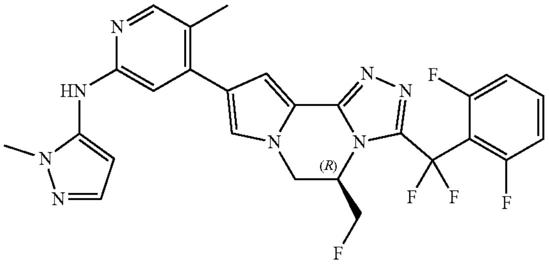 |

-continued
| Compound | Structure |
|---|---|
| 186 | 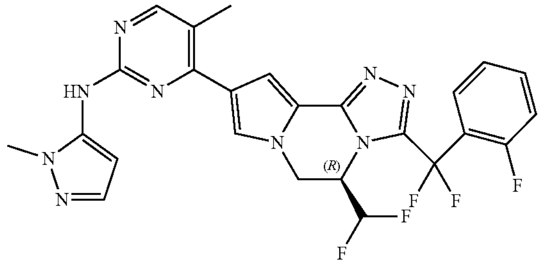 |
| 187 | 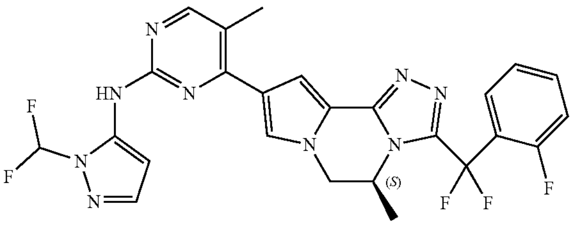 |
| 188 | 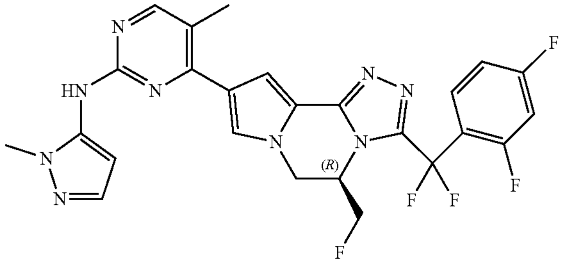 |
| 189 | 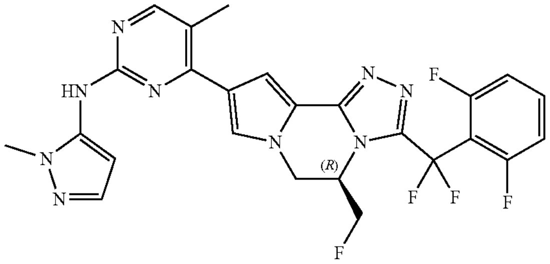 |
| 190 | 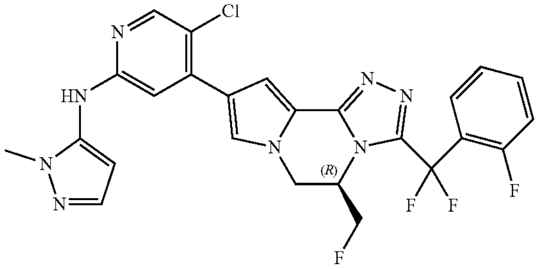 |
| 191 | 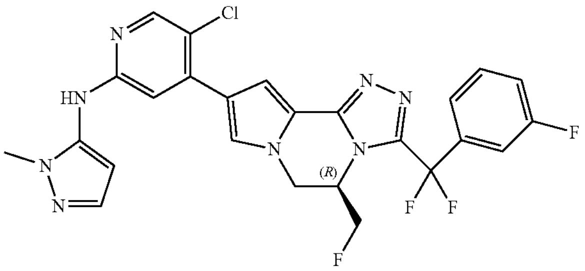 |

-continued
| Compound | Structure |
|---|---|
| 192 | 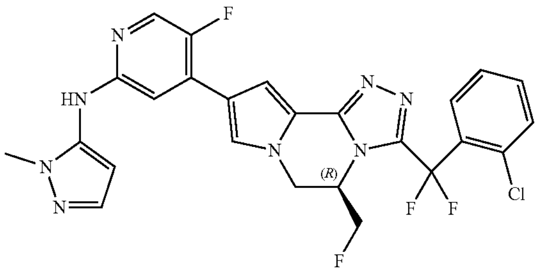 |
| 193 | 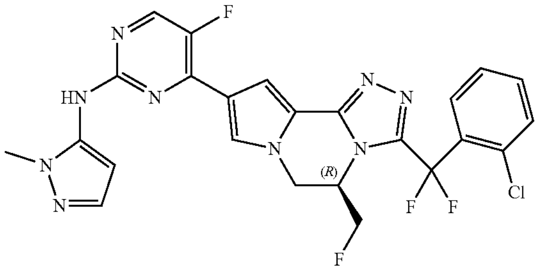 |
| 194 | 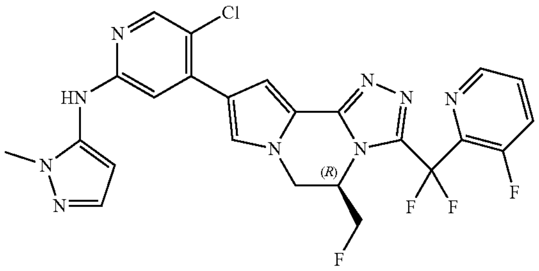 |
| 195 | 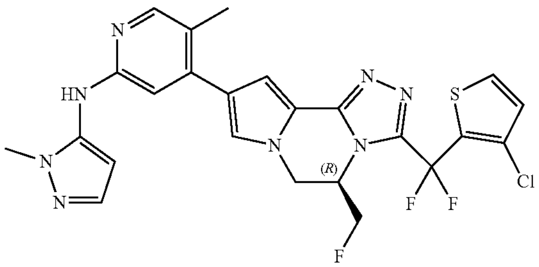 |
| 196 | 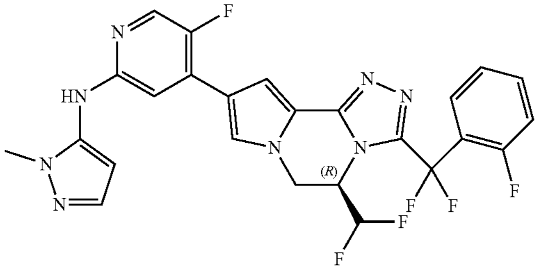 |

-continued
| Compound | Structure |
|---|---|
| 197 | 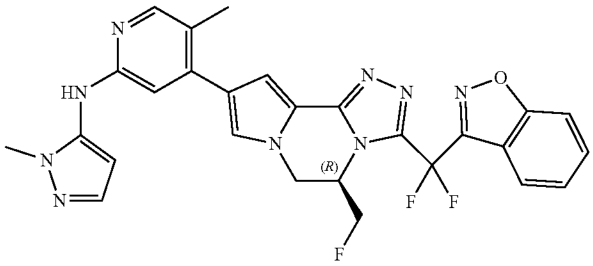 |
| 198 | 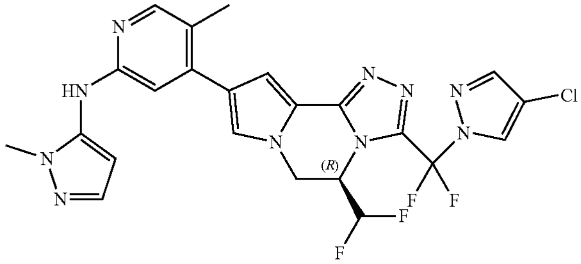 |
| 200 | 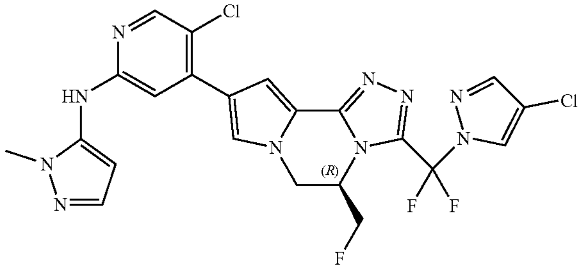 |
| 201 | 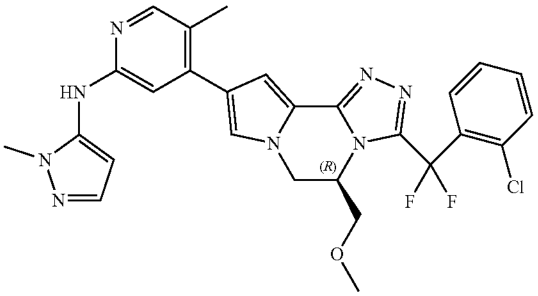 |
| 202 | 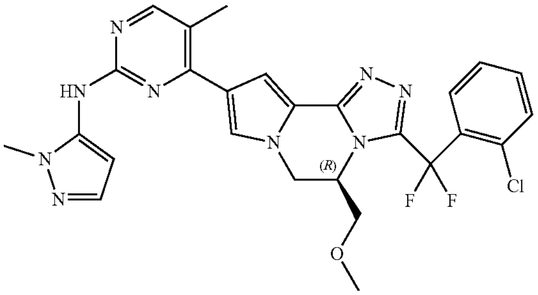 |

-continued
| Compound | Structure |
| --- | --- |
| 203 | 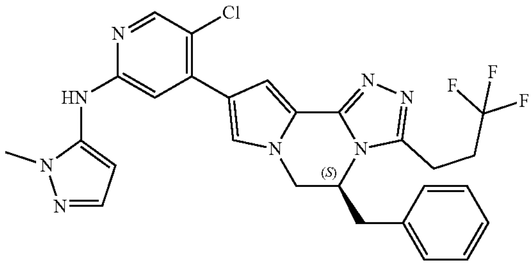 |
| 204 | 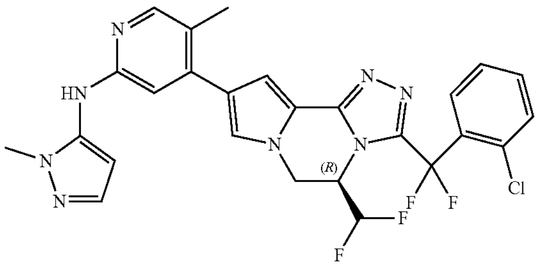 |
| 205 | 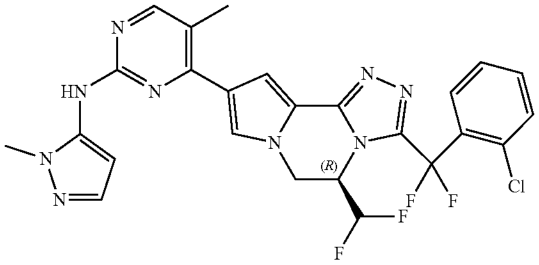 |
| 206 | 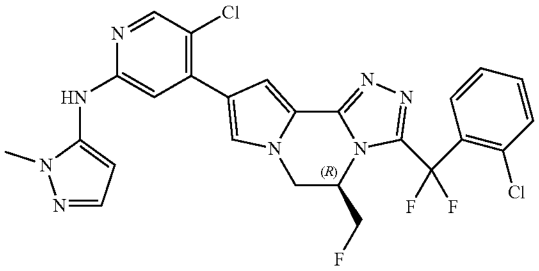 |
| 207 | 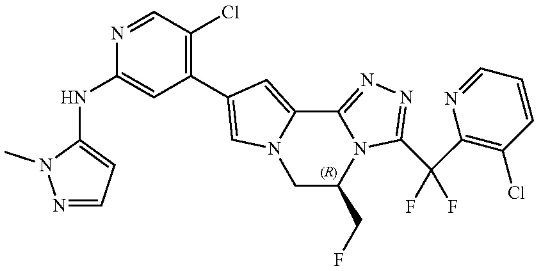 |

-continued
| Compound | Structure |
| --- | --- |
| 208 | 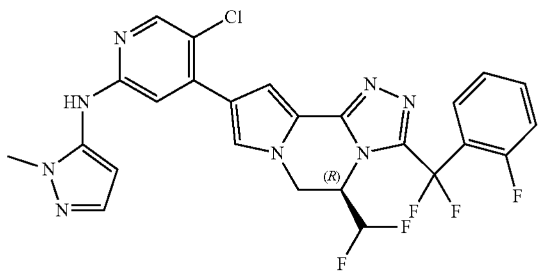 |
| 209 | 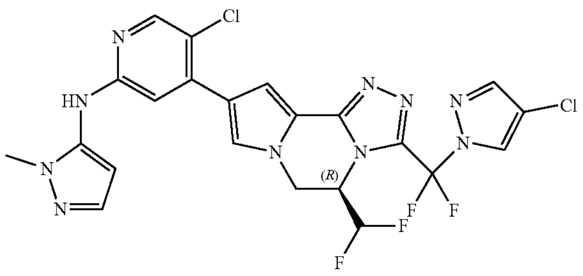 |
| 210 | 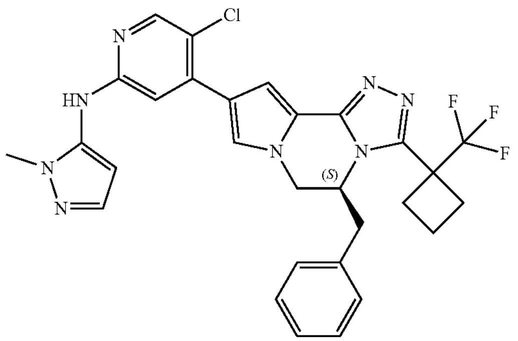 |
| 220 | 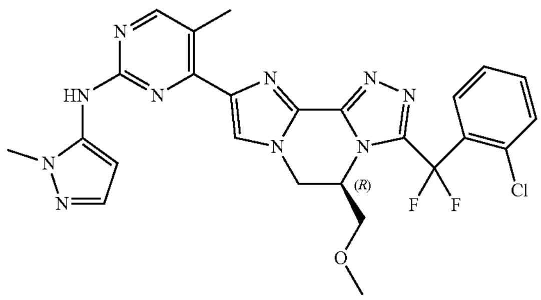 |
| 221 | 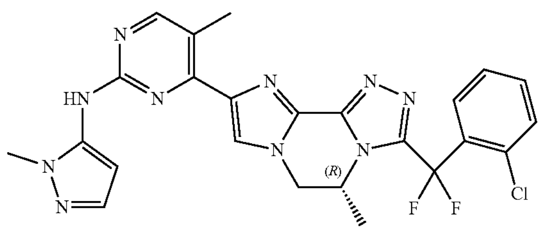 |

-continued
| Compound | Structure |
| --- | --- |
| 222 | 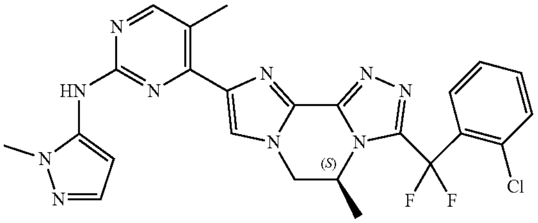 |
| 223 | 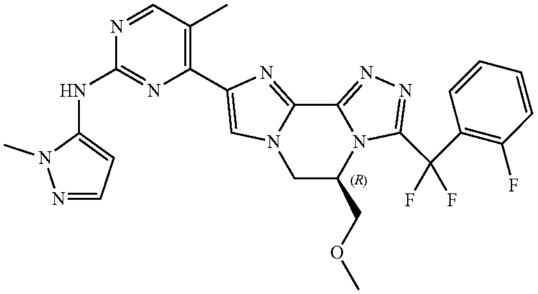 |
| 224 | 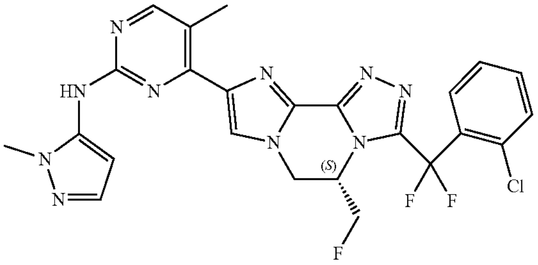 |
| 225 | 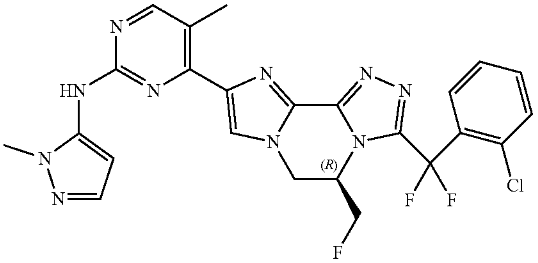 |
| 226 | 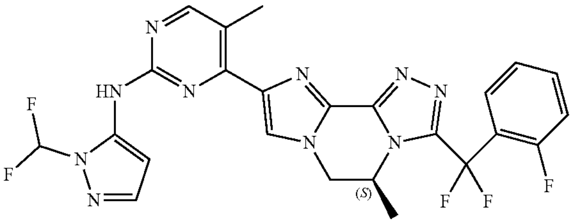 |
| 227 | 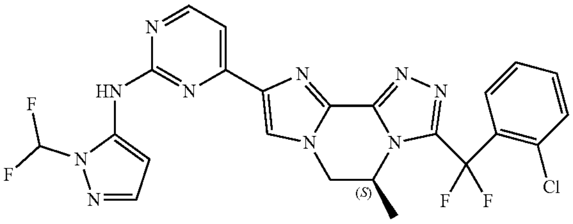 |

-continued
| Compound | Structure |
| --- | --- |
| 228 | 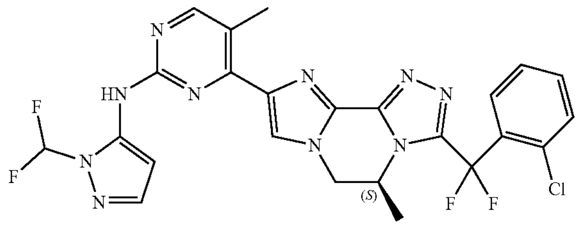 |
| 234 | 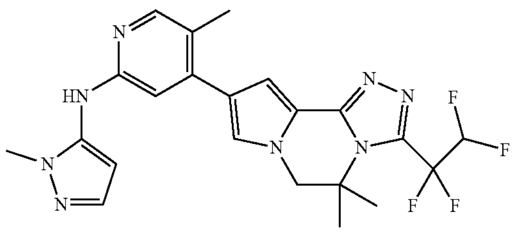 [SMILES: Cc1cnc(Nc2ccnn2C)cc1-c1cc2n(c1)CC(C)(C)n1c-2nnc1C(F)(F)C(F)F] |
| 235 | 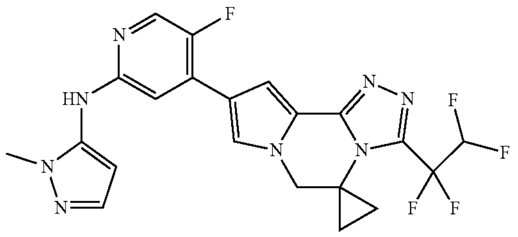 [SMILES: Cn1nccc1Nc1cc(-c2cc3n(c2)CC2(CC2)n2c-3nnc2C(F)(F)C(F)F)c(F)cn1] |
| 238 | 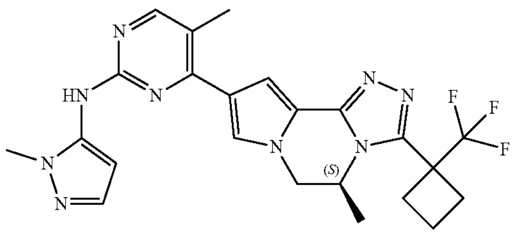 |
| 239 | 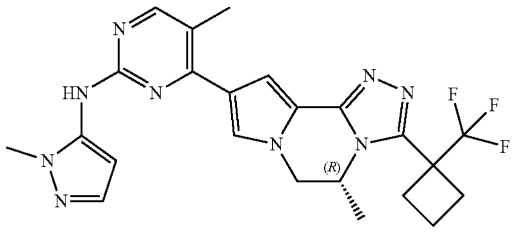 |
| 242 | 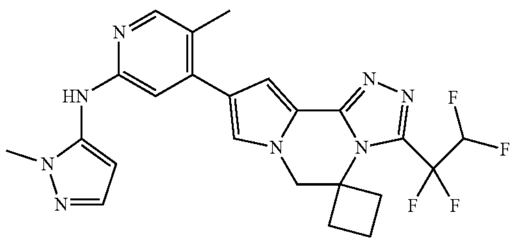 [SMILES: Cc1cnc(Nc2ccnn2C)cc1-c1cc2n(c1)CC1(CCC1)n1c-2nnc1C(F)(F)C(F)F] |

-continued
| Compound | Structure |
| --- | --- |
| 247 | 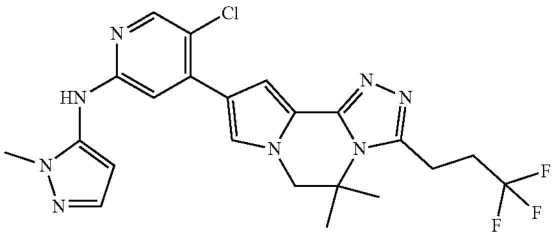 [SMILES: Cn1nccc1Nc1cc(-c2cc3n(c2)CC(C)(C)n2c(CCC(F)(F)F)nnc2-3)c(Cl)cn1] |
| 249 | 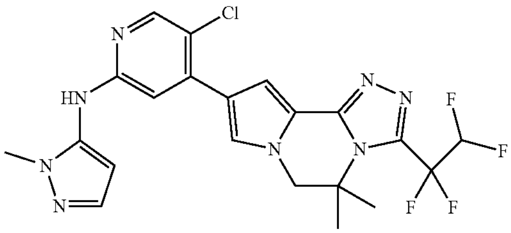 [SMILES: Cn1nccc1Nc1cc(-c2cc3n(c2)CC(C)(C)n2c-3nnc2C(F)(F)C(F)F)c(Cl)cn1] |
| 250 | 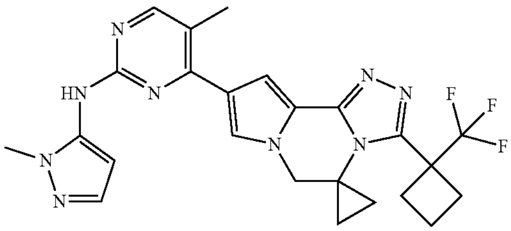 [SMILES: Cc1cnc(Nc2ccnn2C)nc1-c1cc2n(c1)CC1(CC1)n1c-2nnc1C1(C(F)(F)F)CCC1] |
| 253 | 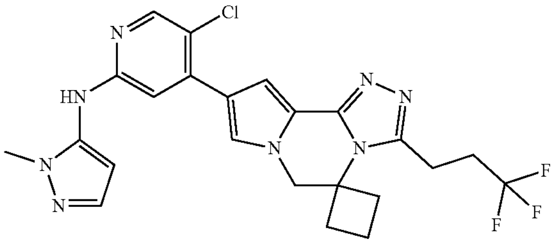 [SMILES: Cn1nccc1Nc1cc(-c2cc3n(c2)CC2(CCC2)n2c(CCC(F)(F)F)nnc2-3)c(Cl)cn1] |
| 256 | 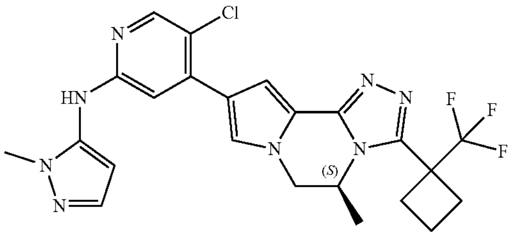 |
| 259 | 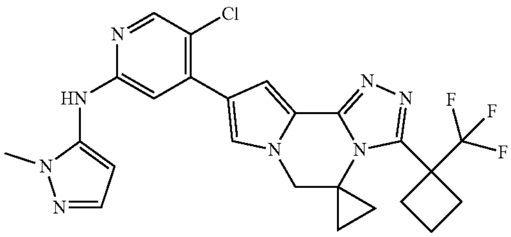 [SMILES: Cn1nccc1Nc1cc(-c2cc3n(c2)CC2(CC2)n2c-3nnc2C2(C(F)(F)F)CCC2)c(Cl)cn1] |

-continued
| Compound | Structure |
|---|---|
| 260 | 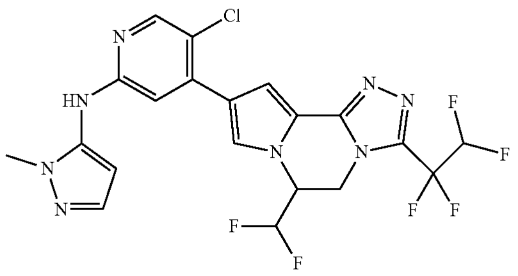 [SMILES: Cn1nccc1Nc1cc(-c2cc3n(c2)C(C(F)F)Cn2c-3nnc2C(F)(F)C(F)F)c(Cl)cn1] |
| 265 | 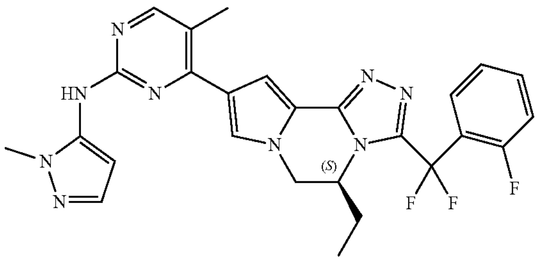 |
| 270 | 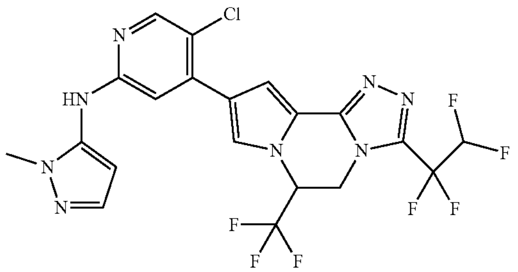 [SMILES: Cn1nccc1Nc1cc(-c2cc3n(c2)C(C(F)(F)F)Cn2c-3nnc2C(F)(F)C(F)F)c(Cl)cn1] |
| 273 | 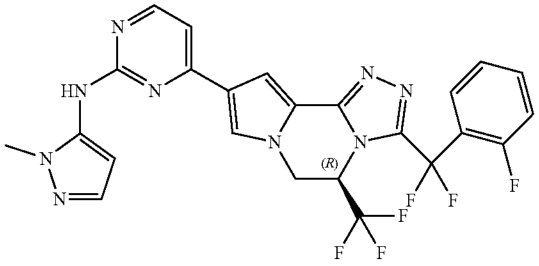 |
| 274 | 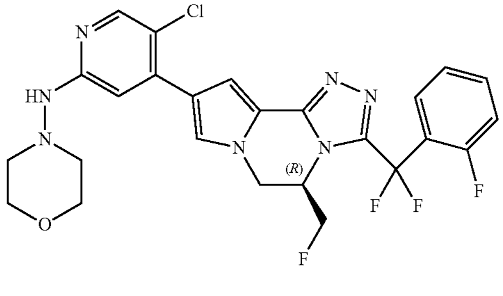 |

-continued
| Compound | Structure |
| --- | --- |
| 280 | 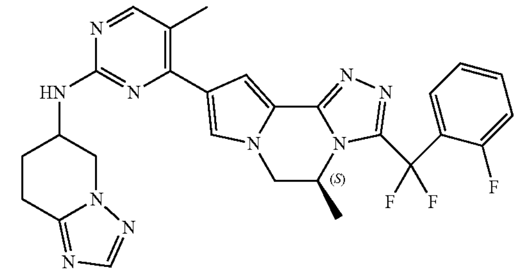 |
| 287 | 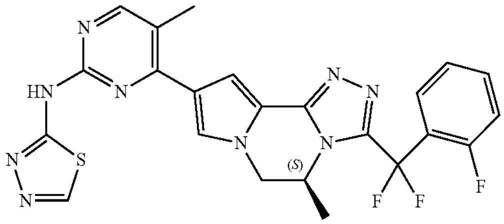 |
| 288 | 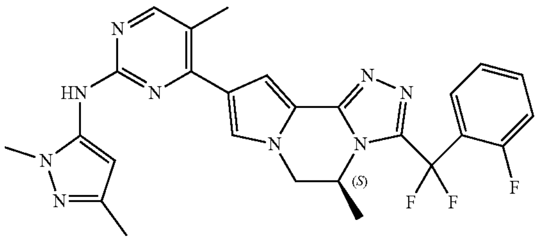 |
| 289 | 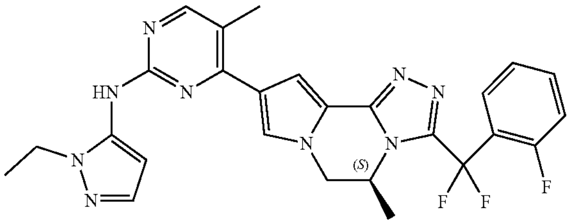 |
| 290 | 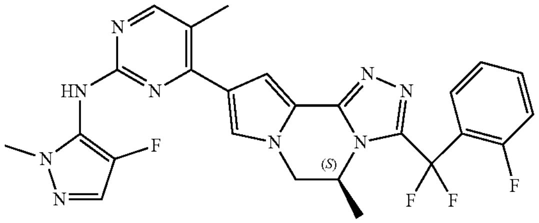 |
| 291 | 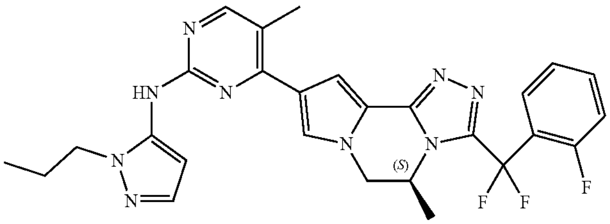

-continued
| Compound | Structure |
|---|---|
| 292 | 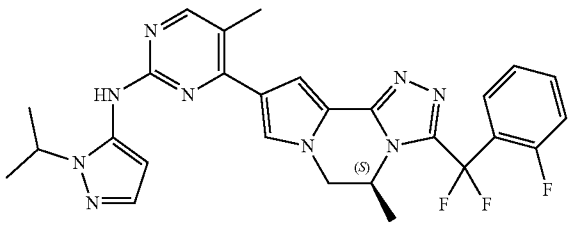 |
| 293 | 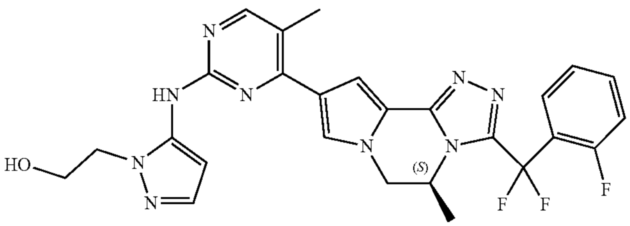 |
| 294 | 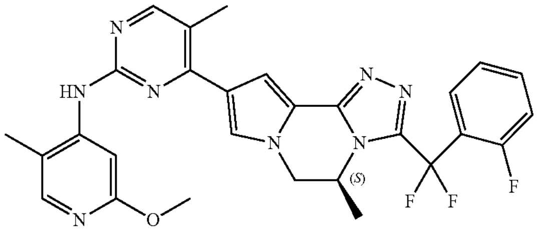 |
| 295 | 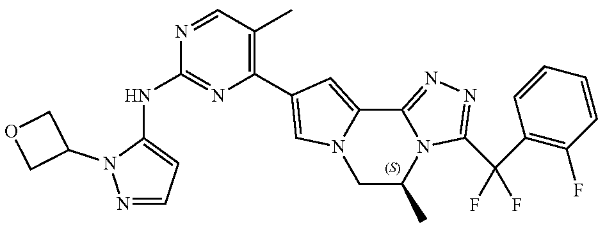 |
| 296 | 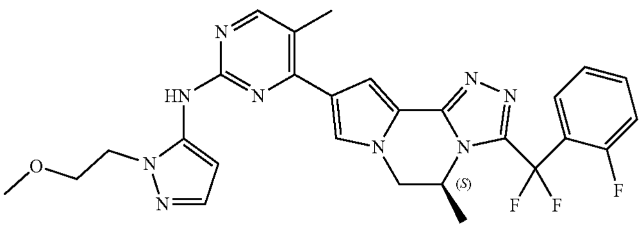 |
| 297 | 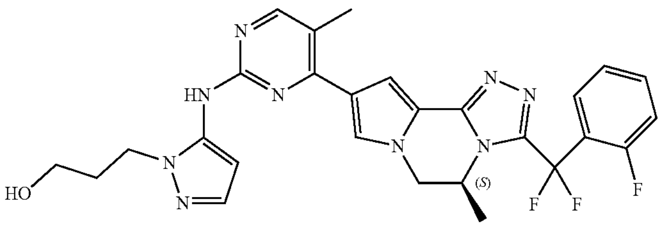 |

-continued

| Compound | Structure |
| --- | --- |
| 298 | 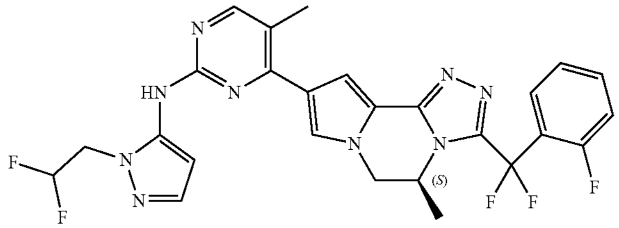 |
| 301 | 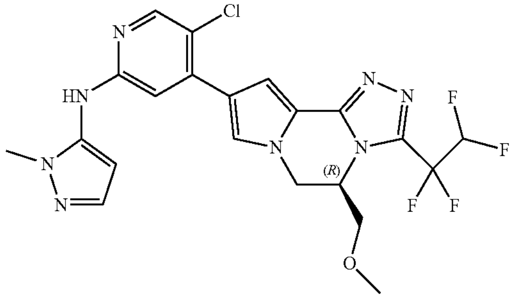 |
| 303 | 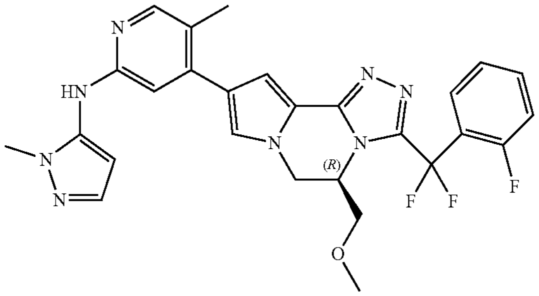 |
| 305 | 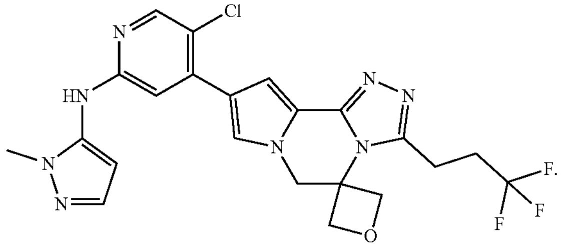 [SMILES: Cn1nccc1Nc1cc(-c2cc3n(c2)CC2(COC2)n2c(CCC(F)(F)F)nnc2-3)c(Cl)cn1] |

Embodiment 31. The compound of formula (I) according to embodiment 1, or a pharmaceutically acceptable salt thereof, or solvates, racemic mixtures, enantiomers, diastereomers, or tautomers of the compound of formula (I) or a pharmaceutically acceptable salt thereof, wherein, n is 1, ------ is single bond, $R_3$, $R_4$, $R_5$, $R_6$, $R_7$, and $R_8$ are independently selected from hydrogen, halo, hydroxy, $C_{1-6}$ alkyl, and $C_{1-6}$ alkoxyl; wherein said $C_{1-6}$ alkyl is optionally substituted with one or more substituents independently selected from hydroxy and $C_{1-6}$ alkoxyl; or any two of $R_3$, $R_4$, $R_5$, $R_6$, $R_7$, and $R_8$ together with the carbon atom they are attached to and the B ring form a 9-12 membered spirocyclic, fused, or bridged ring optionally containing 1-3 ring heteroatoms selected from N, O, or S; wherein said spirocyclic, fused, or bridged ring is optionally substituted with one or more substituents independently selected from halo, hydroxy, amino, $C_{1-6}$ alkyl, and —CN.

Embodiment 32. The compound of formula (I) according to embodiment 31, or a pharmaceutically acceptable salt thereof, or solvates, racemic mixtures, enantiomers, diastereomers, or tautomers of the compound of formula (I) or a pharmaceutically acceptable salt thereof, wherein the compound of formula (I) is the compound of formula (I-3), (I-3)

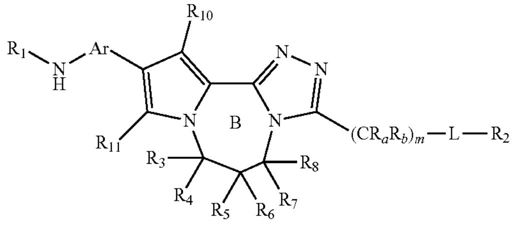

wherein, $R_1$ is selected from $C_{1-6}$ alkyl, —($C_{1-6}$ alkyl)-OH, saturated monocyclic $C_{3-8}$ cycloalkyl, saturated monocyclic 3-8 membered heterocyclyl containing 1 or 2 ring heteroatoms independently selected from N, O and S, and heteroaryl; wherein each of said $C_{3-8}$ cycloalkyl, 3-8 membered heterocyclyl, and heteroaryl is optionally substituted with one or more substituents independently selected from halo, $C_{1-6}$ alkyl optionally substituted with one or more deuterium, $C_{1-6}$ alkoxyl, and $C_{1-6}$ haloalkyl;

Ar is heteroaryl optionally substituted with one or more substituents independently selected from halo, —CN, $C_{1-6}$ alkyl optionally substituted with one or more deuterium, $C_{1-6}$ alkoxyl, and $C_{1-6}$ haloalkyl;

$R_2$ is selected from halo, —CN, $C_{1-6}$ alkyl, $C_{1-6}$ haloalkyl, saturated monocyclic $C_{3-8}$ cycloalkyl, phenyl, or heteroaryl, wherein each of said saturated monocyclic $C_{3-8}$ cycloalkyl, phenyl, or heteroaryl is optionally substituted with one or more substituents independently selected from halo, —CN, $C_{1-6}$ alkyl, $C_{1-6}$ alkoxyl, $C_{1-6}$ haloalkyl, and oxo;

$R_3$, $R_4$, $R_5$, $R_6$, $R_7$, and $R_8$ are independently selected from hydrogen, halo, hydroxy, $C_{1-6}$ alkyl, and $C_{1-6}$ alkoxyl; wherein said $C_{1-6}$ alkyl is optionally substituted with one or more substituents independently selected from hydroxy and $C_{1-6}$ alkoxyl; or any two of $R_3$, $R_4$, $R_5$, $R_6$, $R_7$, and $R_8$ together with the carbon atom they are attached to and the B ring form

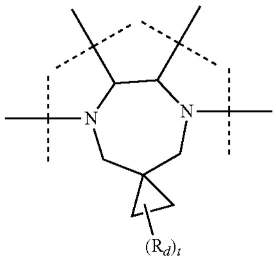,

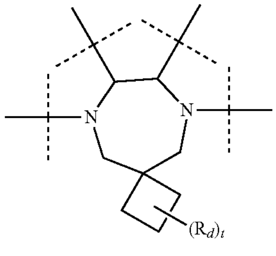,

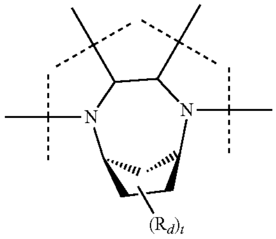,

-continued

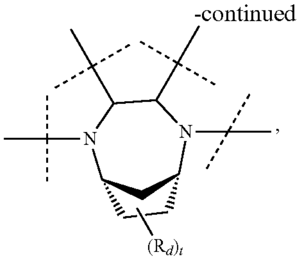, or

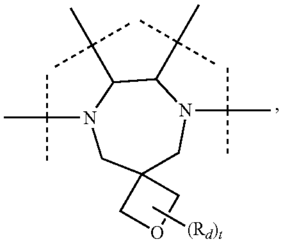, $R_d$ is selected from hydrogen or halo, t is 0, 1, 2, or 3;

$R_{10}$ and $R_{11}$ are independently selected from hydrogen, halo, $C_{1-6}$ alkyl, $C_{1-6}$ alkoxyl, $C_{1-6}$ haloalkyl, and —($C_{1-6}$ alkyl)-OH;

m is 0, 1, or 2;

$R_a$ and $R_b$ are independently selected from hydrogen, halo, hydroxy, or $C_{1-6}$ alkyl; or $R_a$ and $R_b$ together with the carbon atom they are attached to form a saturated $C_{3-6}$ cycloalkyl or a 4-6 membered heterocyclyl, wherein said 4-6 membered heterocyclyl is a saturated monocyclic ring having 4-6 ring atoms with 1 or 2 of the ring atoms being ring heteroatoms independently selected from N, O and S, and the remaining ring atoms being carbon; wherein each of said saturated $C_{3-6}$ cycloalkyl or 4-6 membered heterocyclyl is optionally substituted with one or more substituents selected from halo;

L is absent, or L is NH, O or S;

said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another.

Embodiment 33. The compound of formula (I) according to embodiment 32, or a pharmaceutically acceptable salt thereof, or solvates, racemic mixtures, enantiomers, diastereomers, or tautomers of the compound of formula (I) or a pharmaceutically acceptable salt thereof, wherein, $R_1$ is selected from $C_{1-6}$ alkyl, —($C_{1-6}$ alkyl)-OH, saturated monocyclic $C_{3-8}$ cycloalkyl, saturated monocyclic 3-8 membered heterocyclyl containing 1 or 2 ring heteroatoms independently selected from N, O and S, and heteroaryl; wherein each of said $C_{3-8}$ cycloalkyl, 3-8 membered heterocyclyl, and heteroaryl is optionally substituted with one or more substituents independently selected from halo, $C_{1-6}$ alkoxyl, $C_{1-6}$ haloalkyl, and $C_{1-6}$ alkyl optionally substituted with one or more deuterium;

Ar is heteroaryl, wherein said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, and when the total number of S and O atoms in the heteroaryl group exceeds 1, said S and O heteroatoms are not adjacent to one another; wherein said heteroaryl is optionally substituted with one or more substituents independently selected from halo, —CN, $C_{1-6}$ alkyl optionally substituted with one or more deuterium, $C_{1-6}$ alkoxyl, and $C_{1-6}$ haloalkyl;

$R_2$ is selected from —CN, $C_{1-6}$ haloalkyl, saturated monocyclic $C_{3-8}$ cycloalkyl, phenyl, or heteroaryl, wherein said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another; wherein each of said saturated monocyclic $C_{3-8}$ cycloalkyl, phenyl, or heteroaryl is optionally substituted with one or more substituents independently selected from halo, —CN, $C_{1-6}$ alkyl, and $C_{1-6}$ haloalkyl;

$R_3$, $R_4$, $R_5$, $R_6$, $R_7$, and $R_8$ are independently selected from hydrogen, halo, hydroxy, $C_{1-6}$ alkyl, and $C_{1-6}$ alkoxyl; wherein said $C_{1-6}$ alkyl is optionally substituted with one or more substituents independently selected from hydroxy and $C_{1-6}$ alkoxyl; or any two of $R_3$, $R_4$, $R_5$, $R_6$, $R_7$, and $R_8$ together with the carbon atom they are attached to and the B ring form

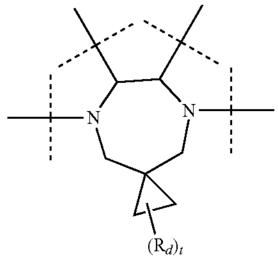
,

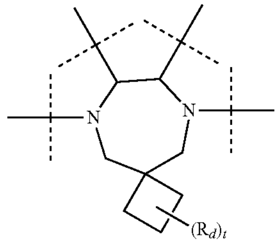
,

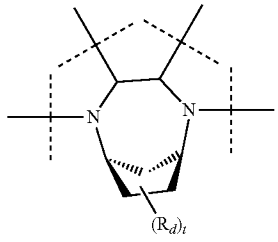
,

-continued

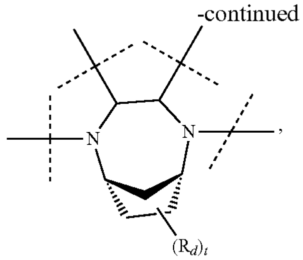
, or

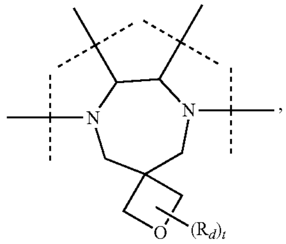
, $R_d$ is selected from hydrogen and halo, t is 0, 1, 2, or 3;

$R_{10}$ and $R_{11}$ are independently selected from hydrogen, halo, and $C_{1-6}$ alkyl;

m is 0, 1, or 2;

$R_a$ and $R_b$ are independently selected from hydrogen, halo, hydroxy, and $C_{1-6}$ alkyl; or $R_a$ and $R_b$ together with the carbon atom they are attached to form a saturated monocyclic $C_{3-6}$ cycloalkyl or a 3-6 membered heterocyclyl, wherein said 3-6 membered heterocyclyl is a saturated monocyclic ring having 3-6 ring atoms with 1 or 2 of the ring atoms being ring heteroatoms independently selected from N, O and S, and the remaining ring atoms being carbon; wherein each of said saturated monocyclic $C_{3-6}$ cycloalkyl or 3-6 membered heterocyclyl is optionally substituted with one or more substituents selected from halo;

L is absent, or L is NH or O.

Embodiment 34. The compound of formula (I) according to embodiment 32, or a pharmaceutically acceptable salt thereof, or solvates, racemic mixtures, enantiomers, diastereomers, or tautomers of the compound of formula (I) or a pharmaceutically acceptable salt thereof, wherein $R_1$ is selected from: (1) $C_{1-6}$ alkyl, (2) —($C_{1-6}$ alkyl)-OH, (3) saturated monocyclic $C_{3-8}$ cycloalkyl, which is optionally substituted with one or more substituents independently selected from halo and $C_{1-6}$ alkoxyl, (4) saturated monocyclic 6 membered heterocyclyl containing 1 or 2 ring heteroatoms independently selected from N, O and S, and (5) heteroaryl selected from pyrazolyl, pyridyl, and isoxazolyl, wherein said heteroaryl is optionally substituted with one or more substituents independently selected from $C_{1-6}$ alkoxyl, $C_{1-6}$ haloalkyl, and $C_{1-6}$ alkyl optionally substituted with one or more deuterium.

Embodiment 35. The compound of formula (I) according to embodiment 32, or a pharmaceutically acceptable salt thereof, or solvates, racemic mixtures, enantiomers, diastereomers, or tautomers of the compound of formula (I) or a pharmaceutically acceptable salt thereof, wherein Ar is heteroaryl selected from pyridyl and pyrimidinyl, wherein said heteroaryl is each optionally substituted with one or more substituents independently selected from halo, —CN, $C_{1-6}$ alkyl optionally substituted with one or more deuterium, $C_{1-6}$ alkoxyl, and $C_{1-6}$ haloalkyl.

Embodiment 36. The compound of formula (I) according to embodiment 35, or a pharmaceutically acceptable salt thereof, or solvates, racemic mixtures, enantiomers, diastereomers, or tautomers of the compound of formula (I) or a pharmaceutically acceptable salt thereof, wherein Ar is (Ib-1)

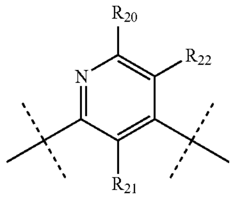

or (Ib-2)

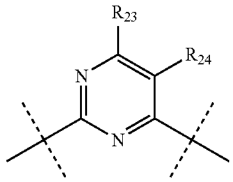

, wherein $R_{20}$, $R_{21}$, $R_{22}$, $R_{23}$, and $R_{24}$ are independently selected from hydrogen, halo, —CN, $C_{1-6}$ alkyl optionally substituted with one or more deuterium, $C_{1-6}$ alkoxyl, and $C_{1-6}$ haloalkyl.

Embodiment 37. The compound of formula (I) according to embodiment 32, or a pharmaceutically acceptable salt thereof, or solvates, racemic mixtures, enantiomers, diastereomers, or tautomers of the compound of formula (I) or a pharmaceutically acceptable salt thereof, wherein $R_2$ is selected from: (1) —CN, (2) $C_{1-6}$ haloalkyl, (3) saturated monocyclic $C_{3-8}$ cycloalkyl, which is optionally substituted with one or more substituents selected from $C_{1-6}$ haloalkyl, (4) phenyl, which is optionally substituted with one or more substituents independently selected from halo and —CN, and (5) heteroaryl selected from 1,2,5-oxadiazolyl, indolinyl, 1,2,3,4-tetrahydroquinolinyl, pyrazolyl, indazolyl, and pyrrolyl, wherein said heteroaryl is each optionally substituted with one or more substituents independently selected from halo, —CN, and $C_{1-6}$ alkyl.

Embodiment 38. The compound of formula (I) according to embodiment 32, or a pharmaceutically acceptable salt thereof, wherein the compound of formula (I) is selected from:

| Compound | Structure |
|---|---|
| 1 | 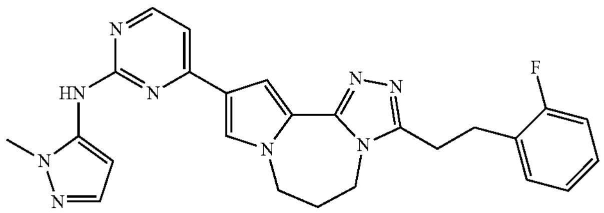 [SMILES: Cn1nccc1Nc1nccc(-c2cc3n(c2)CCCn2c(CCc4ccccc4F)nnc2-3)n1] |
| 4 | 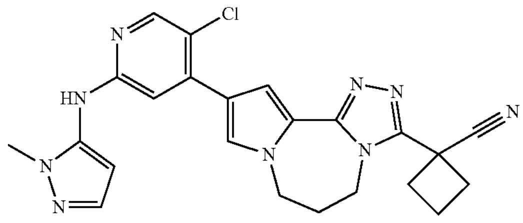 [SMILES: Cn1nccc1Nc1cc(-c2cc3n(c2)CCCn2c-3nnc2C2(C#N)CCC2)c(Cl)cn1] |
| 6 | 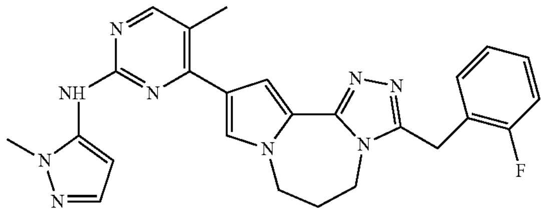 [SMILES: Cc1cnc(Nc2ccnn2C)nc1-c1cc2n(c1)CCCn1c(Cc3ccccc3F)nnc1-2] |
| 8 | 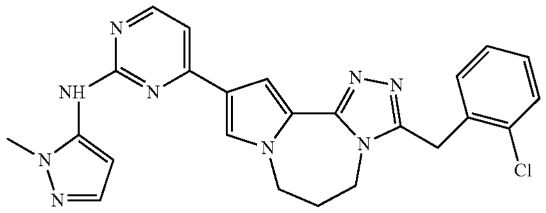 [SMILES: Cn1nccc1Nc1nccc(-c2cc3n(c2)CCCn2c(Cc4ccccc4Cl)nnc2-3)n1] |

-continued
| Compound | Structure |
| --- | --- |
| 10 | 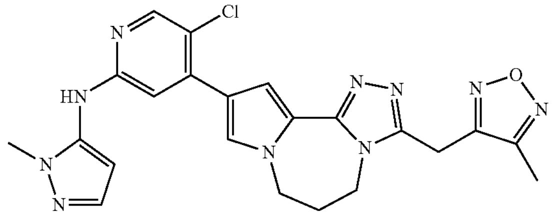 [SMILES: Cc1nonc1Cc1nnc2n1CCCn1cc(-c3cc(Nc4ccnn4C)ncc3Cl)cc1-2] |
| 11 | 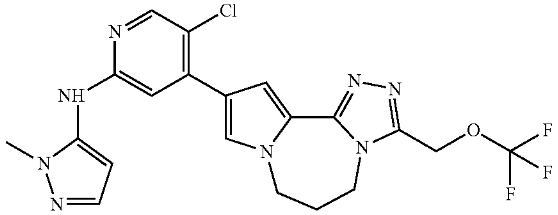 [SMILES: Cn1nccc1Nc1cc(-c2cc3n(c2)CCCn2c(COC(F)(F)F)nnc2-3)c(Cl)cn1] |
| 12 | 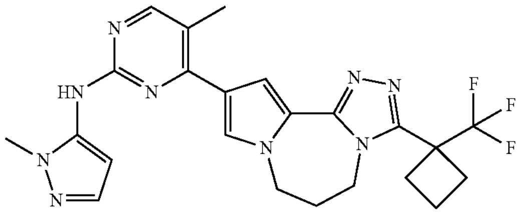 [SMILES: Cc1cnc(Nc2ccnn2C)nc1-c1cc2n(c1)CCCn1c-2nnc1C1(C(F)(F)F)CCC1] |
| 13 | 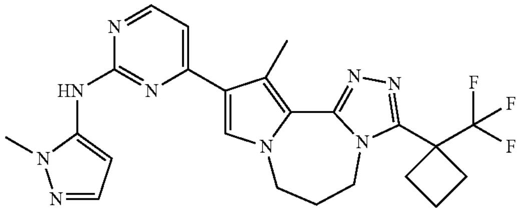 |
| 14 | 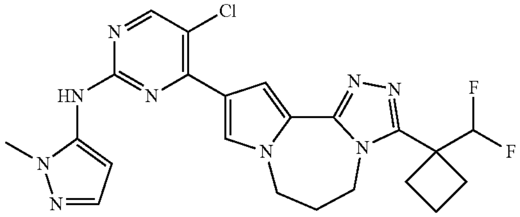 |
| 15 | 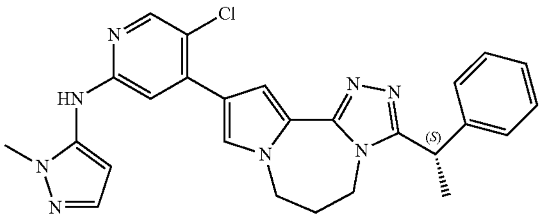 |
| 16 | 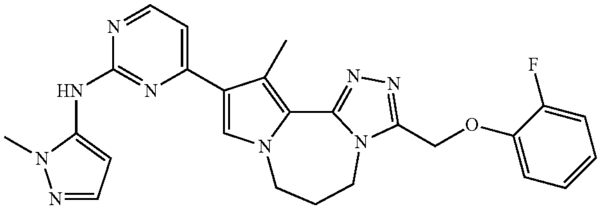 [SMILES: Cc1c(-c2ccnc(Nc3ccnn3C)n2)cn2c1-c1nnc(COc3ccccc3F)n1CCC2] |

-continued
| Compound | Structure |
| --- | --- |
| 17 | 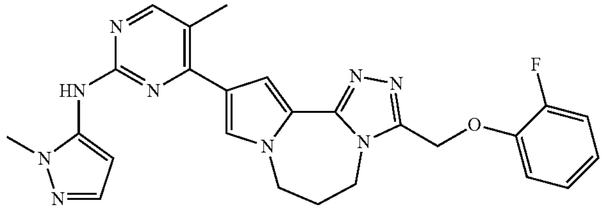 [SMILES: Cc1cnc(Nc2ccnn2C)nc1-c1cc2n(c1)CCCn1c(COc3ccccc3F)nnc1-2] |
| 18 | 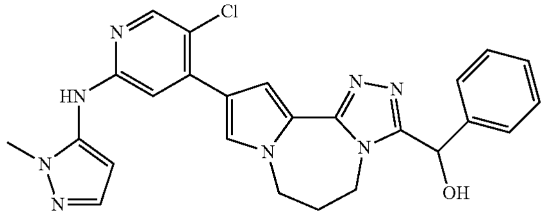 [SMILES: Cn1nccc1Nc1cc(-c2cc3n(c2)CCCn2c-3nnc2C(O)c2ccccc2)c(Cl)cn1] |
| 19 | 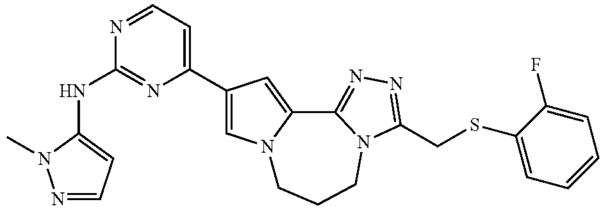 |
| 21 | 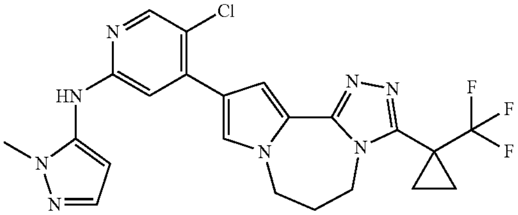 [SMILES: Cn1nccc1Nc1cc(-c2cc3n(c2)CCCn2c-3nnc2C2(C(F)(F)F)CC2)c(Cl)cn1] |
| 22 | 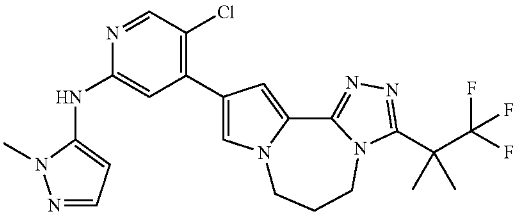 [SMILES: Cn1nccc1Nc1cc(-c2cc3n(c2)CCCn2c-3nnc2C(C)(C)C(F)(F)F)c(Cl)cn1] |
| 24 | 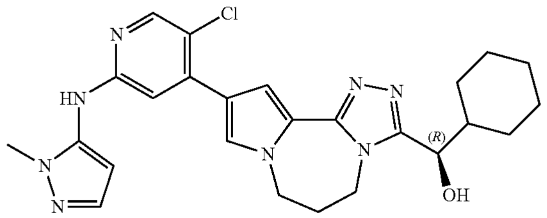 |
| 25 | 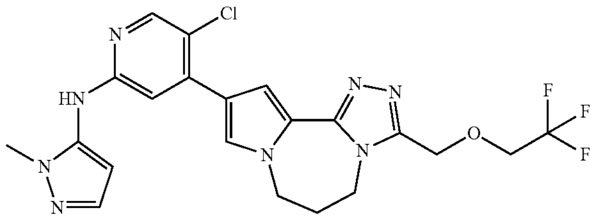 [SMILES: Cn1nccc1Nc1cc(-c2cc3n(c2)CCCn2c(COCC(F)(F)F)nnc2-3)c(Cl)cn1] |

-continued
| Compound | Structure |
|---|---|
| 26 | 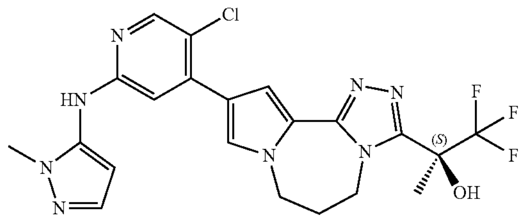 |
| 27 | 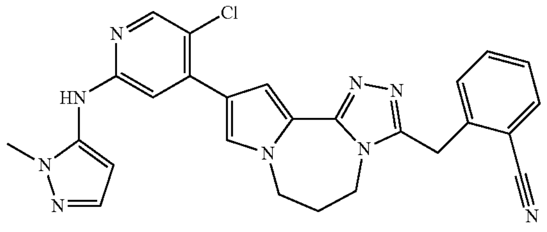 [SMILES: Cn1nccc1Nc1cc(-c2cc3n(c2)CCCn2c(Cc4ccccc4C#N)nnc2-3)c(Cl)cn1] |
| 28 | 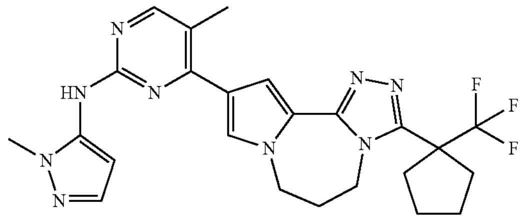 [SMILES: Cc1cnc(Nc2ccnn2C)nc1-c1cc2n(c1)CCCn1c-2nnc1C1(C(F)(F)F)CCCC1] |
| 29 | 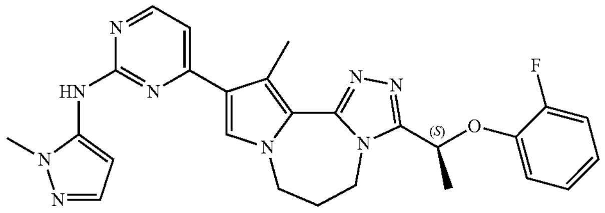 |
| 30 | 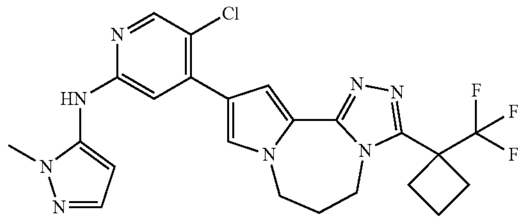 |
| 31 | 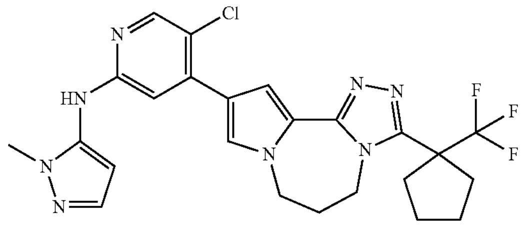 [SMILES: Cn1nccc1Nc1cc(-c2cc3n(c2)CCCn2c-3nnc2C2(C(F)(F)F)CCCC2)c(Cl)cn1] |

-continued
| Compound | Structure |
|---|---|
| 32 | 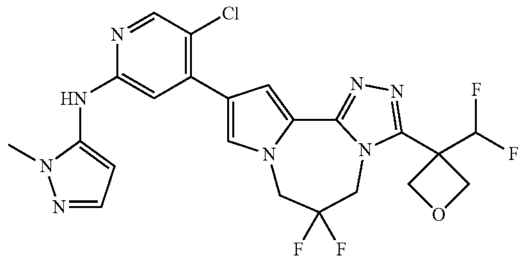 [SMILES: Cn1nccc1Nc1cc(-c2cc3n(c2)CC(F)(F)Cn2c-3nnc2C2(C(F)F)COC2)c(Cl)cn1] |
| 33 | 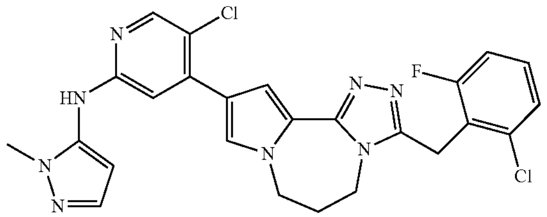 [SMILES: Cn1nccc1Nc1cc(-c2cc3n(c2)CCCn2c(Cc4c(F)cccc4Cl)nnc2-3)c(Cl)cn1] |
| 34 | 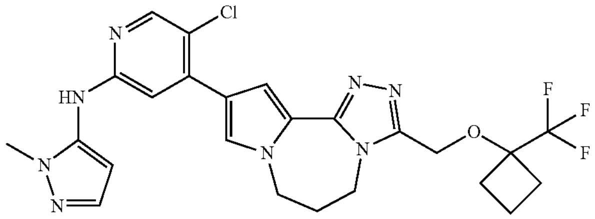 |
| 35 | 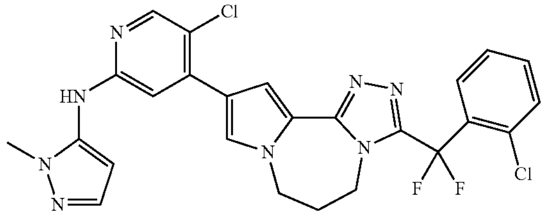 [SMILES: Cn1nccc1Nc1cc(-c2cc3n(c2)CCCn2c-3nnc2C(F)(F)c2ccccc2Cl)c(Cl)cn1] |
| 36 | 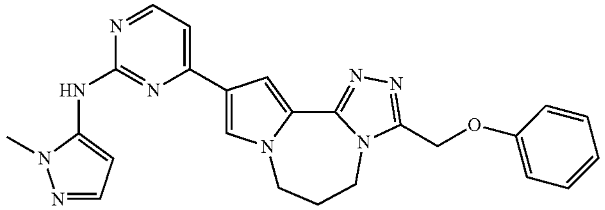 [SMILES: Cn1nccc1Nc1nccc(-c2cc3n(c2)CCCn2c(COc4ccccc4)nnc2-3)n1] |
| 37 | 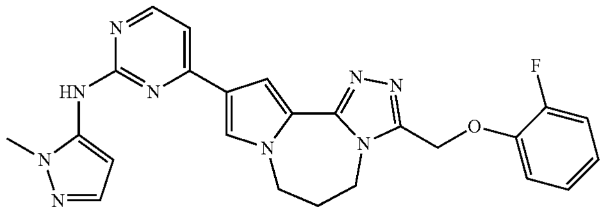 |
| 38 | 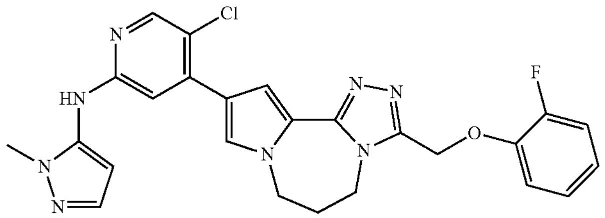 |

-continued
| Compound | Structure |
|---|---|
| 42 | 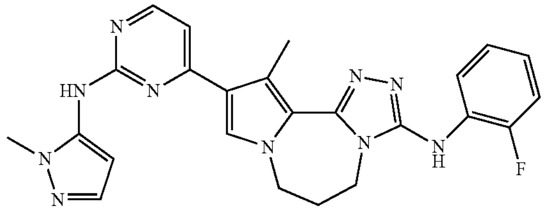 [SMILES: Cc1c(-c2ccnc(Nc3ccnn3C)n2)cn2c1-c1nnc(Nc3ccccc3F)n1CCC2] |
| 43 | 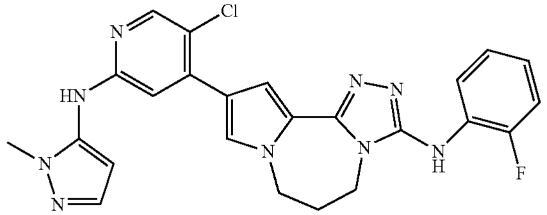 [SMILES: Cn1nccc1Nc1cc(-c2cc3n(c2)CCCn2c(Nc4ccccc4F)nnc2-3)c(Cl)cn1] |
| 44 | 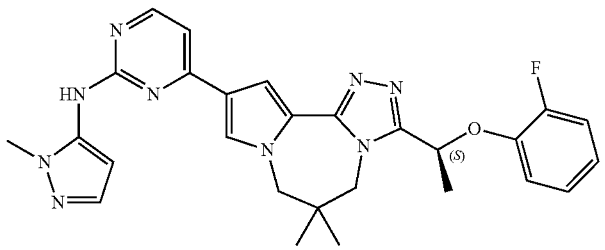 |
| 49 | 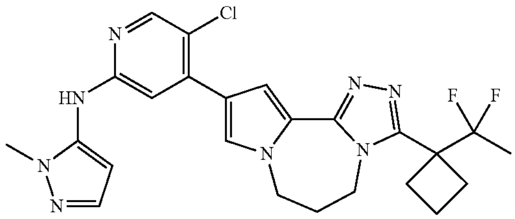 [SMILES: Cn1nccc1Nc1cc(-c2cc3n(c2)CCCn2c-3nnc2C2(C(C)(F)F)CCC2)c(Cl)cn1] |
| 51 | 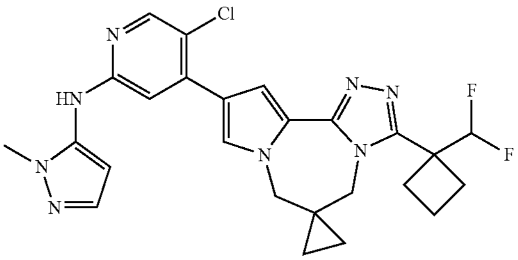 [SMILES: Cn1nccc1Nc1cc(-c2cc3n(c2)CC2(CC2)Cn2c-3nnc2C2(C(F)F)CCC2)c(Cl)cn1] |
| 52 | 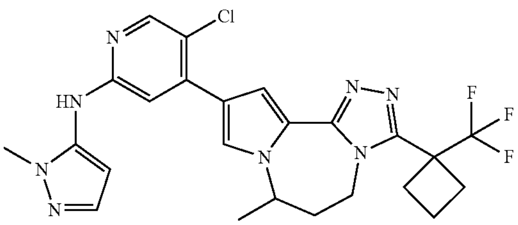 [SMILES: CC1CCn2c(nnc2C2(C(F)(F)F)CCC2)-c2cc(-c3cc(Nc4ccnn4C)ncc3Cl)cn21] |

-continued
| Compound | Structure |
| --- | --- |
| 53 | 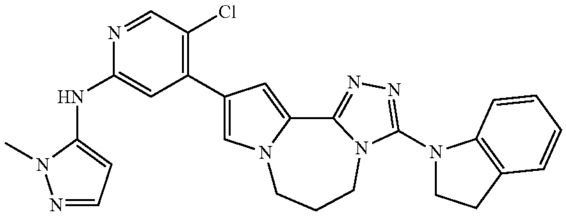 [SMILES: Cn1nccc1Nc1cc(-c2cc3n(c2)CCCn2c-3nnc2N2CCc3ccccc32)c(Cl)cn1] |
| 54 | 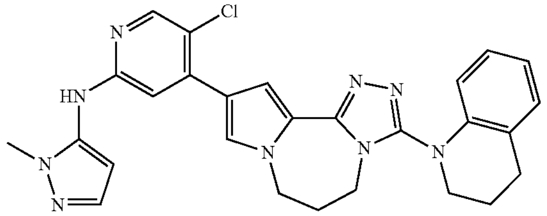 [SMILES: Cn1nccc1Nc1cc(-c2cc3n(c2)CCCn2c-3nnc2N2CCCc3ccccc32)c(Cl)cn1] |
| 55 | 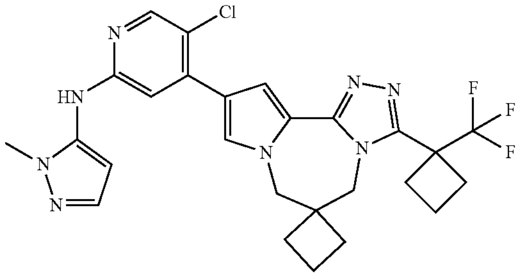 [SMILES: Cn1nccc1Nc1cc(-c2cc3n(c2)CC2(CCC2)Cn2c-3nnc2C2(C(F)(F)F)CCC2)c(Cl)cn1] |
| 59 | 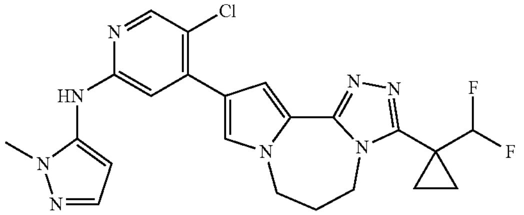 [SMILES: Cn1nccc1Nc1cc(-c2cc3n(c2)CCCn2c-3nnc2C2(C(F)F)CC2)c(Cl)cn1] |
| 60 | 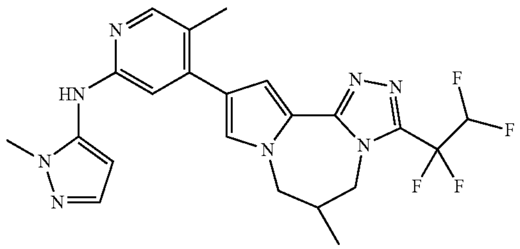 [SMILES: Cc1cnc(Nc2ccnn2C)cc1-c1cc2n(c1)CC(C)Cn1c-2nnc1C(F)(F)C(F)F] |
| 65 | 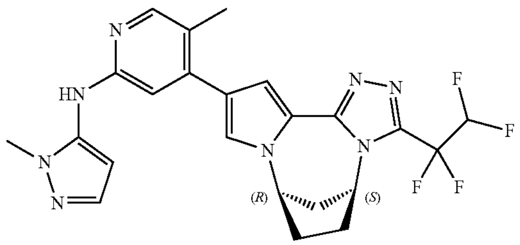 |

-continued
| Compound | Structure |
| --- | --- |
| 66 | 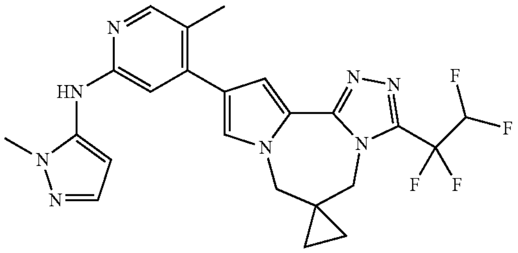 [SMILES: Cc1cnc(Nc2ccnn2C)cc1-c1cc2n(c1)CC1(CC1)Cn1c-2nnc1C(F)(F)C(F)F] |
| 67 | 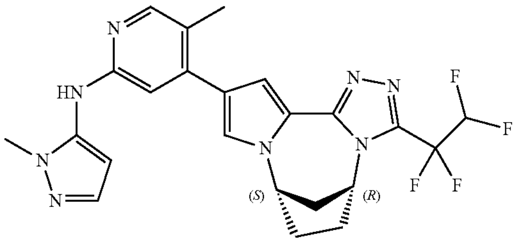 |
| 72 | 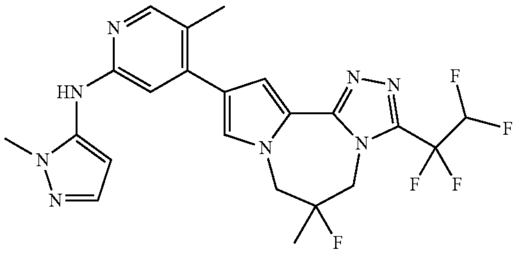 [SMILES: Cc1cnc(Nc2ccnn2C)cc1-c1cc2n(c1)CC(C)(F)Cn1c-2nnc1C(F)(F)C(F)F] |
| 73 | 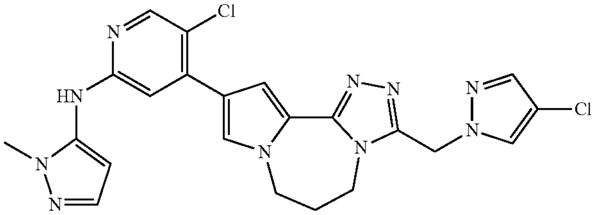 [SMILES: Cn1nccc1Nc1cc(-c2cc3n(c2)CCCn2c(Cn4cc(Cl)cn4)nnc2-3)c(Cl)cn1] |
| 74 | 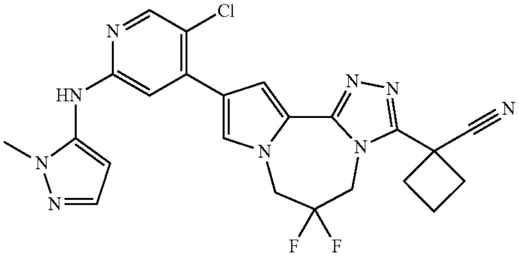 [SMILES: Cn1nccc1Nc1cc(-c2cc3n(c2)CC(F)(F)Cn2c-3nnc2C2(C#N)CCC2)c(Cl)cn1] |
| 75 | 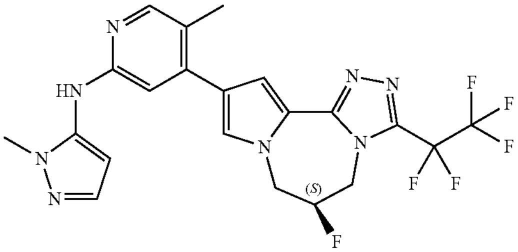 |

-continued
| Compound | Structure |
|---|---|
| 77 | 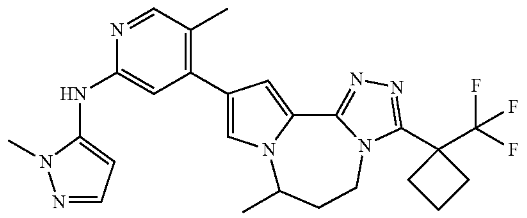 [SMILES: Cc1cnc(Nc2ccnn2C)cc1-c1cc2n(c1)C(C)CCn1c-2nnc1C1(C(F)(F)F)CCC1] |
| 78 | 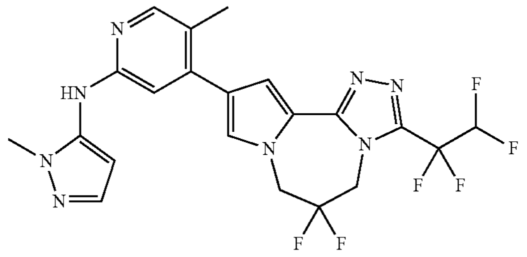 [SMILES: Cc1cnc(Nc2ccnn2C)cc1-c1cc2n(c1)CC(F)(F)Cn1c-2nnc1C(F)(F)C(F)F] |
| 80 | 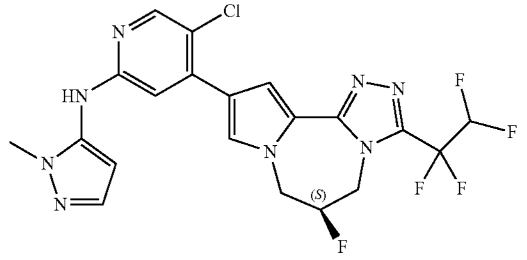 |
| 81 | 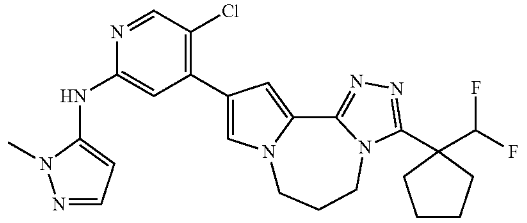 [SMILES: Cn1nccc1Nc1cc(-c2cc3n(c2)CCCn2c-3nnc2C2(C(F)F)CCCC2)c(Cl)cn1] |
| 84 | 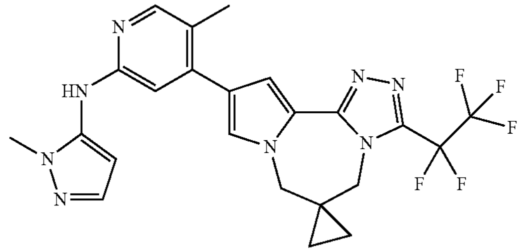 [SMILES: Cc1cnc(Nc2ccnn2C)cc1-c1cc2n(c1)CC1(CC1)Cn1c-2nnc1C(F)(F)C(F)(F)F] |
| 85 | 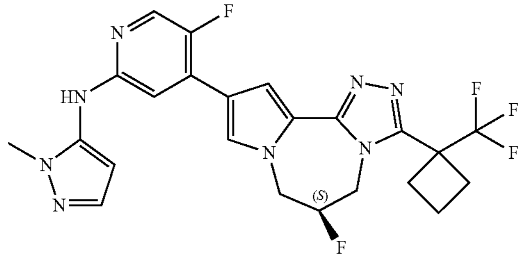 |

-continued
| Compound | Structure |
| --- | --- |
| 87 | 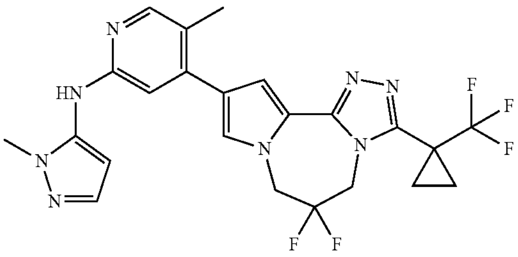 [SMILES: Cc1cnc(Nc2ccnn2C)cc1-c1cc2n(c1)CC(F)(F)Cn1c-2nnc1C1(C(F)(F)F)CC1] |
| 93 | 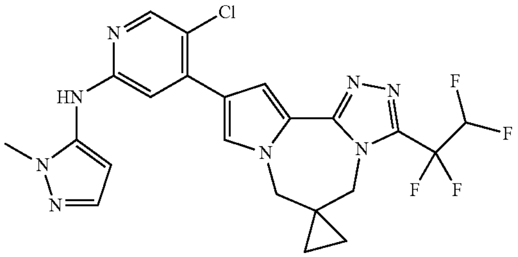 [SMILES: Cn1nccc1Nc1cc(-c2cc3n(c2)CC2(CC2)Cn2c-3nnc2C(F)(F)C(F)F)c(Cl)cn1] |
| 105 | 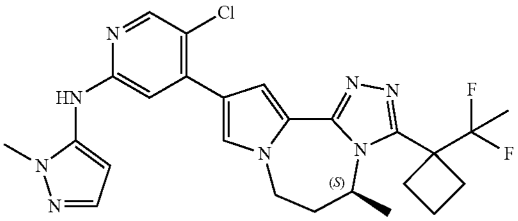 |
| 106 | 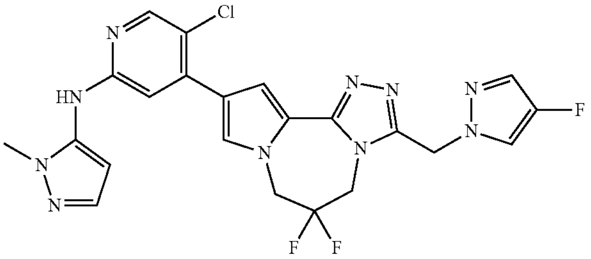 [SMILES: Cn1nccc1Nc1cc(-c2cc3n(c2)CC(F)(F)Cn2c(Cn4cc(F)cn4)nnc2-3)c(Cl)cn1] |
| 107 | 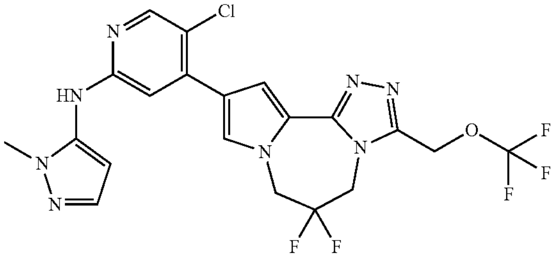 [SMILES: Cn1nccc1Nc1cc(-c2cc3n(c2)CC(F)(F)Cn2c(COC(F)(F)F)nnc2-3)c(Cl)cn1] |
| 113 | 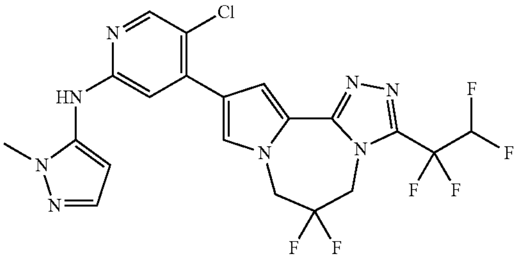 [SMILES: Cn1nccc1Nc1cc(-c2cc3n(c2)CC(F)(F)Cn2c-3nnc2C(F)(F)C(F)F)c(Cl)cn1] |

-continued
| Compound | Structure |
|---|---|
| 115 | 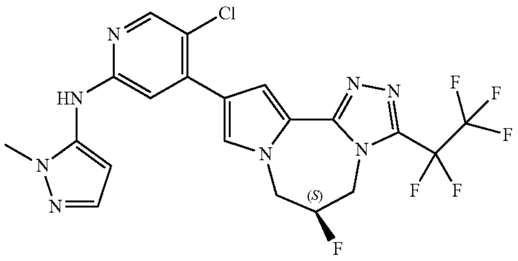 |
| 117 | 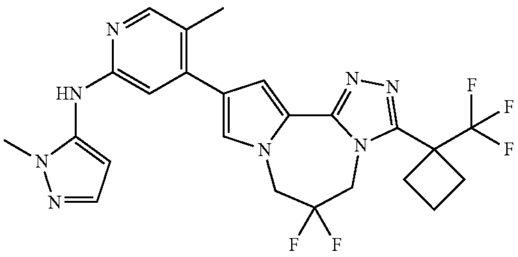 [SMILES: Cc1cnc(Nc2ccnn2C)cc1-c1cc2n(c1)CC(F)(F)Cn1c-2nnc1C1(C(F)(F)F)CCC1] |
| 119 | 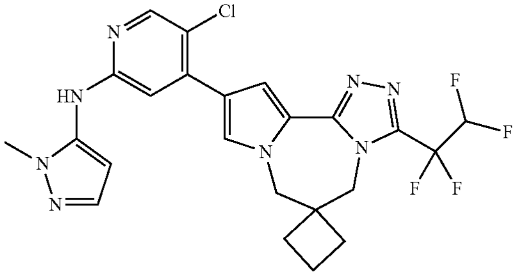 [SMILES: Cn1nccc1Nc1cc(-c2cc3n(c2)CC2(CCC2)Cn2c-3nnc2C(F)(F)C(F)F)c(Cl)cn1] |
| 120 | 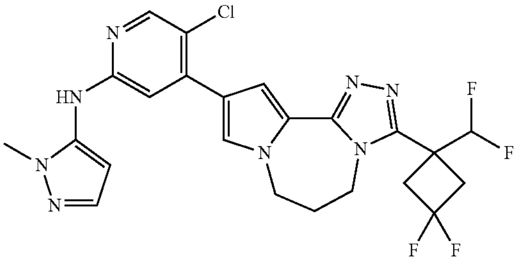 [SMILES: Cn1nccc1Nc1cc(-c2cc3n(c2)CCCn2c-3nnc2C2(C(F)F)CC(F)(F)C2)c(Cl)cn1] |
| 122 | 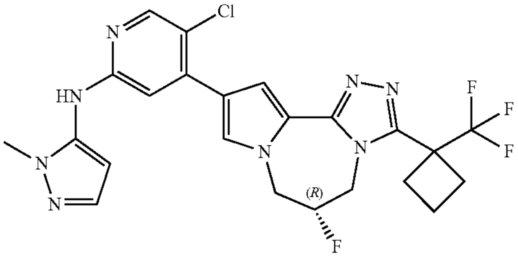 |

-continued
| Compound | Structure |
| --- | --- |
| 123 | 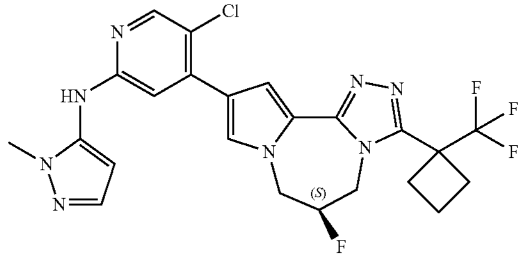 |
| 129 | 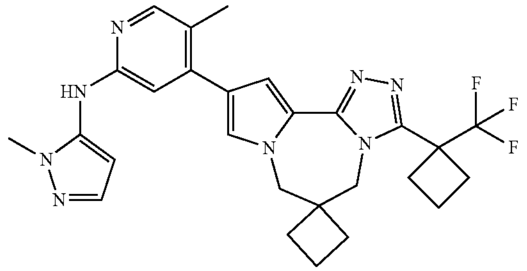 [SMILES: Cc1cnc(Nc2ccnn2C)cc1-c1cc2n(c1)CC1(CCC1)Cn1c-2nnc1C1(C(F)(F)F)CCC1] |
| 132 | 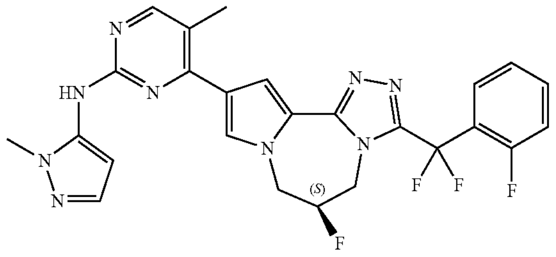 |
| 136 | 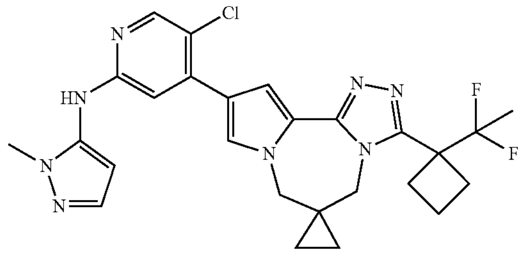 [SMILES: Cn1nccc1Nc1cc(-c2cc3n(c2)CC2(CC2)Cn2c-3nnc2C2(C(C)(F)F)CCC2)c(Cl)cn1] |
| 140 | 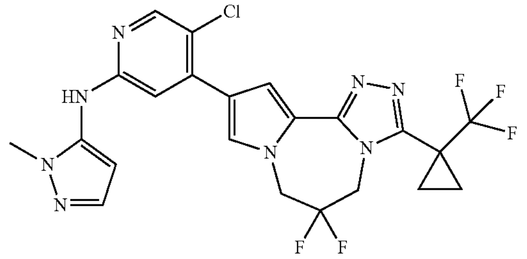 [SMILES: Cn1nccc1Nc1cc(-c2cc3n(c2)CC(F)(F)Cn2c-3nnc2C2(C(F)(F)F)CC2)c(Cl)cn1] |
| 146 | 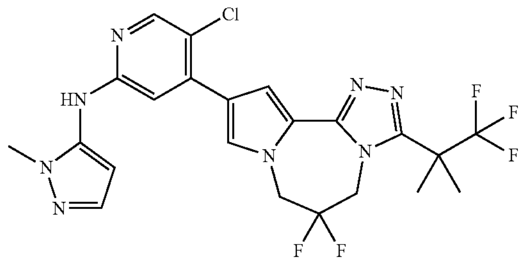 [SMILES: Cn1nccc1Nc1cc(-c2cc3n(c2)CC(F)(F)Cn2c-3nnc2C(C)(C)C(F)(F)F)c(Cl)cn1] |

-continued
| Compound | Structure |
|---|---|
| 147 | 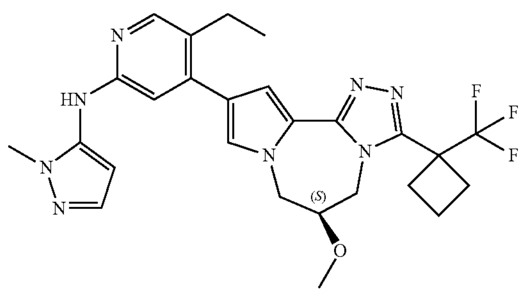 |
| 155 | 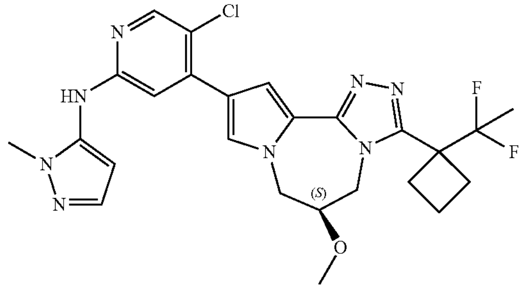 |
| 159 | 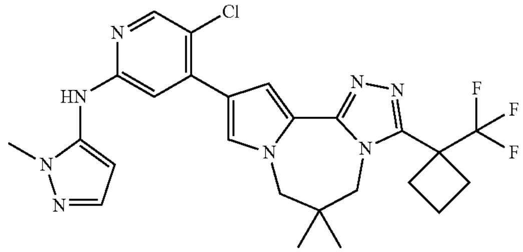 [SMILES: Cn1nccc1Nc1cc(-c2cc3n(c2)CC(C)(C)Cn2c-3nnc2C2(C(F)(F)F)CCC2)c(Cl)cn1] |
| 160 | 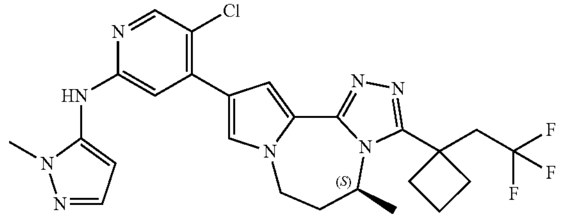 |
| 162 | 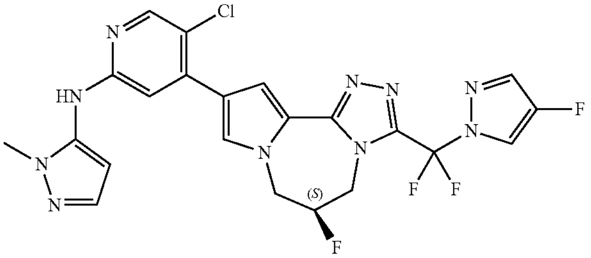 |

-continued
| Compound | Structure |
| --- | --- |
| 165 | 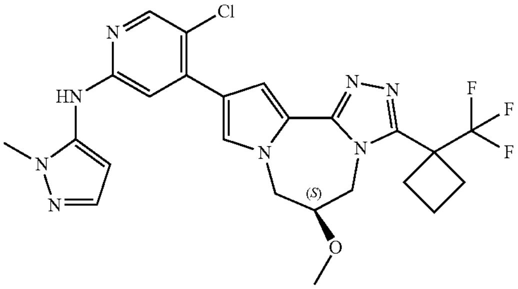 |
| 168 | 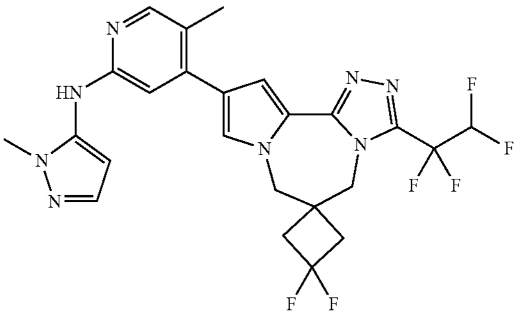 [SMILES: Cc1cnc(Nc2ccnn2C)cc1-c1cc2n(c1)CC1(Cn3c-2nnc3C(F)(F)C(F)F)CC(F)(F)C1] |
| 169 | 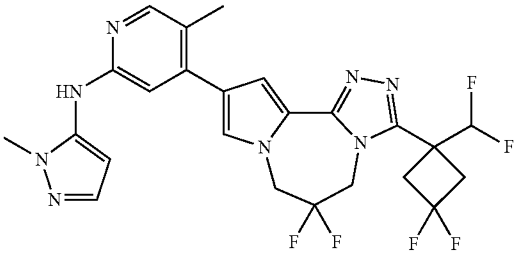 [SMILES: Cc1cnc(Nc2ccnn2C)cc1-c1cc2n(c1)CC(F)(F)Cn1c-2nnc1C1(C(F)F)CC(F)(F)C1] |
| 171 | 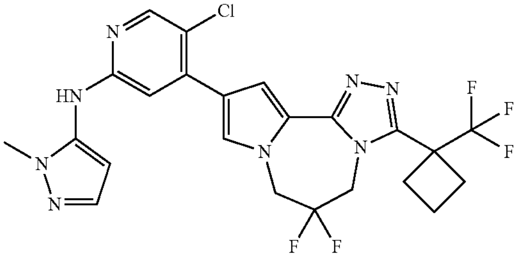 [SMILES: Cn1nccc1Nc1cc(-c2cc3n(c2)CC(F)(F)Cn2c-3nnc2C2(C(F)(F)F)CCC2)c(Cl)cn1] |
| 199 | 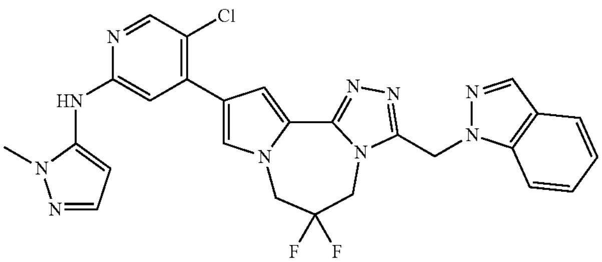 [SMILES: Cn1nccc1Nc1cc(-c2cc3n(c2)CC(F)(F)Cn2c(Cn4ncc5ccccc54)nnc2-3)c(Cl)cn1] |

-continued
| Compound | Structure |
|---|---|
| 211 | 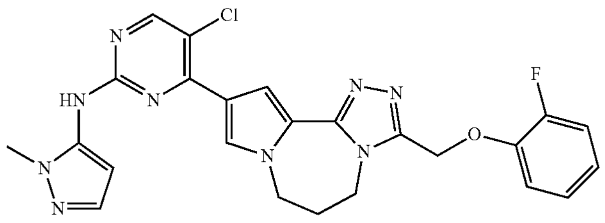 |
| 213 | 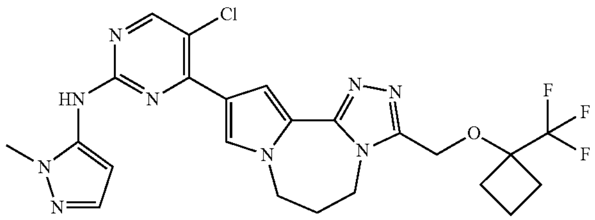 [SMILES: Cn1nccc1Nc1ncc(Cl)c(-c2cc3n(c2)CCCn2c(COC4(C(F)(F)F)CCC4)nnc2-3)n1] |
| 214 | 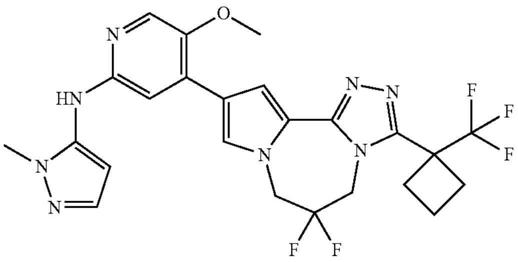 [SMILES: COc1cnc(Nc2ccnn2C)cc1-c1cc2n(c1)CC(F)(F)Cn1c-2nnc1C1(C(F)(F)F)CCC1] |
| 215 | 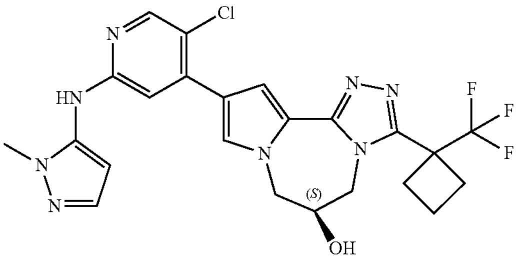 |
| 216 | 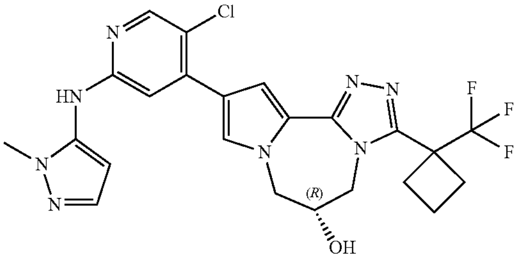 |
| 217 | 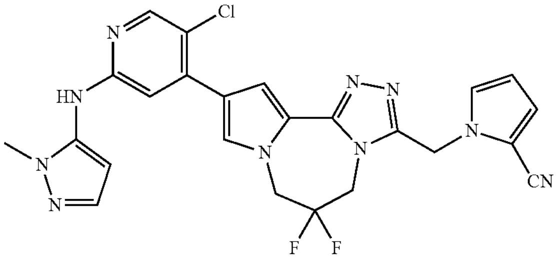 [SMILES: Cn1nccc1Nc1cc(-c2cc3n(c2)CC(F)(F)Cn2c(Cn4cccc4C#N)nnc2-3)c(Cl)cn1] |

-continued
| Compound | Structure |
| --- | --- |
| 218 | 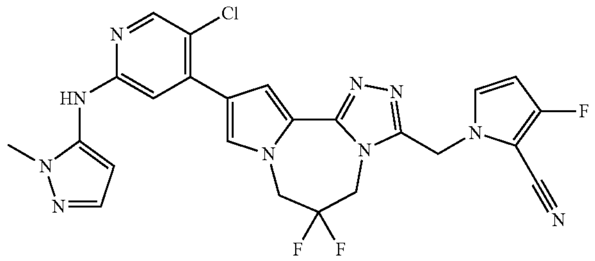 [SMILES: Cn1nccc1Nc1cc(-c2cc3n(c2)CC(F)(F)Cn2c(Cn4ccc(F)c4C#N)nnc2-3)c(Cl)cn1] |
| 219 | 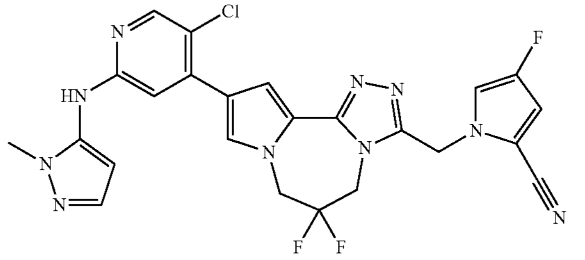 [SMILES: Cn1nccc1Nc1cc(-c2cc3n(c2)CC(F)(F)Cn2c(Cn4cc(F)cc4C#N)nnc2-3)c(Cl)cn1] |
| 229 | 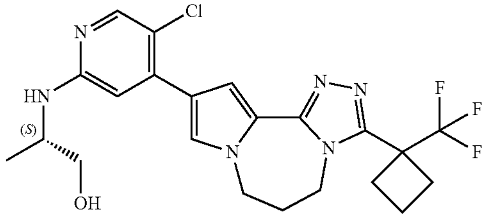 |
| 230 | 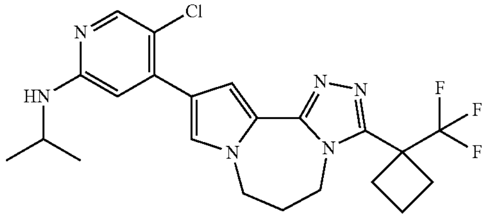 [SMILES: CC(C)Nc1cc(-c2cc3n(c2)CCCn2c-3nnc2C2(C(F)(F)F)CCC2)c(Cl)cn1] |
| 233 | 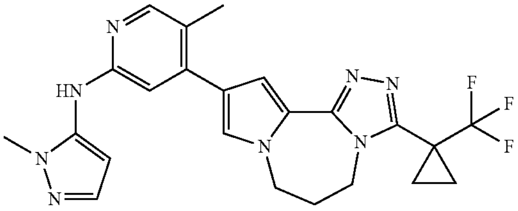 [SMILES: Cc1cnc(Nc2ccnn2C)cc1-c1cc2n(c1)CCCn1c-2nnc1C1(C(F)(F)F)CC1] |
| 237 | 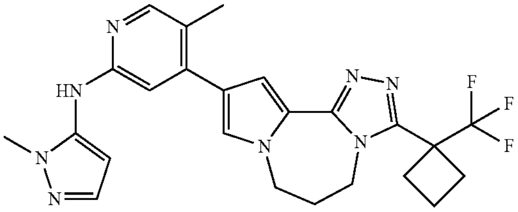 [SMILES: Cc1cnc(Nc2ccnn2C)cc1-c1cc2n(c1)CCCn1c-2nnc1C1(C(F)(F)F)CCC1] |

-continued
| Compound | Structure |
|---|---|
| 240 | 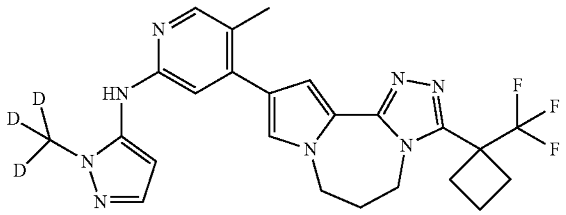 [SMILES: [2H]C([2H])([2H])n1nccc1Nc1cc(-c2cc3n(c2)CCCn2c-3nnc2C2(C(F)(F)F)CCC2)c(C)cn1] |
| 241 | 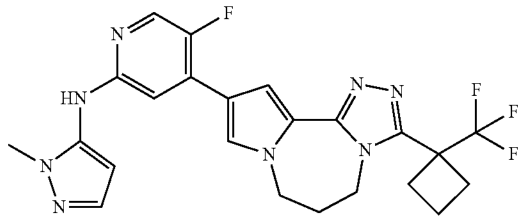 [SMILES: Cn1nccc1Nc1cc(-c2cc3n(c2)CCCn2c-3nnc2C2(C(F)(F)F)CCC2)c(F)cn1] |
| 243 | 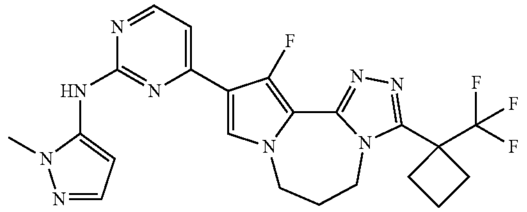 |
| 244 | 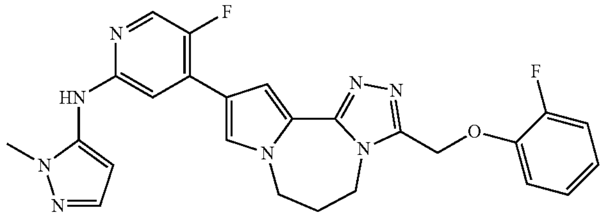 |
| 245 | 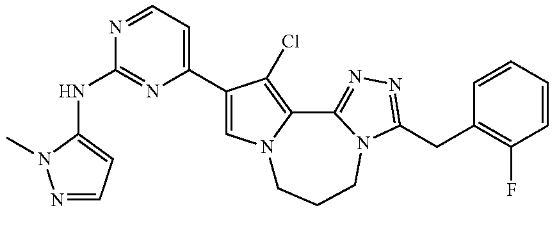 [SMILES: Cn1nccc1Nc1nccc(-c2cn3c(c2Cl)-c2nnc(Cc4ccccc4F)n2CCC3)n1] |
| 246 | 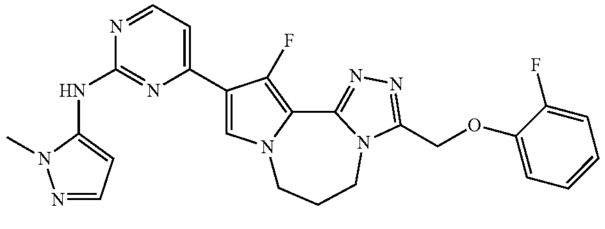 [SMILES: Cn1nccc1Nc1nccc(-c2cn3c(c2F)-c2nnc(COc4ccccc4F)n2CCC3)n1] |
| 248 | 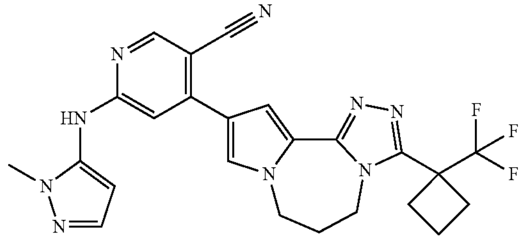 [SMILES: Cn1nccc1Nc1cc(-c2cc3n(c2)CCCn2c-3nnc2C2(C(F)(F)F)CCC2)c(C#N)cn1] |

-continued
| Compound | Structure |
|---|---|
| 251 | 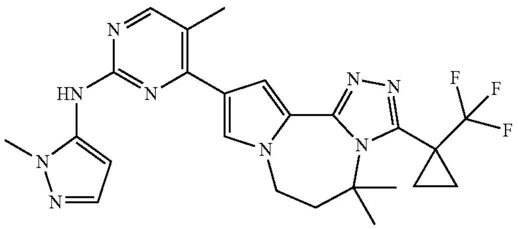 [SMILES: Cc1cnc(Nc2ccnn2C)nc1-c1cc2n(c1)CCC(C)(C)n1c-2nnc1C1(C(F)(F)F)CC1] |
| 252 | 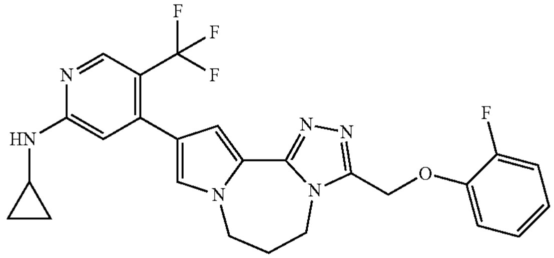 [SMILES: Fc1ccccc1OCc1nnc2n1CCCn1cc(-c3cc(NC4CC4)ncc3C(F)(F)F)cc1-2] |
| 254 | 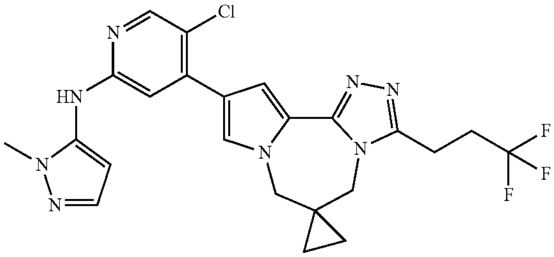 [SMILES: Cn1nccc1Nc1cc(-c2cc3n(c2)CC2(CC2)Cn2c(CCC(F)(F)F)nnc2-3)c(Cl)cn1] |
| 255 | 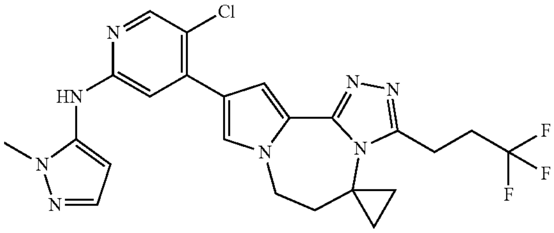 [SMILES: Cn1nccc1Nc1cc(-c2cc3n(c2)CCC2(CC2)n2c(CCC(F)(F)F)nnc2-3)c(Cl)cn1] |
| 257 | 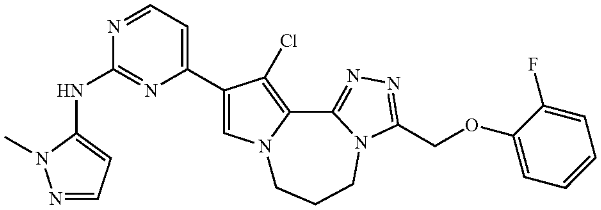 [SMILES: Cn1nccc1Nc1nccc(-c2cn3c(c2Cl)-c2nnc(COc4ccccc4F)n2CCC3)n1] |
| 258 | 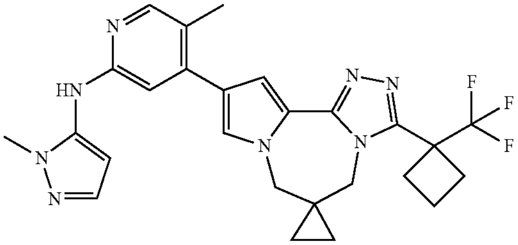 [SMILES: Cc1cnc(Nc2ccnn2C)cc1-c1cc2n(c1)CC1(CC1)Cn1c-2nnc1C1(C(F)(F)F)CCC1] |

-continued
| Compound | Structure |
|---|---|
| 262 | 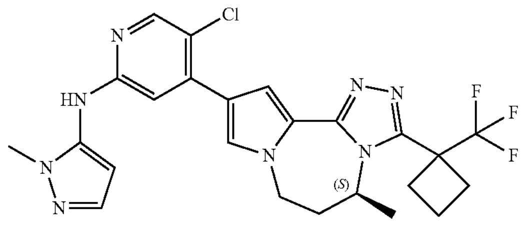 |
| 263 | 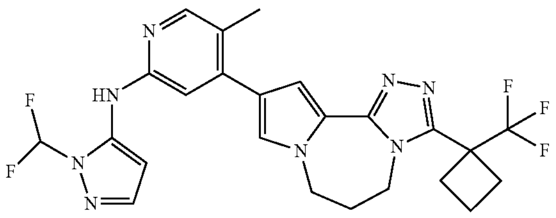 [SMILES: Cc1cnc(Nc2ccnn2C(F)F)cc1-c1cc2n(c1)CCCn1c-2nnc1C1(C(F)(F)F)CCC1] |
| 264 | 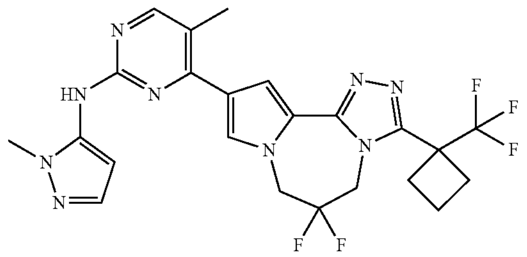 [SMILES: Cc1cnc(Nc2ccnn2C)nc1-c1cc2n(c1)CC(F)(F)Cn1c-2nnc1C1(C(F)(F)F)CCC1] |
| 266 | 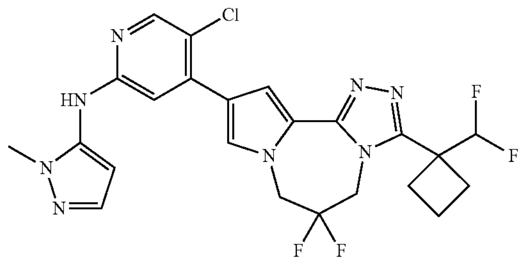 |
| 267 | 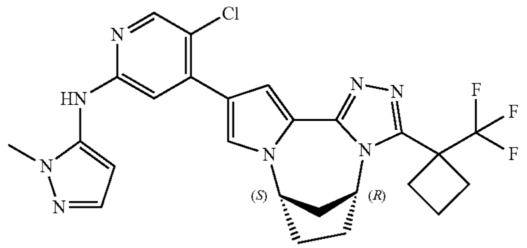 |
| 268 | 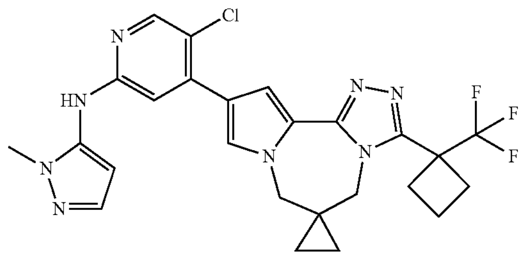 |

-continued
| Compound | Structure |
|---|---|
| 269 | 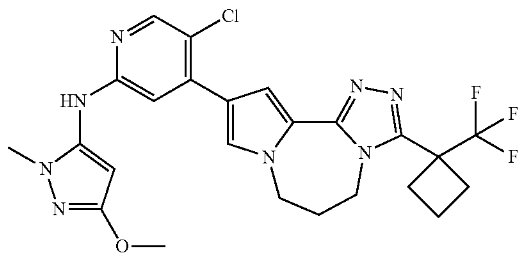 [SMILES: COc1cc(Nc2cc(-c3cc4n(c3)CCCn3c-4nnc3C3(C(F)(F)F)CCC3)c(Cl)cn2)n(C)n1] |
| 271 | 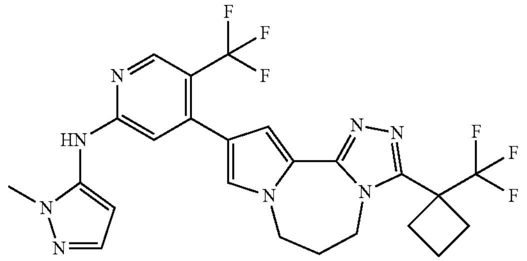 [SMILES: Cn1nccc1Nc1cc(-c2cc3n(c2)CCCn2c-3nnc2C2(C(F)(F)F)CCC2)c(C(F)(F)F)cn1] |
| 272 | 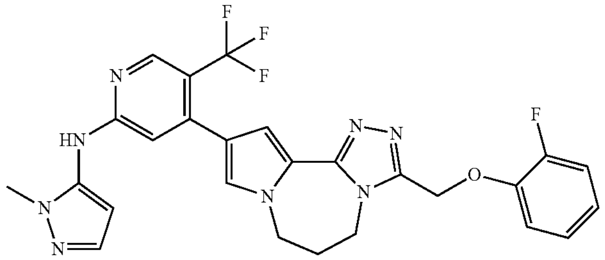 [SMILES: Cn1nccc1Nc1cc(-c2cc3n(c2)CCCn2c(COc4ccccc4F)nnc2-3)c(C(F)(F)F)cn1] |
| 275 | 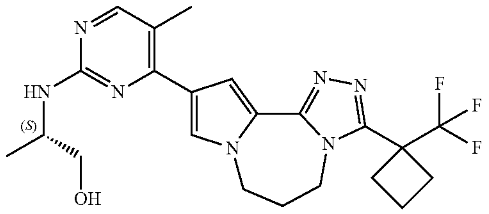 |
| 276 | 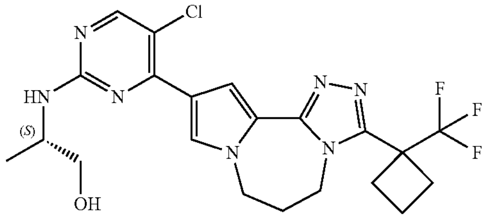 |
| 277 | 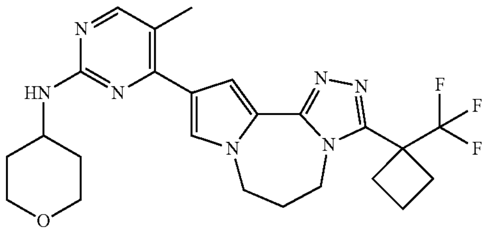 [SMILES: Cc1cnc(NC2CCOCC2)nc1-c1cc2n(c1)CCCn1c-2nnc1C1(C(F)(F)F)CCC1] |

-continued
| Compound | Structure |
| --- | --- |
| 278 | 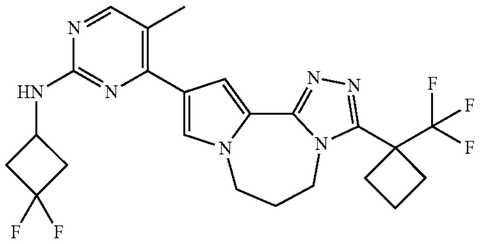 [SMILES: Cc1cnc(NC2CC(F)(F)C2)nc1-c1cc2n(c1)CCCn1c-2nnc1C1(C(F)(F)F)CCC1] |
| 279 | 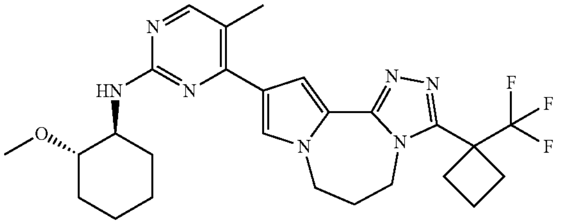 [SMILES: CO[C@H]1CCCC[C@@H]1Nc1ncc(C)c(-c2cc3n(c2)CCCn2c-3nnc2C2(C(F)(F)F)CCC2)n1] |
| 281 | 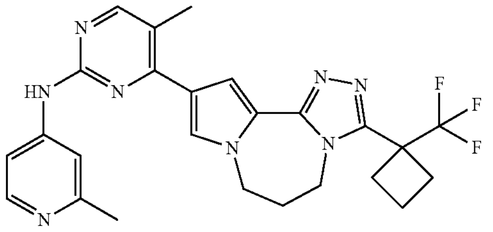 [SMILES: Cc1cc(Nc2ncc(C)c(-c3cc4n(c3)CCCn3c-4nnc3C3(C(F)(F)F)CCC3)n2)ccn1] |
| 284 | 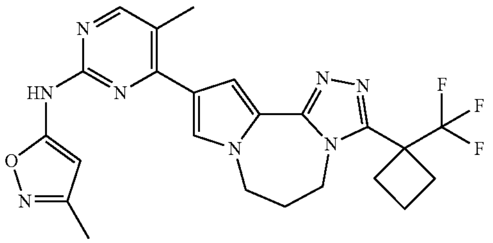 [SMILES: Cc1cc(Nc2ncc(C)c(-c3cc4n(c3)CCCn3c-4nnc3C3(C(F)(F)F)CCC3)n2)on1] |
| 285 | 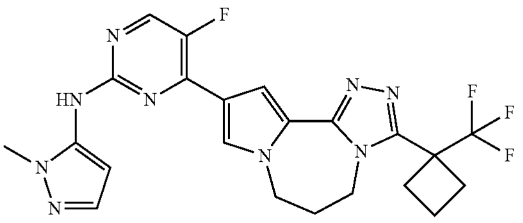 [SMILES: Cn1nccc1Nc1ncc(F)c(-c2cc3n(c2)CCCn2c-3nnc2C2(C(F)(F)F)CCC2)n1] |
| 286 | 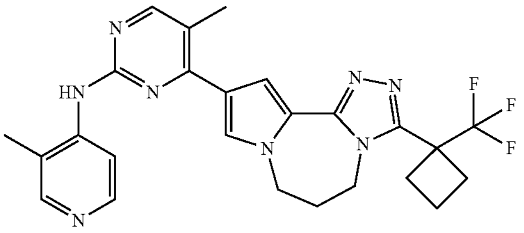 [SMILES: Cc1cnccc1Nc1ncc(C)c(-c2cc3n(c2)CCCn2c-3nnc2C2(C(F)(F)F)CCC2)n1] |

-continued
| Compound | Structure |
| --- | --- |
| 299 | 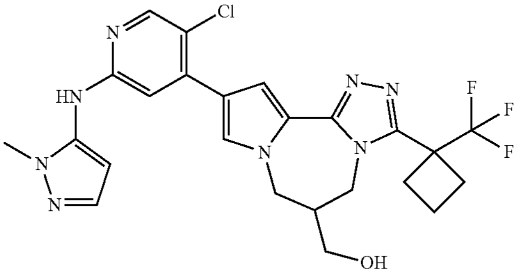 [SMILES: Cn1nccc1Nc1cc(-c2cc3n(c2)CC(CO)Cn2c-3nnc2C2(C(F)(F)F)CCC2)c(Cl)cn1] |
| 300 | 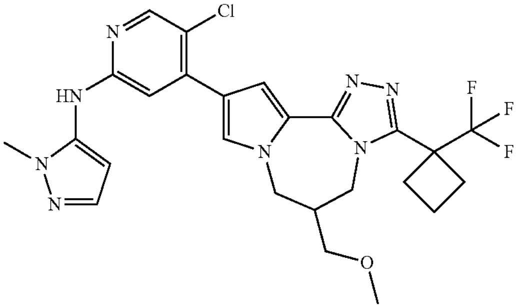 [SMILES: COCC1Cn2cc(-c3cc(Nc4ccnn4C)ncc3Cl)cc2-c2nnc(C3(C(F)(F)F)CCC3)n2C1] |
| 302 | 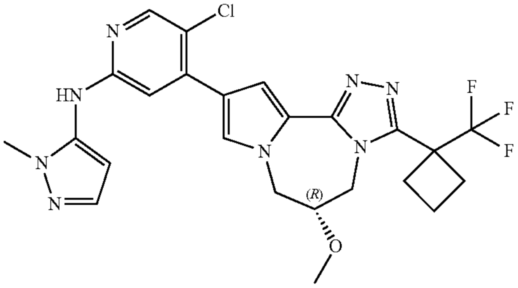 |
| 304 | 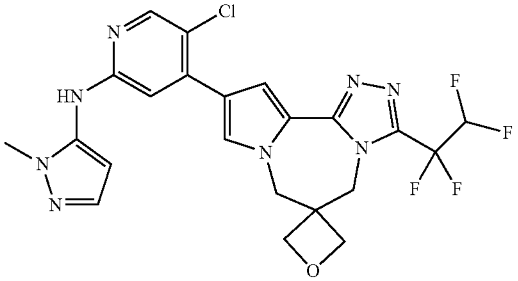 [SMILES: Cn1nccc1Nc1cc(-c2cc3n(c2)CC2(COC2)Cn2c-3nnc2C(F)(F)C(F)F)c(Cl)cn1] |
| 306 | 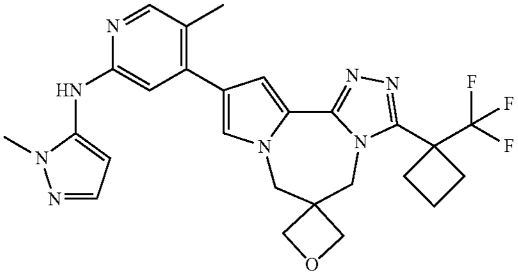 [SMILES: Cc1cnc(Nc2ccnn2C)cc1-c1cc2n(c1)CC1(COC1)Cn1c-2nnc1C1(C(F)(F)F)CCC1] |

-continued

| Compound | Structure |
| --- | --- |
| 307 | 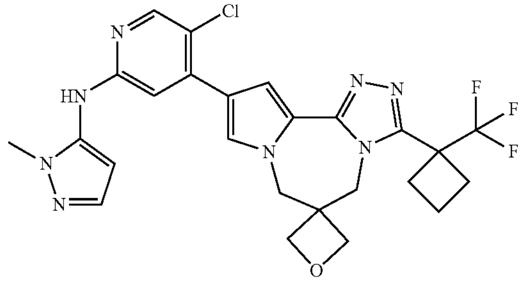 [SMILES: Cn1nccc1Nc1cc(-c2cc3n(c2)CC2(COC2)Cn2c-3nnc2C2(C(F)(F)F)CCC2)c(Cl)cn1] |
| 322 | 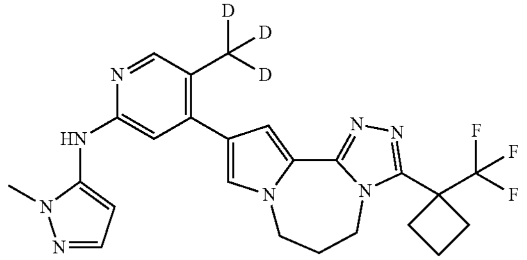 [SMILES: [2H]C([2H])([2H])c1cnc(Nc2ccnn2C)cc1-c1cc2n(c1)CCCn1c-2nnc1C1(C(F)(F)F)CCC1] |

Embodiment 39. A pharmaceutical composition, comprising the compound of any one of embodiments 1-38, or a pharmaceutically acceptable salt thereof, and optionally a pharmaceutically acceptable carrier.

Embodiment 40. A method of in vivo or in vitro inhibiting the activity of ERK, comprising contacting an effective amount of the compound of any one of embodiments 1-38 or a pharmaceutically acceptable salt thereof with ERK.

Embodiment 41. Use of the compound of any one of embodiments 1-38 or a pharmaceutically acceptable salt thereof in the manufacture of a medicament for treating or preventing a disease responsive to inhibition of ERK.

Embodiment 42. The use according to embodiment 41, wherein the medicament is used for treating cancer or an autoimmune disease.

Embodiment 43. The use according to embodiment 42, wherein the cancer is solid tumor or hematologic malignancy, such as leukemia, lymphoma, colorectal cancer, melanoma, glioma, pancreatic cancer, breast cancer, lung cancer (such as non-small cell lung cancer), thyroid cancer (such as papillary thyroid cancer), or ovarian cancer.

Embodiment 44. A method of treating or preventing a disease responsive to inhibition of ERK, comprising administering to the subject in need thereof an effective amount of the compound of any one of embodiments 1-38, or a pharmaceutically acceptable salt thereof.

Embodiment 45. The compound of any one of embodiments 1-38, or a pharmaceutically acceptable salt thereof for use in the treatment or prevention of a disease responsive to inhibition of ERK.

Embodiment 46. The compound of any one of embodiments 1-38, or a pharmaceutically acceptable salt thereof for use as a medicament.

Embodiment 47. The compound according to embodiment 46, or a pharmaceutically acceptable salt thereof for use as a medicament for treating or preventing a disease responsive to inhibition of ERK.

Embodiment 48. The compound according to embodiment 47, or a pharmaceutically acceptable salt thereof for use as a medicament for treating or preventing cancer or an autoimmune disease.

Embodiment 49. The compound according to embodiment 48, or a pharmaceutically acceptable salt thereof, wherein the cancer is solid tumor or hematologic malignancy, such as leukemia, lymphoma, colorectal cancer, melanoma, glioma, pancreatic cancer, breast cancer, lung cancer (such as non-small cell lung cancer), thyroid cancer (such as papillary thyroid cancer), or ovarian cancer.

Embodiment 50. A combination, comprising the compound of any one of embodiments 1-38, or a pharmaceutically acceptable salt thereof, and at least one additional therapeutic agent.

Embodiment 51. The combination according to embodiment 50, wherein said additional therapeutic agent is an anti-neoplastic agent, such as a radiotherapeutic agent, a chemotherapeutic agent, an immunotherapeutic agent, a targeted therapeutic agent.

Embodiment 52. A compound of formula (II):

(II)

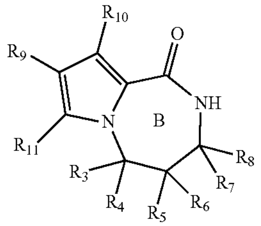

or racemic mixtures or enantiomers thereof, wherein, $R_9$ is a leaving group; $R_{10}$ and $R_{11}$ are independently selected from hydrogen, halo, and $C_{1-6}$ alkyl; $R_3$, $R_4$, $R_5$, $R_6$, $R_7$, and $R_8$ are independently selected from hydrogen, halo, $C_{1-6}$ alkyl, $C_{1-6}$ alkoxyl, or $C_{1-6}$ haloalkyl; or any two of $R_3$, $R_4$, $R_5$, $R_6$, $R_7$, and $R_8$ together with the carbon atom they are attached to and the B ring form

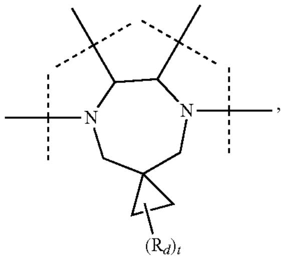

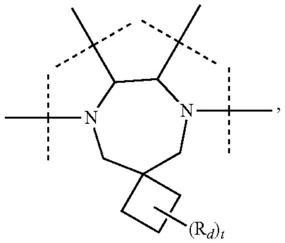

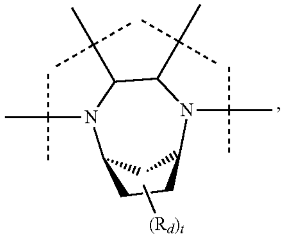

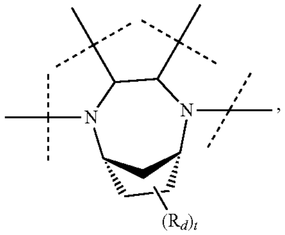

or

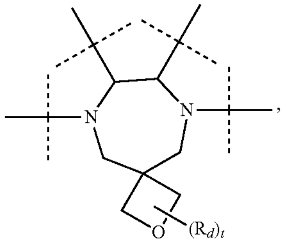

$R_d$ is selected from hydrogen and halo, t is 0, 1, 2, or 3; provided that, when both $R_{10}$ and $R_{11}$ are hydrogen, then $R_3$, $R_4$, $R_5$, $R_6$, $R_7$, and $R_8$ are not all hydrogen, and when one of $R_3$, $R_4$, $R_5$, $R_6$, $R_7$, and $R_8$ is methyl, then the other ones are not all hydrogen.

Embodiment 53. The compound of formula (II) according to embodiment 52, which is selected from:

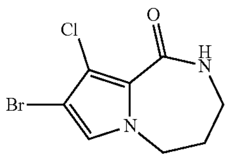

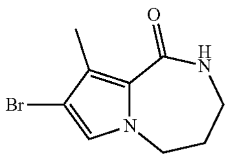

-continued

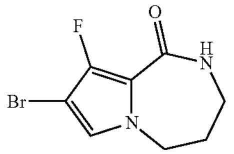

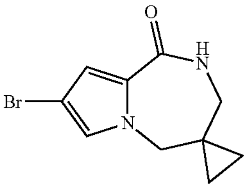

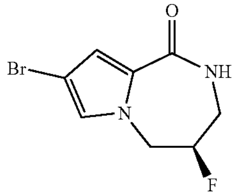

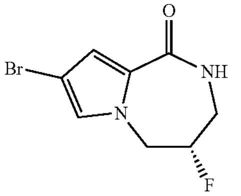

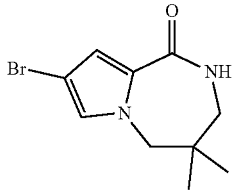

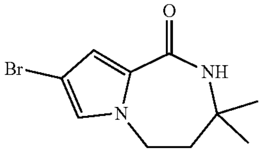

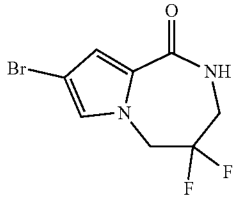

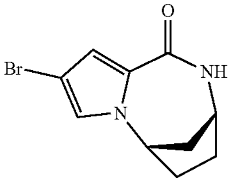

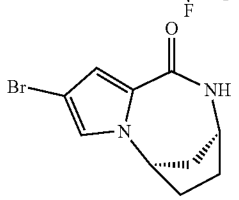

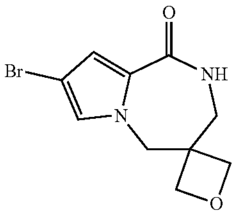

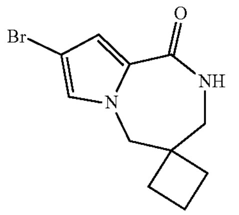

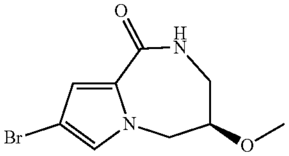

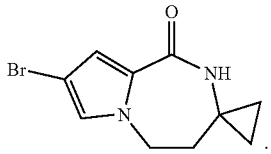

Embodiment 54. A compound of formula (III):

(III)

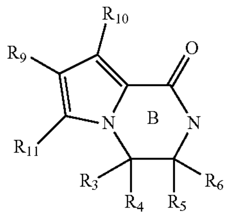

or racemic mixtures or enantiomers thereof, wherein, $R_9$ is a leaving group; $R_{10}$ and $R_{11}$ are independently selected from hydrogen, halo, and $C_{1-6}$ alkyl;

$R_3$, $R_4$, $R_5$, and $R_6$ are independently selected from hydrogen, halo, $C_{1-6}$ alkyl, $C_{1-6}$ alkoxyl, $C_{1-6}$ haloalkyl, or $C_{1-6}$ alkyl optionally substituted with phenyl; or any pair of $R_3$ and $R_4$, or $R_5$ and $R_6$, together with the carbon atom they are attached to form a saturated $C_{3-6}$ cycloalkyl or a saturated 3-4 membered heterocyclyl having 1 or 2 ring heteroatoms selected from N, O and S, thereby together with the B ring forming a spirocyclic ring; provided that, $R_3$, $R_4$, $R_5$, and $R_6$ are not all hydrogen, and when one or two of $R_3$, $R_4$, $R_5$, and $R_6$ is $C_{1-6}$ alkyl, then the other ones are not all hydrogen.

Embodiment 55. The compound of formula (III) according to embodiment 54, which is selected from:

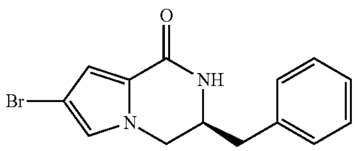

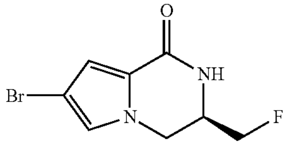

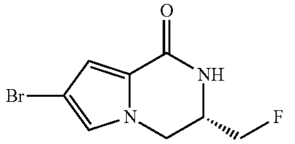

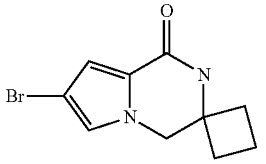

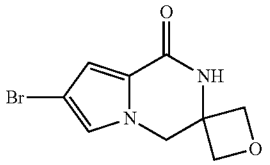

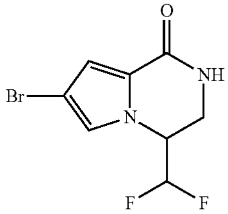

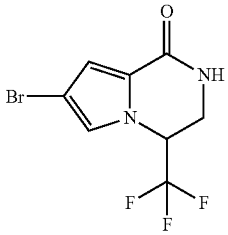

-continued

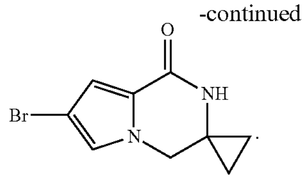

General Synthetic Methods of the Compounds

The compound of formula (I) and/or a pharmaceutically acceptable salt thereof described herein can be synthesized from commercially available starting materials by methods well known in the art and disclosed in the patent application. The synthetic routes given in FIG. 1 illustrate general methods for preparing the compounds disclosed herein, wherein, X is halo; $Z_1$, $Z_2$,

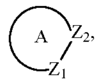

L, $R_1$, $R_2$, $R_3$, $R_4$, $R_5$, $R_6$, $R_7$, $R_8$, $R_a$, $R_b$, m, and n are as defined for the compound of formula (I) and subformula (I-1), (I-2), (I-3) thereof; $R_9$ is as defined for the compound of formula (II), (III).

As shown in FIG. 1, there are mainly three kinds of key reactions for the synthesis of these compounds: the introduction of amino substituent into the Ar ring, the bonding reaction of the Ar ring fragment and the tricyclic system, as well as the construction of triazole ring in the tricyclic system. Accordingly, the synthesis of target compounds can be carried out in different reaction priority according to the practical situation. As shown in route 1, some compounds can be obtained in the order of firstly achieving the bonding reaction, then introducing amino, and finally constructing triazole, such as Example 8; As shown in route 2, some compounds can be obtained in the order of firstly synthesizing triazole to give tricyclic fragment, then achieving the bonding reaction, and finally introducing amino, such as Examples 13 and 14; As shown in route 3, some compounds can be obtained in the order of firstly introducing amino, then achieving the coupling reaction, and finally constructing triazole, such as Examples 1 and 7; As shown in route 4, some compounds can be obtained by combination of the methods of routes 2 and 3, in which the bonding reaction is proceeded finally, such as Example 12.

The compounds obtained by the methods above can be further modified at the peripheral positions to provide other desired compounds. Synthetic chemistry transformations are described, for example, in R. Larock, *Comprehensive Organic Transformations*, VCH Publishers (1989); T. W. Greene and P. G. M. Wuts, *Protective Groups in Organic Synthesis,* 3rd edition, John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Before use, the compound of formula (I) and/or a pharmaceutically acceptable salt thereof described herein can be purified by column chromatography, high performance liquid chromatography, crystallization or other suitable methods.

Pharmaceutical Compositions and Uses

A composition comprising a compound of formula (I) or a pharmaceutically acceptable salt thereof described herein can be administered in various known manners, such as orally, parenterally, by inhalation, or by implantation. The term "parenteral" as used herein includes subcutaneous, intracutaneous, intravenous, intramuscular, intraarticular, intraarterial, intrasynovial, intrasternal, intrathecal, intralesional and intracranial injection or infusion.

An oral composition can be any orally acceptable dosage form including, but not limited to, tablets, capsules, pills, powders, emulsions, and aqueous suspensions, dispersions and solutions. Commonly used carriers for tablets include lactose and corn starch. Lubricants such as magnesium stearate are also typically added to tablets. For oral administration in a capsule form, useful diluents include lactose and dried corn starch. When aqueous suspensions or emulsions are administered orally, the active ingredient can be suspended or dissolved in an oily phase with the aid of emulsifying or suspending agents. If desired, certain sweetening, flavoring, or coloring agents can be added.

A sterile injectable composition (e.g., aqueous or oily suspension) can be formulated according to techniques known in the art using suitable dispersing or wetting agents (for example, Tween 80) and suspending agents. The sterile injectable composition can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium, for example, synthetic mono- or di-glycerides. Fatty acids such as oleic acid and its glyceride derivatives as well as natural pharmaceutically acceptable oils such as olive oil or castor oil (especially in their polyoxyethylated versions) are useful in the preparation of the injectables composition. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation employing benzyl alcohol or other suitable preservatives, absorption enhancers to improve bioavailability, fluorocarbons, and/or other solubilizing or dispersing agents known in the art, and can also be prepared as a solution in saline.

A topical composition can be formulated in form of oil, cream, lotion, ointment, and the like. Suitable carriers for the composition include vegetable or mineral oils, white petrolatum (white soft paraffin), branched chain fats or oils, animal fats and high molecular weight alcohols (namely, an alcohol having a number of carbon atoms greater than 12). In some embodiments, the pharmaceutically acceptable carrier is one in which the active ingredient is soluble. If desired, the composition may comprise emulsifiers, stabilizers, humectants and antioxidants, as well as agents imparting color or fragrance. Additionally, transdermal penetration enhancers may be added into the topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient dissolved in a small amount of an oil such as almond oil is admixed. An example of such a cream is one which includes, by weight, about 40 parts of water, about 20 parts of beeswax, about 40 parts of mineral oil and about 1 part of almond oil. Ointments may be formulated by mixing a solution of the active ingredient in a vegetable oil such as almond oil with warm soft paraffin, and allowing the mixture to cool. An example of such an ointment is one which includes about 30% by weight almond oil and about 70% by weight white soft paraffin.

A pharmaceutically acceptable carrier refers to a carrier that is compatible with the active ingredient of the composition (in some embodiments, capable of stabilizing the active ingredient) and not deleterious to the subject to be treated. For example, solubilizing agents, such as cyclodextrins (which are able to form a specific, more soluble complex with the compound of formula (I) and/or a pharmaceutically acceptable salt thereof described herein), can be utilized as pharmaceutical excipients for delivery of the active ingredient. Examples of other carriers include colloidal silicon dioxide, magnesium stearate, cellulose, sodium lauryl sulfate, and pigments such as D&C Yellow #10.

Suitable in vitro assays can be used to preliminarily evaluate the efficacy of the compound of formula (I) and/or a pharmaceutically acceptable salt thereof described herein, in inhibiting the ERK activity. For example, the compound of formula (I) and/or a pharmaceutically acceptable salt thereof described herein can be contacted with ERK kinase or cell, and its inhibition rate to the ERK activity can be determined. The compound of formula (I) and/or a pharmaceutically acceptable salt thereof described herein can further be examined for additional efficacy in treating or preventing cancer or an autoimmune disease by in vivo assays. For example, the compound of formula (I) and/or a pharmaceutically acceptable salt thereof described herein can be administered to an animal (e.g., a mouse model) having cancer or an autoimmune disease and its therapeutic effects can be assessed. Based on the results, an appropriate dosage range and administration route for animals, such as humans, can also be determined.

The compound of formula (I) and/or a pharmaceutically acceptable salt thereof described herein can be used to achieve a beneficial therapeutic or prophylactic effect, for example, in subjects with cancer.

As used herein, the term "cancer" refers to a cellular disorder characterized by uncontrolled or disregulated cell proliferation, decreased cellular differentiation, inappropriate ability to invade surrounding tissue, and/or ability to establish new growth at other sites. The term "cancer" includes, but is not limited to, solid tumors and hematologic malignancies. The term "cancer" encompasses cancer of skin, tissues, organs, bone, cartilage, blood, and vessels. The term "cancer" further encompasses primary and metastatic cancers.

Non-limiting examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and lung adenocarcinoma; ovarian cancer, including, e.g., progressive epithelial cancer or primary peritoneal cancer; cervical cancer; gastric cancer; esophageal cancer; head and neck cancer, including, e.g., squamous cell cancer of the head and neck; skin cancer, including, e.g., melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; soft tissue sarcoma; and thyroid cancer, such as papillary thyroid cancer.

Non-limiting examples of hematologic malignancies include acute myeloid leukemia (AML); chronic myeloid leukemia (CML), including accelerated CML phase and CML blast phase (CML-BP); acute lymphocytic leukemia (ALL); chronic lymphocytic leukemia (CLL); Hodgkin's lymphoma; non-Hodgkin's lymphoma (NHL), including follicular lymphoma and mantle cell lymphoma (MCL); B-cell lymphoma; T-cell lymphoma; multiple myeloma (MM); Waldenstrom's macroglobulinemia; myelodysplastic syndrome (MDS), including refractory anemia (RA), refractory anemia with ringed siderblasts (RARS), refractory anemia with excess blasts (RAEB), and RAEB in transformation (RAEB-T); and myeloproliferative syndrome.

The compound of formula (I) and/or a pharmaceutically acceptable salt thereof described herein can be used to achieve a beneficial therapeutic or prophylactic effect, for example, in subjects with an autoimmune disease.

The term "autoimmune disease" refers to a disease or condition arising from damage to an individual's own tissues or organs caused by the body's immune response to self-antigens. Examples of autoimmune diseases include, but are not limited to, chronic obstructive pulmonary disease (COPD), allergic rhinitis, lupus erythematosus, myasthenia gravis, multiple sclerosis (MS), rheumatoid arthritis (RA), psoriasis, inflammatory bowel disease (IBD), asthma, idiopathic thrombocytopenic purpura, and myeloproliferative disease, such as myelofibrosis, post-polycythemia vera/essential thrombocythemia myelofibrosis (post-PV/ET myelofibrosis).

In addition, the compound of formula (I) (e.g., the compound of subformula (I-1), (I-2) or (I-3), and Compounds 1-321) and/or a pharmaceutically acceptable salt thereof described herein may be used in combination with additional therapeutic agents in the treatment of cancer. The additional therapeutic agents may be administered separately with the compound of formula (I) and/or a pharmaceutically acceptable salt thereof described herein or may be included with the compound of formula (I) and/or a pharmaceutically acceptable salt thereof described herein in a pharmaceutical composition according to the disclosure, such as a fixed-dose combination drug product. In some embodiments, the additional therapeutic agents are those that are known or discovered to be effective in the treatment of diseases mediated by ERK, such as another ERK inhibitor or a compound that antagonizes another target associated with said particular disease. The combination may serve to increase efficacy (e.g., by including in the combination a compound potentiating the potency or effectiveness of the compound of formula (I) and/or a pharmaceutically acceptable salt thereof described herein), decrease one or more side effects, or decrease the required dose of the compound of formula (I) and/or a pharmaceutically acceptable salt thereof described herein.

In some embodiments, the compound of formula (I) (e.g., the compound of subformula (I-1), (I-2) or (I-3), and Compounds 1-321) and/or a pharmaceutically acceptable salt thereof described herein is administered in combination with an anti-neoplastic agent. As used herein, the term "anti-neoplastic agent" refers to any agent that is administered to a subject suffering from cancer for purposes of treating the cancer. The anti-neoplastic agents include, but are not limited to: radiotherapeutic agents, chemotherapeutic agents, immunotherapeutic agents, targeted therapeutic agents.

Non-limiting examples of chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, mitoxantrone, idarubicin, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; nucleoside mimetics (e.g., 5-fluorouracil, capecitabine, gemcitabine, fludarabine, cytarabine, azacitidine (VIDAZA®), mercaptopurine, thioguanine, pentostatin, and hydroxyurea); paclitaxel, docetaxel, and related analogs; vincristine, vinblastin, and related analogs; thalidomide and related analogs (e.g., CC-5013 and CC-4047).

Non-limiting examples of immunotherapeutic agents or targeted therapeutic agents include MEK inhibitors, RAF inhibitors, mTOR inhibitors, PAK inhibitors, CDK inhibitors, VEGFR inhibitors, PARP inhibitors, ERBB inhibitors, PI3K inhibitors, AKT inhibitors, autophagy inhibitors, immune checkpoint inhibitors such as PD-1 inhibitors, PD-L1 inhibitors, and the like. For example, Trametinib, Cobimetinib, Vemurafenib, Dabrafenib, Rapamycin, Temsirolimus, Everolimus, Palbociclib, Ribociclib, Fruquintinib, Olaparib, Niraparib, Neratinib, Chloroquine, Hydroxychloroquine, LXH254, Selumetinib, LY3214996, Abemaciclib, P1446A-05 (voruciclib), LGX818 (encorafenib), ARRY-162 (binimetinib), Cetuximab, Gefitinib, Panitumumab, BYL719 (Alpelisib), Bevacizumab, Pembrolizumab, Atezolizumab, PDR001 (Spartalizumab), Durvalumab, Nivolumab, Avelumab, Libtayo (Cemiplimab), Tislelizumab, Toripalimab (JS001), Sintilimab, Camrelizumab, and the like.

EXAMPLES

The examples below are intended to be purely illustrate the invention, and should not be contorted to be limiting in any way. Efforts have been made to ensure accuracy with respect to numbers used (for example, amounts, temperature, etc.), but some experimental errors and deviations should be accounted for.

Unless indicated otherwise, parts are parts by weight, temperature is in degrees Centigrade, and pressure is at or near atmospheric. All MS (mass spectrometry) data were measured by agilent 6120 and/or agilent 1100. $^1$H-NMR spectra were recorded on a nuclear magic resonance spectrometer operating at 400 MHz. NMR spectra were obtained as $CDCl_3$ solutions (reported in ppm), using chloroform as the reference standard (7.26 ppm), or using internal standard tetramethylsilane (0.00 ppm) when appropriate. Other NMR solvents were used as needed. When peak multiplicities are reported, the following abbreviations are used: s (singlet), d (doublet), t (triplet), m (multiplet), q (quarter), br (broadened), dd (doublet of doublets) dt (doublet of triplets). Coupling constants, when given, are reported in Herz (Hz).

All reagents, except intermediates, used in this invention are commercially available.

All compound names except the reagents were generated by Chemdraw. If there's any inconsistency between the structure and the name of a compound given in this invention, the structure prevails, unless the context shows that the structure is incorrect and the name is right.

If there's any empty valence in any atom disclosed herein, the empty valence is the hydrogen atom which is omitted for convenience.

In the following examples, the abbreviations below are used:

Boc tert-butyloxycarbonyl
BPIN bis(pinacolato)diboron
CDI N,N'-carbonyldiimidazole
DCM dichloromethane
DIAD diisopropyl azodicarboxylate
DIBAL-H diisobutylaluminium hydride
DIPEA N,N-diisopropylethylamine
DMF N,N-dimethylformamide
EA ethyl acetate
EDCI 1-ethyl-3-(3-dimethylaminopropyl)carbodiimide hydrochloride
Et ethyl
h hour(s)
HATU O-(7-azabenzotriazol-1-yl)-N,N,N',N'-tetramethyluronium hexafluorophosphate
HOBT 1-hydroxybenzotriazole
ISCO TELEDYNE ISCO CombiFlash RF+ Chromatograph System
LDA lithium diisopropylamide
min minute(s)
MeOH methanol
Ms methanesulfonyl
NBS N-bromosuccinimide
NaHMDS sodium bis(trimethylsilyl)amide
PE petroleum ether
$PdCl_2(PPh_3)_2$ bis(triphenylphosphine)palladium(II)dichloride
$Pd_2(dba)_3$ tris(dibenzylideneacetone)dipalladium(O)
$Pd(dppf)Cl_2 \cdot CH_2Cl_2$ 1,1'-bis(diphenylphosphino)ferrocene-palladium(II) dichloride dichloromethane complex
$Pd(OAc)_2$ palladium(II) acetate
$Pd(PPh_3)_4$ tetrakis(triphenylphosphine)palladium(O)
PMB para-methoxybenzyl
$PPh_3$ triphenylphosphine
PTLC Preparative Thin Layer Chromatography
SEM 2-(trimethylsilyl)ethoxymethyl
THF tetrahydrofuran
TBDPS tert-butyldiphenylsilyl
TFA trifluoroacetic acid
Ts p-toluenesulphonyl
Xantphos 4,5-Bis(diphenylphosphino)-9,9-dimethylxanthene Intermediate 1

4-chloro-N-(1-methyl-1H-pyrazol-5-yl)pyrimidin-2-amine

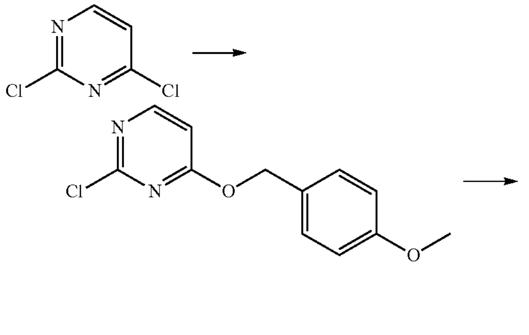

-continued

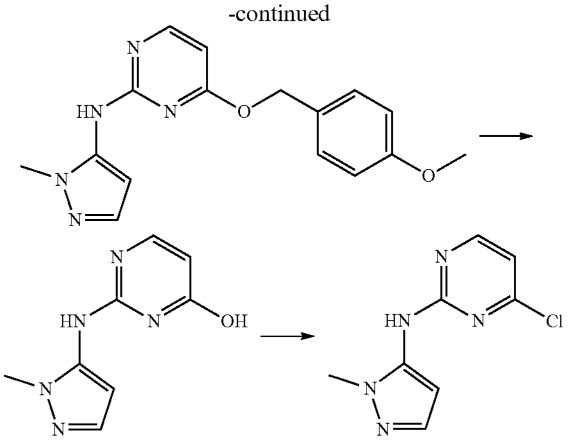

(A) 2-chloro-4-((4-methoxybenzyl)oxy)pyrimidine

To a solution of (4-methoxyphenyl)methanol (40.8 g, 295.3 mmol) in THF (200 mL) was added NaH (16.1 g, 402.5 mmol, 60% dispersion in Paraffin Liquid) in portions at 0° C. The mixture was stirred for 30 min at the same temperature under nitrogen atmosphere. Then the mixture was added slowly into a solution of 2,4-dichloropyrimidine (40.0 g, 268.5 mmol) in THF (200 mL) at 0° C. After addition, the mixture was stirred overnight at room temperature. The reaction was quenched with ice water (200 mL). The mixture was separated and the aqueous layer was extracted with THF (200 mL). The combined organic layers were washed with brine, dried over anhydrous sodium sulfate. After filtration, the filtrate was concentrated to give an off-white solid (73.0 g) which was used directly in the next step.

(B) 4-((4-methoxybenzyl)oxy)-N-(1-methyl-1H-pyrazol-5-yl)pyrimidin-2-amine

To a solution of 2-chloro-4-((4-methoxybenzyl)oxy)pyrimidine (73.0 g, which was obtained from the previous step) and 1-methyl-1H-pyrazol-5-amine (56.6 g, 582.4 mmol) in 1,4-dioxane (730 mL) were added $Pd(OAc)_2$ (3.27 g, 14.6 mmol), Xantphos (16.8 g, 29.1 mmol) and KOAc (85.7 g, 873.6 mmol). The mixture was purged and then stirred overnight at 90° C. under nitrogen atmosphere. After cooling, the mixture was filtered and the filter cake was washed with EA (200 mL). The combined filtrate was washed with brine. After separation, the organic layer was dried over anhydrous sodium sulfate, filtered and concentrated. The residue was purified via ISCO (eluting with methanol in water 0%~100%) to give a slight yellow solid (38.5 g, 42.4% yield). MS (m/z): 312.1 $(M+H)^+$.

(C) 4-chloro-N-(1-methyl-1H-pyrazol-5-yl)pyrimidin-2-amine

To a three-necked round bottom flask were added 4-((4-methoxybenzyl)oxy)-N-(1-methyl-1H-pyrazol-5-yl)pyrimidin-2-amine (38.5 g, 123.7 mmol) and TFA (150 mL). Then the mixture was stirred for 3 h at room temperature. Then the mixture was concentrated to give a brown solid which was suspended in $POCl_3$ (150 mL). The mixture was stirred for 3 h at 100° C. and then concentrated. The residue was poured into ice water, adjusted to PH=8~9 with saturated solution of $NaHCO_3$. The mixture was extracted with EA.

The combined organic layers were washed with brine, dried over anhydrous sodium sulfate, filtered and concentrated to afford a brown solid (23.3 g, 89.6% yield) MS (m/z): 210.0 $(M+H)^+$.

The intermediate below was prepared according to the procedures of intermediate 1 using the corresponding intermediates and reagents under appropriate conditions that could be recognized by one skilled in the art.

| Intermediate | Structure | MS (m/z) $(M + H)^+$ |
|---|---|---|
| 2 | 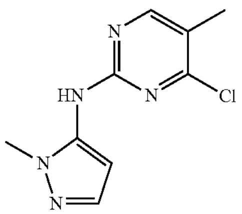 | 224.0 |

Intermediate 3

5-chloro-4-iodo-N-(1-methyl-1H-pyrazol-5-yl)pyridin-2-amine

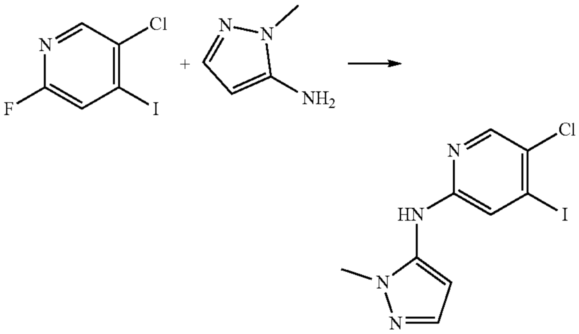

(A) 5-chloro-4-iodo-N-(1-methyl-1H-pyrazol-5-yl) pyridin-2-amine

To a solution of 1-methyl-1H-pyrazol-5-amine (39.4 g, 406 mmol) in anhydrous THF (1500 mL) was added NaHMDS (406 mL, 406 mmol, 1M in THF) at 0° C. under nitrogen atmosphere and the solution was stirred for 30 min. Then 5-chloro-2-fluoro-4-iodopyridine (87 g, 338 mmol) was added and the resulting mixture was refluxed overnight. The reaction was quenched with methanol/water (40 mL, 1:1), concentrated under vacuum. The residue was purified by silica gel chromatography (PE:EA=1:1) and ISCO (eluting with methanol in water 0%—100%) to give the title compound as a light yellow solid (39.8 g, 35% yield). MS (m/z): 334.9 $(M+H)^+$.

The intermediate below was prepared according to the procedures of intermediate 3 using the corresponding intermediates and reagents under appropriate conditions that could be recognized by one skilled in the art.

| Intermediate | Structure | MS (m/z) $(M + H)^+$ |
|---|---|---|
| 4 | 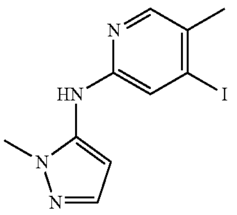 | 314.9 |

Intermediate 5

5-fluoro-4-iodo-N-(1-methyl-1H-pyrazol-5-yl)pyridin-2-amine

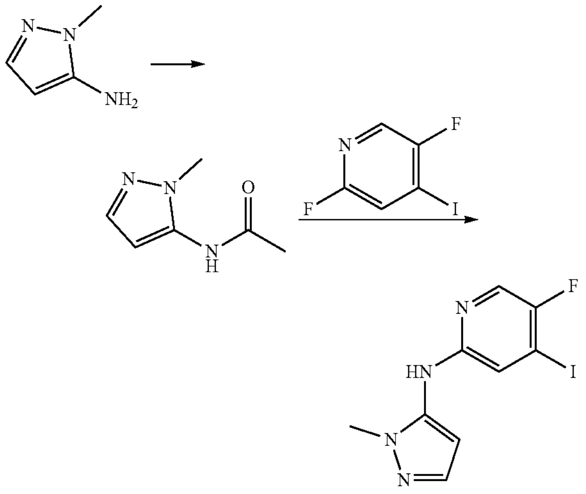

(A) N-(1-methyl-1H-pyrazol-5-yl)acetamide

To a solution of 1-methyl-1H-pyrazol-5-amine (87 g, 90 mmol) and acetic anhydride (101 g, 99 mmol) in EA (1000 mL) was added NaOAc (81 g, 99 mmol) at room temperature. The mixture was stirred at room temperature overnight. Then the mixture was filtered and the cake was washed with EA. The filtrate was concentrated under vacuum. The residue was purified by silica gel chromatography (DCM:MeOH=25:1) to give the title compound as a light yellow solid (98 g, 78% yield). MS (m/z): 140.1 $(M+H)^+$.

(B) 5-fluoro-4-iodo-N-(1-methyl-1H-pyrazol-5-yl) pyridin-2-amine

To a solution of N-(1-methyl-1H-pyrazol-5-yl)acetamide (53 g, 380 mmol) in anhydrous THF/DMF (800 mL, 7:1) was added NaHMDS (354 mL, 354 mmol, 1M in THF) at 0° C. under nitrogen atmosphere and the solution was stirred at room temperature for 30 min. Then 2,5-difluoro-4-iodopyridine (61 g, 253 mmol) was added and the solution was refluxed. The reaction was quenched with methanol/water (200 mL, 1:1), concentrated under vacuum. The residue was dissolved in methanol/water (200 mL, 1:1). Lithium hydroxide monohydrate (11 g, 253 mmol) was added and the solution was stirred at room temperature for 1 h. Solvent was removed by rotary evaporator and the residue was purified by silica gel chromatography (PE:EA=1:1) and ISCO (eluting with methanol in water 0%~100%) to give the title compound as a pink solid (30 g, 37.5% yield). MS (m/z): 319.0 $(M+H)^+$.

Intermediate 6

4-iodo-N-(1-methyl-1H-pyrazol-5-yl)-5-(trifluoromethyl)pyridin-2-amine

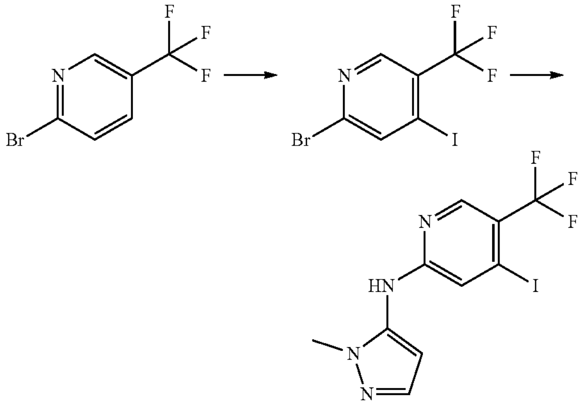

(A) 2-bromo-4-iodo-5-(trifluoromethyl)pyridine

To a solution of diisopropylamine (3.1 g, 30 mmol) in anhydrous THF (150 mL) was added n-butyllithium (12.5 mL, 30 mmol, 2.4 mol/L in THF) at −70° C. under nitrogen atmosphere. The solution was stirred at −10° C. for 30 min. The solution was cooled to −70° C. again and 2-bromo-5-(trifluoromethyl)pyridine (5.6 g, 25 mmol) was added. The resulting dark brown solution was stirred for 2 h at −70° C. Iodine (6.4 g, 25 mmol) was added in portions and the solution was stirred for another 1 h. The reaction was quenched with 10% HOAc (50 mL) and saturated solution of sodium thiosulfate. The mixture was extracted with EA. The organic phases were combined and concentrated under vacuum. The residue was purified by silica gel chromatography (PE:EA=50:1) to give the title compound as a yellow solid (6.1 g, 69% yield). MS (m/z): 351.7, 353.7 $(M+H)^+$.

(B) 4-iodo-N-(1-methyl-1H-pyrazol-5-yl)-5-(trifluoromethyl)pyridin-2-amine

To a solution of N-(1-methyl-1H-pyrazol-5-yl)acetamide (1.1 g, 4 mmol) in anhydrous THF (50 mL) was added sodium hydride (320 mg, 8 mmol, 60% dispersion in Paraffin Liquid) in portions at room temperature under nitrogen atmosphere. The mixture was stirred for 30 min. 2-bromo-4-iodo-5-(trifluoromethyl)pyridine (556 mg, 4 mmol) was added and the mixture was refluxed overnight. The reaction was quenched with methanol. Solvent was removed by rotary evaporator and the residue was purified via ISCO (eluting with methanol in water 0%~100%) and silica gel chromatography (DCM:MeOH=25:1) to give the title compound as a brown gum (640 mg, 44% yield). MS (m/z): 368.9 $(M+H)^+$.

The intermediate below was prepared according to the procedures of intermediate 6 using the corresponding intermediates and reagents under appropriate conditions that could be recognized by one skilled in the art.

| Intermediate | Structure | MS (m/z) $(M + H)^+$ |
|---|---|---|
| 7 | 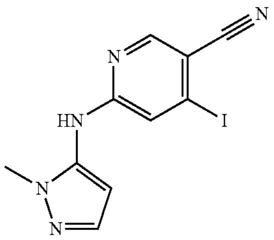 [SMILES: Cn1nccc1Nc1cc(I)c(C#N)cn1] | 326.0 |

Intermediate 8

N-cyclopropyl-4-iodo-5-(trifluoromethyl)pyridin-2-amine

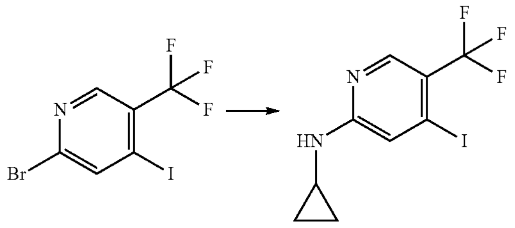 [SMILES: FC(F)(F)c1cnc(Br)cc1I ; FC(F)(F)c1cnc(NC2CC2)cc1I]

(A) N-cyclopropyl-4-iodo-5-(trifluoromethyl)pyridin-2-amine

To a solution of 2-bromo-4-iodo-5-(trifluoromethyl)pyridine (352 mg, 1 mmol) and cyclopropanamine (114 mg, 2 mmol) in anhydrous THF (10 mL) was added DIPEA (390 mg, 3 mmol). The solution was refluxed overnight. Solvent was removed by rotary evaporator and the residue was purified via ISCO (eluting with methanol in water 0%~100%) to give the title compound as a yellow solid (184 mg, 56% yield). MS (m/z): 328.9 $(M+H)^+$.

The intermediates below were prepared according to the procedures of intermediate 8 using the corresponding intermediates and reagents under appropriate conditions that could be recognized by one skilled in the art.

| Intermediate | Structure | MS (m/z) $(M + H)^+$ |
|---|---|---|
| 9 | 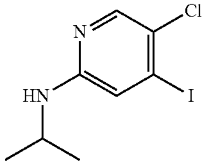 | 296.9 |

-continued

| Intermediate | Structure | MS (m/z) (M + H)$^+$ |
|---|---|---|
| 10 | 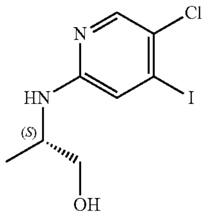 | 312.9 |

Intermediate 11

5-ethyl-4-iodo-N-(1-methyl-1H-pyrazol-5-yl)pyridin-2-amine

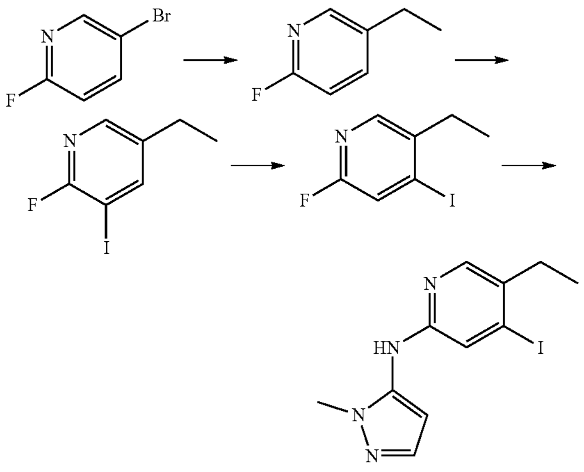

(A) 5-ethyl-2-fluoropyridine

To a solution of 5-bromo-2-fluoropyridine (5.5 g, 31.3 mmol) and triethylborane (1M) (62.6 mL, 62.6 mmol) in DMF (30 mL) was added $K_2CO_3$ (12.9 g, 94 mmol) and $Pd(PPh_3)_4$ (1.8 g, 1.6 mmol). The mixture was degassed and stirred under nitrogen atmosphere at 80° C. overnight, diluted with water, extracted with hexane, washed with water and brine, dried over anhydrous $Na_2SO_4$, concentrated and purified via ISCO (eluting with DCM in PE 0%~100%) to afford the title compound as a yellow liquid (3 g, 77% yield). MS (m/z): 126.0 (M+H)$^+$.

(B) 5-ethyl-2-fluoro-3-iodopyridine

To a solution of 5-ethyl-2-fluoropyridine (1 g, 8 mmol) in THF (20 mL) was added LDA (6 mL, 12 mmol, 2M in THF) dropwise under nitrogen atmosphere at −78° C. After stirring at −78° C. for 1 h, Iodine (3 g, 12 mmol) was added. The mixture was stirred under nitrogen atmosphere at −78° C. for 2 h, quenched with HOAc and aqueous $Na_2SO_3$, extracted with EA. The organic layer was washed with water and brine, dried over anhydrous $Na_2SO_4$, concentrated and purified via ISCO (eluting with EA in PE 0%~100%) to afford the title compound as a yellow oil (1.1 g, 55% yield). MS (m/z): 251.9 (M+H)$^+$.

(C) 5-ethyl-2-fluoro-4-iodopyridine

To a solution of 5-ethyl-2-fluoro-3-iodopyridine (1.1 g, 4.4 mmol) in THF (20 mL) was added LDA (3.3 mL, 6.6 mmol, 2M in THF) dropwise under nitrogen atmosphere at −78° C. The mixture was stirred under nitrogen atmosphere at −78° C. for 2 h, quenched with saturated solution of Ammonium chloride, extracted with EA. The organic layer was washed with water and brine, dried over anhydrous $Na_2SO_4$, concentrated and purified via ISCO (eluting with EA in PE 0%~100%) to afford the title compound as a yellow oil (860 mg, 78% yield).

(D) 5-ethyl-4-iodo-N-(1-methyl-1H-pyrazol-5-yl)pyridin-2-amine

To a solution of 1-methyl-1H-pyrazol-5-amine (648 mg, 6.6 mmol) in THF (40 mL) was added NaHMDS (6.6 mL, 6.6 mmol, 1M in THF) under nitrogen atmosphere. After stirring at room temperature for 1 h, 5-ethyl-2-fluoro-4-iodopyridine (830 mg, 3.3 mmol) was added. The mixture was refluxed overnight, quenched with water and MeOH, concentrated and purified via ISCO (eluting with methanol in water 0%—100%) to afford the title compound as a yellow solid (100 mg, 9% yield). MS (m/z): 328.9 (M+H)$^+$.

Intermediate 12

2-bromo-4-iodo-5-methoxypyridine

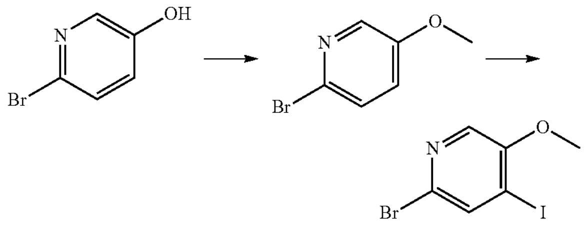

(A) 2-bromo-5-methoxypyridine

To a solution of 6-bromopyridin-3-ol (1.7 g, 10 mmol) in anhydrous DMF (20 mL) was added NaH (600 mg, 15 mmol, 60% dispersion in Paraffin Liquid) in portions at 0° C. under nitrogen atmosphere.

The mixture was stirred for 30 min. Iodomethane (2.1 g, 15 mmol) was added and the mixture was then stirred at room temperature for 1 h. The reaction was quenched with saturated solution of ammonium chloride. The mixture was extracted with EA. The organic phases were combined and concentrated under vacuum. The residue was purified by silica gel chromatography (PE:EA=5:1) to give the title compound as a yellow solid (1.7 g, 91% yield). MS (m/z): 188.0, 190.0 (M+H)$^+$.

(B) 2-bromo-4-iodo-5-methoxypyridine

To a solution of 2-bromo-5-methoxypyridine (1.5 g, 8 mmol) in anhydrous THF (50 mL) was added LDA (4 mL, 8 mmol, 2M in THF) at −70° C. under nitrogen atmosphere. The solution was stirred at −70° C. for 2 h. Iodine (2.1 g, 8 mmol) was added in portions and the solution was stirred for another 1 h. The reaction was quenched with 10% HOAc and saturated solution of sodium thiosulfate. The mixture was extracted with DCM. The organic phases were combined and concentrated under vacuum. The residue was purified by silica gel chromatography (PE:EA=5:1) to give the title compound as a light yellow solid (900 mg, 39% yield). MS (m/z): 313.8, 315.8 $(M+H)^+$.

Intermediate 13

8-bromo-2,3,4,5-tetrahydro-1H-pyrrolo[1,2-a][1,4]diazepin-1-one

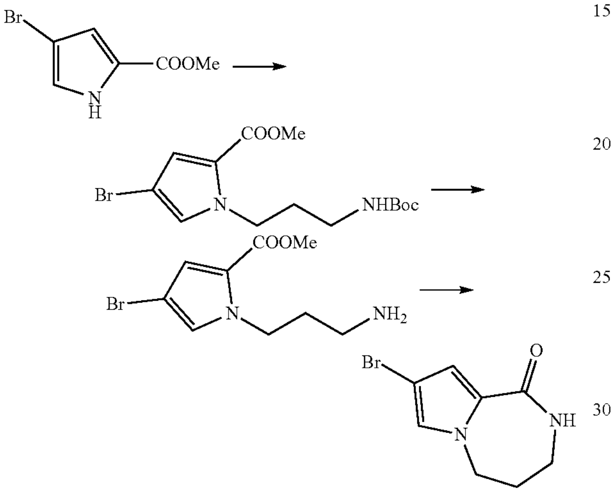

(A) methyl 4-bromo-1-(3-((tert-butoxycarbonyl)amino)propyl)-1H-pyrrole-2-carboxylate To a mixture of methyl 4-bromo-1H-pyrrole-2-carboxylate (100 g, 0.49 mol) and tert-butyl (3-bromopropyl)carbamate (122 g, 0.51 mol) in DMF (500 mL) was added $K_2CO_3$ (169 g, 1.23 mol). The mixture was stirred at room temperature overnight. Then the $K_2CO_3$ was filtered off and the filtrate was diluted with water, extracted by EA. The organic layer was washed with brine, dried over anhydrous $Na_2SO_4$, concentrated to afford the title compound as a yellow solid (166 g, 93.9% yield). MS (m/z): 261.0, 263.0 $(M+H)^+$.

(B) methyl 1-(3-aminopropyl)-4-bromo-1H-pyrrole-2-carboxylate

A mixture of methyl 4-bromo-1-(3-((tert-butoxycarbonyl)amino)propyl)-1H-pyrrole-2-carboxylate (166 g, 0.46 mol) and TFA (200 mL) was heated at 60° C. for 3 h. The mixture was concentrated and the residue was partitioned between saturated solution of $NaHCO_3$ and EA. The organic layer was washed with brine, dried over anhydrous $Na_2SO_4$, concentrated to afford the title compound as a yellow solid (114.37 g, 95.2% yield). MS (m/z): 261.0, 263.0 $(M+H)^+$.

(C) 8-bromo-2,3,4,5-tetrahydro-1H-pyrrolo[1,2-a][1,4]diazepin-1-one

To a mixture of methyl 1-(3-aminopropyl)-4-bromo-1H-pyrrole-2-carboxylate (114 g, 0.44 mol) in MeOH (800 mL) was added $K_2CO_3$ (151 g, 1.10 mol). The mixture was stirred at 80° C. for 3 h. Then the $K_2CO_3$ was filtered off and the filtrate was concentrated. The residue was diluted with water and extracted by EA. The organic layer was washed with brine, dried over anhydrous Na2SO4, concentrated and recrystallized to afford the title compound as a white solid (70.0 g, 69.9% yield). MS (m/z): 228.9/230.9 $(M+H)^+$.

Intermediate 14

8-bromo-9-chloro-2,3,4,5-tetrahydro-1H-pyrrolo[1,2-a][1,4]diazepin-1-one

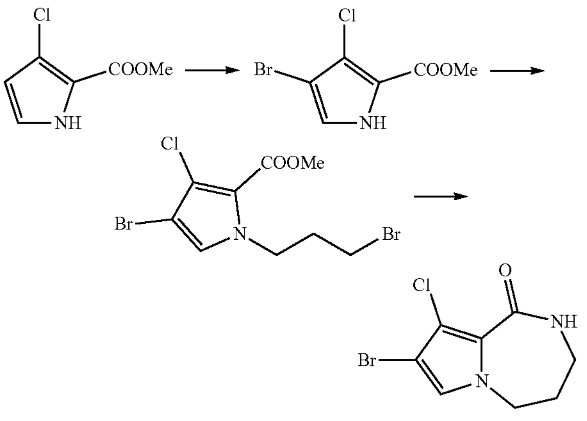

(A) methyl 4-bromo-3-chloro-1H-pyrrole-2-carboxylate

To a mixture of methyl 3-chloro-1H-pyrrole-2-carboxylate (10 g, 62.7 mmol) in DMF (400 mL) was added $Br_2$ (3.2 mL, 62.7 mmol) dropwise at room temperature. The mixture was stirred at room temperature for 8 h. Then the mixture was diluted by water (2.0 L), extracted by EA (3×1.5 L). The organic layer was concentrated, and the residue was then purified via ISCO (eluting with methanol in water 0%—100%) to afford the title compound as a yellow solid (7.0 g, 46.9% yield). MS (m/z): 237.8, 239.8 $(M+H)^+$.

(B) methyl 4-bromo-1-(3-bromopropyl)-3-chloro-1H-pyrrole-2-carboxylate

A mixture of methyl 4-bromo-3-chloro-1H-pyrrole-2-carboxylate (6 g, 25.2 mmol), 1,3-dibromopropane (50.9 g, 252 mmol) and $K_2CO_3$ (7.0 g, 50.4 mmol) in $CH_3CN$ (150 mL) was heated at 70° C. for 3 h. The reaction mixture was concentrated, partitioned between water (200 mL) and EA (200 mL). The aqueous layer was further extracted with EA (2×200 mL). The combined organic layers were concentrated and purified via ISCO (eluting with methanol in water 0%—100%) to afford the title compound as a white solid (4.2 g, 46.3% yield). MS (m/z): 359.8 $(M+H)^+$.

(C) 8-bromo-9-chloro-2,3,4,5-tetrahydro-1H-pyrrolo[1,2-a][1,4]diazepin-1-one

A mixture of methyl 4-bromo-1-(3-bromopropyl)-3-chloro-1H-pyrrole-2-carboxylate (500 mg, 1.39 mmol) in ammonium hydroxide (6 mL) and MeOH (10 mL) was heated at 120° C. for 3 h under microwave. The reaction mixture was concentrated, washed with EA (1 mL) to afford the crude title compound as a white solid (500 mg, used for next step directly). MS (m/z): 262.9, 264.9 $(M+H)^+$.

The intermediate below was prepared according to the procedures of intermediate 14 using the corresponding intermediates and reagents under appropriate conditions that could be recognized by one skilled in the art.

| Intermediate | Structure | MS (m/z) $(M + H)^+$ |
| --- | --- | --- |
| 15 | 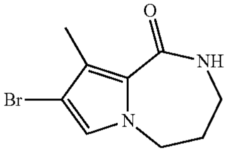 | 242.9/244.9 |

Intermediate 16

8-bromo-9-fluoro-2,3,4,5-tetrahydro-1H-pyrrolo[1,2-a][1,4]diazepin-1-one

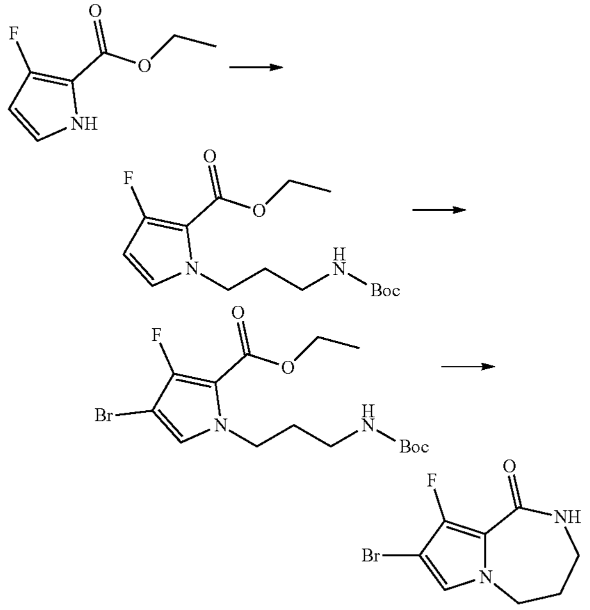

(A) Ethyl 1-(3-((tert-butoxycarbonyl)amino)propyl)-3-fluoro-1H-pyrrole-2-carboxylate A mixture of ethyl 3-fluoro-1H-pyrrole-2-carboxylate (3.14 g, 20 mmol), tert-butyl (3-bromopropyl)carbamate (7.14 g, 30 mmol) and $Cs_2CO_3$ (9.75 g, 30 mmol) in DMF (20 mL) was heated at 80° C. overnight. After cooling to room temperature the mixture was extracted by EA. The organic phase was washed by water and birne, concentrated, purified via ISCO (eluting with methanol in water 0%~100%) to afford the title compound as a yellow solid (6.28 g). MS (m/z):315.1 $(M+H)^+$.

(B) Ethyl 4-bromo-1-(3-((tert-butoxycarbonyl)amino)propyl)-3-fluoro-1H-pyrrole-2-carboxylate To a solution of ethyl 1-(3-((tert-butoxycarbonyl)amino)propyl)-3-fluoro-1H-pyrrole-2-carboxylate (6.28 g, 20 mmol) in DMF (15 mL) was added NBS (3.56 g, 20 mml) in portions under room temperature. The mixture was stirred for 4 h, quenched by aqueous $Na_2SO_3$, extracted by EA, concentrated to afford the crude title compound. MS (m/z): 414.9, 416.9 $(M+23)^+$.

(C) 8-bromo-9-fluoro-2,3,4,5-tetrahydro-1H-pyrrolo[1,2-a][1,4]diazepin-1-one

To a solution of ethyl 4-bromo-1-(3-((tert-butoxycarbonyl)amino)propyl)-3-fluoro-1H-pyrrole-2-carboxylate (6.1 g, 15.5 mmol) in methanol (10 mL) was added concentrated hydrochloric acid (3 mL) and the resulting mixture was stirred at room temperature for 3 h. The mixture was concentrated under vacuum. The residue was adjusted to pH=8 with aqueous $NaHCO_3$, extracted with DCM. The organic phase was concentrated and the residue was dissolved in MeOH (25 mL) and $K_2CO_3$ (6.42 g, 46.5 mmol) was added. The mixture was stirred at 80° C. for 48 h. Then the $K_2CO_3$ was filtered off and the filtrate was concentrated. The residue was purified via ISCO (eluting with EA in PE 50%~100%) to afford the title compound as a white solid (3 g, 78.7% yield). MS (m/z):247.0, 249.0 $(M+H)^+$.

Intermediate 17

7-bromo-3,4-dihydropyrrolo[1,2-a]pyrazin-1(2H)-one

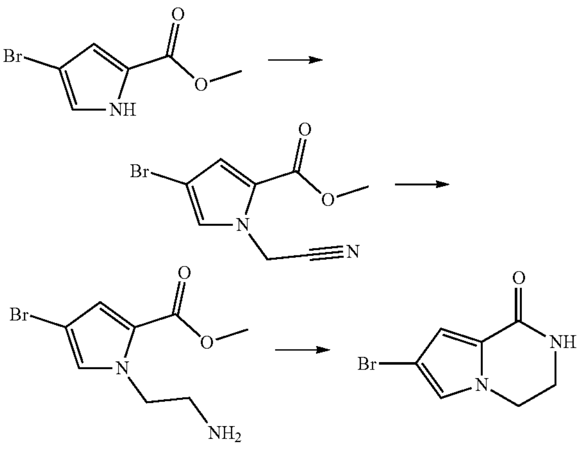

(A) Methyl 4-bromo-1-(cyanomethyl)-1H-pyrrole-2-carboxylate

To a solution of methyl 4-bromo-1H-pyrrole-2-carboxylate (4 g, 19.6 mmol) in DMF (15 mL) was added $K_2CO_3$ (5.4 g, 39.2 mmol) and 2-bromoacetonitrile (2.4 g, 19.6 mmol). The mixture was stirred at 80° C. for 3 h, poured into water and extracted with EA. The organic phase was washed with water and brine, dried over anhydrous Na2SO4 and concentrated to afford the title compound as a yellow solid (5.1 g). MS (m/z): 243.0/245.0 $(M+H)^+$.

(B) Methyl 1-(2-aminoethyl)-4-bromo-1H-pyrrole-2-carboxylate

To a solution of methyl 4-bromo-1-(cyanomethyl)-1H-pyrrole-2-carboxylate (5.1 g, 19.6 mmol) in THF (20 mL)

was added $BH_3 \cdot Me_2S$ (10 mL, 19.6 mmol, 2M in THF) dropwise at room temperature. The mixture was then stirred at 60° C. overnight, quenched with cold aqueous $NaHCO_3$ at 0° C., extracted with EA. The organic phase was washed with water and brine, dried over anhydrous $Na_2SO_4$ and concentrated to afford the title compound as a yellow solid (4.5 g, 93% yield). MS (m/z): 246.9/248.9 $(M+H)^+$.

(C) 7-bromo-3,4-dihydropyrrolo[1,2-a]pyrazin-1 (2H)-one

To a solution of methyl 1-(2-aminoethyl)-4-bromo-1H-pyrrole-2-carboxylate (4.5 g, 18.2 mmol) in MeOH (20 mL) was added ammonium hydroxide (3 mL). The mixture was stirred at room temperature overnight, concentrated and purified via ISCO (eluting with MeOH in DCM 0%—15%) to afford the title compound as a brown solid (3.2 g, 82% yield). MS (m/z): 214.9/216.9 $(M+H)^+$.

Intermediate 18

8'-bromo-2',3'-dihydro-1'H,5'H-spiro[cyclopropane-1,4'-pyrrolo[1,2-a][1,4]diazepin]-1'-one

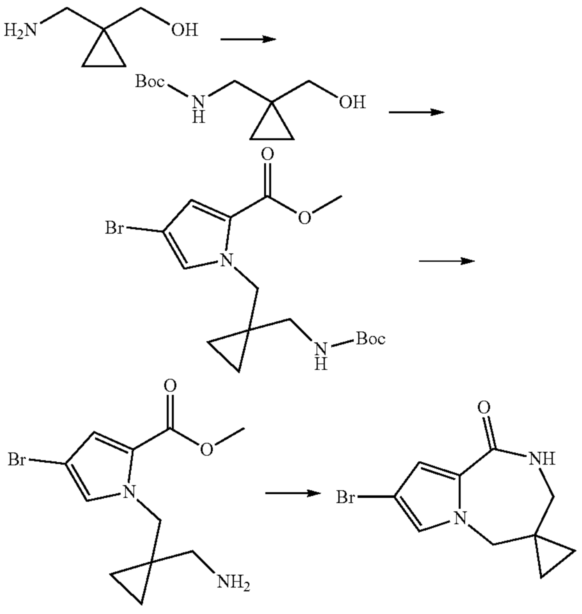

(A) tert-butyl ((1-(hydroxymethyl)cyclopropyl)methyl)carbamate

To a solution of (1-(aminomethyl)cyclopropyl)methanol (5 g, 49.5 mmol) in DCM (40 mL) was added $Boc_2O$ (10.8 g, 49.5 mmol) and DIPEA (12.8 g, 99 mmol). The mixture was stirred at room temperature for 2 h, concentrated and purified via ISCO (eluting with methanol in water 0%—100%) to afford the title compound as a yellow solid (9.4 g, 94% yield).

(B) Methyl 4-bromo-1-((1-(((tert-butoxycarbonyl) amino)methyl)cyclopropyl)methyl)-1H-pyrrole-2-carboxylate To a solution of tert-butyl ((1-(hydroxymethyl)cyclopropyl)methyl)carbamate (4.9 g, 24.5 mmol), methyl 4-bromo-1H-pyrrole-2-carboxylate (5 g, 24.5 mmol) and $PPh_3$ (9.6 g, 36.8 mmol) in THF (20 mL) was added DIAD (7.4 g, 36.8 mmol) dropwise under nitrogen atmosphere at 0° C. The mixture was stirred at room temperature overnight, concentrated and purified via ISCO (eluting with EA in PE 00%-~100%) to afford the title compound as a yellow oil (9.2 g, crude).

(C) 8'-bromo-2',3'-dihydro-1'H,5'H-spiro[cyclopropane-1,4'-pyrrolo[1,2-a][1,4]diazepin]-1'-one A mixture of methyl 4-bromo-1-((1-(((tert-butoxycarbonyl)amino)methyl)cyclopropyl)methyl)-1H-pyrrole-2-carboxylate (9.2 g, 23.8 mmol) in TFA (10 mL) was stirred at room temperature for 2 h. The mixture was concentrated under vacuum. The residue was dissolved in MeOH (30 mL), $K_2CO_3$ (9.8 g, 71.3 mmol) and $Et_3N$ (7.2 g, 71.3 mmol) was added. The mixture was stirred at room temperature overnight, concentrated and purified via ISCO (eluting with methanol in water 00%-~100%) to afford the title compound as a yellow solid (4.5 g, 7400 yield). MS (m/z): 255.0/257.0 $(M+H)^+$.

The intermediates below were prepared according to the procedures of intermediate 18 using the corresponding intermediates and reagents under appropriate conditions that could be recognized by one skilled in the art.

| Intermediate | Structure | MS (m/z) $(M + H)^+$ |
|---|---|---|
| 19 | 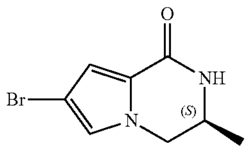 | 229.0/231.0 |
| 20 | 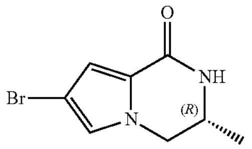 | 228.9/230.9 |
| 21 | 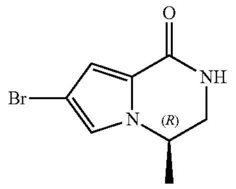 | 229.0/231.0 |
| 22 | 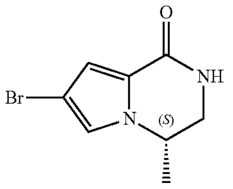 | 229.0/231.0 |
| 23 | 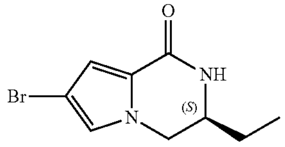 | 243.0/245.0 |

-continued
| Inter-mediate | Structure | MS (m/z) (M + H)+ |
|---|---|---|
| 24 | 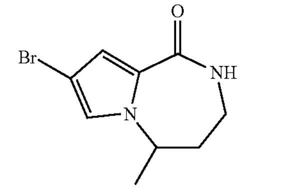 | 243.0/245.0 |
| 25 | 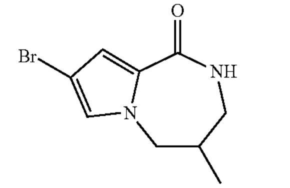 | 243.0/245.0 |
| 26 | 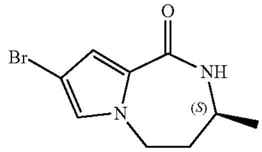 | 242.9/244.9 |
| 27 | 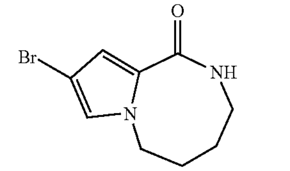 [SMILES: O=C1NCCCCn2cc(Br)cc21] | 243.0/245.0 |
| 28 | 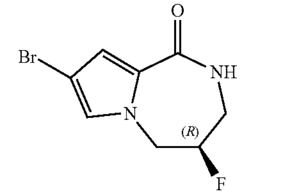 | 247.0/249.0 |
| 29 | 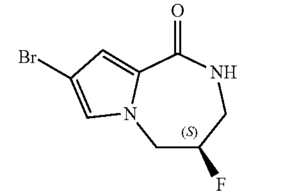 | 246.9/248.9 |
| 30 | 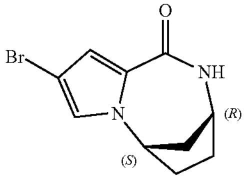 | 255.0/257.0 |
| 31 | 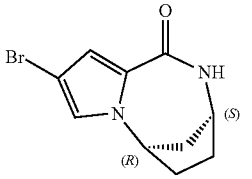 | 255.0/257.0 |
-continued
| Inter-mediate | Structure | MS (m/z) (M + H)+ |
|---|---|---|
| 32 | 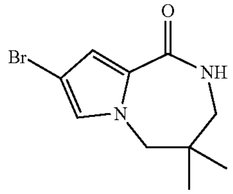 | 257.0/259.0 |
| 33 | 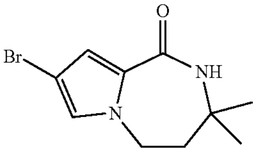 | 257.0/259.0 |
| 34 | 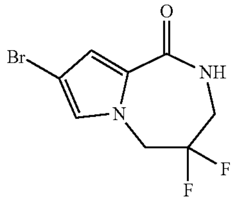 [SMILES: O=C1NCC(F)(F)Cn2cc(Br)cc21] | 264.9/266.9 |
| 35 | 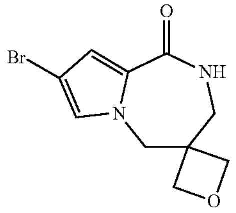 [SMILES: O=C1NCC2(COC2)Cn2cc(Br)cc21] | 270.9/272.9 |
| 36 | 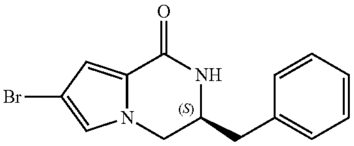 | 304.9/306.9 |
Intermediate 37
(R)-8-bromo-4-methoxy-2,3,4,5-tetrahydro-1H-pyrrolo[1,2-a][1,4]diazepin-1-one
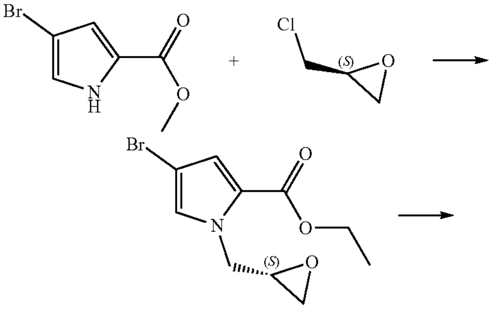

-continued

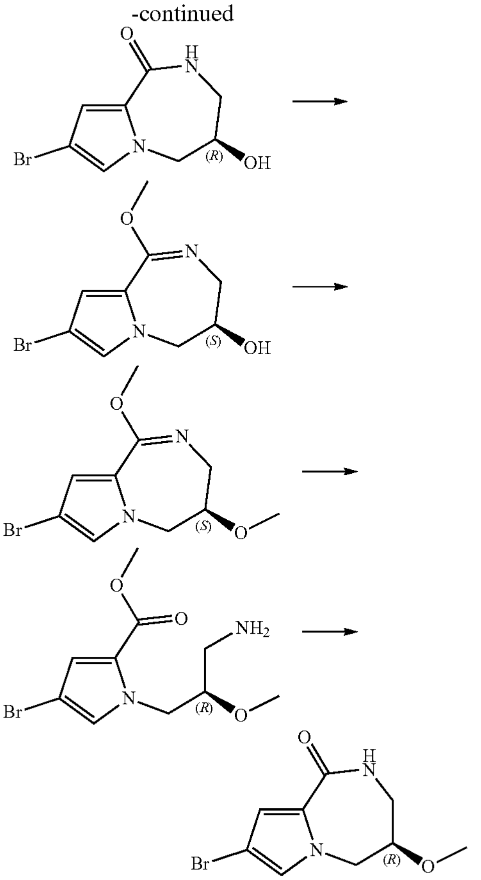

(A) (R)-8-bromo-4-hydroxy-2,3,4,5-tetrahydro-1H-pyrrolo[1,2-a][1,4]diazepin-1-one To a solution of methyl 4-bromo-1H-pyrrole-2-carboxylate (60.0 g, 0.294 mol) and (S)-2-(chloromethyl)oxirane (68.0 g, 0.735 mol) in EtOH (600 mL) was added $Cs_2CO_3$ (115.0 g, 0.352 mol). After stirring at 80° C. for 2 hours, the mixture was diluted with water and extracted with EA. The organic layer was concentrated, the residue was dissolved in EtOH (1000 mL) and ammonium hydroxide (100 mL, 25~28 WT % solution in water) was added. The mixture was stirred at 80° C. for 16 hours. The mixture was concentrated and the residue was recrystallized (EA and EtOH) to give the title compound as a white solid (25 g, 34.7% yield for two steps). MS (m/z): 245.1/247.1 $(M+H)^+$.

(B) (R)-8-bromo-4-methoxy-2,3,4,5-tetrahydro-1H-pyrrolo[1,2-a][1,4]diazepin-1-one To a solution of (R)-8-bromo-4-hydroxy-2,3,4,5-tetrahydro-1H-pyrrolo[1,2-a][1,4]diazepin-1-one (20.0 g, 0.082 mol) in DCM (300 mL) was added $CF_3SO_3Me$ (20.0 g, 0.122 mol). After stirring at 40° C. for 16 hours, the mixture was concentrated. The residue was dissolved in DMF (250 mL) and cooled to 0° C. NaH (10.0 g, 0.255 mol, 60% dispersion in Paraffin Liquid) was added at 0° C. and the mixture was stirred at 0° C. for 30 min, followed by the addition of iodomethane (24.0 g, 0.17 mol). After stirring at room temperature for 3 hours, the mixture was diluted with water and extracted with EA. The organic layer was washed with brine and water, concentrated to give yellow oil which was dissolved in MeOH (300 mL). Concentrated hydrochloric acid (60 mL) was added and the mixture was stirred at 60° C. for 3 hours. The mixture was concentrated and dissolved in MeOH (400 mL) again. $K_2CO_3$ (40.0 g, 0.289 mol) was added and the mixture was stirred at 60° C. for 4 hours. The mixture was filtrated over celite. The filtrate was concentrated and the residue was purified via ISCO (eluting with methanol in water 0%~100%) to afford the title compound as a white solid (10.0 g, 47.7% yield for four steps). MS (m/z): 259.0/261.0 $(M+H)^+$.

Intermediate 38

8'-bromo-2',3'-dihydro-1'H,5'H-spiro[cyclobutane-1, 4'-pyrrolo[1,2-a][1,4]diazepin]-1'-one

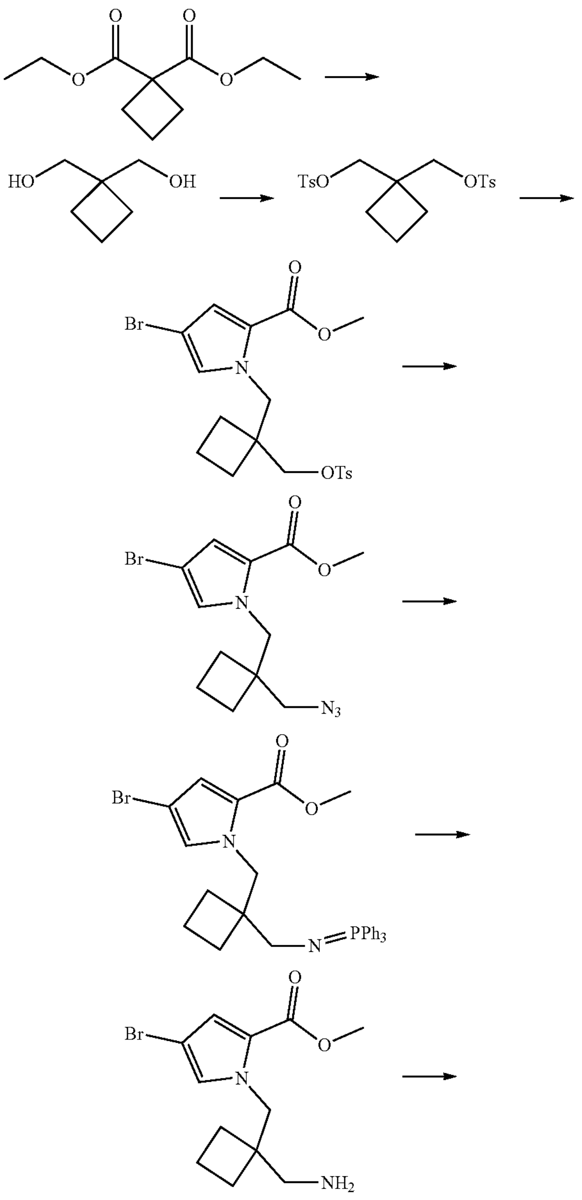

-continued

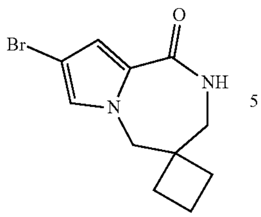

(A) cyclobutane-1,1-diyldimethanol

To a suspension of $LiAlH_4$ (2.3 g, 60 mmol) in THF (30 mL) was added diethyl cyclobutane-1,1-dicarboxylate (8 g, 40 mmol) in THF (40 mL) dropwise under nitrogen atmosphere at 0° C. The mixture was stirred at room temperature overnight, poured into water, adjust to pH=3 with 2N HCl, extracted with EA, washed with water and brine, dried over anhydrous $Na_2SO_4$ and concentrated to afford the title compound as a yellow oil (2.9 g, 63% yield). MS (m/z): 117.1 $(M+H)^+$.

(B) 1,1-bis(4-methylsulfonyloxymethyl)cyclobutane

To a solution of cyclobutane-1,1-diyldimethanol (2.9 g, 25 mmol) in DCM (30 mL) was added TsCl (10.5 g, 55 mmol) and $Et_3N$ (7.6 g, 75 mmol) at 0° C. The mixture was stirred at room temperature for 3 h, poured into water, extracted with DCM, washed with water and brine, dried over anhydrous $Na_2SO_4$, concentrated and purified via ISCO (eluting with EA in PE 0%—100%) to afford the title compound as a white solid (3.5 g, 33% yield).

(C) 8'-bromo-2',3'-dihydro-1'H,5'H-spiro[cyclobutane-1,4'-pyrrolo[1,2-a][1,4]diazepin]-1'-one To a solution of methyl 4-bromo-1H-pyrrole-2-carboxylate (1.7 g, 8.2 mmol) in DMF (10 mL) was added $K_2CO_3$ (3.4 g, 24.7 mmol) and 1,1-bis(4-methylsulfonyloxymethyl) cyclobutane (3.5 g, 8.2 mmol). The mixture was stirred at 100° C. for 5 h, poured into water, extracted with DCM. The organic layer was washed with water and brine, dried over anhydrous $Na_2SO_4$ and concentrated. The obtained yellow oil was dissolved in DMF (10 mL) and $NaN_3$ (1.1 g, 16.4 mmol) was added. The mixture was stirred at 100° C. overnight, poured into water and extracted with EA. The organic layer was washed with water and brine, dried over anhydrous $Na_2SO_4$ and concentrated. The residue was dissolved in EA (30 mL) and $PPh_3$ (2.2 g, 8.2 mmol) was added. The mixture was stirred at room temperature for 1 h, and then concentrated. The residue was dissolved in MeOH (3 mL) and concentrated hydrochloric acid (10 mL) was added. The mixture was refluxed for 3 h, concentrated and re-dissolved in MeOH (10 mL). $K_2CO_3$ (3.4 g, 24.7 mmol) and $Et_3N$ (4.2 g, 41.1 mmol) was added. The mixture was refluxed overnight, concentrated and purified via ISCO (eluting with methanol in water 0%~100%) to afford the title compound as a yellow solid (1.2 g, 54.1% yield). MS (m/z): 269.0/271.0 $(M+H)^+$.

Intermediate 39

(R)-7-bromo-3-(fluoromethyl)-3,4-dihydropyrrolo[1,2-a]pyrazin-1(2H)-one

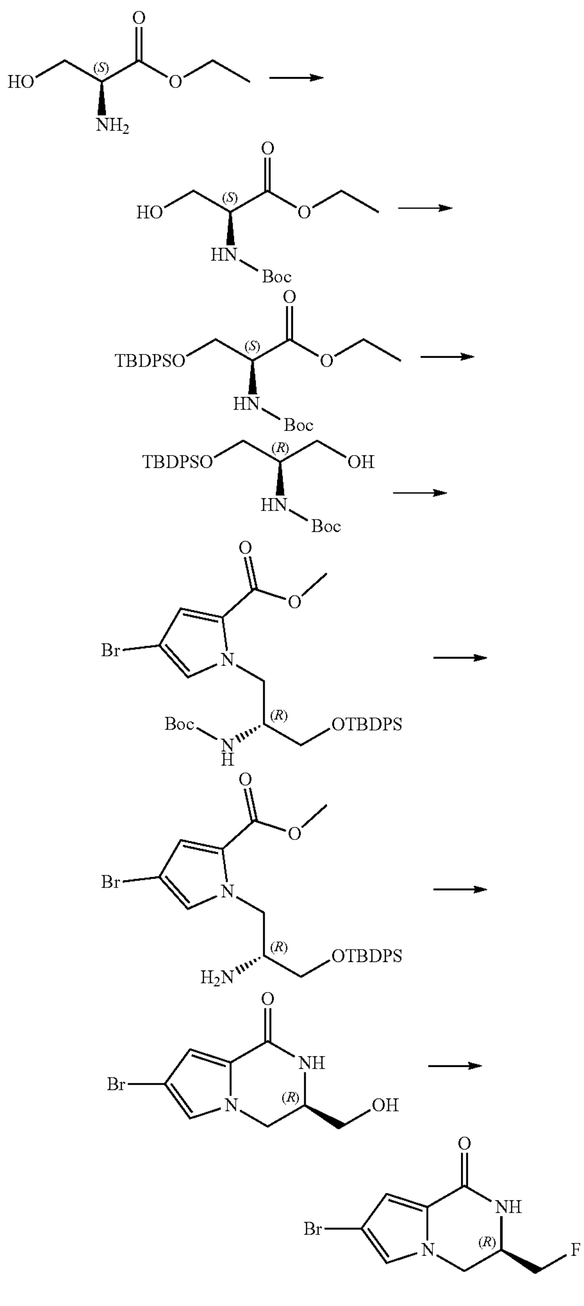

(A) Ethyl N-(tert-butoxycarbonyl)-O-(tert-butyldiphenylsilyl)-L-serinate

To a solution of ethyl L-serinate hydrogen chloride (8.0 g, 47.2 mmol) and $Et_3N$ (9.5 g, 94.3 mmol) in DCM (80 mL) was added $(Boc)_2O$ (20.6 g, 94.3 mmol). The resulting mixture was stirred at room temperature overnight and then diluted with water (100 mL), extracted by DCM (3×100 mL). The combined organic layers were concentrated and re-dissolved in DCM (100 mL). 1H-imidazole (4.7 g, 68.6 mmol) and TBDPSCl (8.3 g, 30.2 mmol) was added at 0° C. The mixture was stirred at room temperature overnight. The reaction mixture was diluted with water (100 mL) and extracted by DCM (3×100 mL). The combined organic layers were concentrated and the residue was purified via ISCO (eluting with methanol in water 0%~100%) to afford the title compound as oil (5.8 g, 26.1% yield). MS (m/z): 372.1 $(M+H-100)^+$.

(B) tert-butyl (R)-(1-((tert-butyldiphenylsilyl)oxy)-3-hydroxypropan-2-yl)carbamate To a solution of ethyl N-(tert-butoxycarbonyl)-O-(tert-butyldiphenylsilyl)-L-serinate (5.4 g, 11.4 mmol) in DCM (40 mL) was added DIBAL-H (22.9 mL, 22.9 mmol, 1M in hexane) slowly at −78° C. The mixture was stirred at −78° C. for 30 min and then at room temperature overnight. The reaction mixture cooled to 0° C. and quenched with 1 mL of water, 1 mL 15% solution of NaOH and 3 mL water. The mixture was stirred at room temperature for 15 min, filtered and the cake was washed with DCM (100 mL). The combined filtrates were concentrated and purified via ISCO (eluting with EA in PE 0%~100%) to afford the title compound as oil (3.1 g, 63.3% yield). MS (m/z):330.1 $(M+H-100)^+$.

(C) Methyl (R)-4-bromo-1-(2-((tert-butoxycarbonyl) amino)-3-((tert-butyldiphenyl silyl)oxy)propyl)-1H-pyrrole-2-carboxylate To a solution of tert-butyl (R)-(1-((tert-butyldiphenylsilyl)oxy)-3-hydroxypropan-2-yl)carbamate (2.5 g, 5.8 mmol), methyl 4-bromo-1H-pyrrole-2-carboxylate (1.2 g, 5.8 mmol) and $PPh_3$ (2.3 g, 8.7 mmol) in anhydrous THF (100 mL) was added DIAD (1.8 g, 8.7 mmol) slowly at 0° C. The mixture was then allowed to rise to room temperature and stirred overnight. The reaction mixture was concentrated, partitioned between water (100 mL) and DCM (100 mL). The aqueous layer was further extracted with DCM (2*100 mL). The combined organic layers were concentrated and purified via ISCO (eluting with EA in PE 0%~100%) to afford the title compound as white solid (2.0 g, 55.8% yield). MS (m/z):515.1/517.1 $(M+H-100)^+$.

(D) (R)-7-bromo-3-(hydroxymethyl)-3,4-dihydropyrrolo[1,2-a]pyrazin-1(2H)-one

A solution of methyl (R)-4-bromo-1-(2-((tert-butoxycarbonyl)amino)-3-((tert-butyldiphenylsilyl)oxy)propyl)-1H-pyrrole-2-carboxylate (2.0 g, 3.2 mmol) in TFA (40 mL) was stirred at room temperature for 2 h. The volatiles were removed under reduce pressure. The residue was dissolved in MeOH (50 mL), $Et_3N$ (1.6 g, 16.2 mmol) and $K_2CO_3$ (2.2 g, 16.2 mmol) was added. The resulting mixture was refluxed for 4 h. The reaction mixture was concentrated, partitioned between water (100 mL) and DCM (100 mL). The aqueous layer was further extracted with DCM (2*100 mL). The combined organic layers were concentrated and purified via ISCO (eluting with methanol in water 0%~100%) to afford the title compound as a white solid (0.35 g, 44.2% yield). MS (m/z):245.0/247.0 $(M+H)^+$.

(E) (R)-7-bromo-3-(fluoromethyl)-3,4-dihydropyrrolo[1,2-a]pyrazin-1(2H)-one

To a mixture of (R)-7-bromo-3-(hydroxymethyl)-3,4-dihydropyrrolo[1,2-a]pyrazin-1(2H)-one (450 mg, 1.84 mmol) in DCM (5 mL) was added diethylaminosulfur trifluoride (593 mg, 3.68 mol) slowly at 0° C. The mixture was allowed to rise to room temperature and stirred overnight under nitrogen atmosphere. Then the mixture was quenched with saturated solution of $NaHCO_3$ and extracted by EA. The organic layer was dried over anhydrous $Na_2SO_4$, concentrated and purified via ISCO (eluting with methanol in water 0%—100%) to afford the title compound as a yellow solid (228 mg, 50.2% yield). MS (m/z): 246.9/248.9 $(M+H)^+$.

The intermediate below was prepared according to the procedures of intermediate 39 using the corresponding intermediates and reagents under appropriate conditions that could be recognized by one skilled in the art.

| Intermediate | Structure | MS (m/z) (M + H)$^+$ |
|---|---|---|
| 40 | 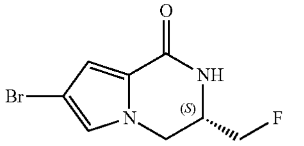 | 247.0/249.0 |

Intermediate 41

7'-Bromo-4'H-spiro[cyclobutane-1,3'-pyrrolo[1,2-a]pyrazin]-1'(2'H)-one

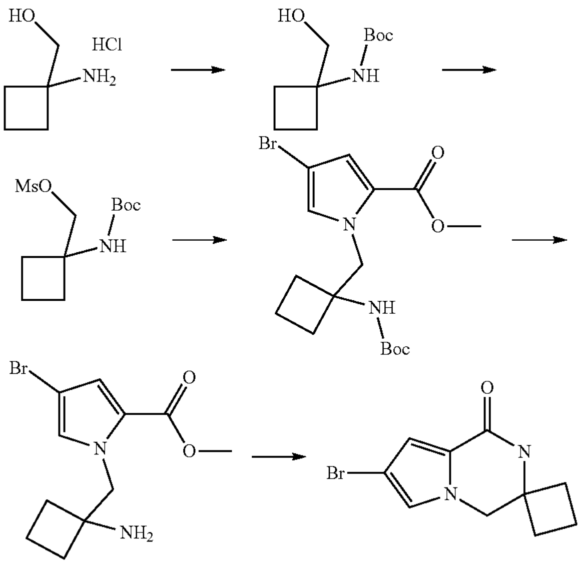

(A) tert-Butyl (1-(hydroxymethyl)cyclobutyl)carbamate

To a solution of (1-aminocyclobutyl)methanol hydrochloride (2 g, 0.015 mol) and $Et_3N$ (6.2 mL, 0.044 mol) in DCM (40 mL) was added $(Boc)_2O$ (3.5 g, 0.016 mol) at 0° C. The reaction was stirred at room temperature for 16 h. The reaction mixture was partitioned between DCM (30 mL) and saturated aqueous ammonium chloride solution (30 mL). The organic layer was washed with brine (30 mL), dried over anhydrous sodium sulfate, filtered, concentrated and recrystallized with PE/EA to afford the title compound as a white solid (2.4 g, 87.8% yield). H NMR (400 MHz, DMSO-d6) δ 6.57 (s, 1H), 4.64 (t, J=5.9 Hz, 1H), 3.39 (d, J=5.9 Hz, 2H), 2.17-2.02 (m, 2H), 1.97-1.85 (m, 2H), 1.75-1.52 (m, 2H), 1.35 (s, 9H).

(B) Methyl 4-bromo-1-((1-((tert-butoxycarbonyl) amino)cyclobutyl)methyl)-1H-pyrrole-2-carboxylate To a solution of tert-butyl (1-(hydroxymethyl)cyclobutyl) carbamate (2.1 g, 0.010 mol) in DCM (50 mL) was added $Et_3N$ (2.8 mL, 0.020 mol) and then MsCl (0.93 mL, 0.012 mol) dropwise at 0° C. The mixture was stirred at room temperature for 2 h. The reaction mixture was partitioned between DCM (30 mL) and saturated solution of ammonium chloride (30 mL). The organic layer was washed with brine (30 mL), dried over anhydrous $Na_2SO_4$, filtered and concentrated. The residue was dissolved in DMF (40 mL), methyl 4-bromo-1H-pyrrole-2-carboxylate (2 g, 0.0096 mol) and $Cs_2CO_3$ (6.3 g, 0.0192 mol) was added. The resulting mixture was stirred at 80° C. for 8 h. The reaction mixture was partitioned between EA (200 mL) and brine (300 mL). The aqueous layer was further extracted with EA (200 mL×2). The combined organic layers were concentrated and purified via ISCO (PE/EA) to afford the title compound as oil (1.6 g, 41% yield). MS (m/z): 287.0/289.0 $(M+H-100)^+$.

(C) 7'-Bromo-4'H-spiro[cyclobutane-1,3'-pyrrolo[1,2-a]pyrazin]-1'(2'H)-one

A mixture of methyl 4-bromo-1-((1-((tert-butoxycarbonyl)amino)cyclobutyl)methyl)-1H-pyrrole-2-carboxylate (1.6 g, 0.0041 mol) in TFA (10 mL) was stirred at room temperature for 2 h. The volatiles were removed under reduce pressure. The residue was dissolved in MeOH (20 mL), $Et_3N$ (3 mL) and $K_2CO_3$ (2 g, 0.0144 mol) was added. The mixture was refluxed for 6 h and then concentrated. The residue was purified via ISCO (eluting with methanol in water 0%~100%) to afford the title compound as a white solid (0.7 g, 66.8% yield). MS (m/z): 255.9/257.9 $(M+H)^+$.

The intermediates below were prepared according to the procedures of intermediate 41 using the corresponding intermediates and reagents under appropriate conditions that could be recognized by one skilled in the art.

| Intermediate | Structure | MS (m/z) $(M + H)^+$ |
|---|---|---|
| 42 | 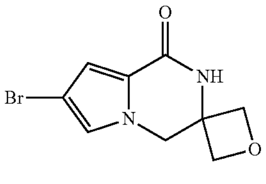 [SMILES: O=C1NC2(COC2)Cn2cc(Br)cc21] | 256.9/258.9 |
| 43 | 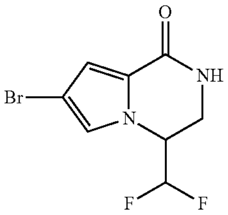 [SMILES: O=C1NCC(C(F)F)n2cc(Br)cc21] | 265.0/267.0 |

-continued

| Intermediate | Structure | MS (m/z) $(M + H)^+$ |
|---|---|---|
| 44 | 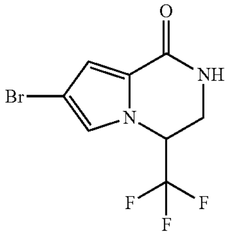 | 282.9/284.9 |

Intermediate 45

7'-bromo-4'H-spiro[cyclopropane-1,3'-pyrrolo[1,2-a]pyrazin]-1'(2'H)-one

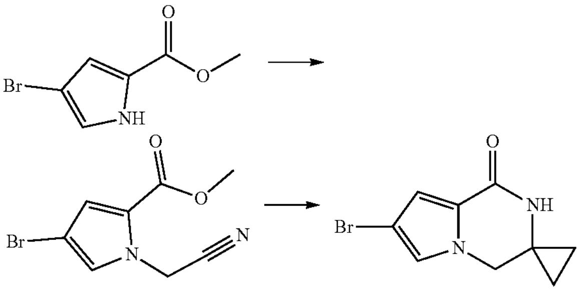

(A) Methyl 4-bromo-1-(cyanomethyl)-1H-pyrrole-2-carboxylate

A mixture of methyl 4-bromo-1H-pyrrole-2-carboxylate (10 g, 49.0 mmol), 2-bromoacetonitrile (6.17 g, 51.5 mmol) and $K_2CO_3$ (10.1 g, 73.5 mmol) in $CH_3CN$ (100 mL) was heated at 80° C. for 3.5 h. The reaction mixture was concentrated, partitioned between water (150 mL) and EA (150 mL). The aqueous layer was further extracted with EA (2*150 mL). The combined organic layers were concentrated to afford the title compound as a white solid (11.0 g, 92.4% yield). MS (m/z): 242.9/244.9 $(M+H)^+$.

(B) 7'-bromo-4'H-spiro[cyclopropane-1,3'-pyrrolo[1,2-a]pyrazin]-1'(2'H)-one

To a mixture of methyl 4-bromo-1-(cyanomethyl)-1H-pyrrole-2-carboxylate (3.0 g, 12.3 mmol) and $Ti(O^iPr)_4$ (5.2 g, 18.2 mmol) in THF (60 mL) was added ethylmagnesium bromide (11 mL, 33 mmol, 3M in THF) dropwise at room temperature. After the addition the mixture was stirred at room temperature for 1 h. Hydrochloric acid (1N, 50 mL) was added, THF was removed under reduced pressure and the aqueous layer was extracted with DCM (3×50 mL). The combined organic layers were concentrated and the residue was purified via ISCO (PE/EA) to afford the title compound as a white solid (0.4 g, 10.1% yield). MS (m/z): 241.0/243.0 $(M+H)^+$. $^1H$ NMR (400 MHz, DMSO-d6) δ 8.01 (brs, 1H), 7.11 (d, J=1.8 Hz, 1H), 6.68 (d, J=1.8 Hz, 1H), 4.01 (s, 2H), 0.84-0.79 (m, 4H).

The intermediate below was prepared according to the procedures of intermediate 45 using the corresponding intermediates and reagents under appropriate conditions that could be recognized by one skilled in the art.

| Intermediate | Structure | MS (m/z) (M + H)+ |
|---|---|---|
| 46 | 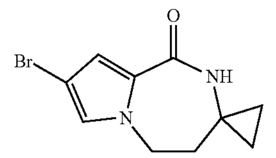 [SMILES: O=C1NC2(CCn3cc(Br)cc31)CC2] | 254.9/256.9 |

Intermediate 47

7-bromo-3-methylpyrrolo[1,2-a]pyrazin-1(2H)-one

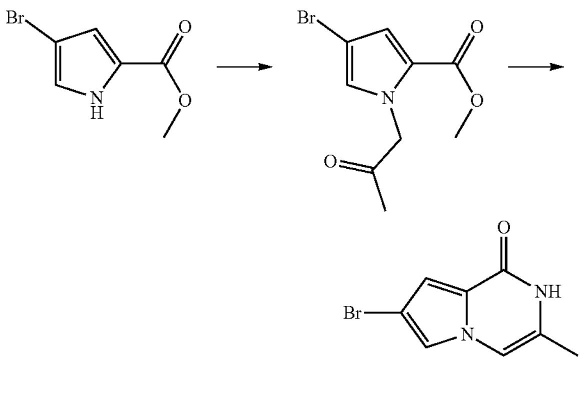

(A) Methyl 4-bromo-1-(2-oxopropyl)-1H-pyrrole-2-carboxylate

To a solution of methyl 4-bromo-1H-pyrrole-2-carboxylate (2.0 g, 0.010 mol) in DMF (10 mL) was added NaH (0.6 g, 0.015 mol, 60% dispersion in Paraffin Liquid) at 0° C. The mixture was stirred at 0° C. for 30 min, and then 1-bromopropan-2-one (1.4 g, 0.010 mol) was added. The mixture was stirred at room temperature for 4 hours, diluted with water and extracted with EA. The organic layer was washed with water and brine, concentrated to give the title compound as yellow oil (2.5 g). MS (m/z): 259.9/261.9 $(M+H)^+$.

(B) 7-bromo-3-methylpyrrolo[1,2-a]pyrazin-1(2H)-one

To a solution of methyl 4-bromo-1-(2-oxopropyl)-1H-pyrrole-2-carboxylate (2.5 g, 0.001 mol) in MeOH (10 mL) was added a solution of ammonium in MeOH (10 mL, 7M). The mixture was sealed in an autoclave and stirred at 120° C. for 16 hours. The mixture was concentrated and the residue was purified via ISCO (eluting with methanol in water 0%~100%) to afford the title compound as a yellow solid (0.5 g, 22.0% yield over two steps). MS (m/z): 227.0/229.0 $(M+H)^+$.

Intermediate 48

1-(trifluoromethyl)cyclobutane-1-carbohydrazide

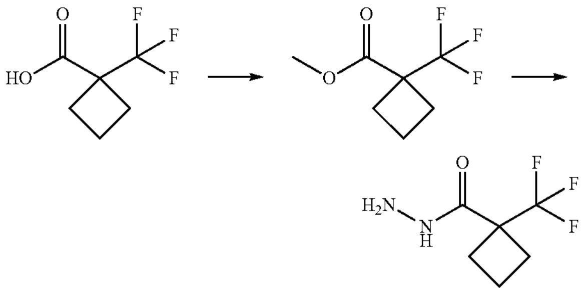

(A) 1-(trifluoromethyl)cyclobutane-1-carbohydrazide

To a solution of 1-(trifluoromethyl)cyclobutane-1-carboxylic acid (20 g, 119 mmol) in MeOH (30 mL) was added concentrated $H_2SO_4$ (0.75 mL). The mixture was refluxed overnight. Hydrazine hydrate (85%, 30 mL) was added. The mixture was refluxed overnight again. The mixture was diluted with EA, washed with water and brine, dried over anhydrous $Na_2SO_4$, concentrated to afford the title compound as a yellow solid (19 g, 68% yield). MS (m/z): 183.0 $(M+H)^+$.

The intermediates below were prepared according to the procedures of intermediate 48 using the corresponding intermediates and reagents under appropriate conditions that could be recognized by one skilled in the art.

| Intermediate | Structure | MS (m/z) (M + H)+ |
|---|---|---|
| 49 | 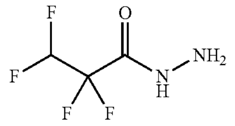 | 161.0 |
| 50 | 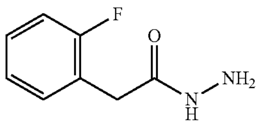 [SMILES: NNC(=O)Cc1ccccc1F] | 169.0 |
| 51 | 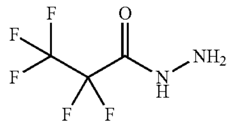 [SMILES: NNC(=O)C(F)(F)C(F)(F)F] | 179.0 |
| 52 | 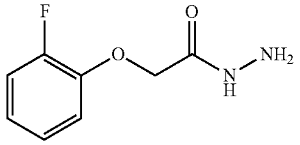 [SMILES: NNC(=O)COc1ccccc1F] | 185.1 |

-continued

| Intermediate | Structure | MS (m/z) (M + H)⁺ |
|---|---|---|
| 53 | 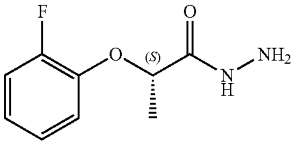 | 199.1 |

Intermediate 54

1-(trifluoromethyl)cyclopropane-1-carbohydrazide

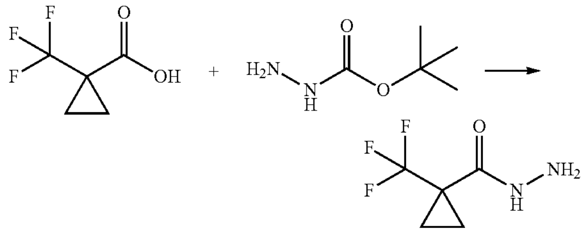

(A) 1-(trifluoromethyl)cyclopropane-1-carbohydrazide

To a solution of 1-(trifluoromethyl)cyclopropane-1-carboxylic acid (5.0 g, 0.033 mol) and tert-butyl hydrazinecarboxylate (5.5 g, 0.033 mol) in DCM (50 mL) was added EDCI (6.3 g, 0.033 mol), HOBT (4.4 g, 0.033 mol) and $Et_3N$ (6.6 g, 0.066 mol). The resulting mixture was stirred at room temperature for 16 hours and then washed with saturated solution of $NaHCO_3$ and water. The organic layer was concentrated in vacuum. The residue was dissolved in THF (80 mL) and concentrated hydrochloric acid (10 mL) was added. The resulting mixture was stirred at room temperature overnight. Then the mixture was concentrated to give the crude title compound as yellow solid (5.0 g). MS (m/z): 169.1 $(M+H)^+$.

Intermediate 55

1-(difluoromethyl)-3,3-difluorocyclobutane-1-carbohydrazide

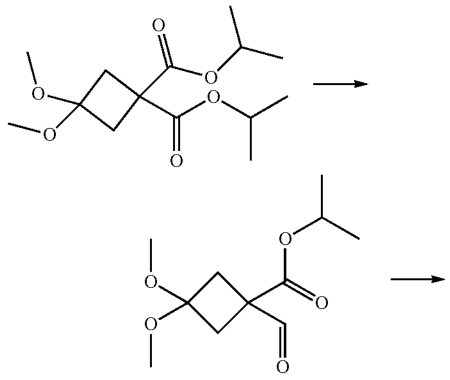

-continued

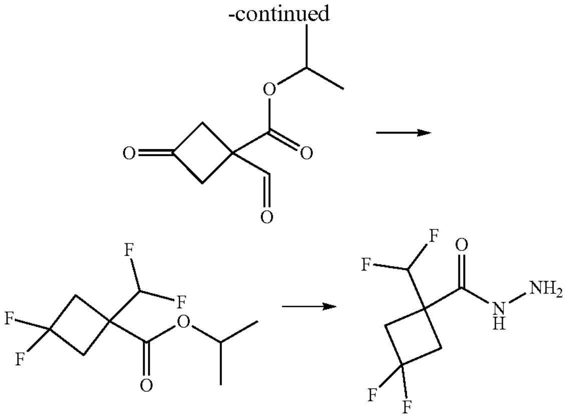

(A) isopropyl 1-formyl-3,3-dimethoxycyclobutane-1-carboxylate

To a mixture of diisopropyl 3,3-dimethoxycyclobutane-1,1-dicarboxylate (5.0 g, 17.34 mmol) in DCM (50 mL) was added DIBAL-H (35 mL, 35.0 mmol) slowly at −78° C. The mixture was stirred at −78° C. for 0.5 h under nitrogen atmosphere. Then the reaction was quenched by 2N HCl and extracted by DCM. The organic layer was washed with brine, dried over anhydrous $Na_2SO_4$, concentrated and purified via ISCO (eluting with EA in PE 0%~100%) to afford the title compound as colorless oil (1.83 g, 45.8% yield). $^1H$ NMR (400 MHz, $CDCl_3$) δ 9.67 (s, 1H), 5.11-5.03 (m, 1H), 3.14 (s, 3H), 3.11 (s, 3H), 2.65-2.58 (m, 4H), 1.24 (d, J=6.3 Hz, 6H).

(B) isopropyl 1-formyl-3-oxocyclobutane-1-carboxylate

A mixture of isopropyl 1-formyl-3,3-dimethoxycyclobutane-1-carboxylate (1.83 g, 7.95 mmol) in 6N HCl (10 mL, 60 mmol) was stirred at room temperature for 24 hours. Then the mixture was extracted by DCM. The organic layer was washed with brine, dried over anhydrous $Na_2SO_4$, concentrated to afford the title compound as colorless oil (950 mg). MS (m/z): 185.1 $(M+H)^+$.

(C) isopropyl 1-(difluoromethyl)-3,3-difluorocyclobutane-1-carboxylate

To a mixture of above isopropyl 1-formyl-3-oxocyclobutane-1-carboxylate (0.95 g) in DCM (5 mL) was added diethylaminosulfur trifluoride (4.46 g, 27.27 mmol) slowly at 0° C. The mixture was then stirred at room temperature under nitrogen atmosphere. The reaction was quenched with saturated solution of $NaHCO_3$ and extracted by DCM. The organic layer was washed with brine, dried over anhydrous $Na_2SO_4$, and concentrated to afford the title compound as brown oil (1.2 g). $^1H$ NMR (400 MHz, $CDCl_3$) δ 6.15 (t, J=56.2 Hz, 1H), 5.15-5.07 (m, 1H), 3.01-2.90 (m, 4H), 1.28 (d, J=6.3 Hz, 6H).

(D) 1-(difluoromethyl)-3,3-difluorocyclobutane-1-carbohydrazide

To a mixture of above isopropyl 1-(difluoromethyl)-3,3-difluorocyclobutane-1-carboxylate (1.20 g) in MeOH (10 mL) was added hydrazine hydrate (85%, 3 mL). The mixture was stirred at 75° C. overnight under nitrogen atmosphere.

Then the MeOH was removed and the residue was extracted by EA. The organic layer was washed with brine, dried over anhydrous $Na_2SO_4$, and concentrated to afford the title compound as yellow oil (1.0 g). MS (m/z): 201.0 $(M+H)^+$.

The intermediates below were prepared according to the procedures of intermediate 55 using the corresponding intermediates and reagents under appropriate conditions that could be recognized by one skilled in the art.

| Intermediate | Structure | MS (m/z) $(M + H)^+$ |
|---|---|---|
| 56 | 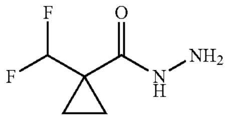 | 151.0 |
| 57 | 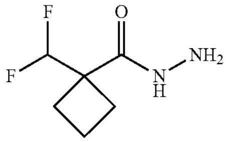 [SMILES: NNC(=O)C1(C(F)F)CCC1] | 165.1 |
| 58 | 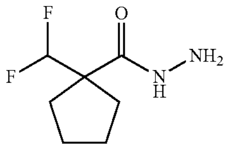 [SMILES: NNC(=O)C1(C(F)F)CCCC1] | 179.1 |

Example 1: Synthesis of Compounds 1-35

Compound 1

4-(3-(2-fluorophenethyl)-6,7-dihydro-5H-pyrrolo[1,2-a][1,2,4]triazolo[3,4-c][1,4]diazepin-10-yl)-N-(1-methyl-1H-pyrazol-5-yl)pyrimidin-2-amine

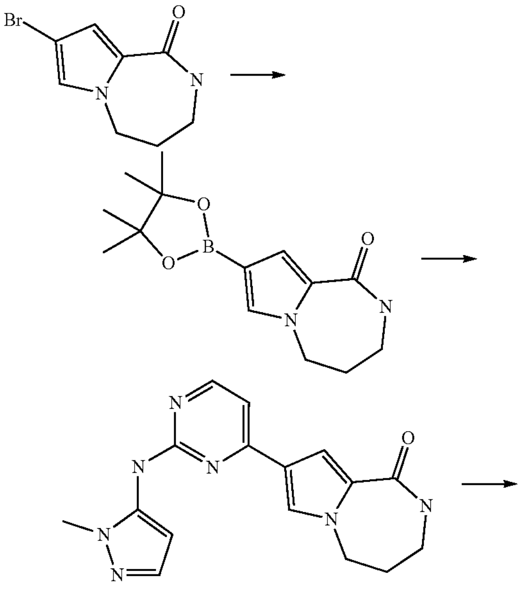

-continued

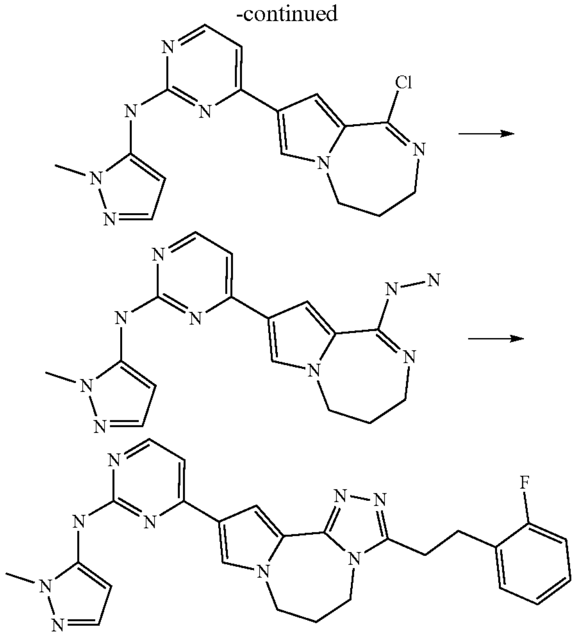

(A) 8-(4,4,5,5-Tetramethyl-1,3,2-dioxaborolan-2-yl)-2,3,4,5-tetrahydro-1H-pyrrolo[1,2-a][1,4]diazepin-1-one A mixture of 8-bromo-2,3,4,5-tetrahydro-1H-pyrrolo[1,2-a][1,4]diazepin-1-one (6 g, 26.19 mmol), 4,4,4',4',5,5,5',5'-octamethyl-2,2'-bi(1,3,2-dioxaborolane) (11.97 g, 47.15 mmol), $Pd_2dba_3$ (2.4 g, 2.62 mmol), tricyclohexylphosphane (1.47 g, 5.24 mmol) and KOAc (7.71 g, 78.58 mmol) in 1,4-dioxane (120 mL) was stirred for 16 h at 100° C. under nitrogen atmosphere. The mixture was filtered and the filtrate was diluted with EA (200 mL), washed with water (100 mL) and brine (100 mL). The collected organic was dried over anhydrous sodium sulfate, filtered, and concentrated. The residue was purified via ISCO (eluting with methanol in water 0%~100%) to afford the title compound as a white solid (3.55 g, 49.1% yield). MS (m/z): 277.0 $(M+H)^+$.

(B) 8-(2-((1-methyl-1H-pyrazol-5-yl)amino)pyrimidin-4-yl)-2,3,4,5-tetrahydro-1H-pyrrolo[1,2-a][1,4]diazepin-1-one To a mixture of 8-(4,4,5,5-tetramethyl-1,3,2-dioxaborolan-2-yl)-2,3,4,5-tetrahydro-1H-pyrrolo[1,2-a][1,4]diazepin-1-one (17.76 g, 64.32 mol) and 4-chloro-N-(1-methyl-1H-pyrazol-5-yl)pyrimidin-2-amine (13.50 g, 64.40 mmol) in 1,4-dioxane/water (380 mL/70 mL) were added Pd(dppf)$Cl_2 \cdot CH_2Cl_2$ (2.63 g, 3.22 mmol) and cesium carbonate (52.40 g, 160.82 mmol). Then the mixture was stirred for 2 h at 90° C. under nitrogen atmosphere. The mixture was filtered, and the filtrate was diluted with EA, washed with water and brine. The organic layer was dried over anhydrous sodium sulfate, filtered, concentrated. The residue was purified via ISCO (eluting with methanol in water 0%~100%) to afford the title compound as a yellow solid (16.6 g, 79.8% yield). MS (m/z): 324.1 $(M+H)^+$.

(C) 4-(1-hydrazineyl-4,5-dihydro-3H-pyrrolo[1,2-a][1,4]diazepin-8-yl)-N-(1-methyl-1H-pyrazol-5-yl)pyrimidin-2-amine A suspension of 8-(2-((1-methyl-1H-pyrazol-5-yl)amino)pyrimidin-4-yl)-2,3,4,5-tetrahydro-1H-pyrrolo[1,2-a][1,4]

diazepin-1-one (8.00 g, 24.74 mmol) in $POCl_3$ (80 mL) was stirred overnight at 100° C. under nitrogen atmosphere. The mixture was concentrated and the residue was poured into cold saturated solution of $NaHCO_3$, extracted with EA. The combined organic layers were washed with water and brine, dried over anhydrous sodium sulfate and concentrated. The residue was dissolved in THF (50 mL) and hydrazine hydrate (50 mL, 85%) was added. Then the mixture was refluxed overnight under nitrogen atmosphere. The mixture was filtered and the filter cake was washed with THF. The organic layer was washed with water and brine, dried over anhydrous sodium sulfate, concentrated to give a brown solid (3.75 g, 47.7% yield) MS (m/z): 338.1 $(M+H)^+$.

(D) 4-(3-(2-fluorophenethyl)-6,7-dihydro-5H-pyrrolo[1,2-a][1,2,4]triazolo[3,4-c][1,4]diazepin-10-yl)-N-(1-methyl-1H-pyrazol-5-yl)pyrimidin-2-amine To a solution of 4-(1-hydrazineyl-4,5-dihydro-3H-pyrrolo[1,2-a][1,4]diazepin-8-yl)-N-(1-methyl-1H-pyrazol-5-yl)pyrimidin-2-amine (100 mg, 0.30 mmol) and 3-(2-fluorophenyl)propanoic acid (60 mg, 0.35 mmol) in 5 mL of DCM was added HATU (113 mg, 0.30 mmol) and $Et_3N$ (58 mg, 0.58 mmol). The mixture was stirred at room temperature for 1 h. The volatiles were removed under reduced pressure and the residue was dissolved in 5 mL of 1,4-dioxane and then stirred at 60° C. for 1 h. The mixture was concentrated, purified via ISCO (eluting with methanol in water 0%~100%) to afford the title compound as a white solid (66.6 mg, 47.1% yield). MS (m/z): 470.3 $(M+H)^+$. $^1H$ NMR (400 MHz, DMSO-d6) δ 9.22 (s, 1H), 8.31 (d, J=5.2 Hz, 1H), 7.68 (d, J=2.0 Hz, 1H), 7.40-7.32 (m, 3H), 7.28-7.23 (m, 1H), 7.18-7.09 (m, 3H), 6.27 (d, J=1.9 Hz, 1H), 4.37-4.23 (m, 2H), 4.17-4.00 (m, 2H), 3.68 (s, 3H), 3.10-2.98 (m, 4H), 2.29-2.13 (m, 2H).

The compounds below were prepared according to the procedures of Compound 1 using the corresponding intermediates and reagents under appropriate conditions that could be recognized by one skilled in the art.

| Compound | Structure | LC-MS (m/z) $(M + H)^+$ | $^1H$ NMR |
|---|---|---|---|
| 2 | 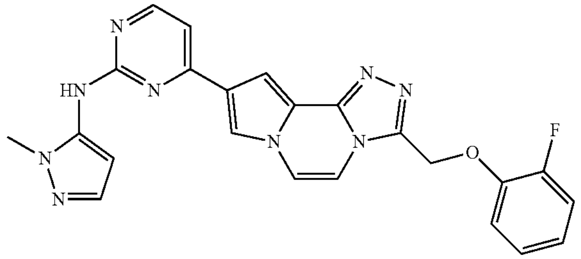 [SMILES: Cn1nccc1Nc1nccc(-c2cc3c4nnc(COc5ccccc5F)n4ccn3c2)n1] | 456.1 | $^1H$ NMR (400 MHz, DMSO-d6) δ 9.36 (s, 1H), 8.43 (d, J = 5.1 Hz, 1H), 8.27 (d, J = 1.5 Hz, 1H), 8.06 (d, J = 6.1 Hz, 1H), 7.83 (d, J = 6.1 Hz, 1H), 7.65 (s, 1H), 7.42 (t, J = 8.0 Hz, 1H), 7.36-7.33 (m, 2H), 7.25-7.13 (m, 2H), 7.03-6.96 (m, 1H), 6.30 (d, J = 1.9 Hz, 1H), 5.63 (s, 2H), 3.69 (s, 3H). |
| 3 | 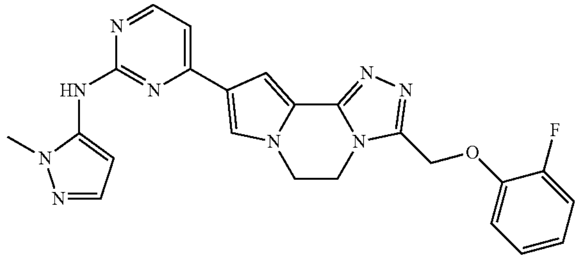 [SMILES: Cn1nccc1Nc1nccc(-c2cc3n(c2)CCn2c(COc4ccccc4F)nnc2-3)n1] | 458.2 | $^1H$ NMR (400 MHz, DMSO-d6) δ 9.26 (s, 1H), 8.33 (d, J = 4.4 Hz, 1H), 7.82 (s, 1H), 7.40 (t, J = 8.0 Hz, 1H), 7.34-7.31 (m, 1H), 7.26 (s, 1H), 7.21 (d, J = 10.4 Hz, 1H), 7.17-7.13 (m, 2H), 7.04-6.96 (m, 1H), 6.28-6.26 (m, 1H), 5.42 (s, 2H), 4.46-4.41 (m, 4H), 3.68 (s, 3H). |
| 4 | 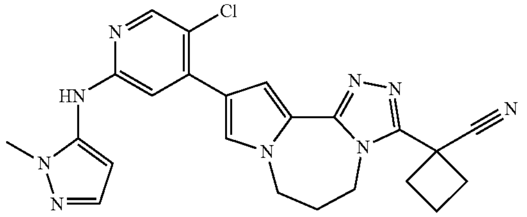 [SMILES: Cn1nccc1Nc1cc(-c2cc3n(c2)CCCn2c-3nnc2C2(C#N)CCC2)c(Cl)cn1] | 460.1 | $^1H$ NMR (400 MHz, DMSO-d6) δ 8.82 (s, 1H), 8.12 (s, 1H), 7.66 (d, J = 2.1 Hz, 1H), 7.31 (d, J = 1.9 Hz, 1H), 7.27 (d, J = 2.1 Hz, 1H), 6.98 (s, 1H), 6.22 (d, J = 1.9 Hz, 1H), 4.47-4.34 (m, 2H), 4.19-4.11 (m, 2H), 3.65 (s, 3H), 3.00-2.80 (m, 4H), 2.41-2.33 (m, 2H), 2.32-2.19 (m, 1H), 2.07-2.03 (m, 1H). |
| 5 | 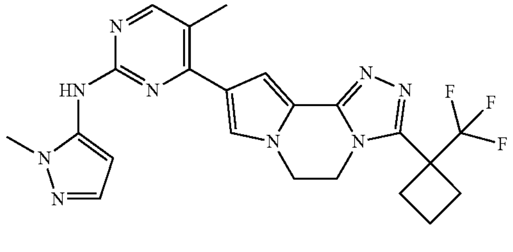 [SMILES: Cc1cnc(Nc2ccnn2C)nc1-c1cc2n(c1)CCn1c-2nnc1C1(C(F)(F)F)CCC1] | 470.2 | $^1H$ NMR (400 MHz, DMSO-d6) δ 8.99 (s, 1H), 8.23 (s, 1H), 7.74 (s, 1H), 7.33 (d, J = 1.6 Hz, 1H), 7.27 (d, J = 1.6 Hz, 1H), 6.26 (d, J = 2.0 Hz, 1H), 4.47-4.39 (m, 2H), 4.29-4.26 (m, 2H), 3.68 (s, 3H), 2.94-2.86 (m, 2H), 2.75-2.67 (m, 2H), 2.34 (s, 3H), 2.19-2.14 (m, 1H), 2.05-1.98 (m, 1H). |

-continued

| Compound | Structure | LC-MS (m/z) (M + H)+ | 1H NMR |
|---|---|---|---|
| 6 | 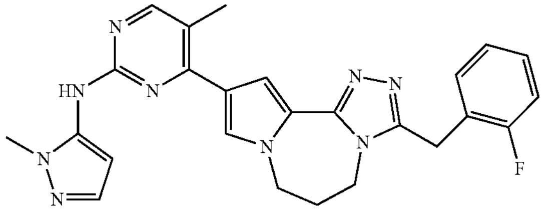 [SMILES: Cc1cnc(Nc2ccnn2C)nc1-c1cc2n(c1)CCCn1c(Cc3ccccc3F)nnc1-2] | 470.2 | 1H NMR (400 MHz, DMSO-d6) δ 9.08 (s, 1H), 8.20 (s, 1H), 7.60 (d, J = 1.8 Hz, 1H), 7.41 (d, J = 1.7 Hz, 1H), 7.33-7.28 (m, 2H), 7.24-7.11 (m, 3H), 6.25 (d, J = 1.7 Hz, 1H), 4.37-4.30 (m, 2H), 4.18 (s, 2H), 4.12-4.06 (m, 2H), 3.66 (s, 3H), 2.30 (s, 3H), 2.28-2.23 (m, 2H). |
| 7 | 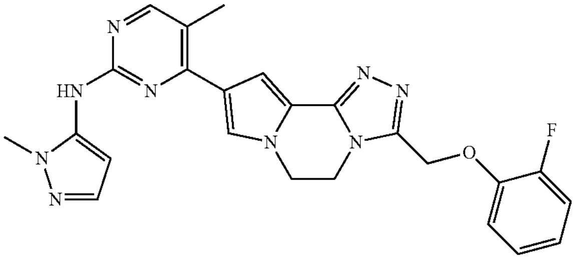 [SMILES: Cc1cnc(Nc2ccnn2C)nc1-c1cc2n(c1)CCn1c(COc3ccccc3F)nnc1-2] | 472.2 | 1H NMR (400 MHz, DMSO-d6) δ 9.12 (s, 1H), 8.23 (s, 1H), 7.76 (d, J = 1.6 Hz, 1H), 7.42-7.38 (m, 1H), 7.33 (d, J = 2.0 Hz, 1H), 7.25 (d, J = 1.2 Hz, 1H), 7.23-7.19 (m, 1H), 7.15 (t, J = 8.0 Hz, 1H), 7.02-6.97 (m, 1H), 6.27 (d, J = 2.0 Hz, 1H), 5.42 (s, 2H), 4.45 (br, 4H), 3.68 (s, 3H), 2.33 (s, 3H). |
| 8 | 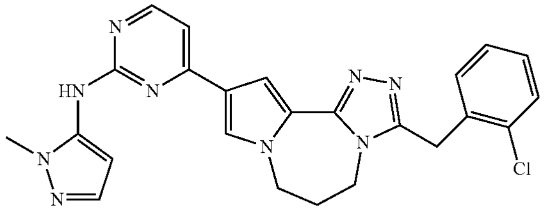 [SMILES: Cn1nccc1Nc1nccc(-c2cc3n(c2)CCCn2c(Cc4ccccc4Cl)nnc2-3)n1] | 472.2 | 1H NMR (400 MHz, DMSO-d6) δ 9.19 (s, 1H), 8.28 (d, J = 5.1 Hz, 1H), 7.66 (s, 1H), 7.51-7.41 (m, 1H), 7.35-7.22 (m, 4H), 7.21-7.13 (m, 1H), 7.07 (d, J = 5.1 Hz, 1H), 6.26-6.24 (m, 1H), 4.39-4.26 (m, 2H), 4.22 (s, 2H), 4.14-4.01 (m, 2H), 3.66 (s, 3H), 2.32-2.18 (m, 2H). |
| 9 | 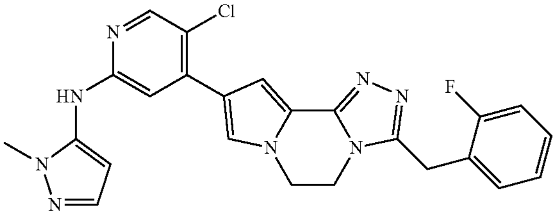 [SMILES: Cn1nccc1Nc1cc(-c2cc3n(c2)CCn2c(Cc4ccccc4F)nnc2-3)c(Cl)cn1] | 475.1 | 1H NMR (400 MHz, DMSO-d6) δ 8.84 (s, 1H), 8.12 (s, 1H), 7.69 (s, 1H), 7.37-7.10 (m, 5H), 6.99 (s, 1H), 6.94 (s, 1H), 6.23-6.20 (m, 1H), 4.41-4.37 (m, 2H), 4.29-4.25 (m, 2H), 4.20 (s, 2H), 3.64 (s, 3H). |
| 10 | 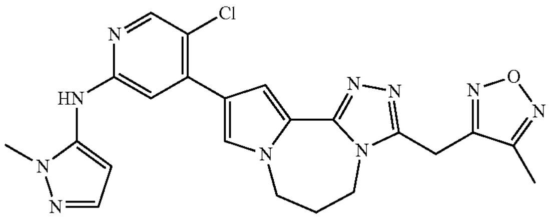 [SMILES: Cc1nonc1Cc1nnc2n1CCCn1cc(-c3cc(Nc4ccnn4C)ncc3Cl)cc1-2] | 477.1 | 1H NMR (400 MHz, DMSO-d6) δ 8.82 (s, 1H), 8.11 (s, 1H), 7.63 (s, 1H), 7.32-7.30 (m, 1H), 7.21 (s, 1H), 6.96 (s, 1H), 6.23-6.21 (m, 1H), 4.45 (s, 2H), 4.40-4.36 (m, 2H), 4.20-4.15 (m, 2H), 3.64 (s, 3H), 2.34-2.28 (m, 5H). |
| 11 | 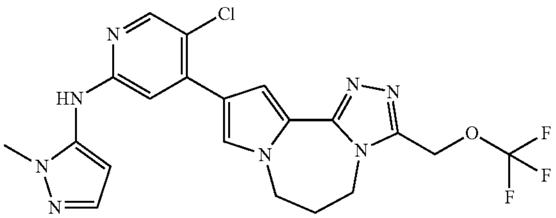 [SMILES: Cn1nccc1Nc1cc(-c2cc3n(c2)CCCn2c(COC(F)(F)F)nnc2-3)c(Cl)cn1] | 479.2 | 1H NMR (400 MHz, DMSO-d6) δ 8.88 (s, 1H), 8.13 (s, 1H), 7.67 (d, J = 2.1 Hz, 1H), 7.32 (d, J = 1.9 Hz, 1H), 7.30 (d, J = 2.1 Hz, 1H), 6.98 (s, 1H), 6.23 (d, J = 1.9 Hz, 1H), 5.43 (s, 2H), 4.48-4.36 (m, 2H), 4.34-4.25 (m, 2H), 3.66 (s, 3H), 2.36-2.33 (m, 2H). |

-continued

| Compound | Structure | LC-MS (m/z) (M + H)+ | 1H NMR |
|---|---|---|---|
| 12 | 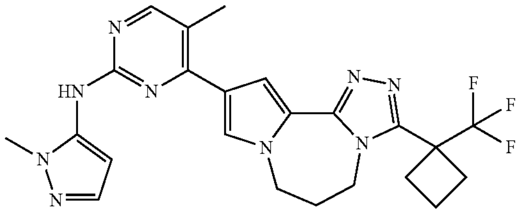 [SMILES: Cc1cnc(Nc2ccnn2C)nc1-c1cc2n(c1)CCCn1c-2nnc1C1(C(F)(F)F)CCC1] | 484.1 | 1H NMR (400 MHz, DMSO-d6) δ 9.08 (s, 1H), 8.21 (s, 1H), 7.66 (d, J = 1.4 Hz, 1H), 7.40 (d, J = 1.4 Hz, 1H), 7.31 (d, J = 1.4 Hz, 1H), 6.25 (d, J = 1.4 Hz, 1H), 4.37-4.28 (m, 2H), 4.08-3.99 (m, 2H), 3.66 (s, 3H), 2.92-2.88 (m, 2H), 2.75-2.66 (m, 2H), 2.35-2.24 (m, 5H), 2.17-2.13 (m, 1H), 2.01-1.97 (m, 1H). |
| 13 | 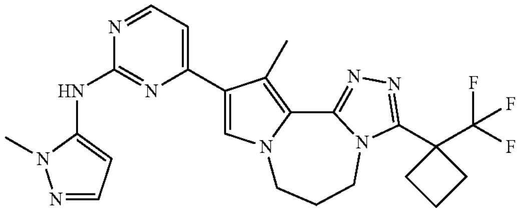 [SMILES: Cc1c(-c2ccnc(Nc3ccnn3C)n2)cn2c1-c1nnc(C3(C(F)(F)F)CCC3)n1CCC2] | 484.1 | 1H NMR (400 MHz, DMSO-d6) δ 9.06 (s, 1H), 8.30 (d, J = 5.3 Hz, 1H), 7.72 (s, 1H), 7.32 (d, J = 1.9 Hz, 1H), 6.99 (d, J = 5.3 Hz, 1H), 6.18 (d, J = 1.9 Hz, 1H), 4.05 (t, J = 6.6 Hz, 2H), 3.86 (t, J = 6.5 Hz, 2H), 3.64 (s, 3H), 2.93-2.89 (m, 2H), 2.79-2.65 (m, 2H), 2.38 (s, 3H), 2.27-2.09 (m, 3H), 2.05-1.94 (m, 1H). |
| 14 | 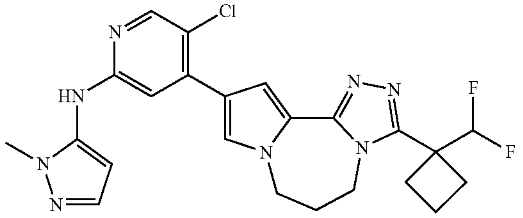 [SMILES: Cn1nccc1Nc1cc(-c2cc3n(c2)CCCn2c-3nnc2C2(C(F)F)CCC2)c(Cl)cn1] | 485.1 | 1H NMR (400 MHz, DMSO-d6) δ 8.82 (s, 1H), 8.12 (s, 1H), 7.66 (s, 1H), 7.33-7.31 (m, 1H), 7.18 (s, 1H), 6.98 (s, 1H), 6.48 (t, J = 55.8 Hz, 1H), 6.23-6.21 (m, 1H), 4.36-4.26 (m, 2H), 4.07-3.99 (m, 2H), 3.65 (s, 3H), 2.75-2.67 (m, 2H), 2.55-2.53 (m, 2H), 2.31-2.25 (m, 2H), 2.19-2.08 (m, 1H), 2.01-1.90 (m, 1H). |
| 15 | 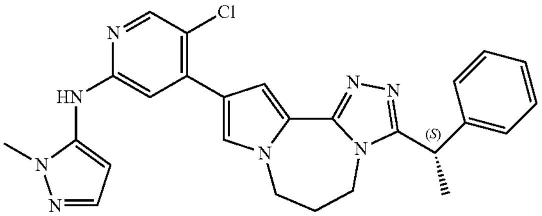 | 485.2 | 1H NMR (400 MHz, DMSO-d6) δ 8.83 (s, 1H), 8.10 (s, 1H), 7.59 (d, J = 2.0 Hz, 1H), 7.34-7.27 (m, 3H), 7.23-7.17 (m, 4H), 6.97 (s, 1H), 6.22 (d, J = 1.9 Hz, 1H), 4.40-4.26 (m, 2H), 4.18-4.09 (m, 2H), 3.65 (s, 3H), 3.61-3.53 (m, 1H), 2.21-2.10 (m, 1H), 2.03-1.94 (m, 1H), 1.63 (d, J = 7.0 Hz, 3H). |
| 16 | 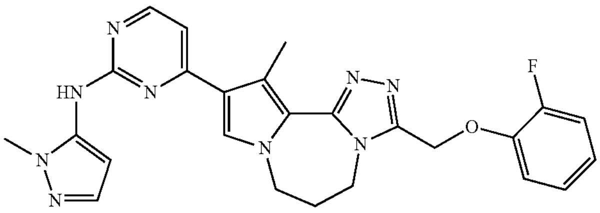 | 486.1 | 1H NMR (400 MHz, DMSO-d6) δ 9.09 (s, 1H), 8.30 (d, J = 3.6 Hz, 1H), 7.72 (s, 1H), 7.44-7.40 (m, 1H), 7.32 (d, J = 1.9 Hz, 1H), 7.27-7.12 (m, 2H), 7.04-6.96 (m, 2H), 6.19 (d, J = 1.9 Hz, 1H), 5.42 (s, 2H), 4.13-4.06 (m, 4H), 3.65 (s, 3H), 2.43 (s, 3H), 2.32-2.28 (m, 2H). |
| 17 | 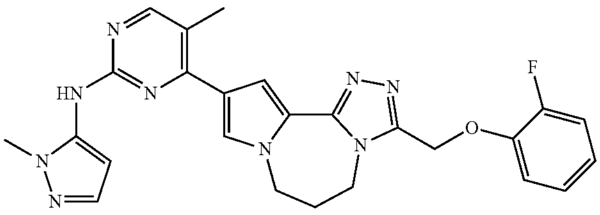 [SMILES: Cc1cnc(Nc2ccnn2C)nc1-c1cc2n(c1)CCCn1c(COc3ccccc3F)nnc1-2] | 486.2 | 1H NMR (400 MHz, DMSO-d6) δ 9.09 (s, 1H), 8.21 (s, 1H), 7.65 (d, J = 1.8 Hz, 1H), 7.48 (d, J = 1.9 Hz, 1H), 7.43-7.39 (m, 1H), 7.32 (d, J = 1.8 Hz, 1H), 7.25-7.14 (m, 2H), 7.02-6.96 (m, 1H), 6.26 (d, J = 1.9 Hz, 1H), 5.40 (s, 2H), 4.46-4.37 (m, 2H), 4.37-4.29 (m, 2H), 3.67 (s, 3H), 2.38-2.28 (m, 5H). |
| 18 | 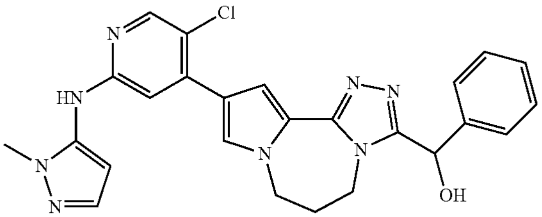 [SMILES: Cn1nccc1Nc1cc(-c2cc3n(c2)CCCn2c-3nnc2C(O)c2ccccc2)c(Cl)cn1] | 487.2 | 1H NMR (400 MHz, DMSO-d6) δ 8.83 (s, 1H), 8.10 (s, 1H), 7.61 (d, J = 2.0 Hz, 1H), 7.38-7.34 (m, 4H), 7.31-7.25 (m, 2H), 7.19 (d, J = 2.0 Hz, 1H), 6.96 (s, 1H), 6.59 (d, J = 5.0 Hz, 1H), 6.21 (d, J = 1.9 Hz, 1H), 6.04 (d, J = 5.0 Hz, 1H), 4.38-4.31 (m, 1H), 4.28-4.25 (m, 1H), 4.24-4.18 (m, 1H), 3.96-3.90 (m, 1H), 3.64 (s, 3H), 2.22-2.12 (m, 1H), 2.12-1.97 (m, 1H). |

-continued

| Compound | Structure | LC-MS (m/z) (M + H)+ | 1H NMR |
| --- | --- | --- | --- |
| 19 | 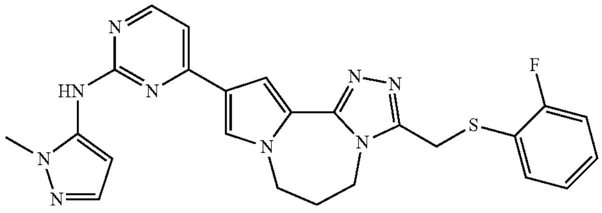 | 488.2 | 1H NMR (400 MHz, DMSO-d6) δ 9.21 (s, 1H), 8.33-8.28 (m, 1H), 7.70 (s, 1H), 7.61-7.57 (m, 1H), 7.34-7.30 (m, 3H), 7.25-7.08 (m, 3H), 6.29-6.25 (m, 1H), 4.43 (m, 2H), 4.38-4.34 (m, 2H), 4.32-4.27 (m, 2H), 3.67 (s, 3H), 2.35-2.31 (m, 2H). |
| 20 | 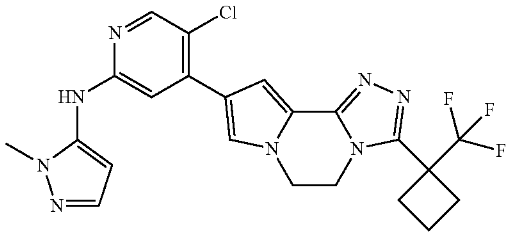 [SMILES: Cn1nccc1Nc1cc(-c2cc3n(c2)CCn2c-3nnc2C2(C(F)(F)F)CCC2)c(Cl)cn1] | 489.0 | 1H NMR (400 MHz, DMSO-d6) δ 8.85 (br, 1H), 8.13 (s, 1H), 7.74 (d, J = 1.2 Hz, 1H), 7.32 (d, J = 1.6 Hz, 1H), 7.07 (d, J = 1.6 Hz, 1H), 6.96 (s, 1H), 6.22 (d, J = 1.6 Hz, 1H), 4.45-4.36 (m, 2H), 4.28-4.25 (m, 2H), 3.65 (s, 3H), 2.92-2.84 (m, 2H), 2.72-2.65 (m, 2H), 2.17-2.10 (m, 1H), 2.05-1.91 (m, 1H). |
| 21 | 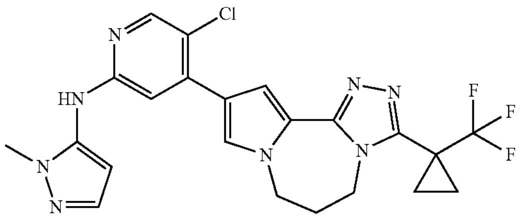 [SMILES: Cn1nccc1Nc1cc(-c2cc3n(c2)CCCn2c-3nnc2C2(C(F)(F)F)CC2)c(Cl)cn1] | 489.1 | 1H NMR (400 MHz, DMSO-d6) δ 8.83 (s, 1H), 8.12 (s, 1H), 7.66 (d, J = 2.1 Hz, 1H), 7.31 (d, J = 1.9 Hz, 1H), 7.24 (d, J = 2.1 Hz, 1H), 6.97 (s, 1H), 6.22 (d, J = 1.9 Hz, 1H), 4.47-4.34 (m, 2H), 4.34-4.21 (m, 2H), 3.65 (s, 3H), 2.40-2.25 (m, 2H), 1.63-1.49 (m, 2H), 1.49-1.35 (m, 2H). |
| 22 | 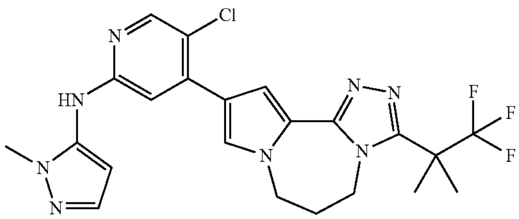 [SMILES: Cn1nccc1Nc1cc(-c2cc3n(c2)CCCn2c-3nnc2C(C)(C)C(F)(F)F)c(Cl)cn1] | 491.1 | 1H NMR (400 MHz, DMSO-d6) δ 8.86 (s, 1H), 8.13 (s, 1H), 7.71 (s, 1H), 7.33-7.30 (m, 1H), 7.12 (s, 1H), 6.97 (s, 1H), 6.24-6.21 (m, 1H), 4.35-4.19 (m, 4H), 3.66 (s, 3H), 2.37-2.24 (m, 2H), 1.72 (s, 6H). |
| 23 | 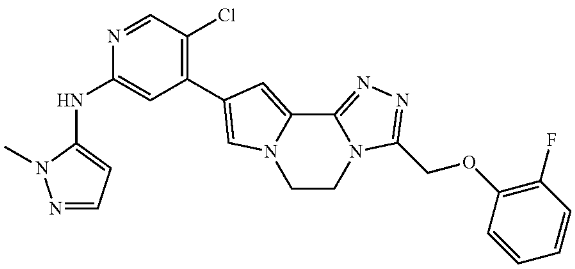 [SMILES: Cn1nccc1Nc1cc(-c2cc3n(c2)CCn2c(COc4ccccc4F)nnc2-3)c(Cl)cn1] | 491.2 | 1H NMR (400 MHz, DMSO-d6) δ 8.87 (s, 1H), 8.14 (s, 1H), 7.74 (d, J = 1.6 Hz, 1H), 7.42-7.37 (m, 1H), 7.33 (d, J = 2.0 Hz, 1H), 7.26-7.19 (m, 1H), 7.15 (t, J = 8.0 Hz, 1H), 7.06 (d, J = 1.6 Hz, 1H), 7.03-6.97 (m, 1H), 6.96 (s, 1H), 6.23 (d, J = 2.0 Hz, 1H), 5.42 (s, 2H), 4.45 (br, 4H), 3.66 (s, 3H). |
| 24 | 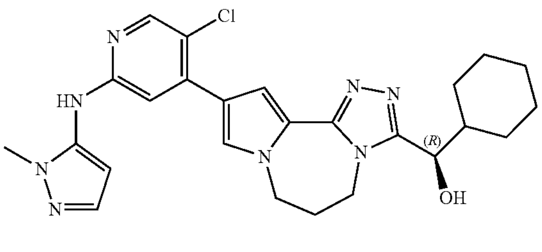 | 493.1 | 1H NMR (400 MHz, DMSO-d6) δ 8.85 (s, 1H), 8.12 (s, 1H), 7.64 (s, 1H), 7.33-7.31 (m, 1H), 7.18 (s, 1H), 6.97 (s, 1H), 6.24-6.21 (m, 1H), 4.46-4.21 (m, 5H), 3.65 (s, 3H), 2.35-2.22 (m, 2H), 2.15-2.04 (m, 1H), 2.01-1.92 (m, 1H), 1.92-1.80 (m, 1H), 1.67-1.75 (m, 1H), 1.66-1.55 (m, 2H), 1.36-1.24 (m, 2H), 1.17-1.01 (m, 3H). |

-continued

| Compound | Structure | LC-MS (m/z) (M + H)+ | 1H NMR |
|---|---|---|---|
| 25 | 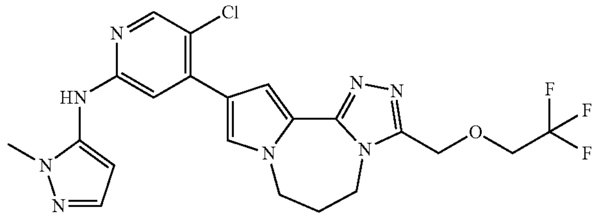 [SMILES: Cn1nccc1Nc1cc(-c2cc3n(c2)CCCn2c(COCC(F)(F)F)nnc2-3)c(Cl)cn1] | 493.1 | $^1$H NMR (400 MHz, DMSO-d6) δ 8.83 (s, 1H), 8.12 (s, 1H), 7.64 (d, J = 1.8 Hz, 1H), 7.32 (d, J = 1.6 Hz, 1H), 7.26 (d, J = 1.8 Hz, 1H), 6.96 (s, 1H), 6.22 (d, J = 1.6 Hz, 1H), 4.86 (s, 2H), 4.45-4.35 (m, 2H), 4.31-4.21 (m, 2H), 4.14 (q, J = 9.3 Hz, 2H), 3.65 (s, 3H), 2.34-2.30 (m, 2H). |
| 26 | 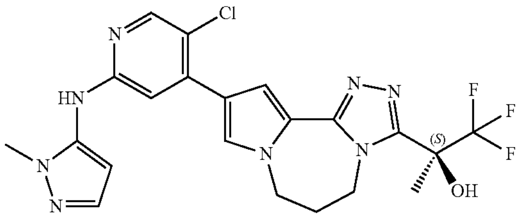 | 493.1 | $^1$H NMR (400 MHz, DMSO-d6) δ 8.82 (s, 1H), 8.12 (s, 1H), 7.70 (d, J = 1.9 Hz, 1H), 7.46 (s, 1H), 7.31 (d, J = 1.9 Hz, 1H), 7.17 (d, J = 1.9 Hz, 1H), 6.97 (s, 1H), 6.22 (d, J = 1.9 Hz, 1H), 4.59-4.35 (m, 2H), 4.33-4.24 (m, 2H), 3.65 (s, 3H), 2.38-2.21 (m, 2H), 1.85 (s, 3H). |
| 27 | 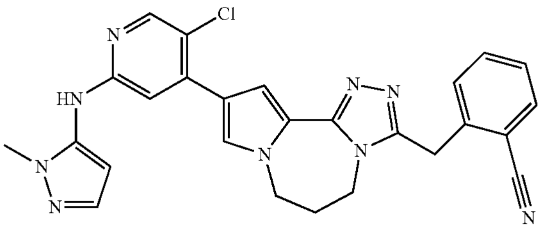 [SMILES: Cn1nccc1Nc1cc(-c2cc3n(c2)CCCn2c(Cc4ccccc4C#N)nnc2-3)c(Cl)cn1] | 496.1 | $^1$H NMR (400 MHz, DMSO-d6) δ 8.82 (s, 1H), 8.11 (s, 1H), 7.85 (d, J = 7.4 Hz, 1H), 7.65-7.63 (m, 2H), 7.48-7.46 (m, 1H), 7.37 (d, J = 7.4 Hz, 1H), 7.31-7.29 (m, 1H), 7.20 (s, 1H), 6.97 (s, 1H), 6.23-6.21 (m, 1H), 4.37-4.35 (m, 4H), 4.17-4.16 (m, 2H), 3.64 (s, 3H), 2.29-2.28 (m, 2H). |
| 28 | 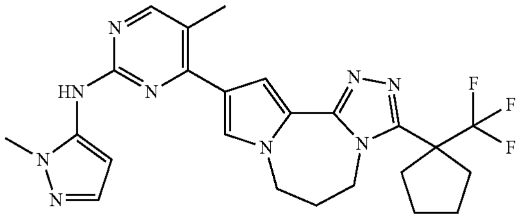 [SMILES: Cc1cnc(Nc2ccnn2C)nc1-c1cc2n(c1)CCCn1c-2nnc1C1(C(F)(F)F)CCCC1] | 498.2 | $^1$H NMR (400 MHz, DMSO-d6) δ 8.96 (s, 1H), 8.21 (s, 1H), 7.68 (d, J = 1.9 Hz, 1H), 7.35-7.27 (m, 2H), 6.25 (d, J = 1.9 Hz, 1H), 4.33-4.16 (m, 4H), 3.68 (s, 3H), 2.72-2.59 (m, 2H), 2.40-2.26 (m, 7H), 1.82-1.60 (m, 4H). |
| 29 | 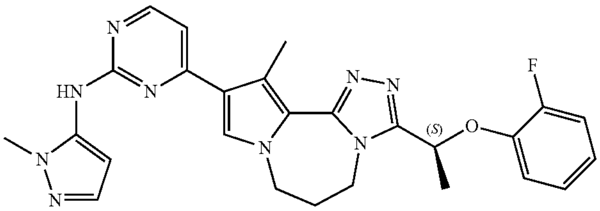 | 500.2 | $^1$H NMR (400 MHz, DMSO-d6) δ 9.08 (s, 1H), 8.29 (d, J = 5.1 Hz, 1H), 7.70 (s, 1H), 7.35-6.98 (m, 6H), 6.20-6.17 (m, 1H), 5.90-5.88 (m, 1H), 4.08-3.98 (m, 4H), 3.64 (s, 3H), 2.39 (s, 3H), 2.23-2.19 (m, 2H), 1.74 (d, J = 6.2 Hz, 3H). |
| 30 | 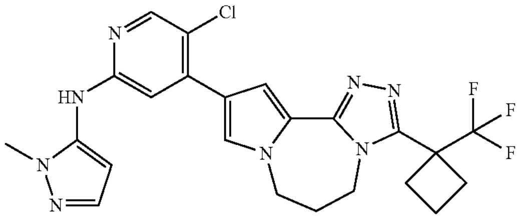 [SMILES: Cn1nccc1Nc1cc(-c2cc3n(c2)CCCn2c-3nnc2C2(C(F)(F)F)CCC2)c(Cl)cn1] | 503.1 | $^1$H NMR (400 MHz, DMSO-d6) δ 8.84 (s, 1H), 8.13 (s, 1H), 7.67 (d, J = 2.0 Hz, 1H), 7.32 (d, J = 1.9 Hz, 1H), 7.20 (d, J = 2.0 Hz, 1H), 6.98 (s, 1H), 6.22 (d, J = 1.9 Hz, 1H), 4.35-4.28 (m, 2H), 4.09-3.97 (m, 2H), 3.65 (s, 3H), 2.92-2.88 (m, 2H), 2.73-2.69 (m, 2H), 2.35-2.24 (m, 2H), 2.22-2.09 (m, 1H), 2.03-1.95 (m, 1H). |

-continued

| Compound | Structure | LC-MS (m/z) (M + H)+ | 1H NMR |
|---|---|---|---|
| 31 | 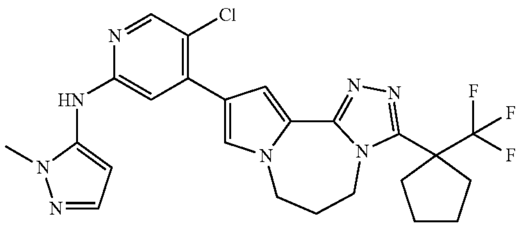 [SMILES: Cn1nccc1Nc1cc(-c2cc3n(c2)CCCn2c-3nnc2C2(C(F)(F)F)CCCC2)c(Cl)cn1] | 517.2 | 1H NMR (400 MHz, DMSO-d6) δ 8.84 (s, 1H), 8.12 (s, 1H), 7.69 (d, J = 1.9 Hz, 1H), 7.31 (d, J = 1.8 Hz, 1H), 7.15 (d, J = 1.9 Hz, 1H), 6.97 (s, 1H), 6.22 (d, J = 1.8 Hz, 1H), 4.27 (t, J = 6.1 Hz, 2H), 4.20 (t, J = 6.1 Hz, 2H), 3.65 (s, 3H), 2.70-2.59 (m, 2H), 2.39-2.26 (m, 4H), 1.78-1.59 (m, 4H). |
| 32 | 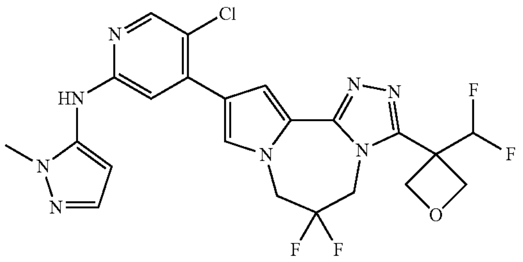 [SMILES: Cn1nccc1Nc1cc(-c2cc3n(c2)CC(F)(F)Cn2c-3nnc2C2(C(F)F)COC2)c(Cl)cn1] | 523.0 | 1H NMR (400 MHz, DMSO-d6) δ 8.86 (s, 1H), 8.15 (s, 1H), 7.87 (d, J = 1.9 Hz, 1H), 7.32 (d, J = 1.9 Hz, 1H), 7.12 (d, J = 1.9 Hz, 1H), 6.94 (s, 1H), 6.70 (t, J = 55.1 Hz, 1H), 6.22 (d, J = 1.9 Hz, 1H), 5.10-4.97 (m, 4H), 4.83 (t, J = 13.2 Hz, 2H), 4.44 (t, J = 12.8 Hz, 2H), 3.64 (s, 3H). |
| 33 | 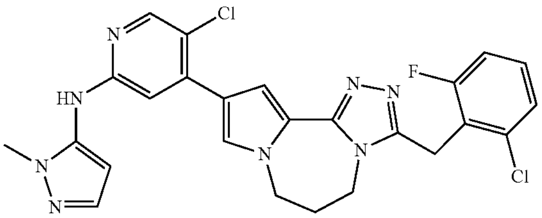 [SMILES: Cn1nccc1Nc1cc(-c2cc3n(c2)CCCn2c(Cc4c(F)cccc4Cl)nnc2-3)c(Cl)cn1] | 523.1 | 1H NMR (400 MHz, DMSO-d6) δ 8.82 (s, 1H), 8.11 (s, 1H), 7.64 (d, J = 2.0 Hz, 1H), 7.43-7.34 (m, 2H), 7.30-7.23 (m, 2H), 7.16 (d, J = 2.0 Hz, 1H), 6.98 (s, 1H), 6.22 (d, J = 1.8 Hz, 1H), 4.42-4.35 (m, 2H), 4.31-4.24 (m, 2H), 4.20 (s, 2H), 3.64 (s, 3H), 2.36-2.32 (m, 2H). |
| 34 | 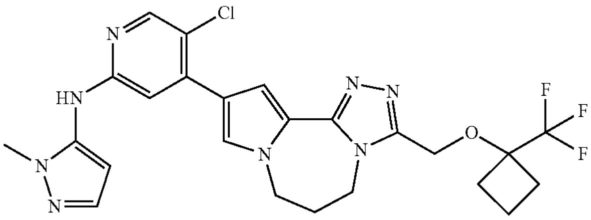 [SMILES: Cn1nccc1Nc1cc(-c2cc3n(c2)CCCn2c(COC4(C(F)(F)F)CCC4)nnc2-3)c(Cl)cn1] | 533.1 | 1H NMR (400 MHz, DMSO-d6) δ 8.81 (s, 1H), 8.12 (s, 1H), 7.64 (s, 1H), 7.33-7.31 (m, 1H), 7.25 (s, 1H), 6.96 (s, 1H), 6.23-6.21 (m, 1H), 4.83 (s, 2H), 4.40-4.38 (m, 2H), 4.26-4.25 (m, 2H), 3.65 (s, 3H), 2.51-2.48 (m, 4H), 2.34-2.30 (m, 4H). |
| 35 | 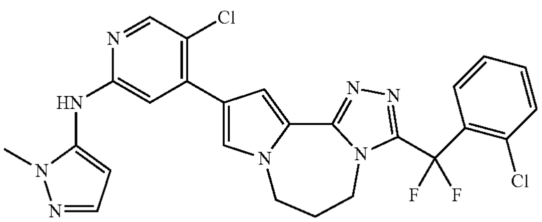 [SMILES: Cn1nccc1Nc1cc(-c2cc3n(c2)CCCn2c-3nnc2C(F)(F)c2ccccc2Cl)c(Cl)cn1] | 541.2 | 1H NMR (400 MHz, DMSO-d6) δ 8.86 (s, 1H), 8.13 (s, 1H), 7.81 (d, J = 7.7 Hz, 1H), 7.72 (s, 1H), 7.66-7.64 (m, 2H), 7.57-7.53 (m, 1H), 7.33-7.31 (m, 2H), 6.99 (s, 1H), 6.23 (s, 1H), 4.54-4.42 (m, 4H), 3.65 (s, 3H), 2.43-2.38 (m, 2H). |

Example 2: Synthesis of Compounds 36-38

Compound 36

N-(1-methyl-1H-pyrazol-5-yl)-4-(3-(phenoxymethyl)-6,7-dihydro-5H-pyrrolo[1,2-a][1,2,4]triazolo[3,4-c][1,4]diazepin-10-yl)pyrimidin-2-amine

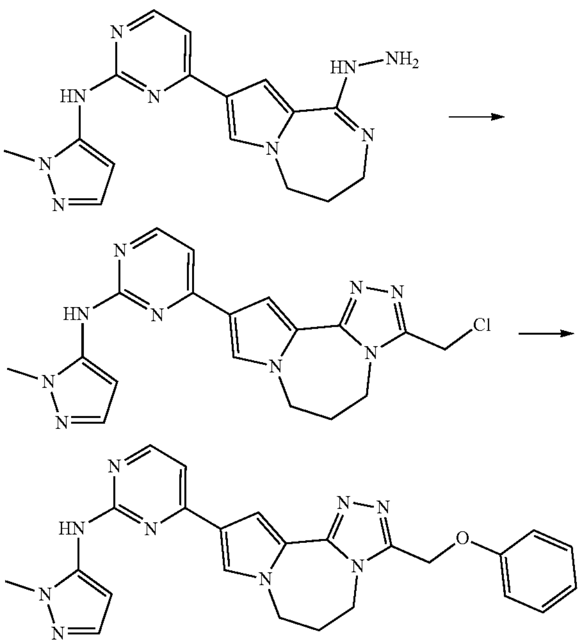

(A) 4-(3-(chloromethyl)-6,7-dihydro-5H-pyrrolo[1,2-a][1,2,4]triazolo[3,4-c][1,4]diazepin-10-yl)-N-(1-methyl-1H-pyrazol-5-yl)pyrimidin-2-amine To a solution of 4-(1-hydrazineyl-4,5-dihydro-3H-pyrrolo[1,2-a][1,4]diazepin-8-yl)-N-(1-methyl-1H-pyrazol-5-yl)pyrimidin-2-amine (500 mg, 1.48 mmol) in DCM (50 mL) was added DIPEA (287 mg, 2.22 mmol) and then 2-chloroacetyl chloride (201 mg, 1.78 mmol) slowly at 0° C. Then the mixture was stirred overnight at room temperature and then refluxed for 3 hours. The mixture was diluted with THF (100 mL) and water (100 mL). The aqueous layer was extracted with THF. The combined organic layers were washed with brine, dried over anhydrous sodium sulfate, concentrated to give brown oil (587 mg) which was used in the next step directly. MS (m/z): 454.2 $(M+H)^+$.

(B) N-(1-methyl-1H-pyrazol-5-yl)-4-(3-(phenoxymethyl)-6,7-dihydro-5H-pyrrolo[1,2-a][1,2,4]triazolo[3,4-c][1,4]diazepin-10-yl)pyrimidin-2-amine To a solution of 4-(3-(chloromethyl)-6,7-dihydro-5H-pyrrolo[1,2-a][1,2,4]triazolo[3,4-c][1,4]diazepin-10-yl)-N-(1-methyl-1H-pyrazol-5-yl)pyrimidin-2-amine (73.4 mg, 0.19 mmol) in DMF (5 mL) was added cesium carbonate (151 mg, 0.46 mmol) and phenol (34.9 mg, 0.37 mmol). The resulting mixture was stirred at 60° C. for 1 h. After cooling, the reaction mixture was directly purified via ISCO (eluting with methanol in water 0%~100%) and PTLC (DCM: MeOH=12/1) to afford the title compound as a light yellow solid (19.1 mg, 22.7+) yield). MS (m/z): 396.2 $(M+H)^+$. $^1$H NMR (400 MHz, DMSO-d6) δ 9.26 (s, 1H), 8.31 (s, 1H), 7.71 (s, 1H), 7.42 (s, 1H), 7.37-7.24 (m, 3H), 7.15-7.04 (m, 3H), 7.03-6.92 (m, 1H), 6.28 (s, 1H), 5.30 (s, 2H), 4.45-4.34 (m, 2H), 4.34-4.24 (m, 2H), 3.68 (s, 3H), 2.38-42.27 (m, 2H).

The compounds below were prepared according to the procedures of Compound 36 using the corresponding intermediates and reagents under appropriate conditions that could be recognized by one skilled in the art.

| Compound | Structure | LC-MS (m/z) (M + H)+ | $^1$H NMR |
|---|---|---|---|
| 37 | 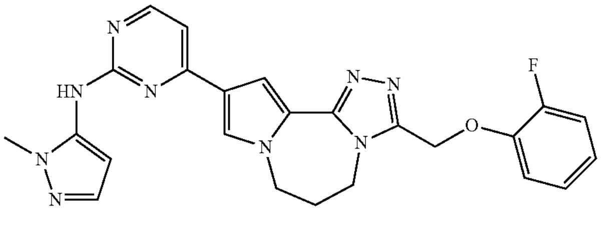 [SMILES: Cn1nccc1Nc1nccc(-c2cc3n(c2)CCCn2c(COc4ccccc4F)nnc2-3)n1] | 472.2 | $^1$H NMR (400 MHz, DMSO-d6) δ 9.22 (s, 1H), 8.30 (d, J = 4.7 Hz, 1H), 7.71 (s, 1H), 7.46-7.36 (m, 2H), 7.32 (s, 1H), 7.25-7.17 (m, 1H), 7.17-7.12 (m, 1H), 7.10 (d, J = 4.7 Hz, 1H), 7.05-6.93 (m, 1H), 6.26 (s, 1H), 5.38 (s, 2H), 4.43-4.35 (m, 2H), 4.35-4.28 (m, 2H), 3.67 (s, 3H), 2.38-2.28 (m, 2H). |
| 38 | 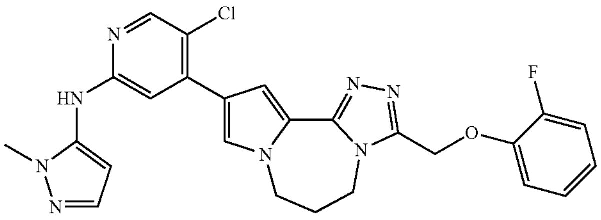 [SMILES: Cn1nccc1Nc1cc(-c2cc3n(c2)CCCn2c(COc4ccccc4F)nnc2-3)c(Cl)cn1] | 505.2 | $^1$H NMR (400 MHz, DMSO-d6) δ 8.83 (s, 1H), 8.12 (s, 1H), 7.65 (s, 1H), 7.46-7.35 (m, 1H), 7.31 (s, 1H), 7.26 (s, 1H), 7.24-7.10 (m, 2H), 7.02-6.93 (m, 2H), 6.22 (s, 1H), 5.39 (s, 2H), 4.47-4.37 (m, 2H), 4.37-4.23 (m, 2H), 3.65 (s, 3H), 2.39-2.26 (m, 2H). |

Example 3: Synthesis of Compounds 39-40

Compound 39

(S)-4-(3-(I-(2-fluorophenoxy)ethyl)pyrrolo[1,2-a][1,2,4]triazolo[3,4-c]pyrazin-9-yl)-N-(1-methyl-1H-pyrazol-5-yl)pyrimidin-2-amine

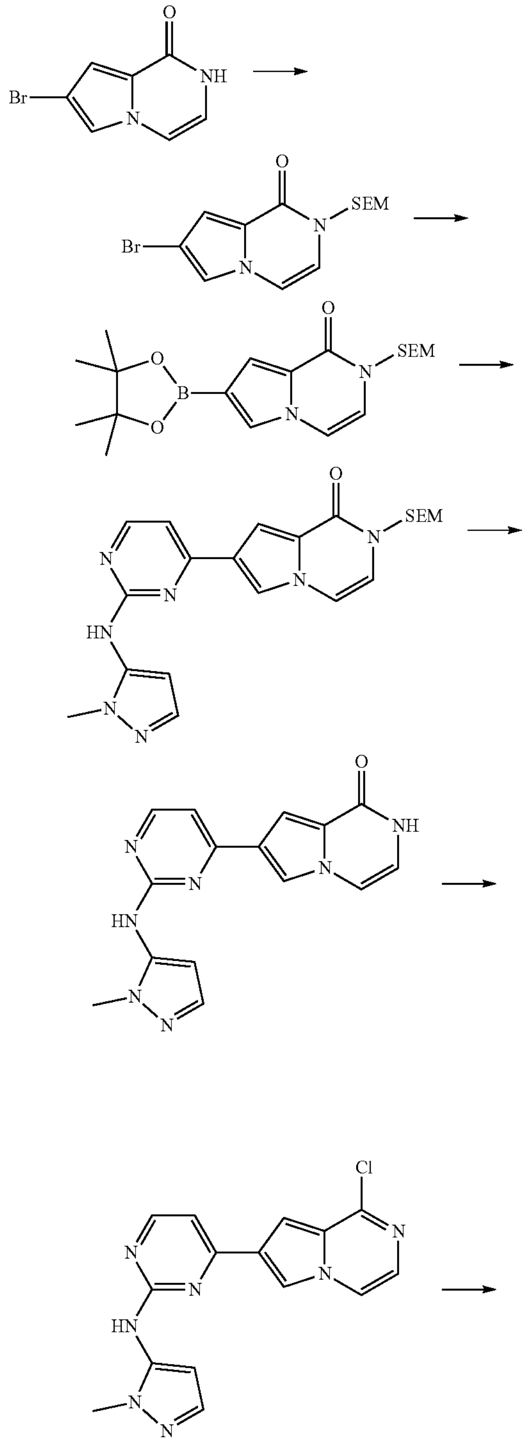

-continued

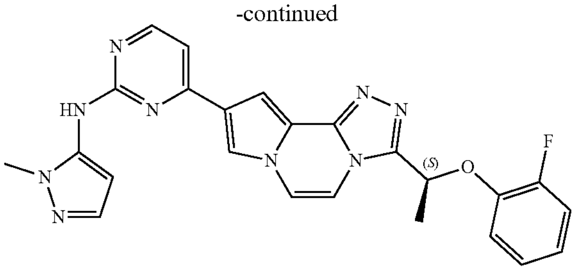

(A) 7-bromo-2-((2-(trimethylsilyl)ethoxy)methyl)pyrrolo[1,2-a]pyrazin-1(2H)-one

To a solution of 7-bromopyrrolo[1,2-a]pyrazin-1(2H)-one (21.3 g, 100 mmol) in anhydrous DMF (100 mL) was added NaH (6 g, 150 mmol, 60% dispersion in Paraffin Liquid) at 0° C. The mixture was stirred at 0° C. for 0.5 h and then 2-(trimethylsilyl)ethoxy methyl chloride (21.6 g, 130 mmol) was added. The mixture was stirred at room temperature overnight and poured into ice-water, extracted by EA, concentrated and purified via ISCO (PE/EA=5:1) to afford the title compound as a yellow solid (16 g, 47% yield).). MS (m/z): 342.9/344.9 $(M+H)^+$.

(B) 7-(4,4,5,5-tetramethyl-1,3,2-dioxaborolan-2-yl)-2-((2-(trimethylsilyl)ethoxy)methyl)pyrrolo[1,2-a]pyrazin-1(2H)-one A mixture of 7-bromo-2-((2-(trimethylsilyl)ethoxy)methyl)pyrrolo[1,2-a]pyrazin-1(2H)-one (8.5 g, 24.8 mmol), BPIN (9.44 g, 37.2 mmol), $Pd_2(dba)_3$ (0.68 g, 7.44 mmol), KOAc (4.86 g, 49.6 mmol) and tricyclohexylphosphine (0.417, 1.488 mmol) in 1,4-dioxane (120 mL) was stirred at 100° C. for 4 hours under nitrogen atmosphere. The mixture was diluted with water and extracted by EA. The organic layer was concentrated, purified via ISCO (PE/EA=5:1) to afford the title compound as a yellow solid (8.1 g, 84% yield). MS (m/z): 391.1 $(M+H)^+$.

(C) 7-(2-((1-methyl-1H-pyrazol-5-yl)amino)pyrimidin-4-yl)-2-((2-(trimethylsilyl)ethoxy)methyl)pyrrolo[1,2-a]pyrazin-1(2H)-one A mixture of 4-chloro-N-(1-methyl-1H-pyrazol-5-yl)pyrimidin-2-amine (627 mg, 3 mmol), 7-(4,4,5,5-tetramethyl-1,3,2-dioxaborolan-2-yl)-2-((2-(trimethylsilyl)ethoxy)methyl)pyrrolo[1,2-a]pyrazin-1(2H)-one (1170 mg, 3 mmol), $Pd(dppf)Cl_2 \cdot CH_2Cl_2$ (122 mg, 0.15 mmol) and $Na_2CO_3$ (636 mg, 3 mmol) in 1,4-dioxane (20 mL) and water (2 mL) was stirred at 100° C. for 3 hours under nitrogen atmosphere. The mixture was diluted with water and extracted by EA. The organic layer was concentrated, purified via ISCO (DCM/MeOH=20:1) to afford the title compound as a brown solid (800 mg, 61% yield). MS (m/z):438.2 $(M+H)^+$.

(D) 7-(2-((1-methyl-1H-pyrazol-5-yl)amino)pyrimidin-4-yl)pyrrolo[1,2-a]pyrazin-1(2H)-one A solution of 7-(2-((1-methyl-1H-pyrazol-5-yl)amino)pyrimidin-4-yl)-2-((2-(trimethylsilyl)ethoxy)methyl)pyrrolo

[1,2-a]pyrazin-1(2H)-one (800 mg, 1.8 mmol) in TFA (3 mL) was stirred at room temperature for 0.5 h. The volatiles were removed under reduced pressure and ammonium hydroxide was added. Filtered and the cake was washed by water, dried to afford the title compound as yellow solid (500 mg). MS (m/z): 380.0 $(M+H)^+$.

(E) (S)-4-(3-(1-(2-fluorophenoxy)ethyl)pyrrolo[1,2-a][1,2,4]triazolo[3,4-c]pyrazin-9-yl)-N-(1-methyl-1H-pyrazol-5-yl)pyrimidin-2-amine A mixture of 7-(2-((1-methyl-1H-pyrazol-5-yl)amino)pyrimidin-4-yl)pyrrolo[1,2-a]pyrazin-1(2H)-one (93 mg, 0.3 mmol) in $POCl_3$ (2 mL) was stirred at 100° C. for 1 h. The volatiles were removed under reduced pressure and aqueous $NaHCO_3$ was added to adjust the PH=8. The aqueous layer was extracted by DCM. The organic layer was dried over anhydrous $Na_2SO_4$, concentrated. The residue was dissolved in EtOH (5 mL) and (S)-2-(2-fluorophenoxy)propanehydrazide (59 mg, 0.30 mmol) was added. The resulting mixture was refluxed for overnight. The volatiles were removed under reduced pressure and the residue was purified via ISCO (eluting with MeOH in water 0~100%) to afford the title compound as a yellow solid (85 mg, 60% yield). MS (m/z): 470.1 $(M+H)^+$. $^1H$ NMR (400 MHz, $CD_3OD$) δ 8.31 (d, J=5.2 Hz, 1H), 8.07 (s, 1H), 7.77 (d, J=6.0 Hz, 1H), 7.98 (d, J=6.0 Hz, 1H), 7.60 (s, 1H), 7.42 (d, J=2.0 Hz, 1H), 7.20-6.97 (m, 5H), 6.35 (d, J=2.0 Hz, 1H), 5.97-5.92 (m, 1H), 3.75 (s, 3H), 1.88 (d, J=6.8 Hz, 3H).

The compound below was prepared according to the procedures of Compound 39 using the corresponding intermediates and reagents under appropriate conditions that could be recognized by one skilled in the art.

Example 4: Synthesis of Compounds 41-43

Compound 41

N-(2-fluorophenyl)-9-(2-((1-methyl-1H-pyrazol-5-yl)amino)pyrimidin-4-yl)pyrrolo[1,2-a][1,2,4]triazolo[3,4-c]pyrazin-3-amine

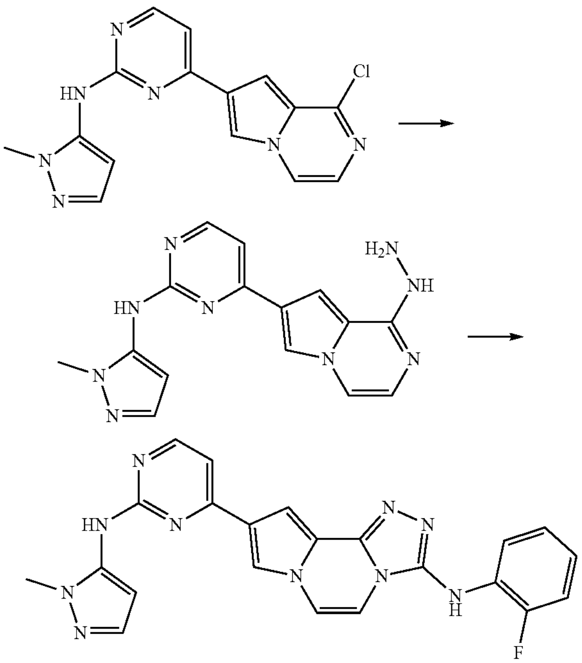

To a solution of 4-(1-chloropyrrolo[1,2-a]pyrazin-7-yl)-N-(1-methyl-1H-pyrazol-5-yl)pyrimidin-2-amine (130 mg, 0.40 mmol) in THF (5 mL) was added hydrazine hydrate (2 mL, 85%) and then the mixture was heated at 80° C. for 4 hours. Then the mixture was extracted with DCM. The combined organic layers were dried over anhydrous sodium

| Compound | Structure | LC-MS (m/z) $(M+H)^+$ | $^1H$ NMR |
|---|---|---|---|
| 40 | 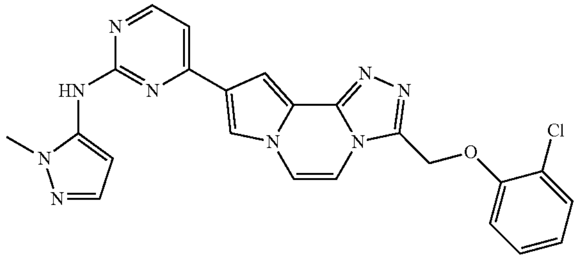 | 472.1 | $^1H$ NMR (400 MHz, DMSO-d6) δ 9.34 (s, 1H), 8.43 (d, J = 5.2 Hz, 1H), 8.26 (d, J = 1.6 Hz, 1H), 8.06 (d, J = 6.0 Hz, 1H), 7.82 (d, J = 6.0 Hz, 1H), 7.65 (s, 1H), 7.44-7.43 (m, 1H), 7.42-7.41 (m, 1H), 7.36-7.31 (m, 3H), 7.04-6.98 (m, 1H), 6.29 (d, J = 1.6 Hz, 1H), 5.66 (s, 2H), 3.69 (s, 3H). |

sulfate and concentrated. The residue was dissolved in DCM (5 mL), 1-fluoro-2-isocyanatobenzene (70 mg, 0.51 mmol) and $POCl_3$ (3 mL) was added and the resulting mixture was heated at 60° C. for 3 h. The volatiles were removed under reduced pressure and the residue was adjusted to pH=8 with aqueous $NaHCO_3$. The aqueous layer was extracted by DCM. The organic layer was dried over anhydrous $Na_2SO_4$, concentrated. The residue was purified via ISCO (eluting with MeOH in water 0~100%) to afford the title compound as a yellow solid (15.0 mg, 10.0% yield). MS (m/z): 441.1 $(M+H)^+$. $^1H$ NMR (400 MHz, DMSO-d6) δ 9.32 (s, 1H), 8.41 (d, J=5.2 Hz, 1H), 8.17 (d, J=1.2 Hz, 1H), 7.89-7.85 (m, 1H), 7.84 (d, J=6.4 Hz, 1H), 7.66 (d, J=6.4 Hz, 1H), 7.50 (s, 1H), 7.34 (d, J=2.0 Hz, 1H), 7.31 (d, J=5.2 Hz, 1H), 7.21-7.18 (m, 1H), 7.11-7.07 (m, 1H), 6.91-6.86 (m, 1H), 6.30 (d, J=2.0 Hz, 1H), 3.69 (s, 3H).

The compounds below were prepared according to the procedures of Compound 41 using the corresponding intermediates and reagents under appropriate conditions that could be recognized by one skilled in the art.

-continued

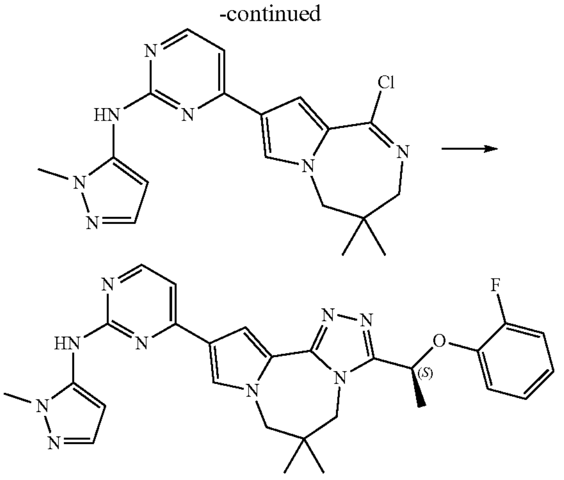

| Compound | Structure | LC-MS (m/z) $(M + H)^+$ | $^1H$ NMR |
|---|---|---|---|
| 42 | 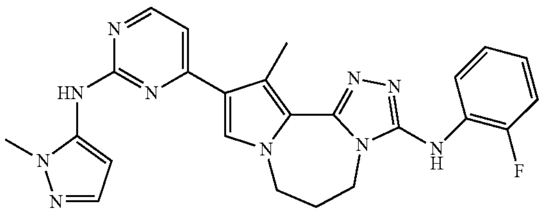 [SMILES: Cc1c(-c2ccnc(Nc3ccnn3C)n2)cn2c1-c1nnc(Nc3ccccc3F)n1CCC2] | 471.0 | $^1H$ NMR (400 MHz, DMSO-d6) δ 9.08 (s, 1H), 8.49 (s, 1H), 8.29 (d, J = 4.7 Hz, 1H), 7.76-7.66 (m, 2H), 7.32 (s, 1H), 7.17-6.92 (m, 4H), 6.19 (s, 1H), 4.13-4.09 (m, 2H), 3.94-3.90 (m, 2H), 3.65 (s, 3H), 2.43 (s, 3H), 2.27-2.24 (m, 2H). |
| 43 | 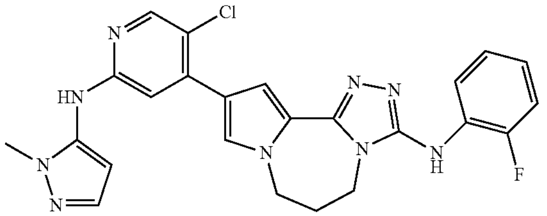 [SMILES: Cn1nccc1Nc1cc(-c2cc3n(c2)CCCn2c(Nc4ccccc4F)nnc2-3)c(Cl)cn1] | 490.1 | $^1H$ NMR (400 MHz, DMSO-d6) δ 8.83 (s, 1H), 8.33 (s, 1H), 8.12 (s, 1H), 7.63 (s, 1H), 7.56-7.52 (m, 1H), 7.32 (s, 1H), 7.24-7.15 (m, 2H), 7.12-7.06 (m, 1H), 6.98 (s, 1H), 6.95-6.88 (m, 1H), 6.23 (s, 1H), 4.43-4.32 (m, 2H), 4.14-4.01 (m, 2H), 3.66 (s, 3H), 2.36-2.27 (m, 2H). |

Example 5: Synthesis of Compounds 44-52

Compound 44

(S)-4-(3-(1-(2-fluorophenoxy)ethyl)-6,6-dimethyl-6,7-dihydro-5H-pyrrolo[1,2-a][1,2,4]triazolo[3,4-c][1,4]diazepin-10-yl)-N-(1-methyl-1H-pyrazol-5-yl)pyrimidin-2-amine

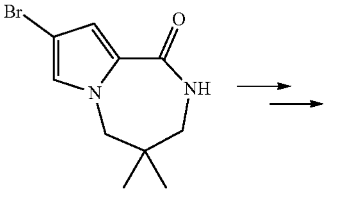

(A) 4-(1-chloro-4,4-dimethyl-4,5-dihydro-3H-pyrrolo[1,2-a][1,4]diazepin-8-yl)-N-(1-methyl-1H-pyrazol-5-yl)pyrimidin-2-amine The title intermediate was prepared according to the procedures of Example 1 using the corresponding intermediates and reagents.

(B) (S)-4-(3-(1-(2-fluorophenoxy)ethyl)-6,6-dimethyl-6,7-dihydro-5H-pyrrolo[1,2-a][1,2,4]triazolo[3,4-c][1,4]diazepin-10-yl)-N-(1-methyl-1H-pyrazol-5-yl)pyrimidin-2-amine A mixture of 4-(1-chloro-4,4-dimethyl-4,5-dihydro-3H-pyrrolo[1,2-a][1,4]diazepin-8-yl)-N-(1-methyl-1H-pyrazol-5-yl)pyrimidin-2-amine (111 mg, 0.3 mmol) and (S)-2-(2-fluorophenoxy)propanehydrazide (59 mg, 0.3 mmol) in EtOH (0 mL) was refluxed overnight. The mixture was concentrated and the residue was purified via ISCO (eluting with MeOH in water 0~100%) to afford the title compound as a yellow solid (40 mg, 260 yield). MS (m/z): 514.2 $(M+H)^+$. $^1H$ NMR (400 MHz, $CD_3OD$) δ 8.26 (d, J=5.2 Hz, 1H), 7.70 (d, J=1.6 Hz, 1H), 7.42 (d, J=2.0 Hz, 1H), 7.38 (d, J=1.6 Hz, 1H), 7.24-7.20 (m, 1H), 7.17-7.09 (m, 2H), 7.07-7.00 (m, 2H), 6.33 (d, J=2.0 Hz, 1H), 5.81-5.76 (m, 1H), 4.00 (s, 2H), 3.92 (s, 2H), 3.74 (s, 3H), 1.81 (d, J=6.8 Hz, 3H), 1.11 (s, 3H), 1.16 (s, 3H).

The compounds below were prepared according to the procedures of Compound 44 using the corresponding intermediates and reagents under appropriate conditions that could be recognized by one skilled in the art.

| Compound | Structure | LC-MS (m/z) $(M + H)^+$ | $^1H$ NMR |
|---|---|---|---|
| 45 | 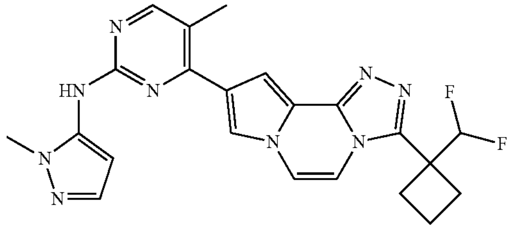 [SMILES: Cc1cnc(Nc2ccnn2C)nc1-c1cc2c3nnc(C4(C(F)F)CCC4)n3ccn2c1] | 450.1 | $^1H$ NMR (400 MHz, DMSO-d6) δ 9.20 (s, 1H), 8.31 (s, 1H), 8.24 (d, J = 1.6 Hz, 1H), 7.92 (d, J = 6.0 Hz, 1H), 7.55 (s, 1H), 7.40 (d, J = 6.0 Hz, 1H), 7.35 (d, J = 2.0 Hz, 1H), 6.56 (t, J = 56 Hz, 1H), 6.28 (d, J = 2.0 Hz, 1H), 3.68 (s, 3H), 2.78-2.60 (m, 4H), 2.38 (s, 3H), 2.22-2.13 (m, 1H), 2.01-1.91 (m, 1H). |
| 46 | 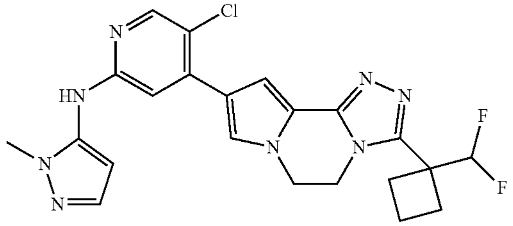 [SMILES: Cn1nccc1Nc1cc(-c2cc3n(c2)CCn2c-3nnc2C2(C(F)F)CCC2)c(Cl)cn1] | 471.0 | $^1H$ NMR (400 MHz, DMSO-d6) δ 8 81 (s, 1H), 8.12 (s, 1H), 7.72 (s, 1H), 7.33-7.30 (m, 1H), 7.03 (s, 1H), 6.95 (s, 1H), 6.46 (t, J = 56.0 Hz, 1H), 6.22-6.20 (m, 1H), 4.38-4.36 (m, 2H), 4.25-4.24 (m, 2H), 3.65 (s, 3H), 2.69-2.67 (m, 2H), 2.52-2.48 (m, 2H), 2.11-2.10 (m, 1H), 1.96-1.93 (m, 1H). |
| 47 | 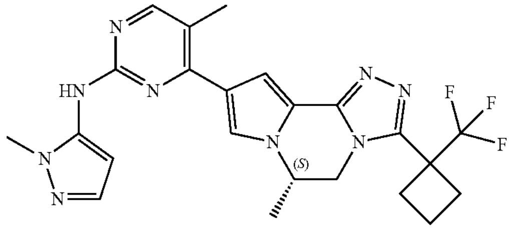 | 484.1 | $^1H$ NMR (400 MHz, DMSO-d6) δ 9.10 (s, 1H), 8.23 (s, 1H), 7.77 (d, J = 1.5 Hz, 1H), 7.33 (d, J = 1.8 Hz, 1H), 7.27 (d, J = 1.5 Hz, 1H), 6.26 (d, J = 1.8 Hz, 1H), 4.77-4.75 (m, 1H), 4.36-4.32 (m, 1H), 4.11-4.07 (m, 1H), 3.67 (s, 3H), 2.88-2.84 (m, 2H), 2.72-2.68 (m, 2H), 2.34 (s, 3H), 2.17-2.13 (m, 1H), 2.02-1.95 (m, 1H), 1.38 (d, J = 6.6 Hz, 3H). |
| 48 | 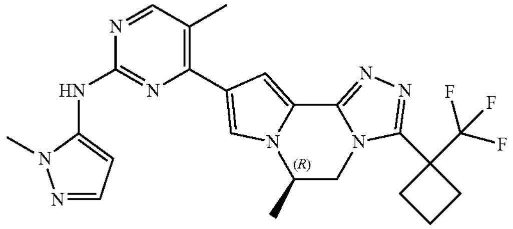 | 484.1 | $^1H$ NMR (400 MHz, DMSO-d6) δ 9.10 (s, 1H), 8.23 (s, 1H), 7.76 (s, 1H), 7.33 (d, J = 1.8 Hz, 1H), 7.27 (s, 1H), 6.26 (d, J = 1.8 Hz, 1H), 4.78-4.74 (m, 1H), 4.36-4.32 (m, 1H), 4.11-4.07 (m, 1H), 3.67 (s, 3H), 2.89-2.83 (m, 2H), 2.75-2.69 (m, 2H), 2.34 (s, 3H), 2.16-2.12 (m, 1H), 2.03-1.95 (m, 1H), 1.36 (d, J = 6.5 Hz, 3H). |
| 49 | 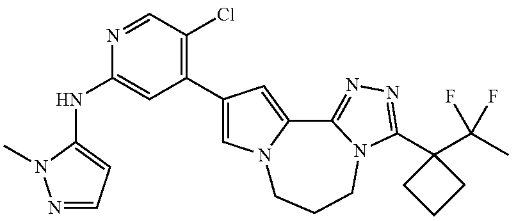 [SMILES: Cn1nccc1Nc1cc(-c2cc3n(c2)CCCn2c-3nnc2C2(C(C)(F)F)CCC2)c(Cl)cn1] | 499.1 | $^1H$ NMR (400 MHz, DMSO-d6) δ 8.81 (s, 1H), 8.11 (s, 1H), 7.66 (d, J = 2.0 Hz, 1H), 7.31 (d, J = 1.9 Hz, 1H), 7.15 (d, J = 2.0 Hz, 1H), 6.95 (s, 1H), 6.21 (d, J = 1.9 Hz, 1H), 4.35-4.24 (m, 2H), 4.08-3.96 (m, 2H), 3.64 (s, 3H), 2.80-2.69 (m, 2H), 2.65-2.59 (m, 2H), 2.30-2.21 (m, 2H), 2.07-1.86 (m, 2H), 1.50 (t, J = 19.2 Hz, 3H). |
| 50 | 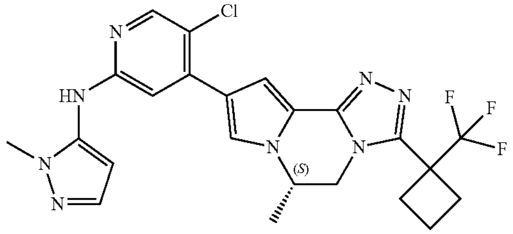 | 503.1 | $^1H$ NMR (400 MHz, DMSO-d6) δ 8.84 (s, 1H), 8.14 (s, 1H), 7.76 (s, 1H), 7.32 (d, J = 1.8 Hz, 1H), 7.08 (s, 1H), 6.98 (s, 1H), 6.23 (d, J = 1.8 Hz, 1H), 4.75-4.71 (m, 1H), 4.36-4.32 (m, 1H), 4.11-4.07 (m, 1H), 3.66 (s, 3H), 2.87-2.83 (m, 2H), 2.73-2.69 (m, 2H), 2.16-2.12 (m, 1H), 2.03-1.99 (m, 1H), 1.40 (d, J = 8.6 Hz, 3H). |

-continued
| Compound | Structure | LC-MS (m/z) (M + H)+ | $^1$H NMR |
|---|---|---|---|
| 51 | 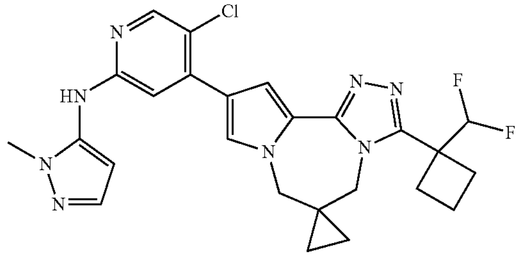 [SMILES: Cn1nccc1Nc1cc(-c2cc3n(c2)CC2(CC2)Cn2c-3nnc2C2(C(F)F)CCC2)c(Cl)cn1] | 511.1 | $^1$H NMR (400 MHz, DMSO-d6) δ 8.83 (s, 1H), 8.11 (s, 1H), 7.53 (d, J = 2.0 Hz, 1H), 7.31 (d, J = 2.0 Hz, 1H), 7.28 (d, J = 2.0 Hz, 1H), 6.98 (s, 1H), 6.42 (t, J = 56 Hz, 1H), 6.22 (d, J = 2.0 Hz, 1H), 4.26 (s, 2H), 3.96 (s, 2H), 3.65 (s, 3H), 2.67-2.60 (m, 2H), 2.52-2.45 (m, 2H), 2.13-2.06 (m, 1H), 1.97-1.85 (m, 1H), 0.74-0.70 (m, 4H). |
| 52 | 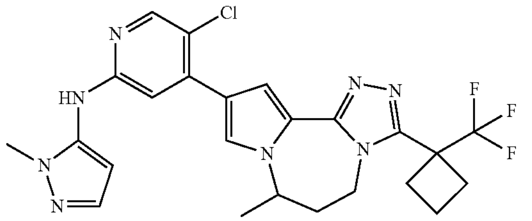 [SMILES: CC1CCn2c(nnc2C2(C(F)(F)F)CCC2)-c2cc(-c3cc(Nc4ccnn4C)ncc3Cl)cn21] | 517.1 | $^1$H NMR (400 MHz, DMSO-d6) δ 8.90 (s, 1H), 8.13 (s, 1H), 7.71 (d, J = 1.6 Hz, 1H), 7.32 (d, J = 1.6 Hz, 1H), 7.19 (d, J = 1.6 Hz, 1H), 7.00 (s, 1H), 6.23 (d, J = 1.6 Hz, 1H), 4.63-4.58 (m, 1H), 4.06-3.99 (m, 2H), 3.66 (s, 3H), 2.95-2.88 (m, 2H), 2.74-2.69 (m, 2H), 2.44-2.39 (m, 1H), 2.24-2.11 (m, 2H), 2.01-1.95 (m, 1H), 1.46 (d, J = 6.4 Hz, 3H). |
Example 6: Synthesis of Compounds 53-54
Compound 53
5-Chloro-4-(3-(indolin-1-yl)-6,7-dihydro-5H-pyrrolo[1,2-a][1,2,4]triazolo[3,4-c][1,4]diazepin-10-yl)-N-(1-methyl-1H-pyrazol-5-yl)pyridin-2-amine
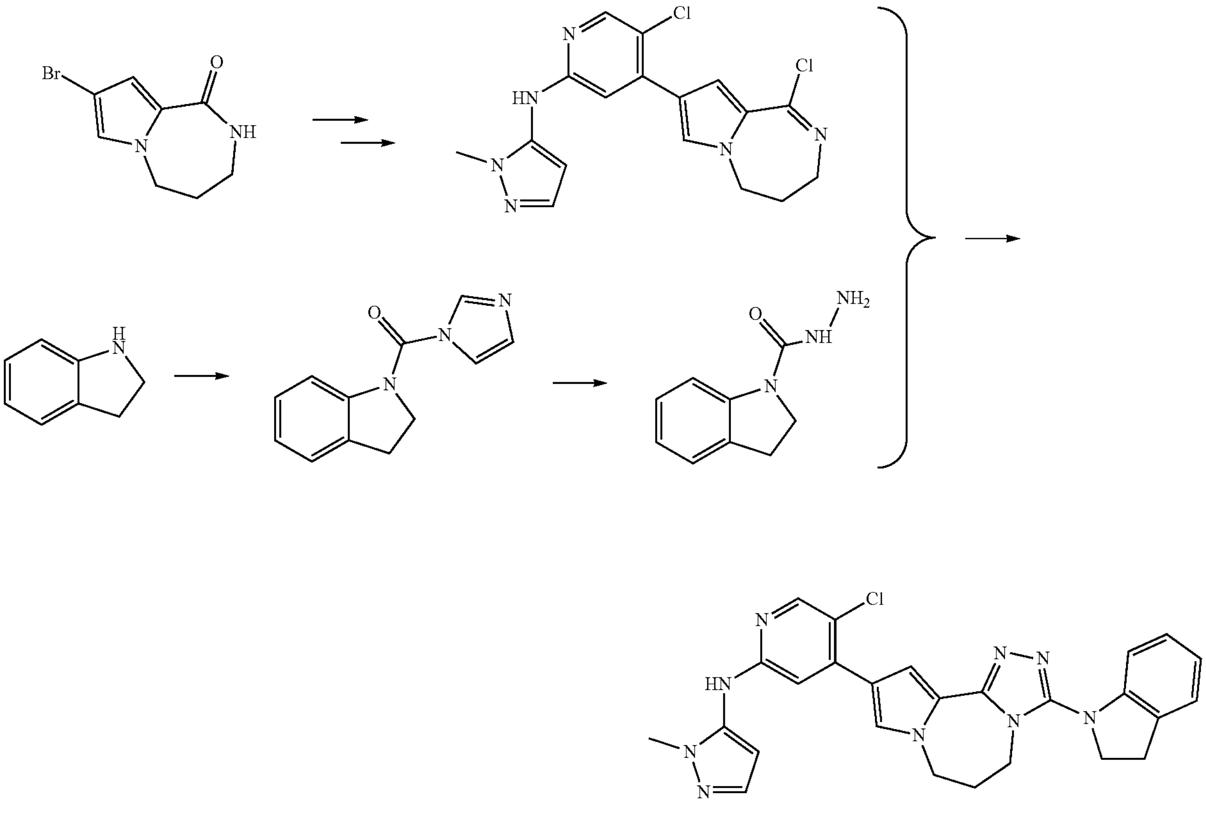

(A) 5-chloro-4-(1-chloro-4,5-dihydro-3H-pyrrolo[1,2-a][1,4]diazepin-8-yl)-N-(1-methyl-1H-pyrazol-5-yl)pyridin-2-amine The title intermediate was prepared according to the procedures of Example 1 using the corresponding intermediates and reagents (B) indoline-1-carbohydrazide To a solution of indoline (500 mg, 4.2 mmol) in DMF (5 mL) and DIPEA (0.76 mL, 4.6 mmol), was added CDI (750 mg, 4.6 mmol) portionwise at 0° C. The reaction mixture was stirred at room temperature for 2 hours and diluted with water (100 mL), extracted by EA (200 mL×2). The combined organic layers were washed with brine (100 mL), dried over anhydrous sodium sulfate, filtered, and concentrated. The residue was dissolved in THF (10 mL) and hydrazine hydrate (20 mL, 85%) was added. The reaction mixture was stirred at room temperature for 1 h. Removed the solvent and the residue was partitioned between EA (50 mL) and brine (30 mL). The organic layer was dried over anhydrous sodium sulfate, filtered, and concentrated to yield the title compound (600 mg, crude), which was used directly in the next step without further purification. MS (m/z): 178.1 $(M+H)^+$.

(C) 5-Chloro-4-(3-(indolin-1-yl)-6,7-dihydro-5H-pyrrolo[1,2-a][1,2,4]triazolo[3,4-c][1,4]diazepin-10-yl)-N-(1-methyl-1H-pyrazol-5-yl)pyridin-2-amine A mixture of 5-chloro-4-(1-chloro-4,5-dihydro-3H-pyrrolo[1,2-a][1,4]diazepin-8-yl)-N-(1-methyl-1H-pyrazol-5-yl)pyridin-2-amine (60 mg, 0.16 mmol) and indoline-1-carbohydrazide (43 mg, 0.24 mmol) in $POCl_3$ (5 mL) was stirred at 60° C. for 3 h and then 90° C. for 4 h. The volatiles were removed under reduced pressure and the residue was adjusted to pH=10 with 2M solution of NaOH, extract with DCM (30 mL×2). The combined organic layers were washed with brine (30 mL), concentrated and purified by PTLC (DCM/MeOH=13/1) to give the title compound as a yellow solid (12 mg, 15% yield). MS (m/z): 498.2 $(M+H)^+$.

$^1$H NMR (400 MHz, DMSO-d6) δ 8.83 (s, 1H), 8.13 (s, 1H), 7.64 (d, J=2.0 Hz, 1H), 7.32 (d, J=1.9 Hz, 1H), 7.25-7.21 (m, 2H), 7.04 (t, J=7.7 Hz, 1H), 6.99 (s, 1H), 6.80 (t, J=7.4 Hz, 1H), 6.68 (d, J=7.9 Hz, 1H), 6.23 (d, J=1.9 Hz, 1H), 4.49-4.40 (m, 2H), 4.14-4.05 (m, 2H), 3.93 (t, J=8.3 Hz, 2H), 3.66 (s, 3H), 3.13 (t, J=8.2 Hz, 2H), 2.34-2.30 (m, 2H).

The compound below was prepared according to the procedures of Compound 53 using the corresponding intermediates and reagents under appropriate conditions that could be recognized by one skilled in the art.

| Compound | Structure | LC-MS (m/z) (M + H)$^+$ | $^1$H NMR |
|---|---|---|---|
| 54 | 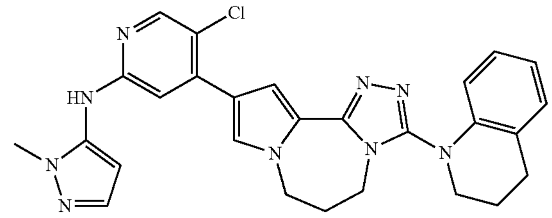 [SMILES: Cn1nccc1Nc1cc(-c2cc3n(c2)CCCn2c-3nnc2N2CCCc3ccccc32)c(Cl)cn1] | 512.2 | $^1$H NMR (400 MHz, DMSO-d6) δ 8.83 (s, 1H), 8.13 (s, 1H), 7.63 (d, J = 2.1 Hz, 1H), 7.32-7.28 (m, 2H), 7.05 (d, J = 7.5 Hz, 1H), 6.99 (s, 1H), 6.93 (t, J = 7.7 Hz, 1H), 6.72 (t, J = 7.4 Hz, 1H), 6.24-6.20 (m, 2H), 4.45-4.36 (m, 2H), 3.97-3.87 (m, 2H), 3.66 (s, 3H), 3.61-3.53 (m, 2H), 2.83 (t, J = 6.4 Hz, 2H), 2.28-2.24 (m, 2H), 2.02-1.98 (m, 2H). |

Example 7: Synthesis of Compounds 55-210

Compound 55

5-chloro-N-(1-methyl-1H-pyrazol-5-yl)-4-(3'-(1-(trifluoromethyl)cyclobutyl)-5'H,7'H-spiro[cyclobutane-1,6'-pyrrolo[1,2-a][1,2,4]triazolo[3,4-c][1,4]diazepin]-10'-yl)pyridin-2-amine

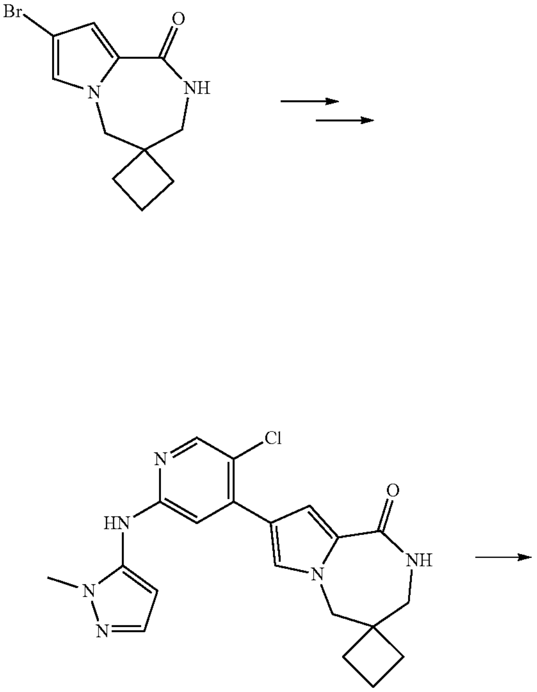

-continued

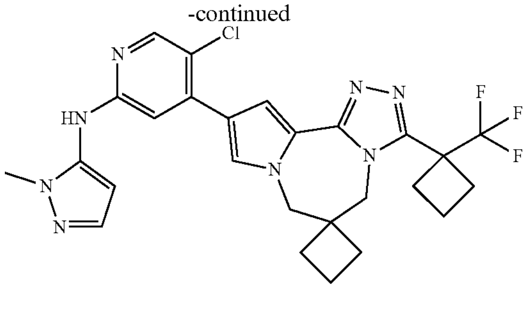

(A) 8'-(5-chloro-2-((1-methyl-1H-pyrazol-5-yl)amino)pyridin-4-yl)-2',3'-dihydro-1'H,5'H-spiro[cyclobutane-1,4'-pyrrolo[1,2-a][1,4]diazepin]-1'-one The title intermediate was prepared according to the procedures of Example 1 using the corresponding intermediates and reagents.

(B) 5-chloro-N-(1-methyl-1H-pyrazol-5-yl)-4-(3'-(1-(trifluoromethyl)cyclobutyl)-5'H,7'H-spiro[cyclobutane-1,6'-pyrrolo[1,2-a][1,2,4]triazolo[3,4-c][1,4]diazepin]-10'-yl)pyridin-2-amine A mixture of 8'-(5-chloro-2-((1-methyl-1H-pyrazol-5-yl)amino)pyridin-4-yl)-2',3'-dihydro-1'H,5'H-spiro[cyclobutane-1,4'-pyrrolo[1,2-a][1,4]diazepin]-1'-one (55 mg, 0.14 mmol) and 1-(trifluoromethyl)cyclobutane-1-carbohydrazide (25 mg, 0.14 mmol) in $POCl_3$ (3 mL) was stirred at 100° C. for 30 min. The volatiles were removed under reduced pressure and the residue was adjusted to pH=8 with solution of $NaHCO_3$, extract with EA. The combined organic layers were washed with water and brine, dried over anhydrous $Na_2SO_4$ and concentrated. The residue was dissolved in EtOH (3 mL) and acetic acid (2 drops) and the resulting mixture was stirred at 100° C. for 1.5 h under microwave. Then the mixture was concentrated and the residue was purified via ISCO (eluting with MeOH in water 0-1000%) and PTLC (DCM/MeOH=15:1) to afford the title compound as a yellow solid (20 mg, 27% yield). MS (m/z): 543.1 (M+H).

$^1$H NMR (400 MHz, DMSO-d6) δ 8.85 (s, 1H), 8.12 (s, 1H), 7.72 (d, J=1.6 Hz, 1H), 7.31 (d, J=1.6 Hz, 1H), 7.20 (d, J=2.0 Hz, 1H), 6.97 (s, 1H), 6.22 (d, J=1.6 Hz, 1H), 4.40 (s, 2H), 4.06 (s, 2H), 3.64 (s, 3H), 2.92-2.85 (m, 2H), 2.80-2.74 (m, 2H), 2.20-2.13 (m, 1H), 2.03-1.96 (m, 2H), 1.894-1.79 (m, 5H).

The compounds below were prepared according to the procedures of Compound 55 using the corresponding intermediates and reagents under appropriate conditions that could be recognized by one skilled in the art.

| Compound | Structure | LC-MS (m/z) $(M + H)^+$ | $^1$H NMR |
|---|---|---|---|
| 56 | 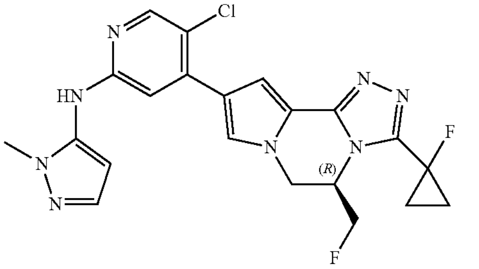 | 457.0 | $^1$H NMR (400 MHz, DMSO-d6) δ 8.83 (s, 1H), 8.13 (s, 1H), 7.78 (d, J = 1.7 Hz, 1H), 7.33 (d, J = 1.9 Hz, 1H), 7.08 (d, J = 1.7 Hz, 1H), 6.96 (s, 1H), 6.23 (d, J = 1.9 Hz, 1H), 5.30-5.21 (m, 1H), 4.83-4.48 (m, 4H), 3.65 (s, 3H), 1.62-1.49 (m, 2H), 1.43-1.28 (m, 2H). |
| 57 | 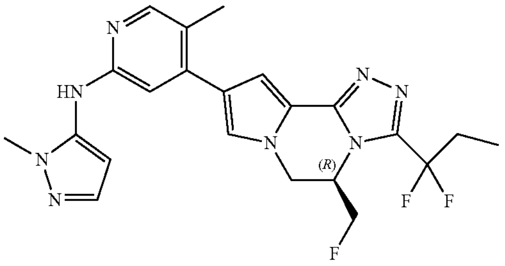 | 457.2 | $^1$H NMR (400 MHz, DMSO-d6) δ 8.52 (s, 1H), 7.95 (s, 1H), 7.52 (s, 1H), 7.30-7.28 (m, 1H), 7.02 (s, 1H), 6.82 (s, 1H), 6.21-6.18 (m, 1H), 5.58-5.19 (m, 1H), 4.76-4.46 (m, 4H), 2.64-2.48 (m, 2H), 2.28 (s, 3H), 1.15-1.04 (m, 3H). |
| 58 | 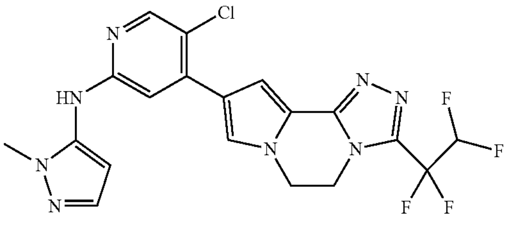 [SMILES: Cn1nccc1Nc1cc(-c2cc3n(c2)CCn2c-3nnc2C(F)(F)C(F)F)c(Cl)cn1] | 467.0 | $^1$H NMR (400 MHz, DMSO-d6) δ 8.88 (s, 1H), 8.14 (s, 1H), 7.80 (s, 1H), 7.32 (d, J = 1.3 Hz, 1H), 7.27-6.93 (m, 3H), 6.22 (d, J = 1.3 Hz, 1H), 4.57 (t, J = 5.7 Hz, 2H), 4.49 (t, J = 5.7 Hz, 2H), 3.65 (s, 3H). |

-continued
| Compound | Structure | LC-MS (m/z) (M + H)+ | 1H NMR |
|---|---|---|---|
| 59 | 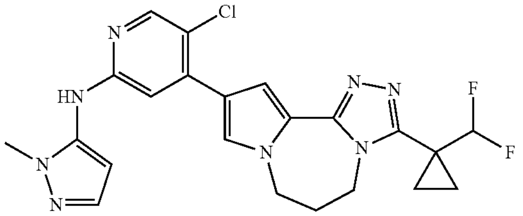 [SMILES: Cn1nccc1Nc1cc(-c2cc3n(c2)CCCn2c-3nnc2C2(C(F)F)CC2)c(Cl)cn1] | 471.1 | 1H NMR (400 MHz, DMSO-d6) δ 8.82 (s, 1H), 8.11 (s, 1H), 7.64 (s, 1H), 7.33-7.30 (m, 1H), 7.21 (s, 1H), 6.96 (s, 1H), 6.22-6.20 (m, 1H), 6.03-5.75 (m, 1H), 4.45-4.29 (m, 2H), 4.29-4.17 (m, 2H), 3.64 (s, 3H), 2.38-2.24 (m, 2H), 1.40-1.26 (m, 2H), 1.26-1.14 (m, 2H). |
| 60 | 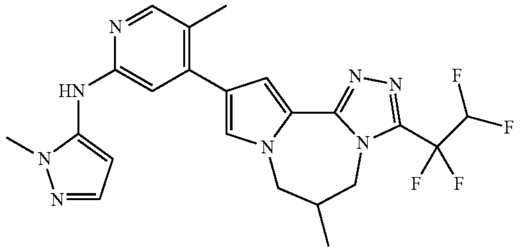 [SMILES: Cc1cnc(Nc2ccnn2C)cc1-c1cc2n(c1)CC(C)Cn1c-2nnc1C(F)(F)C(F)F] | 475.1 | 1H NMR (400 MHz, DMSO-d6) δ 8.51 (s, 1H), 7.93 (s, 1H), 7.46 (d, J = 2.0 Hz, 1H), 7.30-7.02 (m, 1H), 7.28 ( d, J = 1.9 Hz, 1H), 7.16 (d, J = 2.1 Hz, 1H), 6.84 (s, 1H), 6.19 (d, J = 1.9 Hz, 1H), 4.35 (dt, J = 13.9, 3.6 Hz, 2H), 4.12 (ddd, J = 14.0, 7.5, 3.4 Hz, 2H), 3.64 (s, 3H), 2.72-2.61 (m, 1H), 2.28 (d, J = 0.4 Hz, 3H), 1.03 (d, J = 7.0 Hz, 3H). |
| 61 | 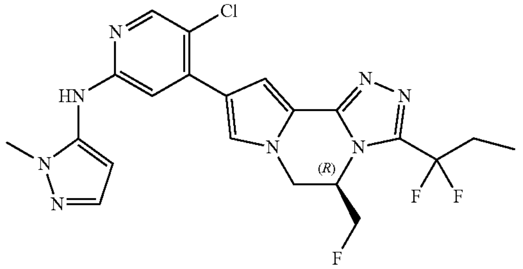 | 477.1 | 1H NMR (400 MHz, DMSO-d6) δ 8.85 (s, 1H), 8.13 (s, 1H), 7.80 (s, 1H), 7.32-7.30 (m, 1H), 7.14 (s, 1H), 6.96 (s, 1H), 6.23-6.21 (m, 1H), 5.46-5.12 (m, 1H), 4.81-4.41 (m, 4H), 3.64 (s, 3H), 2.61-2.49 (m, 2H), 1.11-1.02 (m, 3H). |
| 62 | 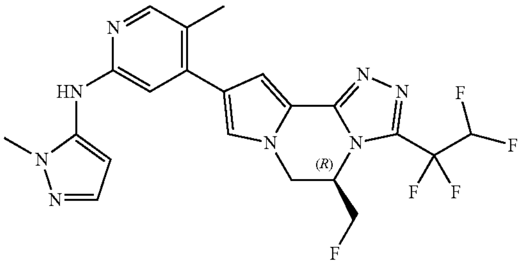 | 479.4 | 1H NMR (400 MHz, DMSO-d6) δ 8.52 (s, 1H), 7.94 (s, 1H), 7.53 (s, 1H), 7.30-7.28 (m, 1H), 7.26-7.00 (m, 1H), 7.08 (s, 1H), 6.81 (s, 1H), 6.20 - 6.18 (m, 1H), 5.37-5.32 (m, 1H), 4.73-4.43 (m, 4H), 3.64 (s, 3H), 2.28 (s, 3H). |
| 63 | 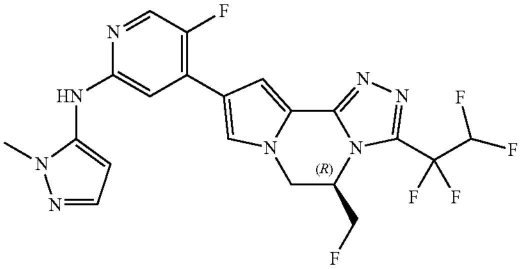 | 483.0 | 1H NMR (400 MHz, DMSO-d6) δ 8.68 (s, 1H), 8.08 (s, 1H), 7.74 (s, 1H), 7.30-7.13 (m, 3H), 7.02 (s, 1H), 6.21-6.19 (m, 1H), 5.35-5.34 (m, 1H), 4.71-4.48 (m, 4H), 3.64 (s, 3H). |

-continued

| Compound | Structure | LC-MS (m/z) (M + H)+ | $^1$H NMR |
|---|---|---|---|
| 64 | 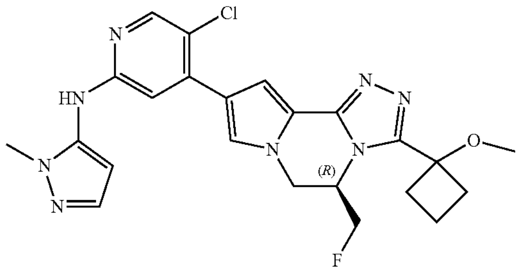 | 483.1 | $^1$H NMR (400 MHz, DMSO-d6) δ 8.80 (s, 1H), 8.12 (s, 1H), 7.77 (s, 1H), 7.32-7.30 (m, 1H), 7.05 (s, 1H), 6.95 (s, 1H), 6.22-6.20 (m, 1H), 4.98-4.95 (m, 1H), 4.68-4.32 (m, 4H), 3.64 (s, 3H), 2.97 (s, 3H), 2.72-2.59 (m, 2H), 2.42-2.21 (m, 2H), 1.84-1.65 (m, 2H). |
| 65 | 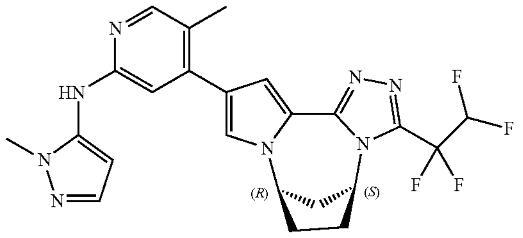 | 487.0 | $^1$H NMR (400 MHz, DMSO-d6) δ 8.52 ( s, 1H), 7.93 (s, 1H), 7.52 (d, J = 2.1 Hz, 1H), 7.31-7.03 ( m, 3H), 6.86 ( s, 1H), 6.20 (d, J = 1.9 Hz, 1H), 5.18-5.12 (m, 2H), 3.64 (s, 3H), 2.63-2.56 (m, 1H), 2.39-2.20 (m, 6H), 2.00-1.89 (m, 2H). |
| 66 | 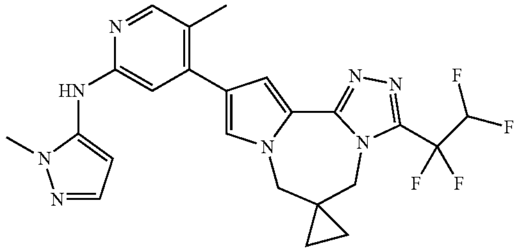 [SMILES: Cc1cnc(Nc2ccnn2C)cc1-c1cc2n(c1)CC1(CC1)Cn1c-2nnc1C(F)(F)C(F)F] | 487.1 | $^1$H NMR (400 MHz, DMSO-d6) δ 8.52 (s, 1H), 7.93 (s, 1H), 7.33 (d, J = 2.0 Hz, 1H), 7.29-7.27 (m, 2H), 7.27-7.00 (m, 1H), 6.86 (s, 1H), 6.20 (d, J = 2.0 Hz, 1H), 4.33 (s, 2H), 4.31 (s, 2H), 3.64 (s, 3H), 2.28 (s, 3H), 0.84-0.79 (m, 2H), 0.78-0.72 (m, 2H). |
| 67 | 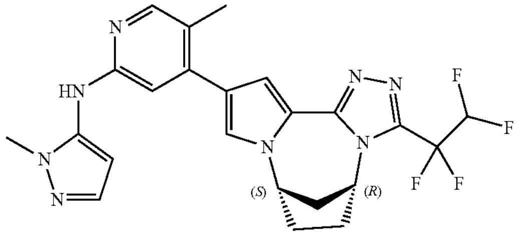 | 487.1 | $^1$H NMR (400 MHz, DMOS-d6) δ 8.53 (s, 1H), 7.92 (s, 1H), 7.51 (d, J = 1.6 Hz, 1H), 7.33-7.04 ( m, 3H), 6.86 (s, 1H), 6.19 (d, J = 1.6 Hz, 1H), 5.16-5.12 (m, 2H), 3.64 (s, 3H), 2.62-2.55 (m, 1H), 2.35-2.23 (m, 6H), 1.97-1.92 (m, 2H). |
| 68 | 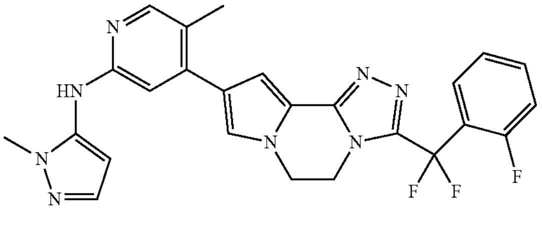 [SMILES: Cc1cnc(Nc2ccnn2C)cc1-c1cc2n(c1)CCn1c-2nnc1C(F)(F)c1ccccc1F] | 491.1 | $^1$H NMR (400 MHz, DMSO-d6) δ 8.57 (s, 1H), 7.95 (s, 1H), 7.73-7.68 (m, 2H), 7.56 (d, J = 1.6 Hz, 1H), 7.47-7.37 (m, 2H), 7.30 (d, J = 2.0 Hz, 1H), 7.03 (d, J = 1.6 Hz, 1H), 6.83 (s, 1H), 6.19 (d, J = 2.0 Hz, 1H), 4.64-4.61 (m, 2H), 4.51-4.48 (m, 2H), 3.65 (s, 3H), 2.29 (s, 3H). |
| 69 | 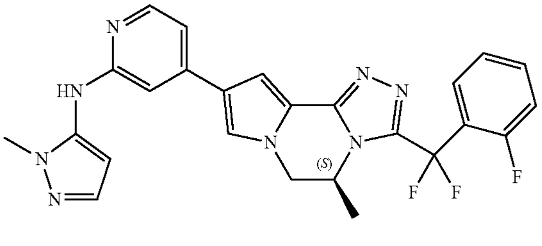 | 491.1 | $^1$H NMR (400 MHz, DMSO-d6) δ 8.64 (s, 1H), 8.03 (d, J = 5.3 Hz, 1H), 7.78-7.64 (m, 3H), 7.46-7.38 (m, 2H), 7.31 (d, J = 1.9 Hz, 1H), 7.20 (d, J = 1.6 Hz, 1H), 7.02 (dd, J = 5.3, 1.4 Hz, 1H), 6.89 (s, 1H), 6.20 (d, J = 1.9 Hz, 1H), 5.27-5.08 (m, 1H), 4.52-4.38 (m, 2H), 3.65 (s, 3H), 1.29 (d, J = 6.6 Hz, 3H). |

-continued
| Compound | Structure | LC-MS (m/z) (M + H)+ | 1H NMR |
|---|---|---|---|
| 70 | 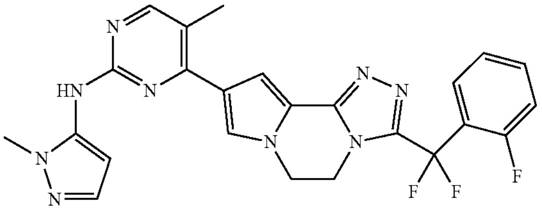 [SMILES: Cc1cnc(Nc2ccnn2C)nc1-c1cc2n(c1)CCn1c-2nnc1C(F)(F)c1ccccc1F] | 492.2 | 1H NMR (400 MHz, DMSO-d6) δ 9.11 (s, 1H), 8.24 (s, 1H), 7.83 (s, 1H), 7.76-7.65 (m, 2H), 7.48-7.36 (m, 2H), 7.35-7.25 (m, 2H), 6.26 (d, J = 1.6 Hz, 1H), 4.70-4.59 (m, 2H), 4.58-4.47 (m, 2H), 3.67 (s, 3H), 2.33 (s, 3H). |
| 71 | 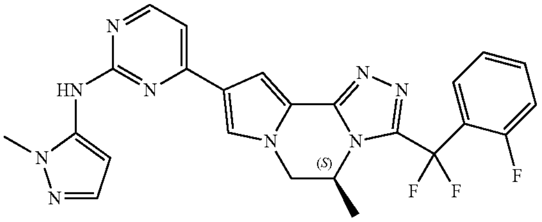 | 492.2 | 1H NMR (400 MHz, DMSO-d6) δ 9.24 (s, 1H), 8.35 (d, J = 5.0 Hz, H), 7.88 (s, 1H), 7.73-7.70 (m, 2H), 7.48-7.29 (m, 4H), 7.17 (d, J = 5.0 Hz, 1H), 6.27 (d, J = 1.9 Hz, 1H), 5.23-5.19 (m, 1H), 4.50-4.47 (m, 2H), 3.67 (s, 3H), 1.29 (d, J = 5.8 Hz, 3H). |
| 72 | 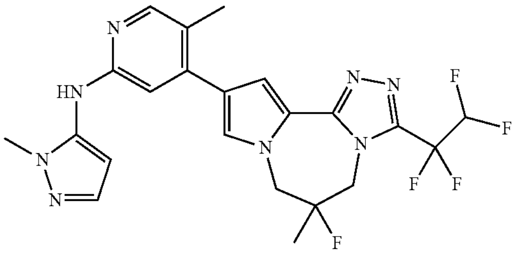 [SMILES: Cc1cnc(Nc2ccnn2C)cc1-c1cc2n(c1)CC(C)(F)Cn1c-2nnc1C(F)(F)C(F)F] | 493.1 | 1H NMR (400 MHz, DMSO-d6) δ 8.56 (s, 1H), 7.95 (s, 1H), 7.60 (s, 1H), 7.31-7.28 (m, 1H), 7.27-7.02 (m, 1H), 7.09 (s, 1H), 6.83 (s, 1H), 6.21-6.18 (m, 1H), 4.56-4.30 (m, 4H), 3.64 (s, 3H), 2.30 (s, 3H), 1.59 (d, J = 21.6 Hz, 3H). |
| 73 | 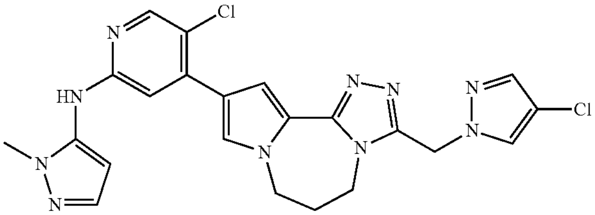 [SMILES: Cn1nccc1Nc1cc(-c2cc3n(c2)CCCn2c(Cn4cc(Cl)cn4)nnc2-3)c(Cl)cn1] | 495.0 | 1H NMR (400 MHz, DMSO-d6) δ 8.83 (s, 1H), 8.10 (s, 1H), 8.07 (s, 1H), 7.62 (s, 1H), 7.57 (s, 1H), 7.31-7.29 (m, 1H), 7.23 (s, 1H), 6.96 (s, 1H), 6.22-6.20 (m, 1H), 5.57 (s, 2H), 4.34 (br, 2H), 4.21 (br, 2H), 3.64 (s, 3H), 2.27 (br, 2H). |
| 74 | 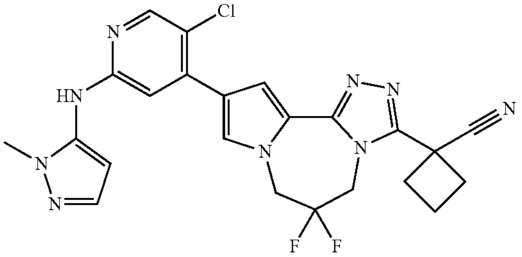 [SMILES: Cn1nccc1Nc1cc(-c2cc3n(c2)CC(F)(F)Cn2c-3nnc2C2(C#N)CCC2)c(Cl)cn1] | 496.0 | 1H NMR (400 MHz, DMSO-d6) δ 8.93 (s, 1H), 8.18 (s, 1H), 7.91 (s, 1H), 7.35-7.33 (m, 1H), 7.15 (s, 1H), 6.99 (s, 1H), 6.25-6.23 (m, 1H), 4.87 (t, J = 12.9 Hz, 2H), 4.59 (t, J = 12.9 Hz, 2H), 3.67 (s, 3H), 3.00-2.90 (m, 4H), 2.36-2.21 (m, 1H), 2.16-2.00 (m, 1H). |
| 75 | 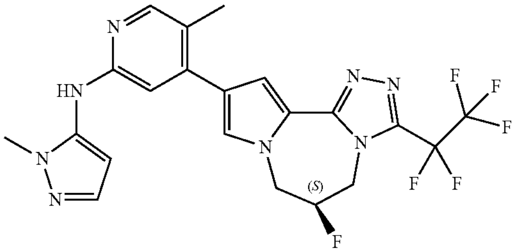 | 497.1 | 1H NMR (400 MHz, DMSO-d6) δ 8.64 (s, 1H), 7.95 (s, 1H), 7.56 (s, 1H), 7.29-7.27 (m, 1H), 7.16 (s, 1H), 6.88 (s, 1H), 6.21-6.19 (m, 1H), 5.64-5.53 (m, 1H), 4.78-4.49 (m, 4H), 3.65 (s, 3H), 2.29 (s, 4H). |

-continued

| Compound | Structure | LC-MS (m/z) (M + H)+ | 1H NMR |
|---|---|---|---|
| 76 | 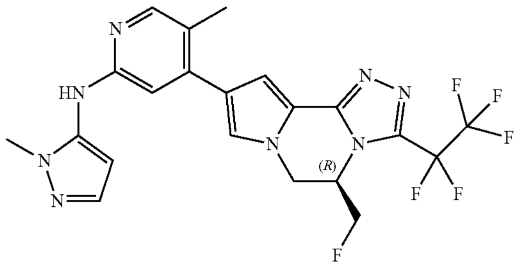 | 497.1 | 1H NMR (400 MHz, DMSO-d6) δ 8.52 (s, 1H), 7.94 (s, 1H), 7.53 (s, 1H), 7.28 (d, J = 1.8 Hz, 1H), 7.10 (s, 1H), 6.81 (s, 1H), 6.18 (d, J = 1.8 Hz, 1H), 5.37-5.35 (m, 1H), 4.74-4.38 (m, 4H), 3.63 (s, 3H), 2.27 (s, 3H). |
| 77 | 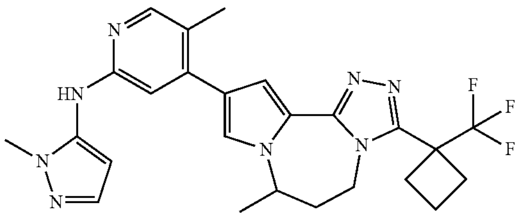 [SMILES: Cc1cnc(Nc2ccnn2C)cc1-c1cc2n(c1)C(C)CCn1c-2nnc1C1(C(F)(F)F)CCC1] | 497.1 | 1H NMR (400 MHz, DMSO-d6) δ 8.52 (s, 1H), 7.92 (s, 1H), 7.43 (d, J = 2.0 Hz, 1H), 7.27 (d, J = 2.0 Hz, 1H), 7.03 (d, J = 2.0 Hz, 1H), 6.84 (s, 1H), 6.19 (d, J = 2.0 Hz, 1H), 4.59-4.55 (m, 1H), 4.04-3.97 (m, 2H), 3.63 (s, 3H), 2.95-2.87 (m, 2H), 2.73-2.67 (m, 2H), 2.44-2.35 (m, 1H), 2.28 (s, 3H), 2.20-2.10 (m, 2H), 2.04-1.92 (m, 1H), 1.45 (d, J = 6.8 Hz, 3H). |
| 78 | 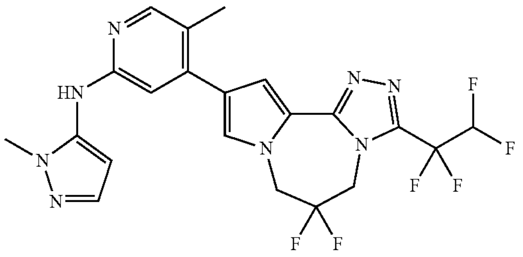 [SMILES: Cc1cnc(Nc2ccnn2C)cc1-c1cc2n(c1)CC(F)(F)Cn1c-2nnc1C(F)(F)C(F)F] | 497.1 | 1H NMR (400 MHz, DMSO-d6) δ 8.57 (s, 1H), 7.98 (s, 1H), 7.69 (d, J = 1.6 Hz, 1H), 7.31-7.04 (m, 1H), 7.30 (d, J = 1.6 Hz, 1H), 7.14 (d, J = 1.6 Hz, 1H), 6.83 (s, 1H), 6.21 (d, J = 2.0 Hz, 1H), 4.87 (t, J = 13.2 Hz, 2H), 4.75 (t, J = 12.4 Hz, 2H), 3.66 (s, 3H), 2.31 (s, 3H). |
| 79 | 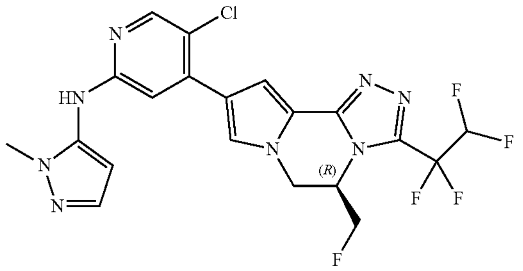 | 499.0 | 1H NMR (400 MHz, DMSO-d6) δ 8.82 (s, 1H), 8.14 (s, 1H), 7.81 (s, 1H), 7.41-6.89 (m, 4H), 6.23-6.21 (m, 1H), 5.37-5.34 (m, 1H), 4.84-4.42 (m, 4H), 3.64 (s, 3H). |
| 80 | 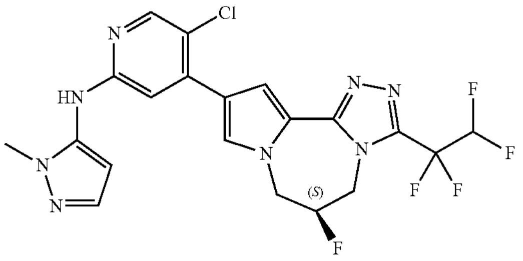 | 499.0 | 1H NMR (400 MHz, DMSO-d6) δ 8.87 (s, 1H), 8.17 (s, 1H), 7.82 (d, J = 1.9 Hz, 1H), 7.42-6.93 (m, 4H), 6.24 (d, J = 1.8 Hz, 1H), 5.73-5.51 (m, 1H), 4.65-4.57(m, 4H), 3.67 (s, 3H). |
| 81 | 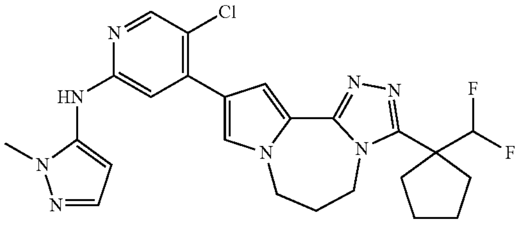 [SMILES: Cn1nccc1Nc1cc(-c2cc3n(c2)CCCn2c-3nnc2C2(C(F)F)CCCC2)c(Cl)cn1] | 499.1 | 1H NMR (400 MHz, DMSO-d6) δ 8.82 (s, 1H), 8.11 (s, 1H), 7.67 (s, 1H), 7.33-7.29 (m, 1H), 7.11 (s, 1H), 6.96 (s, 1H), 6.47-6.10 (m, 2H), 4.32-4.18 (m, 4H), 3.65 (s, 3H), 2.43-2.39 (m, 2H), 2.31-2.27 (m, 2H), 2.20-2.16 (m, 2H), 1.80-1.55 (m, 4H). |

-continued

| Compound | Structure | LC-MS (m/z) (M + H)+ | 1H NMR |
|---|---|---|---|
| 82 | 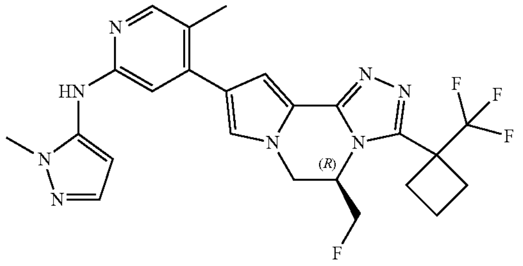 | 501.1 | 1H NMR (400 MHz, DMSO-d6) δ 8.51 (s, 1H), 7.94 (s, 1H), 7.50 (d, J = 1.5 Hz, 1H), 7.29 (d, J = 1.8 Hz, 1H), 6.97 (d, J = 1.5 Hz, 1H), 6.81 (s, 1H), 6.19 (d, J = 1.8 Hz, 1H), 5.05-4.90 (m, 1H), 4.64-4.35 (m, 4H), 3.63 (s, 3H), 3.01-2.87 (m, 2H), 2.70-2.67 (m, 2H), 2.27 (s, 3H), 2.19-2.11 (m, 1H), 2.02-1.98 (m, 1H). |
| 83 | 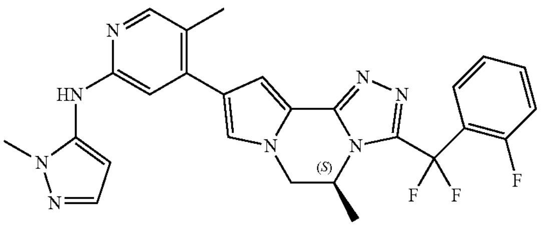 | 505.1 | 1H NMR (400 MHz, DMSO-d6) δ 8.57 (s, 1H), 7.97 (s, 1H), 7.82-7.68 (m, 2H), 7.57 (s, 1H), 7.49-7.39 (m, 2H), 7.32 (d, J = 1.3 Hz, 1H), 7.10 (s, 1H), 6.86 (s, 1H), 6.24-6.20 (m, 1H), 5.26-5.16 (m, 1H), 4.55-4.42 (m, 2H), 3.66 (s, 3H), 2.31 (s, 3H), 1.33 (d, J = 6.5 Hz, 3H). |
| 84 | 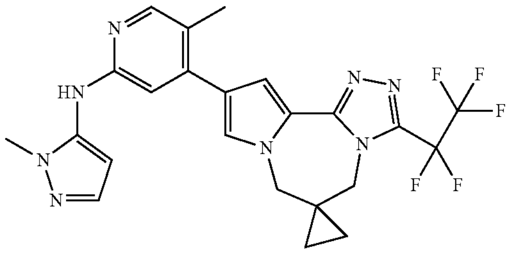 [SMILES: Cc1cnc(Nc2ccnn2C)cc1-c1cc2n(c1)CC1(CC1)Cn1c-2nnc1C(F)(F)C(F)(F)F] | 505.1 | 1H NMR (400 MHz, DMSO-d6) δ 8.52 (s, 1H), 7.92 (s, 1H), 7.33 (d, J = 2.0 Hz, 1H), 7.29-7.27 (m, 2H), 6.84 (s, 1H), 6.19 (d, J = 2.0 Hz, 1H), 4.32 (s, 2H), 4.30 (s, 2H), 3.63 (s, 3H), 2.27 (s, 3H), 0.83 (t, J = 5.6 Hz, 2H), 0.74 (t, J = 5 .6 Hz, 2H). |
| 85 | 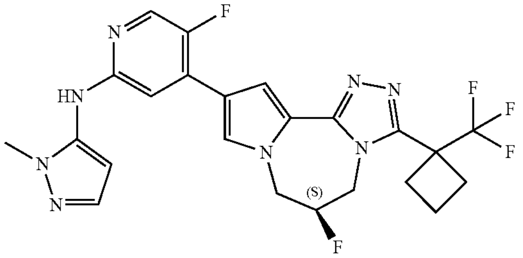 | 505.1 | 1H NMR (400 MHz, DMSO-d6) δ 8.67 (s, 1H), 8.08 (d, J = 3.0 Hz, 1H), 7.70 (t, J = 2.2 Hz, 1H), 7.30 (d, J = 1.9 Hz, 1H), 7.10 (dd, J = 1.8, 0.8 Hz, 1H), 7.02 (d, J = 5.5 Hz, 1H), 6.21 (d, J = 1.9 Hz, 1H), 5.55-5.35 (m, 1H), 4.65-4.43 (m, 2H), 4.40-4.30 (m, 1H), 4.21-4.04 (m, 1H), 2.97 (dd, J = 21.0, 9.8 Hz, 1H), 2.89-2.69 (m, 3H), 2.22-2.11 (m, 1H), 2.07-1.92 (m, 1H). |
| 86 | 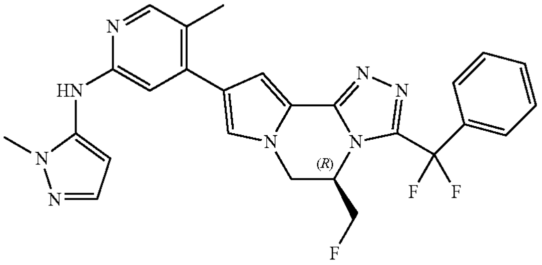 | 505.2 | 1H NMR (400 MHz, DMSO-d6) δ 8.55 (s, 1H), 7.98 (s, 1H), 7.73-7.56 (m, 6H), 7.34-7.31 (m, 1H), 7.07 (s, 1H), 6.84 (s 1H), 6.24-6.21 (m, 1H), 5.39-5.33 (m, 1H), 4.73-4.53 (m, 4H), 3.67 (s, 3H), 2.31 (s, 3H). |
| 87 | 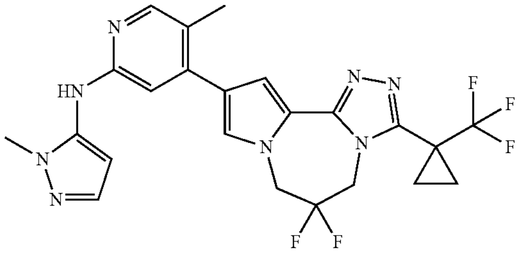 [SMILES: Cc1cnc(Nc2ccnn2C)cc1-c1cc2n(c1)CC(F)(F)Cn1c-2nnc1C1(C(F)(F)F)CC1] | 505.3 | 1H NMR (400 MHz, DMSO-d6) δ 8.55 (s, 1H), 7.95 (s, 1H), 7.61 (d, J = 1.8 Hz, 1H), 7.28 (d, J = 1.9 Hz, 1H), 6.99 (d, J = 1.8 Hz, 1H), 6.80 (s, 1H), 6.19 (d, J = 1.9 Hz, 1H), 4.77 (t, J = 13.2 Hz, 2H), 4.65 (t, J = 13.2 Hz, 2H), 3.64 (s, 3H), 1.63-1.60 (m, 2H), 1.38-1.35 (m, 2H). |

-continued

| Compound | Structure | LC-MS (m/z) (M + H)+ | 1H NMR |
|---|---|---|---|
| 88 | 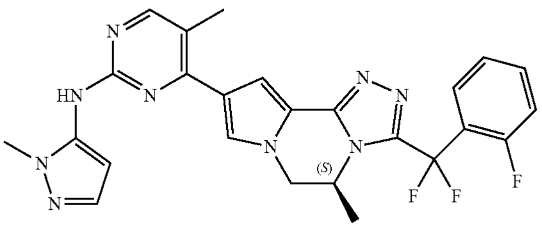 | 506.0 | 1H NMR (400 MHz, DMSO-d6) δ 9.10 (s, 1H), 8.24 (d, J = 0.4 Hz, 1H), 7.84 (d, J = 1.6 Hz, 1H), 7.76-7.68 (m, 2H), 7.45-7.39 (m, 2H), 7.34 (d, J = 1.6 Hz, 1H), 7.32 (d, J = 1.9 Hz, 1H), 6.26 (d, J = 1.9 Hz, 1H), 5.30-5.12 (m, 1H), 4.54-4.49 (m, 2H), 3.67 (s, 3H), 2.33 (s, 3H), 1.29 (d, J = 6.7 Hz, 3H). |
| 89 | 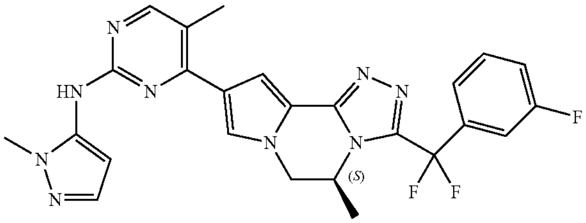 | 506.2 | 1H NMR (400 MHz, DMSO-d6) δ 9.09 (s, 1H), 8.23 (s, 1H), 7.82 (d, J = 1.4 Hz, 1H), 7.64-7.61 (m, 1H), 7.57-7.44 (m, 3H), 7.35-7.32 (m, 2H), 6.25 (d, J = 1.8 Hz, 1H), 5.16-5..13 (m, 1H), 4.52-4.42 (m, 2H), 3.65 (s, 3H), 2.32 (s, 3H), 1.24 (d, J = 6.6 Hz, 3H). |
| 90 | 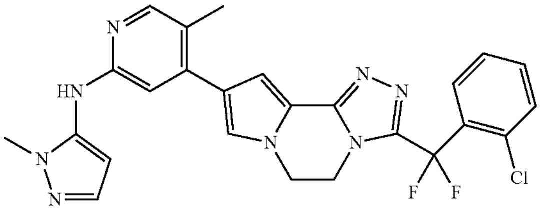 [SMILES: Cc1cnc(Nc2ccnn2C)cc1-c1cc2n(c1)CCn1c-2nnc1C(F)(F)c1ccccc1Cl] | 507.0 | 1H NMR (400 MHz, DMSO-d6) δ 8.56 (s, 1H), 7.95 (s, 1H), 7.84 (d, J = 7.6 Hz, 1H), 7.67-7.63 (m, 2H), 7.60-7.54 (m, 2H), 7.30 (d, J = 2.0 Hz, 1H), 7.03 (d, J = 1.6 Hz, 1H), 6.82 (s, 1H), 6.19 (d, J = 2.0 Hz, 1H), 4.66-4.63 (m, 2H), 4.51-4.48 (m, 2H), 3.65 (s, 3H), 2.29 (s, 3H). |
| 91 | 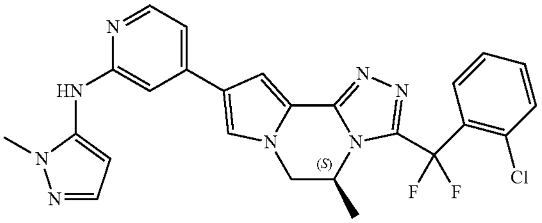 | 507.2 | 1H NMR (400 MHz, DMSO-d6) δ 8.64 (s, 1H), 8.03 (d, J = 5.4 Hz, 1H), 7.86 (d, J = 7.4 Hz, 1H), 7.74 (d, J = 1.6 Hz, 1H), 7.67-7.54 (m, 3H), 7.31 (d, J = 1.9 Hz, 1H), 7.20 (d, J = 1.6 Hz, 1H), 7.02 (dd, J = 5.3, 1.5 Hz, 1H), 6.89 (s, 1H), 6.20 (d, J = 1.9 Hz, 1H), 5.29-5.12 (m, 1H), 4.51-4.39 (m, 2H), 3.65 (s, 3H), 1.31 (d, J = 6.6 Hz, 3H). |
| 92 | 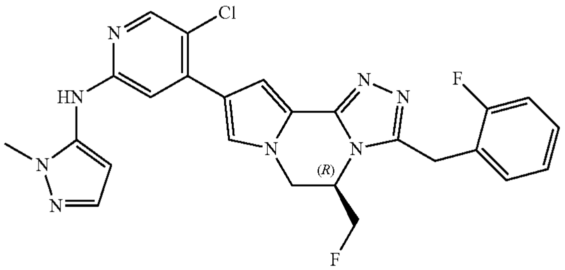 | 507.2 | 1H NMR (400 MHz, DMSO-d6) δ 8.84 (s, 1H), 8.16 (s, 1H), 7.75 (d, J = 1.6 Hz, 1H), 7.42-7.30 (m, 3H), 7.29-7.15 (m, 2H), 7.06 (d, J = 1.6 Hz, 1H), 6.98 (s, 1H), 6.25 (d, J = 1.8 Hz, 1H), 5.27-5.09 (m, 1H), 4.74-4.18 (m, 6H), 3.68 (s, 3H). |
| 93 | 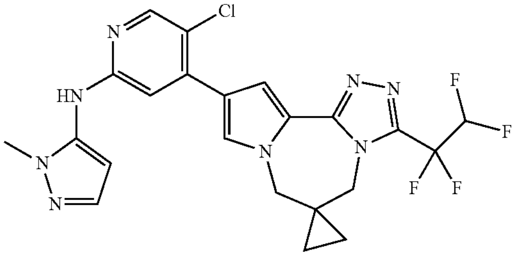 | 507.5 | 1H NMR (400 MHz, DMSO-d6) δ 8.85 (s, 1H), 8.14 (s, 1H), 7.62 (d, J = 2.0 Hz, 1H), 7.42 (d, J = 2.0 Hz, 1H), 7.33 (d, J = 2.0 Hz, 1H), 7.30-7.02 (m, 1H), 7.02 (s, 1H), 6.24 (d, J = 2.0 Hz, 1H), 4.37 (s, 2H), 4.32 (s, 2H), 3.67 (s, 3H), 0.86-0.73 (m, 4H). |

-continued

| Compound | Structure | LC-MS (m/z) (M + H)+ | 1H NMR |
|---|---|---|---|
| 94 | 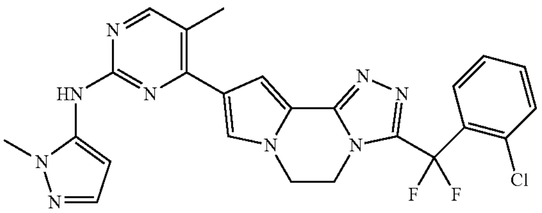 [SMILES: Cc1cnc(Nc2ccnn2C)nc1-c1cc2n(c1)CCn1c-2nnc1C(F)(F)c1ccccc1Cl] | 508.2 | $^1$H NMR (400 MHz, DMSO-d6) δ 9.12 (s, 1H), 8.24 (s, 1H), 7.88-7.80 (m, 2H), 7.69-7.62 (m, 2H), 7.60-7.50 (m, 1H), 7.37-7.25 (m, 2H), 6.26 (d, J = 1.6 Hz, 1H), 4.69-4.60 (m, 2H), 4.59-4.46 (m, 2H), 3.67 (s, 3H), 2.33 (s, 3H). |
| 95 | 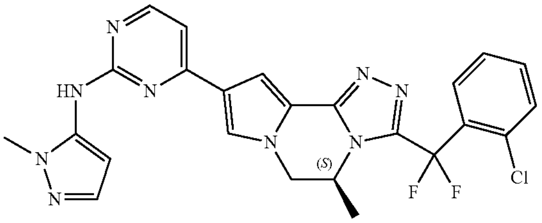 | 508.2 | $^1$H NMR (400 MHz, DMSO-d6) δ 9.28 (s, 1H), 8.38 (d, J = 5.2 Hz, 1H), 7.93-7.90 (m, 2H), 7.68-7.61 (m, 3H), 7.41-7.36 (m, 2H), 7.20 (d, J = 5.2 Hz, 1H), 6.33-6.28 (m, 1H), 5.26-5.24 (m, 1H), 4.55-4.52 (m, 2H), 3.71 (s, 3H), 1.34 (d, J = 6.6 Hz, 3H). |
| 96 | 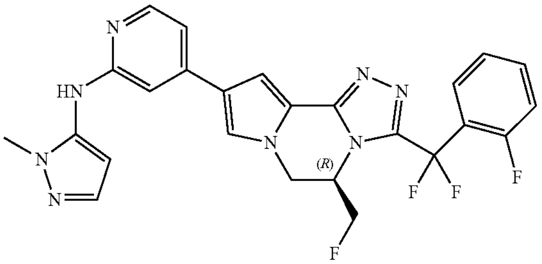 | 509.2 | $^1$H NMR (400 MHz, DMSO-d6) δ 8.72 (s, 1H), 8.05 (d, J = 5.2 Hz, 1H), 7.83-7.67 (m, 3H), 7.52-7.38 (m, 2H), 7.37-7.32 (m, 1H), 7.24 (s, 1H), 7.03 (d, J = 4.7 Hz, 1H), 6.92 (s, 1H), 6.25-6.21 (m, 1H), 5.53-5.34 (m, 1H), 4.81-4.55 (m, 4H), 3.66 (s, 3H). |
| 97 | 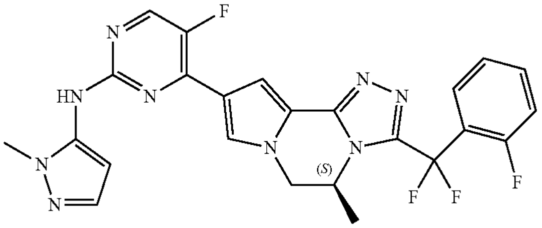 | 510.0 | $^1$H NMR (400 MHz, DMSO-d6) δ 9.35 (s, 1H), 8.46 (d, J = 3.3 Hz, 1H), 7.93 (t, J = 1.7 Hz, 1H), 7.75-7.68 (m, 2H), 7.45-7.39 (m, 2H), 7.34 (d, J = 1.9 Hz, 1H), 7.27 (s, 1H), 6.26 (d, J = 1.8 Hz, 1H), 5.27-5.17 (m, 1H), 4.61-4.48 (m, 2H), 3.67 (s, 3H), 1.28 (d, J = 6.6 Hz, 3H). |
| 98 | 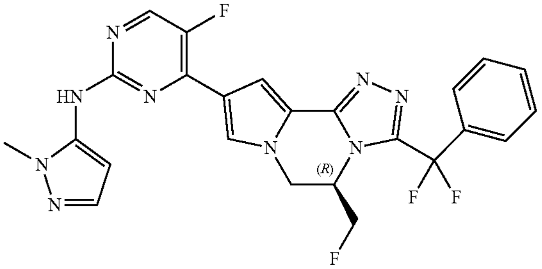 | 510.2 | $^1$H NMR (400 MHz, DMSO-d6) δ 9.37 (s, 1H), 8.47 (d, J = 3.3 Hz, 1H), 7.94-7.91 (m, 1H), 7.72-7.53 (m, 5H), 7.35 (d, J = 3.3 Hz, 1H), 7.25 (s, 1H), 6.27 (d, J = 1.9 Hz, 1H), 5.49-5.35 (m, 1H), 4.87-4.50 (m, 4H), 3.68 (s, 3H). |
| 99 | 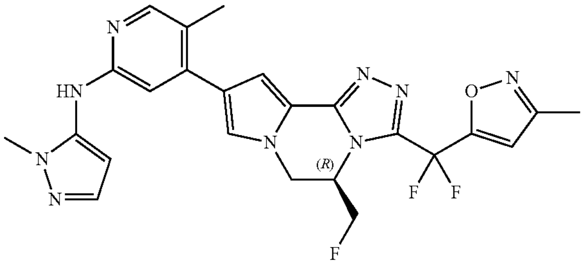 | 510.2 | $^1$H NMR (400 MHz, DMSO-d6) δ 8.51 (s, 1H), 7.95 (s, 1H), 7.55 (d, J = 1.7 Hz, 1H), 7.29 (d, J = 1.9 Hz, 1H), 7.10 (s, 1H), 7.08 (d, J = 1.7 Hz, 1H), 6.81 (s, 1H), 6.19 (d, J = 1.9 Hz, 1H), 5.43-5.30 (m, 1H), 4.73-4.46 (m, 4H), 3.64 (s, 3H), 2.33 (s, 3H), 2.28 (s, 3H). |

-continued

| Compound | Structure | LC-MS (m/z) (M + H)+ | $^1$H NMR |
|---|---|---|---|
| 100 | 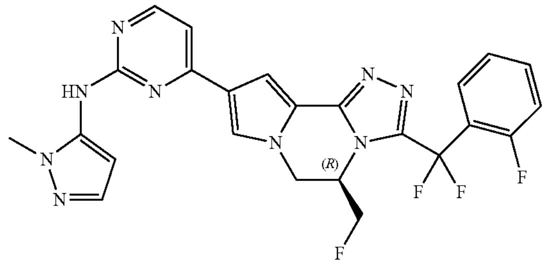 | 510.2 | $^1$H NMR (400 MHz, DMSO-d6) δ 9.24 (s, 1H), 8.34 (d, J = 5.2 Hz, 1H), 7.87 (d, J = 1.6 Hz, 1H), 7.75-7.70 (m, 2H), 7.45-7.42 (m, 2H), 7.36 (d, J = 1.6 Hz, 1H), 7.33 (d, J = 1.9 Hz, 1H), 7.16 (d, J = 5.2 Hz, 1H), 6.27 (d, J = 1.9 Hz, 1H), 5.46-5.35 (m, 1H), 4.80-4.56 (m, 4H), 3.67 (s, 3H). |
| 101 | 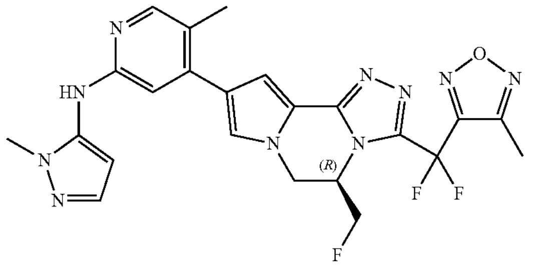 | 511.1 | $^1$H NMR (400 MHz, DMSO-d6) δ 8.52 (s, 1H), 7.94 (s, 1H), 7.56 (d, J = 1.6 Hz, 1H), 7.28 (d, J = 2.0 Hz, 1H), 7.08 (d, J = 1.6 Hz, 1H), 6.81 (s, 1H), 6.18 (d, J = 2.0 Hz, 1H), 5.48-5.37 (m, 1H), 4.77-4.49 (m, 4H), 3.63 (s, 3H), 2.43 (s, 3H), 2.28 (s, 3H). |
| 102 | 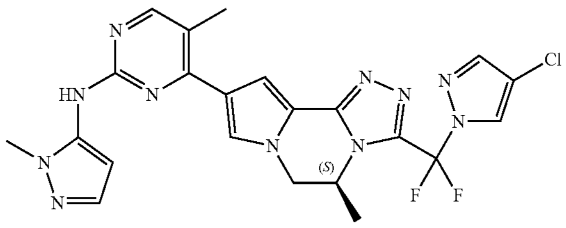 | 512.2 | $^1$H NMR (400 MHz, DMSO-d6) δ 9.13 (s, 1H), 8.87 (s, 1H), 8.25 (s, 1H), 8.02 (s, 1H), 7.83 (d, J = 1.6 Hz, 1H), 7.37 (d, J = 1.6 Hz, 1H), 7.33 (d, J = 1.8 Hz, 1H), 6.26 (d, J = 1.8 Hz, 1H), 4.93-4.80 (m, 1H), 4.48-4.34 (m, 2H), 3.67 (s, 3H), 2.33 (s, 3H), 1.14 (d, J = 6.7 Hz, 3H). |
| 103 | 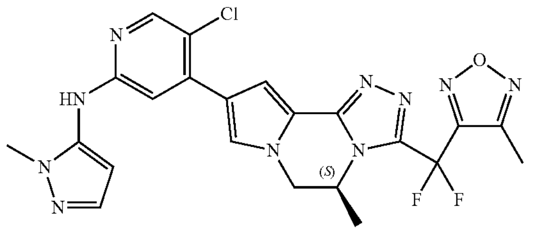 | 513.0 | $^1$H NMR (400 MHz, DMSO-d6) δ 8.85 (s, 1H), 8.15 (s, 1H), 7.85 (d, J = 1.6 Hz, 1H), 7.31 (d, J = 1.9 Hz, 1H), 7.21 (d, J = 1.6 Hz, 1H), 6.97 (s, 1H), 6.22 (d, J = 1.9 Hz, 1H), 5.26-5.17 (m, 1H), 4.51 (d, J = 2.8 Hz, 2H), 3.64 (s, 3H), 2.43 (s, 3H), 1.33 (d, J = 6.7 Hz, 3H). |
| 104 | 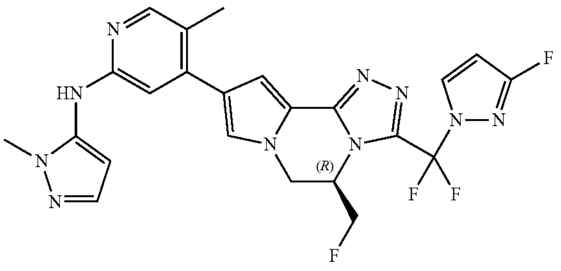 | 513.1 | $^1$H NMR (400 MHz, DMSO-d6) δ 8.53 (s, 1H), 8.37 (t, J = 2.8 Hz, 1H), 7.96 (s, 1H), 7.55 (d, J = 1.7 Hz, 1H), 7.30 (d, J = 1.9 Hz, 1H), 7.10 (d, J = 1.7 Hz, 1H), 6.83 (s, 1H), 6.52 (dd, J = 5.8, 3.0 Hz, 1H), 6.21 (d, J = 1.9 Hz, 1H), 5.26-5.14 (m, 1H), 4.66 (d, J = 14.2 Hz, 1H), 4.64-4.42 (m, 3H), 3.65 (s, 3H), 2.30 (s, 3H). |
| 105 | 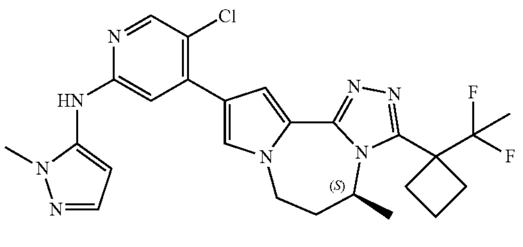 | 513.1 | $^1$H NMR (400 MHz, DMSO-d6) δ 8.83 (s, 1H), 8.12 (s, 1H), 7.71 (d, J = 2.0 Hz, 1H), 7.31 (d, J = 1 9 Hz, 1H), 7 05 (d, J = 2.0 Hz, 1H), 6.97 (s, 1H), 6.22 (d, J = 1.9 Hz, 1H), 4.59-4.48 (m, 1H), 4.46-4.37 (m, 1H), 4.21-4.11 (m, 1H), 3.64 (s, 3H), 2.83-2.79 (m, 1H), 2.71-2.54 (m, 3H), 2.38-2.16 (m, 2H), 2.07-1.88 (m, 2H), 1.49 (t, J = 19.2 Hz, 3H), 1.05 (d, J = 7.0 Hz, 3H). |

-continued

| Compound | Structure | LC-MS (m/z) (M + H)+ | ¹H NMR |
|---|---|---|---|
| 106 | 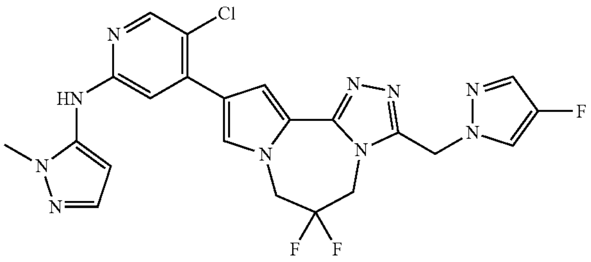 [SMILES: Cn1nccc1Nc1cc(-c2cc3n(c2)CC(F)(F)Cn2c(Cn4cc(F)cn4)nnc2-3)c(Cl)cn1] | 515.0 | ¹H NMR (400 MHz, DMSO-d6) δ 8.89 (s, 1H), 8.17 (s, 1H), 8.01 (d, J = 3.6 Hz, 1H), 7.89 (s, 1H), 7.55 (d, J = 3.6 Hz, 1H), 7.35-7.33 (m, 1H), 7.15 (s, 1H), 6.97 (s, 1H), 6.25-6.23 (m, 1H), 5.62 (s, 2H), 4.89-4.64 (m, 4H), 3.67 (s, 3H). |
| 107 | 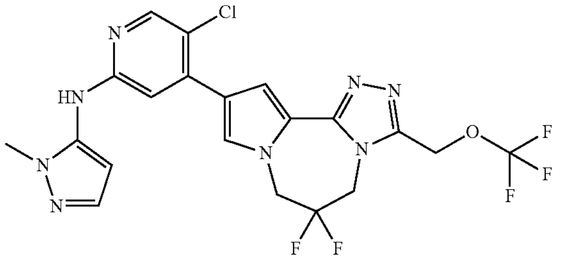 [SMILES: Cn1nccc1Nc1cc(-c2cc3n(c2)CC(F)(F)Cn2c(COC(F)(F)F)nnc2-3)c(Cl)cn1] | 515.0 | ¹H NMR (400 MHz, DMSO-d6) δ 8.90 (s, 1H), 8.16 (s, 1H), 7.90 (d, J = 1.8 Hz, 1H), 7.32 (d, J = 1.9 Hz, 1H), 7.17 (d, J = 1.8 Hz, 1H), 6.97 (s, 1H), 6.23 (d, J = 1.9 Hz, 1H), 5.51 (s, 2H), 4.82 (t, J = 13.2 Hz, 2H), 4.72 (t, J = 13.2 Hz, 2H), 3.66 (s, 3H). |
| 108 | 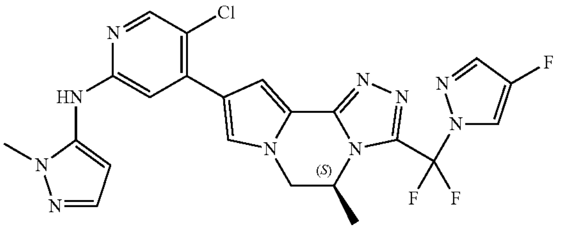 | 515.0 | ¹H NMR (400 MHz, DMSO-d6) δ 8.90 (s, 1H), 8.74 (d, J = 4.2 Hz, 1H), 8.14 (s, 1H), 8.00 (d, J = 4.2 Hz, 1H), 7.82 (d, J = 1.4 Hz, 1H), 7.32 (d, J = 1.8 Hz, 1H), 7.22 (d, J = 1.4 Hz, 1H), 7.00 (s, 1H), 6.23 (d, J = 1.8 Hz, 1H), 4.91-4.74 (m, 1H), 4.48-4.30 (m, 2H), 3.65 (s, 3H), 1.14 (d, J = 6.6 Hz, 3H). |
| 109 | 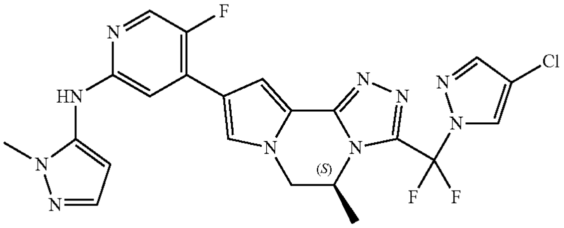 | 515.2 | ¹H NMR (400 MHz, DMSO-d6) δ 8.86 (s, 1H), 8.71 (s, 1H), 8.09 (d, J = 2.9 Hz, 1H), 8.01 (s, 1H), 7.86-7.69 (m, 1H), 7.30 (d, J = 1.9 Hz, 1H), 7.21 (s, 1H), 7.06 (d, J = 5.5 Hz, 1H), 6.21 (d, J = 1.9 Hz, 1H), 4.93-4.84 (m, 1H), 4.54-4.31 (m, 2H), 3.65 (s, 3H), 1.14 (d, J = 6.7 Hz, 3H). |
| 110 | 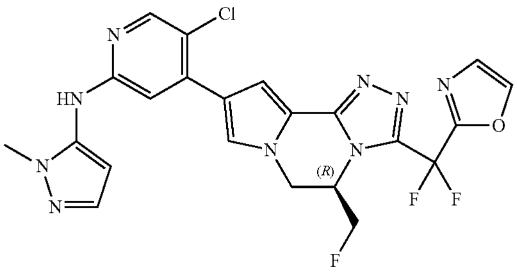 | 516.0 | ¹H NMR (400 MHz, DMSO-d6) δ 8.85 (s, 1H), 8.50-8.48 (m, 1H), 8.14 (s, 1H), 7.82 (d, J = 1.5 Hz, 1H), 7.56-7.54 (m, 1H), 7.32 (d, J = 1.9 Hz, 1H), 7.19 (d, J = 1.5 Hz, 1H), 6.96 (s, 1H), 6.22 (d, J = 1.8 Hz, 1H), 5.44-5.32 (m, 1H), 4.76-4.49 (m, 4H), 3.65 (s, 3H). |
| 111 | 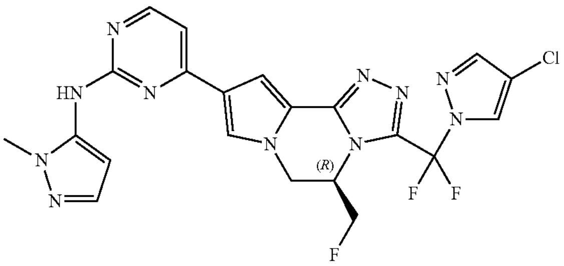 | 516.0 | ¹H NMR (400 MHz, DMSO-d6) δ 9.25 (s, 1H), 8.80 (s, 1H), 8.35 (d, J = 5.2 Hz, 1H), 8.01 (s, 1H), 7.85 (d, J = 1.3 Hz, 1H), 7.41 (d, J = 1.3 Hz, 1H), 7.33 (d, J = 1.8 Hz, 1H), 7.17 (d, J = 5.2 Hz, 1H), 6.27 (d, J = 1.8 Hz, 1H), 5.16-5.11 (m, 1H), 4.77-4.36 (m, 4H), 3.67 (s, 3H). |

-continued

| Compound | Structure | LC-MS (m/z) (M + H)+ | $^1$H NMR |
|---|---|---|---|
| 112 | 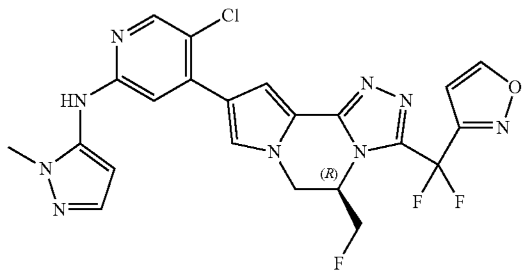 | 516.2 | $^1$H NMR (400 MHz, DMSO-d6) δ 9.27 (s, 1H), 8.84 (s, 1H), 8.16-8.14 (m, 1H), 7.84 (d, J = 1.6 Hz, 1H), 7.33 (d, J = 1.9 Hz, 1H), 7.20 (d, J = 1.6 Hz, 1H), 7.13 (d, J = 1.7 Hz, 1H), 6.97 (s, 1H), 6.24 (d, J = 1.9 Hz, 1H), 5.42-5.36 (m, 1H), 4.81-4.51 (m, 4H), 3.66 (s, 3H). |
| 113 | 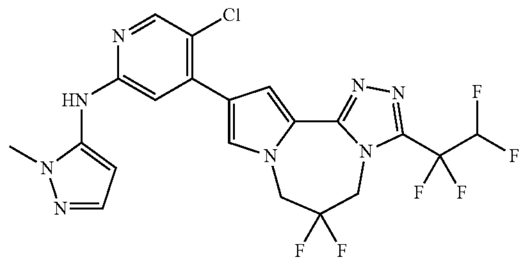 [SMILES: Cn1nccc1Nc1cc(-c2cc3n(c2)CC(F)(F)Cn2c-3nnc2C(F)(F)C(F)F)c(Cl)cn1] | 517.0 | $^1$H NMR (400 MHz, DMSO-d6) δ 8.90 (s, 1H), 8.18 (s, 1H), 7.96 (d, J = 1.6 Hz, 1H), 7.40-6.89 (m, 4H), 6.24 (d, J = 1.8 Hz, 1H), 4.92 (t, J = 13.2 Hz, 2H), 4.76 (t, J = 12.6 Hz, 2H), 3.66 (s, 3H). |
| 114 | 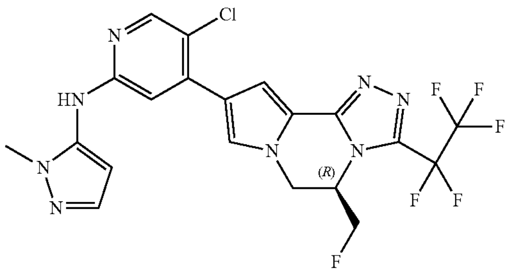 | 517.0 | $^1$H NMR (400 MHz, DMSO-d6) δ 8.82 (s, 1H), 8.14 (s, 1H), 7.82 (d, J = 1.6 Hz, 1H), 7.32 (d, J = 1.9 Hz, 1H), 7.23 (d, J = 1.6 Hz, 1H), 6.95 (s, 1H), 6.22 (d, J = 1.9 Hz, 1H), 5.48-5.28 (m, 1H), 4.77-4.40 (m, 4H), 3.64 (s, 3H). |
| 115 | 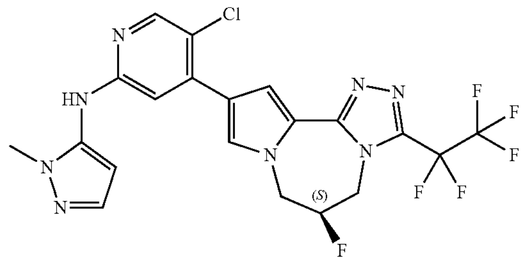 | 517.1 | $^1$H NMR (400 MHz, DMSO-d6) δ 8.98 (s, 1H), 8.15 (s, 1H), 7.83 (d, J = 1.9 Hz, 1H), 7.32 (d, J = 1.9 Hz, 1H), 7.28 (d, J = 1.9 Hz, 1H), 7.03 (s, 1H), 6.23 (d, J = 1.9 Hz, 1H), 5.64-5.53 (m, 1H), 4.70-4.57 (m, 4H), 3.66 (s, 3H). |
| 116 | 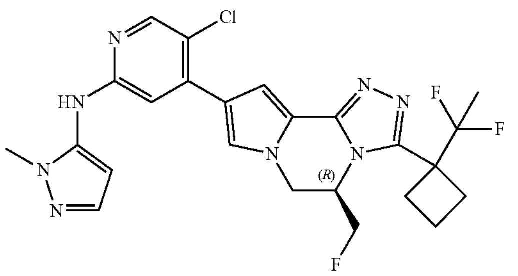 | 517.5 | $^1$H NMR (400 MHz, DMSO-d6) δ 8.82 (s, 1H), 8.13 (s, 1H), 7.78 (s, 1H), 7.33-7.30 (m, 1H), 7.06 (s, 1H), 6.96 (s, 1H), 6.23--6.21 (m, 1H), 4.93-4.91 (m, 1H), 4.65-4.40 (m, 4H), 3.65 (s, 3H), 2.79-2.77 (m, 2H), 2.61-2.59 (m, 2H), 2.05-1.83 (m, 2H), 1.48 (t, J = 19.2 Hz, 3H). |

-continued

| Compound | Structure | LC-MS (m/z) (M + H)+ | $^1$H NMR |
|---|---|---|---|
| 117 | 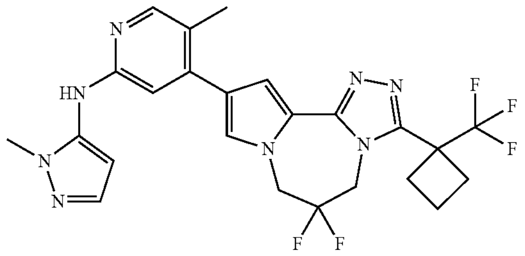 [SMILES: Cc1cnc(Nc2ccnn2C)cc1-c1cc2n(c1)CC(F)(F)Cn1c-2nnc1C1(C(F)(F)F)CCC1] | 519.3 | $^1$H NMR (400 MHz, DMSO-d6) δ 8.54 (s, 1H), 7.95 (s, 1H), 7.60 (d, J = 1.7 Hz, 1H), 7.29 (d, J = 1.8 Hz, 1H), 6.99 (d, J = 1.7 Hz, 1H), 6.80 (s, 1H), 6.18 (d, J = 1.8 Hz, 1H), 4.78 (t, J = 13.2 Hz, 2H), 4.47 (t, J = 13.2 Hz, 2H), 3.64 (s, 3H), 2.89-2.86 (m, 2H), 2.83-2.78 (m, 2H), 2.29 (s, 3H), 2.19-2.11 (m, 1H), 2.03-1.98 (m, 1H). |
| 118 | 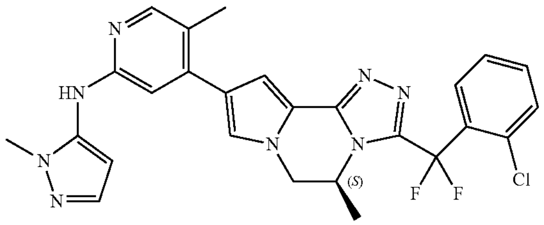 | 521.1 | $^1$H NMR (400 MHz, DMSO-d6) δ 8.53 (s, 1H), 7.95 (s, 1H), 7.86 (d, J = 7.5 Hz, 1H), 7.69-7.62 (m, 2H), 7.60-7.55 (m, 2H), 7.29 (d, J = 1.8 Hz, 1H), 7.05 (d, J = 1.5 Hz, 1H), 6.83 (s, 1H), 6.19 (d, J = 1.8 Hz, 1H), 5.28-5.11 (m, 1H), 4.57-4.39 (m, 2H), 3.64 (s, 3H), 2.29 (s, 3H), 1.32 (d, J = 6.6 Hz, 3H). |
| 119 | 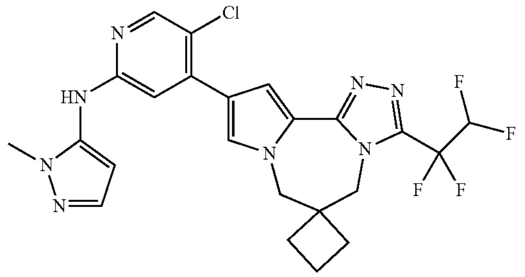 [SMILES: Cn1nccc1Nc1cc(-c2cc3n(c2)CC2(CCC2)Cn2c-3nnc2C(F)(F)C(F)F)c(Cl)cn1] | 521.1 | $^1$H NMR (400 MHz, DMSO-d6) δ 8.85 (s, 1H), 8.13 (s, 1H), 7.79 (d, J = 2.0 Hz, 1H), 7.30 (d, J = 2.0 Hz, 1H), 7.28 (d, J = 2.0 Hz, 1H), 7.29-7.02 (m, 1H), 6.98 (s, 1H), 6.22 (d, J = 2.0 Hz, 1H), 4.45 (s, 2H), 4.37 (s, 2H), 3.64 (s, 3H), 2.02-1.80 (m, 6H). |
| 120 | 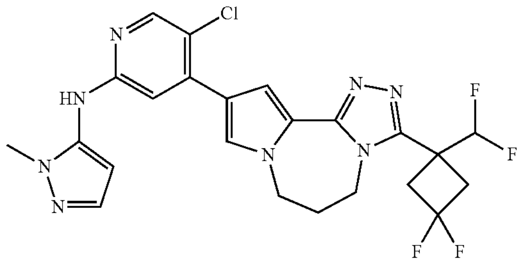 [SMILES: Cn1nccc1Nc1cc(-c2cc3n(c2)CCCn2c-3nnc2C2(C(F)F)CC(F)(F)C2)c(Cl)cn1] | 521.1 | $^1$H NMR (400 MHz, DMSO-d6) δ 8.83 (s, 1H), 8.12 (s, 1H), 7.67 (d, J = 1.9 Hz, 1H), 7.32 (d, J = 1.6 Hz, 1H), 7.22 (d, J = 1.9 Hz, 1H), 6.98 (s, 1H), 6.50 (t, J = 55.6 Hz, 1H), 6.22 (d, J = 1.6 Hz, 1H), 4.43-4.26 (m, 2H), 4.17-4.03 (m, 2H), 3.65 (s, 3H), 3.46-3.43 (m, 4H), 2.33-2.30 (m, 2H). |
| 121 | 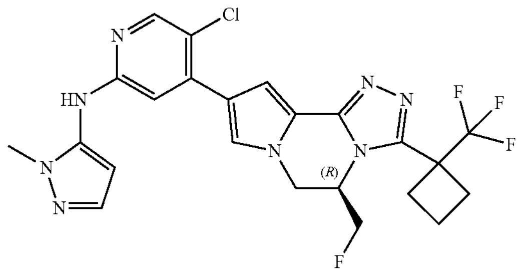 | 521.1 | $^1$H NMR (400 MHz, DMSO-d6) δ 8.86 (s, 1H), 8.13 (s, 1H), 7.79 (s, 1H), 7.32-7.30 (m, 1H), 7.10 (s, 1H), 6.96 (s, 1H), 6.23-6.21 (m, 1H), 4.98-4.97 (m, 1H), 4.72-4.33 (m, 4H), 3.64 (s, 3H), 2.96-2.93 (m, 2H), 2.69-2.67 (m, 2H), 2.14-1.99 (m, 2H). |

-continued
| Compound | Structure | LC-MS (m/z) (M + H)+ | 1H NMR |
|---|---|---|---|
| 122 | 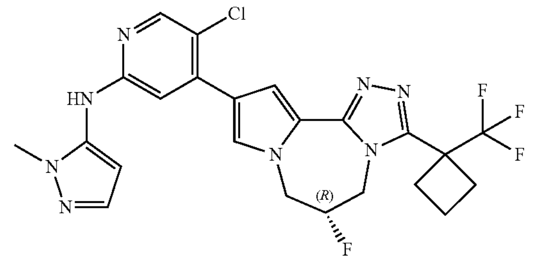 | 521.1 | 1H NMR (400 MHz, DMSO-d6) δ 8.95 (s, 1H), 8.12 (s, 1H), 7.76 (s, 1H), 7.31-7.29 (m, 1H), 7.09 (s, 1H), 7.01 (s, 1H), 6.22-6.20 (m, 1H), 5.50-5.39 (m, 1H), 4.64-4.28 (m, 3H), 4.13-4.11 (m, 1H), 3.65 (s, 3H), 2.95-2.93 (m, 1H), 2.81-2.76 (m, 3H), 2.16-2.13 (m, 1H), 2.01-1.99 (m, 1H). |
| 123 | 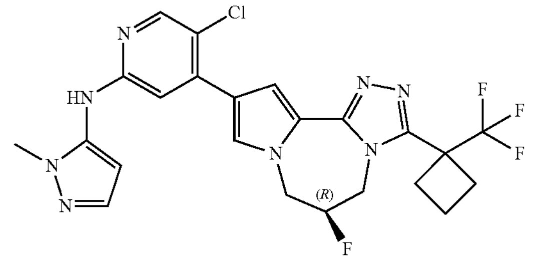 | 521.5 | 1H NMR (400 MHz, DMSO-d6) δ 8.85 (s, 1H), 8.16 (s, 1H), 7.79 (s, 1H), 7.35-7.33 (m, 1H), 7.13 (s, 1H), 6.97 (s, 1H), 6.25-6.23 (m, 1H), 5.53-5.41 (m, 1H), 4.63-4.30 (m, 3H), 4.22-4.11 (m, 1H), 3.67 (s, 3H), 3.00-2.97 (m, 1H), 2.83-2.79 (m, 3H), 2.19-2.16 (m, 1H), 2.02-1.99 (m, 1H). |
| 124 | 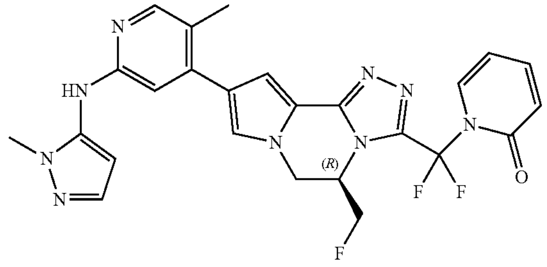 | 522.0 | 1H NMR (400 MHz, DMSO-d6) δ 8.51 (s, 1H), 8.10 (d, J = 7.1 Hz, 1H), 7.95 (s, 1H), 7.69-7.60 (m, 1H), 7.54 (d, J = 1.5 Hz, 1H), 7.29 (d, J = 1.8 Hz, 1H), 7.03 (d, J = 1.5 Hz, 1H), 6.82 (s, 1H), 6.51-6.44 (m, 2H), 6.19 (d, J = 1.8 Hz, 1H), 5.50-5.37 (m, 1H), 4.85-4.61 (m, 3H), 4.57-4.46 (m, 1H), 3.64 (s, 3H), 2.29 (s, 3H). |
| 125 | 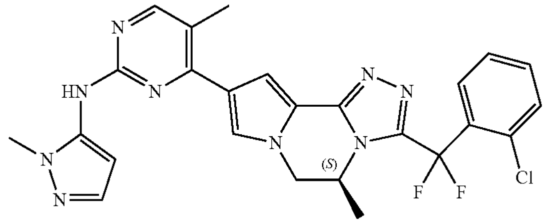 | 522.2 | 1H NMR (400 MHz, DMSO-d6) δ 9.13 (s, 1H), 8.25 (s, 1H), 7.89-7.84 (m, 2H), 7.68-7.64 (m, 2H), 7.62-7.55 (m, 1H), 7.35-7.32 (m, 2H), 6.27 (d, J = 1.8 Hz, 1H), 5.28-5.20 (m, 1H), 4.58-4.48 (m, 2H), 3.68 (s, 3H), 2.35 (s, 3H), 1.32 (d, J = 6.6 Hz, 3H). |
| 126 | 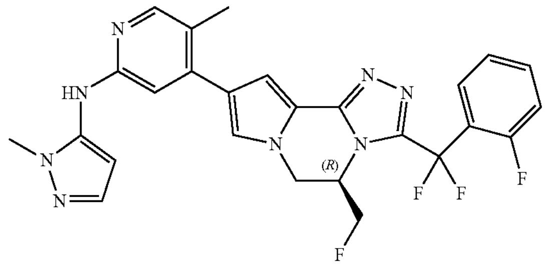 | 523.1 | 1H NMR (400 MHz, DMSO-d6) δ 8.50 (s, 1H), 7.94 (s, 1H), 7.75-7.68 (m, 2H), 7.56 (d, J = 1.5 Hz, 1H), 7.42-7.39 (m, 2H), 7.29 (d, J = 1.8 Hz, 1H), 7.04 (d, J = 1.5 Hz, 1H), 6.81 (s, 1H), 6.19 (d, J = 1.8 Hz, 1H), 5.49-5.33 (m, 1H), 4.76-4.54 (m, 4H), 3.64 (s, 3H), 2.28 (s, 3H). |

-continued
| Compound | Structure | LC-MS (m/z) (M + H)+ | 1H NMR |
|---|---|---|---|
| 127 | 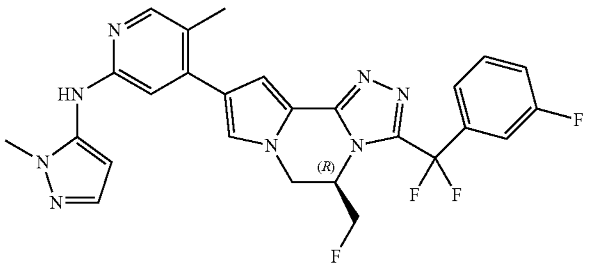 | 523.2 | 1H NMR (400 MHz, DMSO-d6) δ 8.56 (s, 1H), 7.97 (s, 1H), 7.66-7.51 (m, 5H), 7.34-7.30 (m, 1H), 7.07 (s, 1H), 6.85 (s, 1H), 6.24-6.20 (m, 1H), 5.41-4.38 (m, 1H), 4.73-4.58 (m, 4H), 3.67 (s, 3H), 2.31 (s, 3H). |
| 128 | 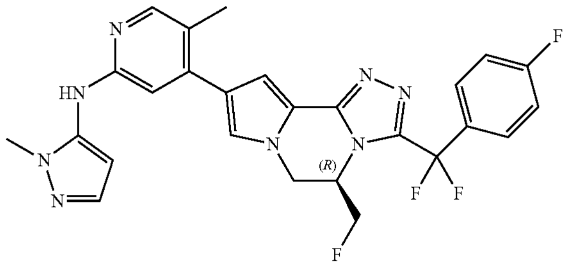 | 523.2 | 1H NMR (400 MHz, DMSO-d6) δ 8.54 (s, 1H), 7.95 (s, 1H), 7.75-7.71 (m, 2H), 7.56 (s, 1H), 7.43-7.40 (m, 2H), 7.31-7.28 (m, 1H), 7.04 (s, 1H), 6.83 (s, 1H), 6.22-6.19 (m, 1H), 5.37-5.33 (m, 1H), 4.67-4.54 (m, 4H), 3.65 (s, 3H), 2.29 (s, 3H). |
| 129 | 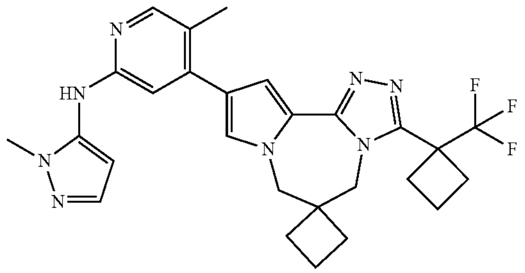 [SMILES: Cc1cnc(Nc2ccnn2C)cc1-c1cc2n(c1)CC1(CCC1)Cn1c-2nnc1C1(C(F)(F)F)CCC1] | 523.2 | 1H NMR (400 MHz, DMSO-d6) δ 8.54 (s, 1H), 7.93 (s, 1H), 7.45 (d, J = 1.6 Hz, 1H), 7.29 (d, J = 1.6 Hz, 1H), 7.07 (d, J = 2.0 Hz, 1H), 6.85 (s, 1H), 6.20 (d, J = 2.0 Hz, 1H), 4.38 (s, 2H), 4.06 (s, 2H), 3.64 (s, 3H), 2.93-2.85 (m, 2H), 2.81-2.75 (m, 2H), 2.29 (s, 3H), 2.21-2.14 (m, 1H), 2.04-1.96 (m, 2H), 1.92-1.77 (m, 5H). |
| 130 | 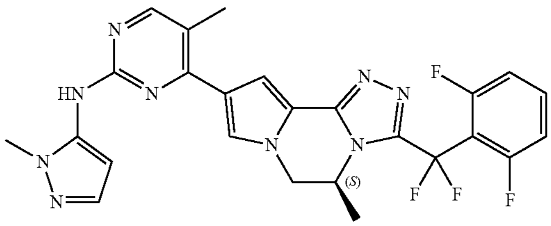 | 524.0 | 1H NMR (400 MHz, DMSO-d6) δ 9.12 (s, 1H), 8.24 (s, 1H), 7.86 (d, J = 1.5 Hz, 1H), 7.80-7.70 (m, 1H), 7.40-7.24 (m, 4H), 6.26 (d, J = 1.8 Hz, 1H), 5.32-5.14 (m, 1H), 4.58-4.48(m, 2H), 3.66 (s, 3H), 2.33 (s, 3H), 1.31 (d, J = 6.7 Hz, 3H). |
| 131 | 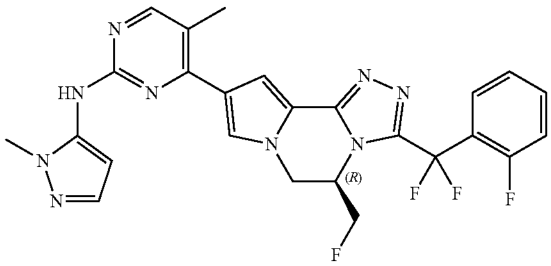 | 524.0 | 1H NMR (400 MHz, DMSO-d6) δ 9.10 (s, 1H), 8.24 (s, 1H), 7.84 (d, J = 1.6 Hz, 1H), 7.76-7.66 (m, 2H), 7.45-7.39 (m, 2H), 7.32-7.31 (m, 2H), 6.25 (d, J = 2.0 Hz, 1H), 5.45-5.39 (m, 1H), 4.84-4.55 (m, 4H), 3.66 (s, 3H), 2.33 (s, 3H). |

-continued

| Compound | Structure | LC-MS (m/z) (M + H)+ | $^1$H NMR |
|---|---|---|---|
| 132 | 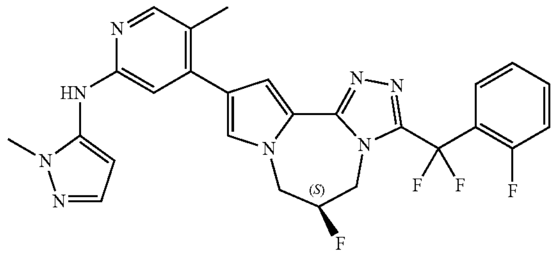 | 524.1 | $^1$H NMR (400 MHz, DMSO-d6) δ 9.11 (s, 1H), 8.23 (s, 1H), 7.80 (d, J = 1.7 Hz, 1H), 7.74-7.66 (m, 2H), 7.50-7.32 (m, 3H), 7.30 (d, J = 1.8 Hz, 1H), 6.24 (d, J = 1.7 Hz, 1H), 5.68-5.50 (m, 1H), 4.83-4.48 (m, 4H), 3.66 (s, 3H), 2.32 (s, 3H). |
| 133 | 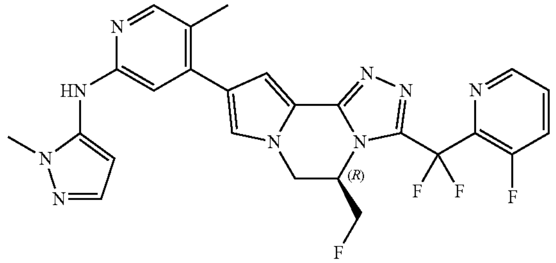 | 524.2 | $^1$H NMR (400 MHz, DMSO-d6) δ 8.55 (d, J = 4.5 Hz, 1H), 8.51 (s, 1H), 8.09-7.99 (m, 1H), 7.96 (s, 1H), 7.86-7.77 (m, 1H), 7.56 (d, J = 1.6 Hz, 1H), 7.30 (d, J = 1.9 Hz, 1H), 7.05 (d, J = 1.6 Hz, 1H), 6.83 (s, 1H), 6.20 (d, J = 1.9 Hz, 1H), 5.50-5.20 (m, 1H), 4.77-4.49 (m, 4H), 3.65 (s, 3H), 2.30 (s, 3H). |
| 134 | 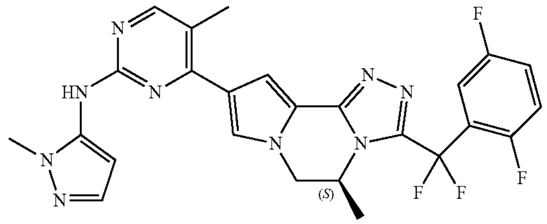 | 524.2 | $^1$H NMR (400 MHz, DMSO-d6) δ 9.12 (s, 1H), 8.25 (s, 1H), 7.86 (d, J = 1.5 Hz, 1H), 7.71-7.45 (m, 3H), 7.35 (d, J = 1.5 Hz, 1H), 7.33 (d, J = 1.9 Hz, 1H), 6.27 (d, J = 1.9 Hz, 1H), 5.33-5.14 (m, 1H), 4.54-4.51 (m, 2H), 3.67 (s, 3H), 2.34 (s, 3H), 1.30 (d, J = 6.7 Hz, 3H). |
| 135 | 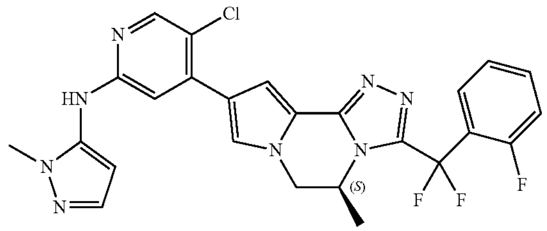 | 525.0 | $^1$H NMR (400 MHz, DMSO-d6) δ 8.85 (s, 1H), 8.16 (s, 1H), 7.85 (d, J = 1.5 Hz, 1H), 7.78-7.68 (m, 2H), 7.50-7.36 (m, 2H), 7.33 (d, J = 1.8 Hz, 1H), 7.18 (d, J = 1.6 Hz, 1H), 6.99 (s, 1H), 6.24 (d, J = 1.8 Hz, 1H), 5.26-5.17 (m, 1H), 4.54-4.48 (m, 2H), 3.66 (s, 3H), 1.31 (d, J = 6.6 Hz, 3H). |
| 136 | 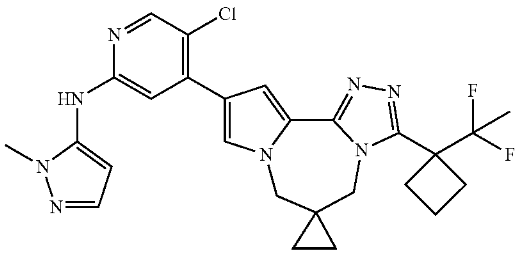 [SMILES: Cn1nccc1Nc1cc(-c2cc3n(c2)CC2(CC2)Cn2c-3nnc2C2(C(C)(F)F)CCC2)c(Cl)cn1] | 525.1 | $^1$H NMR (400 MHz, DMSO-d6) δ 8.85 (s, 1H), 8.11 (s, 1H), 7.53 (s, 1H), 7.31-7.29 (m, 1H), 7.27 (s, 1H), 6.97 (s, 1H), 6.22-6.20 (m, 1H), 4.24 (s, 2H), 3.97 (s, 2H), 3.64 (s, 3H), 2.71-2.52 (m, 4H), 2.02-1.95 (m, 1H), 1.91-1.85 (m, 1H), 1.49 (t, J = 19.2 Hz, 3H), 0.72-0.65 (m, 4H). |
| 137 | 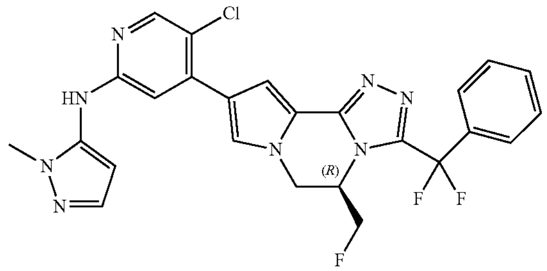 | 525.2 | $^1$H NMR (400 MHz, DMSO-d6) δ 8.89 (s, 1H), 8.17 (s, 1H), 7.85 (d, J = 1.6 Hz, 1H), 7.70-7.59 (m, 5H), 7.35 (d, J = 1.9 Hz, 1H), 7.19 (d, J = 1.6 Hz, 1H), 7.00 (s, 1H), 6.26 (d, J = 1.9 Hz, 1H), 5.40-5.35 (m, 1H), 4.81-4.50 (m, 4H), 3.68 (s, 3H). |

-continued

| Compound | Structure | LC-MS (m/z) (M + H)+ | $^1$H NMR |
|---|---|---|---|
| 138 | 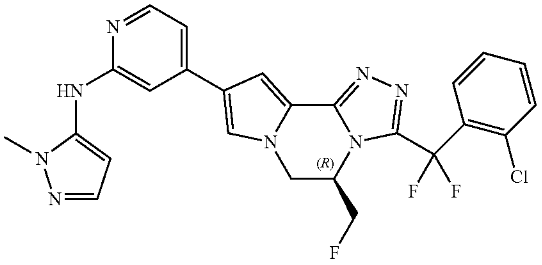 | 525.2 | $^1$H NMR (400 MHz, DMSO-d6) δ 8.77 (s, 1H), 8.06 (d, J = 5.4 Hz, 1H), 7.90 (d, J = 7.6 Hz, 1H), 7.78 (d, J = 1.3 Hz, 1H), 7.70-7.65 (m, 2H), 7.64-7.58 (m, 1H), 7.34 (d, J = 1.8 Hz, 1H), 7.23 (d, J = 1.3 Hz, 1H), 7.05 (d, J = 5.4 Hz, 1H), 6.95 (s, 1H), 6.24 (d, J = 1.8 Hz, 1H), 5.49-5.43 (m, 1H), 4.78-4.61 (m, 4H), 3.68 (s, 3H). |
| 139 | 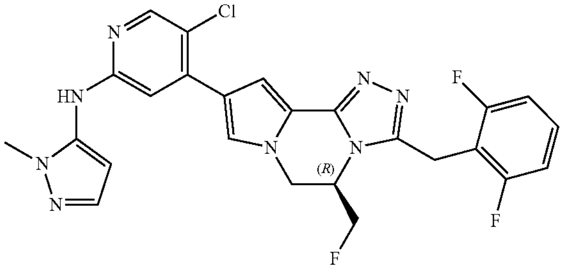 | 525.2 | $^1$H NMR (400 MHz, DMSO-d6) δ 8.82 (s, 1H), 8.14 (s, 1H), 7.74 (d, J = 1.7 Hz, 1H), 7.49-7.37 (m, 1H), 7.33 (d, J = 1.9 Hz, 1H), 7.20-7.09 (m, 2H), 7.05 (d, J = 1.7 Hz, 1H), 6.97 (s, 1H), 6.23 (d, J = 1.9 Hz, 1H), 5.30-5.25 (m, 1H), 4.79-4.61 (m, 2H), 4.56-4.36 (m, 2H), 4.26-4.14 (m, 2H), 3.65 (s, 3H). |
| 140 | 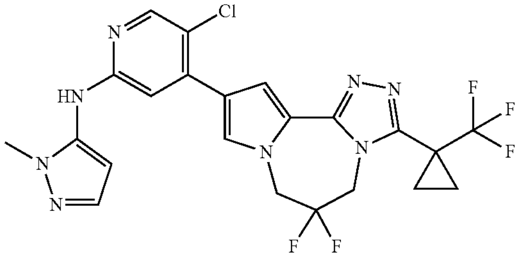 | 525.2 | $^1$H NMR (400 MHz, DMSO-d6) δ 8.93 (s, 1H), 8.21 (m, 1H), 7.91 (d, J = 1.9 Hz, 1H), 7.36 (d, J = 1.8 Hz, 1H), 7.15 (d, J = 1.9 Hz, 1H), 6.99 (s, 1H), 6.26 (d, J = 1.8 Hz, 1H), 4.86 (t, J = 13.2 Hz, 2H), 4.70 (t, J = 13.2 Hz, 2H), 3.69 (s, 3H), 1.66-1.63 (m, 2H), 1.42-1.41 (m, 2H). |
| 141 | 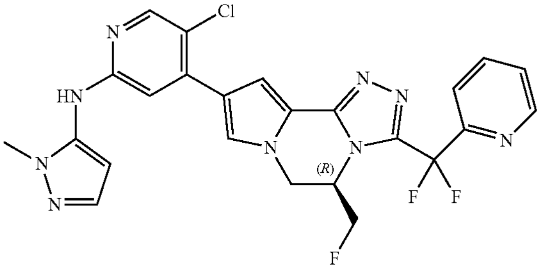 | 526.0 | $^1$H NMR (400 MHz, DMSO-d6) δ 8.87 (s, 1H), 8.68 (d, J = 4.6 Hz, 1H), 8.13 (s, 1H), 8.10-8.03 (m, 1H), 7.91 (d, J = 7.9 Hz, 1H), 7.82 (d, J = 1.6 Hz, 1H), 7.66-7.59 (m, 1H), 7.31 (d, J = 1.9 Hz, 1H), 7.14 (d, J = 1.6 Hz, 1H), 6.98 (s, 1H), 6.22 (d, J = 1.9 Hz, 1H), 5.55-5.29 (m, 1H), 4.79-4.52 (m, 4H), 3.64 (s, 3H). |
| 142 | 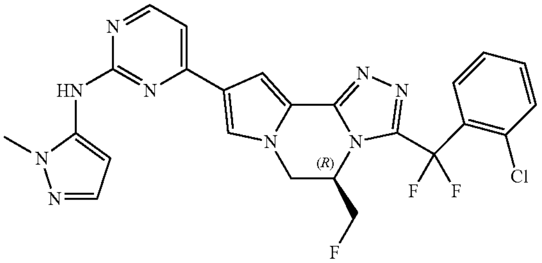 | 526.2 | $^1$H NMR (400 MHz, DMSO-d6) δ 9.28 (s, 1H), 8.38 (d, J = 5.2 Hz, 1H), 7.92-7.90 (m, 2H), 7.69-7.66 (m, 2H), 7.63-7.60 (m, 1H), 7.43-7.34 (m, 2H), 7.20 (d, J = 5.2 Hz, 1H), 6.32-6.29 (m, 1H), 5.50-5.44 (m, 1H), 4.84-4.58 (m, 4H), 3.71 (s, 3H). |

-continued

| Compound | Structure | LC-MS (m/z) (M + H)+ | $^1$H NMR |
|---|---|---|---|
| 143 | 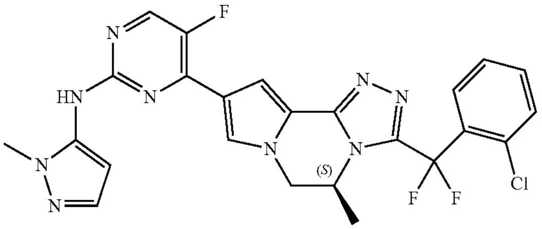 | 526.2 | $^1$H NMR (400 MHz, DMSO-d6) δ 9.36 (s, 1H), 8.47 (d, J = 3.3 Hz, 1H), 7.94 (s, 1H), 7.87 (d, J = 7.5 Hz, 1H), 7.68-7.65 (m, 2H), 7.61-7.54 (m, 1H), 7.35 (d, J = 1.9 Hz, 1H), 7.28 (s, 1H), 6.27 (d, J = 1.9 Hz, 1H), 5.32-5.20 (m, 1H), 4.62-4.60 (m, 2H), 3.68 (s, 3H), 1.31 (d, J = 6.6 Hz, 3H). |
| 144 | 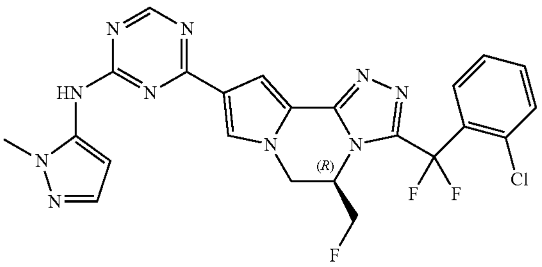 | 527.0 | $^1$H NMR (400 MHz, DMSO-d6) δ 10.01 (s, 1H), 8.61 (s, 1H), 7.98 (s, 1H), 7.89-7.86 (m, 1H), 7.67-7.65 (m, 2H), 7.60-7.56 (m, 1H), 7.37 (s, 1H), 7.20 (brs, 1H), 6.35 (brs, 1H), 5.50-5.44 (m, 1H), 4.84 (d, J = 14.2 Hz, 1H), 4.73 (d, J = 4.7 Hz, 1H), 4.65-4.60 (m, 2H), 3.68 (s, 3H). |
| 145 | 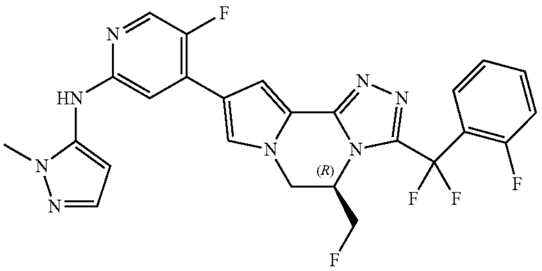 | 527.1 | $^1$H NMR (400 MHz, DMSO-d6) δ 8.67 (s, 1H), 8.11-8.06 (m, 1H), 7.79-7.65 (m, 3H), 7.46-7.37 (m, 2H), 7.30 (d, J = 1.9 Hz, 1H), 7.15 (s, 1H), 7.03 (d, J = 5.2 Hz, 1H), 6.20 (d, J = 1.9 Hz, 1H), 5.44-5.40 (m, 1H), 4.81-4.56 (m, 4H), 3.64 (s, 3H). |
| 146 | 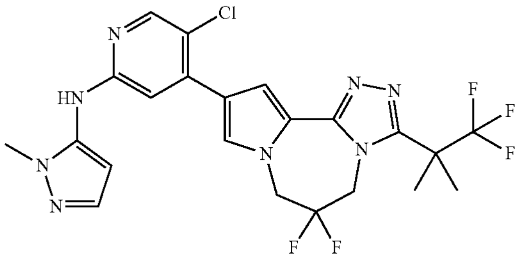 [SMILES: Cn1nccc1Nc1cc(-c2cc3n(c2)CC(F)(F)Cn2c-3nnc2C(C)(C)C(F)(F)F)c(Cl)cn1] | 527.1 | $^1$H NMR (400 MHz, DMSO-d6) δ 8.87 (s, 1H), 8.11 (s, 1H), 7.88 (d, J = 2.0 Hz, 1H), 7.28 (d, J = 1.6 Hz, 1H), 7.12 (d, J = 2.0 Hz, 1H), 6.89 (s, 1H), 6.24 (d, J = 1.9 Hz, 1H), 4.83-4.72 (m, 4H), 3.65 (s, 3H), 1.74 (s, 6H). |
| 147 | 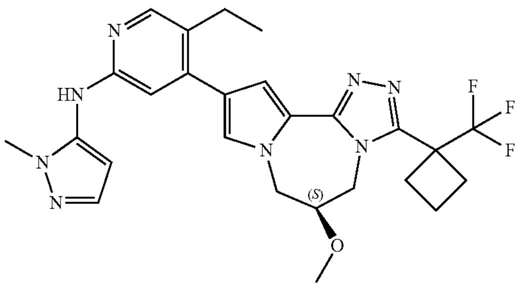 | 527.5 | $^1$H NMR (400 MHz, DMSO-d6) δ 8.57 (s, 1H), 7.98 (s, 1H), 7.39 (s, 1H), 7.31-7.29 (m, 1H), 6.91 (s, 1H), 6.75 (s, 1H), 6.22-6.20 (m, 1H), 4.44-4.08 (m, 4H), 3.93-3.88 (m, 1H), 3.66 (s, 3H), 3.05-2.97 (m, 1H), 2.87-2.67 (m, 5H), 2.21-2.14 (m, 1H), 2.05-1.97 (m, 1H), 1.14 (t, J = 7.2 Hz, 3H). |

-continued

| Compound | Structure | LC-MS (m/z) (M + H)+ | ¹H NMR |
|---|---|---|---|
| 148 | 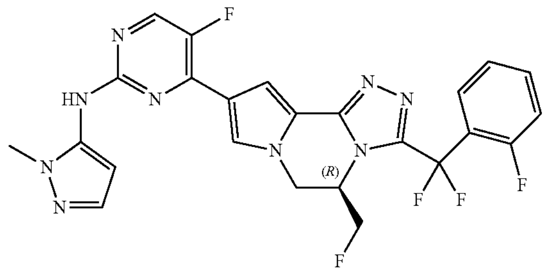 | 528.0 | ¹H NMR (400 MHz, DMSO-d6) δ 9.35 (s, 1H), 8.46 (d, J = 3.3 Hz, 1H), 7.93 (s, 1H), 7.77-7.67 (m, 2H), 7.48-7.39 (m, 2H), 7.34 (d, J = 1.9 Hz, 1H), 7.25 (s, 1H), 6.25 (d, J = 1.8 Hz, 1H), 5.48-5.39 (m, 1H), 4.88-4.56 (m, 4H), 3.67 (s, 3H). |
| 149 | 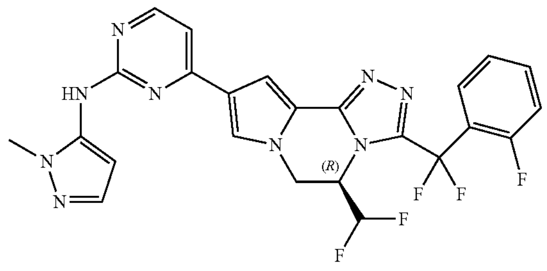 | 528.0 | ¹H NMR (400 MHz, DMSO-d6) δ 9.29 (s, 1H), 8.38 (d, J = 5.2 Hz, 1H), 7.93 (s, 1H), 7.83-7.66 (m, 2H), 7.48-7.39 (m, 3H), 7.37 (d, J = 2.0 Hz, 1H), 7.20 (d, J = 5.2 Hz, 1H), 6.61-6.26 (m, 2H), 5.74-5.55 (m, 1H), 4.97-4.85 (m, 1H), 4.78-4.62 (m, 1H), 3.70 (s, 3H). |
| 150 | 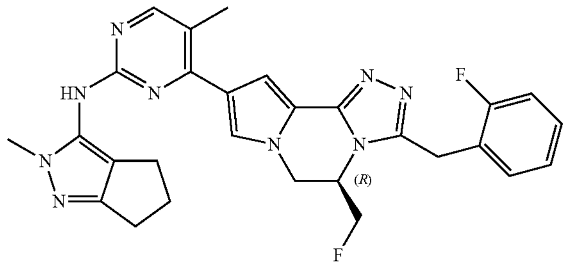 | 528.1 | ¹H NMR (400 MHz, DMSO-d6) δ 8.91 (s, 1H), 8.18 (s, 1H), 7.70 (s, 1H), 7.40-7.28 (m, 2H), 7.27-7.04 (m, 3H), 5.25-5.07 (m, 1H), 4.71-4.10 (m, 7H), 3.58 (s, 3H), 2.61-2.51 (m, 2H), 2.46-2.40 (m, 2H), 2.35-2.20 (m, 5H). |
| 151 | 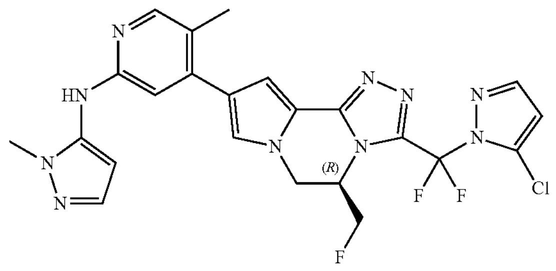 | 528.9 | ¹H NMR (400 MHz, DMSO-d6) δ 8.53 (s, 1H), 7.97 (s, 1H), 7.86 (d, J = 1.8 Hz, 1H), 7.55 (d, J = 1.6 Hz, 1H), 7.31 (d, J = 1.9 Hz, 1H), 7.10 (d, J = 1.6 Hz, 1H), 6.88 (d, J = 1.8 Hz, 1H), 6.83 (s, 1H), 6.21 (d, J = 1.9 Hz, 1H), 5.20-5.08 (m, 1H), 4.69 (d, J = 14.0 Hz, 1H), 4.62 (d, J = 5.1 Hz, 1H), 4.50 (d, J = 5.1 Hz, 1H), 4.44-4.43 (m, 1H), 3.66 (s, 3H), 2.30 (s, 3H). |
| 152 | 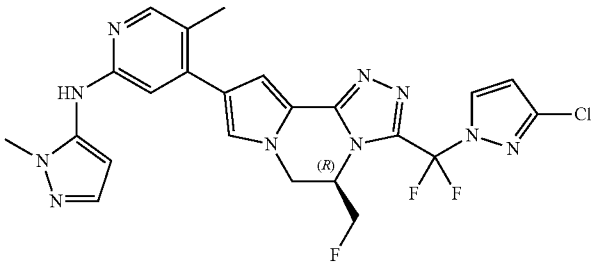 | 529.0 | ¹H NMR (400 MHz, DMSO-d6) δ 8.52 (s, 1H), 8.49 (d, J = 2.7 Hz, 1H), 7.96 (s, 1H), 7.54 (s, 1H), 7.30 (s, 1H), 7.10 (s, 1H), 6.82 (s, 1H), 6.79 (d, J = 2.7 Hz, 1H), 6.20 (s, 1H), 5.27-5.14 (m, 1H), 4.70-4.38 (m, 4H), 3.65 (s, 3H), 2.29 (s, 3H). |

-continued

| Compound | Structure | LC-MS (m/z) (M + H)+ | 1H NMR |
|---|---|---|---|
| 153 | 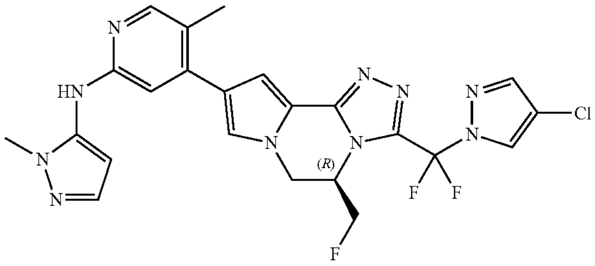 | 529.2 | 1H NMR (400 MHz, DMSO-d6) δ 8.80 (s, 1H), 8.51 (s, 1H), 8.01 (s, 1H), 7.95 (s, 1H), 7.53 (d, J = 1.6 Hz, 1H), 7.29 (d, J = 1.9 Hz, 1H), 7.08 (d, J = 1.6 Hz, 1H), 6.81 (s, 1H), 6.19 (d, J = 1.9 Hz, 1H), 5.21-5.05 (m, 1H), 4.69-4.40 (m, 4H), 3.64 (s, 3H), 2.28 (s, 3H). |
| 154 | 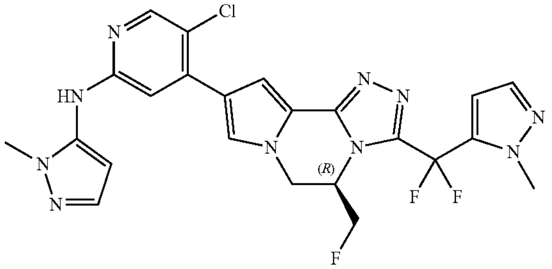 | 529.2 | 1H NMR (400 MHz, DMSO-d6) δ 8.84 (s, 1H), 8.14 (s, 1H), 7.82 (d, J = 1.6 Hz, 1H), 7.57 (d, J = 1.8 Hz, 1H), 7.32 (d, J = 1.9 Hz, 1H), 7.18 (d, J = 1.6 Hz, 1H), 6.96 (s, 1H), 6.71 (d, J = 1.8 Hz, 1H), 6.22 (d, J = 1.9 Hz, 1H), 5.42-5.23 (m, 1H), 4.75-4.52 (m, 4H), 3.84 (s, 3H), 3.64 (s, 3H). |
| 155 | 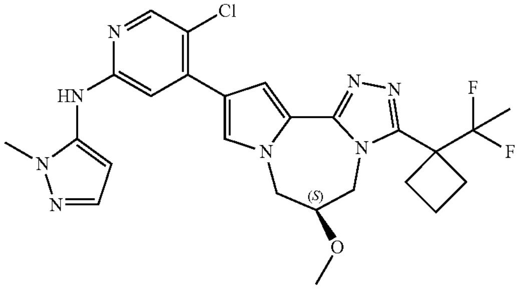 | 529.5 | 1H NMR (400 MHz, DMSO-d6) δ 8.83 (s, 1H), 8.12 (s, 1H), 7.73 (s, 1H), 7.32-7.30 (m, 1H), 7.04 (s, 1H), 6.95 (s, 1H), 6.23-6.21 (m, 1H), 4.41 (d, J = 14.6 Hz, 1H), 4.22 (d, J = 14.6 Hz, 1H), 4.17-3.99 (m, 2H), 3.81-3.78 (m, 1H), 3.65 (s, 3H), 3.34 (s, 3H), 2.90-2.86 (m, 1H), 2.65-2.61 (m, 3H), 2.02-1.98 (m, 1H), 1.93-1.89 (m, 1H), 1.51 (t, J = 19.1 Hz, 3H). |
| 156 | 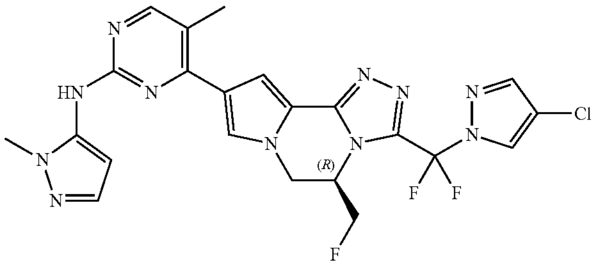 | 530.2 | 1H NMR (400 MHz, DMSO-d6) δ 9.12 (s, 1H), 8.81 (s, 1H), 8.24 (s, 1H), 8.01 (s, 1H), 7.82 (d, J = 1.5 Hz, 1H), 7.37 (d, J = 1.5 Hz, 1H), 7.33 (d, J = 1.9 Hz, 1H), 6.26 (d, J = 1.9 Hz, 1H), 5.26-5.05 (m, 1H), 4.77-4.41 (m, 4H), 3.67 (s, 3H), 2.32 (s, 3H). |
| 157 | 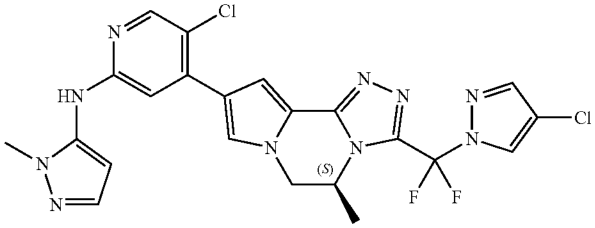 | 530.9 | 1H NMR (400 MHz, DMSO-d6) δ 8.89 (s, 1H), 8.85 (s, 1H), 8.14 (s, 1H), 8.01 (s, 1H), 7.82 (s, 1H), 7.32 (d, J = 1.8 Hz, 1H), 7.22 (d, J = 1.0 Hz, 1H), 6.99 (s, 1H), 6.23 (d, J = 1.8 Hz, 1H), 4.92-4.82 (m, 1H), 4.48-4.30 (m, 2H), 3.65 (s, 3H), 1.14 (d, J = 6.6 Hz, 3H). |

-continued

| Compound | Structure | LC-MS (m/z) (M + H)+ | $^1$H NMR |
|---|---|---|---|
| 158 | 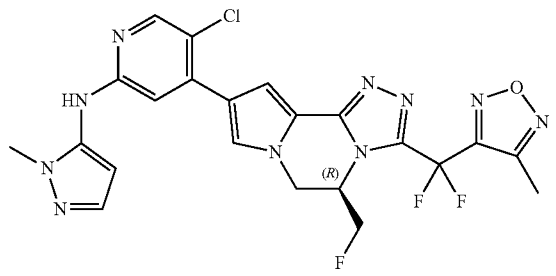 | 531.0 | $^1$H NMR (400 MHz, DMSO-d6) δ 8.88 (s, 1H), 8.14 (s, 1H), 7.83 (d, J = 1.6 Hz, 1H), 7.31 (d, J = 2.0 Hz, 1H), 7.20 (d, J = 1.6 Hz, 1H), 6.98 (s, 1H), 6.22 (d, J = 2.0 Hz, 1H), 5.49-5.39 (m, 1H), 4.79-4.52 (m, 4H), 3.64 (s, 3H), 2.44 (s, 3H). |
| 159 | 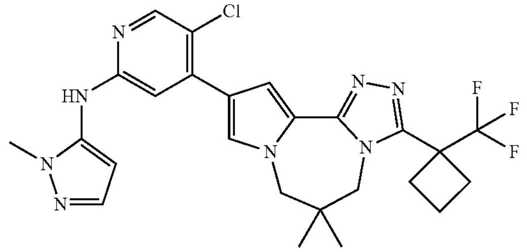 [SMILES: Cn1nccc1Nc1cc(-c2cc3n(c2)CC(C)(C)Cn2c-3nnc2C2(C(F)(F)F)CCC2)c(Cl)cn1] | 531.1 | $^1$H NMR (400 MHz, DMSO-d6) δ 8.85 (s, 1H), 8.11 (s, 1H), 7.63 (d, J = 2.0 Hz, 1H), 7.30 (d, J = 2.0 Hz, 1H), 7.20 (d, J = 2.0 Hz, 1H), 6.98 (s, 1H), 6.21 (d, J = 2.0 Hz, 1H), 4.10 (s, 2H), 3.79 (s, 2H), 3.64 (s, 3H), 2.92-2.84 (m, 2H), 2.77-2.67 (m, 2H), 2.18-2.11 (m, 1H), 2.02-1.95 (m, 1H), 1.02 (s, 6H). |
| 160 | 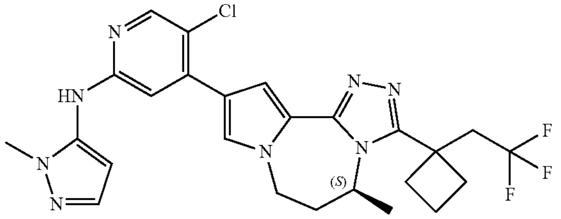 | 531.1 | $^1$H NMR (400 MHz, DMSO-d6) δ 8.86 (s, 1H), 8.15 (s, 1H), 7.71 (s, 1H), 7.35-7.33 (m, 1H), 7.09 (s, 1H), 7.00 (s, 1H), 6.26-6.24 (m, 1H), 4.62-4.58 (m, 1H), 4.47-4.43(m, 1H), 4.20-4.17 (m, 1H), 3.68 (s, 3H), 3.16-3.05 (m, 2H), 2.78-2.68 (m, 2H), 2.39-2.28 (m, 4H), 2.18-2.16 (m, 1H), 1.94-1.90 (m, 1H), 1.12 (d, J = 6.5 Hz, 3H). |
| 161 | 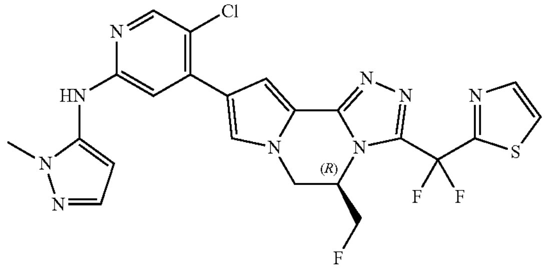 | 532.1 | $^1$H NMR (400 MHz, DMSO-d6) δ 8.87 (s, 1H), 8.17 (d, J = 3.1 Hz, 1H), 8.14 (s, 1H), 8.10-8.04 (m, 1H), 7.82 (d, J = 1.7 Hz, 1H), 7.32 (d, J = 1.9 Hz, 1H), 7.18 (d, J = 1.7 Hz, 1H), 6.97 (s, 1H), 6.22 (d, J = 1.9 Hz, 1H), 5.47-5.33 (m, 1H), 4.80-4.52 (m, 4H), 3.64 (s, 3H). |
| 162 | 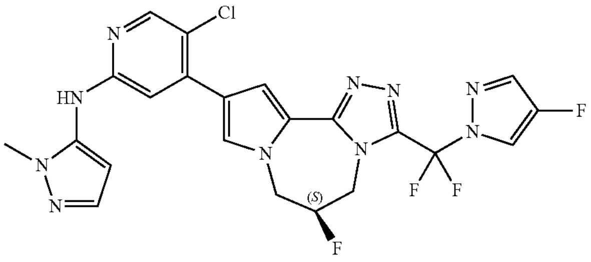 | 533.0 | $^1$H NMR (400 MHz, DMSO-d6) δ 8.85 (s, 1H), 8.77 (d, J = 4.4 Hz, 1H), 8.14 (s, 1H), 8.00 (d, J = 4.4 Hz, 1H), 7.79 (d, J = 1.8 Hz, 1H), 7.32 (d, J = 1.8 Hz, 1H), 7.29 (d, J = 1.8 Hz, 1H), 6.96 (s, 1H), 6.22 (d, J = 1.8 Hz, 1H), 5.44 (d, J = 44.1 Hz, 1H), 4.72-4.52 (m, 2H), 4.43-4.19 (m, 2H), 3.65 (s, 3H). |

-continued

| Compound | Structure | LC-MS (m/z) $(M + H)^+$ | $^1H$ NMR |
|---|---|---|---|
| 163 | 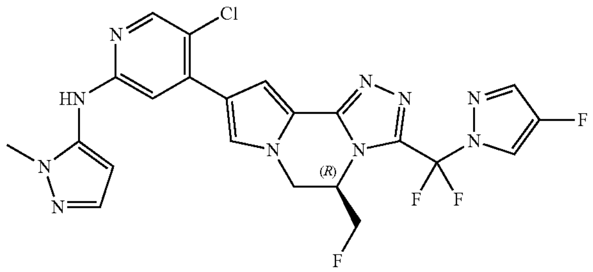 | 533.0 | $^1H$ NMR (400 MHz, DMSO-d6) δ 8.83 (s, 1H), 8.70 (d, J = 4.4 Hz, 1H), 8.14 (s, 1H), 8.00 (d, J = 4.1 Hz, 1H), 7.81 (d, J = 1.5 Hz, 1H), 7.32 (d, J = 1.8 Hz, 1H), 7.20 (d, J = 1.5 Hz, 1H), 6.95 (s, 1H), 6.22 (d, J = 1.8 Hz, 1H), 5.13-5.07 (m, 1H), 4.73-4.44 (m, 4H), 3.64 (s, 3H). |
| 164 | 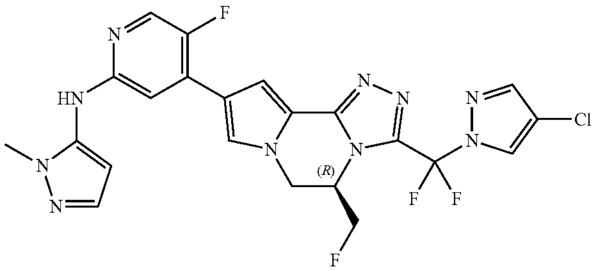 | 533.0 | $^1H$ NMR (400 MHz, DMSO-d6) δ 8.80 (s, 1H), 8.72 (s, 1H), 8.07 (s, 1H), 8.00 (s, 1H), 7.73 (s, 1H), 7.31-7.28 (m, 1H), 7.20 (s, 1H), 7.05 (d, J = 5.0 Hz, 1H), 6.21-6.19 (m, 1H), 5.31-5.01 (m, 1H), 4.77-4.42 (m, 4H), 3.65 (s, 3H). |
| 165 | 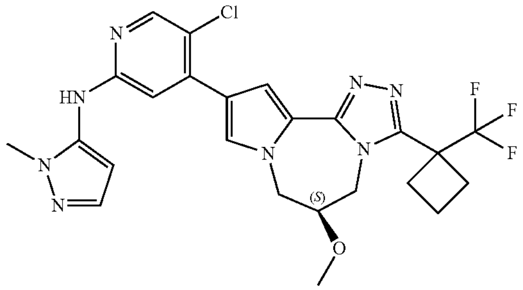 | 533.1 | $^1H$ NMR (400 MHz, DMSO-d6) δ 8.86 (s, 1H), 8.12 (s, 1H), 7.74 (d, J = 1.8 Hz, 1H), 7.31 (d, J = 1.9 Hz, 1H), 7.09 (d, J = 1.8 Hz, 1H), 6.95 (s, 1H), 6.21 (d, J = 1.9 Hz, 1H), 4.43-4.39 (m, 1H), 4.31-4.24 (m, 1H), 4.17-4.06 (m, 2H), 3.93-3.83 (m, 1H), 3.64 (s, 3H), 3.27 (s, 3H), 3.00-2.97 (m, 1H), 2.79-2.75 (m, 3H), 2.19-2.10 (m, 1H), 2.03-1.99 (m, 1H). |
| 166 | 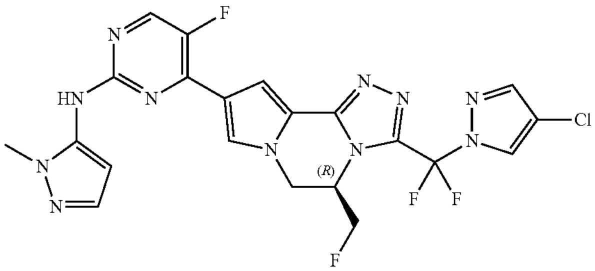 | 534.0 | $^1H$ NMR (400 MHz, DMSO-d6) δ 9.37 (s, 1H), 8.81 (s, 1H), 8.46 (d, J = 3.3 Hz, 1H), 8.01 (s, 1H), 7.91 (t, J = 1.8 Hz, 1H), 7.34 (d, J = 1.9 Hz, 1H), 7.29 (s, 1H), 6.26 (d, J = 1.9 Hz, 1H), 5.22-5.12 (m, 1H), 4.80 (d, J = 14.0 Hz, 1H), 4.52-4.45 (m, 3H), 3.67 (s, 3H). |
| 167 | 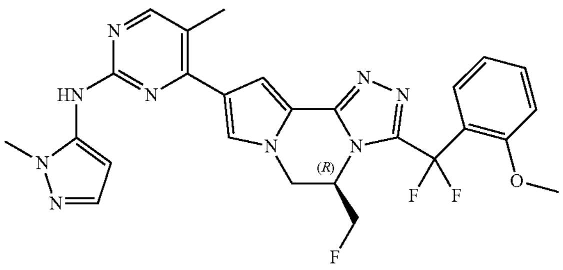 | 536.0 | $^1H$ NMR (400 MHz, DMSO-d6) δ 9.14 (s, 1H), 8.27 (s, 1H), 7.87 (s, 1H), 7.72-7.57 (m, 2H), 7.37-7.30 (m, 2H), 7.24-7.10 (m, 2H), 6.30-6.27 (m, 1H), 5.45-5.37 (m, 1H), 4.91-4.50 (m, 4H), 3.70 (s, 3H), 3.67 (s, 3H), 2.36 (s, 3H). |

-continued

| Compound | Structure | LC-MS (m/z) (M + H)+ | 1H NMR |
|---|---|---|---|
| 168 | 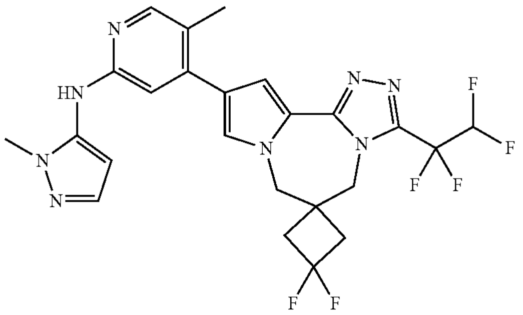 [SMILES: Cc1cnc(Nc2ccnn2C)cc1-c1cc2n(c1)CC1(Cn3c-2nnc3C(F)(F)C(F)F)CC(F)(F)C1] | 537.1 | 1H NMR (400 MHz, DMSO-d6) δ 8.54 (s, 1H), 7.94 (s, 1H), 7.55 (d, J = 2.0 Hz, 1H), 7.31-7.03 (m, 1H), 7.28 (d, J = 2.0 Hz, 1H), 7.17 (d, J = 2.0 Hz, 1H), 6.85 (s, 1H), 6.20 (d, J = 2.0 Hz, 1H), 4.50 (s, 2H), 4.47 (s, 2H), 3.64 (s, 3H), 2.74-2.55 (m, 4H), 2.29 (s, 3H). |
| 169 | 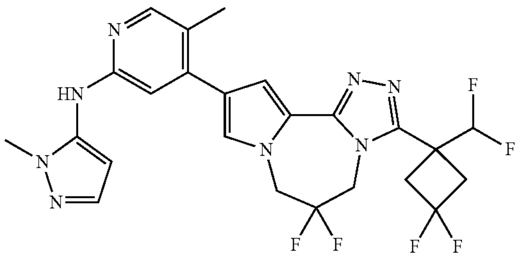 [SMILES: Cc1cnc(Nc2ccnn2C)cc1-c1cc2n(c1)CC(F)(F)Cn1c-2nnc1C1(C(F)F)CC(F)(F)C1] | 537.1 | 1H NMR (400 MHz, DMSO-d6) δ 8.54 (s, 1H), 7.95 (s, 1H), 7.60 (d, J = 1.7 Hz, 1H), 7.28 (d, J = 1.8 Hz, 1H), 7.00 (d, J = 1.7 Hz, 1H), 6.80 (s, 1H), 6.46 (t, J = 55.2 Hz, 1H), 6.18 (d, J = 1.8 Hz, 1H), 4.78 (t, J = 13.2 Hz, 2H), 4.54 (t, J = 12.7 Hz, 2H), 3.63 (s, 3H), 3.44-3.35 (m, 4H), 2.28 (s, 3H). |
| 170 | 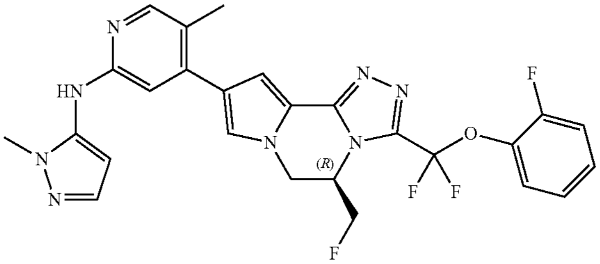 | 539.1 | 1H NMR (400 MHz, DMSO-d6) δ 8.57 (s, 1H), 7.95 (s, 1H), 7.66-7.24 (m, 6H), 7.08 (s, 1H), 6.84 (s, 1H), 6.20 (s, 1H), 5.52-5.35 (m, 1H), 4.74-4.58 (m, 4H), 3.65 (s, 3H), 2.30 (s, 3H). |
| 171 | 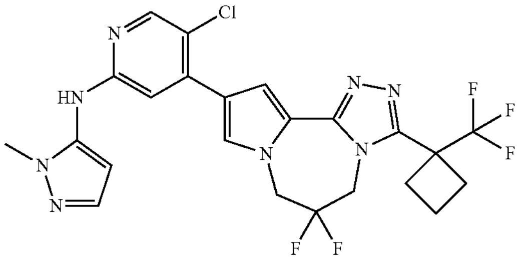 [SMILES: Cn1nccc1Nc1cc(-c2cc3n(c2)CC(F)(F)Cn2c-3nnc2C2(C(F)(F)F)CCC2)c(Cl)cn1] | 539.1 | 1H NMR (400 MHz, DMSO-d6) δ 8.90 (s, 1H), 8.14 (s, 1H), 7.87 (d, J = 2.0 Hz, 1H), 7.31 (d, J = 2.0 Hz, 1H), 7.11 (d, J = 2.0 Hz, 1H), 6.95 (s, 1H), 6.22 (d, J = 2.0 Hz, 1H), 4.82 (t, J = 13.2 Hz, 2H), 4.48 (t, J = 12.8 Hz, 2H), 3.64 (s, 3H), 2.91-2.73 (m, 4H), 2.21-2.09 (m, 1H), 2.04-1.93 (m, 1H). |
| 172 | 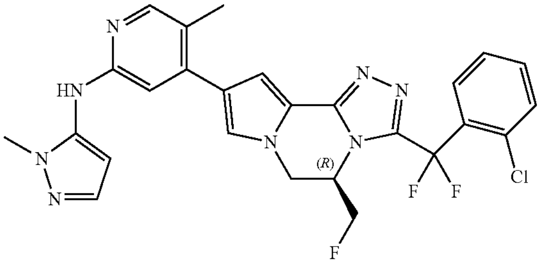 | 539.2 | 1H NMR (400 MHz, DMSO-d6) δ 8.56 (s, 1H), 7.98 (s, 1H), 7.90 (d, J = 7.6 Hz, 1H), 7.71-7.68 (m, 2H), 7.64-7.56 (m, 2H), 7.32 (d, J = 1.7 Hz, 1H), 7.07 (d, J = 1.3 Hz, 1H), 6.84 (s, 1H), 6.22 (d, J = 1.7 Hz, 1H), 5.50-5.44 (m, 1H), 4.78-4.60 (m, 4H), 3.67 (s, 3H), 2.32 (s, 3H). |

-continued

| Compound | Structure | LC-MS (m/z) (M + H)+ | $^1$H NMR |
|---|---|---|---|
| 173 | 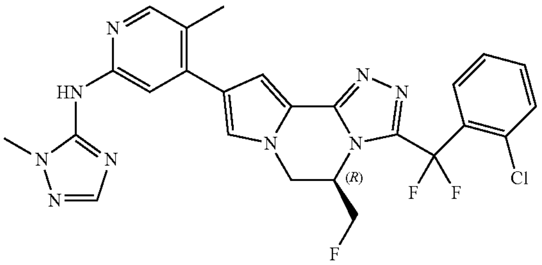 | 540.0 | $^1$H NMR (400 MHz, DMSO-d6) δ 9.54 (s, 1H), 8.06 (s, 1H), 7.96-7.81 (m, 2H), 7.78-7.46 (m, 5H), 7.08 (s, 1H), 5.54-5.36 (m, 1H), 4.84-4.54 (m, 4H), 3.71 (s, 3H), 2.34 (s, 3H). |
| 174 | 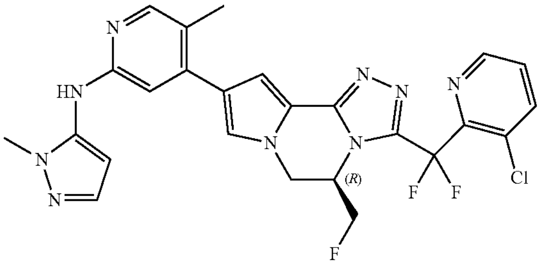 | 540.0 | $^1$H NMR (400 MHz, DMSO-d6) δ 8.65 (dd, J = 4.6, 1.3 Hz, 1H), 8.53 (s, 1H), 8.21 (dd, J = 8.2, 1.3 Hz, 1H), 7.96 (s, 1H), 7.73 (dd, J = 8.2, 4.6 Hz, 1H), 7.56 (d, J = 1.6 Hz, 1H), 7.30 (d, J = 1.9 Hz, 1H), 7.06 (d, J = 1.6 Hz, 1H), 6.83 (s, 1H), 6.20 (d, J = 1.9 Hz, 1H), 5.37-5.27 (m, 1H), 4.74-4.65 (m, 2H), 4.62-4.53 (m, 2H), 3.65 (s, 3H), 2.30 (s, 3H). |
| 175 | 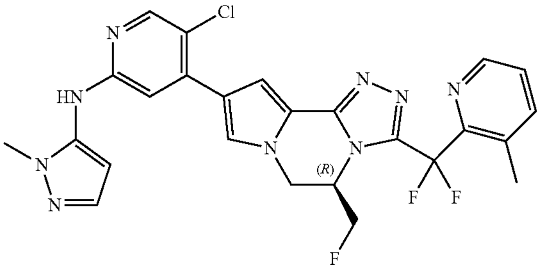 | 540.0 | $^1$H NMR (400 MHz, DMSO-d6) δ 8.85 (s, 1H), 8.43 (d, J = 3.7 Hz, 1H), 8.14 (s, 1H), 7.88 (d, J = 7.8 Hz, 1H), 7.82 (s, 1H), 7.61-7.47 (m, 1H), 7.33-7.30 (m, 1H), 7.15 (s, 1H), 6.97 (s, 1H), 6.24-6.21 (m, 1H), 5.33-5.10 (m, 1H), 4.76-4.46 (m, 4H), 3.64 (s, 3H), 2.45-2.43 (m, 3H). |
| 176 | 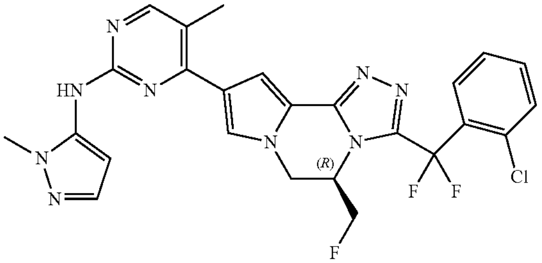 | 540.2 | $^1$H NMR (400 MHz, DMSO-d6) δ 9.15 (s, 1H), 8.27 (s, 1H), 7.94-7.86 (m, 2H), 7.69-7.66 (m, 2H), 7.64-7.57 (m, 1H), 7.36-7.34 (m, 2H), 6.29 (d, J = 1.7 Hz, 1H), 5.51-5.45 (m, 1H), 4.87-4.62 (m, 4H), 3.69 (s, 3H), 2.36 (s, 3H). |
| 177 | 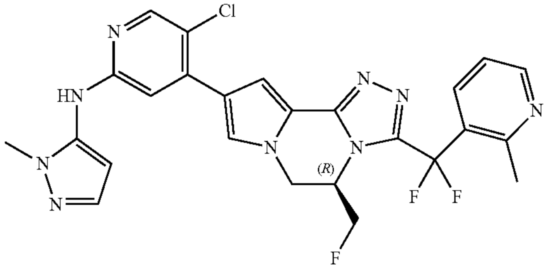 | 540.2 | $^1$H NMR (400 MHz, DMSO-d6) δ 8.93 (s, 1H), 8.66 (d, J = 4.1 Hz, 1H), 8.14 (s, 1H), 8.02 (d, J = 8.0 Hz, 1H), 7.84 (d, J = 1.7 Hz, 1H), 7.43 (t, J = 8.0 Hz, 1H), 7.31 (d, J = 1.9 Hz, 1H), 7.17 (d, J = 1.7 Hz, 1H), 7.01 (s, 1H), 6.22 (d, J = 1.9 Hz, 1H), 5.44-5.41 (m, 1H), 4.75-4.59 (m, 4H), 3.65 (s, 3H), 2.42 (s, 3H). |

-continued
| Compound | Structure | LC-MS (m/z) (M + H)+ | 1H NMR |
|---|---|---|---|
| 178 | 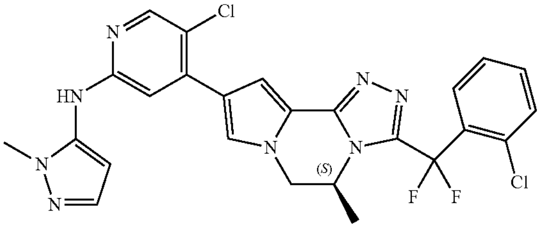 | 541.0 | 1H NMR (400 MHz, DMSO-d6) δ 8.85 (s, 1H), 8.16 (s, 1H), 7.89-7.84 (m, 2H), 7.68-7.65 (m, 2H), 7.61-7.55 (m, 1H), 7.33 (d, J =1.9 Hz, 1H), 7.18 (d, J = 1.7 Hz, 1H), 6.98 (s, 1H), 6.24 (d, J = 1.9 Hz, 1H), 5.30-5.16 (m, 1H), 4.53-4.48 (m, 2H), 3.66 (s, 3H), 1.33 (d, J = 6.7 Hz, 3H). |
| 179 | 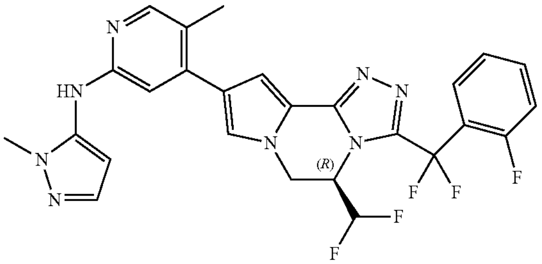 | 541.1 | 1H NMR (400 MHz, DMSO-d6) δ 8.54 (s, 1H), 7.94 (s, 1H), 7.76-7.66 (m, 2H), 7.59 (d, J = 1.6 Hz, 1H), 7.46-7.36 (m, 2H), 7.29 (d, J = 1.9 Hz, 1H), 7.06 (d, J = 1.6 Hz, 1H), 6.82 (s, 1H), 6.57-6.25 (m, 1H), 6.19 (d, J = 1.9 Hz, 1H), 5.67-5.54 (m, 1H), 4.88-4.78 (m, 1H), 4.73-4.62 (m, 1H), 3.64 (s, 3H), 2.28 (s, 3H). |
| 180 | 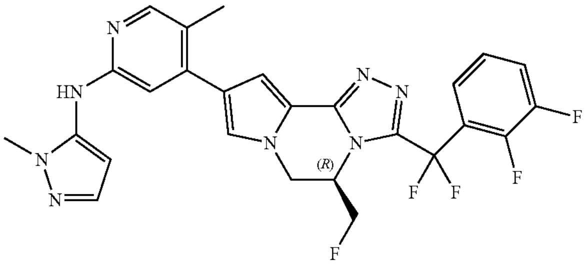 | 541.2 | 1H NMR (400 MHz, DMSO-d6) δ 8.53 (s, 1H), 7.96 (s, 1H), 7.84-7.74 (m, 1H), 7.62-7.54 (m, 2H), 7.49-7.41 (m, 1H), 7.32-7.28 (m, 1H), 7.06 (s, 1H), 6.83 (s, 1H), 6.23-6.18 (m, 1H), 5.51-5.36 (m, 1H), 4.79-4.55 (m, 4H), 3.65 (s, 3H), 2.29 (s, 3H). |
| 181 | 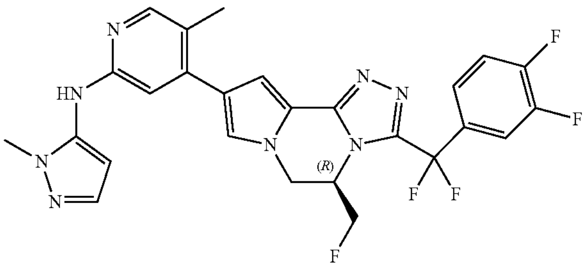 | 541.2 | 1H NMR (400 MHz, DMSO-d6) δ 8.51 (s, 1H), 7.95 (s, 1H), 7.91-7.78 (m, 1H), 7.71-7.51 (m, 3H), 7.30 (d, J = 1.8 Hz, 1H), 7.05 (d, J = 1.5 Hz, 1H), 6.82 (s, 1H), 6.20 (d, J = 1.8 Hz, 1H), 5.41-5.31 (m, 1H), 4.76-4.51 (m, 4H), 3.64 (s, 3H), 2.29 (s, 3H). |
| 182 | 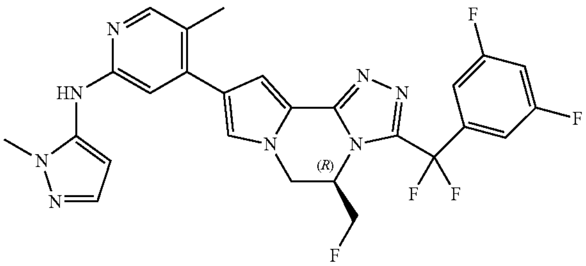 | 541.2 | 1H NMR (400 MHz, DMSO-d6) δ 8.52 (s, 1H), 7.95 (s, 1H), 7.63-7.52 (m, 2H), 7.50-7.46 (m, 2H), 7.30 (d, J = 1.9 Hz, 1H), 7.05 (d, J = 1.6 Hz, 1H), 6.82 (s, 1H), 6.20 (d, J = 1.9 Hz, 1H), 5.43-5.33 (m, 1H), 4.74-4.51 (m, 4H), 3.64 (s, 3H), 2.29 (s, 3H). |

-continued
| Compound | Structure | LC-MS (m/z) (M + H)+ | 1H NMR |
|---|---|---|---|
| 183 | 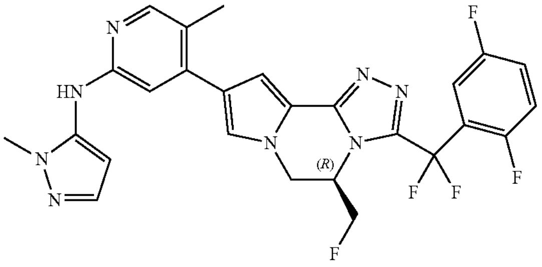 | 541.2 | 1H NMR (400 MHz, DMSO-d6) δ 8.51 (s, 1H), 7.95 (s, 1H), 7.69-7.47 (m, 4H), 7.29 (d, J = 1.9 Hz, 1H), 7.05 (d, J = 1.6 Hz, 1H), 6.82 (s, 1H), 6.20 (d, J = 1.9 Hz, 1H), 5.51-5.35 (m, 1H), 4.74-4.57 (m, 4H), 3.64 (s, 3H), 2.29 (s, 3H). |
| 184 | 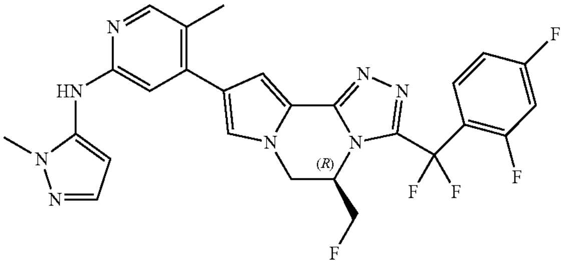 | 541.2 | 1H NMR (400 MHz, DMSO-d6) δ 8.58 (s, 1H), 7.96 (s, 1H), 7.91-7.78 (m, 1H), 7.61-7.47 (m, 2H), 7.37-7.27 (m, 2H), 7.09 (d, J = 1.2 Hz, 1H), 6.85 (s, 1H), 6.22 (d, J = 1.8 Hz, 1H), 5.52-5.34 (m, 1H), 4.78-4.59 (m, 4H), 3.66 (s, 3H), 2.30 (s, 3H). |
| 185 | 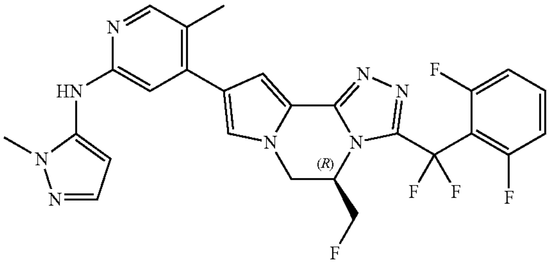 | 541.2 | 1H NMR (400 MHz, DMSO-d6) δ 8.58 (s, 1H), 7.96 (s, 1H), 7.86-7.68 (m, 1H), 7.57 (s, 1H), 7.45-7.28 (m, 3H), 7.10 (s, 1H), 6.85 (s, 1H), 6.23-6.20 (m, 1H), 5.52-5.35 (m, 1H), 4.91-4.56 (m, 4H), 3.66 (s, 3H), 2.30 (s, 3H). |
| 186 | 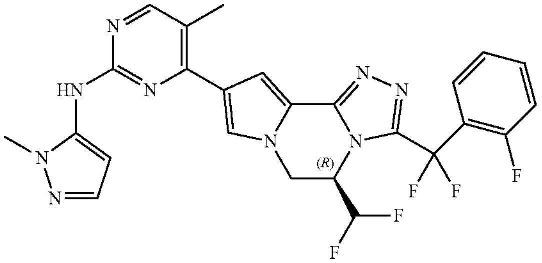 | 542.0 | 1H NMR (400 MHz, DMSO-d6) δ 9.12 (s, 1H), 8.25 (s, 1H), 7.88 (s, 1H), 7.77-7.67 (m, 2H), 7.46-7.38 (m, 2H), 7.36-7.31 (m, 2H), 6.58-6.23 (m, 2H), 5.70-5.56 (m, 1H), 4.98-4.88 (m, 1H), 4.76-4.65 (m, 1H), 3.67 (s, 3H), 2.33 (s, 3H). |
| 187 | 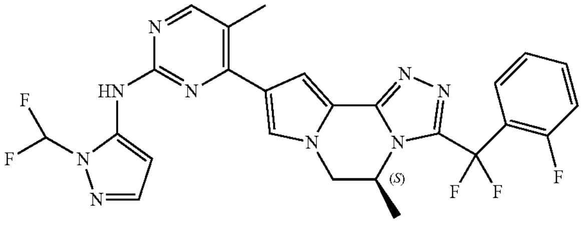 | 542.1 | 1H NMR (400 MHz, DMSO-d6) δ 9.64 (s, 1H), 8.30 (s, 1H), 7.88-7.85 (m, 1H), 7.78-7.63 (m, 3H), 7.61-7.17 (m, 4H), 6.46 (s, 1H), 5.30-5.10 (m, 1H), 4.52 (brs, 2H), 2.35 (s, 3H), 1.29 (d, J = 5.1 Hz, 3H). |

-continued
| Compound | Structure | LC-MS (m/z) (M + H)+ | $^1$H NMR |
|---|---|---|---|
| 188 | 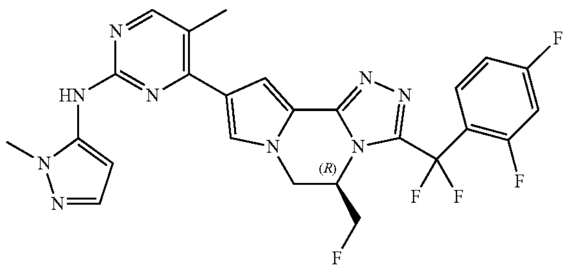 | 542.2 | $^1$H NMR (400 MHz, DMSO-d6) δ 9.12 (s, 1H), 8.25 (s, 1H), 7.96-7.76 (m, 2H), 7.59-7.45 (m, 1H), 7.43-7.22 (m, 3H), 6.30-6.26 (m, 1H), 5.53-5.36 (m, 1H), 4.87-4.59 (m, 4H), 3.69 (s, 3H), 2.34 (s, 3H). |
| 189 | 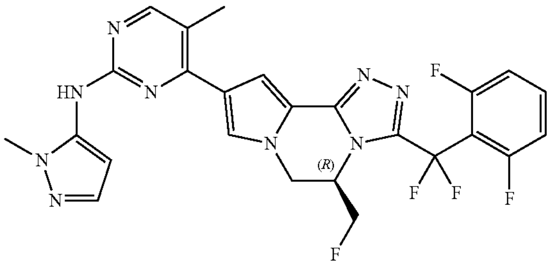 | 542.2 | $^1$H NMR (400 MHz, DMSO-d6) δ 9.11 (s, 1H), 8.25 (s, 1H), 7.91-7.70 (m, 2H), 7.56-7.22 (m, 4H), 6.31-6.25 (m, 1H), 5.54-5.37 (m, 1H), 4.89-4.51 (m, 4H), 3.67 (s, 3H), 2.34 (s, 3H). |
| 190 | 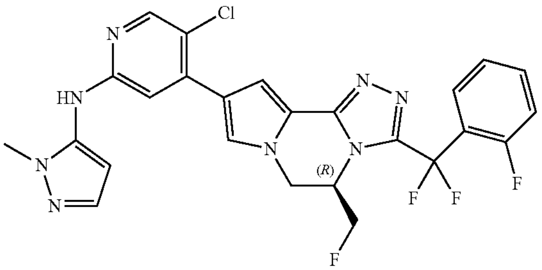 | 543.1 | $^1$H NMR (400 MHz, DMSO-d6) δ 8.85 (s, 1H), 8.18 (s, 1H), 7.87 (d, J = 1.0 Hz, 1H), 7.85-7.69 (m, 2H), 7.48-7.42 (m, 2H), 7.35 (d, J = 1.6 Hz, 1H), 7.20 (s, 1H), 6.99 (s, 1H), 6.26 (d, J = 1.6 Hz, 1H), 5.48-5.42 (m, 1H), 4.85-4.57 (m, 4H), 3.68 (s, 3H). |
| 191 | 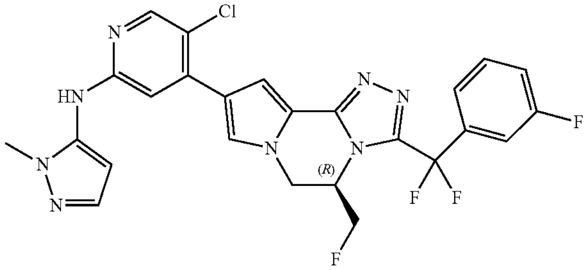 | 543.2 | $^1$H NMR (400 MHz, DMSO-d6) δ 8.89 (s, 1H), 8.15 (s, 1H), 7.84 (d, J = 1.5 Hz, 1H), 7.68-7.59 (m, 1H), 7.57-7.49 (m, 3H), 7.33 (d, J = 1.9 Hz, 1H), 7.17 (d, J = 1.5 Hz, 1H), 6.99 (s, 1H), 6.24 (d, J = 1.9 Hz, 1H), 5.42-5.36 (m, 1H), 4.79-4.54 (m, 4H), 3.66 (s, 3H). |
| 192 | 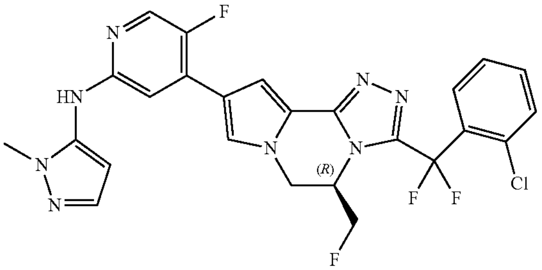 | 543.2 | $^1$H NMR (400 MHz, DMSO-d6) δ 8.67 (s, 1H), 8.09 (d, J = 2.9 Hz, 1H), 7.88 (d, J = 7.4 Hz, 1H), 7.77 (s, 1H), 7.70-7.52 (m, 3H), 7.31 (d, J = 1.8 Hz, 1H), 7.17 (s, 1H), 7.03 (d, J = 5.5 Hz, 1H), 6.21 (d, J = 1.8 Hz, 1H), 5.49-5.43 (m, 1H), 4.82-4.61 (m, 4H), 3.65 (s, 3H). |

-continued

| Compound | Structure | LC-MS (m/z) (M + H)+ | $^1$H NMR |
|---|---|---|---|
| 193 | 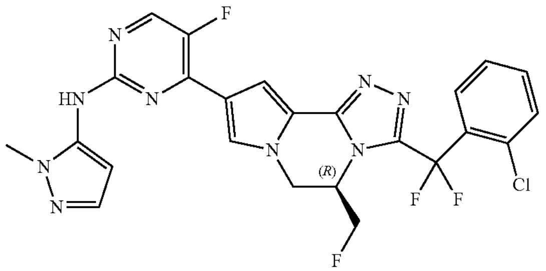 | 544.2 | $^1$H NMR (400 MHz, DMSO-d6) δ 9.36 (s, 1H), 8.47 (d, J = 3.3 Hz, 1H), 7.94 (d, J = 1.7 Hz, 1H), 7.88 (d, J = 7.4 Hz, 1H), 7.69-7.63 (m, 2H), 7.61-7.56 (m, 1H), 7.35 (d, J =1.9 Hz, 1H), 7.27 (s, 1H), 6.27 (d, J = 1.9 Hz, 1H), 5.51-5.45 (m, 1H), 4.93-4.58 (m, 4H), 3.68 (s, 3H). |
| 194 | 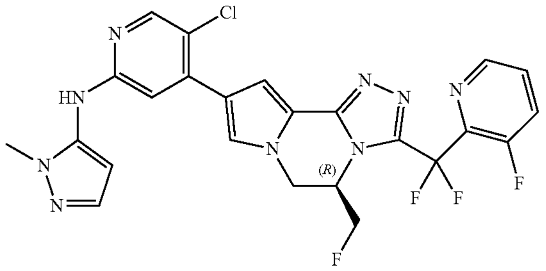 | 544.2 | $^1$H NMR (400 MHz, DMSO-d6) δ 8.86 (s, 1H), 8.53 (d, J = 4.6 Hz, 1H), 8.14 (s, 1H), 8.08-7.98 (m, 1H), 7.88-7.74 (m, 2H), 7.32 (d, J = 1.8 Hz, 1H), 7.17 (d, J = 1.3 Hz, 1H), 6.97 (s, 1H), 6.22 (d, J = 1.8 Hz, 1H), 5.52-5.18 (m, 1H), 4.80-4.53 (m, 4H), 3.65 (s, 3H). |
| 195 | 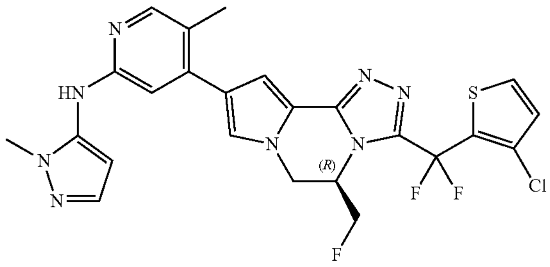 | 544.9 | $^1$H NMR (400 MHz, DMSO-d6) δ 8.53 (s, 1H), 8.01 (d, J = 5.3 Hz, 1H), 7.96 (s, 1H), 7.56 (d, J = 1.6 Hz, 1H), 7.34-7.24 (m, 2H), 7.07 (d, J = 1.6 Hz, 1H), 6.83 (s, 1H), 6.20 (d, J = 1.9 Hz, 1H), 5.44-5.22 (m, 1H), 4.74-4.53 (m, 4H), 3.65 (s, 3H), 2.29 (s, 3H). |
| 196 | 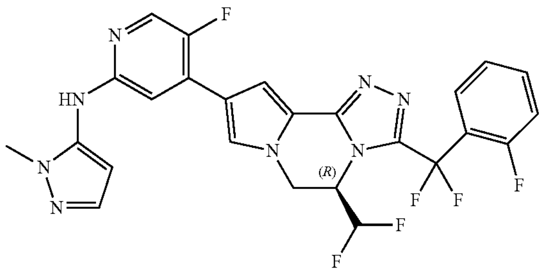 | 545.0 | $^1$H NMR (400 MHz, DMSO-d6) δ 8.72 (s, 1H), 8.07 (d, J = 2.9 Hz, 1H), 7.77 (s, 1H), 7.74-7.64 (m, 2H), 7.44-7.36 (m, 2H), 7.29 (d, J = 1.9 Hz, 1H), 7.22 (s, 1H), 7.01 (d, J = 5.5 Hz, 1H), 6.54-6.26 (m, 1H), 6.19 (d, J = 1.9 Hz, 1H), 5.67-5.55 (m, 1H), 4.92-4.87 (m, 1H), 4.71-4.59 (m, 1H), 3.63 (s, 3H). |
| 197 | 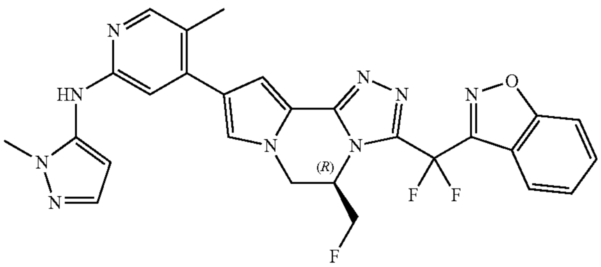 | 546.1 | $^1$H NMR (400 MHz, DMSO-d6) δ 8.53 (s, 1H), 7.97 (d, J = 8.4 Hz, 1H), 7.96 (s, 1H), 7.88 (d, J = 8.0 Hz, 1H), 7.84-7.80 (m, 1H), 7.58 (d, J = 1.6 Hz, 1H), 7.57-7.52 (m, 1H), 7.30 (d, J = 2.0 Hz, 1H), 7.08 (d, J = 1.6 Hz, 1H), 6.83 (s, 1H), 6.20 (d, J = 2.0 Hz, 1H), 5.53-5.42 (m, 1H), 4.80-4.56 (m, 4H), 3.65 (s, 3H), 2.30 (s, 3H). |

-continued

| Compound | Structure | LC-MS (m/z) (M + H)+ | 1H NMR |
| --- | --- | --- | --- |
| 198 | 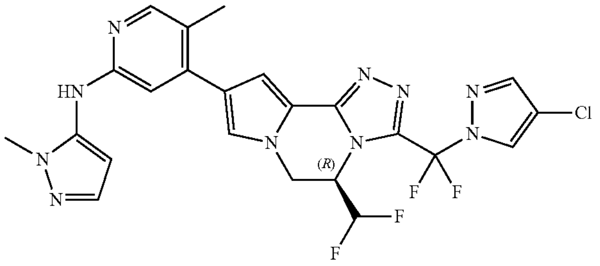 | 547.0 | 1H NMR (400 MHz, DMSO-d6) δ 8.78 (s, 1H), 8.55 (s, 1H), 8.03 (s, 1H), 7.98 (s, 1H), 7.60 (d, J = 1.6 Hz, 1H), 7.32 (d, J = 1.9 Hz, 1H), 7.13 (d, J = 1.6 Hz, 1H), 6.84 (s, 1H), 6.52-6.25 (m, 1H), 6.22 (d, J = 1.9 Hz, 1H), 5.45-5.32 (m, 1H), 4.88-4.77 (m, 1H), 4.64-4.51 (m, 1H), 3.67 (s, 3H), 2.31 (s, 3H). |
| 199 | 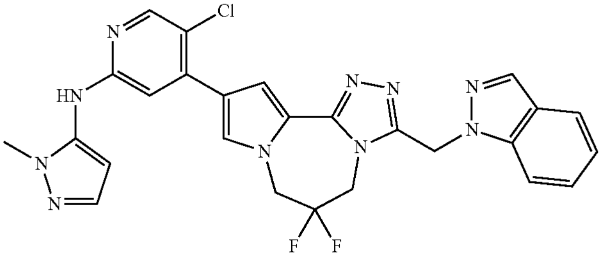 [SMILES: Cn1nccc1Nc1cc(-c2cc3n(c2)CC(F)(F)Cn2c(Cn4ncc5ccccc54)nnc2-3)c(Cl)cn1] | 547.4 | 1H NMR (400 MHz, DMSO-d6) δ 8.89 (s, 1H), 8.15 (s, 1H), 8.14 (d, J = 0.8 Hz, 1H), 7.86 (d, J = 1.6 Hz, 1H), 7.79-7.74 (m, 2H), 7.47-7.41 (m, 1H), 7.32 (d, J = 2.0 Hz, 1H), 7.20-7.14 (m, 1H), 7.12 (d, J = 2.0 Hz, 1H), 6.96 (s, 1H), 6.23 (d, J = 2.0 Hz, 1H), 5.98 (s, 2H), 4.79-4.70 (m, 4H), 3.65 (s, 3H). |
| 200 | 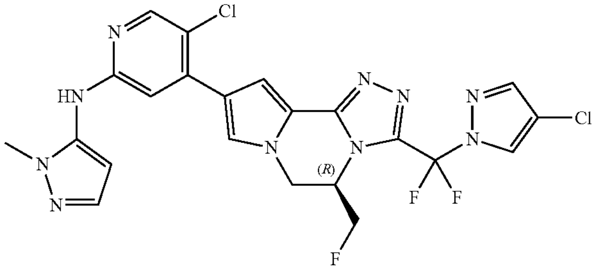 | 549.1 | 1H NMR (400 MHz, DMSO-d6) δ 8.83 (s, 1H), 8.80 (s, 1H), 8.14 (s, 1H), 8.01 (s, 1H), 7.81 (d, J = 1.6 Hz, 1H), 7.32 (d, J = 1.9 Hz, 1H), 7.20 (d, J = 1.6 Hz, 1H), 6.96 (s, 1H), 6.22 (d, J = 1.9 Hz, 1H), 5.17-5.12 (m, 1H), 4.75-4.40 (m, 4H), 3.65 (s, 3H). |
| 201 | 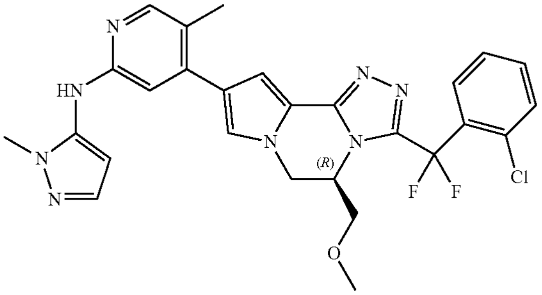 | 551.2 | 1H NMR (400 MHz, DMSO-d6) δ 8.51 (s, 1H), 7.94 (s, 1H), 7.86 (d, J = 7.6 Hz, 1H), 7.66-7.63 (m, 2H), 7.57-7.54 (m, 2H), 7.28 (d, J = 2.0 Hz, 1H), 7.02 (d, J = 1.2 Hz, 1H), 6.82 (s, 1H), 6.18 (d, J = 2.0 Hz, 1H), 5.23-5.18 (m, 1H), 4.67-4.39 (m, 2H), 3.63 (s, 3H), 3.49-3.41 (m, 2H), 3.20 (s, 3H), 2.28 (s, 3H). |
| 202 | 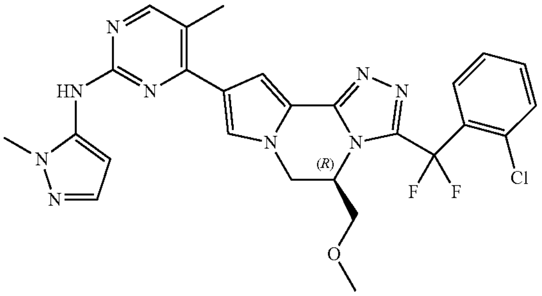 | 552.2 | 1H NMR (400 MHz, DMSO-d6) δ 9.09 (s, 1H), 8.23 (s, 1H), 7.88-7.84 (m, 2H), 7.66-7.62 (m, 2H), 7.59-7.53 (m, 1H), 7.34-7.26 (m, 2H), 6.25 (d, J = 2.0 Hz, 1H), 5.23-5.19 (m, 1H), 4.76-4.42 (m, 2H), 3.66 (s, 3H), 3.50-3.41 (m, 2H), 3.18 (s, 3H), 2.32 (s, 3H). |

-continued

| Compound | Structure | LC-MS (m/z) (M + H)+ | $^1$H NMR |
|---|---|---|---|
| 203 | 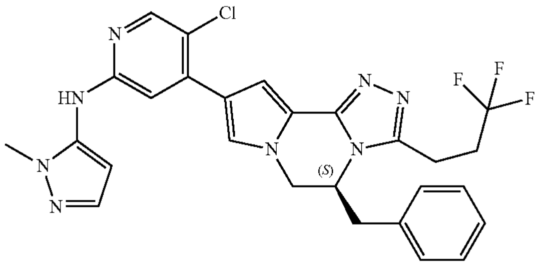 | 553.1 | $^1$H NMR (400 MHz, DMSO-d6) δ 8.89 (s, 1H), 8.14 (s, 1H), 7.78 (d, J = 1.6 Hz, 1H), 7.33 (d, J = 2.0 Hz, 1H), 7.25-7.22 (m, 3H), 7.07 (d, J = 1.6 Hz, 1H), 6.99 (s, 1H), 6.92-6.89 (m, 2H), 6.24 (d, J = 2.0 Hz, 1H), 5.01-4.89 (m, 1H), 4.59 (d, J = 14 Hz, 1H), 4.34-4.25 (m, 1H), 3.66 (s, 3H), 3.00-2.96(m, 2H), 2.66-2.56 (m, 2H), 2.36-2.24 (m, 2H). |
| 204 | 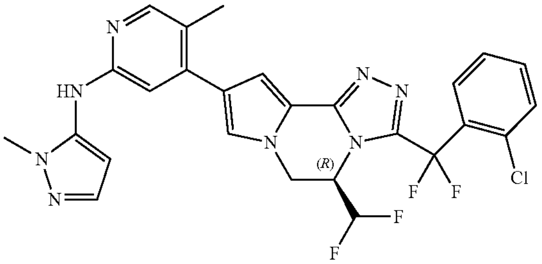 | 557.0 | $^1$H NMR (400 MHz, DMSO-d6) δ 8.54 (s, 1H), 7.95 (s, 1H), 7.92-7.83 (m, 1H), 7.68-7.52 (m, 4H), 7.29 (d, J = 1.8 Hz, 1H), 7.06 (d, J = 1.4 Hz, 1H), 6.81 (s, 1H), 6.57-6.19 (m, 1H), 6.19 (d, J = 1.8 Hz, 1H), 5.71-5.58 (m, 1H), 4.89-4.77 (m, 1H), 4.74-4.60 (m, 1H), 3.64 (s, 3H), 2.28 (s, 3H). |
| 205 | 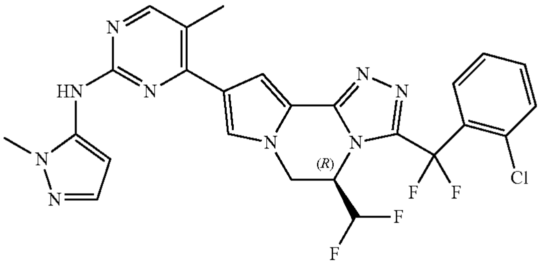 | 557.9 | $^1$H NMR (400 MHz, DMSO-d6) δ 9.12 (s, 1H), 8.25 (s, 1H), 7.97-7.82 (m, 2H), 7.70-7.53 (m, 3H), 7.37-7.28 (m, 2H), 6.59-6.23 (m, 2H), 5.75-5.59 (m, 1H), 5.01-4.87 (m, 1H), 4.76-4.63 (m, 1H), 3.68 (s, 3H), 2.34 (s, 3H). |
| 206 | 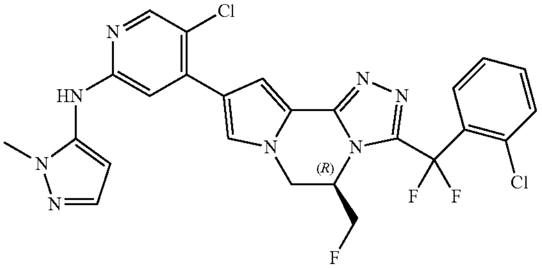 | 559.0 | $^1$H NMR (400 MHz, DMSO-d6) δ 8.85 (s, 1H), 8.16 (s, 1H), 7.90-7.84 (m, 2H), 7.69-7.50 (m, 3H), 7.33 (d, J = 1.9 Hz, 1H), 7.17 (d, J = 1.6 Hz, 1H), 6.97 (s, 1H), 6.24 (d, J = 1.9 Hz, 1H), 5.51-5.41 (m, 1H), 4.82-4.60 (m, 4H), 3.66 (s, 3H). |
| 207 | 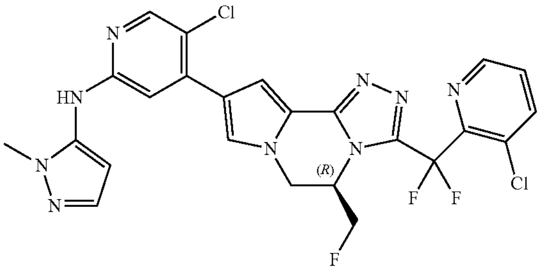 | 559.9 | $^1$H NMR (400 MHz, DMSO-d6) δ 8.86 (s, 1H), 8.64 (dd, J = 4.6, 1.2 Hz, 1H), 8.20 (dd, J = 8.2, 1.2 Hz, 1H), 8.14 (s, 1H), 7.83 (d, J = 1.7 Hz, 1H), 7.74-7.70 (m, 1H), 7.32 (d, J = 1.9 Hz, 1H), 7.17 (d, J = 1.7 Hz), 6.97 (s, 1H), 6.22 (d, J = 1.9 Hz, 1H), 5.39-5.25 (m, 1H), 4.81-4.72 (m, 1H), 4.72-4.64 (m, 1H), 4.63-4.52 (m, 2H), 3.65 (s, 3H). |

-continued

| Compound | Structure | LC-MS (m/z) (M + H)+ | $^1$H NMR |
|---|---|---|---|
| 208 | 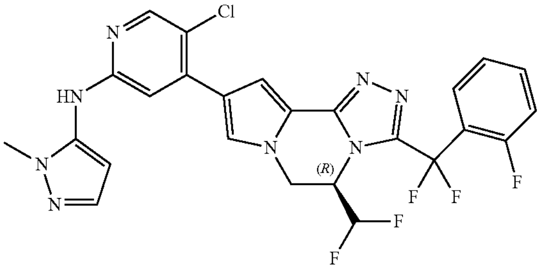 | 561.0 | $^1$H NMR (400 MHz, DMSO-d6) δ 8.90 (s, 1H), 8.16 (s, 1H), 7.88 (s, 1H), 7.77-7.65 (m, 2H), 7.48-7.37 (m, 2H), 7.33 (d, J = 1.8 Hz, 1H), 7.19 (d, J = 1.4 Hz, 1H), 6.99 (s, 1H), 6.57-6.29 (m, 1H), 6.24 (d, J = 1.8 Hz, 1H), 5.70-5.56 (m, 1H), 4.96-4.85 (m, 1H), 4.75-4.64 (m, 1H), 3.66 (s, 3H). |
| 209 | 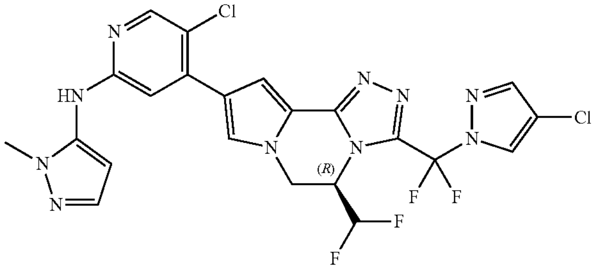 | 567.0 | $^1$H NMR (400 MHz, DMSO-d6) δ 8.89 (s, 1H), 8.78 (s, 1H), 8.18 (s, 1H), 8.03 (s, 1H), 7.88 (s, 1H), 7.35 (d, J = 1.3 Hz, 1H), 7.25 (s, 1H), 7.00 (s, 1H), 6.57-6.18 (m, 2H), 5.48-5.33 (m, 1H), 4.96-4.82 (m, 1H), 4.66-4.52 (m, 1H), 3.68 (s, 3H). |
| 210 | 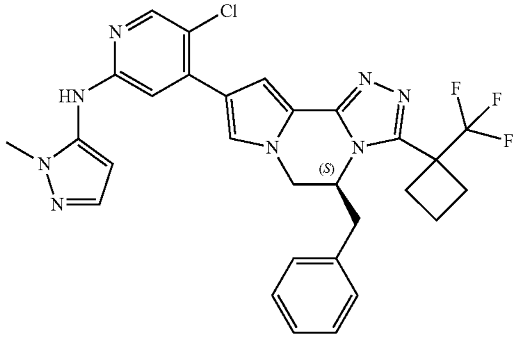 | 579.1 | $^1$H NMR (400 MHz, DMSO-d6) δ 8.91 (s, 1H), 8.17 (s, 1H), 7.82 (d, J = 1.6 Hz, 1H), 7.34 (d, J = 1.6 Hz, 1H), 7.33-7.25 (m, 3H), 7.11 (d, J = 2.0 Hz, 1H), 7.06-7.02 (m, 2H), 7.01 (s, 1H), 6.26 (d, J = 1.6 Hz, 1H), 4.76-4.71 (m, 1H), 4.25 (d, J = 2.4 Hz, 2H), 3.68 (s, 3H), 3.03-2.93 (m, 2H), 2.93-2.70 (m, 3H), 2.65-2.51 (m, 1H), 2.24-2.12 (m, 1H), 2.04-1.93 (m, 1H). |

Example 8: Synthesis of Compounds 211-214

Compound 211

5-chloro-4-(3-((2-fluorophenoxy)methyl)-6,7-dihydro-5H-pyrrolo[1,2-a][1,2,4]triazolo[3,4-c][1,4]diazepin-10-yl)-N-(1-methyl-1H-pyrazol-5-yl)pyrimidin-2-amine

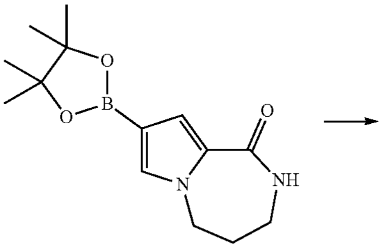

-continued

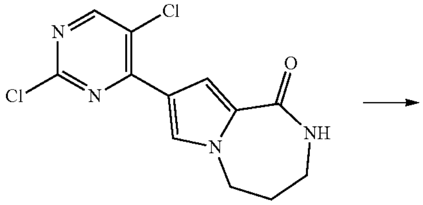

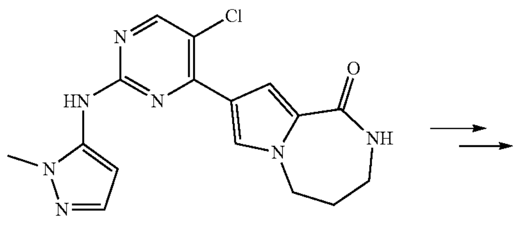

-continued

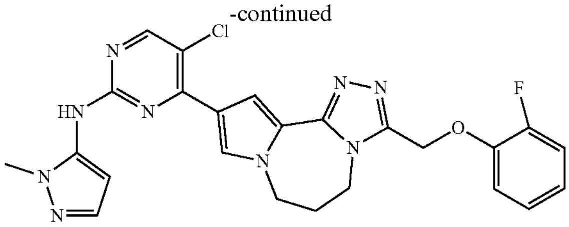

(A) 8-(2,5-dichloropyrimidin-4-yl)-2,3,4,5-tetrahydro-1H-pyrrolo[1,2-a][1,4]diazepin-1-one A mixture of 8-(4,4,5,5-tetramethyl-1,3,2-dioxaborolan-2-yl)-2,3,4,5-tetrahydro-1H-pyrrolo[1,2-a][1,4]diazepin-1-one (2.70 g, 9.78 mmol), Pd(dppf)$Cl_2$·$CH_2Cl_2$ (799 mg, 0.98 mmol), 2,4,5-trichloropyrimidine (1.97 g, 10.76 mmol) and cesium carbonate (9.56 g, 29.33 mmol) in 1,4-dioxane/water (120 mL/30 mL) was degassed and then stirred at 80° C. for 3 hours under nitrogen atmosphere. The mixture was diluted with DCM, washed with water and brine. The organic layer was dried over anhydrous sodium sulfate, concentrated. The residue was suspended in EA, stirred for 30 min, then filtered and the cake was dried in vacuum to afford the title compound as a yellow solid (2.85 g). MS (m/z): 296.9 $(M+H)^+$.

(B) 8-(5-chloro-2-((1-methyl-1H-pyrazol-5-yl)amino)pyrimidin-4-yl)-2,3,4,5-tetrahydro-1H-pyrrolo[1,2-a][1,4]diazepin-1-one A mixture of 8-(2,5-dichloropyrimidin-4-yl)-2,3,4,5-tetrahydro-1H-pyrrolo[1,2-a][1,4]diazepin-1-one (2.80 g, 9.46 mmol), 1-methyl-1H-pyrazol-5-amine (4.59 g, 47.28 mmol), $Pd_2dba_3$ (0.87 g, 0.95 mmol) and Xantphos (1.09 g, 1.89 mmol) and cesium carbonate (9.24 g, 28.36 mmol) in 1,4-dioxane (140 mL) was degassed and stirred at 100° C. for 6 h under nitrogen atmosphere. The mixture was filtered, and the filtrate was extracted with EA and water. The combined organic layers were washed with water and brine, dried over anhydrous sodium sulfate, concentrated. The residue was purified via ISCO (eluting with methanol in water 0%~100%) to afford the title compound as a yellow solid (1.52 g, 45.0% yield). MS (m/z): 358.0 $(M+H)^+$.

(C) 5-chloro-4-(3-((2-fluorophenoxy)methyl)-6,7-dihydro-5H-pyrrolo[1,2-a][1,2,4]triazolo[3,4-c][1,4]diazepin-10-yl)-N-(1-methyl-1H-pyrazol-5-yl)pyrimidin-2-amine The title compound was prepared according to the procedures of Example 1 using the corresponding intermediates and reagents. MS (m/z): 506.2 $(M+H)^+$.

$^1$H NMR (400 MHz, DMSO-d6) δ 9.48 (s, 1H), 8.43 (s, 1H), 7.97 (d, J=2.0 Hz, 1H), 7.60 (d, J=2.0 Hz, 1H), 7.44-7.39 (m, 1H), 7.36 (d, J=1.9 Hz, 1H), 7.25-7.20 (m, 1H), 7.19-7.13 (m, 1H), 7.04-6.96 (m, 1H), 6.26 (d, J=1.9 Hz, 1H), 5.40 (s, 2H), 4.50-4.41 (m, 2H), 4.37-4.30 (m, 2H), 3.68 (s, 3H), 2.40-2.30 (m, 2H).

The compounds below were prepared according to the procedures of Compound 211 using the corresponding intermediates and reagents under appropriate conditions that could be recognized by one skilled in the art.

| Compound | Structure | LC-MS (m/z) $(M + H)^+$ | $^1$H NMR |
|---|---|---|---|
| 212 | 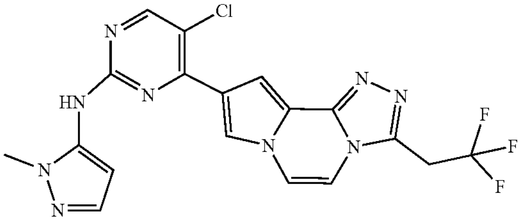 [SMILES: Cn1nccc1Nc1ncc(Cl)c(-c2cc3c4nnc(CC(F)(F)F)n4ccn3c2)n1] | 447.9 | $^1$H NMR (400 MHz, DMSO-d6) δ 9.59 (s, 1H), 8.55 – 8.53 (m, 2H), 8.10 (d, J = 6.0 Hz, 1H), 7.91 (d, J = 6.0 Hz, 1H), 7.64 (s, 1H), 7.38 (d, J = 1.9 Hz, 1H), 6.28 (d, J = 1.9 Hz, 1H), 4.38 (q, J = 10.8 Hz, 2H), 3.69 (s, 3H). |
| 213 | 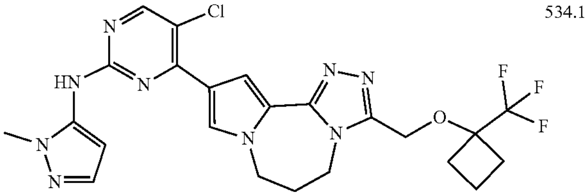 | 534.1 | $^1$H NMR (400 MHz, DMSO-d6) δ 9.45 (s, 1H), 8.42 (s, 1H), 7.95 (d, J = 1.9 Hz, 1H), 7.58 (d, J = 1.9 Hz, 1H), 7.35 (d, J = 1.8 Hz, 1H), 6.25 (d, J = 1.8 Hz, 1H), 4.83 (s, 2H), 4.47 – 4.38 (m, 2H), 4.30 – 4.21 (m, 2H), 3.67 (s, 3H), 2.59 – 2.50 (m, 2H), 2.37 – 2.25 (m, 4H), 1.94 – 1.82 (m, 1H), 1.81 – 1.67 (m, 1H). |
| 214 | 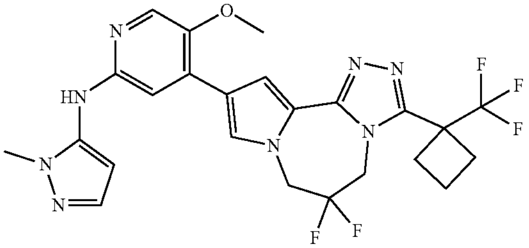 [SMILES: COc1cnc(Nc2ccnn2C)cc1-c1cc2n(c1)CC(F)(F)Cn1c-2nnc1C1(C(F)(F)F)CCC1] | 535.1 | $^1$H NMR (400 MHz, DMSO-d6) δ 8.44 (s, 1H), 7.90 (s, 1H), 7.82 (s, 1H), 7.26 (s, 1H), 7.10 (s, 1H), 7.02 (s, 1H), 6.19 (s, 1H), 4.79 (t, J = 13.2 Hz, 2H), 4.45 (t, J = 12.4 Hz, 2H), 3.87 (s, 3H), 3.64 (s, 3H), 2.91 – 2.83 (m, 2H), 2.80 – 2.74 (m, 2H), 2.18 – 2.11 (m, 1H), 2.04 – 1.93 (m, 1H). |

Example 9: Synthesis of Compounds 215-216

Compound 215

(S)-10-(5-chloro-2-((1-methyl-1H-pyrazol-5-yl) amino)pyridin-4-yl)-3-(1-(trifluoromethyl)cyclobutyl)-6,7-dihydro-5H-pyrrolo[1,2-a][1,2,4]triazolo[3,4-c][1,4]diazepin-6-ol

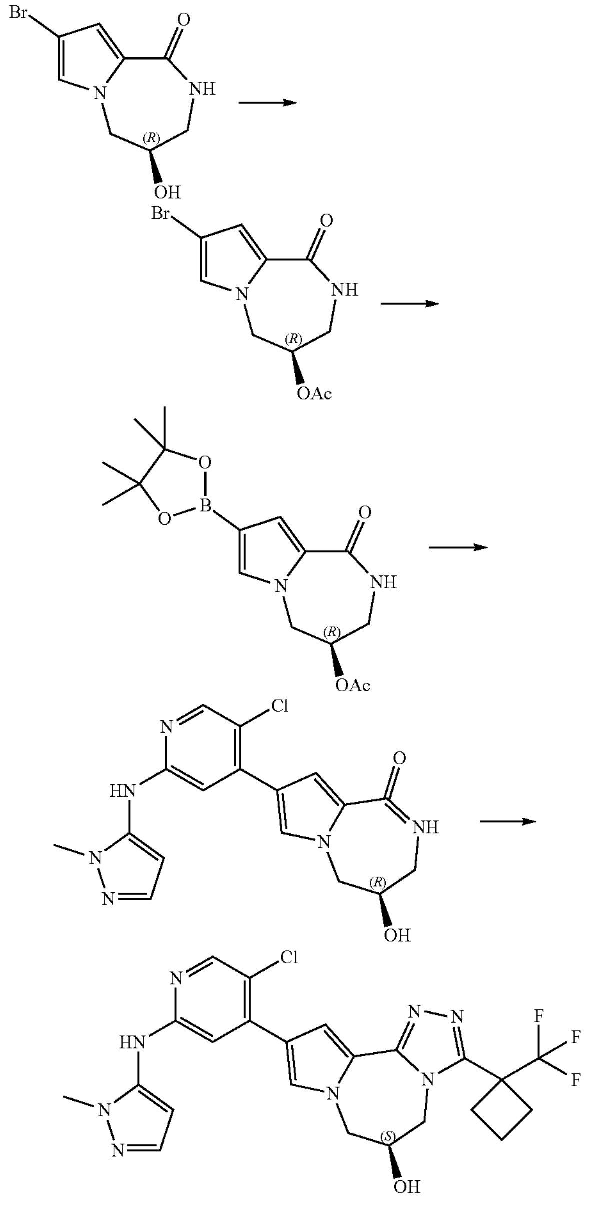

(A) (R)-8-bromo-1-oxo-2,3,4,5-tetrahydro-1H-pyrrolo[1,2-a][1,4]diazepin-4-yl acetate To a solution of (R)-8-bromo-4-hydroxy-2,3,4,5-tetrahydro-1H-pyrrolo[1,2-a][1,4]diazepin-1-one (1.5 g, 0.006 mol) and $Ac_2O$ (0.7 g, 0.006 mol) in THF (50 mL) was added $Et_3N$ (1.3 g, 0.012 mol) and N,N-dimethylpyridin-4-amine (40 mg, 0.300 mmol). After stirring at 50° C. for 1 hour, the mixture was concentrated and the residue was dissolved in DCM. Then the organic layer was washed with saturated solution of $NaHCO_3$ and water, concentrated to give the title compound as yellow oil (1.5 g, 88.2% yield). MS (m/z): 287.0/289.0 $(M+H)^+$.

(B) (R)-1-oxo-8-(4,4,5,5-tetramethyl-1,3,2-dioxaborolan-2-yl)-2,3,4,5-tetrahydro-1H-pyrrolo[1,2-a][1,4]diazepin-4-yl acetate A mixture of (R)-8-bromo-1-oxo-2,3,4,5-tetrahydro-1H-pyrrolo[1,2-a][1,4]diazepin-4-yl acetate (200 mg, 0.669 mmol), $Pd_2(dba)_3$ (32 mg, 0.035 mmol), tricyclohexylphosphane (10 mg, 0.035 mmol), BPIN (178 mg, 0.669 mmol) and KOAc (137 mg, 1.398 mmol) in 1,4-dioxane (10 mL) was stirred at 100° C. for 16 hours under nitrogen atmosphere. The mixture was filtrated and the filtrate was concentrated. The residue was purified via ISCO (eluting with methanol in water 0%~100%) to afford the title compound as a white solid (150 mg, 64.2% yield). MS (m/z): 335.1 $(M+H)^+$.

(C) (R)-8-(5-chloro-2-((1-methyl-1H-pyrazol-5-yl) amino)pyridin-4-yl)-4-hydroxy-2,3,4,5-tetrahydro-1H-pyrrolo[1,2-a][1,4]diazepin-1-one A mixture of (R)-1-oxo-8-(4,4,5,5-tetramethyl-1,3,2-dioxaborolan-2-yl)-2,3,4,5-tetrahydro-1H-pyrrolo[1,2-a][1,4]diazepin-4-yl acetate (150 mg, 0.449 mmol), $Pd(dppf)Cl_2$ (16 mg, 0.023 mmol), $Na_2CO_3$ (95 mg, 0.898 mmol) and 5-chloro-4-iodo-N-(1-methyl-1H-pyrazol-5-yl)pyridin-2-amine (150 mg, 0.449 mmol) in 1,4-dioxane (5 mL) and water (1 mL) was stirred at 80° C. for 2 hours under nitrogen atmosphere. The mixture was diluted with water and extracted with DCM. The organic layer was concentrated and the residue was purified via ISCO (eluting with methanol in water 0%~100%) to afford the title compound as a white solid (100 mg, 59.9% yield). MS (m/z): 373.1 $(M+H)^+$.

(D) (S)-10-(5-chloro-2-((1-methyl-1H-pyrazol-5-yl) amino)pyridin-4-yl)-3-(1-(trifluoromethyl)cyclobutyl)-6,7-dihydro-5H-pyrrolo[1,2-a][1,2,4]triazolo[3,4-c][1,4]diazepin-6-ol A mixture of (R)-8-(5-chloro-2-((1-methyl-1H-pyrazol-5-yl)amino)pyridin-4-yl)-4-hydroxy-2,3,4,5-tetrahydro-1H-pyrrolo[1,2-a][1,4]diazepin-1-one (100 mg, 0.269 mmol), 1-(trifluoromethyl)cyclobutane-1-carbohydrazide (49 mg, 0.269 mmol) in $POCl_3$ (5 mL) was stirred at 80° C. for 2 hours. The mixture was concentrated and the residue was dissolved in DCM and MeOH. Then the organic layer was washed with saturated solution of $NaHCO_3$ and water, concentrated and the residue was dissolved in NMP (5 mL). A drop of HOAc was added and the mixture was stirred at 130° C. in microwave for 30 minutes. Then the reaction mixture was directly purified via ISCO (eluting with methanol in water 0%~100%) to afford the title compound as a light yellow solid (20 mg, 14.4% yield). MS (m/z): 519.0 $(M+H)^+$.

$^1$H NMR (400 MHz, DMSO-d6) δ 8.85 (s, 1H), 8.12 (s, 1H), 7.70 (s, 1H), 7.31 (s, 1H), 7.07 (s, 1H), 6.96 (s, 1H), 6.21 (s, 1H), 4.45-4.28 (m, 2H), 4.14-4.01 (m, 2H), 3.82-3.7 (m, 1H), 3.03-2.86 (m, 2H), 2.73-2.69 (m, 2H), 2.16-2.12 (m, 1H), 2.03-2.00 (m, 1H).

The compound below was prepared according to the procedures of Compound 215 using the corresponding intermediates and reagents under appropriate conditions that could be recognized by one skilled in the art.

| Compound | Structure | LC-MS (m/z) (M + H)$^+$ | $^1$H NMR |
|---|---|---|---|
| 216 | 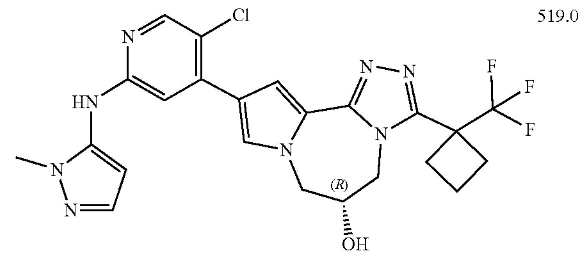 | 519.0 | $^1$H NMR (400 MHz, DMSO-d6) δ 8.88 (s, 1H), 8.14 (s, 1H), 7.72 (s, 1H), 7.32 (s, 1H), 7.09 (s, 1H), 6.97 (s, 1H), 6.23 (s, 1H), 4.47 - 4.29 (m, 2H), 4.16 - 4.02 (m, 2H), 3.83-3.80 (m, 1H), 3.66 (s, 3H), 3.04 - 2.89 (m, 2H), 2.74-2.71 (m, 2H), 2.18-2.15 (m, 1H), 2.04-2.01 (m, 1H). |

Example 10: Synthesis of Compounds 217-219

Compound 217

1-((10-(5-chloro-2-((1-methyl-1H-pyrazol-5-yl)amino)pyridin-4-yl)-6,6-difluoro-6,7-dihydro-5H-pyrrolo[1,2-a][1,2,4]triazolo[3,4-c][1,4]diazepin-3-yl)methyl)-1H-pyrrole-2-carbonitrile

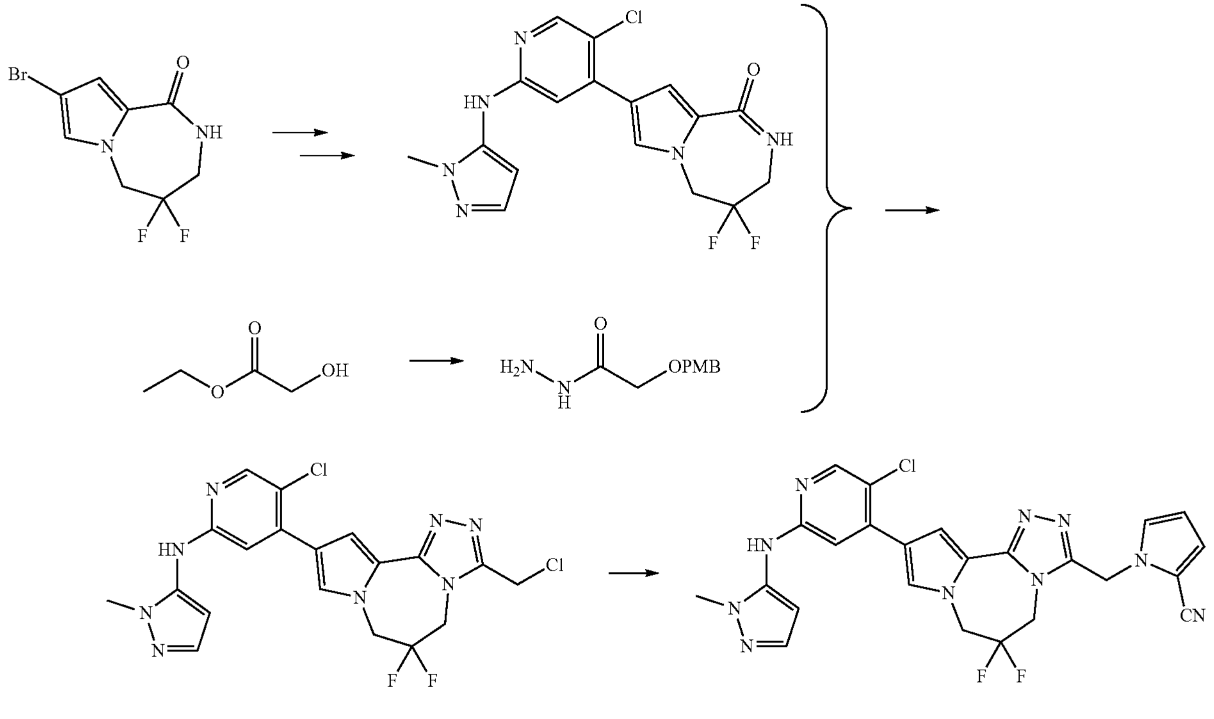

(A) 8-(5-chloro-2-((1-methyl-1H-pyrazol-5-yl)amino)pyridin-4-yl)-4,4-difluoro-2,3,4,5-tetrahydro-1H-pyrrolo[1,2-a][1,4]diazepin-1-one The title intermediate was prepared according to the procedures of Example 1 using the corresponding intermediates and reagents.

(B) 2-((4-methoxybenzyl)oxy)acetohydrazide

To a solution of ethyl 2-hydroxyacetate (3.1 g, 30 mmol) in anhydrous DMF (50 mL) was added NaH (1.5 g, 36 mmol, 60% dispersion in Paraffin Liquid) in portions at 5° C. under nitrogen atmosphere. The mixture was stirred for 1 h. 1-(chloromethyl)-4-methoxybenzene (5.6 g, 36 mmol) was added dropwise and the mixture was stirred at room temperature for 12 h. The reaction was quenched with saturated solution of ammonium chloride, and then concentrated under vacuum. The residue was purified by silica gel chromatography (PE:EA=4:1) to give a yellow oil. The oil was dissolved in ethanol (100 mL) and hydrazine hydrate (4.5 g, 85%) was added. The solution was refluxed for 2 h. Solvent was removed by rotary evaporator and the residue was purified via ISCO (eluting with methanol in water 0%~100%) to afford the title compound as yellow oil (3.7 g, 59% yield). MS (m/z): 121.1 (M+H)$^+$.

(C) 5-chloro-4-(3-(chloromethyl)-6,6-difluoro-6,7-dihydro-5H-pyrrolo[1,2-a][1,2,4]triazolo[3,4-c][1,4]diazepin-10-yl)-N-(1-methyl-1H-pyrazol-5-yl)pyridin-2-amine A mixture of 8-(5-chloro-2-((1-methyl-1H-pyrazol-5-yl)amino)pyridin-4-yl)-4,4-difluoro-2,3,4,5-tetrahydro-1H-pyrrolo[1,2-a][1,4]diazepin-1-one (784 mg, 2 mmol) and 2-((4-methoxybenzyl)oxy)acetohydrazide (841 mg, 4 mmol) in $POCl_3$ (10 mL) was stirred at 100° C. for 2 h under nitrogen atmosphere. Solvent was removed by rotary evaporator and the residue was dissolved in DCM, washed with saturated aqueous sodium bicarbonate. The aqueous phase was extracted with DCM. The organic phases were combined, dried over anhydrous sodium sulfate, and then concentrated under vacuum. The residue was dissolved in a solution of acetic acid (2 drops) in n-BuOH (20 mL). The solution was stirred at 130° C. for 2 h, and then concentrated under vacuum. The residue was purified via ISCO (eluting with methanol in water 0%~100%) to afford the title compound as yellow solid (380 mg, 41% yield). MS (m/z): 465.1, 467.1 $(M+H)^+$.

(D) 1-((10-(5-chloro-2-((1-methyl-1H-pyrazol-5-yl)amino)pyridin-4-yl)-6,6-difluoro-6,7-dihydro-5H-pyrrolo[1,2-a][1,2,4]triazolo[3,4-c][1,4]diazepin-3-yl)methyl)-1H-pyrrole-2-carbonitrile A mixture of 5-chloro-4-(3-(chloromethyl)-6,6-difluoro-6,7-dihydro-5H-pyrrolo[1,2-a][1,2,4]triazolo[3,4-c][1,4]diazepin-10-yl)-N-(1-methyl-1H-pyrazol-5-yl)pyridin-2-amine (80 mg, 0.17 mmol), 1H-pyrrole-2-carbonitrile (19 mg, 0.21 mmol) and Cesium carbonate (166 mg, 0.51 mmol) in acetonitrile (10 mL) was stirred at room temperature under nitrogen atmosphere overnight. The reaction was quenched with diluted aqueous HCl, and then neutralized by saturated aqueous sodium bicarbonate to PH=8. The mixture was extracted with DCM/MeOH (10:1). The organic phases were combined, and then concentrated under vacuum. The residue was purified via ISCO (eluting with methanol in water 0%~100%) and PTLC (DCM/MeOH=10:1) to give the title compound as a light yellow solid (19.1 mg, 22% yield). MS (m/z): 521.1 $(M+H)^+$.

$^1H$ NMR (400 MHz, DMSO-d6) δ 8.87 (s, 1H), 8.14 (s, 1H), 7.87 (d, J=1.9 Hz, 1H), 7.31 (d, J=1.9 Hz, 1H), 7.25 (dd, J=2.7, 1.6 Hz, 1H), 7.13 (d, J=1.9 Hz, 1H), 6.98 (dd, J=4.0, 1.6 Hz, 1H), 6.96 (s, 1H), 6.23 (dd, J=4.0, 2.7 Hz, 1H), 6.21 (d, J=1.9 Hz, 1H), 5.60 (s, 2H), 4.80-4.69 (m, 4H), 3.64 (s, 3H).

The compounds below were prepared according to the procedures of Compound 217 using the corresponding intermediates and reagents under appropriate conditions that could be recognized by one skilled in the art.

| Compound | Structure | LC-MS (m/z) $(M + H)^+$ | $^1H$ NMR |
|---|---|---|---|
| 218 | 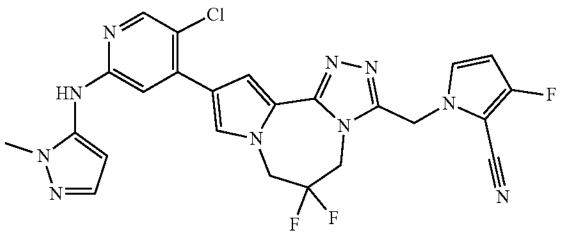 [SMILES: Cn1nccc1Nc1cc(-c2cc3n(c2)CC(F)(F)Cn2c(Cn4ccc(F)c4C#N)nnc2-3)c(Cl)cn1] | 539.0 | $^1H$ NMR (400 MHz, DMSO-d6) δ 9.02 (s, 1H), 8.13 (s, 1H), 7.87 (d, J = 1.7 Hz, 1H), 7.30 (d, J = 1.8 Hz, 1H), 7.23 (dd, J = 5.0, 3.3 Hz, 1H), 7.13 (d, J = 1.8 Hz, 1H), 7.04 (s, 1H), 6.22 - 6.21 (m, 2H), 5.57 (s, 2H), 4.81 - 4.69 (m, 4H), 3.65 (s, 3H). |
| 219 | 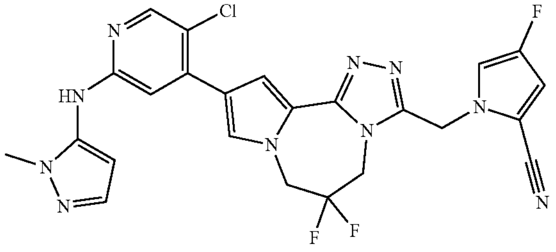 [SMILES: Cn1nccc1Nc1cc(-c2cc3n(c2)CC(F)(F)Cn2c(Cn4cc(F)cc4C#N)nnc2-3)c(Cl)cn1] | 539.0 | $^1H$ NMR (400 MHz, DMSO-d6) δ 8.85 (s, 1H), 8.14 (s, 1H), 7.87 (d, J = 1.7 Hz, 1H), 7.31 (d, J = 1.8 Hz, 1H), 7.29 - 7.24 (m, 1H), 7.13 (d, J = 1.8 Hz, 1H), 6.97 (d, J = 2.0 Hz, 1H), 6.95 (s, 1H), 6.21 (d, J = 1.8 Hz, 1H), 5.55 (s, 2H), 4.83 - 4.67 (m, 4H), 3.64 (s, 3H). |

Example 11: Synthesis of Compounds 220-228

Compound 220

(R)-4-(3-((2-chlorophenyl)difluoromethyl)-5-(methoxymethyl)-5,6-dihydroimidazo[1,2-a][1,2,4]triazolo[3,4-c]pyrazin-9-yl)-5-methyl-N-(1-methyl-1H-pyrazol-5-yl)pyrimidin-2-amine

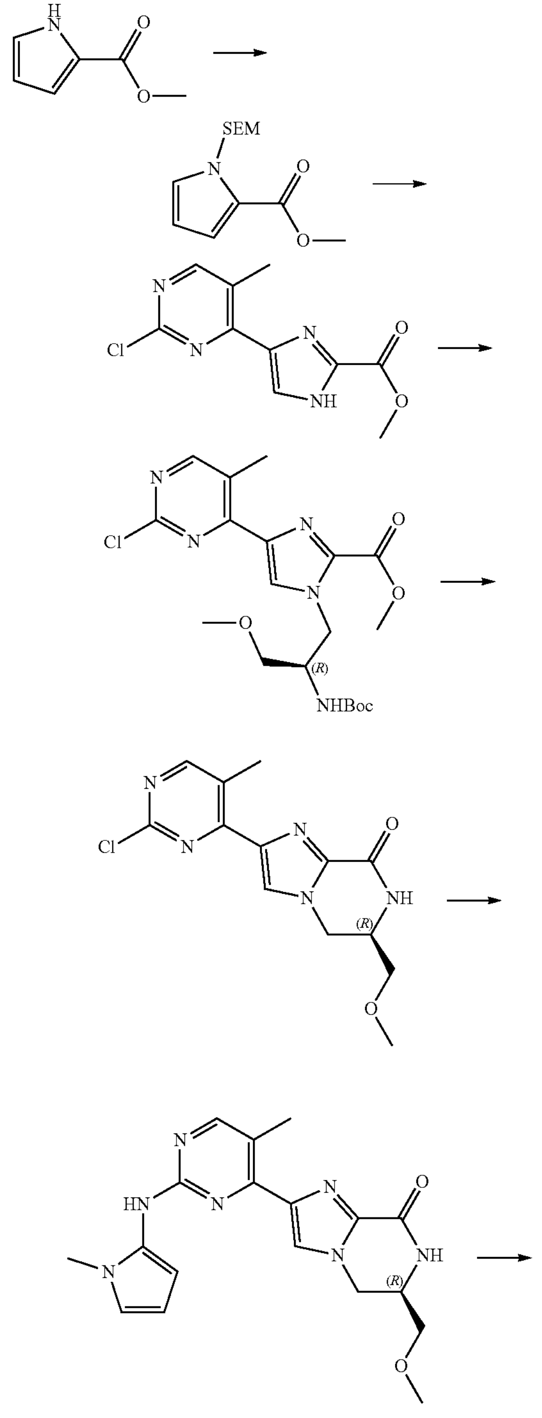

-continued

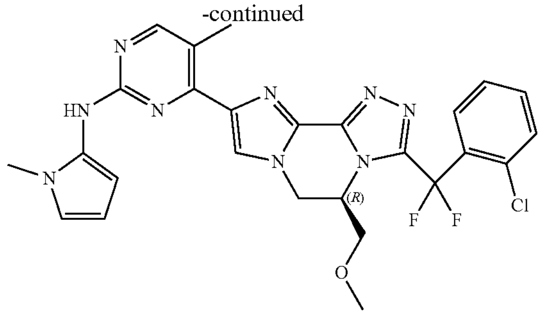

(A) Methyl 1-((2-(trimethylsilyl)ethoxy)methyl)-1H-imidazole-2-carboxylate

To a solution of methyl 1H-imidazole-2-carboxylate (10 g, 79.3 mmol) and $K_2CO_3$ in acetone (300 mL) was added (2-(chloromethoxy)ethyl)trimethylsilane (14.3 g, 85.6 mmol). The resulting mixture was stirred at room temperature for 16 hours. The reaction mixture was filtered and the filtrate was concentrated. The residue was purified via silica gel chromatography (PE:EA=2:1) to afford the title compound as yellow oil (11.9 g, 58.5% yield). MS (m/z): 257.0 $(M+H)^+$.

(B) Methyl 4-(2-chloro-5-methylpyrimidin-4-yl)-1H-imidazole-2-carboxylate

To a mixture of methyl 1-((2-(trimethylsilyl)ethoxy)methyl)-1H-imidazole-2-carboxylate (16.6 g, 64.7 mmol), BPIN (32.8 g, 129.2 mmol), (1,5-cyclooctadiene)(methoxy)iridium(I) Dimer (2.2 g, 3.3 mmol) and 3,4,7,8-tetramethyl-1,10-phenanthroline (1.5 g, 6.5 mmol) was added anhydrous THF (110 mL) and the resulting mixture was degassed three times with nitrogen. Then the mixture was refluxed overnight under nitrogen atmosphere. The mixture was filtered and the filtrate was concentrated. The residue was dissolved in DMF (400 mL), $Pd(PPh_3)_4$ (3.8 g, 3.3 mmol), CuI (1.3 g, 6.5 mmol), Cs2CO3 (15.8 g, 97.0 mmol) and 2,4-dichloro-5-methyl pyrimidine (15.8 g, 97.0 mmol) was added. The resulting mixture was degassed three times with nitrogen. Then the mixture was stirred at 90° C. overnight under nitrogen atmosphere. The mixture was filtered and the filtrate was concentrated. The residue was dissolved in TFA (100 mL) and refluxed for 2 h. The volatiles were removed and the residue was neutralized with saturated solution of $NaHCO_3$ and then extracted with DCM/MeOH (10:1). The combined organic layers were concentrated and the residue was purified via silica gel chromatography (DCM:MeOH=10:1) to afford the title compound as an off-white solid (15.2 g, 92.9% yield). MS (m/z): 253.0 $(M+H)^+$.

(C) Methyl (R)-1-(2-((tert-butoxycarbonyl)amino)-3-methoxypropyl)-4-(2-chloro-5-methylpyrimidin-4-yl)-1H-imidazole-2-carboxylate To a solution of methyl 4-(2-chloro-5-methylpyrimidin-4-yl)-1H-imidazole-2-carboxylate (2.5 g, 9.9 mmol), tert-butyl (R)-(1-hydroxy-3-methoxypropan-2-yl)carbamate (2.3 g, 12.0 mmol) and $PPh_3$ (5.3 g, 20.0 mmol) in anhydrous THF (100 mL) was added DIAD (4.6 g, 20.0 mmol) dropwise at 0° C. The resulting mixture was stirred at room temperature overnight under nitrogen atmosphere. The mixture was concentrated and the residue was purified via silica gel chromatography (PE:EA=2:1) to afford the title compound as yellow gum (2.5 g, 57.4% yield). MS (m/z): 440.0 $(M+H)^+$.

(D) (R)-2-(2-chloro-5-methylpyrimidin-4-yl)-6-(methoxymethyl)-6,7-dihydroimidazo[1,2-a]pyrazin-8(5H)-one A mixture of methyl (R)-1-(2-((tert-butoxycarbonyl)amino)-3-methoxypropyl)-4-(2-chloro-5-methylpyrimidin-4-yl)-1H-imidazole-2-carboxylate (2.5 g, 5.7 mmol) and TFA (15 mL) in DCM (20 mL) was stirred at room temperature for 3 hours. The mixture was concentrated and the residue was dissolved in MeOH (10 mL) and a solution of ammonium in MeOH (30 mL, 7M) was added. The resulting mixture was stirred at room temperature for 2 hours. The mixture was concentrated and the residue was purified via silica gel chromatography (DCM:MeOH=20:1) to afford the title compound as a yellow compound (1.21 g, 69.2% yield). MS (m/z): 308.0 $(M+H)^+$.

(E) (R)-6-(methoxymethyl)-2-(5-methyl-2-((1-methyl-1H-pyrazol-5-yl)amino)pyrimidin-4-yl)-6,7-dihydroimidazo[1,2-a]pyrazin-8(5H)-one To a solution of 1-methyl-1H-pyrazol-5-amine (0.12 g, 1.24 mmol) in THF (10 mL) was added NaHMDS (0.5 mL, 1.0 mmol, 2M in THF) at room temperature and the resulting mixture was further stirred for 20 min under nitrogen atmosphere. (R)-2-(2-chloro-5-methylpyrimidin-4-yl)-6-(methoxymethyl)-6,7-dihydroimidazo[1,2-a]pyrazin-8(5H)-one (0.12 g, 0.39 mmol) was added and the mixture was refluxed for overnight. The reaction was quenched with 4N HCl. The volatiles were removed and the residue was neutralized with saturated solution of $NaHCO_3$. The solvent was removed and the residue was purified via silica gel chromatography (DCM:MeOH=10:1) to afford the title compound as a yellow solid (0.118 g, 82.1% yield). MS (m/z): 369.2 $(M+H)^+$.

(F) (R)-4-(3-((2-chlorophenyl)difluoromethyl)-5-(methoxymethyl)-5,6-dihydroimidazo[1,2-a][1,2,4]triazolo[3,4-c]pyrazin-9-yl)-5-methyl-N-(1-methyl-1H-pyrazol-5-yl)pyrimidin-2-amine The title compound was prepared according to the procedures of Example 7 using the corresponding intermediates and reagents. MS (m/z): 553.0 $(M+H)^+$.

$^1$H NMR (400 MHz, DMSO-d6) δ 9.22 (s, 1H), 8.32 (s, 1H), 8.12 (s, 1H), 7.89 (d, J=7.5 Hz, 1H), 7.70-7.64 (m, 2H), 7.62-7.54 (m, 1H), 7.32 (d, J=1.8 Hz, 1H), 6.30 (d, J=1.8 Hz, 1H), 5.38-5.32 (m, 1H), 4.87 (d, J=14.0 Hz, 1H), 4.69 (dd, J=14.0, 5.1 Hz, 1H), 3.69 (s, 3H), 3.62-3.51 (m, 2H), 3.13 (s, 3H), 2.52 (s, 3H).

The compounds below were prepared according to the procedures of Compound 220 using the corresponding intermediates and reagents under appropriate conditions that could be recognized by one skilled in the art.

| Compound | Structure | LC-MS (m/z) $(M + H)^+$ | $^1$H NMR |
|---|---|---|---|
| 221 | 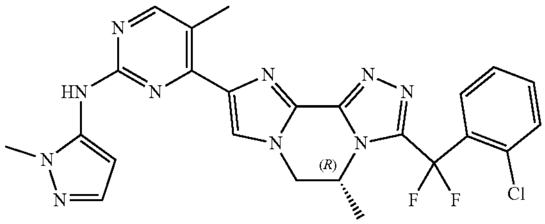 | 523.0 | $^1$H NMR (400 MHz, DMSO-d6) δ 9.22 (s, 1H), 8.33 (s, 1H), 8.12 (s, 1H), 7.89 (d, J = 7.5 Hz, 1H), 7.69-7.64 (m, 2H), 7.63-7.55 (m, 1H), 7.32 (d, J = 1.9 Hz, 1H), 6.30 (d, J = 1.9 Hz, 1H), 5.42-5.26 (m, 1H), 4.75-4.60 (m, 2H), 3.69 (s, 3H), 2.53 (s, 3H), 1.34 (d, J = 6.7 Hz, 3H). |
| 222 | 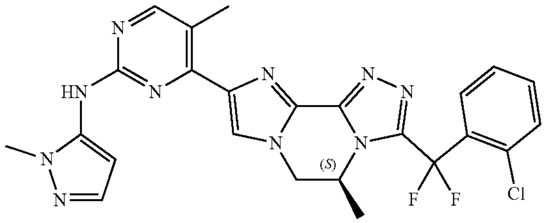 | 523.2 | $^1$H NMR (400 MHz, DMSO-d6) δ 9.21 (s, 1H), 8.33 (s, 1H), 8.12 (s, 1H), 7.89 (d, J = 7.7 Hz, 1H), 7.76-7.64 (m, 2H), 7.63-7.53 (m, 1H), 7.37-7.26 (m, 1H), 6.30 (s, 1H), 5.44-5.24 (m, 1H), 4.78-4.56 (m, 2H), 3.69 (s, 3H), 2.54 (s, 3H), 1.35 (d, J = 6.7 Hz, 3H). |
| 223 | 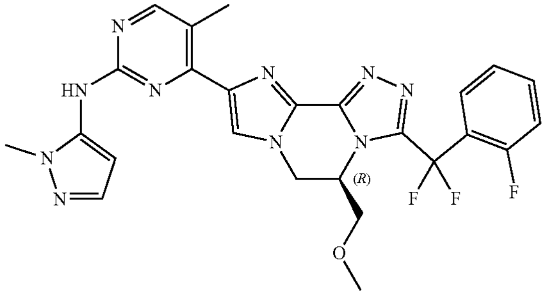 | 537.1 | $^1$H NMR (400 MHz, DMSO-d6) δ 9.20 (s, 1H), 8.32 (d, J = 0.6 Hz, 1H), 8.12 (s, 1H), 7.81-7.67 (m, 2H), 7.50-7.38 (m, 2H), 7.32 (d, J = 1.9 Hz, 1H), 6.30 (d, J = 1.9 Hz, 1H), 5.32 (dd, J = 10.3, 4.8 Hz, 1H), 4.86 (d, J = 14.0 Hz, 1H), 4.69 (dd, J = 14.0, 5.1 Hz, 1H), 3.69 (s, 3H), 3.58-3.51 (m, 2H), 3.12 (s, 3H), 2.53 (d, J = 0.5 Hz, 3H). |

-continued
| Compound | Structure | LC-MS (m/z) (M + H)+ | $^1$H NMR |
|---|---|---|---|
| 224 | 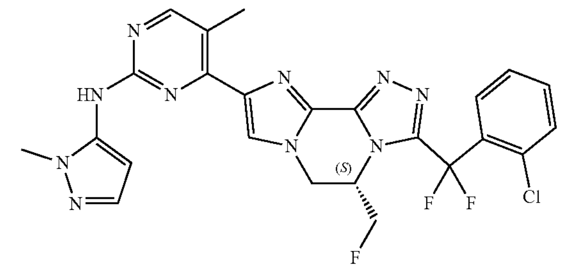 | 541.0 | $^1$H NMR (400 MHz, DMSO-d6) δ 9.22 (s, 1H), 8.32 (s, 1H), 8.10 (s, 1H), 7.90 (d, J = 7.4 Hz, 1H), 7.69-7.65 (m, 2H), 7.63-7.56 (m, 1H), 7.33 (d, J = 1.8 Hz, 1H), 6.30 (d, J = 1.8 Hz, 1H), 5.62-5.53 (m, 1H), 4.98 (d, J = 14.2 Hz, 1H), 4.87-4.62 (m, 3H), 3.69 (s, 3H), 2.52 (s, 3H). |
| 225 | 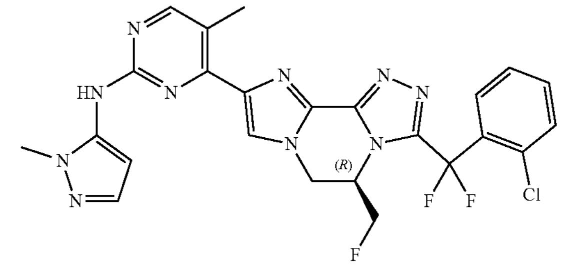 | 541.0 | $^1$H NMR (400 MHz, DMSO-d6) δ 9.22 (s, 1H), 8.32 (s, 1H), 8.10 (s, 1H), 7.90 (d, J = 7.3 Hz, 1H), 7.70-7.58 (m, 2H), 7.61-7.51 (m, 1H), 7.32 (s, 1H), 6.30 (s, 1H), 5.60-5.54 (m, 1H), 4.98 (d, J = 14.4 Hz, 1H), 4.87-4.62 (m, 3H), 3.68 (s, 3H), 2.52 (s, 3H). |
| 226 | 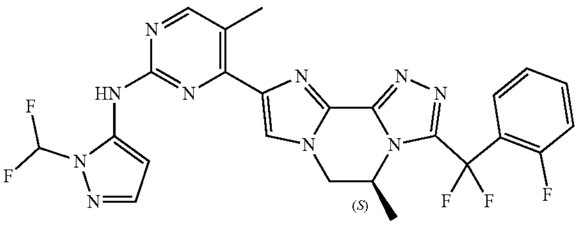 | 543.0 | $^1$H NMR (400 MHz, DMSO-d6) δ 9.76 (s, 1H), 8.39 (s, 1H), 8.16 (s, 1H), 7.92-7.58 (m, 4H), 7.49-7.39 (m, 2H), 6.53 (s, 1H), 5.37-5.23 (m, 1H), 4.73-4.63 (m, 2H), 2.55 (s, 3H), 1.33 (d, J = 6.7 Hz, 3H). |
| 227 | 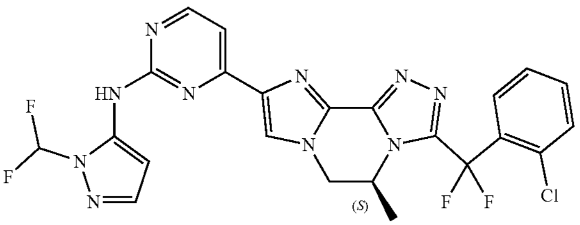 | 545.0 | $^1$H NMR (400 MHz, DMSO-d6) δ 8.39 (d, J = 5.2 Hz, 1H), 8.12 (s, 1H), 7.92-7.85 (m, 2H), 7.76 (s, 1H), 7.69-7.65 (m, 2H), 7.64-7.55 (m, 2H), 7.23-7.13 (m, 1H), 6.48 (s, 1H), 5.37-5.32 (m, 1H), 4.71-4.61 (m, 2H), 1.35 (d, J = 6.7 Hz, 3H). |
| 228 | 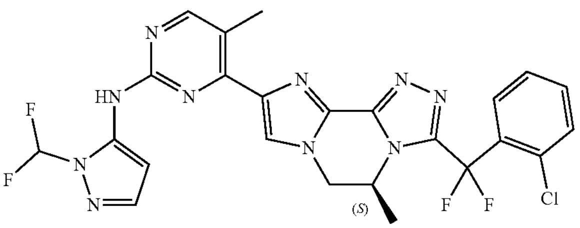 | 559.0 | $^1$H NMR (400 MHz, DMSO-d6) δ 9.76 (s, 1H), 8.39 (s, 1H), 8.17 (s, 1H), 7.91-7.87 (m, 1H), 7.78-7.70 (m, 2H), 7.68-7.66 (m, 2H), 7.62-7.57 (m, 1H), 6.54 (d, J = 1.6 Hz, 1H), 5.39-5.31 (m, 1H), 4.74-4.63 (m, 2H), 2.56 (s, 3H), 1.35 (d, J = 6.7 Hz, 3H). |

Example 12: Synthesis of Compounds 229-274, 322

Compound 229

(S)-2-((5-chloro-4-(3-(1-(trifluoromethyl)cyclobutyl)-6,7-dihydro-5H-pyrrolo[1,2-a][1,2,4]triazolo[3,4-c][1,4]diazepin-10-yl)pyridin-2-yl)amino)propan-1-ol

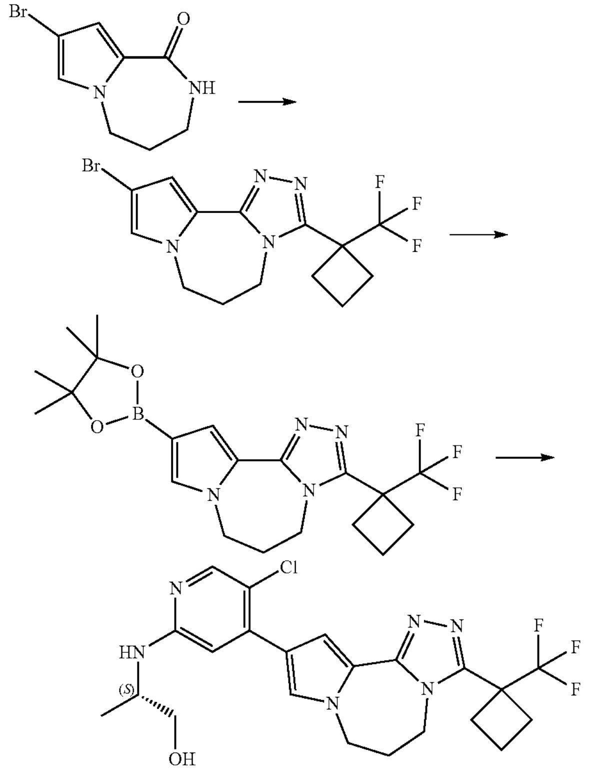

(A) 10-(4,4,5,5-tetramethyl-1,3,2-dioxaborolan-2-yl)-3-(1-(trifluoromethyl)cyclobutyl)-6,7-dihydro-5H-pyrrolo[1,2-a][1,2,4]triazolo[3,4-c][1,4]diazepine The title intermediate was prepared according to the procedures of Example 1 using the corresponding intermediates and reagents. MS (m/z): 423.1 $(M+H)^+$.

(B) (S)-2-((5-chloro-4-(3-(1-(trifluoromethyl)cyclobutyl)-6,7-dihydro-5H-pyrrolo[1,2-a][1,2,4]triazolo[3,4-c][1,4]diazepin-10-yl)pyridin-2-yl)amino)propan-1-ol A mixture of 10-(4,4,5,5-tetramethyl-1,3,2-dioxaborolan-2-yl)-3-(1-(trifluoromethyl)cyclobutyl)-6,7-dihydro-5H-pyrrolo[1,2-a][1,2,4]triazolo[3,4-c][1,4]diazepine (85 mg, 0.2 mmol), (S)-2-((5-chloro-4-iodopyridin-2-yl)amino)propan-1-ol (94 mg, 0.3 mmol), $Pd(PPh_3)_4$ (23 mg, 0.02 mmol) and $Na_2CO_3$ (63 mg, 0.6 mmol) in 1,4-dioxane/water (10 mL, 4:1) was stirred at 80° C. under nitrogen atmosphere for 2 h. Solvent was removed by rotary evaporator and the residue was purified via ISCO (eluting with methanol in water 0%~100%) and PTLC (DCM:MeOH=10:1) to give the title compound as a light yellow solid (39 mg, 41H yield). MS (m/z): 481.1 $(M+H)^+$.

$^1$H NMR (400 MHz, DMSO-d6) δ 7.95 (s, 1H), 7.61 (d, J=2.0 Hz, 1H), 7.18 (d, J=2.0 Hz, 1H), 6.71 (s, 1H), 6.32 (d, J=7.8 Hz, 1H), 4.69 (t, J=5.5 Hz, 1H), 4.32 (t, J=6.0 Hz, 2H), 4.05 (t, J=6.0 Hz, 2H), 3.92-3.86 (m, 1H), 3.49-3.43 (m, 1H), 3.30-3.24 (m, 1H), 2.95-2.87 (m, 2H), 2.79-2.68 (m, 2H), 2.35-2.26 (m, 2H), 2.23-2.10 (m, 1H), 2.05-1.96 (m, 1H), 1.11 (d, J=6.6 Hz, 3H).

The compounds below were prepared according to the procedures of Compound 229 using the corresponding intermediates and reagents under appropriate conditions that could be recognized by one skilled in the art.

| Compound | Structure | LC-MS (m/z) $(M + H)^+$ | $^1$H NMR |
|---|---|---|---|
| 230 | 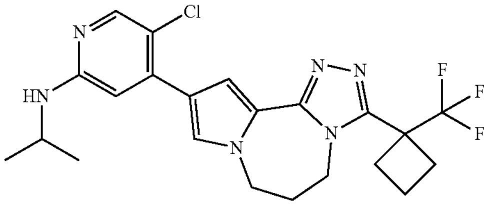 [SMILES: CC(C)Nc1cc(-c2cc3n(c2)CCCn2c-3nnc2C2(C(F)(F)F)CCC2)c(Cl)cn1] | 465.1 | $^1$H NMR (400 MHz, DMSO-d6) δ 7.95 (s, 1H), 7.59 (d, J = 2.0 Hz, 1H), 7.17 (d, J = 2.1 Hz, 1H), 6.64 (s, 1H), 6.38 (d, J = 7.7 Hz, 1H), 4.35-4.27 (m, 2H), 4.07-4.04 (m, 2H), 4.01-3.89 (m, 1H), 2.90 (dd, J = 21.1, 9.9 Hz, 2H), 2.74-2.69 (m, 2H), 2.34-2.22 (m, 2H), 2.19-2.12 (m, 1H), 2.04-1.95 (m, 1H), 1.12 (d, J = 6.4 Hz, 6H). |
| 231 | 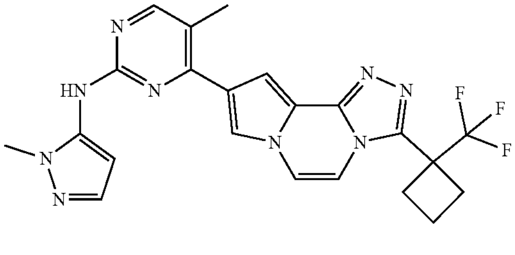 [SMILES: Cc1cnc(Nc2ccnn2C)nc1-c1cc2c3nnc(C4(C(F)(F)F)CCC4)n3ccn2c1] | 468.1 | $^1$H NMR (400 MHz, DMSO-d6) δ 9.21 (s, 1H), 8.32 (s, 1H), 8.26 (d, J = 1.6 Hz, 1H), 7.97 (d, J = 6.0 Hz, 1H), 7.59 (d, J = 0.8 Hz, 1H), 7.46 (d, J = 6.0 Hz, 1H), 7.35 (d, J = 2.0 Hz, 1H), 6.28 (d, J = 2.0 Hz, 1H), 3.68 (s, 3H), 2.96-2.89 (m, 2H), 2.86-2.79 (m, 2H), 2.39 (s, 3H), 2.21-2.14 (m, 1H), 2.05-1.96 (m, 1H). |

-continued

| Compound | Structure | LC-MS (m/z) (M + H)+ | 1H NMR |
|---|---|---|---|
| 232 | 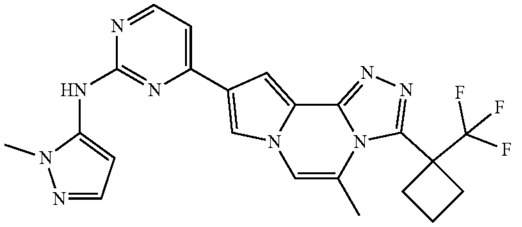 [SMILES: Cc1cn2cc(-c3ccnc(Nc4ccnn4C)n3)cc2c2nnc(C3(C(F)(F)F)CCC3)n12] | 468.1 | 1H NMR (400 MHz, DMSO-d6) δ 9.33 (s, 1H), 8.41 (d, J = 5.2 Hz, 1H), 8.12 (d, J = 1.6 Hz, 1H), 7.82 (s, 1H), 7.62 (d, J = 1.6 Hz 1H), 7.35-7.32 (m, 2H), 6.29 (d, J = 1.9 Hz, 1H), 3.69 (d, J = 1.7 Hz, 3H), 3.20-3.16 (m, 2H), 2.83-2.79 (m, 2H), 2.41 (s, 3H), 2.16-2.12 (m, 1H), 1.96-1.92 (m, 1H). |
| 233 | 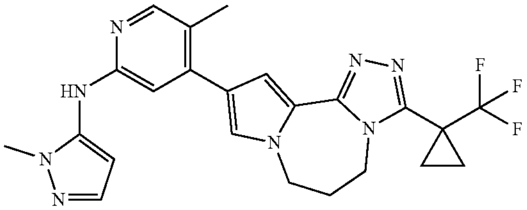 [SMILES: Cc1cnc(Nc2ccnn2C)cc1-c1cc2n(c1)CCCn1c-2nnc1C1(C(F)(F)F)CC1] | 469.2 | 1H NMR (400 MHz, DMSO-d6) δ 8.51 (s, 1H), 7.92 (s, 1H), 7.38 (s, 1H), 7.29-7.26 (m, 1H), 7.11 (s, 1H), 6.84 (s, 1H), 6.20-6.17 (m, 1H), 4.38-4.32 (m, 2H), 4.31-4.20 (m, 2H), 3.64 (s, 3H), 2.38-2.22 (m, 5H), 1.63-1.47 (m, 2H), 1.48-1.32 (m, 2H). |
| 234 | 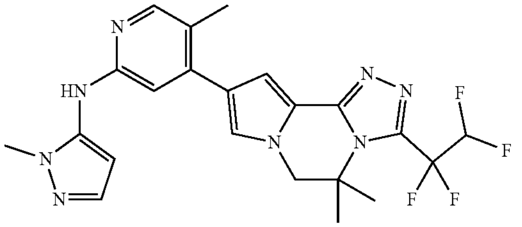 [SMILES: Cc1cnc(Nc2ccnn2C)cc1-c1cc2n(c1)CC(C)(C)n1c-2nnc1C(F)(F)C(F)F] | 475.2 | 1H NMR (400 MHz, DMSO-d6) δ 8.52 (s, 1H), 7.95 (s, 1H), 7.49-7.08 (m, 4H), 6.83 (s, 1H), 6.20-6.18 (m, 1H), 4.38 (s, 2H), 3.64 (s, 3H), 2.29 (s, 3H), 1.56 (s, 6H). |
| 235 | 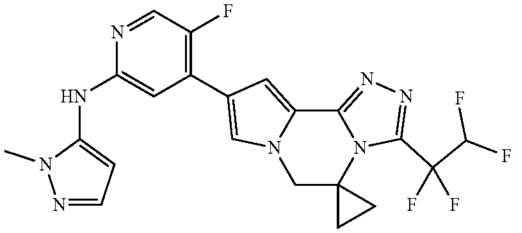 [SMILES: Cn1nccc1Nc1cc(-c2cc3n(c2)CC2(CC2)n2c-3nnc2C(F)(F)C(F)F)c(F)cn1] | 477.2 | 1H NMR (400 MHz, DMSO-d6) δ 8.72 (s, 1H), 8.12 (d, J = 2.4 Hz, 1H), 7.67 (s, 1H), 7.38-7.23 (m, 3H), 7.09 (d, J = 4.2 Hz, 1H), 6.24 (d, J = 1.6 Hz, 1H), 4.45 (s, 2H), 3.68 (s, 3H), 1.62-1.52 (m, 2H), 1.41-1.32 (m, 2H). |
| 236 | 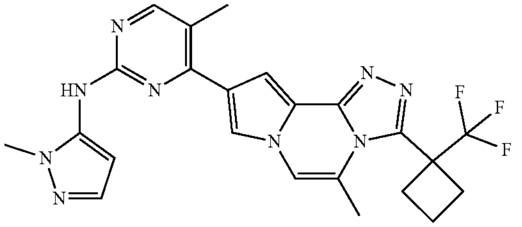 [SMILES: Cc1cnc(Nc2ccnn2C)nc1-c1cc2c3nnc(C4(C(F)(F)F)CCC4)n3c(C)cn2c1] | 482.1 | 1H NMR (400 MHz, DMSO-d6) 9.20 (s, 1H), 8.31 (s, 1H), 8.09 (d, J = 1.5 Hz, 1H), 7.81 (s, 1H), 7.53 (d, J = 1.5 Hz, 1H), 7.34 (d, J = 1.9 Hz, 1H), 6.28 (d, J = 1.9 Hz, 1H), 3.68 (s, 3H), 3.25-3.20 (m, 2H), 2.85-2.80 (m, 2H), 2.42 (s, 3H), 2.39 (s, 3H), 2.20-2.13 (m, 1H), 1.98-1.94 (m, 1H). |
| 237 | 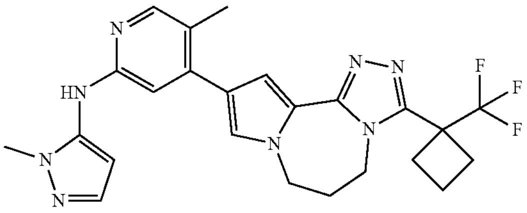 [SMILES: Cc1cnc(Nc2ccnn2C)cc1-c1cc2n(c1)CCCn1c-2nnc1C1(C(F)(F)F)CCC1] | 483.2 | 1H NMR (400 MHz, DMSO-d6) δ 8.51 (s, 1H), 7.94 (s, 1H), 7.40 (d, J = 2.0 Hz, 1H), 7.29 (d, J = 1.9 Hz, 1H), 7.08 (d, J = 2.0 Hz, 1H), 6.84 (s, 1H), 6.20 (d, J = 1.9 Hz, 1H), 4.37-4.27 (m, 2H), 4.11-3.99 (m, 2H), 3.65 (s, 3H), 2.96-2.84 (m, 2H), 2.79-2.66 (m, 2H), 2.32-2.27 (m, 5H), 2.21-2.11 (m, 1H), 2.04-1.95 (m, 1H). |

-continued

| Compound | Structure | LC-MS (m/z) (M + H)+ | 1H NMR |
|---|---|---|---|
| 238 | 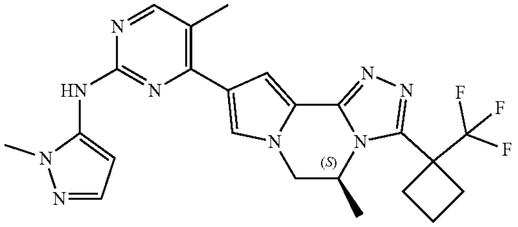 | 484.1 | 1H NMR (400 MHz, DMSO-d6) δ 9.09 (s, 1H), 8.23 (s, 1H), 7.79 (s, 1H), 7.34-7.32 (m, 1H), 7.28 (s, 1H), 6.27-6.25 (m, 1H), 4.82-4.73 (m, 1H), 4.46-4.39 (m, 1H), 4.35-4.28 (m, 1H), 3.67 (s, 2H), 2.98-2.84 (m, 2H), 2.79-2.63 (m, 2H), 2.33 (s, 3H), 2.22-2.10 (m, 1H), 2.07-1.92 (m, 1H), 1.18 (d, J = 6.4 Hz, 3H). |
| 239 | 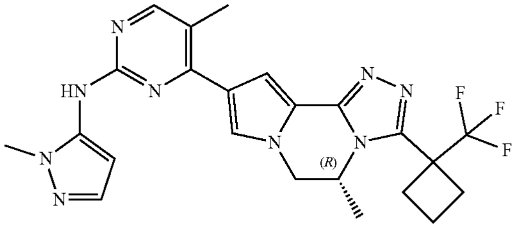 | 484.1 | 1H NMR (400 MHz, DMSO-d6) δ 9.09 (s, 1H), 8.23 (s, 1H), 7.79 (s, 1H), 7.33 (d, J = 1.8 Hz, 1H), 7.28 (s, 1H), 6.27 (d, J = 1.8 Hz, 1H), 4.81-4.75 (m, 1H), 4.45-4.41 (m, 1H), 4.34-4.30 (m, 1H), 3.68 (s, 3H), 2.98-2.82 (m, 2H), 2.81-2.63 (m, 2H), 2.33 (s, 3H), 2.16-2.12 (m, 1H), 2.02-1.98 (m, 1H), 1.19 (d, J = 6.9 Hz, 3H). |
| 240 | 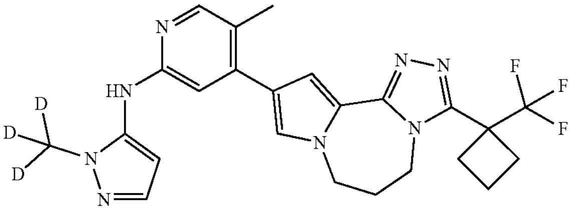 [SMILES: [2H]C([2H])([2H])n1nccc1Nc1cc(-c2cc3n(c2)CCCn2c-3nnc2C2(C(F)(F)F)CCC2)c(C)cn1] | 486.1 | 1H NMR (400 MHz, DMSO-d6) δ 8.53 (s, 1H), 7.93 (s, 1H), 7.40 (d, J = 2.0 Hz, 1H), 7.29 (d, J = 1.9 Hz, 1H), 7.08 (d, J = 2.1 Hz, 1H), 6.85 (s, 1H), 6.20 (d, J = 1.9 Hz, 1H), 4.35-4.29 (m, 2H), 4.08-4.02 (m, 2H), 2.94-2.87 (m, 2H), 2.77-2.67 (m, 2H), 2.32-2.27 (m, 2H), 2.29 (s, 3H), 2.19-2.12 (m, 1H), 2.02-1.95 (m, 1H). |
| 241 | 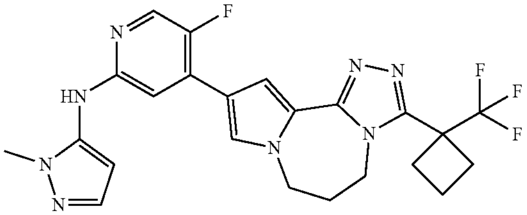 [SMILES: Cn1nccc1Nc1cc(-c2cc3n(c2)CCCn2c-3nnc2C2(C(F)(F)F)CCC2)c(F)cn1] | 487.1 | 1H NMR (400 MHz, DMSO-d6) δ 8.67 (s, 1H), 8.07 (d, J = 3.0 Hz, 1H), 7.59 (t, J = 2.3 Hz, 1H), 7.30 (d, J = 1.9 Hz, 1H), 7.19 (d, J = 1.1 Hz, 1H), 7.04 (d, J = 5.5 Hz, 1H), 6.22 (d, J = 1.9 Hz, 1H), 4.36-4.32 (m, 2H), 4.07-4.03 (m, 2H), 3.66 (s, 3H), 2.95-2.87 (m, 2H), 2.77-2.67 (m, 2H), 2.34-2.24 (m, 2H), 2.19-2.12 (m, 1H), 2.03-1.95 (m, 1H), |
| 242 | 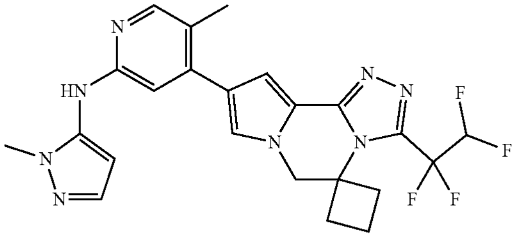 [SMILES: Cc1cnc(Nc2ccnn2C)cc1-c1cc2n(c1)CC1(CCC1)n1c-2nnc1C(F)(F)C(F)F] | 487.2 | 1H NMR (400 MHz, DMSO-d6) δ 8.51 (s, 1H), 7.95 (s, 1H), 7.54 (s, 1H), 7.47-7.13 (m, 2H), 7.06 (s, 1H), 6.82 (s, 1H), 6.19-6.17 (m, 1H), 4.47 (s, 2H), 3.63 (s, 3H), 2.79-2.65 (m, 2H), 2.29 (s, 3H), 2.25-2.17 (m, 2H), 2.12-1.87 (m, 2H). |
| 243 | 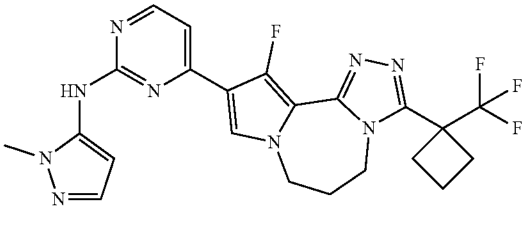 [SMILES: Cn1nccc1Nc1nccc(-c2cn3c(c2F)-c2nnc(C4(C(F)(F)F)CCC4)n2CCC3)n1] | 488.1 | 1H NMR (400 MHz, $CD_3OD$) δ 8.35 (d, J = 5.2 Hz, 1H), 7.55 (d, J = 4.8 Hz, 1H), 7.43 (d, J = 2.0 Hz, 1H), 7.14 (d, J = 4.8 Hz, 1H), 6.33 (d, J = 2.4 Hz, 1H), 4.25-4.22 (m, 2H), 4.13-4.09 (m, 2H), 3.75 (s, 3H), 3.02-2.94 (m, 2H), 2.88-2.81 (m, 2H), 2.43-2.38 (m, 2H), 2.32-2.25 (m, 1H), 2.17-2.08 (m, 1H). |

-continued

| Compound | Structure | LC-MS (m/z) $(M + H)^+$ | $^1H$ NMR |
|---|---|---|---|
| 244 | 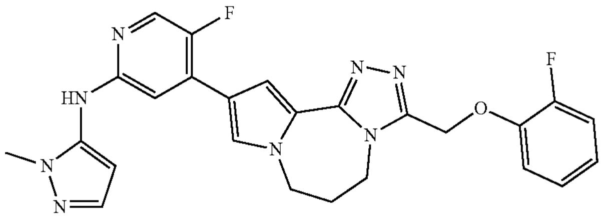 [SMILES: Cn1nccc1Nc1cc(-c2cc3n(c2)CCCn2c(COc4ccccc4F)nnc2-3)c(F)cn1] | 489.1 | $^1H$ NMR (400 MHz, DMSO-d6) δ 8.66 (s, 1H), 8.06 (d, J = 3.0 Hz, 1H), 7.56 (t, J = 2.2 Hz, 1H), 7.40 (td, J = 8.5, 1.5 Hz, 1H), 7.30 (d, J = 1.9 Hz, 1H), 7.24 (d, J = 1.7 Hz, 1H), 7.23-7.12 (m, 2H), 7.03-6.96 (m, 2H), 6.21 (d, J = 1.9 Hz, 1H), 5.38 (s, 2H), 4.41 (t, J = 5.2 Hz, 2H), 4.33 (t, J = 5.6 Hz, 2H), 3.65 (s, 3H), 2.36-2.31 (m, 2H). |
| 245 | 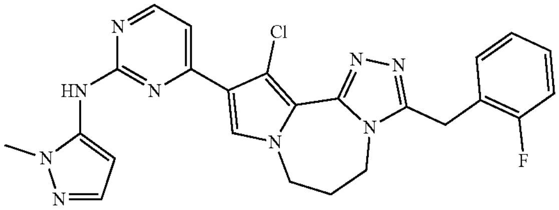 [SMILES: Cn1nccc1Nc1nccc(-c2cn3c(c2Cl)-c2nnc(Cc4ccccc4F)n2CCC3)n1] | 490.1 | $^1H$ NMR (400 MHz, DMSO-d6) δ 9.28 (s, 1H), 8.41 (d, J = 5.2 Hz, 1H), 7.69 (s, 1H), 7.36-7.29 (m, 3H), 7.29-7.13 (m, 3H), 6.27 (d, J = 1.8 Hz, 1H), 4.24 (s, 2H), 4.10 (t, J = 6.3 Hz, 2H), 3.98 (t, J = 6.6 Hz, 2H), 3.67 (s, 3H), 2.16-2.06 (m, 2H). |
| 246 | 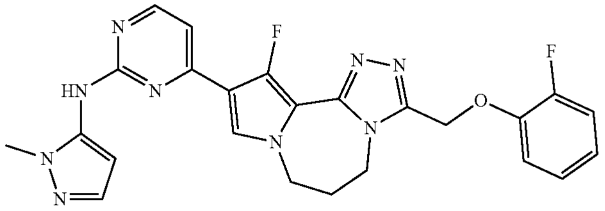 [SMILES: Cn1nccc1Nc1nccc(-c2cn3c(c2F)-c2nnc(COc4ccccc4F)n2CCC3)n1] | 490.2 | $^1H$ NMR (400 MHz, $CD_3OD$) δ 8.32 (d, J = 5.2 Hz, 1H), 7.46 (d, J = 4.8 Hz, 1H), 7.42 (d, J = 2.0 Hz, 1H), 7.31-7.27 (m, 1H), 7.14-7.10 (m, 3H), 7.03-6.98 (m, 1H), 6.32-6.31 (m, 1H), 5.39 (s, 2H), 4.42-4.39 (m, 2H), 4.32-4.29 (m, 2H), 3.74 (s, 3H), 2.49-2.43 (m, 2H). |
| 247 | 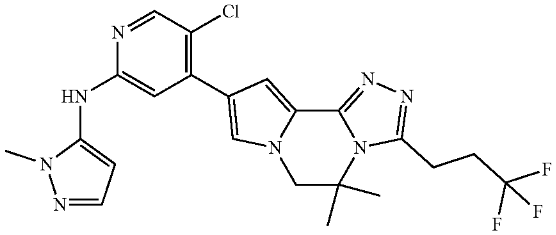 [SMILES: Cn1nccc1Nc1cc(-c2cc3n(c2)CC(C)(C)n2c(CCC(F)(F)F)nnc2-3)c(Cl)cn1] | 491.1 | $^1H$ NMR (400 MHz, DMSO-d6) δ 8.82 (s, 1H), 8.13 (s, 1H), 7.66 (s, 1H), 7.33-7.30 (m, 1H), 7.02-6.96 (m, 2H), 6.23-6.21 (m, 1H), 4.25 (s, 2H), 3.65 (s, 3H), 3.16-3.12 (m, 2H), 2.90-2.86 (m, 2H), 1.53 (s, 6H). |
| 248 | 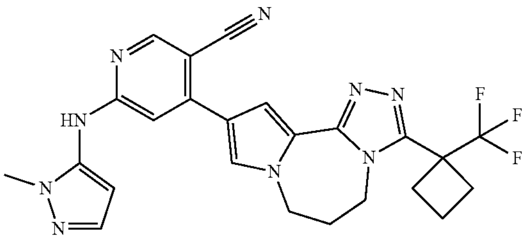 [SMILES: Cn1nccc1Nc1cc(-c2cc3n(c2)CCCn2c-3nnc2C2(C(F)(F)F)CCC2)c(C#N)cn1] | 494.1 | $^1H$ NMR (400 MHz, DMSO-d6) δ 9.47 (brs, 1H), 8.50 (s, 1H), 7.69 (d, J = 2.0 Hz, 1H), 7.37 (d, J = 1.8 Hz, 1H), 7.31 (d, J = 2.0 Hz, 1H), 6.92 (s, 1H), 6.27 (d, J = 1.9 Hz, 1H), 4.34 (t, J = 6.0 Hz, 2H), 4.05 (t, J = 6.0 Hz, 2H), 3.66 (s, 3H), 2.94-2.87 (m, 2H), 2.77-2.68 (m, 2H), 2.34-2.26 (m, 2H), 2.19-2.12 (m, 1H), 2.03-1.95 (m, 1H). |
| 249 | 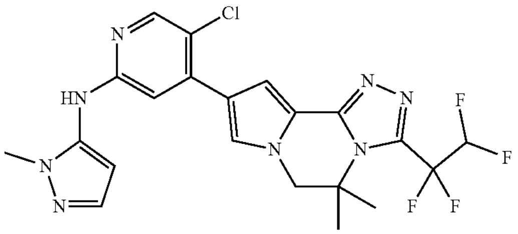 | 495.1 | $^1H$ NMR (400 MHz, DMSO-d6) δ 8.88 (s, 1H), 8.18 (s, 1H), 7.79 (s, 1H), 7.44-7.16 (m, 3H), 7.02 (s, 1H), 6.26 (d, J = 2.0 Hz, 1H), 4.45 (s, 2H), 3.68 (s, 3H), 1.60 (s, 6H). |

-continued

| Compound | Structure | LC-MS (m/z) (M + H)+ | 1H NMR |
|---|---|---|---|
| 250 | 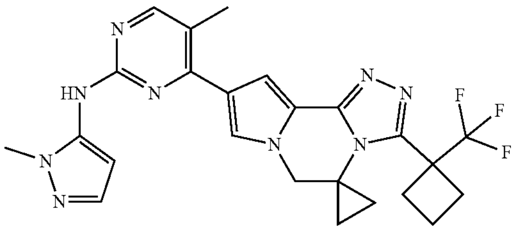 [SMILES: Cc1cnc(Nc2ccnn2C)nc1-c1cc2n(c1)CC1(CC1)n1c-2nnc1C1(C(F)(F)F)CCC1] | 496.2 | 1H NMR (400 MHz, DMSO-d6) δ 9.09 (s, 1H), 8.23 (s, 1H), 7.67 (s, 1H), 7.36-7.24 (m, 2H), 6.26 (s, 1H), 4.37-4.21 (m, 2H), 3.67 (s, 3H), 2.96-2.81 (m, 2H), 2.80-2.70 (m, 2H), 2.33 (s, 3H), 2.09-1.90 (m, 2H), 1.35-1.19 (m, 4H). |
| 251 | 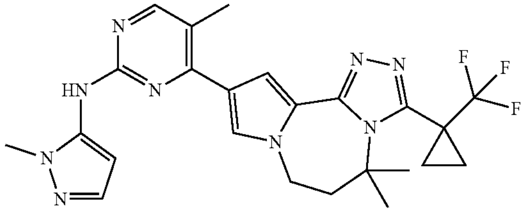 [SMILES: Cc1cnc(Nc2ccnn2C)nc1-c1cc2n(c1)CCC(C)(C)n1c-2nnc1C1(C(F)(F)F)CC1] | 498.2 | 1H NMR (400 MHz, DMSO-d6) δ 9.08 (s, 1H), 8.22 (d, J = 0.4 Hz, 1H), 7.68 (d, J = 2.0 Hz, 1H), 7.40 (d, J = 2.0 Hz, 1H), 7.31 (d, J = 2.0 Hz, 1H), 6.26 (d, J = 2.0 Hz, 1H), 4.43-4.26 (m, 2H), 3.67 (s, 3H), 2.44-2.41 (m, 1H), 2.36-2.31 (m, 1H), 2.32 (s, 3H), 1.71-1.60 (m, 4H), 1.62 (s, 3H), 1.58 (s, 3H). |
| 252 | 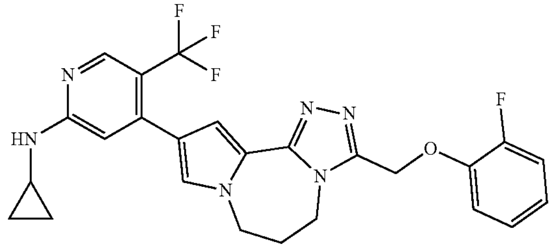 [SMILES: Fc1ccccc1OCc1nnc2n1CCCn1cc(-c3cc(NC4CC4)ncc3C(F)(F)F)cc1-2] | 499.1 | 1H NMR (400 MHz, DMSO-d6) δ 8.28 (s, 1H), 7.44 (d, J = 2.5 Hz, 1H), 7.43-7.35 (m, 1H), 7.26 (d, J = 1.9 Hz, 1H), 7.25-7.16 (m, 1H), 7.16-7.10 (m, 1H), 7.07 (d, J = 1.7 Hz, 1H), 7.02-6.95 (m, 1H), 6.61 (s, 1H), 5.38 (s, 2H), 4.41-4.37 (m, 2H), 4.34-4.31 (m, 2H), 2.59 (brs, 1H), 2.38-2.28 (m, 2H), 0.74-0.68 (m, 2H), 0.48-0.42 (m, 2H). |
| 253 | 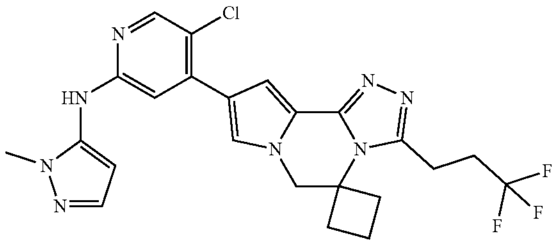 [SMILES: Cn1nccc1Nc1cc(-c2cc3n(c2)CC2(CCC2)n2c(CCC(F)(F)F)nnc2-3)c(Cl)cn1] | 503.0 | 1H NMR (400 MHz, DMSO-d6) δ 8.81 (s, 1H), 8.14 (s, 1H), 7.74 (d, J = 1.7 Hz, 1H), 7.33 (d, J = 2.0 Hz, 1H), 7.01 (d, J = 1.7 Hz, 1H), 6.96 (s, 1H), 6.23 (d, J = 2.0 Hz, 1H), 4.53 (s, 2H), 3.65 (s, 3H), 3.33-3.32 (m, 2H), 2.96-2.83 (m, 2H), 2.80-2.67 (m, 2H), 2.20-2.08 (m, 2H), 2.04-1.91 (m, 2H). |
| 254 | 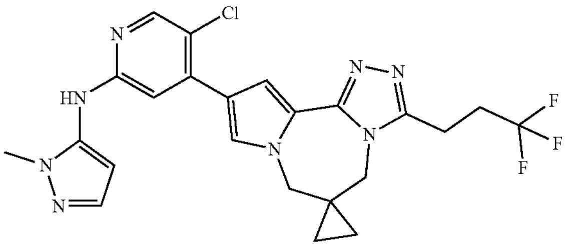 [SMILES: Cn1nccc1Nc1cc(-c2cc3n(c2)CC2(CC2)Cn2c(CCC(F)(F)F)nnc2-3)c(Cl)cn1] | 503.1 | 1H NMR (400 MHz, DMSO-d6) δ 8.80 (s, 1H), 8.11 (s, 1H), 7.51 (d, J = 2.0 Hz, 1H), 7.32 (d, J = 2.0 Hz, 1H), 7.24 (d, J = 2.0 Hz, 1H), 6.99 (s, 1H), 6.23 (d, J = 2.0 Hz, 1H), 4.29 (s, 2H), 4.07 (s, 2H), 3.65 (s, 3H), 2.95-2.91 (m, 2H), 2.83-2.73 (m, 2H), 0.79-0.77 (m, 2H), 0.71-0.66 (m, 2H). |
| 255 | 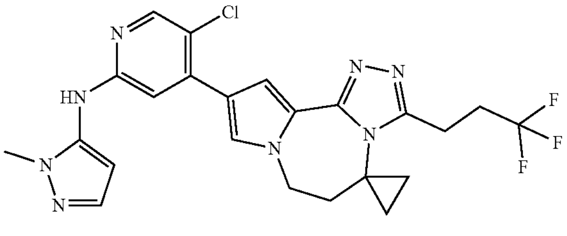 [SMILES: Cn1nccc1Nc1cc(-c2cc3n(c2)CCC2(CC2)n2c(CCC(F)(F)F)nnc2-3)c(Cl)cn1] | 503.1 | 1H NMR (400 MHz, DMSO-d6) δ 8.83 (s, 1H), 8.12 (s, 1H), 7.77 (d, J = 1.8 Hz, 1H), 7.32 (d, J = 1.7 Hz, 1H), 6.99 (s, 1H), 6.90 (d, J = 1.8 Hz, 1H), 6.22 (d, J = 1.7 Hz, 1H), 4.09 (t, J = 6.7 Hz, 2H), 3.65 (s, 3H), 3.08-3.04 (m, 2H), 2.86-2.79 (m, 2H), 2.21 (t, J = 6.7 Hz, 2H), 0.98-0.93 (m, 2H), 0.83-0.79 (m, 2H). |

-continued

| Compound | Structure | LC-MS (m/z) (M + H)+ | $^1$H NMR |
|---|---|---|---|
| 256 | 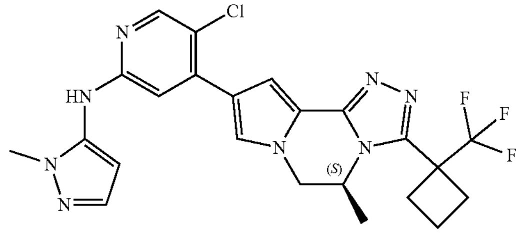 | 503.2 | $^1$H NMR (400 MHz, DMSO-d6) δ 8.84 (s, 1H), 8.14 (s, 1H), 7.79 (s, 1H), 7.32 (d, J = 1.8 Hz, 1H), 7.10 (d, J = 1.3 Hz, 1H), 6.99 (s, 1H), 6.23 (d, J = 1.8 Hz, 1H), 4.83-4.72 (m, 1H), 4.43-4.37 (m, 1H), 4.33-4.26 (m, 1H), 3.66 (s, 2H), 2.98-2.83 (m, 2H), 2.79-2.61 (m, 2H), 2.21-2.10 (m, 1H), 2.07-1.92 (m, 1H), 1.18 (d, J = 6.4 Hz, 3H). |
| 257 | 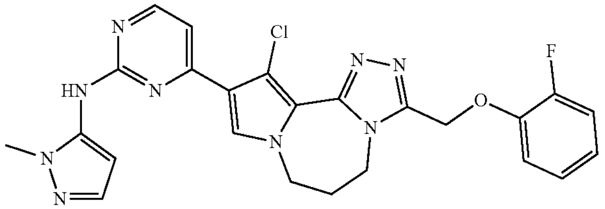 | 506.0 | $^1$H NMR (400 MHz, DMSO-d6) δ 9.31 (s, 1H), 8.43 (m, 1H), 7.74 (s, 1H), 7.47-7.37 (m, 1H), 7.37-7.29 (m, 2H), 7.30-7.10 (m, 2H), 7.05-6.95 (m, 1H), 6.30-6.27 (m, 1H), 5.45 (s, 2H), 4.25-4.09 (m, 4H), 3.68 (s, 3H), 2.35-2.26 (m, 2H). |
| 258 | 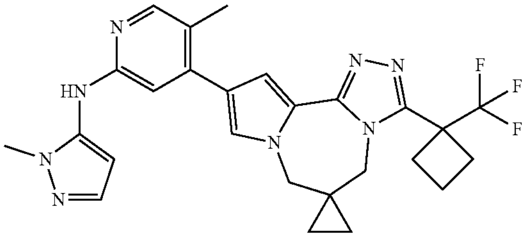 [SMILES: Cc1cnc(Nc2ccnn2C)cc1-c1cc2n(c1)CC1(CC1)Cn1c-2nnc1C1(C(F)(F)F)CCC1] | 509.1 | $^1$H NMR (400 MHz, DMSO-d6) δ 8.54 (s, 1H), 7.92 (s, 1H), 7.28 (d, J = 2.0 Hz, 1H), 7.27 (d, J = 2.0 Hz, 1H), 7.17 (d, J = 2.0 Hz, 1H), 6.85 (s, 1H), 6.20 (d, J = 2.0 Hz, 1H), 4.25 (s, 2H), 3.98 (s, 2H), 3.64 (s, 3H), 2.85-2.77 (m, 2H), 2.72-2.65 (m, 2H), 2.27 (s, 3H), 2.16-2.09 (m, 1H), 2.01-1.92 (m, 1H), 0.74-0.72 (m, 4H). |
| 259 | 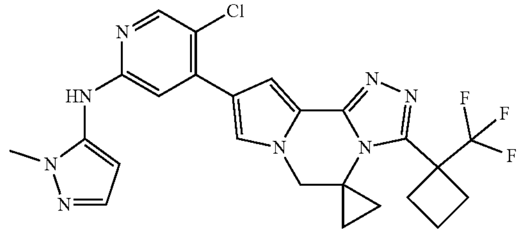 [SMILES: Cn1nccc1Nc1cc(-c2cc3n(c2)CC2(CC2)n2c-3nnc2C2(C(F)(F)F)CCC2)c(Cl)cn1] | 515.2 | $^1$H NMR (400 MHz, DMSO-d6) δ 8.83 (s, 1H), 8.14 (s, 1H), 7.66 (s, 1H), 7.32 (d, J = 1.7 Hz, 1H), 7.13 (d, J = 1.3 Hz, 1H), 6.99 (s, 1H), 6.23 (d, J = 1.7 Hz, 1H), 4.32-4.22 (m, 2H), 3.66 (s, 3H), 3.00-2.82 (m, 2H), 2.78-2.70 (m, 2H), 2.12-2.00 (m, 1H), 2.00-1.89 (m, 1H), 1.33-1.16 (m, 4H). |
| 260 | 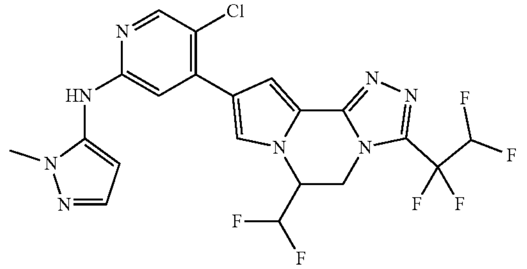 [SMILES: Cn1nccc1Nc1cc(-c2cc3n(c2)C(C(F)F)Cn2c-3nnc2C(F)(F)C(F)F)c(Cl)cn1] | 517.1 | $^1$H NMR (400 MHz, DMSO-d6) δ 8.87 (s, 1H), 8.18 (s, 1H), 7.87 (d, J = 1.6 Hz, 1H), 7.35 (d, J = 1.6 Hz, 1H), 7.31-6.94 (m, 3H), 6.61-6.30 (m, 1H), 6.25 (d, J = 2.0 Hz, 1H), 5.64-5.50 (m, 1H), 4.92-4.87 (m, 1H), 4.78-4.61 (m, 1H), 3.68 (s, 3H). |
| 261 | 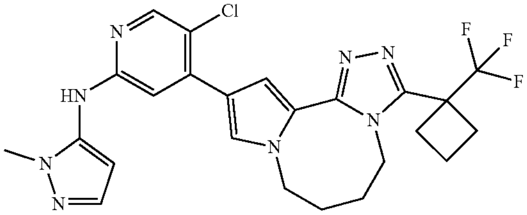 [SMILES: Cn1nccc1Nc1cc(-c2cc3n(c2)CCCCn2c-3nnc2C2(C(F)(F)F)CCC2)c(Cl)cn1] | 517.1 | $^1$H NMR (400 MHz, DMSO-d6) δ 8.81 (s, 1H), 8.11 (s, 1H), 7.71 (d, J = 2.0 Hz, 1H), 7.31 (d, J = 1.9 Hz, 1H), 6.91 (s, 1H), 6.81 (d, J = 2.0 Hz, 1H), 6.20 (d, J = 1.9 Hz, 1H), 4.03-3.95 (m, 2H), 3.82-3.72 (m, 2H), 3.63 (s, 3H), 2.98-2.88 (m, 2H), 2.76-2.67 (m, 2H), 2.21-2.11 (m, 1H), 2.05-1.98 (m, 1H), 1.94-1.88 (m, 2H), 1.85-1.80 (m, 2H). |

-continued

| Compound | Structure | LC-MS (m/z) (M + H)+ | 1H NMR |
|---|---|---|---|
| 262 | 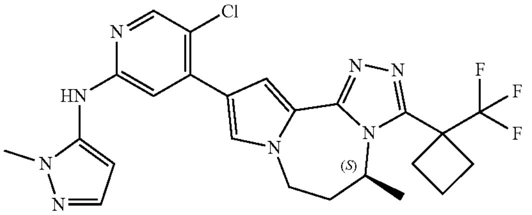 | 517.2 | 1H NMR (400 MHz, DMSO-d6) δ 8.96 (s, 1H), 8.13 (s, 1H), 7.73 (s, 1H), 7.33-7.30 (m, 1H), 7.09 (s, 1H), 6.98 (s, 1H), 6.24-6.22 (m, 1H), 4.52-4-43 (m, 2H), 4.22-4.21 (m, 1H), 3.65 (s, 3H), 2.93-2.84 (m, 2H), 2.75-2.74 (m, 2H), 2.33-2.31 (m, 2H), 2.17-2.15 (m, 1H), 2.05-2.03 (m, 1H), 1.10 (d, J = 6.3 Hz, 3H). |
| 263 | 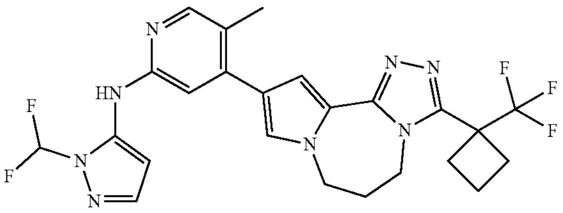 [SMILES: Cc1cnc(Nc2ccnn2C(F)F)cc1-c1cc2n(c1)CCCn1c-2nnc1C1(C(F)(F)F)CCC1] | 519.1 | 1H NMR (400 MHz, DMSO-d6) δ 9.10 (s, 1H), 7.98 (s, 1H), 7.71 (t, J = 57.2 Hz, 1H), 7.64 (s, 1H), 7.43 (d, J = 1.9 Hz, 1H), 7.12 (d, J = 2.0 Hz, 1H), 7.02 (s, 1H), 6.45-6.41 (m, 1H), 4.38-4.29 (m, 2H), 4.10-4.01 (m, 2H), 2.95-2.87 (m, 2H), 2.77-2.68 (m, 2H), 2.32 (s, 3H), 2.30-2.74 (m, 2H), 2.22-2.10 (m, 1H), 2.05-1.95 (m, 1H). |
| 264 | 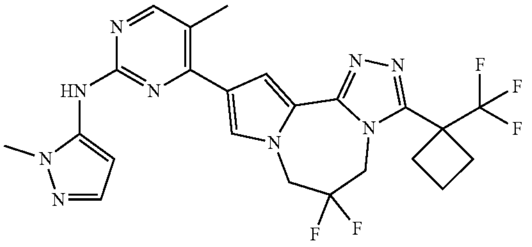 [SMILES: Cc1cnc(Nc2ccnn2C)nc1-c1cc2n(c1)CC(F)(F)Cn1c-2nnc1C1(C(F)(F)F)CCC1] | 520.1 | 1H NMR (400 MHz, DMSO-d6) δ 9.13 (s, 1H), 8.26 (d, J = 0.8 Hz, 1H), 7.89 (d, J = 2.0 Hz, 1H), 7.32 (d, J = 2.0 Hz, 1H), 7.28 (d, J = 2.0 Hz, 1H), 6.26 (d, J = 2.0 Hz, 1H), 4.84 (t, J = 13.2 Hz, 2H), 4.47 (t, J = 12.8 Hz, 2H), 3.67 (s, 3H), 2.97-2.84 (m, 2H), 2.82-2.75 (m, 2H), 2.33 (s, 3H), 2.20-2.13 (m, 1H), 2.04-1.95 (m, 1H). |
| 265 | 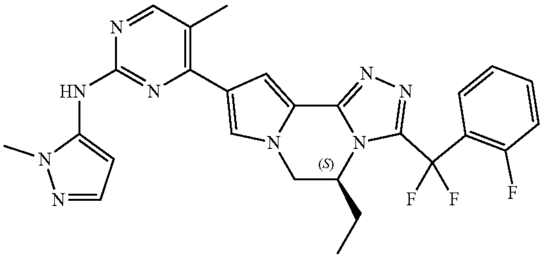 | 520.3 | 1H NMR (400 MHz, DMSO-d6) δ 9.13 (s, 1H), 8.25 (s, 1H), 7.91 (s, 1H), 7.81-7.65 (m, 2H), 7.46-7.40 (m, 2H), 7.33 (s, 2H), 6.27 (s, 1H), 5.02-4.89 (m, 1H), 4.74 (d, J = 13.6 Hz, 1H), 4.48-4.42 (m, 1H), 3.67 (s, 3H), 2.34 (s, 3H), 1.70-1.44 (m, 2H), 0.90 (t, J = 7.4 Hz, 3H). |
| 266 | 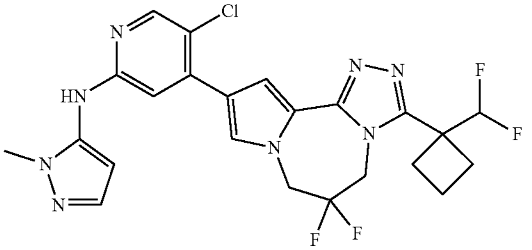 [SMILES: Cn1nccc1Nc1cc(-c2cc3n(c2)CC(F)(F)Cn2c-3nnc2C2(C(F)F)CCC2)c(Cl)cn1] | 521.0 | 1H NMR (400 MHz, DMSO-d6) δ 8.87 (s, 1H), 8.15 (s, 1H), 7.86 (d, J = 2.0 Hz, 1H), 7.31 (d, J = 2.0 Hz, 1H), 7.08 (d, J = 2.0 Hz, 1H), 6.95 (s, 1H), 6.47 (t, J = 56.0 Hz, 1H), 6.22 (d, J = 2.0 Hz, 1H), 4.80 (t, J = 13.2 Hz, 2H), 4.45 (t, J = 12.8 Hz, 2H), 3.65 (s, 3H), 2.73-2.56 (m, 4H), 2.16-2.09 (m, 1H), 1.98-1.90 (m, 1H). |
| 267 | 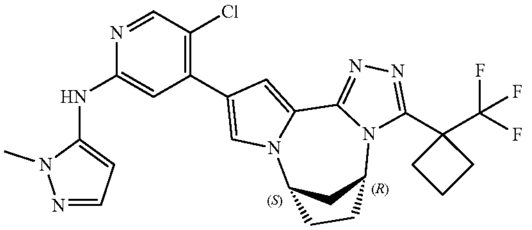 | 529.1 | 1H NMR (400 MHz, DMSO-d6) δ 8.84 (s, 1H), 8.12 (s, 1H), 7.71 (d, J = 2.1 Hz, 1H), 7.31 (d, J = 1.9 Hz, 2H), 7.00 (s, 1H), 6.23 (d, J = 1.9 Hz, 1H), 5.14-5.10 (m, 1H), 4.76-4.71 (m, 1H), 3.65 (s, 3H), 2.95-2.80 (m, 2H), 2.79-2.67 (m, 2H), 2.52-2.48 (m, 1H), 2.34-2.27 (m, 2H), 2.18-2.14 (m, 2H), 2.00-1.94 (m, 2H), 1.90-1.77 (m, 1H). |

-continued

| Compound | Structure | LC-MS (m/z) (M + H)+ | $^1$H NMR |
|---|---|---|---|
| 268 | 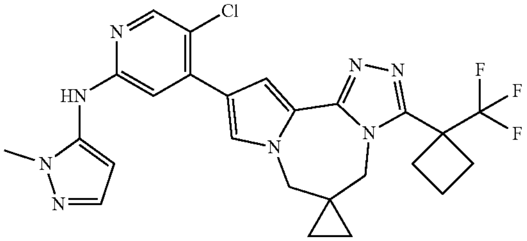 [SMILES: Cn1nccc1Nc1cc(-c2cc3n(c2)CC2(CC2)Cn2c-3nnc2C2(C(F)(F)F)CCC2)c(Cl)cn1] | 529.1 | $^1$H NMR (400 MHz, DMSO-d6) δ 8.86 (s, 1H), 8.12 (s, 1H), 7.56 (d, J = 1.2 Hz, 1H), 7.34-7.28 (m, 2H), 7.00 (s, 1H), 6.23 (d, J = 1.6 Hz, 1H), 4.28 (s, 2H), 3.99 (s, 2H), 3.65 (s, 3H), 2.86-2.78 (m, 2H), 2.72-2.65(m, 2H), 2.16-2.09 (m, 1H), 1.99-1.93 (m, 1H), 0.75-0.72 (m, 4H). |
| 269 | 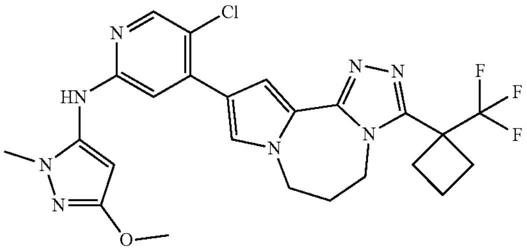 [SMILES: COc1cc(Nc2cc(-c3cc4n(c3)CCCn3c-4nnc3C3(C(F)(F)F)CCC3)c(Cl)cn2)n(C)n1] | 533.1 | $^1$H NMR (400 MHz, DMSO-d6) δ 8.89 (s, 1H), 8.13 (s, 1H), 7.68 (d, J = 2.0 Hz, 1H), 7.20 (d, J = 2.0 Hz, 1H), 7.01 (s, 1H), 5.71 (s, 1H), 4.38-4.27 (m, 2H), 4.08-3.99 (m, 2H), 3.70 (s, 3H), 3.51 (s, 3H), 2.91-2.87 (m, 2H), 2.76-2.65 (m, 2H), 2.31-2.25 (m, 2H), 2.16-2.12 (m, 1H), 1.99-1.95 (m, 1H). |
| 270 | 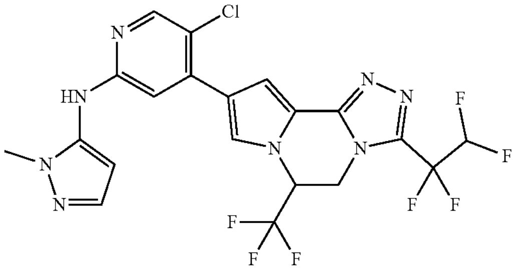 [SMILES: Cn1nccc1Nc1cc(-c2cc3n(c2)C(C(F)(F)F)Cn2c-3nnc2C(F)(F)C(F)F)c(Cl)cn1] | 535.0 | $^1$H NMR (400 MHz, DMSO-d6) δ 8.88 (s, 1H), 8.15 (s, 1H), 7.93 (d, J = 1.5 Hz, 1H), 7.31 (d, J = 1.9 Hz, 1H), 7.29-7.03 (m, 1H), 7.26 (d, J = 1.5 Hz, 1H), 6.97 (s, 1H), 6.23-6.20 (m, 2H), 5.05 (d, J = 14.9 Hz, 1H), 4.79 (d, J = 11.7 Hz, 1H), 3.64 (s, 3H). |
| 271 | 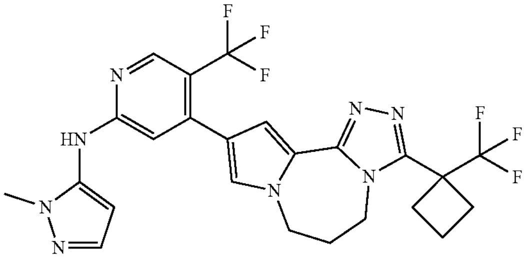 [SMILES: Cn1nccc1Nc1cc(-c2cc3n(c2)CCCn2c-3nnc2C2(C(F)(F)F)CCC2)c(C(F)(F)F)cn1] | 537.1 | $^1$H NMR (400 MHz, DMSO-d6) δ 9.31 (brs, 1H), 8.43 (s, 1H), 7.36 (d, J = 1.9 Hz, 1H), 7.32 (d, J = 1.9 Hz, 1H), 7.04 (d, J = 1.8 Hz, 1H), 6.83 (s, 1H), 6.27 (d, J = 1.9 Hz, 1H), 4.33 (t, J = 5.6 Hz, 2H), 4.05 (t, J = 5.6 Hz, 2H), 3.66 (s, 3H), 2.93-2.86 (m, 2H), 2.76-2.66 (m, 2H), 2.30-2.26 (m, 2H), 2.16-2.10 (m, 1H), 2.03-1.95 (m, 1H). |
| 272 | 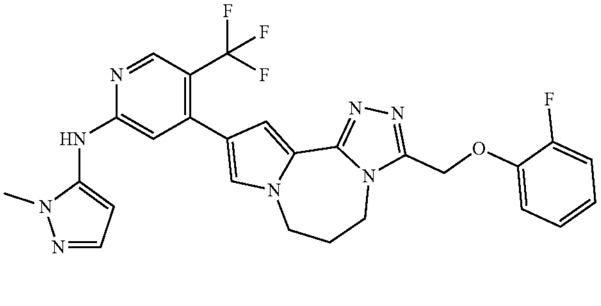 [SMILES: Cn1nccc1Nc1cc(-c2cc3n(c2)CCCn2c(COc4ccccc4F)nnc2-3)c(C(F)(F)F)cn1] | 539.1 | $^1$H NMR (400 MHz, DMSO-d6) δ 9.28 (s, 1H), 8.43 (s, 1H), 7.40 (td, J = 8.5, 1.5 Hz, 1H), 7.36 (d, J = 1.9 Hz, 1H), 7.30 (d, J = 1.9 Hz, 1H), 7.24-7.22 (m, 1H), 7.14 (t, J = 11.1, Hz, 1H), 7.09 (d, J = 1.7 Hz, 1H), 7.02-7.69 (m, 1H), 6.82 (s, 1H), 6.27 (d, J = 1.9 Hz, 1H), 5.39 (s, 2H), 4.42-4.32 (m, 4H), 3.66 (s, 3H), 2.36-2.32 (m, 2H), . |

-continued

| Compound | Structure | LC-MS (m/z) (M + H)+ | $^1$H NMR |
|---|---|---|---|
| 273 | 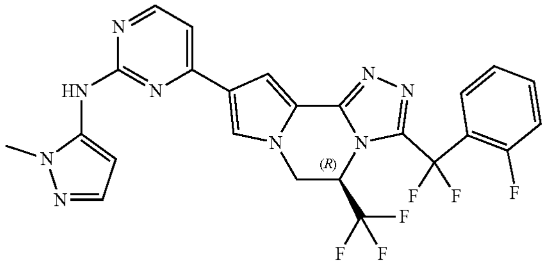 | 546.0 | $^1$H NMR (400 MHz, DMSO-d6) δ 9.28 (s, 1H), 8.37 (d, J = 5.2 Hz, 1H), 7.99 (d, J = 0.9 Hz, 1H), 7.79-7.66 (m, 2H), 7.49-7.38 (m, 3H), 7.34 (d, J = 1.8 Hz, 1H), 7.18 (d, J = 5.2 Hz, 1H), 6.36-6.27 (m, 2H), 5.10-5.05 (m, 1H), 4.88-4.76 (m, 1H), 3.68 (s, 3H). |
| 274 | 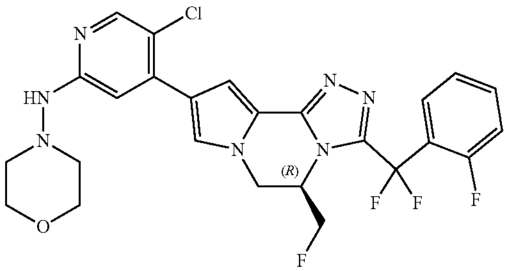 | 548.0 | $^1$H NMR (400 MHz, DMSO-d6) δ 8.03 (s, 1H), 7.83 (d, J = 1.6 Hz, 1H), 7.78-7.68 (m, 2H), 7.57 (s, 1H), 7.47-7.39 (m, 2H), 7.22 (d, J = 1.6 Hz, 1H), 7.02 (s, 1H), 5.50-5.36 (m, 1H), 4.83-4.57 (m, 4H), 3.67 (br, 4H), 2.74 (br, 4H). |
| 322 | 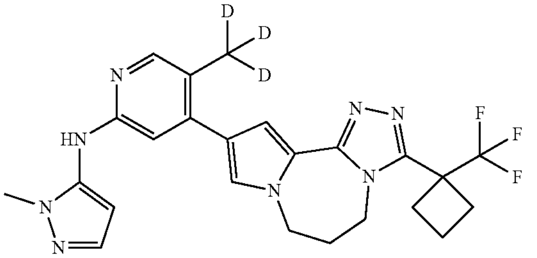 [SMILES: [2H]C([2H])([2H])c1cnc(Nc2ccnn2C)cc1-c1cc2n(c1)CCCn1c-2nnc1C1(C(F)(F)F)CCC1] | 486.3 | $^1$H NMR (400 MHz, DMSO-d6) δ 8.53 (s, 1H), 7.92 (s, 1H), 7.40 (d, J = 2.0 Hz, 1H), 7.28 (d, J = 1.9 Hz, 1H), 7.07 (d, J = 2.0 Hz, 1H), 6.84 (s, 1H), 6.19 (d, J = 1.9 Hz, 1H), 4.34-4.28 (m, 2H), 4.06-4.01 (m, 2H), 3.64 (s, 3H), 2.93-2.86 (m, 2H), 2.75-2.67 (m, 2H), 2.33-2.25 (m, 2H), 2.21-2.09 (m, 1H), 2.01-1.96 (m, 1H). |

Example 13: Synthesis of Compounds 275-280

Compound 275

(S)-2-((5-methyl-4-(3-(1-(trifluoromethyl)cyclobutyl)-6,7-dihydro-5H-pyrrolo[1,2-a][1,2,4]triazolo[3,4-c][1,4]diazepin-10-yl)pyrimidin-2-yl)amino)propan-1-ol

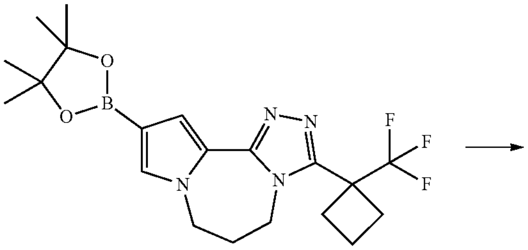

-continued

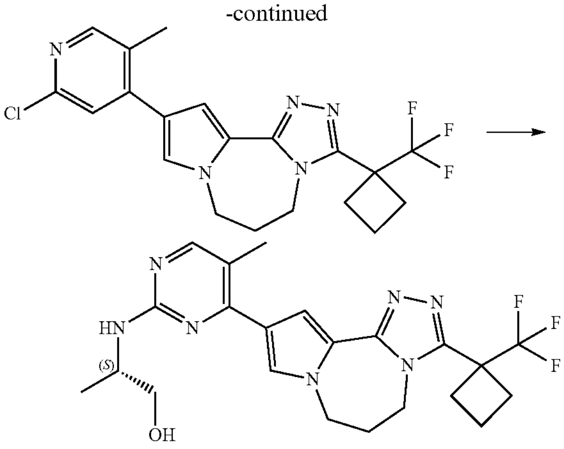

(A) 10-(2-chloro-5-methylpyrimidin-4-yl)-3-(1-(trifluoromethyl)cyclobutyl)-6,7-dihydro-5H-pyrrolo[1,2-a][1,2,4]triazolo[3,4-c][1,4]diazepine A mixture of 10-(4,4,5,5-tetramethyl-1,3,2-dioxaborolan-2-yl)-3-(1-(trifluoromethyl)cyclobutyl)-6,7-dihydro-5H-pyrrolo[1,2-a][1,2,4]triazolo[3,4-c][1,4]diazepine (2.0 g, 4.7 mmol), 2,4-dichloro-5-methylpyrimidine (620 mg, 3.8 mmol), Pd(dppf)$Cl_2$·$CH_2Cl_2$ (300 mg, 0.40 mmol) and $Na_2CO_3$ (1.0 g, 9.4 mmol) in 1,4-dioxane (40 mL) and water (8 mL) was stirred at 90° C. for 4 hours. The resulting mixture was concentrated, purified via ISCO (eluting with methanol in water 0%~100%) to afford the title compound as a white solid (500 mg, 25.0% yield). MS (m/z): 423.0.

(B) (S)-2-((5-methyl-4-(3-(1-(trifluoromethyl)cyclobutyl)-6,7-dihydro-5H-pyrrolo[1,2-a][1,2,4]triazolo[3,4-c][1,4]diazepin-10-yl)pyrimidin-2-yl)amino)propan-1-ol A mixture of 10-(2-chloro-5-methylpyrimidin-4-yl)-3-(1-(trifluoromethyl)cyclobutyl)-6,7-dihydro-5H-pyrrolo[1,2-a][1,2,4]triazolo[3,4-c][1,4]diazepine (50 mg, 0.12 mmol), (S)-2-aminopropan-1-ol (44 mg, 0.59 mmol) and DIPEA (76 mg, 0.59 mmol) in NMP (2 mL) was stirred at 180° C. for 2.5 hours under microwave. The resulting mixture was purified directly via ISCO (eluting with methanol in water 0%~100%) and PTLC (DCM:MeOH=15:1) to afford the title compound as a white solid (8.0 mg, 14.7% yield). MS (m/z): 462.1 $(M+H)^+$.

$^1$H NMR (400 MHz, DMSO-d6) δ 8.03 (s, 1H), 7.62 (d, J=1.7 Hz, 1H), 7.40 (d, J=1.7 Hz, 1H), 6.15 (d, J=8.1 Hz, 1H), 4.58 (s, 1H), 4.37-4.29 (m, 2H), 4.09-3.95 (m, 3H), 3.53-3.45 (m, 1H), 3.40-3.32 (m, 2H), 2.97-2.86 (m, 2H), 2.74-2.71 (m, 2H), 2.35-2.28 (m, 2H), 2.25 (s, 3H), 2.21-2.11 (m, 1H), 2.04-1.94 (m, 1H), 1.14 (d, J=6.6 Hz, 3H).

The compounds below were prepared according to the procedures of Compound 275 using the corresponding intermediates and reagents under appropriate conditions that could be recognized by one skilled in the art.

| Compound | Structure | LC-MS (m/z) $(M + H)^+$ | $^1$H NMR |
|---|---|---|---|
| 276 | 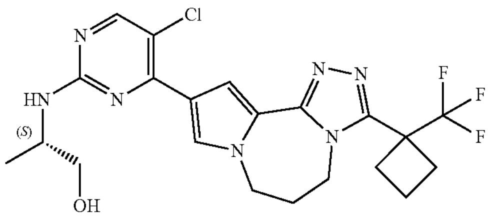 | 482.1 | $^1$H NMR (400 MHz, DMSO-d6) δ 8.22 (s, 1H), 7.96 (d, J = 2.0 Hz, 1H), 7.55 (d, J = 2.0 Hz, 1H), 6.86 (d, J = 8.2 Hz, 1H), 4.75 (br, 1H), 4.37-4.31 (m, 2H), 4.08-4.02 (m, 2H), 4.02-3.96 (m, 1H), 3.51-3.44 (m, 1H), 3.39-3.36 (m, 1H), 2.95-2.86 (m, 2H), 2.76-2.65 (m, 2H), 2.33-2.25 (m, 2H), 2.22-2.09 (m, 1H), 2.02-1.94 (m, 1H), 1.13 (d, J = 6.6 Hz, 3H). |
| 277 | 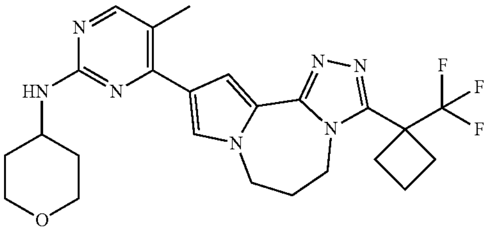 [SMILES: Cc1cnc(NC2CCOCC2)nc1-c1cc2n(c1)CCCn1c-2nnc1C1(C(F)(F)F)CCC1] | 488.2 | $^1$H NMR (400 MHz, DMSO-d6) δ 8.04 (s, 1H), 7.63 (d, J = 1.9 Hz, 1H), 7.40 (d, J = 1.9 Hz, 1H), 6.51 (d, J = 7.6 Hz, 1H), 4.38-4.28 (m, 2H), 4.08-3.82 (m, 5H), 3.43-3.37 (m, 2H), 2.93-2.89 (m, 2H), 2.79-2.66 (m, 2H), 2.33-2.30 (m, 2H), 2.25 (s, 3H), 2.18-2.14 (m, 1H), 2.00-1.93 (m, 1H), 1.88-1.82 (m, 2H), 1.53-1.49 (m, 2H). |
| 278 | 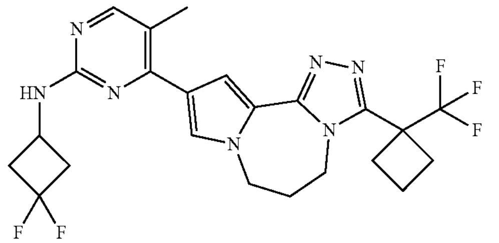 [SMILES: Cc1cnc(NC2CC(F)(F)C2)nc1-c1cc2n(c1)CCCn1c-2nnc1C1(C(F)(F)F)CCC1] | 494.1 | $^1$H NMR (400 MHz, DMSO-d6) δ 8.08 (s, 1H), 7.66 (s, 1H), 7.40 (s, 1H), 7.23 (d, J = 6.3 Hz, 1H), 4.36-4.31 (m, 2H), 4.23-4.16 (m, 1H), 4.09-3.98 (m, 2H), 2.97-2.85 (m, 4H), 2.76-2.67 (m, 2H), 2.66-2.57 (m, 2H), 2.33-2.27 (m, 2H), 2.25(s, 3H), 2.20-2.11 (m, 1H), 2.02-1.94 (m, 1H). |
| 279 | 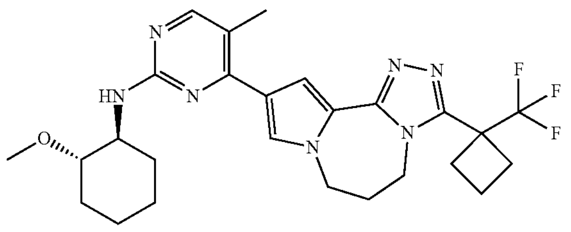 [SMILES: CO[C@H]1CCCC[C@@H]1Nc1ncc(C)c(-c2cc3n(c2)CCCn2c-3nnc2C2(C(F)(F)F)CCC2)n1] | 518.2 | $^1$H NMR (400 MHz, DMSO-d6) δ 8.04 (s, 1H), 7.62 (d, J = 1.9 Hz, 1H), 7.41 (d, J = 1.9 Hz, 1H), 6.63 (d, J = 8.0 Hz, 1H), 4.36-4.29 (m, 2H), 4.08-3.92 (m, 4H), 3.83-3.74 (m, 1H), 3.42-3.29 (m, 5H), 3.19-3.07 (m, 1H), 2.93-2.89 (m, 2H), 2.75-2.71 (m, 2H), 2.35-2.23 (m, 5H), 2.22-2.10 (m, 1H), 2.04-1.99 (m, 2H), 1.55-1.41 (m, 1H). |

-continued

| Compound | Structure | LC-MS (m/z) (M + H)+ | $^1$H NMR |
| --- | --- | --- | --- |
| 280 | 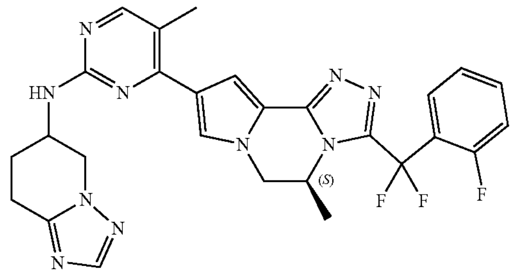 | 547.0 | $^1$H NMR (400 MHz, DMSO-d6) δ 8.13 (s, 1H), 7.86 (s, 1H), 7.84 (d, J = 1.4 Hz, 1H), 7.77-7.66 (m, 2H), 7.46-7.37 (m, 3H), 7.07 (d, J = 6.6 Hz, 1H), 5.26-5.14 (m, 1H), 4.57-4.45 (m, 3H), 4.45-4.35 (m, 1H), 4.16-4.01 (m, 1H), 3.11-2.96 (m, 1H), 2.94-2.83 (m, 1H), 2.29 (s, 3H), 2.22-1.96 (m, 2H), 1.30 (d, J = 6.6 Hz, 3H). |

Example 14: Synthesis of Compounds 281-298

Compound 281

5-methyl-N-(2-methylpyridin-4-yl)-4-(3-(1-(trifluoromethyl)cyclobutyl)-6,7-dihydro-5H-pyrrolo[1,2-a][1,2,4]triazolo[3,4-c][1,4]diazepin-10-yl)pyrimidin-2-amine

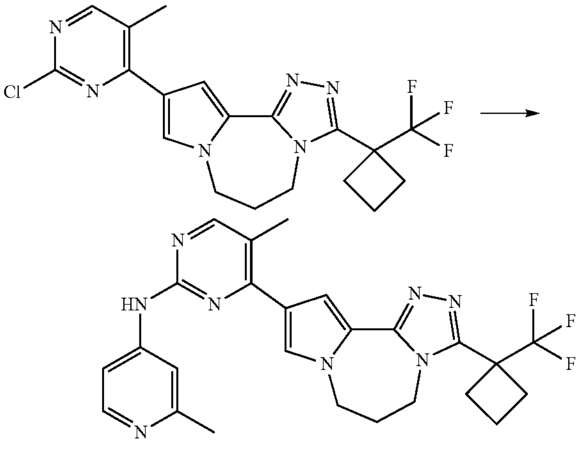

A mixture of 10-(2-chloro-5-methylpyrimidin-4-yl)-3-(1-(trifluoromethyl)cyclobutyl)-6,7-dihydro-5H-pyrrolo[1,2-a][1,2,4]triazolo[3,4-c][1,4]diazepine (30 mg, 0.07 mmol), 2-methylpyridin-4-amine (15 mg, 0.14 mmol), $Pd_2(dba)_3$ (16 mg, 0.007 mmol), Xantphos (4.1 mg, 0.007 mmol) and $Cs_2CO_3$ (69 mg, 0.21 mmol)) in 1,4-dioxane (2 mL) was stirred at 150° C. for 30 min under microwave. The mixture was concentrated, partitioned between water (10 mL) and DCM (10 mL). The aqueous layer was extracted with DCM (10 mL×2). The combined organic layers were concentrated and purified via PTLC (DCM:MeOH=15:1) to afford the title compound as a white solid (8.5 mg, 24.2% yield). MS (m/z): 495.1 $(M+H)^+$.

$^1$H NMR (400 MHz, DMSO-d6) δ 9.63 (s, 1H), 8.34 (s, 1H), 8.19 (d, J=5.7 Hz, 1H), 7.73 (d, J=6.0 Hz, 2H), 7.59-7.54 (m, 1H), 7.55-7.52 (m, 1H), 4.42-4.35 (m, 2H), 4.11-4.05 (m, 2H), 2.98-2.89 (m, 2H), 2.76-2.72 (m, 2H), 2.41 (s, 3H), 2.38 (s, 3H), 2.34-2.30 (m, 2H), 2.23-2.12 (m, 1H), 2.05-1.95 (m, 1H).

The compounds below were prepared according to the procedures of Compound 281 using the corresponding intermediates and reagents under appropriate conditions that could be recognized by one skilled in the art.

| Compound | Structure | LC-MS (m/z) (M + H)+ | $^1$H NMR |
| --- | --- | --- | --- |
| 282 | 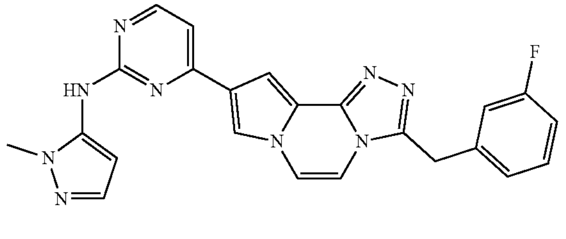 [SMILES: Cn1nccc1Nc1nccc(-c2cc3c4nnc(Cc5cccc(F)c5)n4ccn3c2)n1] | 440.0 | $^1$H NMR (400 MHz, DMSO-d6) δ 9.33 (s, 1H), 8.42 (d, J = 5.1 Hz, 1H), 8.20 (s, 1H), 7.95 (d, J = 6.0 Hz, 1H), 7.70 (d, J = 6.0 Hz, 1H), 7.59 (s, 1H), 7.39-7.30 (m, 3H), 7.22-7.02 (m, 3H), 6.32-6.27 (m, 1H), 4.46 (s, 2H), 3.69 (s, 3H). |

-continued

| Compound | Structure | LC-MS (m/z) (M + H)+ | 1H NMR |
| --- | --- | --- | --- |
| 283 | 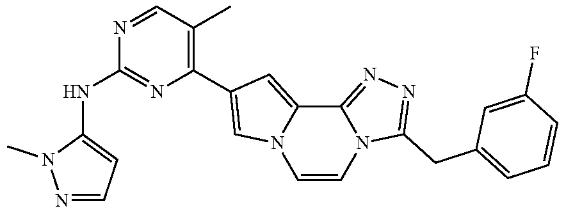 [SMILES: Cc1cnc(Nc2ccnn2C)nc1-c1cc2c3nnc(Cc4cccc(F)c4)n3ccn2c1] | 454.1 | 1H NMR (400 MHz, DMSO-d6) δ 9.20 (s, 1H), 8.30 (s, 1H), 8.18 (s, 1H), 7.94 (d, J = 6.0 Hz, 1H), 7.69 (d, J = 6.0 Hz, 1H), 7.51 (s, 1H), 7.41-7.30 (m, 2H), 7.22-6.99 (m, 3H), 6.28 (d, J = 1.5 Hz, 1H), 4.46 (s, 2H), 3.68 (s, 3H), 2.38 (s, 3H). |
| 284 | 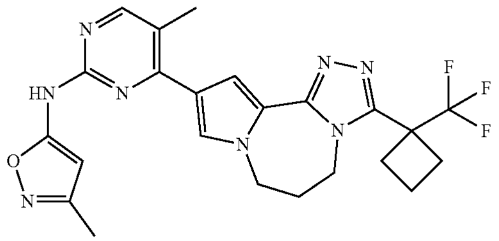 [SMILES: Cc1cc(Nc2ncc(C)c(-c3cc4n(c3)CCCn3c-4nnc3C3(C(F)(F)F)CCC3)n2)on1] | 485.1 | 1H NMR (400 MHz, DMSO-d6) δ 8.33 (s, 1H), 7.76 (d, J = 1.8 Hz, 1H), 7.47 (d, J = 1.8 Hz, 1H), 6.20 (s, 1H), 4.41-4.33 (m, 2H), 4.10-4.01 (m, 2H), 2.96-2.85 (m, 2H), 2.76-2.68 (m, 2H), 2.36 (s, 3H), 2.34-2.29 (m, 2H), 2.20-2.11 (m, 4H), 2.03-1.95 (m, 1H). |
| 285 | 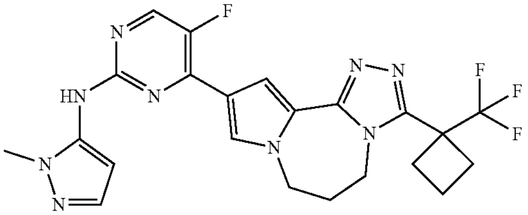 [SMILES: Cn1nccc1Nc1ncc(F)c(-c2cc3n(c2)CCCn2c-3nnc2C2(C(F)(F)F)CCC2)n1] | 488.1 | 1H NMR (400 MHz, DMSO-d6) δ 9.33 (s, 1H), 8.43 (d, J = 3.3 Hz, 1H), 7.76 (s, 1H), 7.40-7.32 (m, 2H), 6.26 (d, J = 1.8 Hz, 1H), 4.40-4.31 (m, 2H), 4.07-4.01 (m, 2H), 3.68 (s, 3H), 2.93-2.89 (m, 2H), 2.79-2.67 (m, 2H), 2.36-2.24 (m, 2H), 2.21-1.98 (m, 2H). |
| 286 | 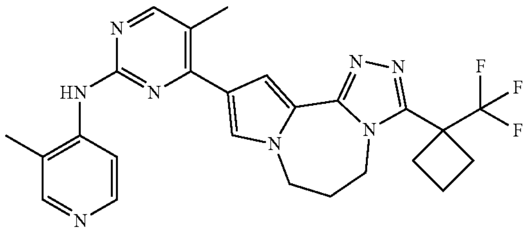 [SMILES: Cc1cnccc1Nc1ncc(C)c(-c2cc3n(c2)CCCn2c-3nnc2C2(C(F)(F)F)CCC2)n1] | 495.2 | 1H NMR (400 MHz, DMSO-d6) δ 8.46 (s, 1H), 8.33 (s, 1H), 8.28-8.22 (m, 2H), 8.14 (d, J = 5.7 Hz, 1H), 7.75 (d, J = 1.5 Hz, 1H), 7.47 (d, J = 1.5 Hz, 1H), 4.41-4.31 (m, 2H), 4.09-4.02 (m, 2H), 2.97-2.85 (m, 2H), 2.78-2.68 (m, 2H), 2.37 (s, 3H), 2.34-2.29 (m, 2H), 2.29 (s, 3H), 2.20-2.11 (m, 1H), 2.02-1.96 (m, 1H). |
| 287 | 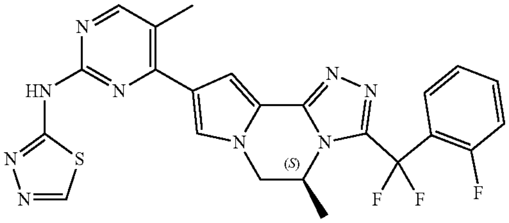 | 510.0 | 1H NMR (400 MHz, DMSO-d6) δ 11.84 (brs, 1H), 9.03 (s, 1H), 8.43 (s, 1H), 8.03 (d, J = 1.6 Hz, 1H), 7.80-7.67 (m, 2H), 7.57 (d, J = 1.6 Hz, 1H), 7.47-7.39 (m, 2H), 5.30-5.20 (m, 1H), 4.62-4.53 (m, 2H), 2.42 (s, 3H), 1.32 (d, J = 6.7 Hz, 3H). |
| 288 | 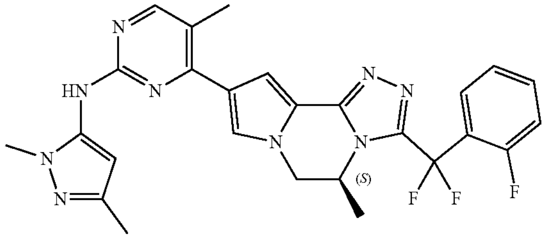 | 520.1 | 1H NMR (400 MHz, DMSO-d6) δ 9.02 (s, 1H), 8.22 (s, 1H), 7.84 (d, J = 1.2 Hz, 1H), 7.76-7.65 (m, 2H), 7.46-7.37 (m, 2H), 7.34 (d, J = 1.2 Hz, 1H), 6.02 (s, 1H), 5.26-5.15 (m, 1H), 4.56-4.47 (m, 2H), 3.57 (s, 3H), 2.32 (s, 3H), 2.08 (s, 3H), 1.29 (d, J = 6.6 Hz, 3H). |

-continued

| Compound | Structure | LC-MS (m/z) (M + H)+ | 1H NMR |
|---|---|---|---|
| 289 | 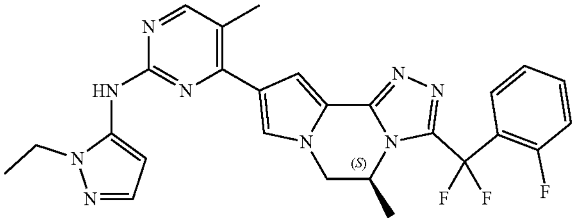 | 520.1 | 1H NMR (400 MHz, DMSO-d6) δ 9.04 (s, 1H), 8.23 (s, 1H), 7.84 (d, J = 1.5 Hz, 1H), 7.77-7.65 (m, 2H), 7.48-7.37 (m, 2H), 7.36 (d, J = 1.8 Hz, 1H), 7.34 (d, J = 1.5 Hz, 1H), 6.25 (d, J = 1.8 Hz, 1H), 5.28-5.13 (m, 1H), 4.57-4.46 (m, 2H), 4.05-4.00 (m, 2H), 2.33 (s, 3H), 1.33-1.23 (m, 6H). |
| 290 | 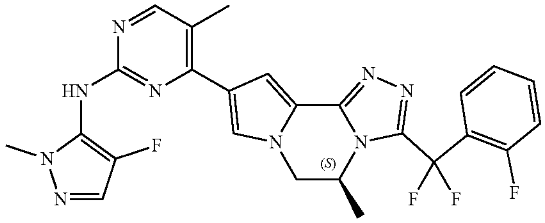 | 524.1 | 1H NMR (400 MHz, DMSO-d6) δ 8.92 (s, 1H), 8.20 (s, 1H), 7.81 (d, J = 1.4 Hz, 1H), 7.77-7.67 (m, 2H), 7.46-7.37 (m, 3H), 7.26 (s, 1H), 5.25-5.12 (m, 1H), 4.55-4.45 (m, 2H), 3.58 (s, 3H), 2.32 (s, 3H), 1.28 (d, J = 6.7 Hz, 3H). |
| 291 | 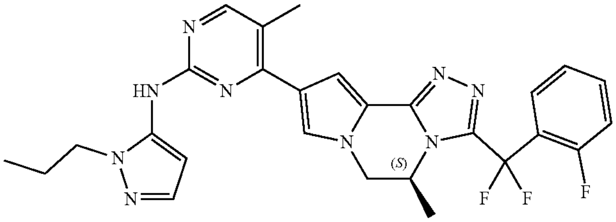 | 534.1 | 1H NMR (400 MHz, DMSO-d6) δ 9.06 (s, 1H), 8.23 (s, 1H), 7.84 (d, J = 1.4 Hz, 1H), 7.76-7.66 (m, 2H), 7.47-7.37 (m, 2H), 7.35 (d, J = 1.8 Hz, 1H), 7.34 (d, J = 1.4 Hz, 1H), 6.27 (d, J = 1.8 Hz, 1H), 5.26-5.13 (m, 1H), 4.59-4.46 (m, 2H), 3.97 (t, J = 7.2 Hz, 2H), 2.33 (s, 3H), 1.74-1.63 (m, 2H), 1.29 (d, J = 6.6 Hz, 3H), 0.78 (t, J = 7.4 Hz, 3H). |
| 292 | 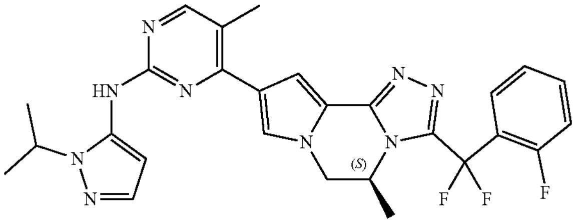 | 534.1 | 1H NMR (400 MHz, DMSO-d6) δ 8.93 (s, 1H), 8.20 (s, 1H), 7.82 (s, 1H), 7.77-7.66 (m, 2H), 7.47-7.35 (m, 3H), 7.32 (d, J = 1.1 Hz, 1H), 6.18 (d, J = 1.6 Hz, 1H), 5.22- 5.17 (m, H), 4.57-4.45 (m, 3H), 2.32 (s, 3H), 1.34-1.26 (m, 9H). |
| 293 | 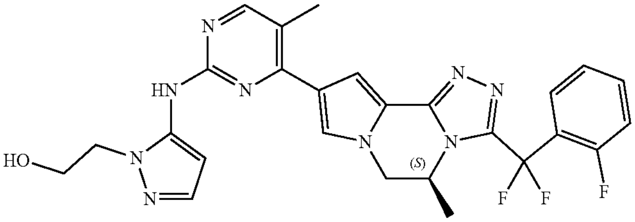 | 536.0 | 1H NMR (400 MHz, DMSO-d6) δ 8.22 (s, 1H), 7.86 (d, J = 1.2 Hz, 1H), 7.77-7.66 (m, 2H), 7.47-7.37 (m, 2H), 7.35 (d, J = 1.6 Hz, 1H), 7.32 (d, J = 1.2 Hz, 1H), 6.35 (d, J = 1.6 Hz, 1H), 5.25-5.15 (m, 1H), 4.54-4.49 (m, 2H), 4.10 (t, J = 5.8 Hz, 2H), 3.69 (t, J = 5.8 Hz, 2H), 2.33 (s, 3H), 1.29 (d, J = 6.7 Hz, 3H). |
| 294 | 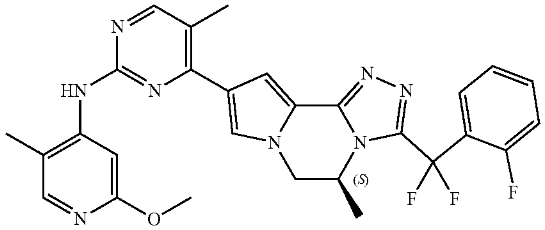 | 547.0 | 1H NMR (400 MHz, DMSO-d6) δ 8.38 (s, 1H), 8.30 (s, 1H), 7.93 (d, J = 1.3 Hz, 1H), 7.83 (s, 1H), 7.78-7.68 (m, 3H), 7.49-7.39 (m, 3H), 5.31-5.12 (m, 1H), 4.61-4.43 (m, 2H), 3.79 (s, 3H), 2.39 (s, 3H), 2.21 (s, 3H), 1.32 (d, J = 6.6 Hz, 3H). |

-continued

| Compound | Structure | LC-MS (m/z) (M + H)+ | $^1$H NMR |
|---|---|---|---|
| 295 | 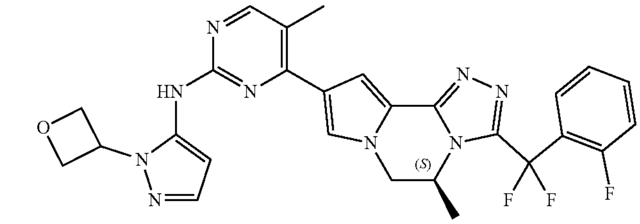 | 548.0 | $^1$H NMR (400 MHz, DMSO-d6) δ 9.14 (s, 1H), 8.21 (s, 1H), 7.82 (d, J = 1.4 Hz, 1H), 7.77-7.65 (m, 2H), 7.54 (d, J = 1.7 Hz, 1H), 7.47-7.35 (m, 2H), 7.29 (d, J = 1.4 Hz, 1H), 6.24 (d, J = 1.7 Hz, 1H), 5.54-5.42 (m, 1H), 5.25-5.14 (m, 1H), 4.94-4.85 (m, 2H), 4.81-4.71 (m, 2H), 4.56-4.46 (m, 2H), 2.32 (s, 3H), 1.28 (d, J = 6.7 Hz, 3H). |
| 296 | 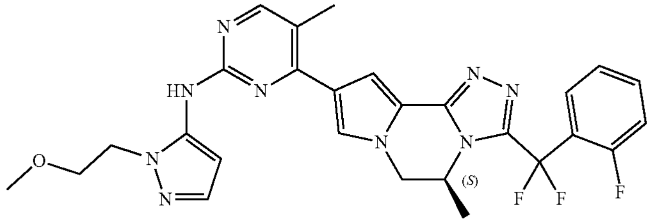 | 550.1 | $^1$H NMR (400 MHz, DMSO-d6) δ 8.98 (s, 1H), 8.24 (s, 1H), 7.86 (s, 1H), 7.81-7.61 (m, 2H), 7.50-7.25 (m, 4H), 6.32 (s, 1H), 5.29-5.09 (m, 1H), 4.61-4.41 (m, 2H), 4.30-4.10 (m, 2H), 3.72-3.56 (m, 2H), 3.19 (s, 3H), 2.34 (s, 3H), 1.29 (d, J = 5.9 Hz, 3H). |
| 297 | 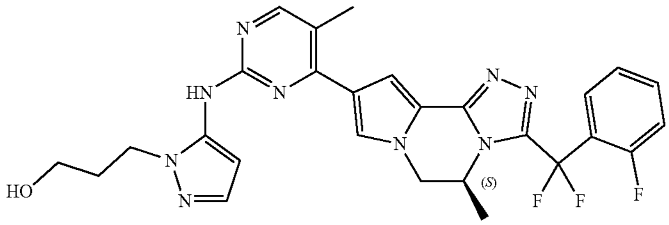 | 550.1 | $^1$H NMR (400 MHz, DMSO-d6) δ 9.04 (s, 1H), 8.23 (s, 1H), 7.85 (s, 1H), 7.77-7.65 (m, 2H), 7.48-7.31 (m, 4H), 6.28 (d, J = 1.7 Hz, 1H), 5.26-5.12 (m, 1H), 4.81-4.63 (m, 1H), 4.58-4.44 (m, 2H), 4.06 (t, J = 7.0 Hz, 2H), 3.37-3.33 (m, 2H), 2.33 (s, 3H), 1.90-1.77 (m, 2H), 1.29 (d, J = 6.6 Hz, 3H). |
| 298 | 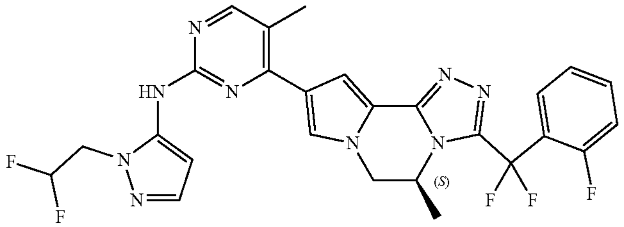 | 556.1 | $^1$H NMR (400 MHz, DMSO-d6) δ 9.30 (s, 1H), 8.26 (s, 1H), 7.87 (d, J = 1.5 Hz, 1H), 7.78-7.66 (m, 2H), 7.46-7.38 (m, 3H), 7.36 (d, J = 1.5 Hz, 1H), 6.45-6.11 (m, 2H), 5.25-5.15 (m, 1H), 4.63-4.49 (m, 4H), 2.34 (s, 3H), 1.29 (d, J = 6.6 Hz, 3H). |

Example 15: Synthesis of Compounds 299

Compound 299

(10-(5-chloro-2-((1-methyl-1H-pyrazol-5-yl)amino)pyridin-4-yl)-3-(1-(trifluoromethyl)cyclobutyl)-6,7-dihydro-5H-pyrrolo[1,2-a][1,2,4]triazolo[3,4-c][1,4]diazepin-6-yl)methanol

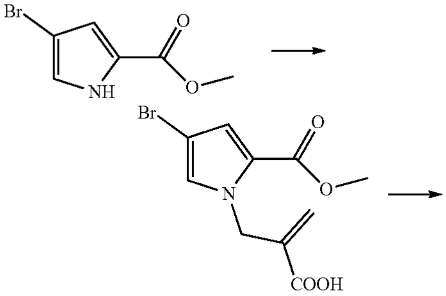

-continued

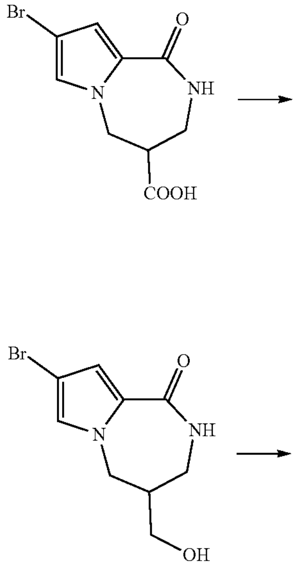

-continued

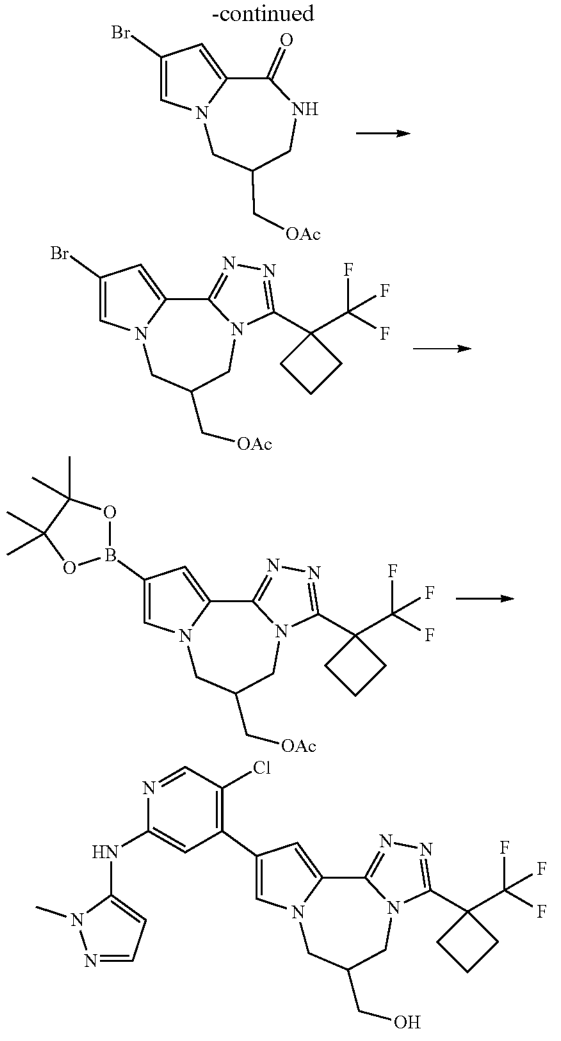

(A) 8-bromo-1-oxo-2,3,4,5-tetrahydro-1H-pyrrolo[1,2-a][1,4]diazepine-4-carboxylic acid To a mixture of methyl 4-bromo-1H-pyrrole-2-carboxylate (5.0 g, 24.5 mmol) in DMF (100 mL) was added NaH (3.43 g, 85.7 mmol, 60% dispersion in Paraffin Liquid) slowly at 0° C. The reaction mixture was stirred for 0.5 h and then 3-bromo-2-(bromomethyl)propanoic acid was added. The reaction was stirred at room temperature for 2 h under nitrogen atmosphere. Then the reaction was quenched by saturated solution of ammonium chloride, adjusted the pH<4 by diluted HCl and extracted by EA. The organic layer was washed with brine, dried and concentrated. To the residue was added ammonium hydroxide (50 mL) and the resulting mixture was stirred at 100° C. overnight. The mixture was concentrated and purified via ISCO (eluting with methanol in water 0%~100%) to afford the title compound as a yellow solid (1.30 g, 16.1% yield). MS (m/z): 273.0/275.0 $(M+H)^+$.

(B) 8-bromo-4-(hydroxymethyl)-2,3,4,5-tetrahydro-1H-pyrrolo[1,2-a][1,4]diazepin-1-one To a mixture of 8-bromo-1-oxo-2,3,4,5-tetrahydro-1H-pyrrolo[1,2-a][1,4]diazepine-4-carboxylic acid (800 mg, 2.93 mmol) in THF (10 mL) was added $BH_3 \cdot Me_2S$ (4.5 mL, 9.0 mmol) at 0° C. The reaction was stirred at 50° C. for 3 h under nitrogen atmosphere. Then the reaction was quenched by MeOH, concentrated and purified via ISCO (eluting with methanol in water 0%~100%) to afford the title compound as a yellow solid (250 mg, 32.8% yield). MS (m/z): 259.0/261.0 $(M+H)^+$.

(C) (10-bromo-3-(1-(trifluoromethyl)cyclobutyl)-6,7-dihydro-5H-pyrrolo[1,2-a][1,2,4]triazolo[3,4-c][1,4]diazepin-6-yl)methyl acetate To a mixture of 8-bromo-4-(hydroxymethyl)-2,3,4,5-tetrahydro-1H-pyrrolo[1,2-a][1,4]diazepin-1-one (250 mg, 0.96 mmol) in DCM (10 mL) was added $Et_3N$ (194.3 mg, 1.92 mmol), $Ac_2O$ (148 mg, 1.44 mmol) and N,N-dimethylpyridin-4-amine (12 mg, 0.096 mmol) at 0° C. The reaction was stirred at room temperature for 2 h under nitrogen atmosphere. Then the reaction was quenched by water and extracted by DCM. The organic layer was washed with brine, dried and concentrated. The residue was mixed with 1-(trifluoromethyl)cyclobutane-1-carbohydrazide (210 mg, 1.15 mmol) and $POCl_3$ (5 mL). The resulting mixture was stirred at 70° C. for 2 h. The volatiles were removed and the residue was dissolved in DCM and MeOH. Then the organic layer was washed with saturated solution of $NaHCO_3$ and dried over anhydrous $Na_2SO_4$, concentrated. The residue was dissolved in NMP (5 mL) and 2 drop of HOAc was added. The resulting mixture was stirred at 130° C. for 0.5 h under microwave. Then the reaction mixture was purified directly via ISCO (eluting with methanol in water 0%~100%) to afford the title compound as a yellow solid (220 mg, 51.0% yield). MS (m/z): 447.0/449.0 $(M+H)^+$.

(D) (10-(4,4,5,5-tetramethyl-1,3,2-dioxaborolan-2-yl)-3-(1-(trifluoromethyl)cyclobutyl)-6,7-dihydro-5H-pyrrolo[1,2-a][1,2,4]triazolo[3,4-c][1,4]diazepin-6-yl)methyl acetate A mixture of (10-bromo-3-(1-(trifluoromethyl)cyclobutyl)-6,7-dihydro-5H-pyrrolo[1,2-a][1,2,4]triazolo[3,4-c][1,4]diazepin-6-yl)methyl acetate (80 mg, 0.18 mmol) and BPIN (91 mg, 0.36 mmol), $Pd_2(dba)_3$ (16 mg, 0.018 mmol), tricyclohexylphosphane (10 mg, 0.036 mmol) and potassium acetate (53 mg, 0.54 mmol) in 1,4-dioxane (8 mL) was stirred at 100° C. for 5 h under nitrogen atmosphere. The reaction was diluted with water and extracted by DCM. The organic layer was dried, concentrated in vacuum and purified via ISCO (eluting with methanol in water 0%~100%) to afford the title compound as a white solid (10 mg, 11.1% yield). MS (m/z): 495.1 $(M+H)^+$.

(E) (10-(5-chloro-2-((1-methyl-1H-pyrazol-5-yl)amino)pyridin-4-yl)-3-(1-(trifluoromethyl)cyclobutyl)-6,7-dihydro-5H-pyrrolo[1,2-a][1,2,4]triazolo[3,4-c][1,4]diazepin-6-yl)methanol A mixture of (10-(4,4,5,5-tetramethyl-1,3,2-dioxaborolan-2-yl)-3-(1-(trifluoromethyl)cyclobutyl)-6,7-dihydro-5H-pyrrolo[1,2-a][1,2,4]triazolo[3,4-c][1,4]diazepin-6-yl)methyl acetate (10 mg, 0.02 mmol), 5-chloro-4-iodo-N-(1-methyl-1H-pyrazol-5-yl)pyridin-2-amine (9 mg, 0.024 mmol), $Pd(dppf)Cl_2 \cdot CH_2Cl_2$ (2 mg, 0.002 mmol) and sodium carbonate (6.4 mg, 0.06 mmol) in 1,4-dioxane (8 mL) and water (2 mL) was degassed and stirred at 80° C. for 1 hour under nitrogen atmosphere. The mixture was then concentrated and the residue was purified via ISCO (eluting with methanol in water 0%~100%) to afford the title compound as a light yellow solid (3.0 mg, 28.0% yield). MS (m/z): 533.0 $(M+H)^+$.

$^1H$ NMR (400 MHz, DMSO-d6) δ 8.86 (s, 1H), 8.14 (s, 1H), 7.70 (s, 1H), 7.33 (s, 1H), 7.14 (s, 1H), 6.98 (s, 1H), 6.24 (s, 1H), 5.06 (t, J=5.0 Hz, 1H), 4.32-4.17 (m, 2H), 4.14-4.09 (m, 1H), 3.75-3.69 (m, 1H), 3.67 (s, 3H), 3.50-3.36 (m, 3H), 2.97-2.89 (m, 2H), 2.77-2.72 (m, 2H), 2.19-2.14 (m, 1H), 2.08-1.94 (m, 1H).

Example 16: Synthesis of Compounds 300-303

Compound 300

5-chloro-4-(6-(methoxymethyl)-3-(1-(trifluoromethyl)cyclobutyl)-6,7-dihydro-5H-pyrrolo[1,2-a][1,2,4]triazolo[3,4-c][1,4]diazepin-10-yl)-N-(1-methyl-H-pyrazol-5-yl)pyridin-2-amine

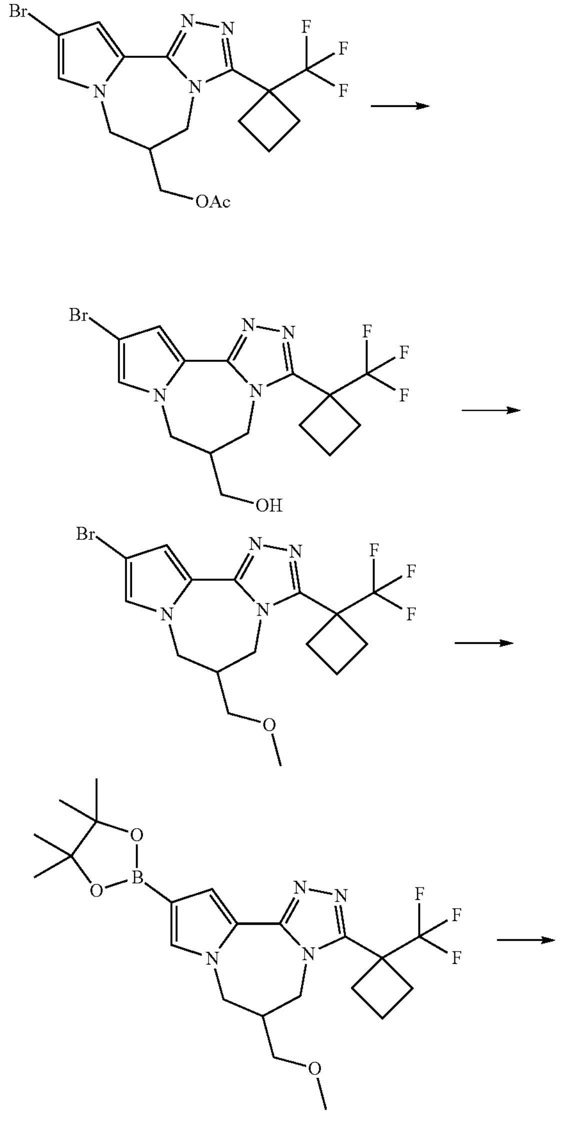

-continued

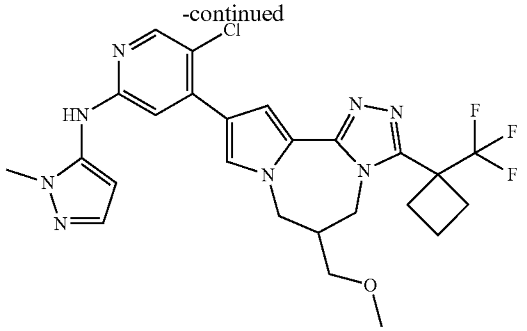

(A) 10-bromo-6-(methoxymethyl)-3-(1-(trifluoromethyl)cyclobutyl)-6,7-dihydro-5H-pyrrolo[1,2-a][1,2,4]triazolo[3,4-c][1,4]diazepine A mixture of (10-bromo-3-(1-(trifluoromethyl)cyclobutyl)-6,7-dihydro-5H-pyrrolo[1,2-a][1,2,4]triazolo[3,4-c][1,4]diazepin-6-yl)methyl acetate (140 mg, 0.31 mmol) and $Na_2CO_3$ (99 mg, 0.93 mmol) in THF (3 mL) and water (3 mL) was stirred at room temperature for 0.5 h. Then the mixture was diluted with water and extracted by DCM. The organic layer was washed with brine, dried and concentrated. The residue was dissolved in THF (10 mL) and cooled to 0° C. NaH (20 mg, 0.50 mmol, 60% dispersion in Paraffin Liquid) was added and the mixture was stirred for other 20 min. Iodomethane was added and the reaction was stirred at room temperature for 0.5 h. Then the reaction was quenched by saturated ammonium chloride and extracted by DCM. The organic layer was concentrated and purified via ISCO (eluting with methanol in water 0%—100%) to afford the title compound as a white solid (110 mg, 83.8% yield). MS (m/z): 419.0/421.0 $(M+H)^+$.

(B) 5-chloro-4-(6-(methoxymethyl)-3-(1-(trifluoromethyl)cyclobutyl)-6,7-dihydro-5H-pyrrolo[1,2-a][1,2,4]triazolo[3,4-c][1,4]diazepin-10-yl)-N-(1-methyl-1H-pyrazol-5-yl)pyridin-2-amine The title compound was prepared according to the procedures of Example 15 using the corresponding intermediates and reagents. MS (m/z): 547.1 $(M+H)^+$.

$^1H$ NMR (400 MHz, DMSO-d6) δ 8.83 (s, 1H), 8.12 (s, 1H), 7.67 (s, 1H), 7.31 (s, 1H), 7.12 (s, 1H), 6.96 (s, 1H), 6.21 (s, 1H), 4.23 (d, J=4.3 Hz, 2H), 4.08-4.05 (m, 1H), 3.82-3.72 (m, 1H), 3.64 (s, 3H), 3.36-3.30 (m, 2H), 3.24 (s, 3H), 2.93-2.85 (m, 2H), 2.75-2.68 (m, 3H), 2.18-2.13 (m, 1H), 2.03-1.97 (m, 1H).

The compounds below were prepared according to the procedures of Compound 300 using the corresponding intermediates and reagents under appropriate conditions that could be recognized by one skilled in the art.

| Compound | Structure | LC-MS (m/z) $(M + H)^+$ | $^1H$ NMR |
| --- | --- | --- | --- |
| 301 | 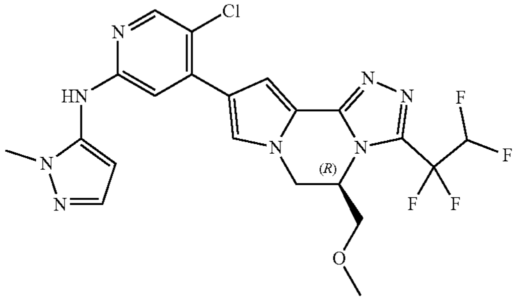 | 511.1 | $^1H$ NMR (400 MHz, DMSO-d6) δ 8.84 (s, 1H), 8.14 (s, 1H), 7.82 (d, J = 1.6 Hz, 1H), 7.31 (d, J = 2.0 Hz, 1H), 7.19 (d, J = 1.6 Hz, 1H), 6.96 (s, 1H), 6.22 (d, J = 1.6 Hz, 1H), 5.20-5.12 (m, 1H), 4.64 (d, J = 13.2 Hz, 1H), 4.51-4.46 (m, 1H), 3.64 (s, 3H), 3.48-3.44 (m, 1H), 3.37-3.31 (m, 2H), 3.16 (s, 3H). |
| 302 | 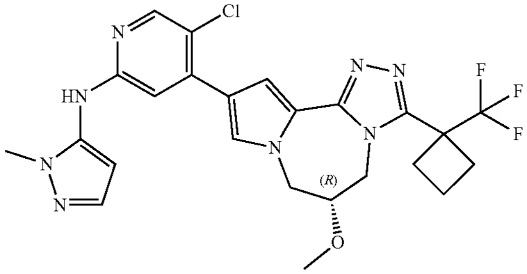 | 533.3 | $^1H$ NMR (400 MHz, DMSO-d6) δ 8.88 (s, 1H), 8.13 (s, 1H), 7.75 (d, J = 1.8 Hz, 1H), 7.32 (d, J = 1.9 Hz, 1H), 7.09 (d, J = 1.8 Hz, 1H), 6.96 (s, 1H), 6.23 (d, J = 1.9 Hz, 1H), 4.46-4.42 (m, 1H), 4.32-4.22 (m, 1H), 4.16-4.12 (m, 2H), 3.93-3.83 (m, 1H), 3.65 (s, 3H), 3.41 (s, 3H), 2.99-2.96 (m, 1H), 2.83-2.79 (m, 3H), 2.17-2.13 (m, 1H), 2.01-1.98 (m, 1H). |
| 303 | 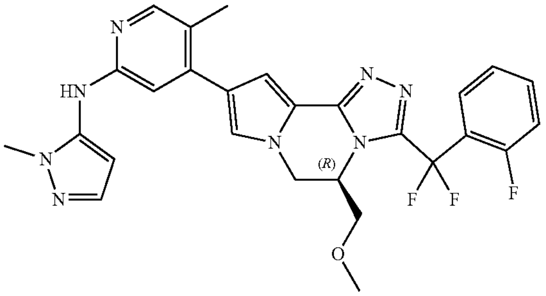 | 535.3 | $^1H$ NMR (400 MHz, DMSO-d6) δ 8.53 (s, 1H), 7.95 (s, 1H), 7.75-7.67 (m, 2H), 7.59 (d, J = 1.2 Hz, 1H), 7.45-7.39(m, 2H), 7.29 (d, J = 1.6 Hz, 1H), 7.03 (d, J = 1.2 Hz, 1H), 6.83 (s, 1H), 6.20 (d, J = 1.6 Hz, 1H), 5.23-5.13 (m, 1H), 4.68-4.44 (m, 2H), 3.64 (s, 3H), 3.48-3.40 (m, 2H), 3.20 (s, 3H), 2.29 (s, 3H). |

Example 17: Synthesis of Compounds 304-321

Compound 304

5-chloro-N-(1-methyl-1H-pyrazol-5-yl)-4-(3'-(1,1,2,2-tetrafluoroethyl)-5'H,7'H-spiro[oxetane-3,6'-pyrrolo[1,2-a][1,2,4]triazolo[3,4-c][1,4]diazepin]-10'-yl)pyridin-2-amine

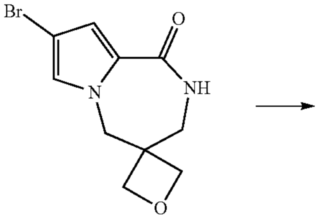

-continued

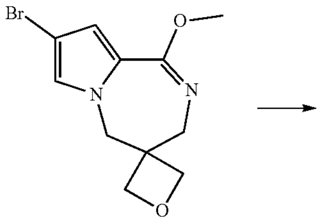

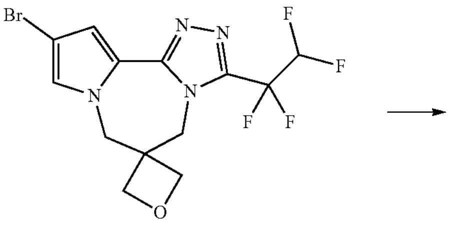

-continued

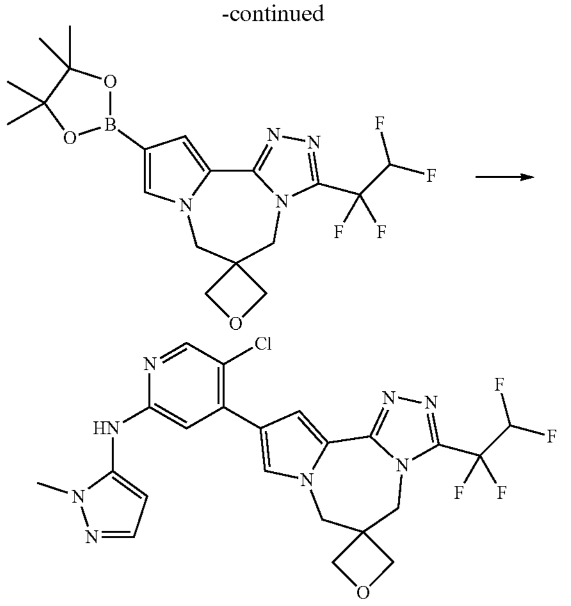

(A) 10'-bromo-3'-(1,1,2,2-tetrafluoroethyl)-5'H,7'H-spiro[oxetane-3,6'-pyrrolo[1,2-a][1,2,4]triazolo[3,4-c][1,4]diazepine]

To a solution of 8'-bromo-2',3'-dihydro-1'H,5'H-spiro[oxetane-3,4'-pyrrolo[1,2-a][1,4]diazepin]-1'-one (400 mg, 1.48 mmol) in DCM (30 mL) was added $CF_3SO_3Me$ (291 mg, 1.77 mmol) and then the mixture was stirred overnight at reflux temperature under nitrogen atmosphere. The reaction was quenched with water and extracted with DCM. The combined organic layers were washed with water and brine, dried over anhydrous sodium sulfate and concentrated. The residue was dissolved in propan-2-ol (20 mL), 2,2,3,3-tetrafluoropropanehydrazide (283 mg, 1.77 mmol) and HOAc (2 drops) was added. Then the mixture was purged with nitrogen atmosphere and stirred at 70° C. for 3 h and then 90° C. for 3 h. The mixture was concentrated and the residue was purified via ISCO (eluting with methanol in water 0%~100%) to give an off-white solid (203 mg, 34.7% yield). MS (m/z): 394.9/396.9 $(M+H)^+$.

(B) 5-chloro-N-(1-methyl-1H-pyrazol-5-yl)-4-(3'-(1,1,2,2-tetrafluoroethyl)-5'H,7'H-spiro[oxetane-3,6'-pyrrolo[1,2-a][1,2,4]triazolo[3,4-c][1,4]diazepin]-10'-yl)pyridin-2-amine The title compound was prepared according to the procedures of Example 15 using the corresponding intermediates and reagents. MS (m/z): 523.0 $(M+H)^+$.

$^1$H NMR (400 MHz, DMSO-d6) δ 8.83 (s, 1H), 8.15 (s, 1H), 7.89 (s, 1H), 7.62-7.14 (m, 3H), 6.98 (s, 1H), 6.23 (s, 1H), 4.73 (s, 2H), 4.66 (s, 2H), 4.51-4.42 (m, 2H), 4.41-4.31 (m, 2H), 3.64 (s, 3H).

The compounds below were prepared according to the procedures of Compound 304 using the corresponding intermediates and reagents under appropriate conditions that could be recognized by one skilled in the art.

| Compound | Structure | LC-MS (m/z) $(M + H)^+$ | $^1$H NMR |
|---|---|---|---|
| 305 | 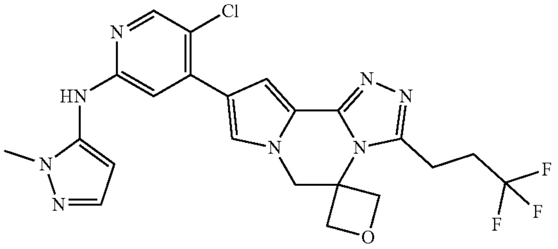 [SMILES: Cn1nccc1Nc1cc(-c2cc3n(c2)CC2(COC2)n2c(CCC(F)(F)F)nnc2-3)c(Cl)cn1] | 505.1 | $^1$H NMR (400 MHz, DMSO-d6) δ 8.83 (s, 1H), 8.13 (s, 1H), 7.72 (d, J = 1.6 Hz, 1H), 7.32 (d, J = 1.9 Hz, 1H), 7.02 (d, J = 1.6 Hz, 1H), 6.94 (s, 1H), 6.22 (d, J = 1.9 Hz, 1H), 5.03-4.99 (m, 2H), 4.83-4.70 (m, 4H), 3.65 (s, 3H), 3.49-3.40 (m, 2H), 3.05-2.89 (m, 2H). |
| 306 | 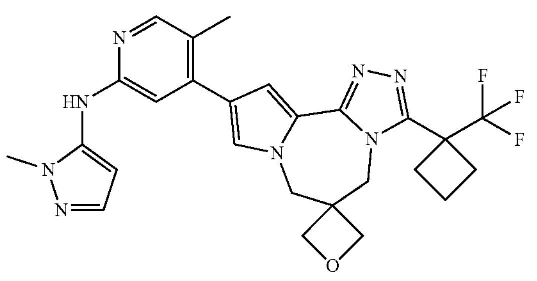 [SMILES: Cc1cnc(Nc2ccnn2C)cc1-c1cc2n(c1)CC1(COC1)Cn1c-2nnc1C1(C(F)(F)F)CCC1] | 525.1 | $^1$H NMR (400 MHz, DMSO-d6) δ 8.56 (s, 1H), 7.95 (s, 1H), 7.60 (d, J = 1.4 Hz, 1H), 7.30 (d, J = 1.5 Hz, 1H), 7.04 (d, J = 1.4 Hz, 1H), 6.85 (s, 1H), 6.21 (d, J = 1.5 Hz, 1H), 4.65 (s, 2H), 4.47 (d, J = 6.5 Hz, 2H), 4.39-4.29 (m, 4H), 3.66 (s, 3H), 2.98-2.87 (m, 2H), 2.86-2.76 (m, 2H), 2.31 (s, 3H), 2.25-2.14 (m, 1H), 2.07-1.93 (m, 1H). |

-continued

| Compound | Structure | LC-MS (m/z) (M + H)+ | 1H NMR |
|---|---|---|---|
| 307 | 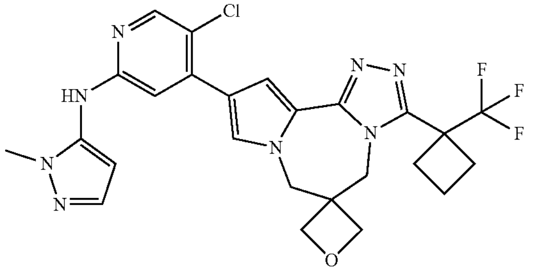 [SMILES: Cn1nccc1Nc1cc(-c2cc3n(c2)CC2(COC2)Cn2c-3nnc2C2(C(F)(F)F)CCC2)c(Cl)cn1] | 545.1 | 1H NMR (400 MHz, DMSO-d6) δ 8.90 (s, 1H), 8.14 (s, 1H), 7.86 (d, J = 1.5 Hz, 1H), 7.33 (d, J = 1.5 Hz, 1H), 7.18 (d, J = 1.5 Hz, 1H), 6.98 (s, 1H), 6.23 (d, J = 1.5 Hz, 1H), 4.67 (s, 2H), 4.45 (d, J = 6.4 Hz, 2H), 4.39-4.26 (m, 4H), 3.66 (s, 3H), 3.00-2.85 (m, 2H), 2.86-2.72 (m, 2H), 2.26-2.12 (m, 1H), 2.07-1.91 (m, 1H). |

The compounds below were prepared according to the procedures of above examples using the corresponding intermediates and reagents under appropriate conditions that could be recognized by one skilled in the art.

| Compound | Structure | LC-MS (m/z) (M + H)+ |
|---|---|---|
| 308 | 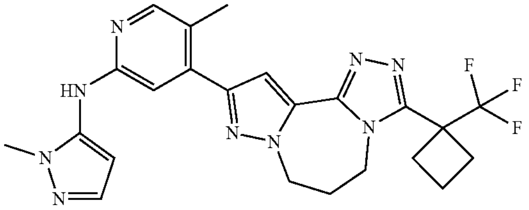 [SMILES: Cc1cnc(Nc2ccnn2C)cc1-c1cc2n(n1)CCCn1c-2nnc1C1(C(F)(F)F)CCC1] | 484.1 |
| 309 | 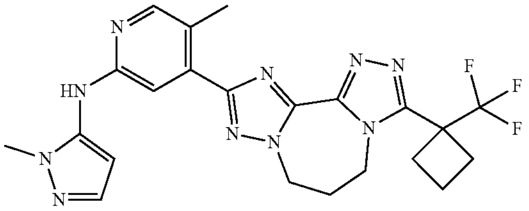 [SMILES: Cc1cnc(Nc2ccnn2C)cc1-c1nc2n(n1)CCCn1c-2nnc1C1(C(F)(F)F)CCC1] | 485.1 |
| 310 | 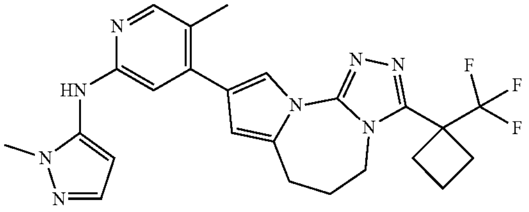 [SMILES: Cc1cnc(Nc2ccnn2C)cc1-c1cc2n(c1)-c1nnc(C3(C(F)(F)F)CCC3)n1CCC2] | 483.1 |
| 311 | 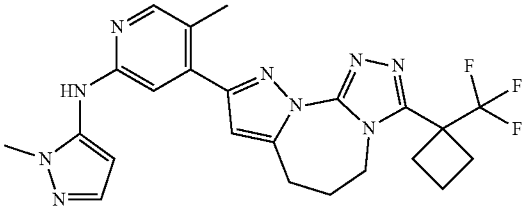 [SMILES: Cc1cnc(Nc2ccnn2C)cc1-c1cc2n(n1)-c1nnc(C3(C(F)(F)F)CCC3)n1CCC2] | 484.1 |

-continued
| Compound | Structure | LC-MS (m/z) (M + H)+ |
| --- | --- | --- |
| 312 | 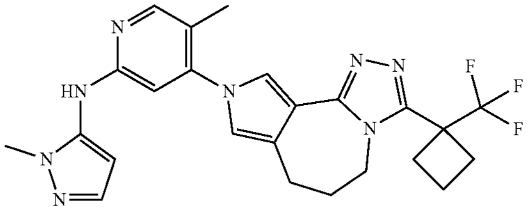 [SMILES: Cc1cnc(Nc2ccnn2C)cc1-n1cc2c(c1)-c1nnc(C3(C(F)(F)F)CCC3)n1CCC2] | 483.1 |
| 313 | 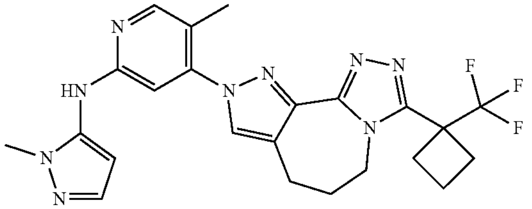 [SMILES: Cc1cnc(Nc2ccnn2C)cc1-n1cc2c(n1)-c1nnc(C3(C(F)(F)F)CCC3)n1CCC2] | 484.1 |
| 314 | 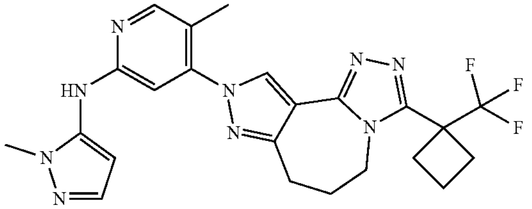 [SMILES: Cc1cnc(Nc2ccnn2C)cc1-n1cc2c(n1)CCCn1c-2nnc1C1(C(F)(F)F)CCC1] | 484.1 |
| 315 | 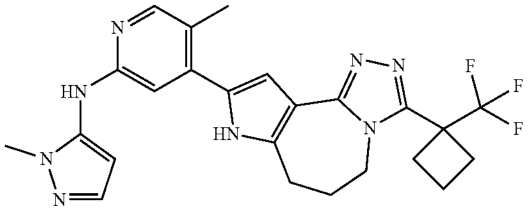 [SMILES: Cc1cnc(Nc2ccnn2C)cc1-c1cc2c([nH]1)CCCn1c-2nnc1C1(C(F)(F)F)CCC1] | 483.1 |
| 316 | 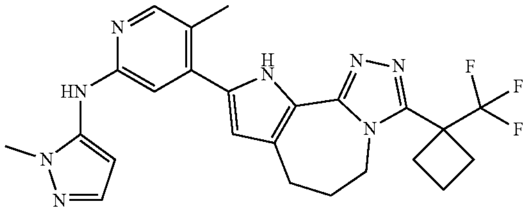 [SMILES: Cc1cnc(Nc2ccnn2C)cc1-c1cc2c([nH]1)-c1nnc(C3(C(F)(F)F)CCC3)n1CCC2] | 483.1 |
| 317 | 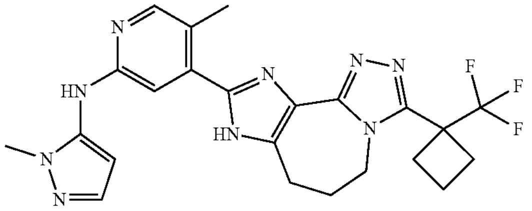 [SMILES: Cc1cnc(Nc2ccnn2C)cc1-c1nc2c([nH]1)CCCn1c-2nnc1C1(C(F)(F)F)CCC1] | 484.1 |
| 318 | 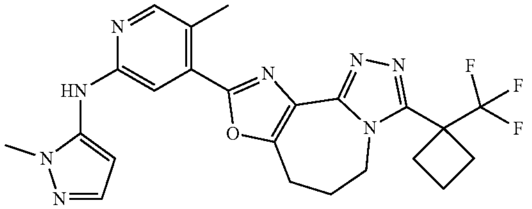 [SMILES: Cc1cnc(Nc2ccnn2C)cc1-c1nc2c(o1)CCCn1c-2nnc1C1(C(F)(F)F)CCC1] | 485.1 |

-continued

| Compound | Structure | LC-MS (m/z) $(M + H)^+$ |
|---|---|---|
| 319 | 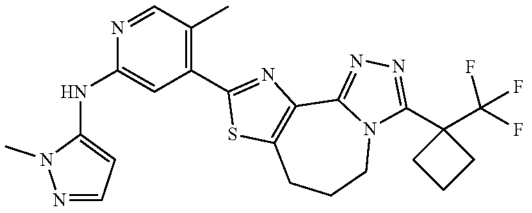 [SMILES: Cc1cnc(Nc2ccnn2C)cc1-c1nc2c(s1)CCCn1c-2nnc1C1(C(F)(F)F)CCC1] | 501.1 |
| 320 | 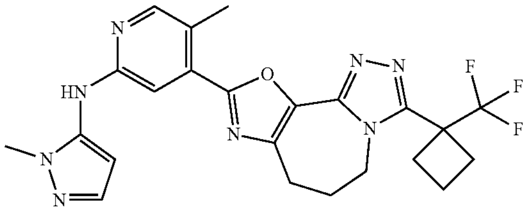 [SMILES: Cc1cnc(Nc2ccnn2C)cc1-c1nc2c(o1)-c1nnc(C3(C(F)(F)F)CCC3)n1CCC2] | 485.1 |
| 321 | 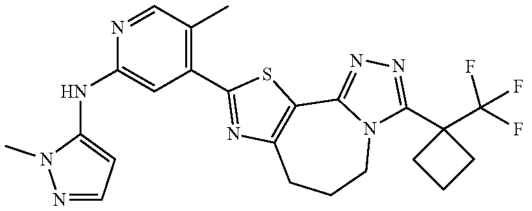 [SMILES: Cc1cnc(Nc2ccnn2C)cc1-c1nc2c(s1)-c1nnc(C3(C(F)(F)F)CCC3)n1CCC2] | 501.1 |

Example 18: Z-Lyte Kinase Assay of ERK2

1. Materials and Reagents:

| | Vender | Cat Number |
|---|---|---|
| Z-lyte assay kit-Ser/Thr3 | Invitrogen | PV3176 |
| Z-LYTE Ser/Thr3 Peptide | Invitrogen | PV3200 |
| Z-LYTE Ser/Thr3 Phospho-peptide | Invitrogen | PV3215 |
| 5X Kinase Buffer | Invitrogen | PV3189 |
| 10 mM ATP | Invitrogen | PV3227 |
| Development Reagent A | Invitrogen | PV3295 |
| Development Buffer | Invitrogen | P3127 |
| Stop Reagent | Invitrogen | P3094 |
| MAPK1(ERK2) enzyme | Invitrogen | PV3313 |
| 384-well plate(black) | Corning | 3575 |
| Victor3 | PerkinElmer ™ | |

2. Reaction Steps:
Plate Map

| 1 | Ref cpd Cons (μM) | Cpd 1 Cons (μM) | Cpd 2 Cons (μM) | . . . | Cpd N Cons (μM) |
|---|---|---|---|---|---|
| C1 | 1.00E+00 | 1.00E+00 | 1.00E+00 | | 1.00E+00 |
| | 1.00E+00 | 1.00E+00 | 1.00E+00 | | 1.00E+00 |
| | 3.33E−01 | 3.33E−01 | 3.33E−01 | | 3.33E−01 |
| | 3.33E−01 | 3.33E−01 | 3.33E−01 | | 3.33E−01 |
| C2 | 1.11E−01 | 1.11E−01 | 1.11E−01 | | 1.11E−01 |
| | 1.11E−01 | 1.11E−01 | 1.11E−01 | | 1.11E−01 |
| | 3.70E−02 | 3.70E−02 | 3.70E−02 | | 3.70E−02 |
| | 3.70E−02 | 3.70E−02 | 3.70E−02 | | 3.70E−02 |
| C3 | 1.23E−02 | 1.23E−02 | 1.23E−02 | | 1.23E−02 |
| | 1.23E−02 | 1.23E−02 | 1.23E−02 | | 1.23E−02 |
| | 4.12E−03 | 4.12E−03 | 4.12E−03 | | 4.12E−03 |
| | 4.12E−03 | 4.12E−03 | 4.12E−03 | | 4.12E−03 |
| | 1.37E−03 | 1.37E−03 | 1.37E−03 | | 1.37E−03 |
| | 1.37E−03 | 1.37E−03 | 1.37E−03 | | 1.37E−03 |

-continued

| 1 | Ref cpd Cons (μM) | Cpd 1 Cons (μM) | Cpd 2 Cons (μM) | . . . | Cpd N Cons (μM) |
|---|---|---|---|---|---|
| | 4.57E−04 | 4.57E−04 | 4.57E−04 | | 4.57E−04 |
| | 4.57E−04 | 4.57E−04 | 4.57E−04 | | 4.57E−04 |

3. Solution Preparation
   1) 1.33× Kinase Buffer: Dilute 5× Kinase Buffer to 1.33× with $ddH_2O$
   2) 4× Test Compounds: Serially dilute the test compounds to 4 folds of the concentrations desired, keeping the DMSO concentration at 8%. The final concentrations are 1, 0.33, 0.11, 0.037, 0.012, 0.004, 0.0014, 0.00046 μM, and the final concentration of DMSO is 2%.
   3) Kinase/Peptide Mixture (P/K solution): Prepare Kinase/Peptide Mixture by diluting the kinase to 0.6 μg/ml and the Z-LYTE™ Ser/Thr3 peptide to 4 μM in 1.33× Kinase Buffer. Mix gently by pipetting.
   4) Phospho-peptide Solution (PP solution): Add 0.4 μl of Z-LYTE™ Ser/Thr3 Phospho-peptide to 99.6 μl of 1.33× Kinase Buffer.
   5) ATP Solution: Prepare ATP Solution by diluting the 10 mM of ATP in 1.33× Kinase Buffer to 100 μM.
   6) Development Solution: Dilute Development Reagent A with Development Buffer as 1:1024.
4. Reaction
   1) Kinase reaction (10 μl of Volume)
   a. In a 384-well plate, add 2.5 μl of 4× test Cpds to each well except C1, C2, C3 wells Add 2.5 μl of 8% DMSO to C1, C2, C3 wells
   b. Put the plate on ice
   c. Add 5 μl of P/K mixture to each test Cpd wells and C1, C2 wells d. Add 5 μl of PP Solution to C3 well e. Add 2.5 μl of 1.33× kinase buffer to C1 and C3 wells f. Add 2.5 μl of 4×ATP Solution to each test Cpd wells and C2 well, respectively. Shake the plate for 30 Sec and centrifuge (1500 rpm, 1 min)

g. Seal the plate to protect from the light and incubate the plate for 1 hour at RT (25-30° C.)

2) Development reaction a. Add 5 μl of the Development solution to all wells b. Shake the plate for 30 sec and centrifuge (1500 rpm, 1 min)

c. Seal the plate to protect from the light and incubate the plate for 1 hour at RT (25-30° C.)

3) Stop and read a. Add 5 μl of the Stop reagent to all wells b. Shake the plate for 30 sec and centrifuge (1500 rpm, 1 min)

c. Measure the value of coumarin (Ex400 nm, Em445 nm) and fluorescein (Ex400 nm, Em520 nm), respectively.

5. Data Analysis

Emission Ratio(ER)=Coumarin Emission (445 nm)/Fluorescein Emission (520 nm)

$$\%\ \text{Phosphorylation}=1-[ER\times C3_{520nm}-C3_{445nm}]/[(C1_{445nm}-C3_{445nm})+ER\times(C3_{520nm}-C1_{520nm})]$$

$$\text{Inhibition rate (IR)}=1-\%\ \text{Pho}_{test\ Cpd}\%\ \text{Pho}_{C2}$$

6. $IC_{50}$ Value: determine $IC_{50}$ with add-in software for Microsoft Excel, XLfit™ (version 2.0) from ID Business Solutions (Guildford, UK)

Example 19: p-RSK (Thr359) Acumen Assay in Colo205

1. Cell Line colo205 (SIBS)

2. Material and Reagent

Phospho-p90RSK (Thr359) (D1E9) Rabbit mAb: cell signal, #8753

Alexa Fluor® 488 donkey anti-rabbit IgG: invitrogen, #A-21206

Propidium Iodide: Sigma, #p4170

4% Paraformaldehyde: SCRC, #DF021

10% Triton X-100: PIERCE, #28314

96-well plate (black with clear bottom): BD, #354640

Acumen® eX3 (A Multilaser Microplate Cytometer For Enhanced High Content Screening): TTP LabTech 3. Acumen Assay Protocol Seed 4000 cells in 100 μl 10% FBS/well into 96-well plate, incubate at 37° C., 5% $CO_2$, overnight.

Dilute the compound to 3, 1, 0.33, 0.11, 0.037, 0.012, 0.004, 0.001 μM, keeping the DMSO concentration at 5%. Add 10 μl of diluted compound per well and incubate at 37° C., 5% $CO_2$ for 1 hour.

Add 100 μl of 4% pre-warmed Paraformaldehyde (2% final), and incubate for 45 min at room temperature.

Remove paraformaldehyde solutions. Add 100 μl of ice-cold 0.1% Triton to fixed cells at room temperature for 30 min.

Wash twice with 150 μl PBS and incubate with 100 μl blocking buffer (1% BSA, in PBS) for 2~3 hours at room temperature, seal the plate.

Wash once with PBS and incubate with 35 μl p-RSK (Thr359) (1:1000 dilution) overnight at 4° C. Seal the plate.

Wash twice with PBS and incubate for 1.5 hours at room temperature with 35 μl of Alexa Fluor® 488 donkey anti-rabbit IgG at a 1:1,000 dilution in antibody dilution buffer (0.1% BSA, in PBS). Cover plate in foil to keep out of light.

Wash twice with 150 μl PBS. Add 35 μl of 1.5 μM Propidium Iodide stock to each well to determine cell number, seal the plate.

Incubate at room temperature for 30 min. Load the plate into the Acumen Explorer and scan with the appropriate instrument settings.

4. Data Analysis $$\text{Inhibition (\%)} = 100 - \frac{Percentage_{compound\ well} - Percentage_{min\ well} \times 100}{Percentage_{max\ well} - Percentage_{min\ well}}$$

Note:

$Percentage_{compound\ well}$ represents the positive percentage of cells treated by compound.

$Percentage_{min\ well}$ represents the positive percentage of cells treated with 3 uM GDC0994.

$Percentage_{max\ well}$ represents the positive percentage of cells without compounds treatment.

5. $IC_{50}$ Value: determine $IC_{50}$ with add-in software for Microsoft Excel, XLfit™ (version 2.0) from ID Business Solutions (Guildford, UK)

Results

| | Example 18 | Example 19 |
|---|---|---|
| Compound | $IC_{50}$ (nM) | $IC_{50}$ (nM) |
| 1 | A | E |
| 2 | A | D |
| 3 | A | D |
| 4 | A | E |
| 5 | A | E |
| 6 | B | D |
| 7 | A | D |
| 8 | A | E |
| 9 | A | D |
| 10 | A | E |
| 11 | A | D |
| 12 | A | D |
| 13 | A | E |
| 14 | A | D |
| 15 | B | D |
| 16 | A | D |
| 17 | A | D |
| 18 | B | E |
| 19 | A | D |
| 20 | A | D |
| 21 | A | E |
| 22 | A | E |
| 23 | B | D |
| 24 | B | E |
| 25 | A | E |
| 26 | A | D |
| 27 | A | D |
| 28 | A | D |
| 29 | A | D |
| 30 | A | D |
| 31 | B | D |
| 32 | A | D |
| 33 | C | D |
| 34 | C | E |
| 35 | C | D |
| 36 | A | E |
| 37 | A | D |
| 38 | C | D |
| 39 | B | D |

-continued

| Compound | Example 18 IC$_{50}$ (nM) | Example 19 IC$_{50}$ (nM) |
|---|---|---|
| 40 | A | D |
| 41 | A | E |
| 42 | A | E |
| 43 | B | D |
| 44 | C | E |
| 45 | A | D |
| 46 | A | D |
| 47 | A | D |
| 48 | A | E |
| 49 | A | D |
| 50 | A | E |
| 51 | A | D |
| 52 | A | D |
| 53 | B | E |
| 54 | B | D |
| 55 | B | D |
| 56 | A | D |
| 57 | A | E |
| 58 | A | D |
| 59 | A | D |
| 60 | A | D |
| 61 | A | D |
| 62 | A | D |
| 63 | A | D |
| 64 | A | E |
| 65 | A | D |
| 66 | A | D |
| 67 | A | D |
| 68 | B | E |
| 69 | A | E |
| 70 | A | D |
| 71 | A | D |
| 72 | B | D |
| 73 | A | E |
| 74 | A | D |
| 75 | A | E |
| 76 | A | E |
| 77 | A | D |
| 78 | A | D |
| 79 | A | D |
| 80 | A | D |
| 81 | A | D |
| 82 | A | D |
| 83 | C | D |
| 84 | B | E |
| 85 | A | D |
| 86 | B | D |
| 87 | A | D |
| 88 | A | D |
| 89 | A | D |
| 90 | B | D |
| 91 | B | D |
| 92 | B | D |
| 93 | B | D |
| 94 | A | D |
| 95 | B | D |
| 96 | B | D |
| 97 | B | D |
| 98 | A | D |
| 99 | A | E |
| 100 | A | D |
| 101 | A | D |
| 102 | A | D |
| 103 | B | D |
| 104 | A | D |
| 105 | B | D |
| 106 | A | D |
| 107 | A | E |
| 108 | A | D |
| 109 | A | E |
| 110 | A | E |
| 111 | A | E |
| 112 | B | D |
| 113 | B | E |

-continued

| Compound | Example 18 IC$_{50}$ (nM) | Example 19 IC$_{50}$ (nM) |
|---|---|---|
| 114 | A | E |
| 115 | B | E |
| 116 | B | E |
| 117 | A | D |
| 118 | C | D |
| 119 | B | E |
| 120 | A | D |
| 121 | A | D |
| 122 | A | D |
| 123 | A | D |
| 124 | A | D |
| 125 | B | D |
| 126 | B | D |
| 127 | B | D |
| 128 | B | D |
| 129 | A | D |
| 130 | B | E |
| 131 | A | D |
| 132 | B | D |
| 133 | A | D |
| 134 | B | D |
| 135 | B | D |
| 136 | C | D |
| 137 | C | D |
| 138 | B | D |
| 139 | A | D |
| 140 | A | D |
| 141 | A | D |
| 142 | B | D |
| 143 | C | D |
| 144 | A | D |
| 145 | A | D |
| 146 | A | D |
| 147 | A | E |
| 148 | B | D |
| 149 | A | D |
| 150 | A | D |
| 151 | A | D |
| 152 | A | D |
| 153 | A | D |
| 154 | A | D |
| 155 | B | D |
| 156 | A | D |
| 157 | B | D |
| 158 | B | D |
| 159 | B | D |
| 160 | A | D |
| 161 | A | D |
| 162 | B | D |
| 163 | A | D |
| 164 | A | D |
| 165 | B | D |
| 166 | A | D |
| 167 | A | D |
| 168 | B | E |
| 169 | A | D |
| 170 | C | E |
| 171 | C | D |
| 172 | B | D |
| 173 | B | E |
| 174 | A | D |
| 175 | A | E |
| 176 | B | D |
| 177 | C | D |
| 178 | C | D |
| 179 | C | D |
| 180 | C | D |
| 181 | B | E |
| 182 | B | E |
| 183 | A | D |
| 184 | B | D |
| 185 | C | D |
| 186 | B | D |
| 187 | C | D |

-continued

| | Example 18 | Example 19 |
|---|---|---|
| Compound | $IC_{50}$ (nM) | $IC_{50}$ (nM) |
| 188 | B | D |
| 189 | B | D |
| 190 | C | D |
| 191 | B | E |
| 192 | C | D |
| 193 | B | D |
| 194 | A | D |
| 195 | A | D |
| 196 | B | D |
| 197 | B | E |
| 198 | A | D |
| 199 | B | E |
| 200 | B | D |
| 201 | C | D |
| 202 | B | D |
| 203 | B | D |
| 204 | C | D |
| 205 | C | D |
| 206 | C | D |
| 207 | A | D |
| 208 | C | D |
| 209 | B | D |
| 210 | C | E |
| 211 | B | D |
| 212 | A | D |
| 213 | A | D |
| 214 | B | E |
| 215 | A | D |
| 216 | A | D |
| 217 | A | D |
| 218 | B | D |
| 219 | A | E |
| 220 | A | D |
| 221 | A | D |
| 222 | A | D |
| 223 | A | D |
| 224 | A | D |
| 225 | A | D |
| 226 | A | D |
| 227 | A | D |
| 228 | A | D |
| 229 | A | D |
| 230 | B | E |
| 231 | A | D |
| 232 | A | D |
| 233 | A | D |
| 234 | A | E |
| 235 | B | D |
| 236 | A | D |
| 237 | A | D |
| 238 | A | E |
| 239 | A | E |
| 240 | A | D |
| 241 | A | E |
| 242 | B | E |
| 243 | A | E |
| 244 | B | D |
| 245 | A | D |
| 246 | A | D |
| 247 | A | D |
| 248 | B | E |
| 249 | B | D |
| 250 | A | D |
| 251 | A | D |
| 252 | C | E |
| 253 | A | D |
| 254 | A | D |
| 255 | A | E |
| 256 | A | D |
| 257 | B | D |
| 258 | A | D |
| 259 | B | D |
| 260 | B | E |
| 261 | C | D |

-continued

| | Example 18 | Example 19 |
|---|---|---|
| Compound | $IC_{50}$ (nM) | $IC_{50}$ (nM) |
| 262 | B | D |
| 263 | A | D |
| 264 | A | E |
| 265 | C | E |
| 266 | A | D |
| 267 | C | E |
| 268 | A | D |
| 269 | B | E |
| 270 | C | D |
| 271 | B | D |
| 272 | C | D |
| 273 | B | E |
| 274 | C | D |
| 275 | A | D |
| 276 | A | D |
| 277 | A | D |
| 278 | A | E |
| 279 | A | E |
| 280 | B | E |
| 281 | A | D |
| 282 | A | E |
| 283 | A | D |
| 284 | A | E |
| 285 | A | E |
| 286 | B | D |
| 287 | B | D |
| 288 | C | D |
| 289 | C | D |
| 290 | B | E |
| 291 | C | D |
| 292 | C | E |
| 293 | B | D |
| 294 | C | E |
| 295 | B | D |
| 296 | B | D |
| 297 | C | D |
| 298 | C | D |
| 299 | A | D |
| 300 | B | D |
| 301 | A | E |
| 302 | A | D |
| 303 | B | E |
| 304 | A | D |
| 305 | A | E |
| 306 | A | D |
| 307 | A | D |

Note:
A≤5, 5<B≤10, C>10; D≤100, E>100.

The invention claimed is:

1. A compound of formula (I):

(I)

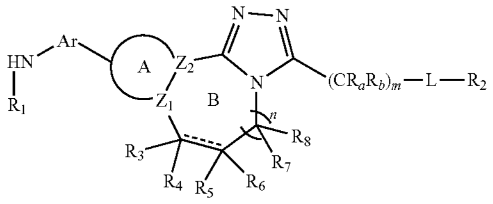

or a pharmaceutically acceptable salt thereof, or a solvate, a racemic mixture, an enantiomer, a diastereomer, or a tautomer of the compound of formula (I) or a pharmaceutically acceptable salt thereof, wherein $Z_1$ and $Z_2$ are independently N or C,

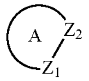

is a 5 membered heteroaryl containing 1, 2, 3, or 4 ring heteroatoms selected from N, O or S; said 5 membered heteroaryl is optionally substituted with one or more substituents independently selected from deuterium, halo, hydroxy, amino, —NH($C_{1-6}$ alkyl), —N($C_{1-6}$ alkyl)$_2$, —CN, mercapto, $C_{1-6}$ alkyl, $C_{2-6}$ alkenyl, $C_{2-6}$ alkynyl, $C_{1-6}$ alkoxyl, $C_{1-6}$ haloalkyl, —($C_{1-6}$ alkyl)-OH, and —($C_{1-6}$ alkyl)-O—($C_{1-6}$ alkyl), wherein each of said $C_{1-6}$ alkyl, $C_{1-6}$ alkoxyl, and $C_{1-6}$ haloalkyl is optionally substituted with one or more deuterium;

L is absent, or L is —$NR_c$, O, or S;

$R_c$ is hydrogen or $C_{1-6}$ alkyl;

Ar is a heteroaryl optionally substituted with one or more substituents independently selected from deuterium, halo, hydroxy, amino, —NH($C_{1-6}$ alkyl), —N($C_{1-6}$ alkyl)$_2$, —CN, mercapto, $C_{1-6}$ alkyl, $C_{2-6}$ alkenyl, $C_{2-6}$ alkynyl, $C_{1-6}$ alkoxyl, $C_{1-6}$ haloalkyl, —($C_{1-6}$ alkyl)-OH, —($C_{1-6}$ alkyl)-O—($C_{1-6}$ alkyl), $C_{3-8}$ cycloalkyl, 3-8 membered heterocyclyl, phenyl, and heteroaryl, wherein each of said $C_{1-6}$ alkyl, $C_{1-6}$ alkoxyl, $C_{1-6}$ haloalkyl, $C_{3-8}$ cycloalkyl, 3-8 membered heterocyclyl, phenyl, and heteroaryl is optionally substituted with one or more deuterium;

$R_1$ is selected from hydrogen, $C_{1-6}$ alkyl optionally substituted with one or more deuterium, $C_{2-6}$ alkenyl, $C_{2-6}$ alkynyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-($C_{3-8}$ cycloalkyl), —($C_{1-6}$ alkyl)-(3-8 membered heterocyclyl), —($C_{1-6}$ alkyl)-phenyl, —($C_{1-6}$ alkyl)-heteroaryl, $C_{3-8}$ cycloalkyl, 3-8 membered heterocyclyl, phenyl, and heteroaryl, wherein each of said $C_{2-6}$ alkenyl, $C_{2-6}$ alkynyl, $C_{3-8}$ cycloalkyl, 3-8 membered heterocyclyl, phenyl, and heteroaryl is optionally substituted with one or more substituents independently selected from deuterium, halo, —CN, hydroxy, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{3-8}$ cycloalkyl, 3-8 membered heterocyclyl, phenyl, heteroaryl, $C_{1-6}$ alkyl optionally substituted with one or more deuterium, $C_{1-6}$ alkoxyl, and $C_{1-6}$ haloalkyl;

$R_2$ is selected from hydrogen, deuterium, halo, hydroxy, amino, —NH($C_{1-6}$ alkyl), —N($C_{1-6}$ alkyl)$_2$, —CN, mercapto, $C_{1-6}$ alkyl optionally substituted with one or more deuterium, $C_{2-6}$ alkenyl, $C_{2-6}$ alkynyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-($C_{3-8}$ cycloalkyl), —($C_{1-6}$ alkyl)-(3-8 membered heterocyclyl), —($C_{1-6}$ alkyl)-phenyl, —($C_{1-6}$ alkyl)-heteroaryl, $C_{3-8}$ cycloalkyl, 3-8 membered heterocyclyl, phenyl, and heteroaryl, wherein each of said $C_{2-6}$ alkenyl, $C_{2-6}$ alkynyl, $C_{3-8}$ cycloalkyl, 3-8 membered heterocyclyl, phenyl, and heteroaryl is optionally substituted with one or more substituents independently selected from deuterium, halo, —CN, hydroxy, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{1-6}$ alkyl, $C_{1-6}$ alkoxyl, $C_{1-6}$ haloalkyl, and oxo;

$R_a$ and $R_b$ are independently selected from hydrogen, deuterium, halo, hydroxy, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), —CN, mercapto, $C_{1-6}$ alkyl, $C_{1-6}$ alkoxyl, and $C_{1-6}$ haloalkyl; or $R_a$ and $R_b$ together with the carbon atom they are attached to form $C_{3-6}$ cycloalkyl or 3-6 membered heterocyclyl, wherein each of said $C_{3-6}$ cycloalkyl or 3-6 membered heterocyclyl is optionally substituted with one or more substituents independently selected from deuterium, halo, —CN, hydroxy, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{1-6}$ alkyl, $C_{1-6}$ alkoxyl, and $C_{1-6}$ haloalkyl;

------ is double bond or single bond, and when ------ is double bond, $R_3$ and $R_5$ are absent;

$R_3$, $R_4$, $R_5$, $R_6$, $R_7$, and $R_8$ are independently selected from hydrogen, deuterium, halo, hydroxy, —CN, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{1-6}$ alkyl, —($C_{1-6}$ alkyl)-phenyl, $C_{1-6}$ alkoxyl, and $C_{1-6}$ haloalkyl; or any two of $R_3$, $R_4$, $R_5$, $R_6$, $R_7$, and $R_8$ together with the carbon atom they are attached to and the B ring form a 8-13 membered spirocyclic, fused, or bridged ring optionally containing 1-3 ring heteroatoms independently selected from N, O, or S; wherein said spirocyclic, fused, or bridged ring is optionally substituted with one or more substituents independently selected from deuterium, halo, —CN, hydroxy, mercapto, amino, —NH($C_{1-6}$ alkyl), —N($C_{1-6}$ alkyl)$_2$, —($C_{1-6}$ alkyl)-OH, —($C_{1-6}$ alkyl)-O—($C_{1-6}$ alkyl), $C_{1-6}$ alkyl, $C_{1-6}$ alkoxyl, and $C_{1-6}$ haloalkyl; or $R_3$ and $R_4$ together, $R_5$ and $R_6$ together, or $R_7$ and $R_8$ together are oxo;

n is 0, 1, or 2; and m is 0, 1, 2, 3, 4, or 5.

2. The compound of formula (I) according to claim 1, or a pharmaceutically acceptable salt thereof, or a solvate, a racemic mixture, an enantiomer, a diastereomer, or a tautomer of the compound of formula (I) or a pharmaceutically acceptable salt thereof, wherein

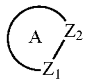

is selected from:

(Ia-1)

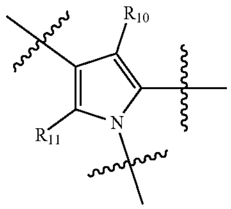

, (Ia-2)

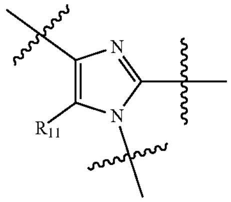

,

-continued
(Ia-3)
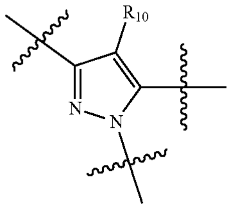
,
(Ia-4)
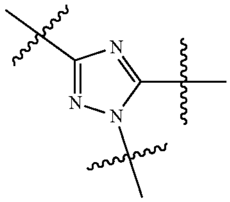
,
(Ia-5)
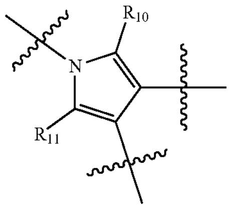
,
(Ia-6)
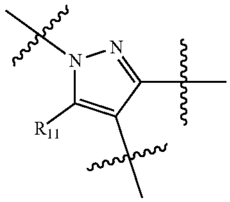
,
(Ia-7)
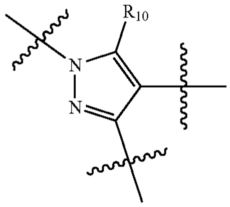
,
(Ia-8)
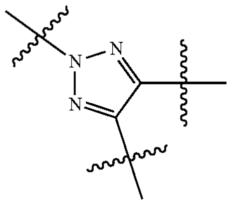
,
(Ia-9)
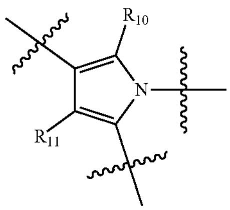
,
-continued
(Ia-10)
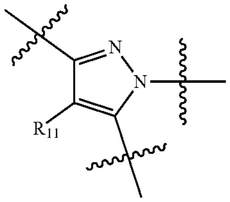
,
(Ia-11)
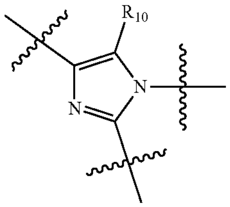
,
(Ia-12)
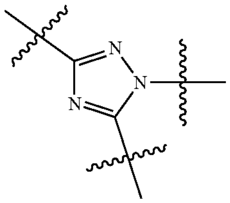
,
(Ia-13)
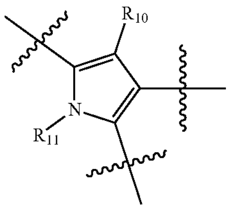
,
(Ia-14)
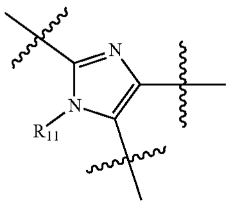
,
(Ia-15)
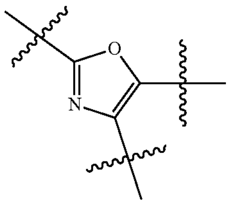
,
(Ia-16)
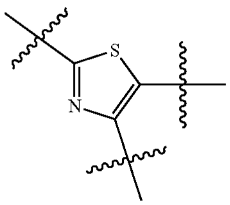
, -continued (Ia-17)

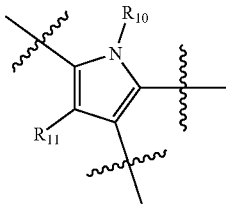

, (Ia-18)

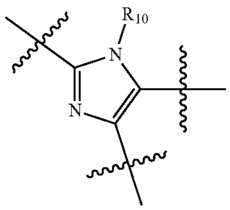

, (Ia-19)

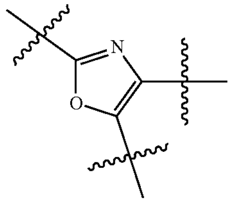

, and (Ia-20)

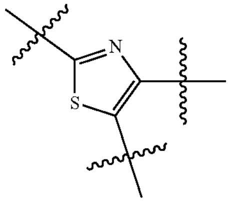

, wherein the wavy lines represent the attachment points of

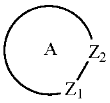

, and wherein $R_{10}$ and $R_{11}$ are independently selected from hydrogen, deuterium, halo, hydroxy, amino, —CN, mercapto, $C_{1-6}$ alkyl, $C_{1-6}$ alkoxyl, $C_{1-6}$ haloalkyl, —($C_{1-6}$ alkyl)-OH, and —($C_{1-6}$ alkyl)-O—($C_{1-6}$ alkyl), wherein each of said $C_{1-6}$ alkyl, $C_{1-6}$ alkoxyl, and $C_{1-6}$ haloalkyl is optionally substituted with one or more deuterium.

3. The compound of formula (I) according to claim 1, or a pharmaceutically acceptable salt thereof, or a solvate, a racemic mixture, an enantiomer, a diastereomer, or a tautomer of the compound of formula (I) or a pharmaceutically acceptable salt thereof, wherein

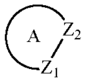

is selected from:

(Ia-1)

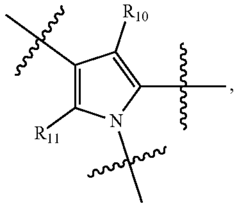

, (Ia-2)

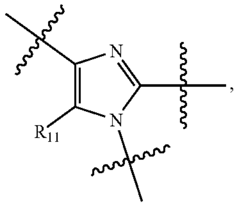

, (Ia-3)

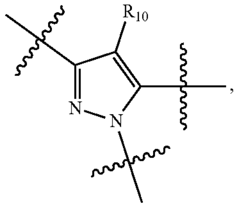

, (Ia-4)

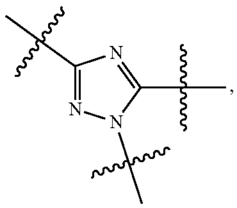

, (Ia-5)

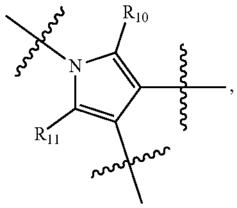

, (Ia-6)

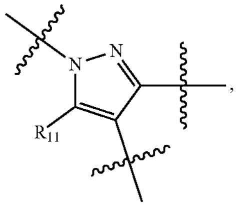

, (Ia-7)

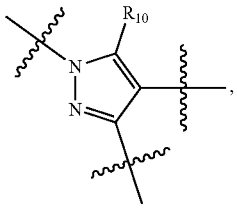

,

-continued (Ia-9)

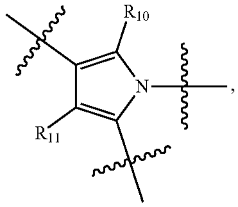, (Ia-10)

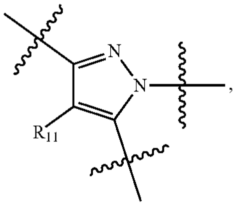, (Ia-13)

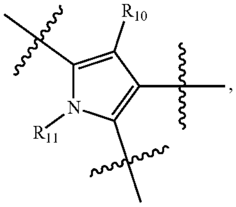, (Ia-14)

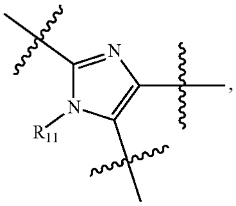, (Ia-15)

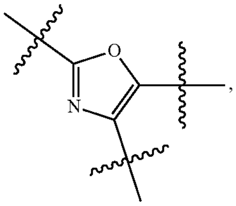, (Ia-16)

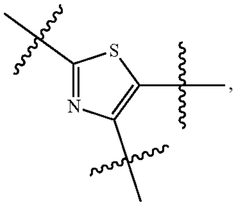, (Ia-17)

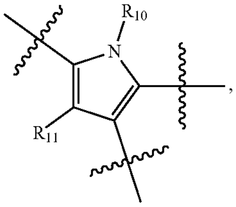,

-continued (Ia-19)

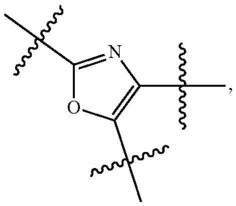, and (Ia-20)

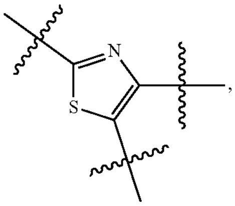, wherein the wavy lines represent the attachment points of Z

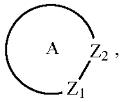, and wherein $R_{10}$ and $R_{11}$ are independently selected from hydrogen, halo, —CN, $C_{1-6}$ alkyl, $C_{1-6}$ alkoxyl, and $C_{1-6}$ haloalkyl.

4. The compound of formula (I) according to claim 3, or a pharmaceutically acceptable salt thereof, or a solvate, a racemic mixture, an enantiomer, a diastereomer, or a tautomer of the compound of formula (I) or a pharmaceutically acceptable salt thereof, wherein

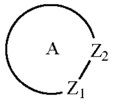

is (Ia-1)

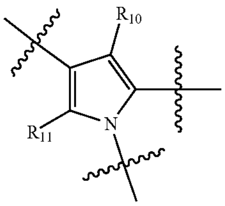, and $R_{10}$ and $R_{11}$ are independently selected from hydrogen, halo, and $C_{1-6}$ alkyl, and wherein the wavy lines represent the attachment points of

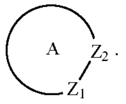

5. The compound of formula (I) according to claim 1, or a pharmaceutically acceptable salt thereof, or a solvate, a racemic mixture, an enantiomer, a diastereomer, or a tautomer of the compound of formula (I) or a pharmaceutically acceptable salt thereof, wherein Ar is a monocyclic heteroaryl having 5 or 6 ring atoms with 1, 2 or 3 of the ring atoms being ring heteroatoms independently selected from N, O, and S, and the remaining ring atoms being carbon; each of which is optionally substituted with one or more substituents independently selected from deuterium, halo, hydroxy, amino, —CN, mercapto, $C_{1-6}$ alkyl, $C_{1-6}$ alkoxyl, $C_{1-6}$ haloalkyl, —($C_{1-6}$ alkyl)-OH, —($C_{1-6}$ alkyl)-O—($C_{1-6}$ alkyl), $C_{3-8}$ cycloalkyl, 3-8 membered heterocyclyl, phenyl, and heteroaryl, wherein each of said $C_{1-6}$ alkyl, $C_{1-6}$ alkoxyl, $C_{1-6}$ haloalkyl, $C_{3-8}$ cycloalkyl, 3-8 membered heterocyclyl, phenyl, and heteroaryl is optionally substituted with one or more deuterium.

6. The compound of formula (I) according to claim 5, or a pharmaceutically acceptable salt thereof, or a solvate, a racemic mixture, an enantiomer, a diastereomer, or a tautomer of the compound of formula (I) or a pharmaceutically acceptable salt thereof, wherein Ar is selected from pyridyl, pyrimidinyl, pyridazinyl, pyrazinyl, 1,3,5-triazinyl, 1,2,4-triazolyl, and thiazolyl, each of which is optionally substituted with one or more substituents independently selected from halo, —CN, $C_{1-6}$ alkyl optionally substituted with one or more deuterium, $C_{1-6}$ alkoxyl, and $C_{1-6}$ haloalkyl.

7. The compound of formula (I) according to claim 6, or a pharmaceutically acceptable salt thereof, a solvate, a racemic mixture, an enantiomer, a diastereomer, or a tautomer of the compound of formula (I) or a pharmaceutically acceptable salt thereof, wherein Ar is (Ib-1)

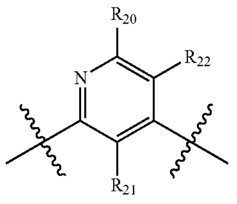

or (Ib-2)

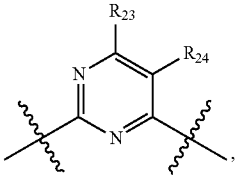

, wherein the wavy lines represent the attachment points of Ar, and wherein $R_{20}$, $R_{21}$, $R_{22}$, $R_{23}$, and $R_{24}$ are independently selected from hydrogen, halo, —CN, $C_{1-6}$ alkyl optionally substituted with one or more deuterium, $C_{1-6}$ alkoxyl, and $C_{1-6}$ haloalkyl.

8. The compound of formula (I) according to claim 1, or a pharmaceutically acceptable salt thereof, or a solvate, a racemic mixture, an enantiomer, a diastereomer, or a tautomer of the compound of formula (I) or a pharmaceutically acceptable salt thereof, wherein $R_1$ is selected from $C_{1-6}$ alkyl, —($C_{1-6}$ alkyl)-OH, saturated monocyclic $C_{3-8}$ cycloalkyl, saturated monocyclic 3-8 membered heterocyclyl containing 1 or 2 ring heteroatoms independently selected from N, O and S, and heteroaryl, wherein said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another, and wherein each of said $C_{3-8}$ cycloalkyl, 3-8 membered heterocyclyl, and heteroaryl is optionally substituted with one or more substituents independently selected from halo, ($C_{1-6}$ alkyl)-OH, —($C_{1-6}$ alkyl)-O—($C_{1-6}$ alkyl), 3-6 membered heterocyclyl, $C_{1-6}$ alkyl optionally substituted with one or more deuterium, $C_{1-6}$ alkoxyl, or $C_{1-6}$ haloalkyl.

9. The compound of formula (I) according to claim 8, or a pharmaceutically acceptable salt thereof, or a solvate, a racemic mixture, an enantiomer, a diastereomer, or a tautomer of the compound of formula (I) or a pharmaceutically acceptable salt thereof, wherein $R_1$ is a heteroaryl selected from pyrazolyl, pyridyl, isoxazolyl, 1,2,4-triazolyl, 1,3,4-thiadiazolyl, 2,4,5,6-tetrahydrocyclopentadieno[c]pyrazolyl, and 5,6,7,8-tetrahydro[1,2,4]triazolo[1,5-a]pyridyl, wherein said heteroaryl is each optionally substituted with one or more substituents independently selected from $C_{1-6}$ alkyl optionally substituted with one or more deuterium, $C_{1-6}$ haloalkyl, $C_{1-6}$ alkoxyl, halo, —($C_{1-6}$ alkyl)-OH, —($C_{1-6}$ alkyl)-O—($C_{1-6}$ alkyl), and 3-6 membered heterocyclyl.

10. The compound of formula (I) according to claim 9, or a pharmaceutically acceptable salt thereof, or a solvate, a racemic mixture, an enantiomer, a diastereomer, or a tautomer of the compound of formula (I) or a pharmaceutically acceptable salt thereof, wherein $R_1$ is pyrazolyl, which is optionally substituted with one or more substituents independently selected from $C_{1-6}$ alkyl optionally substituted with one or more deuterium, $C_{1-6}$ haloalkyl, $C_{1-6}$ alkoxyl, halo, —($C_{1-6}$ alkyl)-OH, —($C_{1-6}$ alkyl)-O—($C_{1-6}$ alkyl), and oxetanyl.

11. The compound of formula (I) according to claim 1, or a pharmaceutically acceptable salt thereof, or a solvate, a racemic mixture, an enantiomer, a diastereomer, or a tautomer of the compound of formula (I) or a pharmaceutically acceptable salt thereof, wherein $R_2$ is selected from halo, —CN, $C_{1-6}$ alkyl, $C_{1-6}$ haloalkyl, saturated monocyclic $C_{3-8}$ cycloalkyl, phenyl, and heteroaryl, wherein said heteroaryl is a monocyclic aromatic hydrocarbon radical having 5 or 6 ring atoms with 1, 2 or 3 of the ring atoms being ring heteroatoms independently selected from N, O, and S, and the remaining ring atoms being carbon, or a bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another, and wherein each of said $C_{3-8}$ cycloalkyl, phenyl, and heteroaryl is optionally substituted with one or more substituents independently selected from halo, —CN, $C_{1-6}$ alkyl, $C_{1-6}$ alkoxyl, $C_{1-6}$ haloalkyl, and oxo.

12. The compound of formula (I) according to claim 11, or a pharmaceutically acceptable salt thereof, or a solvate, a racemic mixture, an enantiomer, a diastereomer, or a tautomer of the compound of formula (I) or a pharmaceutically acceptable salt thereof, wherein $R_2$ is phenyl, wherein said phenyl is optionally substituted with one or more substituents independently selected from halo, —CN, and $C_{1-6}$ alkoxyl.

13. The compound of formula (I) according to claim 11, or a pharmaceutically acceptable salt thereof, or a solvate, a racemic mixture, an enantiomer, a diastereomer, or a tautomer of the compound of formula (I) or a pharmaceutically acceptable salt thereof, wherein $R_2$ is a heteroaryl selected from 1,2,5-oxadiazolyl, indolyl, indolinyl, quinolinyl, isoquinolinyl, tetrahydroquinolinyl, tetrahydroisoquinolinyl, pyrazolyl, oxazolyl, isoxazolyl, pyridyl, thiazolyl, isothiazolyl, benzo[d]isoxazolyl, thienyl, indazolyl, and pyrrolyl, each of which is optionally substituted with one or more substituents independently selected from $C_{1-6}$ alkyl, halo, oxo, and —CN.

14. The compound of formula (I) according to claim 11, or a pharmaceutically acceptable salt thereof, or a solvate, a racemic mixture, an enantiomer, a diastereomer, or a tautomer of the compound of formula (I) or a pharmaceutically acceptable salt thereof, wherein $R_2$ is a saturated monocyclic $C_{3-8}$ cycloalkyl optionally substituted with one or more substituents independently selected from $C_{1-6}$ haloalkyl.

15. The compound of formula (I) according to claim 1, or a pharmaceutically acceptable salt thereof, or a solvate, a racemic mixture, an enantiomer, a diastereomer, or a tautomer of the compound of formula (I) or a pharmaceutically acceptable salt thereof, wherein m is 0, 1, or 2.

16. The compound of formula (I) according to claim 1, or a pharmaceutically acceptable salt thereof, or a solvate, a racemic mixture, an enantiomer, a diastereomer, or a tautomer of the compound of formula (I) or a pharmaceutically acceptable salt thereof, wherein $R_a$ and $R_b$ are independently selected from hydrogen, halo, hydroxy, and $C_{1-6}$ alkyl; or $R_a$ and $R_b$ together with the carbon atom they are attached to form a saturated monocyclic $C_{3-6}$ cycloalkyl or a 3-6 membered heterocyclyl, wherein said 3-6 membered heterocyclyl is a saturated monocyclic ring having 3-6 ring atoms with 1 or 2 of the ring atoms being ring heteroatoms independently selected from N, O and S, and the remaining ring atoms being carbon; wherein each of said saturated monocyclic $C_{3-6}$ cycloalkyl or 3-6 membered heterocyclyl is optionally substituted with one or more substituents selected from halo.

17. The compound of formula (I) according to claim 1, or a pharmaceutically acceptable salt thereof, or a solvate, a racemic mixture, an enantiomer, a diastereomer, or a tautomer of the compound of formula (I) or a pharmaceutically acceptable salt thereof, wherein L is absent, or L is NH, O or S.

18. The compound of formula (I) according to claim 1, or a pharmaceutically acceptable salt thereof, wherein the compound of formula (I) is selected from:

| Compound No. | Structure |
|---|---|
| 1 | 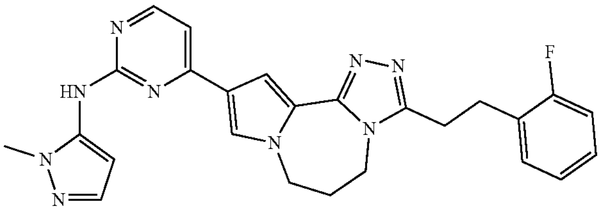, |
| 2 | 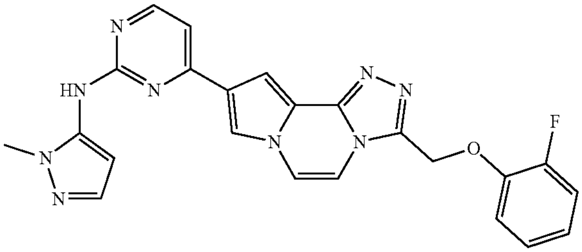, |
| 3 | 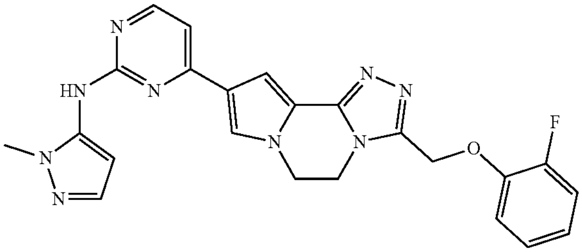, |

-continued
| Compound No. | Structure |
| --- | --- |
| 4 | 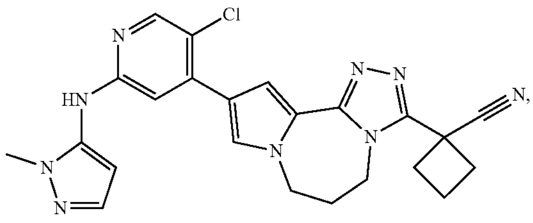 [SMILES: Cn1nccc1Nc1cc(-c2cc3n(c2)CCCn2c-3nnc2C2(C#N)CCC2)c(Cl)cn1], |
| 5 | 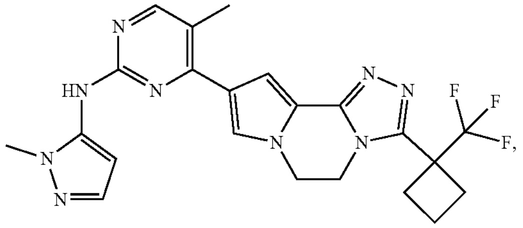 [SMILES: Cc1cnc(Nc2ccnn2C)nc1-c1cc2n(c1)CCn1c-2nnc1C1(C(F)(F)F)CCC1], |
| 6 | 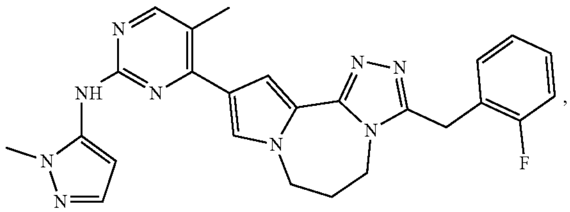 [SMILES: Cc1cnc(Nc2ccnn2C)nc1-c1cc2n(c1)CCCn1c(Cc3ccccc3F)nnc1-2], |
| 7 | 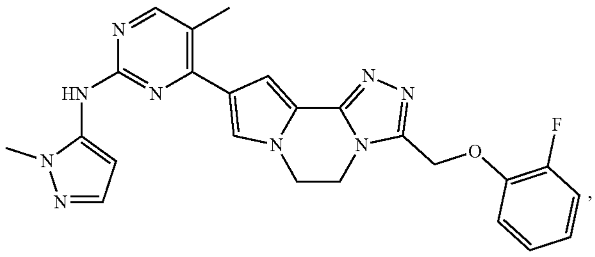 [SMILES: Cc1cnc(Nc2ccnn2C)nc1-c1cc2n(c1)CCn1c(COc3ccccc3F)nnc1-2], |
| 8 | 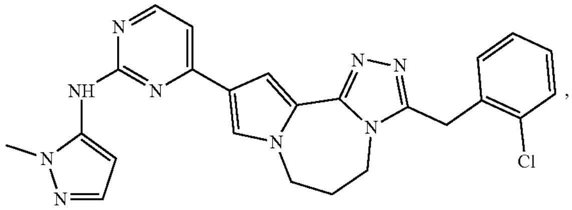 [SMILES: Cn1nccc1Nc1nccc(-c2cc3n(c2)CCCn2c(Cc4ccccc4Cl)nnc2-3)n1], |
| 9 | 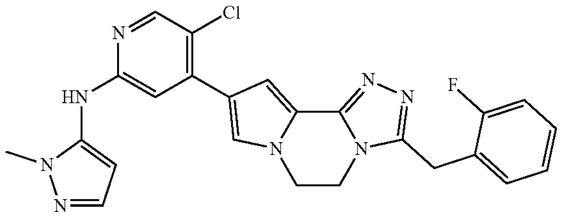, |

-continued
| Compound No. | Structure |
|---|---|
| 10 | 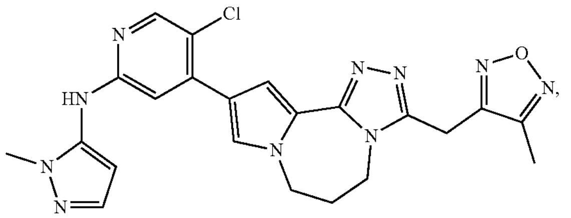 [SMILES: Cc1nonc1Cc1nnc2n1CCCn1cc(-c3cc(Nc4ccnn4C)ncc3Cl)cc1-2] |
| 11 | 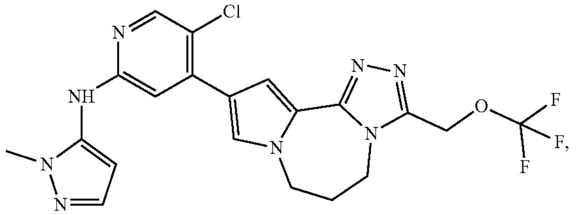 [SMILES: Cn1nccc1Nc1cc(-c2cc3n(c2)CCCn2c(COC(F)(F)F)nnc2-3)c(Cl)cn1] |
| 12 | 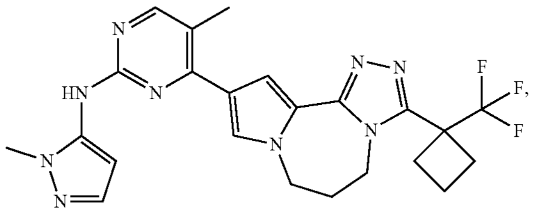 [SMILES: Cc1cnc(Nc2ccnn2C)nc1-c1cc2n(c1)CCCn1c-2nnc1C1(C(F)(F)F)CCC1] |
| 13 | 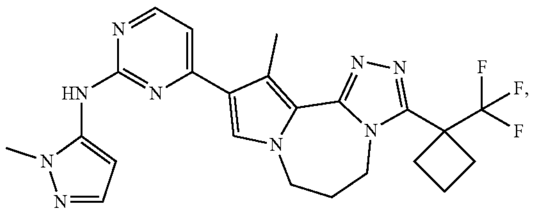 [SMILES: Cc1c(-c2ccnc(Nc3ccnn3C)n2)cn2c1-c1nnc(C3(C(F)(F)F)CCC3)n1CCC2] |
| 14 | 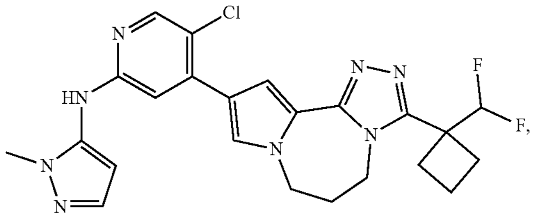 [SMILES: Cn1nccc1Nc1cc(-c2cc3n(c2)CCCn2c-3nnc2C2(C(F)F)CCC2)c(Cl)cn1] |
| 15 | 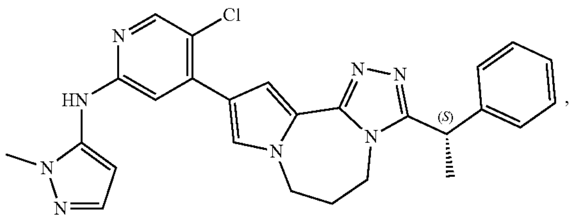 |
| 16 | 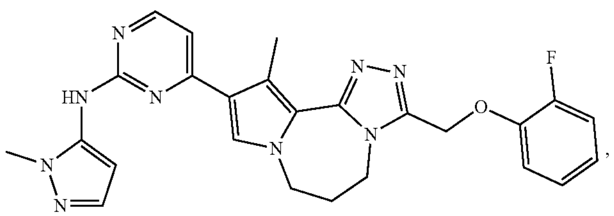 [SMILES: Cc1c(-c2ccnc(Nc3ccnn3C)n2)cn2c1-c1nnc(COc3ccccc3F)n1CCC2] |

-continued
| Compound No. | Structure |
|---|---|
| 17 | 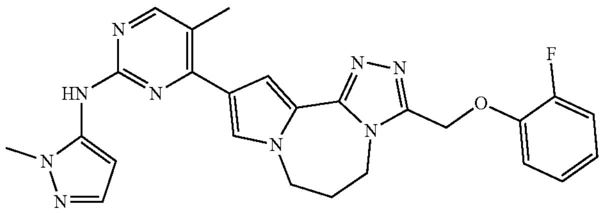, |
| 18 | 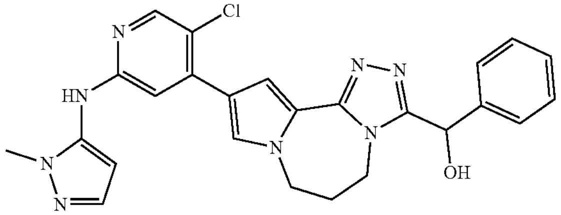, |
| 19 | 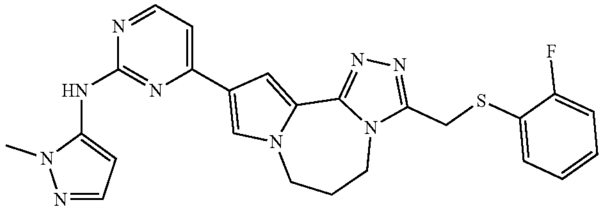, |
| 20 | 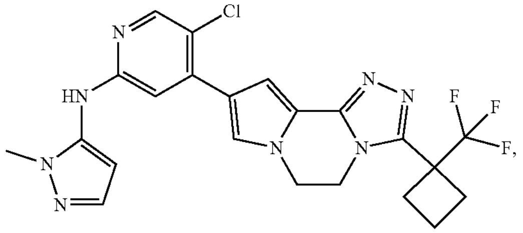 [SMILES: Cn1nccc1Nc1cc(-c2cc3n(c2)CCn2c-3nnc2C2(C(F)(F)F)CCC2)c(Cl)cn1] |
| 21 | 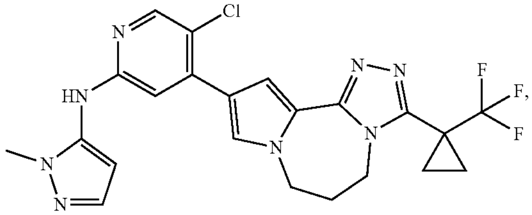 [SMILES: Cn1nccc1Nc1cc(-c2cc3n(c2)CCCn2c-3nnc2C2(C(F)(F)F)CC2)c(Cl)cn1] |
| 22 | 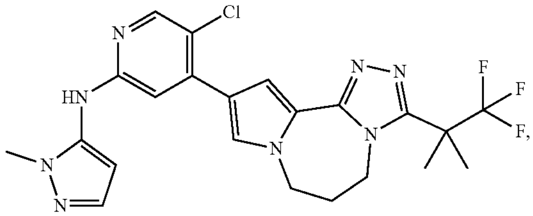 [SMILES: Cn1nccc1Nc1cc(-c2cc3n(c2)CCCn2c-3nnc2C(C)(C)C(F)(F)F)c(Cl)cn1] |

-continued
| Compound No. | Structure |
|---|---|
| 23 | 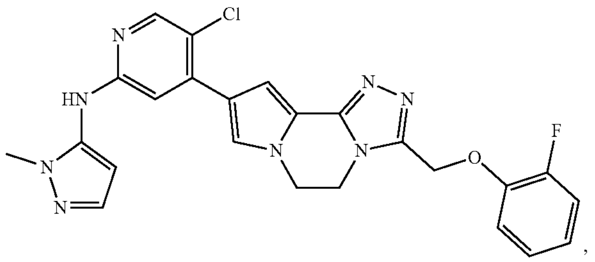 [SMILES: Cn1nccc1Nc1cc(-c2cc3n(c2)CCn2c(COc4ccccc4F)nnc2-3)c(Cl)cn1] |
| 24 | 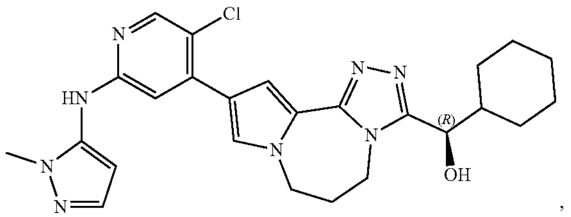 |
| 25 | 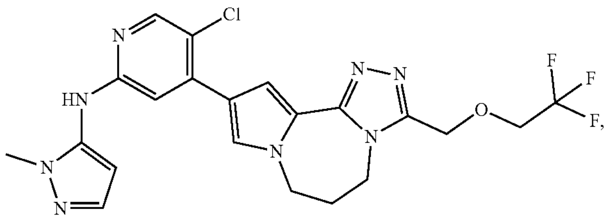 [SMILES: Cn1nccc1Nc1cc(-c2cc3n(c2)CCCn2c(COCC(F)(F)F)nnc2-3)c(Cl)cn1] |
| 26 | 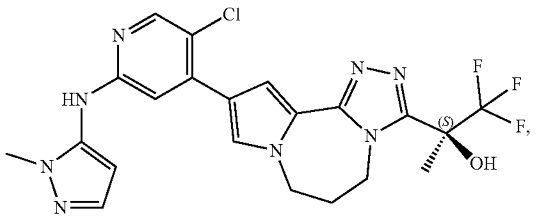 |
| 27 | 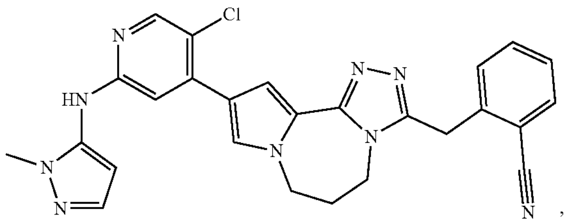 [SMILES: Cn1nccc1Nc1cc(-c2cc3n(c2)CCCn2c(Cc4ccccc4C#N)nnc2-3)c(Cl)cn1] |
| 28 | 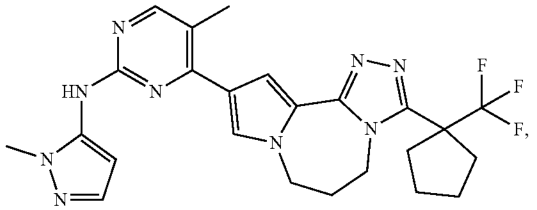 [SMILES: Cc1cnc(Nc2ccnn2C)nc1-c1cc2n(c1)CCCn1c-2nnc1C1(C(F)(F)F)CCCC1] |
| 29 | 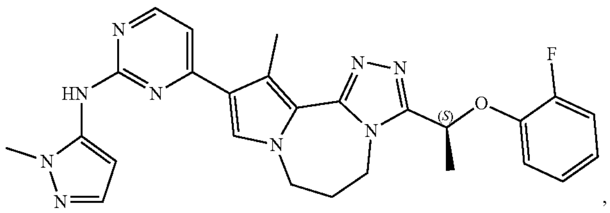 |

-continued
| Compound No. | Structure |
|---|---|
| 30 | 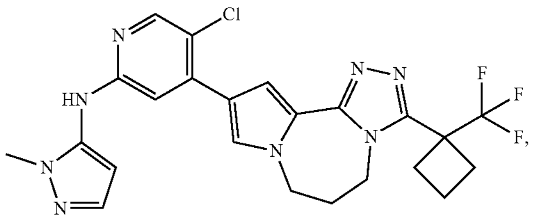 [SMILES: Cn1nccc1Nc1cc(-c2cc3n(c2)CCCn2c-3nnc2C2(C(F)(F)F)CCC2)c(Cl)cn1] |
| 31 | 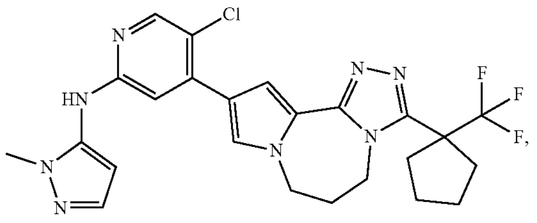 [SMILES: Cn1nccc1Nc1cc(-c2cc3n(c2)CCCn2c-3nnc2C2(C(F)(F)F)CCCC2)c(Cl)cn1] |
| 32 | 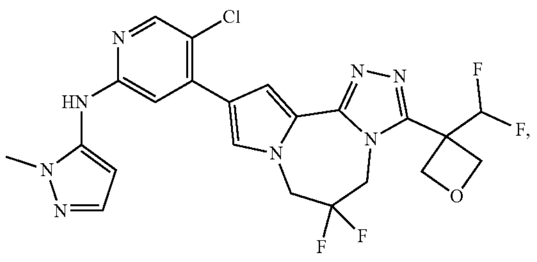 [SMILES: Cn1nccc1Nc1cc(-c2cc3n(c2)CC(F)(F)Cn2c-3nnc2C2(C(F)F)COC2)c(Cl)cn1] |
| 33 | 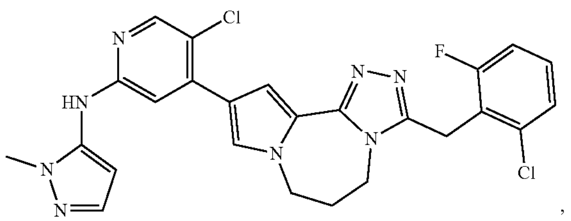 [SMILES: Cn1nccc1Nc1cc(-c2cc3n(c2)CCCn2c(Cc4c(F)cccc4Cl)nnc2-3)c(Cl)cn1] |
| 34 | 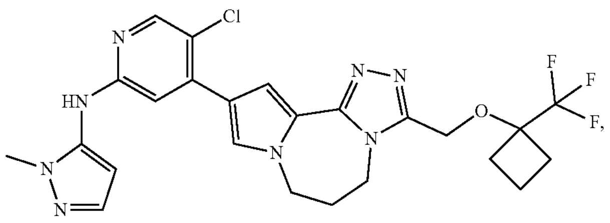 |
| 35 | 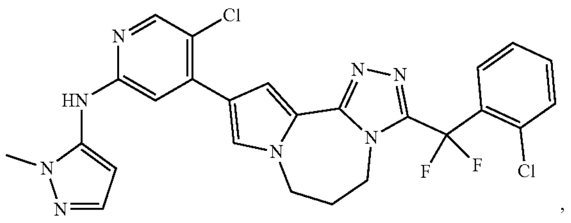 [SMILES: Cn1nccc1Nc1cc(-c2cc3n(c2)CCCn2c-3nnc2C(F)(F)c2ccccc2Cl)c(Cl)cn1] |

-continued
| Compound No. | Structure |
| --- | --- |
| 36 | 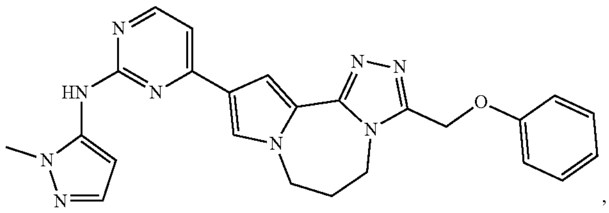 [SMILES: Cn1nccc1Nc1nccc(-c2cc3n(c2)CCCn2c(COc4ccccc4)nnc2-3)n1] , |
| 37 | 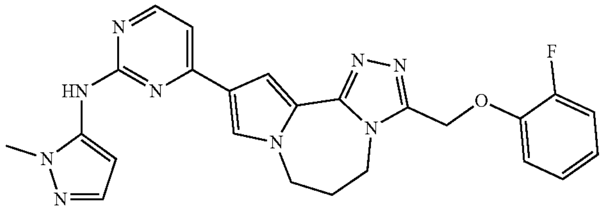 , |
| 38 | 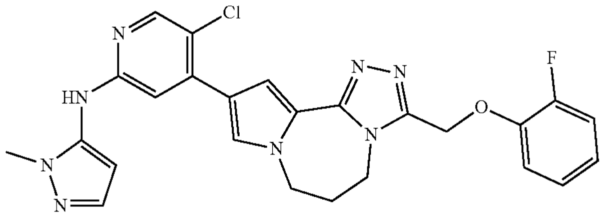 , |
| 39 | 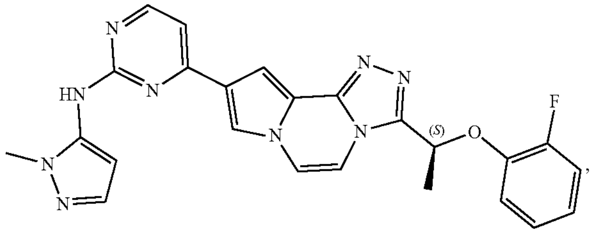 , |
| 40 | 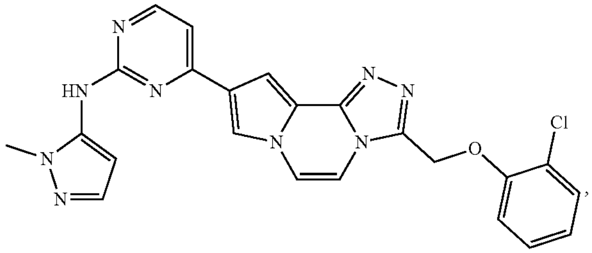 [SMILES: Cn1nccc1Nc1nccc(-c2cc3c4nnc(COc5ccccc5Cl)n4ccn3c2)n1] , |
| 41 | 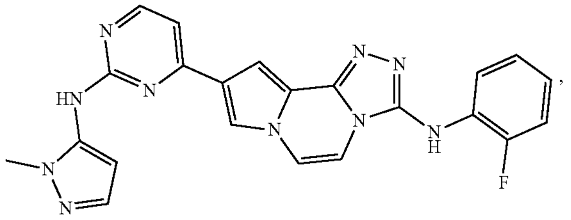 [SMILES: Cn1nccc1Nc1nccc(-c2cc3c4nnc(Nc5ccccc5F)n4ccn3c2)n1] , |

-continued
| Compound No. | Structure |
| --- | --- |
| 42 | 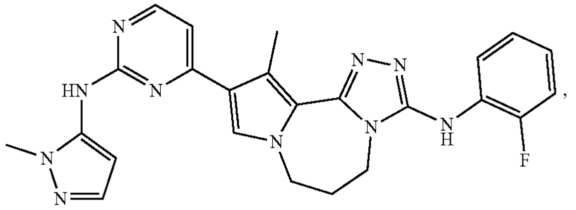 [SMILES: Cc1c(-c2ccnc(Nc3ccnn3C)n2)cn2c1-c1nnc(Nc3ccccc3F)n1CCC2] |
| 43 | 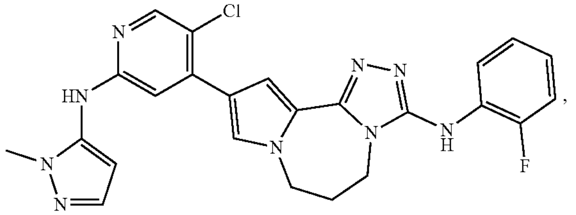 [SMILES: Cn1nccc1Nc1cc(-c2cc3n(c2)CCCn2c(Nc4ccccc4F)nnc2-3)c(Cl)cn1] |
| 44 | 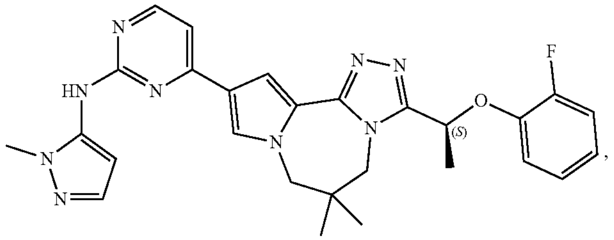 |
| 45 | 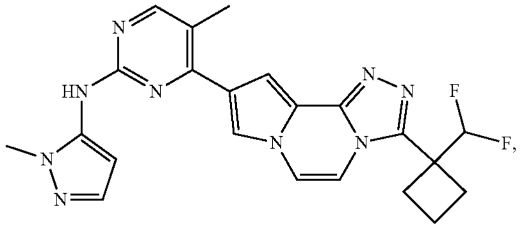 [SMILES: Cc1cnc(Nc2ccnn2C)nc1-c1cc2c3nnc(C4(C(F)F)CCC4)n3ccn2c1] |
| 46 | 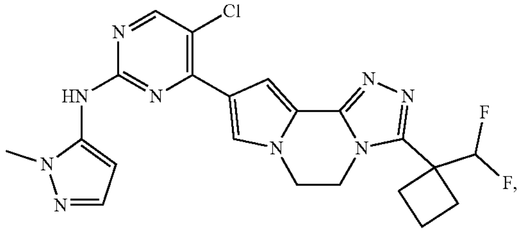 [SMILES: Cn1nccc1Nc1ncc(Cl)c(-c2cc3n(c2)CCn2c-3nnc2C2(C(F)F)CCC2)n1] |
| 47 | 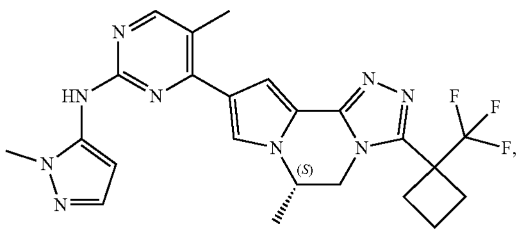 |

-continued
| Compound No. | Structure |
|---|---|
| 48 | 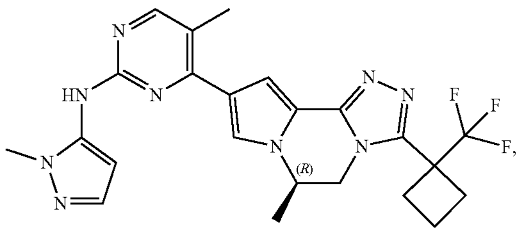 |
| 49 | 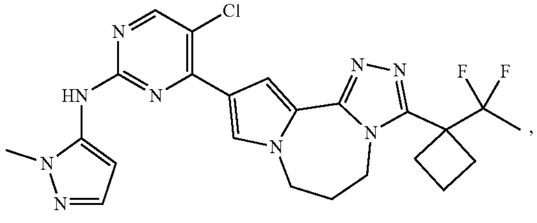 [SMILES: Cn1nccc1Nc1ncc(Cl)c(-c2cc3n(c2)CCCn2c-3nnc2C2(C(C)(F)F)CCC2)n1] |
| 50 | 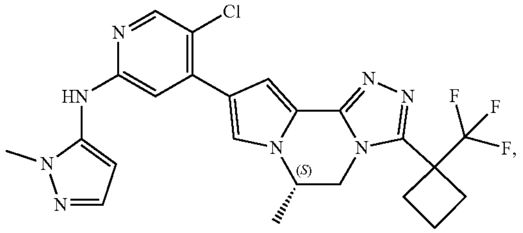 |
| 51 | 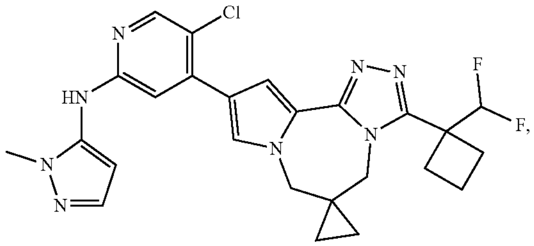 [SMILES: Cn1nccc1Nc1cc(-c2cc3n(c2)CC2(CC2)Cn2c-3nnc2C2(C(F)F)CCC2)c(Cl)cn1] |
| 52 | 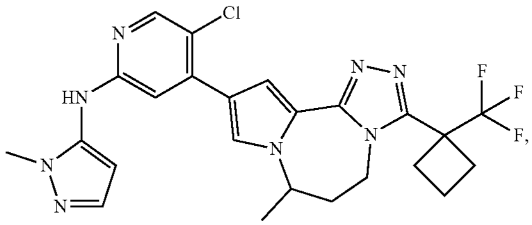 [SMILES: CC1CCn2c(nnc2C2(C(F)(F)F)CCC2)-c2cc(-c3cc(Nc4ccnn4C)ncc3Cl)cn21] |
| 53 | 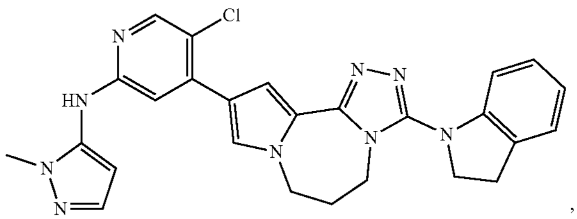 [SMILES: Cn1nccc1Nc1cc(-c2cc3n(c2)CCCn2c-3nnc2N2CCc3ccccc32)c(Cl)cn1] |

-continued
| Compound No. | Structure |
|---|---|
| 54 | 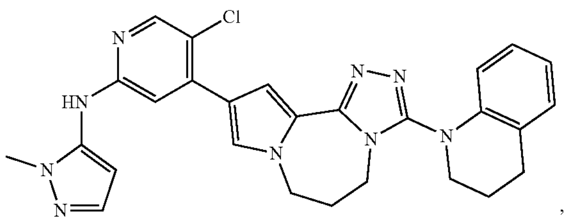 [SMILES: Cn1nccc1Nc1cc(-c2cc3n(c2)CCCn2c-3nnc2N2CCCc3ccccc32)c(Cl)cn1], |
| 55 | 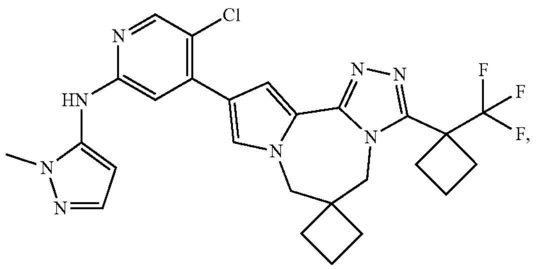 [SMILES: Cn1nccc1Nc1cc(-c2cc3n(c2)CC2(CCC2)Cn2c-3nnc2C2(C(F)(F)F)CCC2)c(Cl)cn1] |
| 56 | 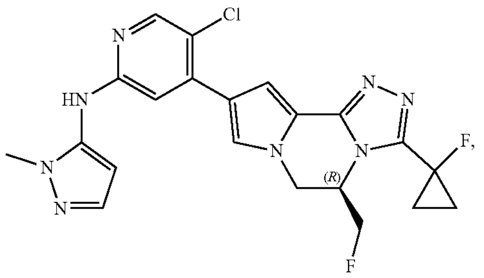 |
| 57 | 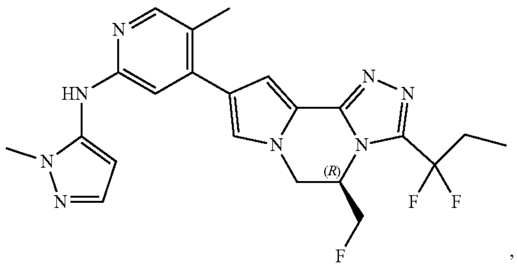, |
| 58 | 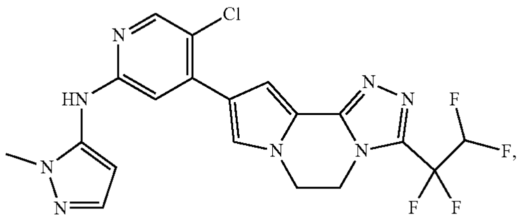 [SMILES: Cn1nccc1Nc1cc(-c2cc3n(c2)CCn2c-3nnc2C(F)(F)C(F)F)c(Cl)cn1] |
| 59 | 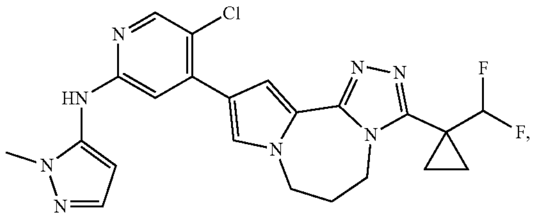 [SMILES: Cn1nccc1Nc1cc(-c2cc3n(c2)CCCn2c-3nnc2C2(C(F)F)CC2)c(Cl)cn1] |

-continued
| Compound No. | Structure |
|---|---|
| 60 | 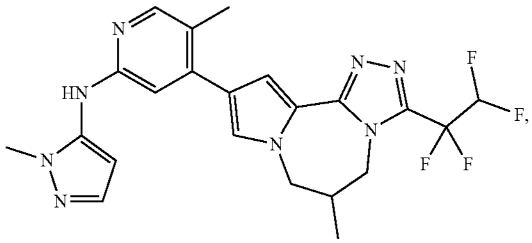 [SMILES: Cc1cnc(Nc2ccnn2C)cc1-c1cc2n(c1)CC(C)Cn1c-2nnc1C(F)(F)C(F)F] |
| 61 | 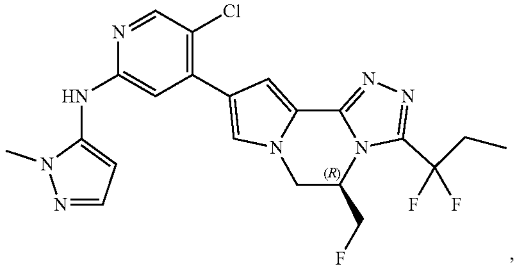 , |
| 62 | 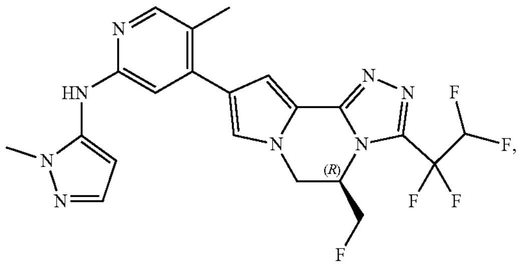 |
| 63 | 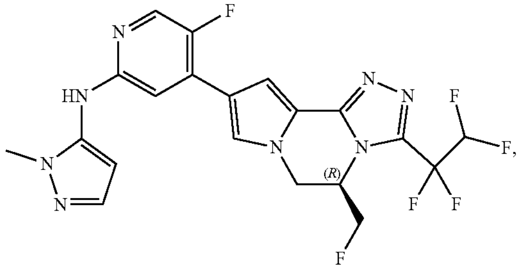 |
| 64 | 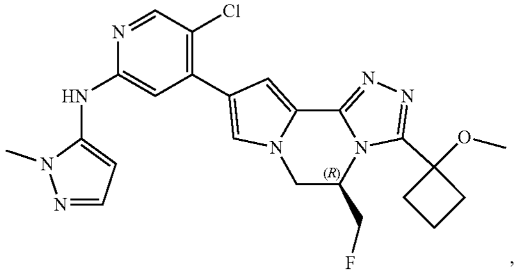 , |
| 65 | 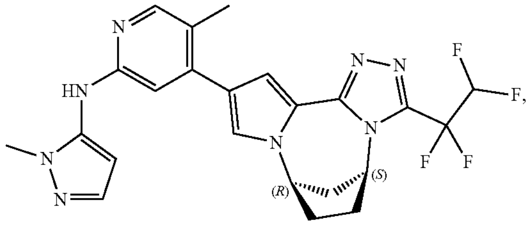 |

-continued
| Compound No. | Structure |
|---|---|
| 66 | 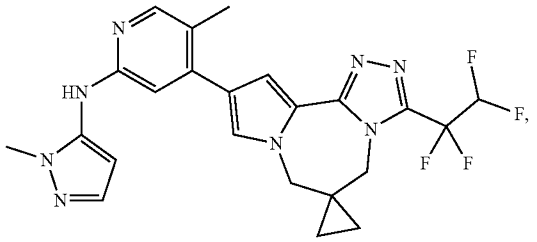 [SMILES: Cc1cnc(Nc2ccnn2C)cc1-c1cc2n(c1)CC1(CC1)Cn1c-2nnc1C(F)(F)C(F)F] |
| 67 | 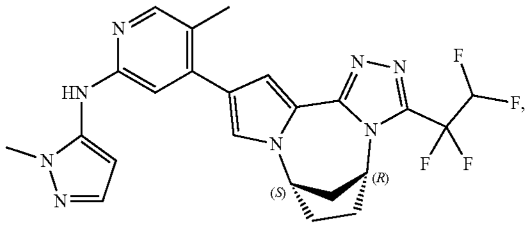 |
| 68 | 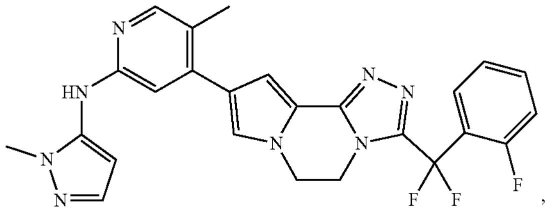 [SMILES: Cc1cnc(Nc2ccnn2C)cc1-c1cc2n(c1)CCn1c-2nnc1C(F)(F)c1ccccc1F] |
| 69 | 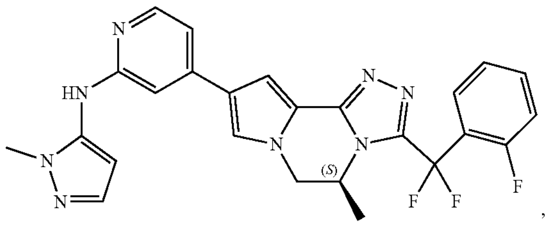 |
| 70 | 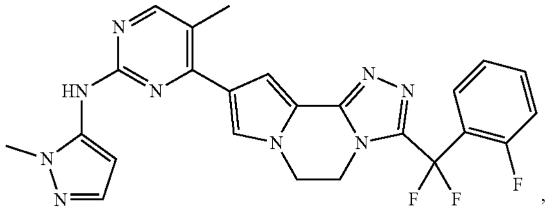 [SMILES: Cc1cnc(Nc2ccnn2C)nc1-c1cc2n(c1)CCn1c-2nnc1C(F)(F)c1ccccc1F] |
| 71 | 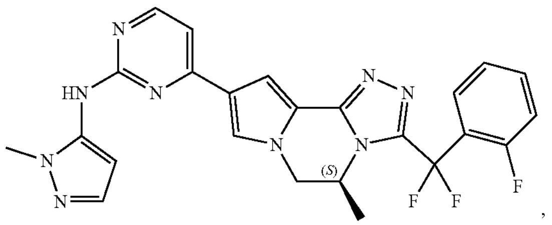 |

-continued
| Compound No. | Structure |
|---|---|
| 72 | 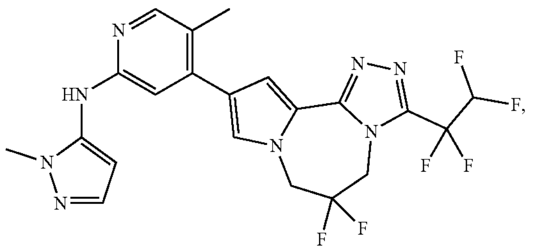 [SMILES: Cc1cnc(Nc2ccnn2C)cc1-c1cc2n(c1)CC(F)(F)Cn1c-2nnc1C(F)(F)C(F)F] |
| 73 | 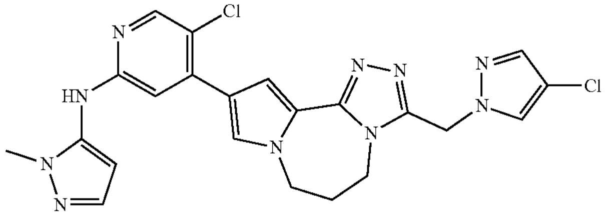 [SMILES: Cn1nccc1Nc1cc(-c2cc3n(c2)CCCn2c(Cn4cc(Cl)cn4)nnc2-3)c(Cl)cn1] |
| 74 | 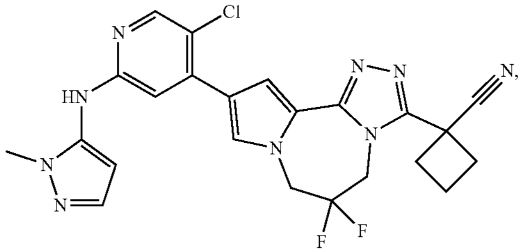 [SMILES: Cn1nccc1Nc1cc(-c2cc3n(c2)CC(F)(F)Cn2c-3nnc2C2(C#N)CCC2)c(Cl)cn1] |
| 75 | 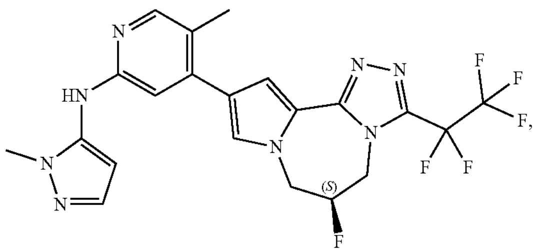 |
| 76 | 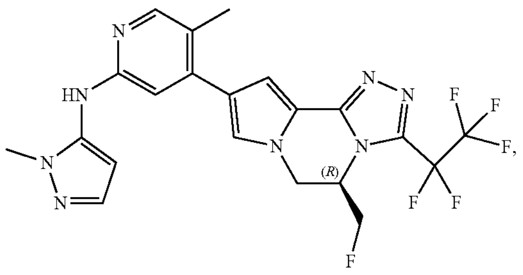 |
| 77 | 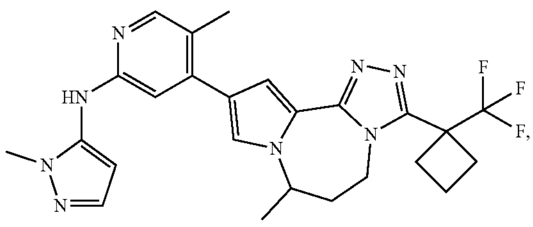 [SMILES: Cc1cnc(Nc2ccnn2C)cc1-c1cc2n(c1)C(C)CCn1c-2nnc1C1(C(F)(F)F)CCC1] |

-continued
| Compound No. | Structure |
|---|---|
| 78 | 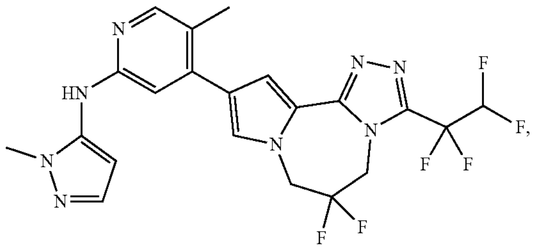 [SMILES: Cc1cnc(Nc2ccnn2C)cc1-c1cc2n(c1)CC(F)(F)Cn1c-2nnc1C(F)(F)C(F)F] |
| 79 | 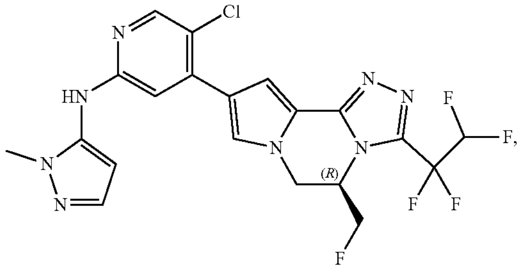 |
| 80 | 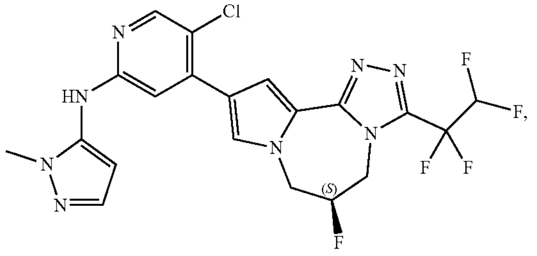 |
| 81 | 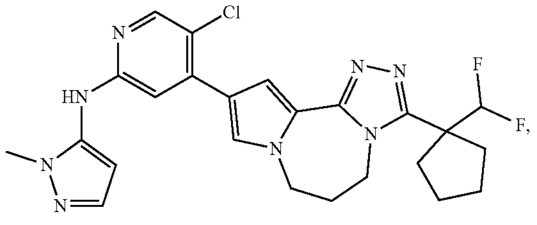 [SMILES: Cn1nccc1Nc1cc(-c2cc3n(c2)CCCn2c-3nnc2C2(C(F)F)CCCC2)c(Cl)cn1] |
| 82 | 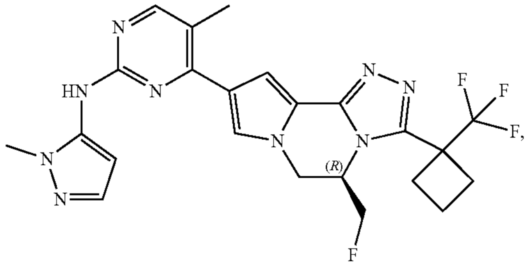 |
| 83 | 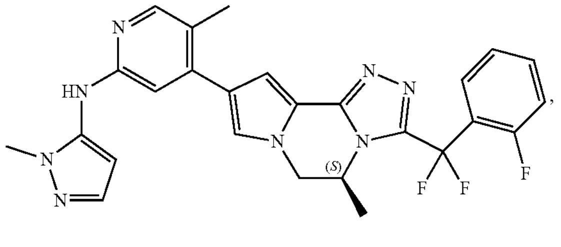 |

-continued
| Compound No. | Structure |
|---|---|
| 84 | 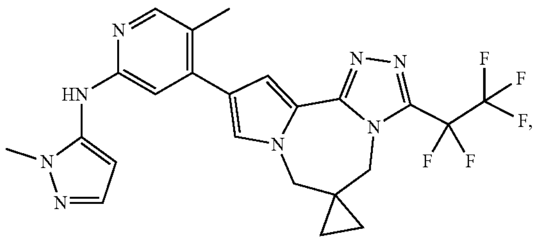 [SMILES: Cc1cnc(Nc2ccnn2C)cc1-c1cc2n(c1)CC1(CC1)Cn1c-2nnc1C(F)(F)C(F)(F)F] |
| 85 | 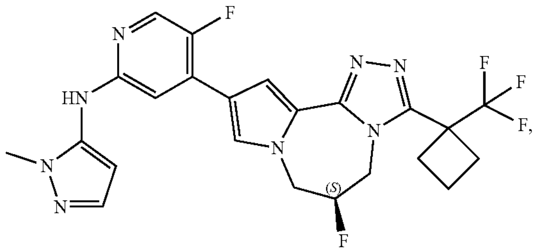 |
| 86 | 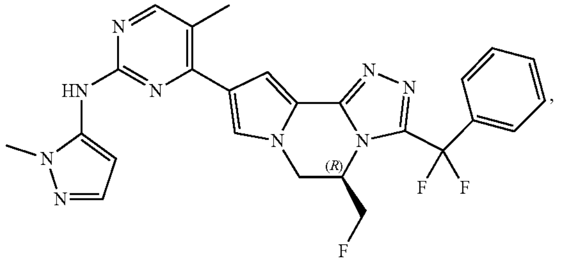 |
| 87 | 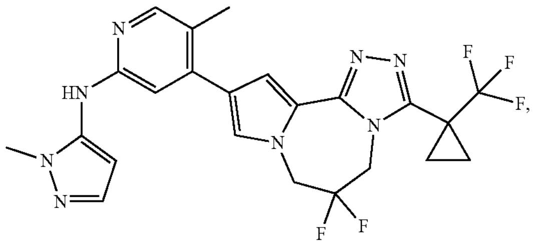 [SMILES: Cc1cnc(Nc2ccnn2C)cc1-c1cc2n(c1)CC(F)(F)Cn1c-2nnc1C1(C(F)(F)F)CC1] |
| 88 | 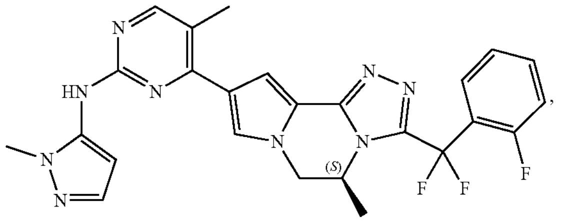 |
| 89 | 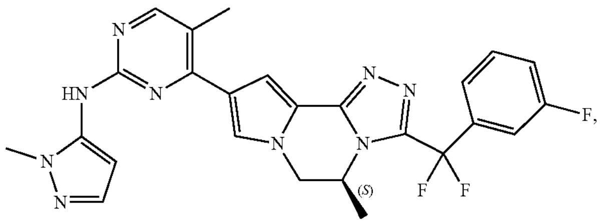 |

-continued
| Compound No. | Structure |
| --- | --- |
| 90 | 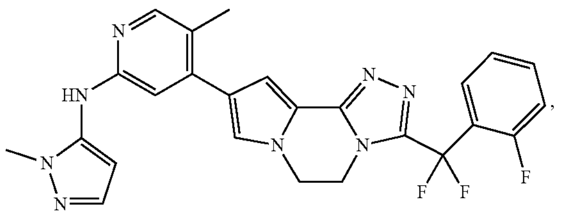 [SMILES: Cc1cnc(Nc2ccnn2C)cc1-c1cc2n(c1)CCn1c-2nnc1C(F)(F)c1ccccc1F] |
| 91 | 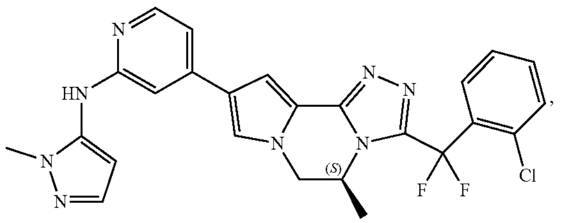 |
| 92 | 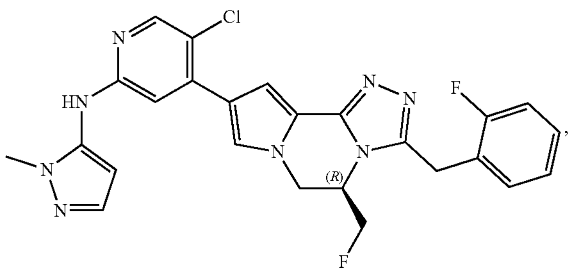 |
| 93 | 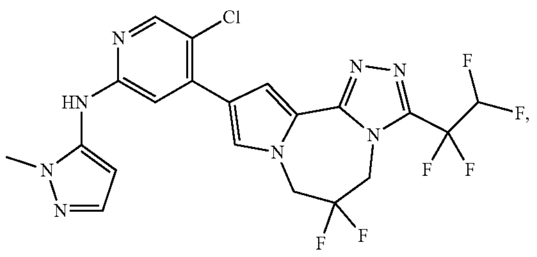 [SMILES: Cn1nccc1Nc1cc(-c2cc3n(c2)CC(F)(F)Cn2c-3nnc2C(F)(F)C(F)F)c(Cl)cn1] |
| 94 | 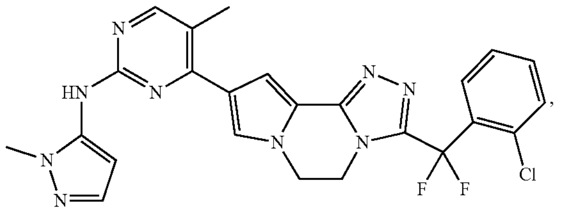 [SMILES: Cc1cnc(Nc2ccnn2C)nc1-c1cc2n(c1)CCn1c-2nnc1C(F)(F)c1ccccc1Cl] |
| 95 | 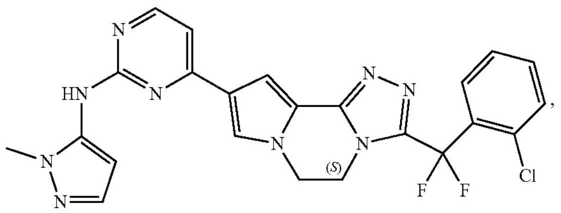 |

-continued
| Compound No. | Structure |
|---|---|
| 96 | 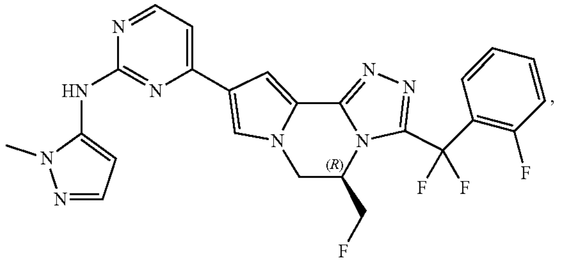 |
| 97 | 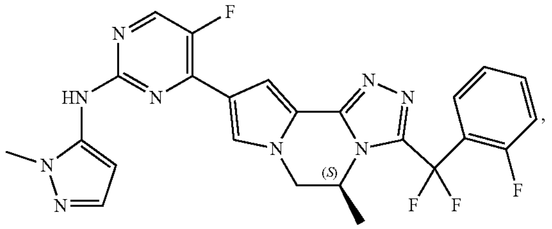 |
| 98 | 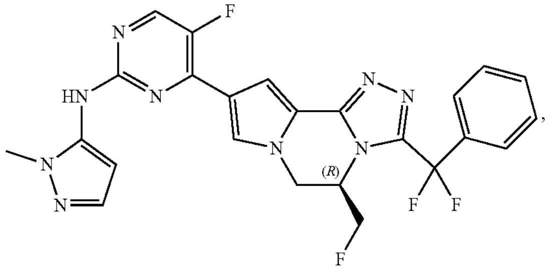 |
| 99 | 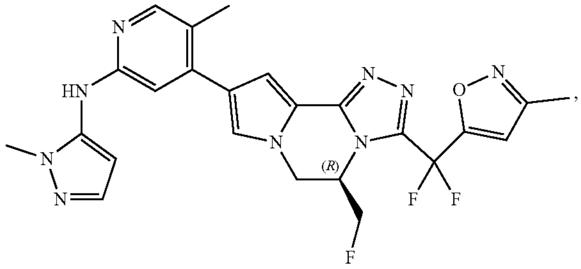 |
| 100 | 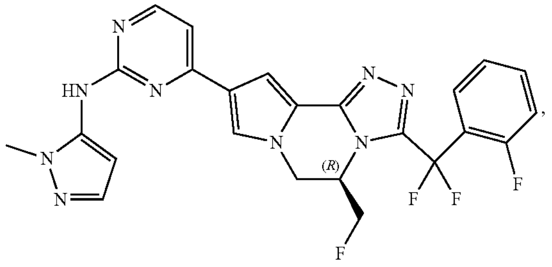 |
| 101 | 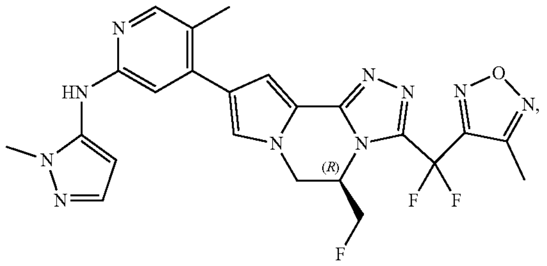 |

-continued
| Compound No. | Structure |
| --- | --- |
| 102 | 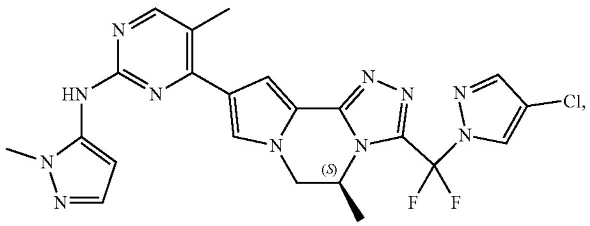 |
| 103 | 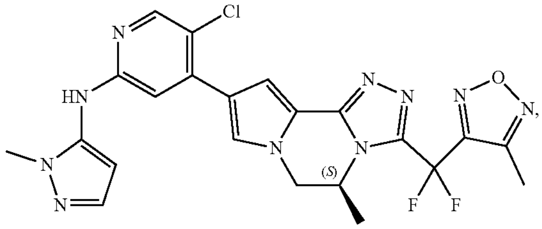 |
| 104 | 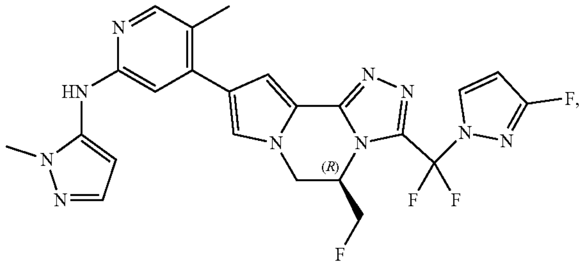 |
| 105 | 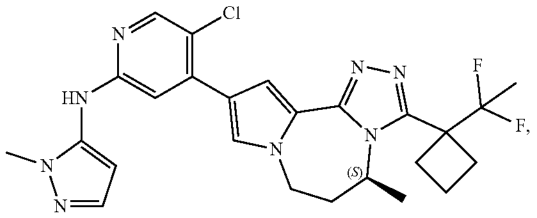 |
| 106 | 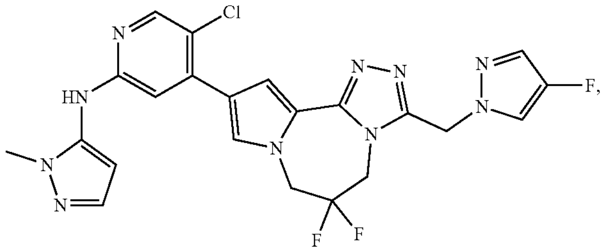 [SMILES: Cn1nccc1Nc1cc(-c2cc3n(c2)CC(F)(F)Cn2c(Cn4cc(F)cn4)nnc2-3)c(Cl)cn1] |
| 107 | 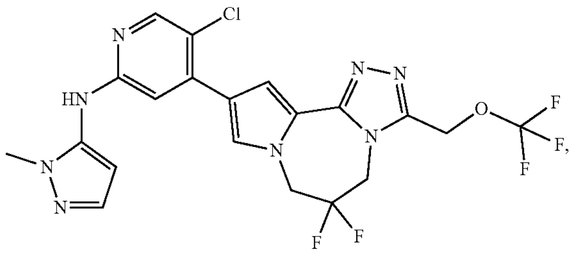 [SMILES: Cn1nccc1Nc1cc(-c2cc3n(c2)CC(F)(F)Cn2c(COC(F)(F)F)nnc2-3)c(Cl)cn1] |

-continued
| Compound No. | Structure |
|---|---|
| 108 | 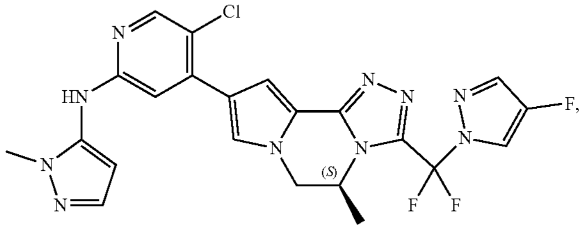 |
| 109 | 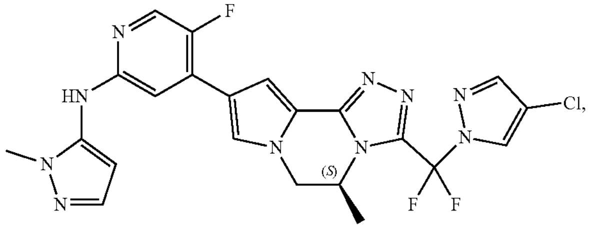 |
| 110 | 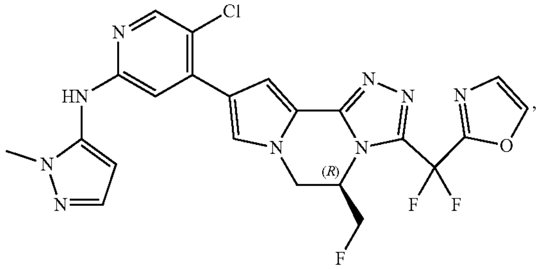 |
| 111 | 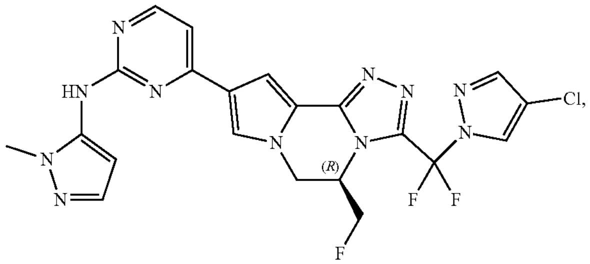 |
| 112 | 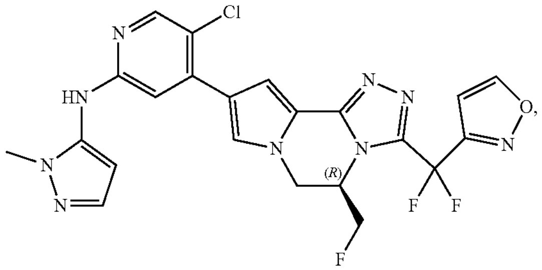 |
| 113 | 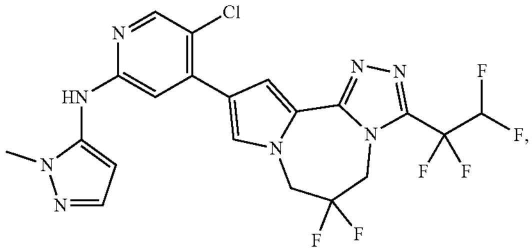 [SMILES: Cn1nccc1Nc1cc(-c2cc3n(c2)CC(F)(F)Cn2c-3nnc2C(F)(F)C(F)F)c(Cl)cn1] |

-continued
| Compound No. | Structure |
|---|---|
| 114 | 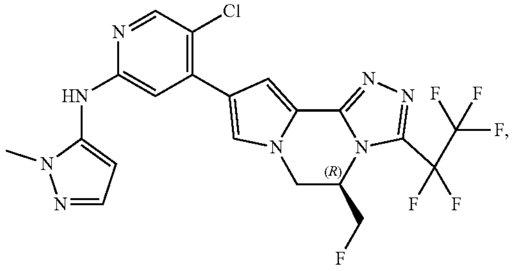 |
| 115 | 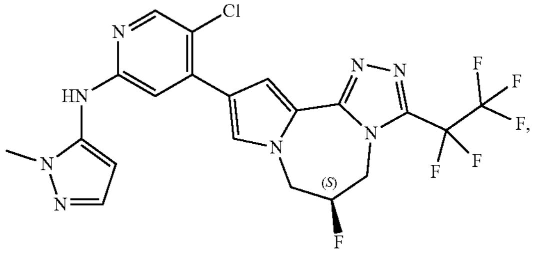 |
| 116 | 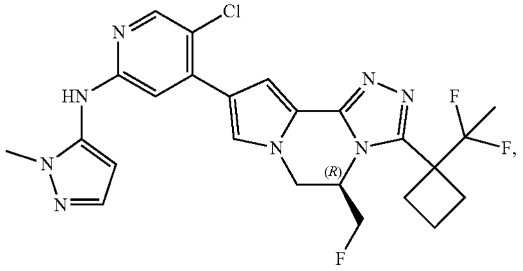 |
| 117 | 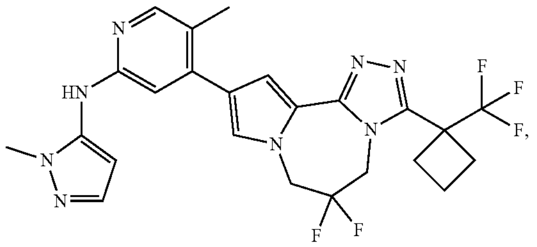 [SMILES: Cc1cnc(Nc2ccnn2C)cc1-c1cc2n(c1)CC(F)(F)Cn1c-2nnc1C1(C(F)(F)F)CCC1] |
| 118 | 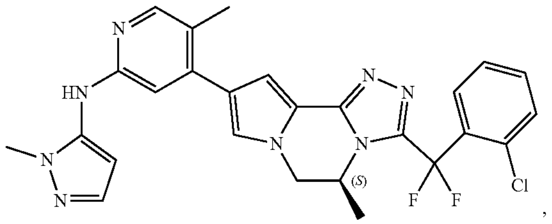 |
| 119 | 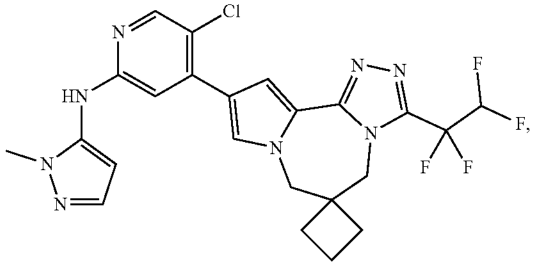 [SMILES: Cn1nccc1Nc1cc(-c2cc3n(c2)CC2(CCC2)Cn2c-3nnc2C(F)(F)C(F)F)c(Cl)cn1] |

-continued
| Compound No. | Structure |
|---|---|
| 120 | 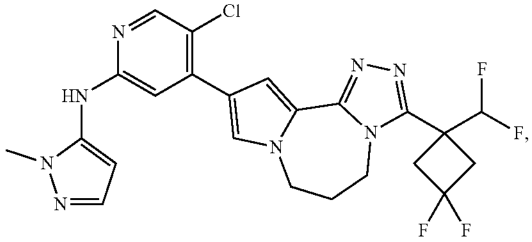 [SMILES: Cn1nccc1Nc1cc(-c2cc3n(c2)CCCn2c-3nnc2C2(C(F)F)CC(F)(F)C2)c(Cl)cn1] |
| 121 | 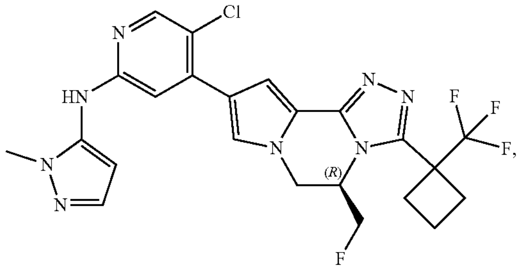 |
| 122 | 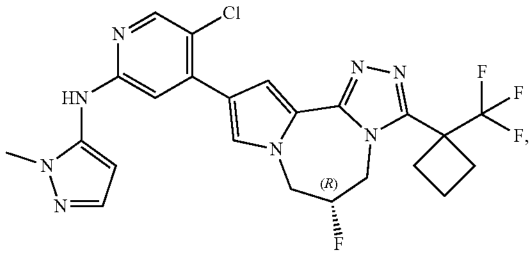 |
| 123 | 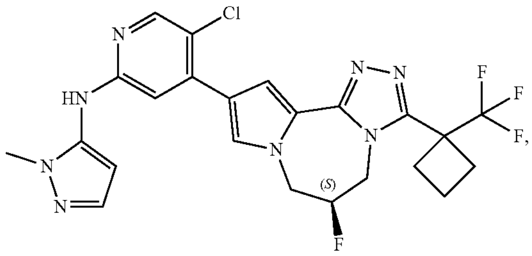 |
| 124 | 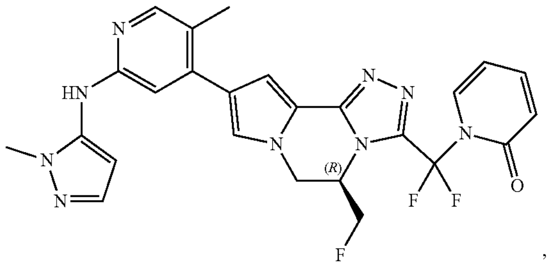 |
| 125 | 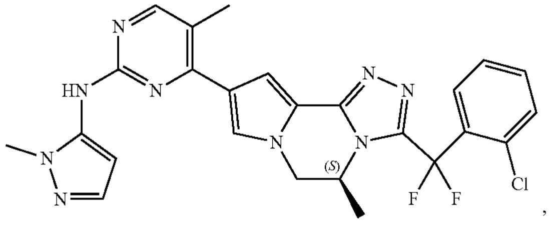 |

-continued
| Compound No. | Structure |
| --- | --- |
| 126 | 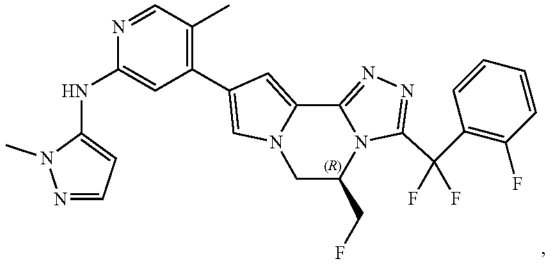 |
| 127 | 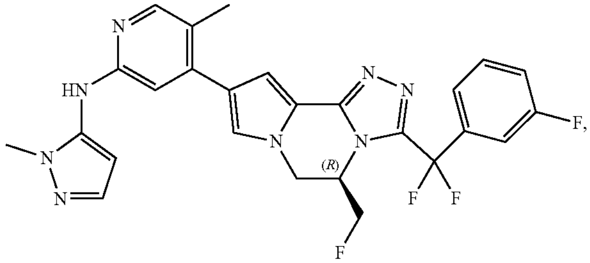 |
| 128 | 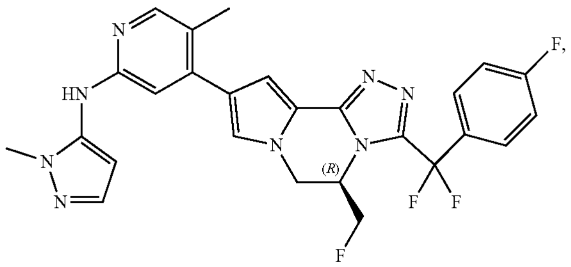 |
| 129 | 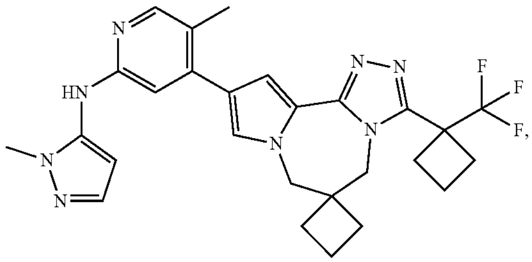 [SMILES: Cc1cnc(Nc2ccnn2C)cc1-c1cc2n(c1)CC1(CCC1)Cn1c-2nnc1C1(C(F)(F)F)CCC1] |
| 130 | 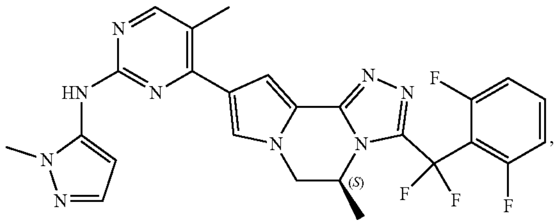 |
| 131 | 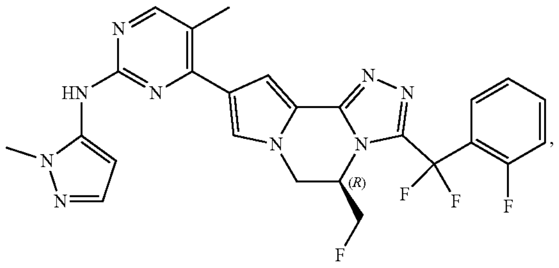 |

-continued
| Compound No. | Structure |
| --- | --- |
| 132 | 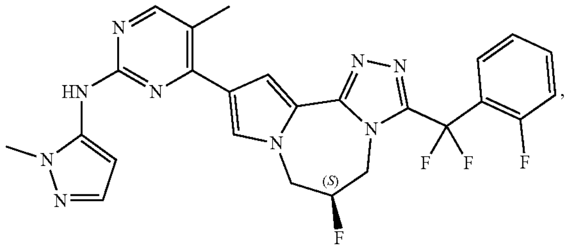 |
| 133 | 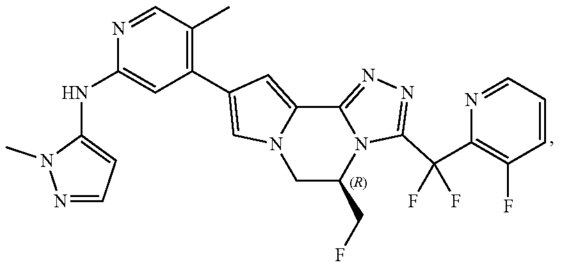 |
| 134 | 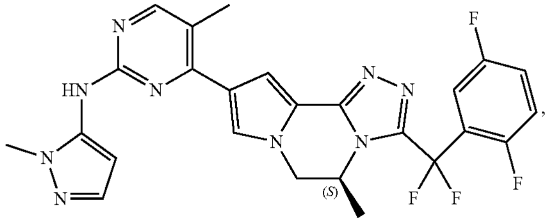 |
| 135 | 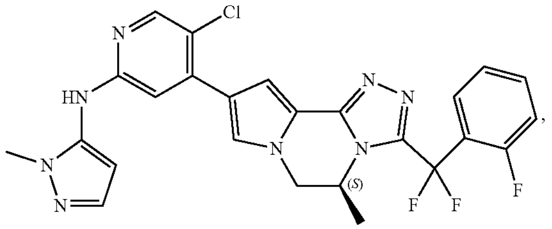 |
| 136 | 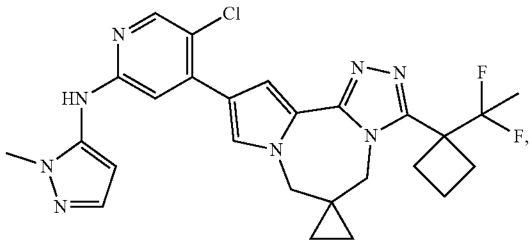 [SMILES: Cn1nccc1Nc1cc(-c2cc3n(c2)CC2(CC2)Cn2c-3nnc2C2(C(C)(F)F)CCC2)c(Cl)cn1] |
| 137 | 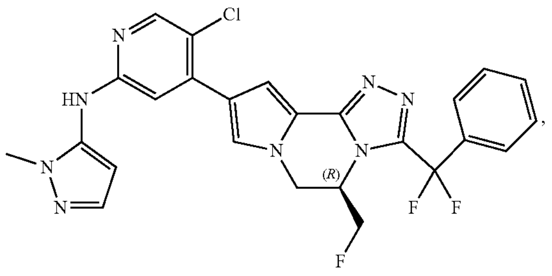 |

-continued
| Compound No. | Structure |
|---|---|
| 138 | 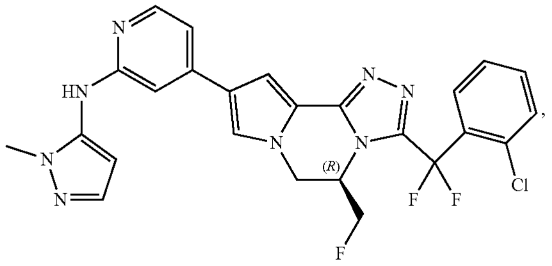 |
| 139 | 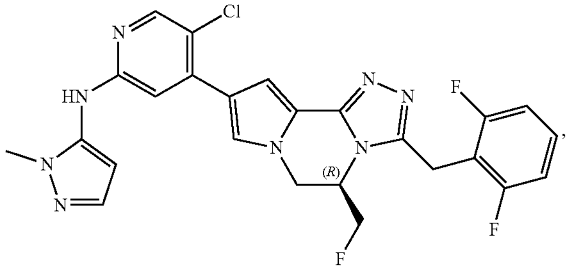 |
| 140 | 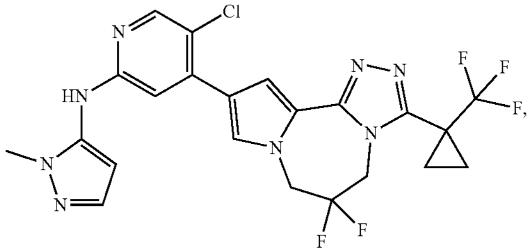 [SMILES: Cn1nccc1Nc1cc(-c2cc3n(c2)CC(F)(F)Cn2c-3nnc2C2(C(F)(F)F)CC2)c(Cl)cn1] |
| 141 | 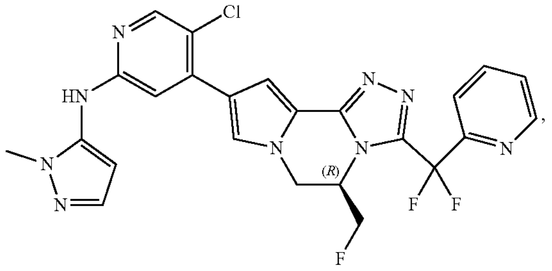 |
| 142 | 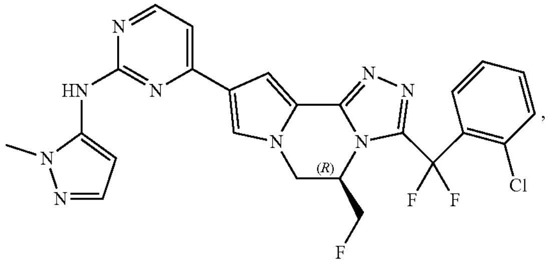 |
| 143 | 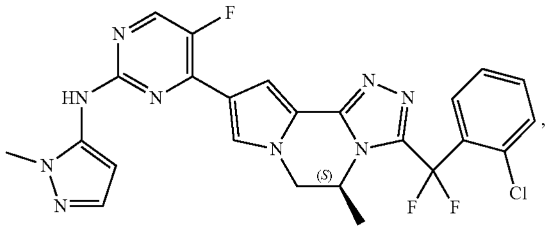 |

-continued
| Compound No. | Structure |
|---|---|
| 144 | 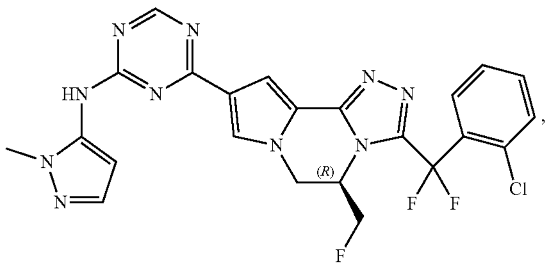 |
| 145 | 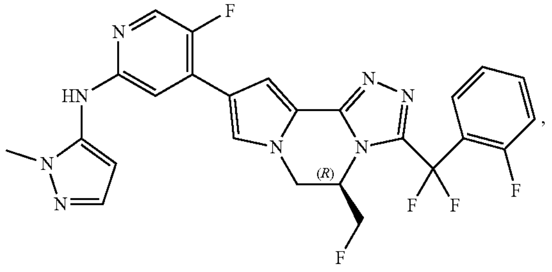 |
| 146 | 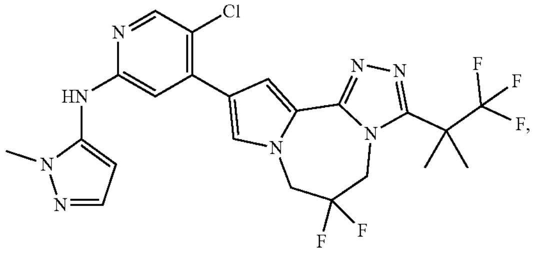 [SMILES: Cn1nccc1Nc1cc(-c2cc3n(c2)CC(F)(F)Cn2c-3nnc2C(C)(C)C(F)(F)F)c(Cl)cn1] |
| 147 | 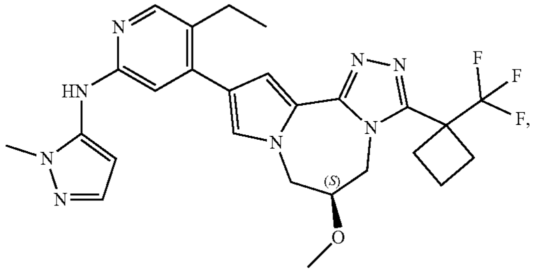 |
| 148 | 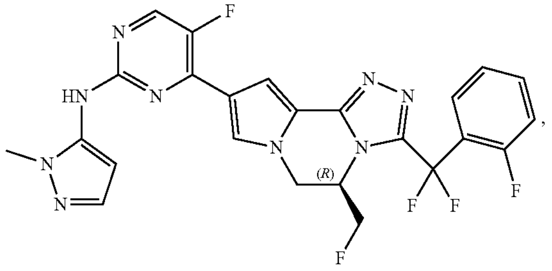 |

-continued
| Compound No. | Structure |
|---|---|
| 149 | 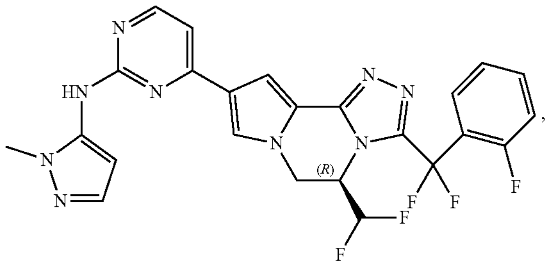 |
| 150 | 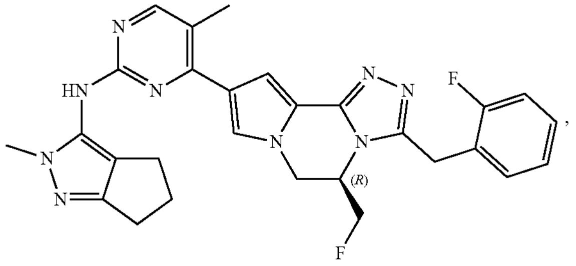 |
| 151 | 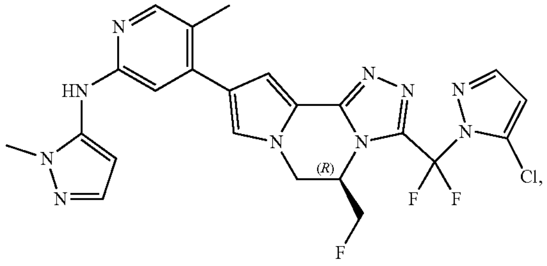 |
| 152 | 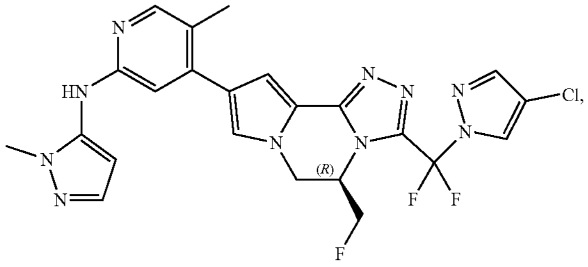 |
| 153 | 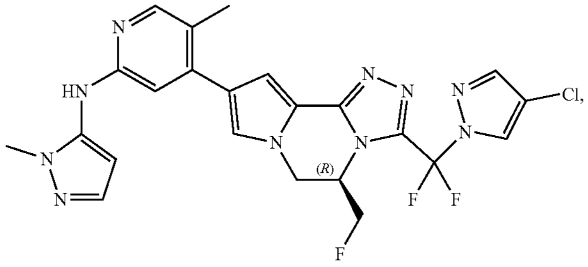 |

-continued
| Compound No. | Structure |
|---|---|
| 154 | 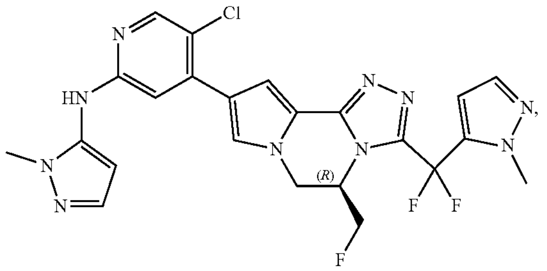 |
| 155 | 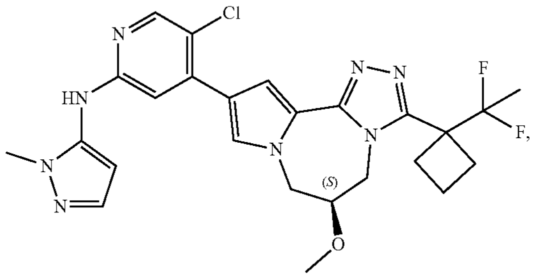 |
| 156 | 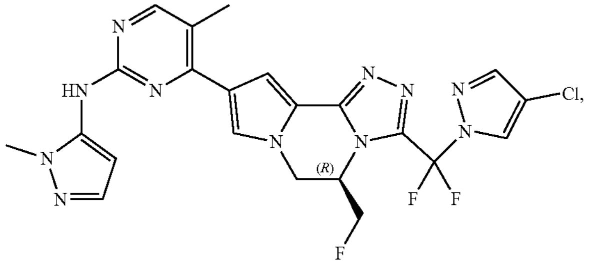 |
| 157 | 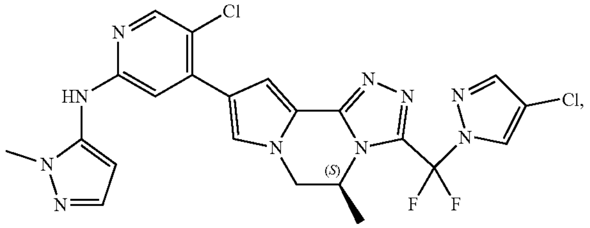 |
| 158 | 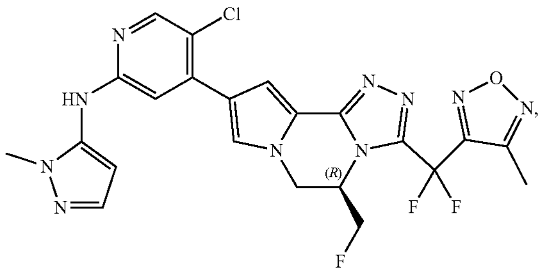 |
| 159 | 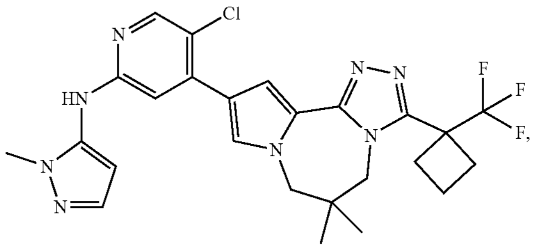 [SMILES: Cn1nccc1Nc1cc(-c2cc3n(c2)CC(C)(C)Cn2c-3nnc2C2(C(F)(F)F)CCC2)c(Cl)cn1] |

-continued
| Compound No. | Structure |
|---|---|
| 160 | 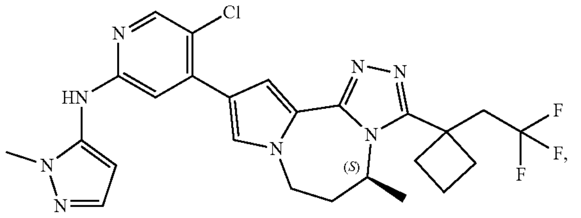 |
| 161 | 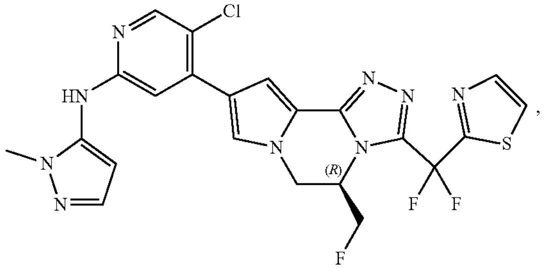 |
| 162 | 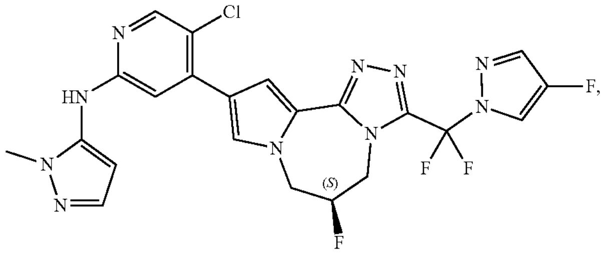 |
| 163 | 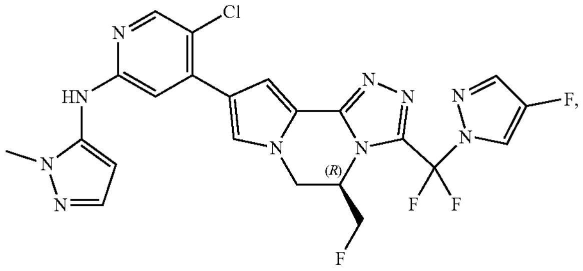 |
| 164 | 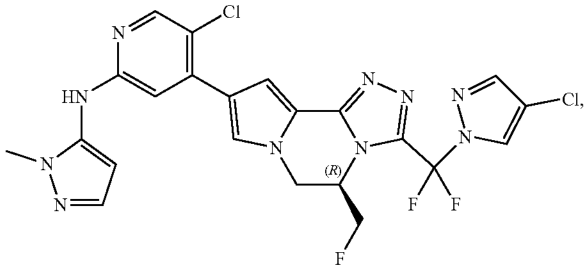 |

-continued
| Compound No. | Structure |
|---|---|
| 165 | 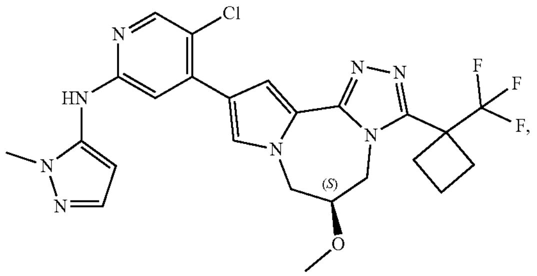 |
| 166 | 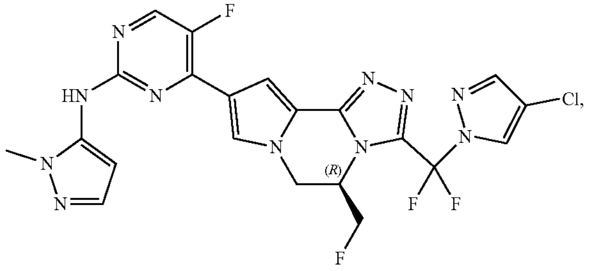 |
| 167 | 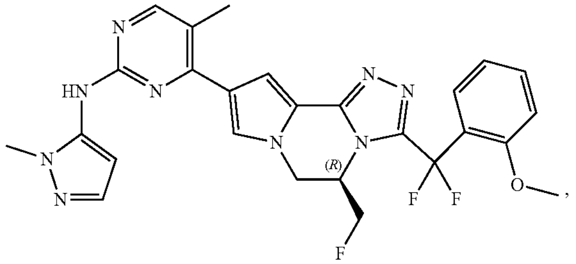 |
| 168 | 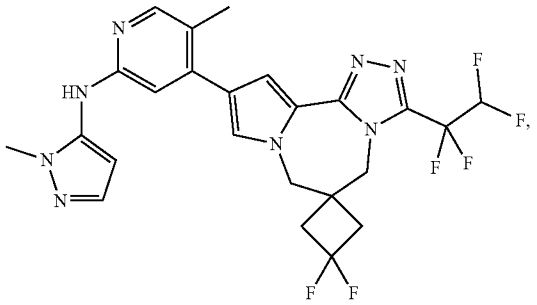 [SMILES: Cc1cnc(Nc2ccnn2C)cc1-c1cc2n(c1)CC1(Cn3c-2nnc3C(F)(F)C(F)F)CC(F)(F)C1] |
| 169 | 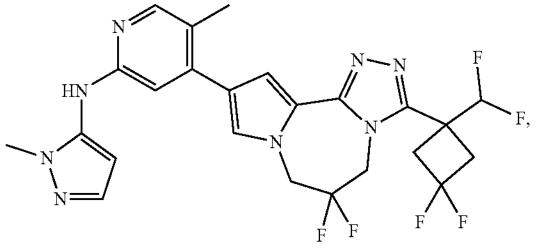 [SMILES: Cc1cnc(Nc2ccnn2C)cc1-c1cc2n(c1)CC(F)(F)Cn1c-2nnc1C1(C(F)F)CC(F)(F)C1] |

-continued
| Compound No. | Structure |
|---|---|
| 170 | 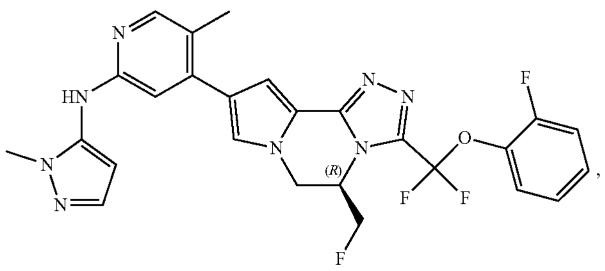 |
| 171 | 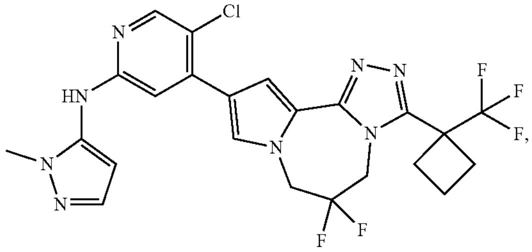 [SMILES: Cn1nccc1Nc1cc(-c2cc3n(c2)CC(F)(F)Cn2c-3nnc2C2(C(F)(F)F)CCC2)c(Cl)cn1] |
| 172 | 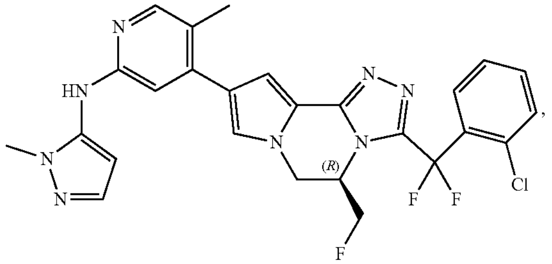 |
| 173 | 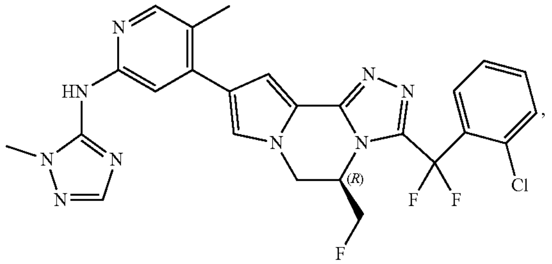 |
| 174 | 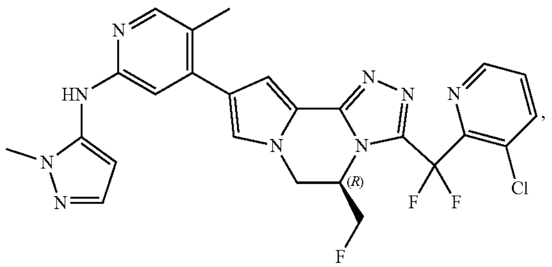 |

-continued
| Compound No. | Structure |
|---|---|
| 175 | 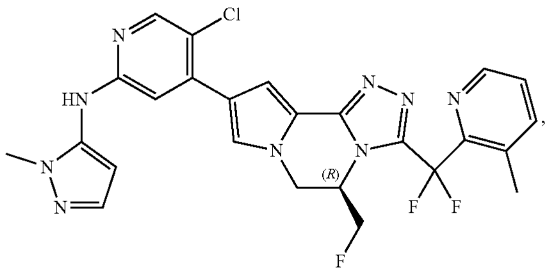 |
| 176 | 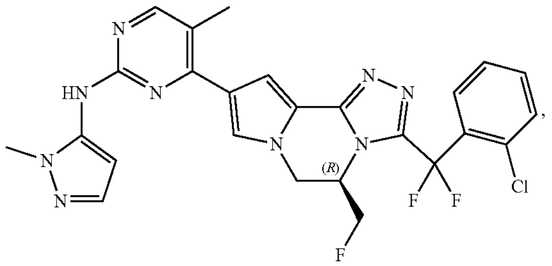 |
| 177 | 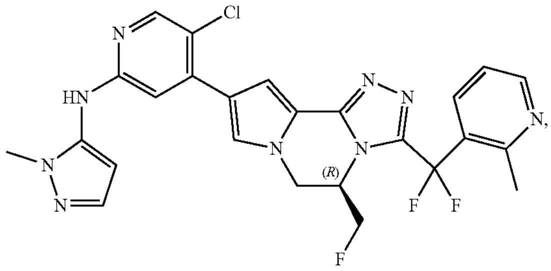 |
| 178 | 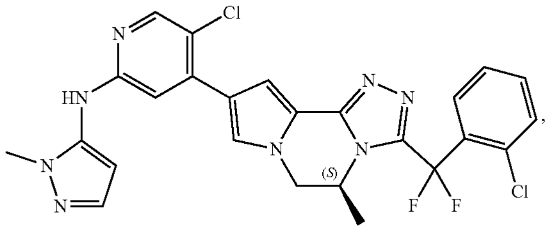 |
| 179 | 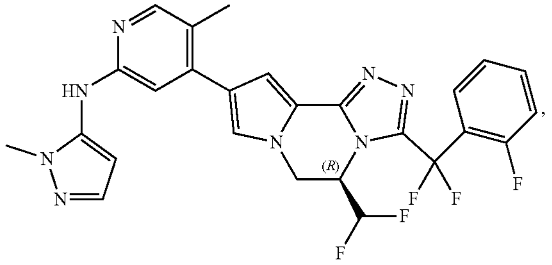 |

-continued
| Compound No. | Structure |
|---|---|
| 180 | 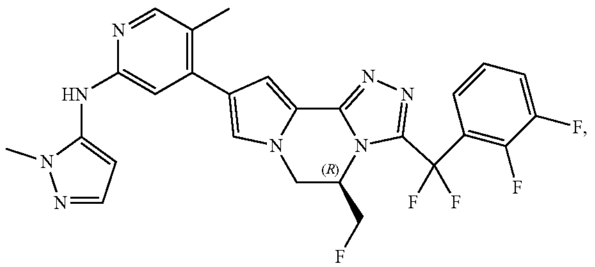 |
| 181 | 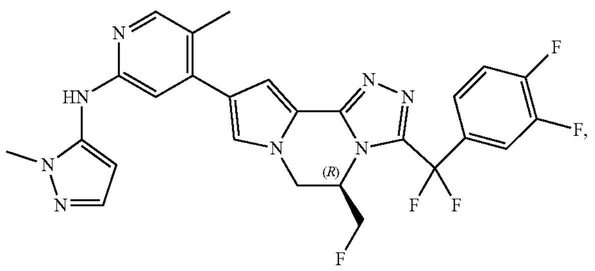 |
| 182 | 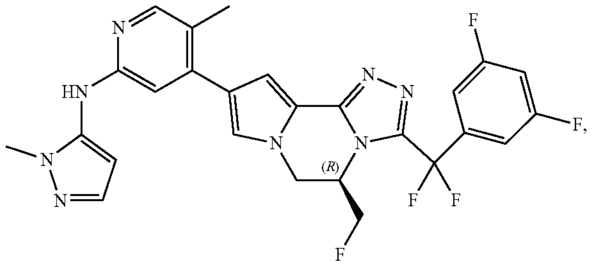 |
| 183 | 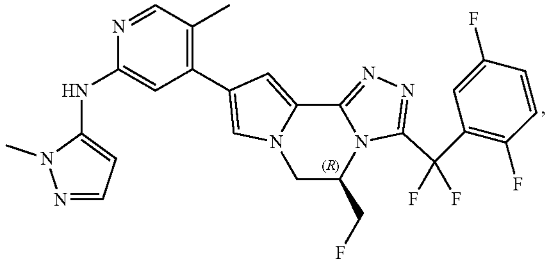 |
| 184 | 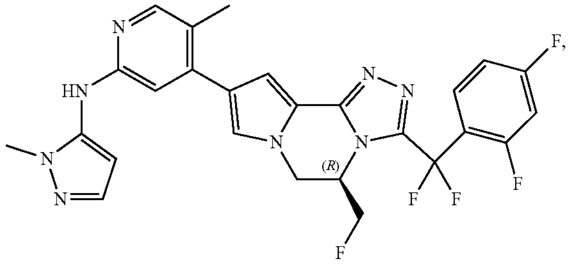 |

-continued
| Compound No. | Structure |
|---|---|
| 185 | 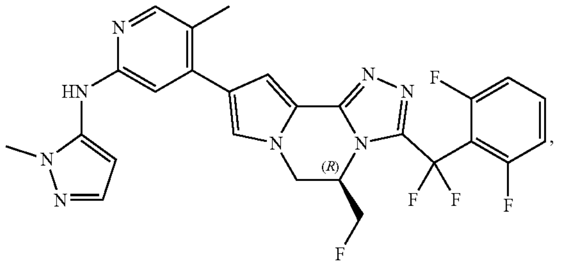 |
| 186 | 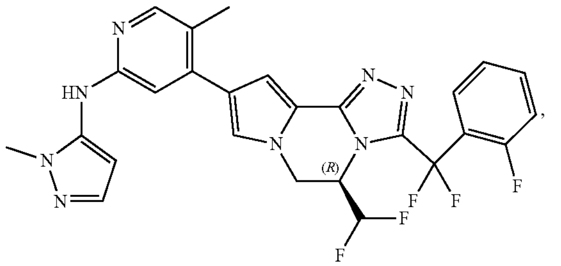 |
| 187 | 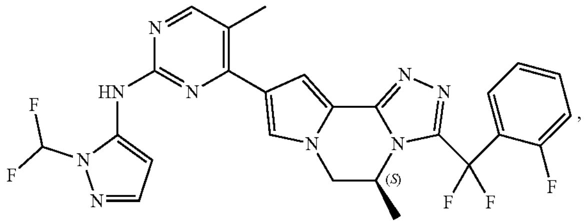 |
| 188 | 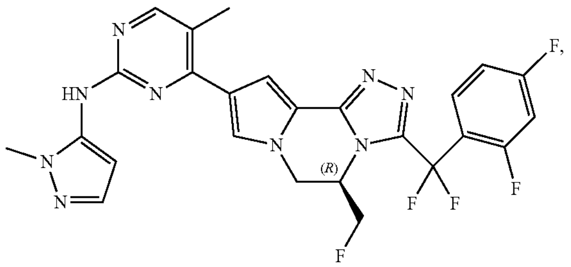 |
| 189 | 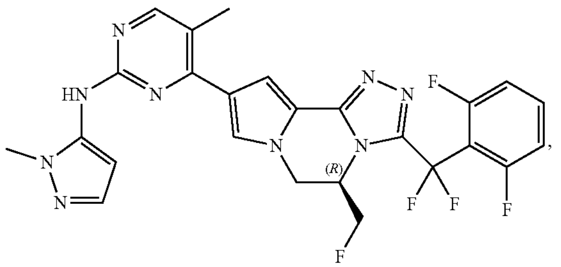 |
| 190 | 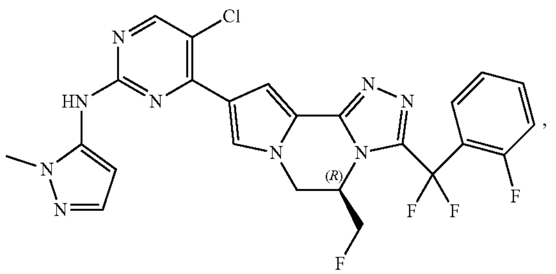 |

-continued
| Compound No. | Structure |
|---|---|
| 191 | 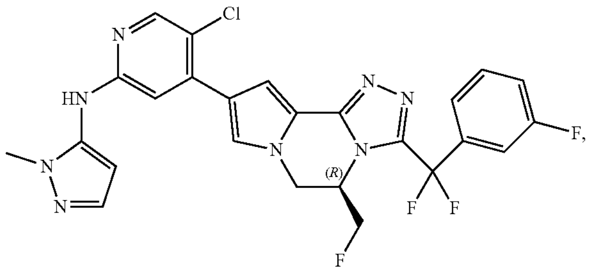 |
| 192 | 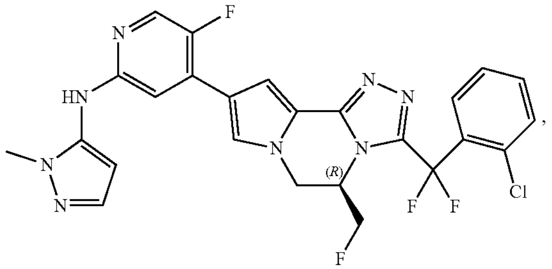 |
| 193 | 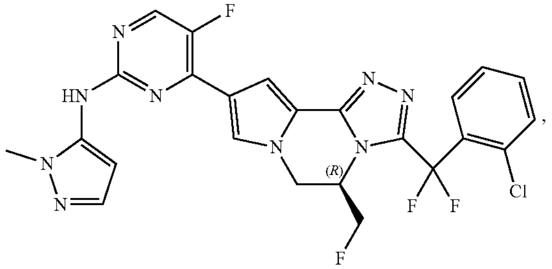 |
| 194 | 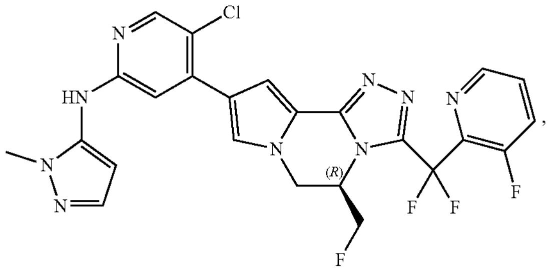 |
| 195 | 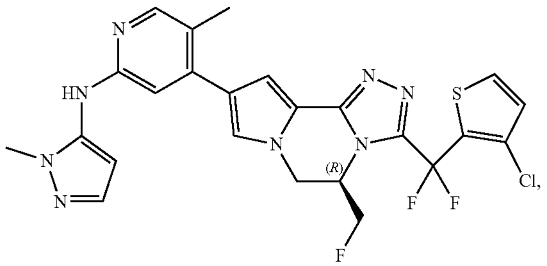 |

-continued
| Compound No. | Structure |
|---|---|
| 196 | 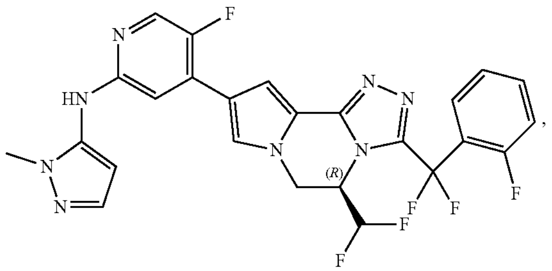 |
| 197 | 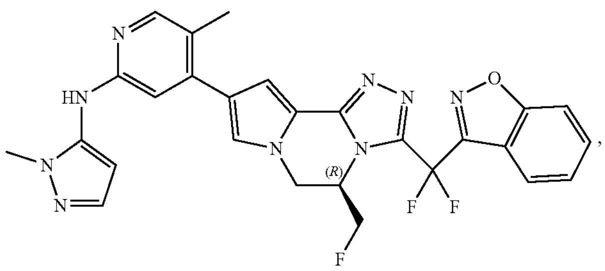 |
| 198 | 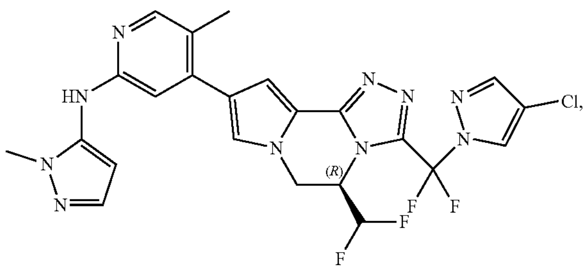 |
| 199 | 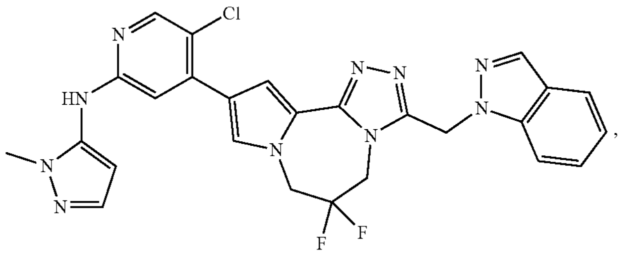 [SMILES: Cn1nccc1Nc1cc(-c2cc3n(c2)CC(F)(F)Cn2c(Cn4ncc5ccccc54)nnc2-3)c(Cl)cn1] |
| 200 | 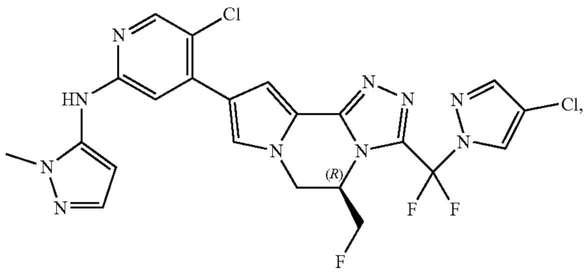 |

-continued
| Compound No. | Structure |
| --- | --- |
| 201 | 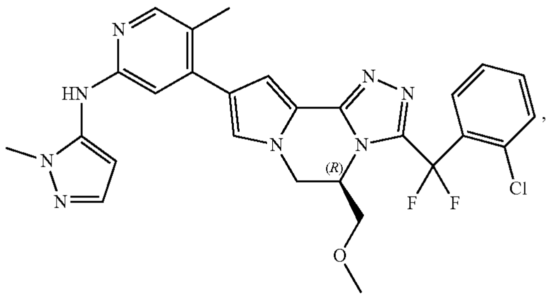 |
| 202 | 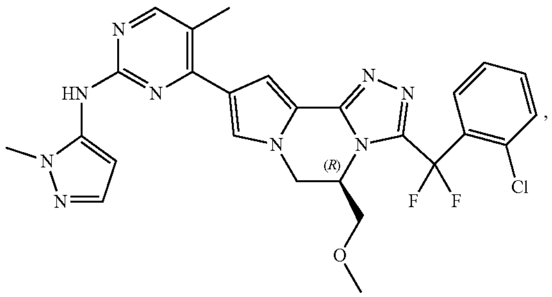 |
| 203 | 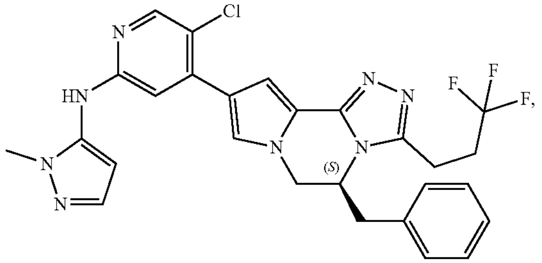 |
| 204 | 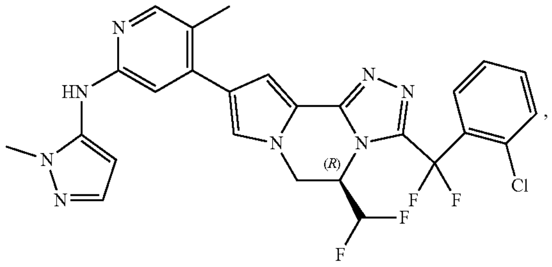 |
| 205 | 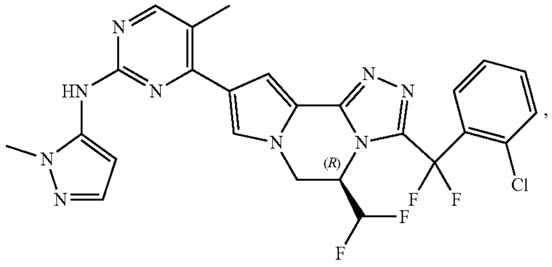 |

-continued
| Compound No. | Structure |
| --- | --- |
| 206 | 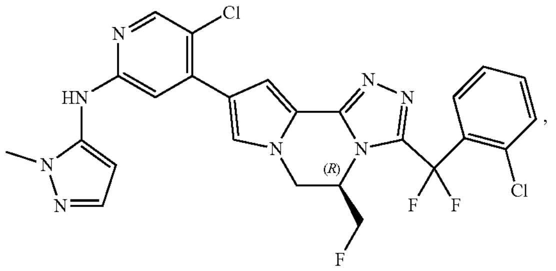 |
| 207 | 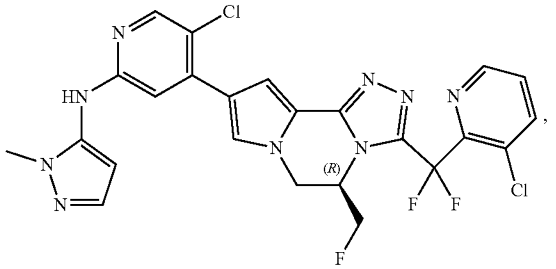 |
| 208 | 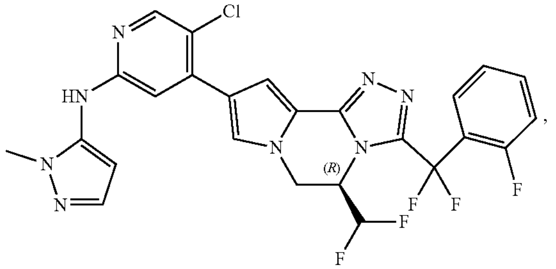 |
| 209 | 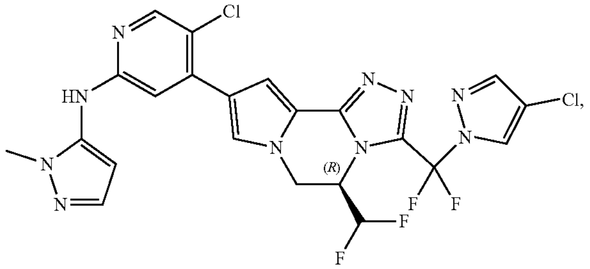 |
| 210 | 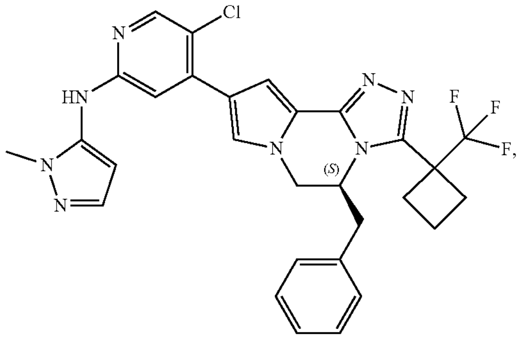 |

-continued
| Compound No. | Structure |
|---|---|
| 211 | 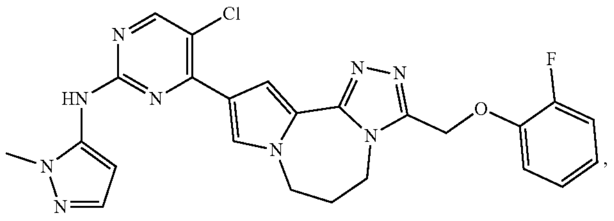 [SMILES: Cn1nccc1Nc1ncc(Cl)c(-c2cc3n(c2)CCCn2c(COc4ccccc4F)nnc2-3)n1] |
| 212 | 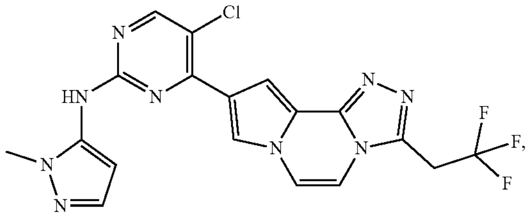 [SMILES: Cn1nccc1Nc1ncc(Cl)c(-c2cc3c4nnc(CC(F)(F)F)n4ccn3c2)n1] |
| 213 | 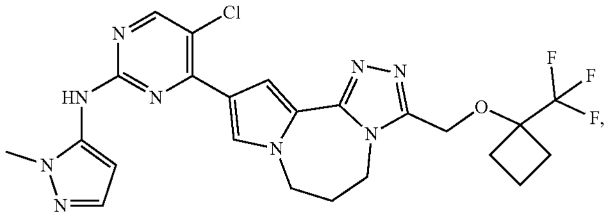 [SMILES: Cn1nccc1Nc1ncc(Cl)c(-c2cc3n(c2)CCCn2c(COC4(C(F)(F)F)CCC4)nnc2-3)n1] |
| 214 | 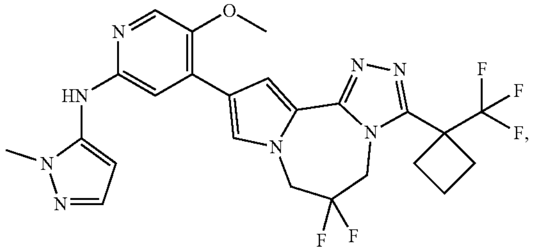 [SMILES: COc1cnc(Nc2ccnn2C)cc1-c1cc2n(c1)CC(F)(F)Cn1c-2nnc1C1(C(F)(F)F)CCC1] |
| 215 | 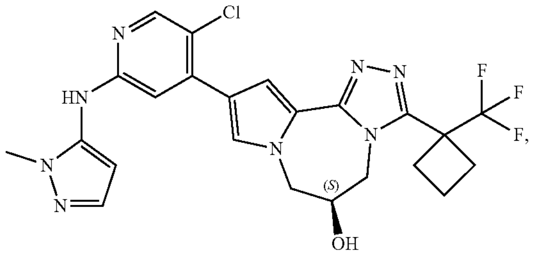 |
| 216 | 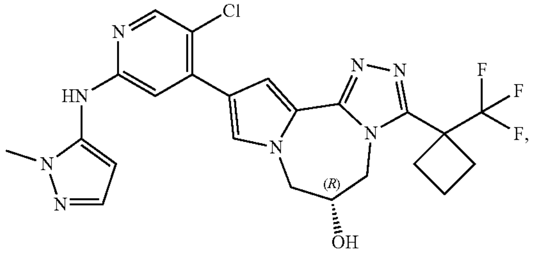 |

-continued
| Compound No. | Structure |
|---|---|
| 217 | 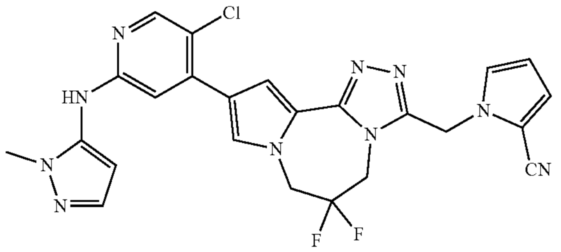 [SMILES: Cn1nccc1Nc1cc(-c2cc3n(c2)CC(F)(F)Cn2c(Cn4cccc4C#N)nnc2-3)c(Cl)cn1] |
| 218 | 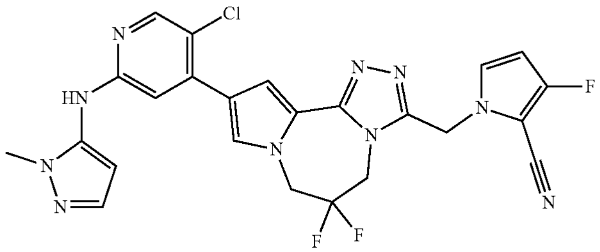 [SMILES: Cn1nccc1Nc1cc(-c2cc3n(c2)CC(F)(F)Cn2c(Cn4ccc(F)c4C#N)nnc2-3)c(Cl)cn1] |
| 219 | 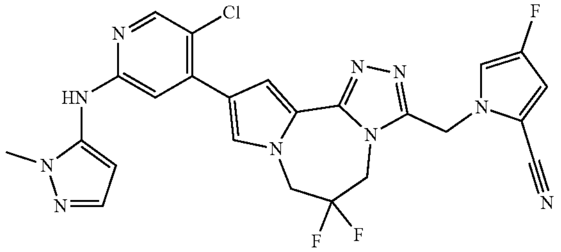 [SMILES: Cn1nccc1Nc1cc(-c2cc3n(c2)CC(F)(F)Cn2c(Cn4cc(F)cc4C#N)nnc2-3)c(Cl)cn1] |
| 220 | 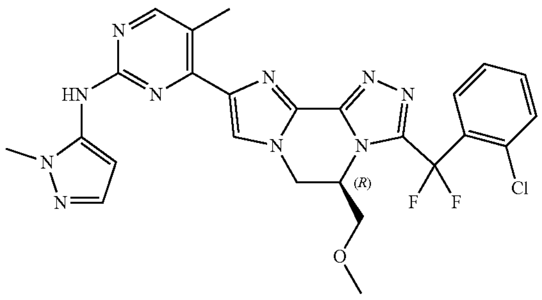 |
| 221 | 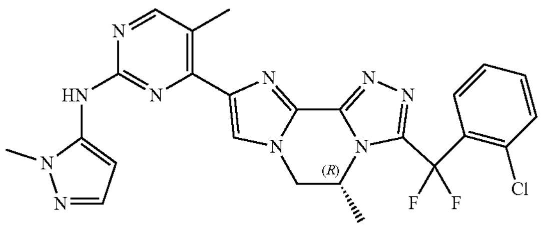 |
| 222 | 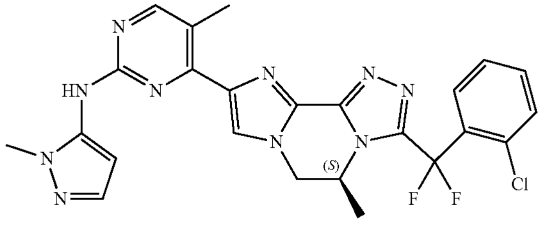 |

-continued
| Compound No. | Structure |
|---|---|
| 223 | 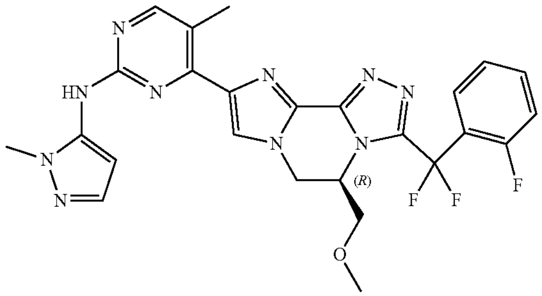 |
| 224 | 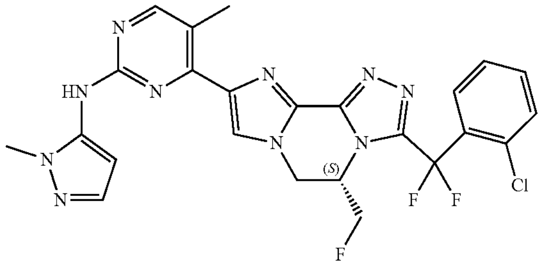 |
| 225 | 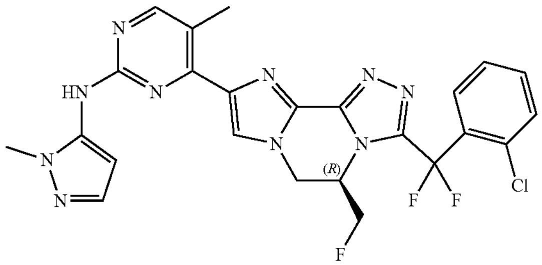 |
| 226 | 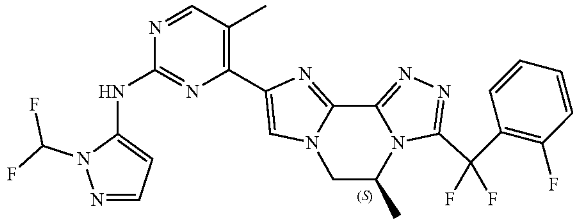 |
| 227 | 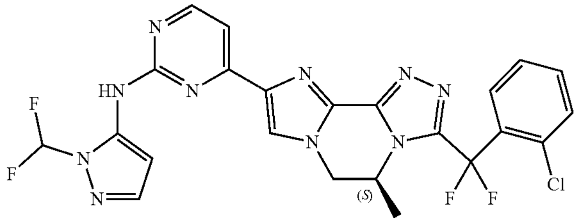 |
| 228 | 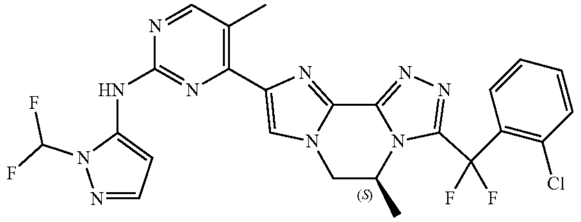 |

-continued
| Compound No. | Structure |
|---|---|
| 229 | 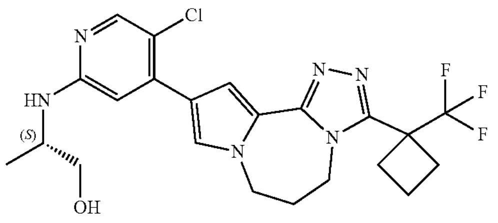 |
| 230 | 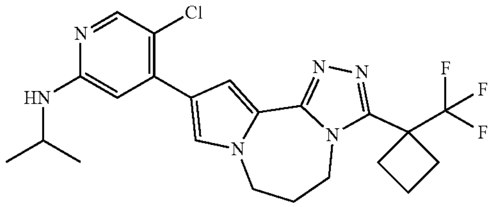 [SMILES: CC(C)Nc1cc(-c2cc3n(c2)CCCn2c-3nnc2C2(C(F)(F)F)CCC2)c(Cl)cn1] |
| 231 | 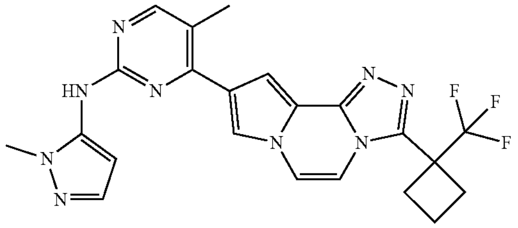 [SMILES: Cc1cnc(Nc2ccnn2C)nc1-c1cc2c3nnc(C4(C(F)(F)F)CCC4)n3ccn2c1] |
| 232 | 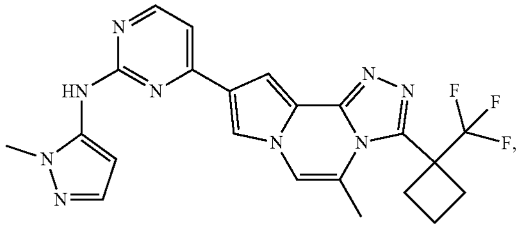 [SMILES: Cc1cn2cc(-c3ccnc(Nc4ccnn4C)n3)cc2c2nnc(C3(C(F)(F)F)CCC3)n12] |
| 233 | 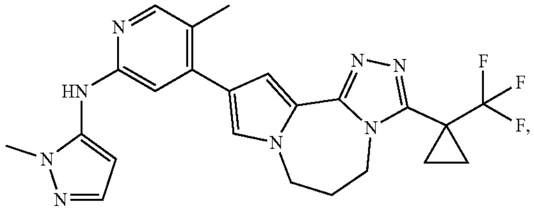 [SMILES: Cc1cnc(Nc2ccnn2C)cc1-c1cc2n(c1)CCCn1c-2nnc1C1(C(F)(F)F)CC1] |
| 234 | 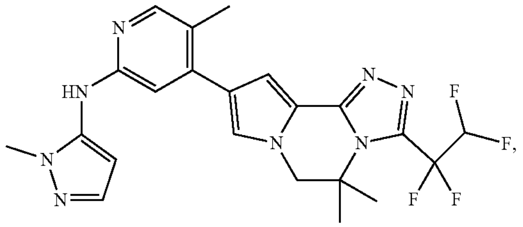 [SMILES: Cc1cnc(Nc2ccnn2C)cc1-c1cc2n(c1)CC(C)(C)n1c-2nnc1C(F)(F)C(F)F] |

-continued
| Compound No. | Structure |
| --- | --- |
| 235 | 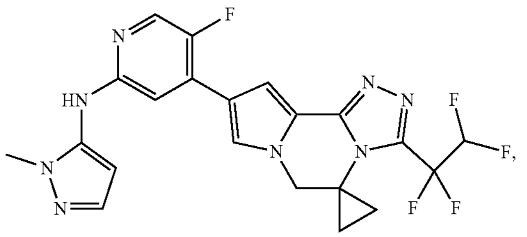 [SMILES: Cn1nccc1Nc1cc(-c2cc3n(c2)CC2(CC2)n2c-3nnc2C(F)(F)C(F)F)c(F)cn1] |
| 236 | 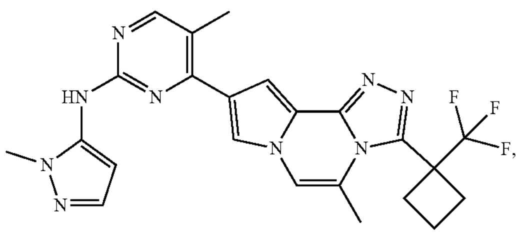 [SMILES: Cc1cnc(Nc2ccnn2C)nc1-c1cc2c3nnc(C4(C(F)(F)F)CCC4)n3c(C)cn2c1] |
| 237 | 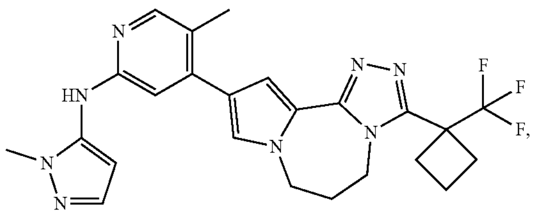 [SMILES: Cc1cnc(Nc2ccnn2C)cc1-c1cc2n(c1)CCCn1c-2nnc1C1(C(F)(F)F)CCC1] |
| 238 | 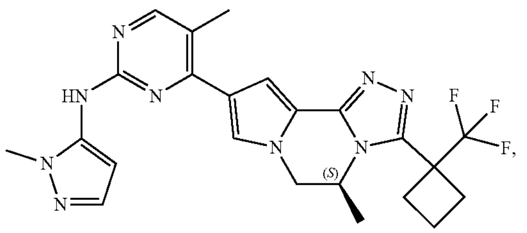 |
| 239 | 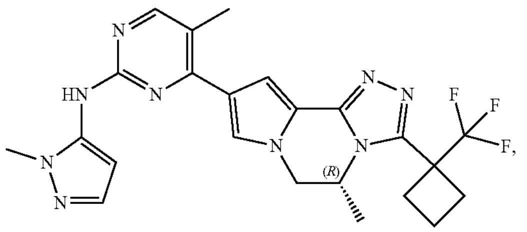 |
| 240 | 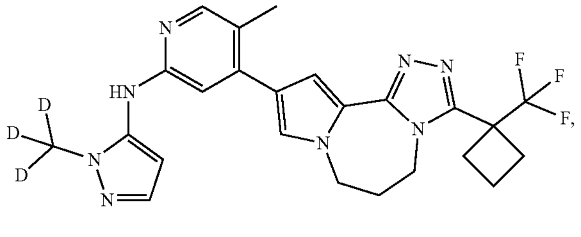 [SMILES: [2H]C([2H])([2H])n1nccc1Nc1cc(-c2cc3n(c2)CCCn2c-3nnc2C2(C(F)(F)F)CCC2)c(C)cn1] |

-continued
| Compound No. | Structure |
|---|---|
| 241 | 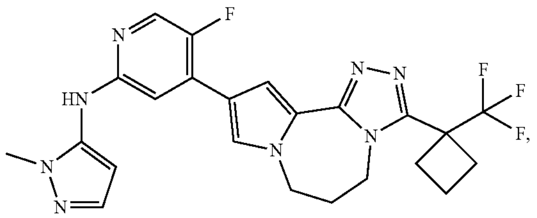 [SMILES: Cn1nccc1Nc1cc(-c2cc3n(c2)CCCn2c-3nnc2C2(C(F)(F)F)CCC2)c(F)cn1] |
| 242 | 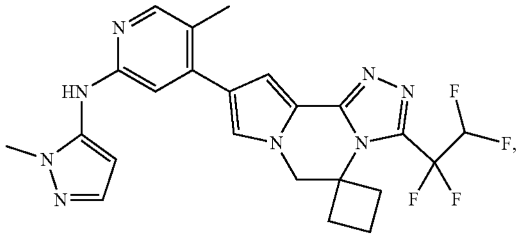 [SMILES: Cc1cnc(Nc2ccnn2C)cc1-c1cc2n(c1)CC1(CCC1)n1c-2nnc1C(F)(F)C(F)F] |
| 243 | 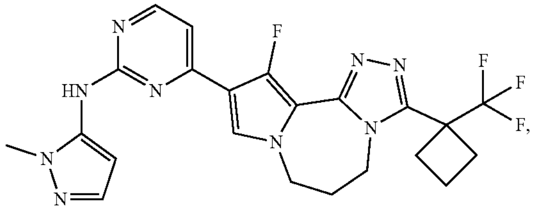 [SMILES: Cn1nccc1Nc1nccc(-c2cn3c(c2F)-c2nnc(C4(C(F)(F)F)CCC4)n2CCC3)n1] |
| 244 | 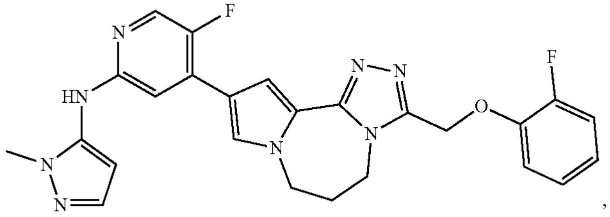 [SMILES: Cn1nccc1Nc1cc(-c2cc3n(c2)CCCn2c(COc4ccccc4F)nnc2-3)c(F)cn1] |
| 245 | 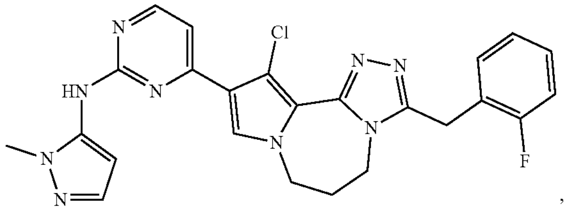 [SMILES: Cn1nccc1Nc1nccc(-c2cn3c(c2Cl)-c2nnc(Cc4ccccc4F)n2CCC3)n1] |
| 246 | 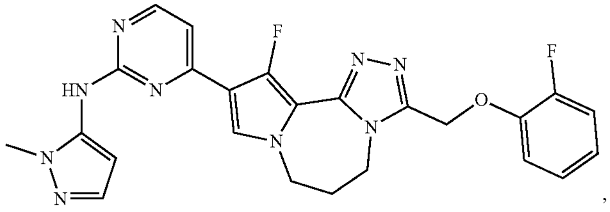 [SMILES: Cn1nccc1Nc1nccc(-c2cn3c(c2F)-c2nnc(COc4ccccc4F)n2CCC3)n1] |
| 247 | 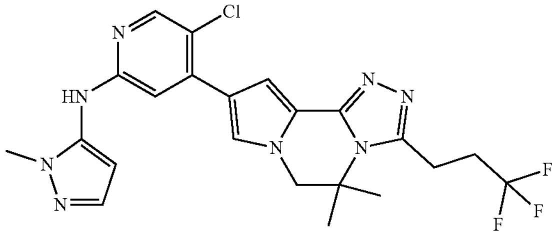 [SMILES: Cn1nccc1Nc1cc(-c2cc3n(c2)CC(C)(C)n2c(CCC(F)(F)F)nnc2-3)c(Cl)cn1] |

-continued
| Compound No. | Structure |
| --- | --- |
| 248 | 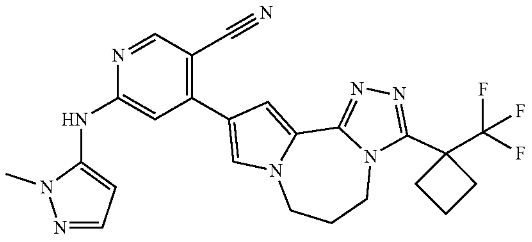 [SMILES: Cn1nccc1Nc1cc(-c2cc3n(c2)CCCn2c-3nnc2C2(C(F)(F)F)CCC2)c(C#N)cn1] |
| 249 | 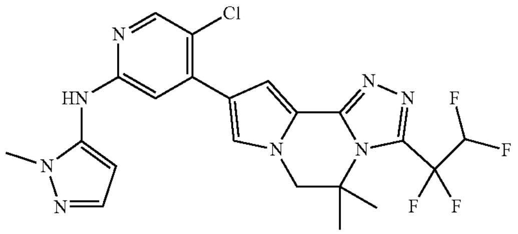 [SMILES: Cn1nccc1Nc1cc(-c2cc3n(c2)CC(C)(C)n2c-3nnc2C(F)(F)C(F)F)c(Cl)cn1] |
| 250 | 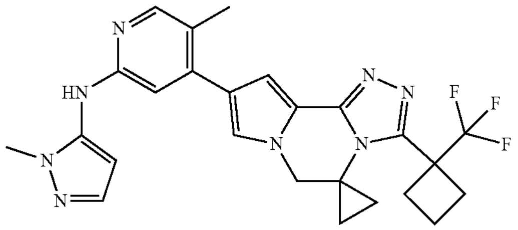 [SMILES: Cc1cnc(Nc2ccnn2C)cc1-c1cc2n(c1)CC1(CC1)n1c-2nnc1C1(C(F)(F)F)CCC1] |
| 251 | 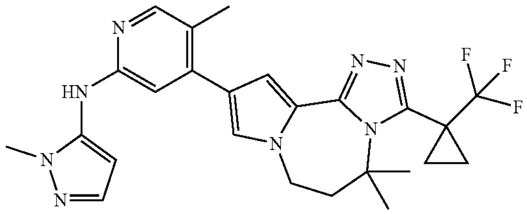 [SMILES: Cc1cnc(Nc2ccnn2C)cc1-c1cc2n(c1)CCC(C)(C)n1c-2nnc1C1(C(F)(F)F)CC1] |
| 252 | 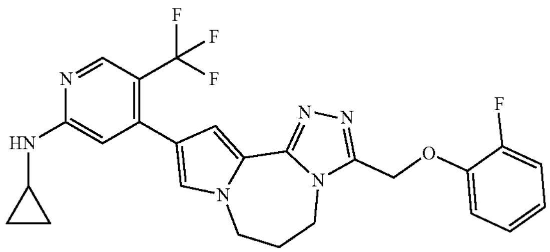 [SMILES: Fc1ccccc1OCc1nnc2n1CCCn1cc(-c3cc(NC4CC4)ncc3C(F)(F)F)cc1-2] |
| 253 | 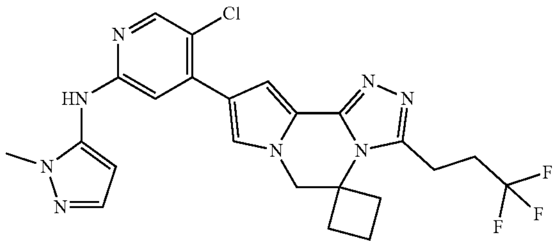 [SMILES: Cn1nccc1Nc1cc(-c2cc3n(c2)CC2(CCC2)n2c(CCC(F)(F)F)nnc2-3)c(Cl)cn1] |

-continued
| Compound No. | Structure |
|---|---|
| 254 | 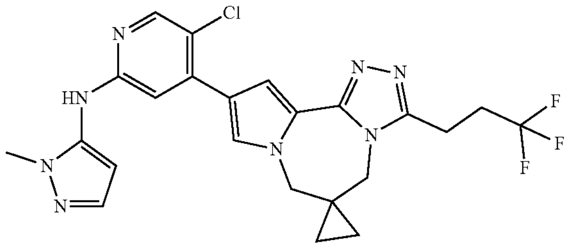 [SMILES: Cn1nccc1Nc1cc(-c2cc3n(c2)CC2(CC2)Cn2c(CCC(F)(F)F)nnc2-3)c(Cl)cn1] |
| 255 | 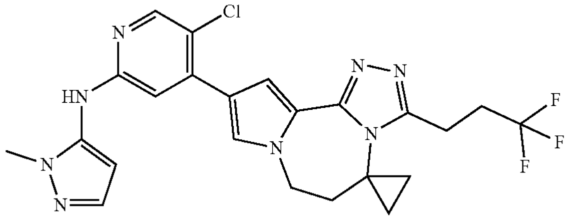 [SMILES: Cn1nccc1Nc1cc(-c2cc3n(c2)CCC2(CC2)n2c(CCC(F)(F)F)nnc2-3)c(Cl)cn1] |
| 256 | 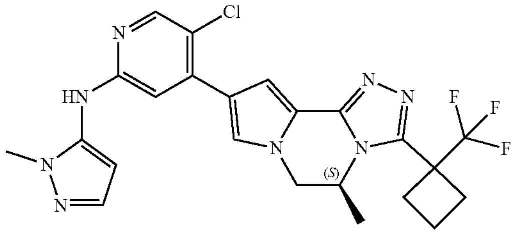 |
| 257 | 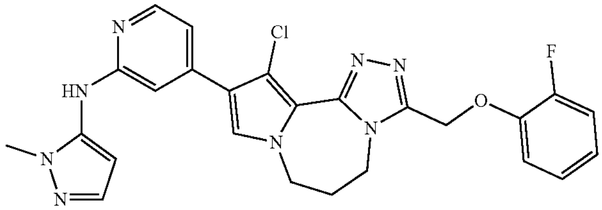 [SMILES: Cn1nccc1Nc1cc(-c2cn3c(c2Cl)-c2nnc(COc4ccccc4F)n2CCC3)ccn1] |
| 258 | 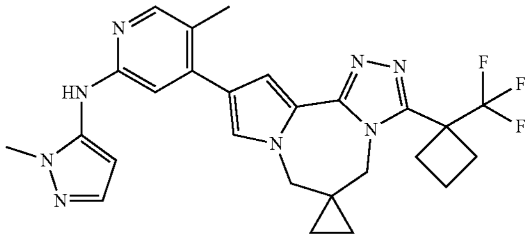 [SMILES: Cc1cnc(Nc2ccnn2C)cc1-c1cc2n(c1)CC1(CC1)Cn1c-2nnc1C1(C(F)(F)F)CCC1] |
| 259 | 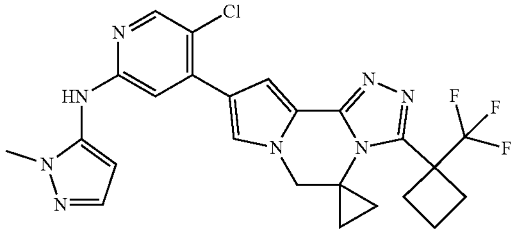 [SMILES: Cn1nccc1Nc1cc(-c2cc3n(c2)CC2(CC2)n2c-3nnc2C2(C(F)(F)F)CCC2)c(Cl)cn1] |

-continued
| Compound No. | Structure |
|---|---|
| 260 | 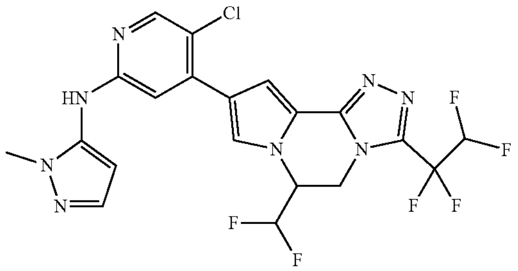 [SMILES: Cn1nccc1Nc1cc(-c2cc3n(c2)C(C(F)F)Cn2c-3nnc2C(F)(F)C(F)F)c(Cl)cn1] |
| 261 | 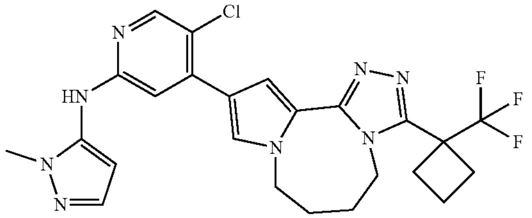 [SMILES: Cn1nccc1Nc1cc(-c2cc3n(c2)CCCCn2c-3nnc2C2(C(F)(F)F)CCC2)c(Cl)cn1] |
| 262 | 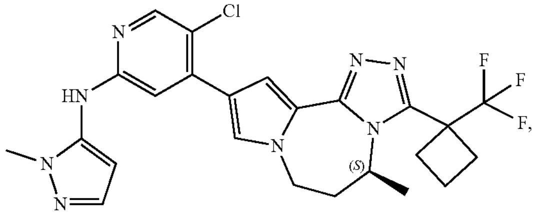 |
| 263 | 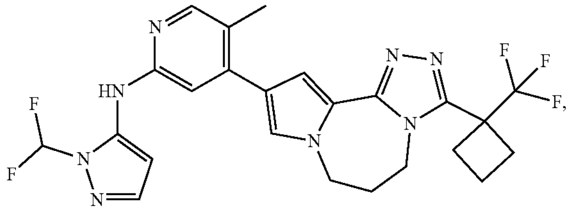 [SMILES: Cc1cnc(Nc2ccnn2C(F)F)cc1-c1cc2n(c1)CCCn1c-2nnc1C1(C(F)(F)F)CCC1] |
| 264 | 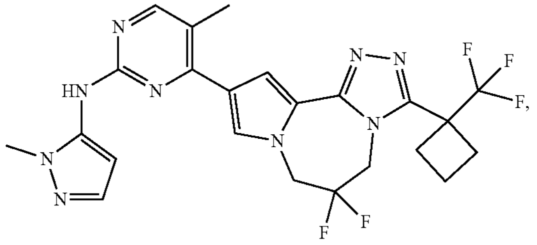 [SMILES: Cc1cnc(Nc2ccnn2C)nc1-c1cc2n(c1)CC(F)(F)Cn1c-2nnc1C1(C(F)(F)F)CCC1] |
| 265 | 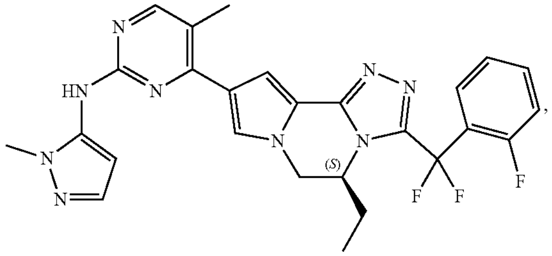 |

-continued
| Compound No. | Structure |
| --- | --- |
| 266 | 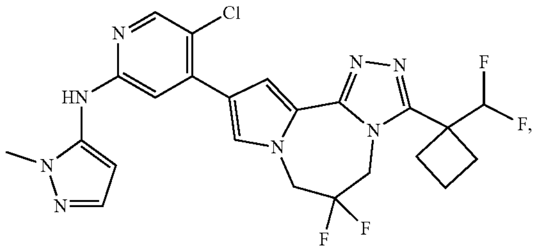 [SMILES: Cn1nccc1Nc1cc(-c2cc3n(c2)CC(F)(F)Cn2c-3nnc2C2(C(F)F)CCC2)c(Cl)cn1] |
| 267 | 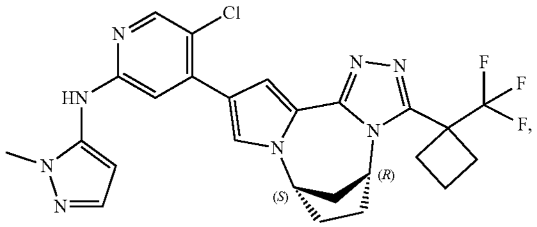 |
| 268 | 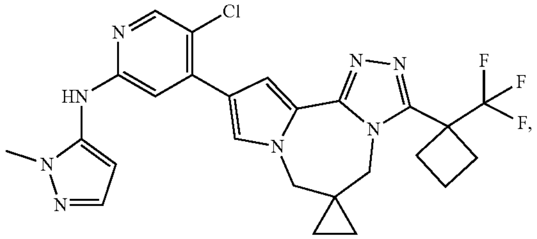 [SMILES: Cn1nccc1Nc1cc(-c2cc3n(c2)CC2(CC2)Cn2c-3nnc2C2(C(F)(F)F)CCC2)c(Cl)cn1] |
| 269 | 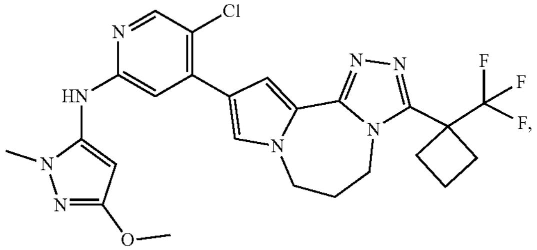 [SMILES: COc1cc(Nc2cc(-c3cc4n(c3)CCCn3c-4nnc3C3(C(F)(F)F)CCC3)c(Cl)cn2)n(C)n1] |
| 270 | 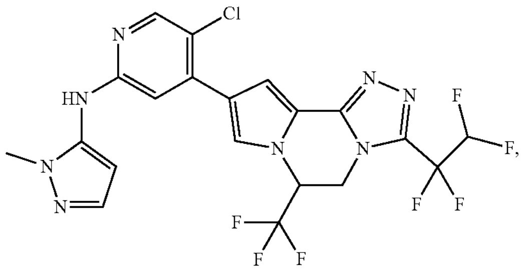 [SMILES: Cn1nccc1Nc1cc(-c2cc3n(c2)C(C(F)(F)F)Cn2c-3nnc2C(F)(F)C(F)F)c(Cl)cn1] |
| 271 | 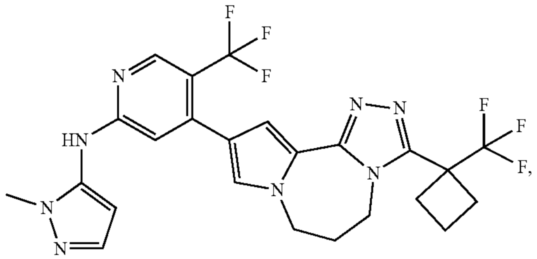 [SMILES: Cn1nccc1Nc1cc(-c2cc3n(c2)CCCn2c-3nnc2C2(C(F)(F)F)CCC2)c(C(F)(F)F)cn1] |

-continued
| Compound No. | Structure |
|---|---|
| 272 | 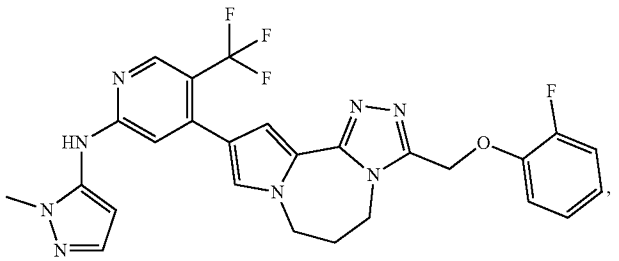 [SMILES: Cn1nccc1Nc1cc(-c2cc3n(c2)CCCn2c(COc4ccccc4F)nnc2-3)c(C(F)(F)F)cn1] |
| 273 | 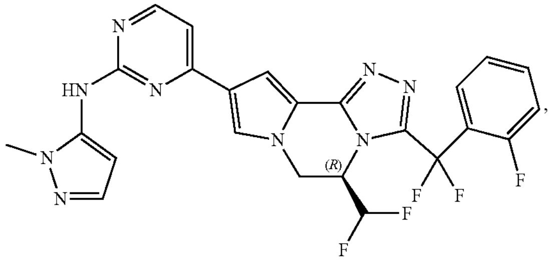 |
| 274 | 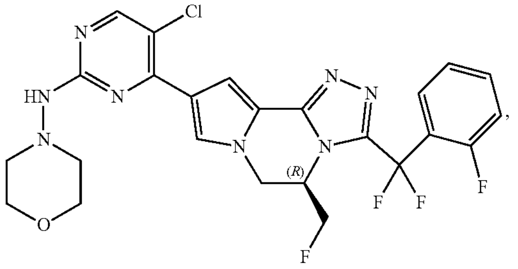 |
| 275 | 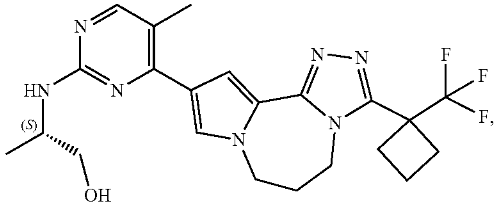 |
| 276 | 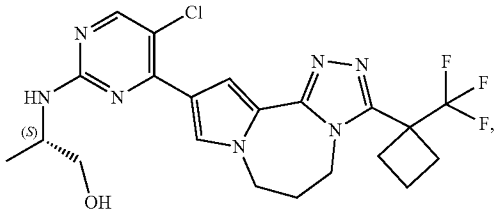 |
| 277 | 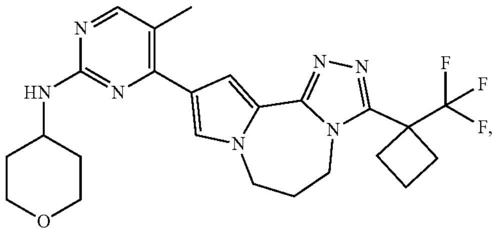 [SMILES: Cc1cnc(NC2CCOCC2)nc1-c1cc2n(c1)CCCn1c-2nnc1C1(C(F)(F)F)CCC1] |

-continued
| Compound No. | Structure |
|---|---|
| 278 | 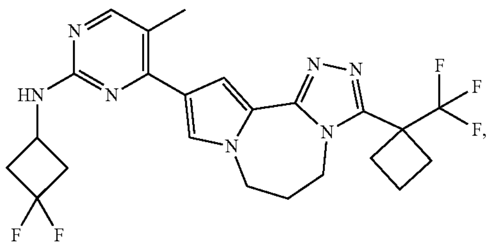 [SMILES: Cc1cnc(NC2CC(F)(F)C2)nc1-c1cc2n(c1)CCCn1c-2nnc1C1(C(F)(F)F)CCC1] |
| 279 | 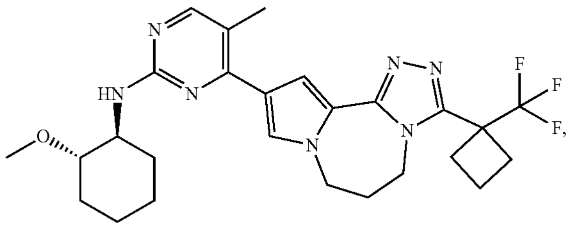 [SMILES: CO[C@H]1CCCC[C@@H]1Nc1ncc(C)c(-c2cc3n(c2)CCCn2c-3nnc2C2(C(F)(F)F)CCC2)n1] |
| 280 | 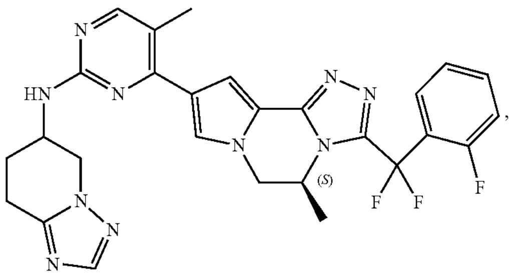 |
| 281 | 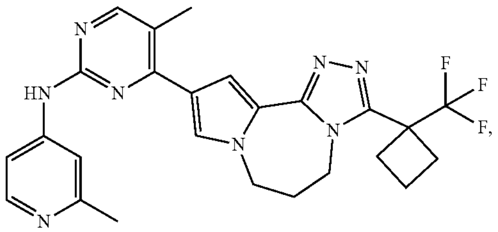 [SMILES: Cc1cc(Nc2ncc(C)c(-c3cc4n(c3)CCCn3c-4nnc3C3(C(F)(F)F)CCC3)n2)ccn1] |
| 282 | 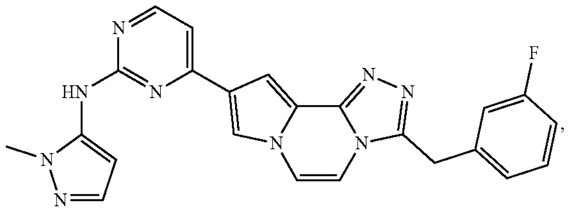 [SMILES: Cn1nccc1Nc1nccc(-c2cc3c4nnc(Cc5cccc(F)c5)n4ccn3c2)n1] |
| 283 | 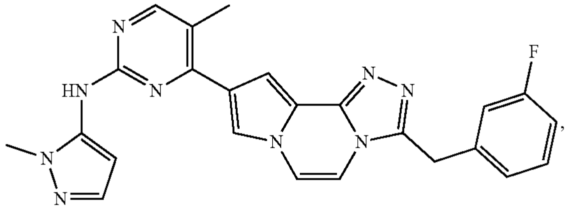 [SMILES: Cc1cnc(Nc2ccnn2C)nc1-c1cc2c3nnc(Cc4cccc(F)c4)n3ccn2c1] |

-continued
| Compound No. | Structure |
|---|---|
| 284 | 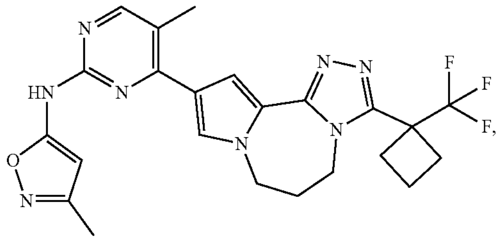 [SMILES: Cc1cc(Nc2ncc(C)c(-c3cc4n(c3)CCCn3c-4nnc3C3(C(F)(F)F)CCC3)n2)on1] |
| 285 | 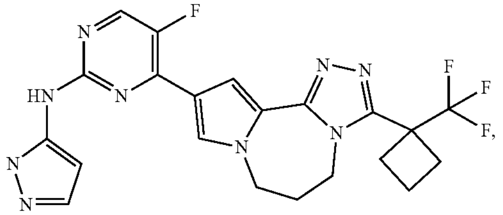 [SMILES: Fc1cnc(Nc2ccn[nH]2)nc1-c1cc2n(c1)CCCn1c-2nnc1C1(C(F)(F)F)CCC1] |
| 286 | 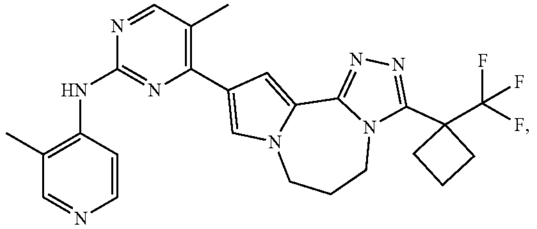 [SMILES: Cc1cnccc1Nc1ncc(C)c(-c2cc3n(c2)CCCn2c-3nnc2C2(C(F)(F)F)CCC2)n1] |
| 287 | 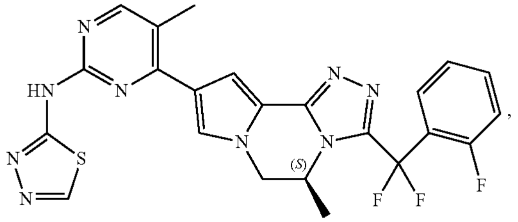 |
| 288 | 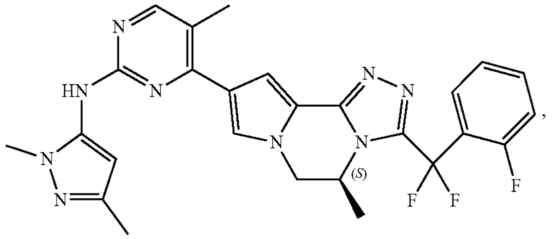 |
| 289 | 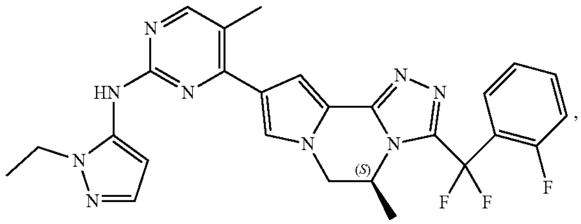 |

-continued
| Compound No. | Structure |
|---|---|
| 290 | 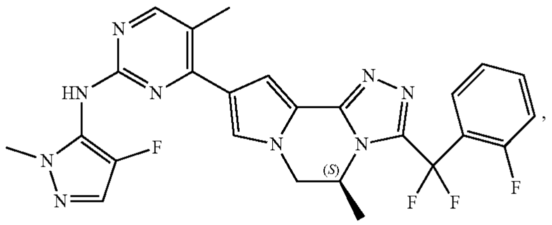 |
| 291 | 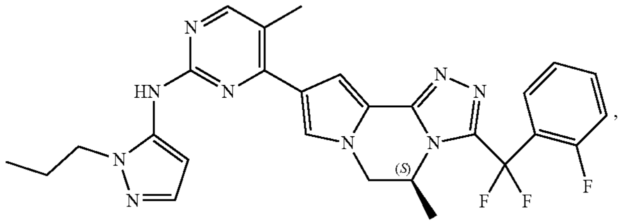 |
| 292 | 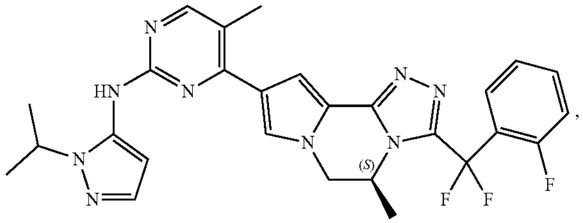 |
| 293 | 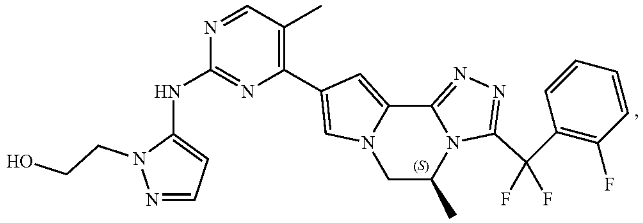 |
| 294 | 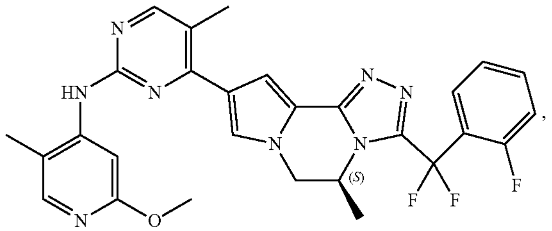 |
| 295 | 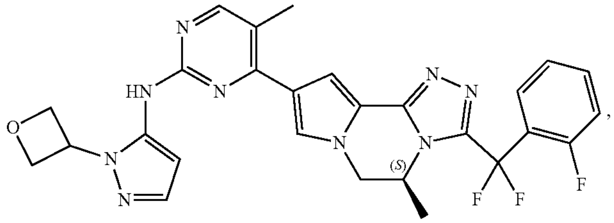 |

-continued
| Compound No. | Structure |
|---|---|
| 296 | 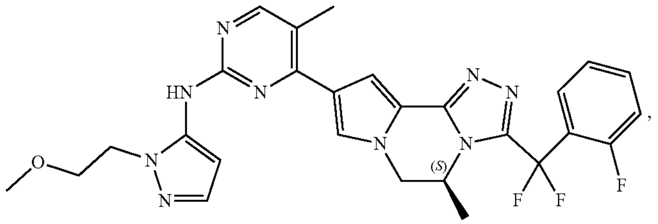 |
| 297 | 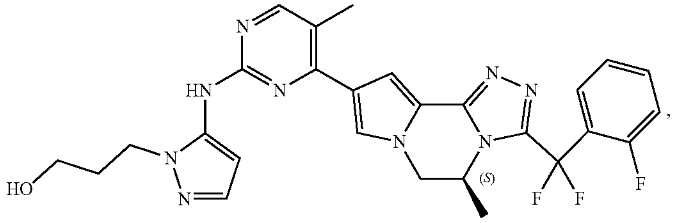 |
| 298 | 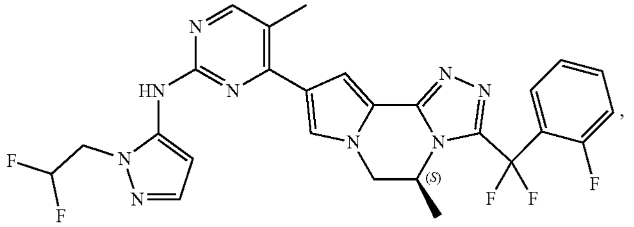 |
| 299 | 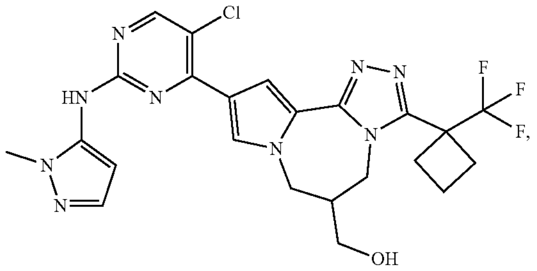 [SMILES: Cn1nccc1Nc1ncc(Cl)c(-c2cc3n(c2)CC(CO)Cn2c-3nnc2C2(C(F)(F)F)CCC2)n1] |
| 300 | 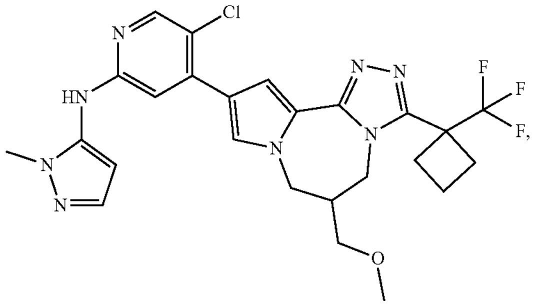 [SMILES: COCC1Cn2cc(-c3cc(Nc4ccnn4C)ncc3Cl)cc2-c2nnc(C3(C(F)(F)F)CCC3)n2C1] |
| 301 | 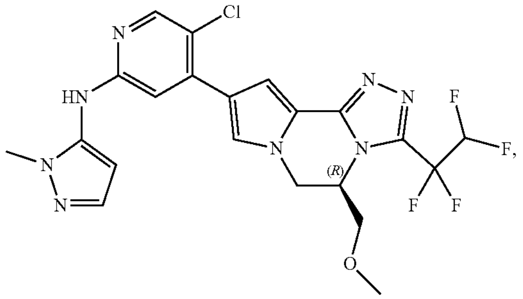 |

-continued
| Compound No. | Structure |
| --- | --- |
| 302 | 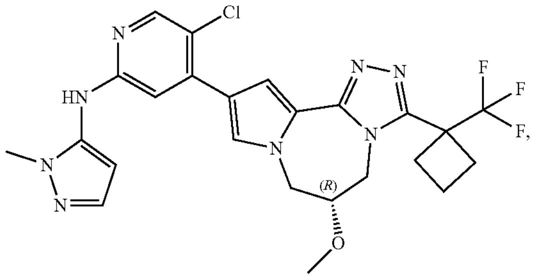 |
| 303 | 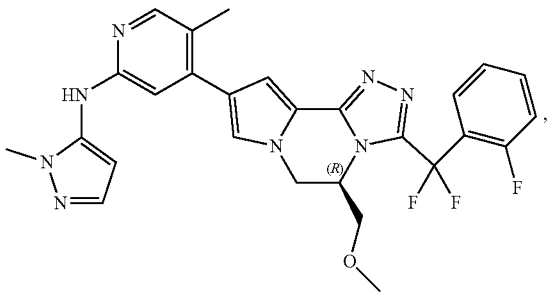 |
| 304 | 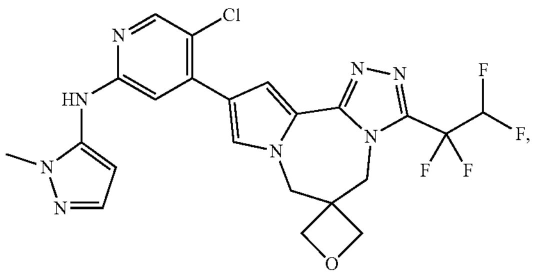 [SMILES: Cn1nccc1Nc1cc(-c2cc3n(c2)CC2(COC2)Cn2c-3nnc2C(F)(F)C(F)F)c(Cl)cn1] |
| 305 | 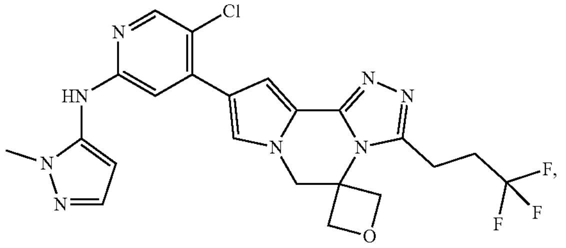 [SMILES: Cn1nccc1Nc1cc(-c2cc3n(c2)CC2(COC2)n2c(CCC(F)(F)F)nnc2-3)c(Cl)cn1] |
| 306 | 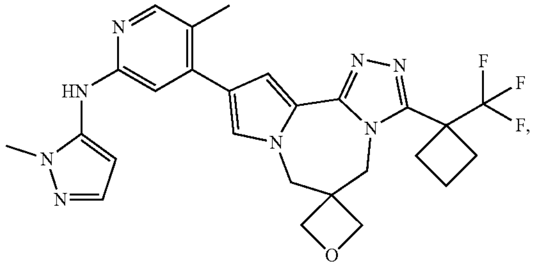 [SMILES: Cc1cnc(Nc2ccnn2C)cc1-c1cc2n(c1)CC1(COC1)Cn1c-2nnc1C1(C(F)(F)F)CCC1] |

-continued
| Compound No. | Structure |
|---|---|
| 307 | 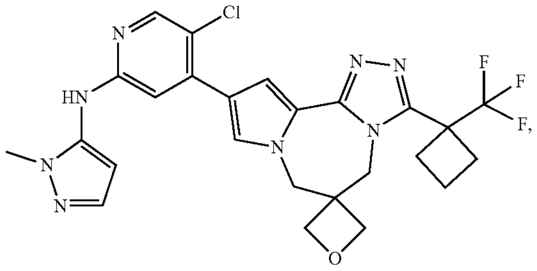 [SMILES: Cn1nccc1Nc1cc(-c2cc3n(c2)CC2(COC2)Cn2c-3nnc2C2(C(F)(F)F)CCC2)c(Cl)cn1] |
| 308 | 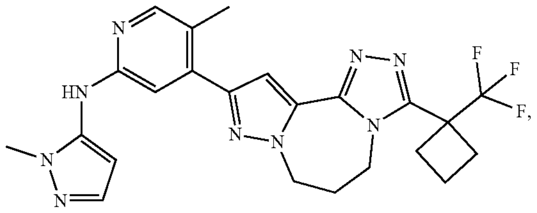 [SMILES: Cc1cnc(Nc2ccnn2C)cc1-c1cc2n(n1)CCCn1c-2nnc1C1(C(F)(F)F)CCC1] |
| 309 | 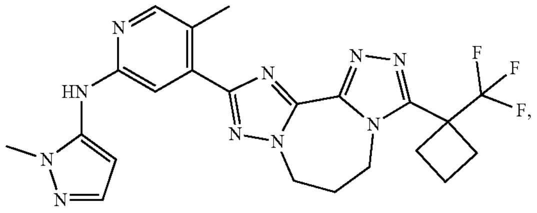 [SMILES: Cc1cnc(Nc2ccnn2C)cc1-c1nc2n(n1)CCCn1c-2nnc1C1(C(F)(F)F)CCC1] |
| 310 | 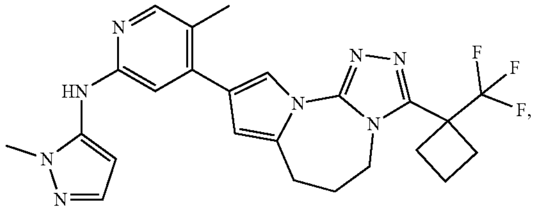 [SMILES: Cc1cnc(Nc2ccnn2C)cc1-c1cc2n(c1)-c1nnc(C3(C(F)(F)F)CCC3)n1CCC2] |
| 311 | 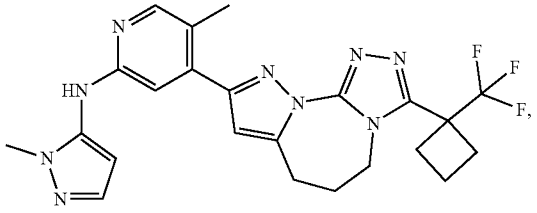 [SMILES: Cc1cnc(Nc2ccnn2C)cc1-c1cc2n(n1)-c1nnc(C3(C(F)(F)F)CCC3)n1CCC2] |
| 312 | 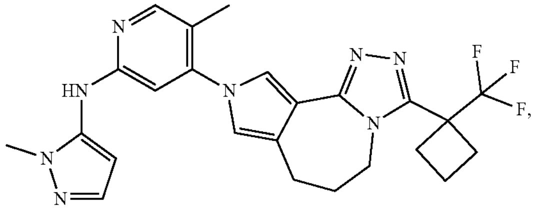 [SMILES: Cc1cnc(Nc2ccnn2C)cc1-n1cc2c(c1)-c1nnc(C3(C(F)(F)F)CCC3)n1CCC2] |
| 313 | 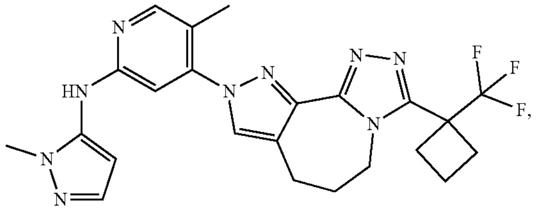 [SMILES: Cc1cnc(Nc2ccnn2C)cc1-n1cc2c(n1)-c1nnc(C3(C(F)(F)F)CCC3)n1CCC2] |

-continued
| Compound No. | Structure |
| --- | --- |
| 314 | 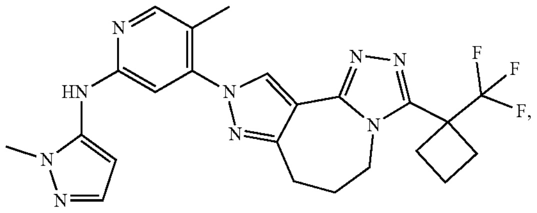 [SMILES: Cc1cnc(Nc2ccnn2C)cc1-n1cc2c(n1)CCCn1c-2nnc1C1(C(F)(F)F)CCC1] |
| 315 | 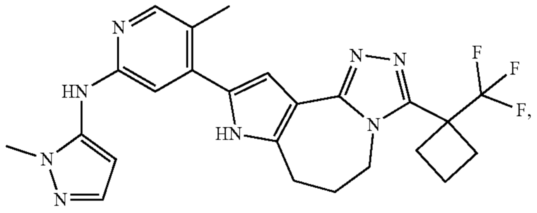 [SMILES: Cc1cnc(Nc2ccnn2C)cc1-c1cc2c([nH]1)CCCn1c-2nnc1C1(C(F)(F)F)CCC1] |
| 316 | 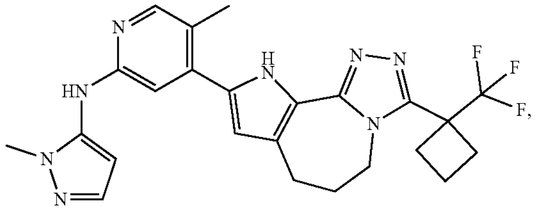 [SMILES: Cc1cnc(Nc2ccnn2C)cc1-c1cc2c([nH]1)-c1nnc(C3(C(F)(F)F)CCC3)n1CCC2] |
| 317 | 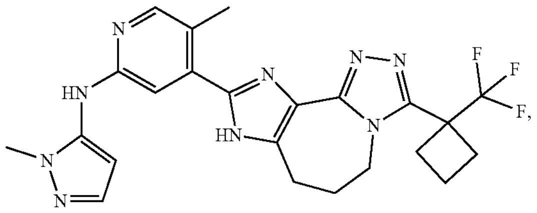 [SMILES: Cc1cnc(Nc2ccnn2C)cc1-c1nc2c([nH]1)CCCn1c-2nnc1C1(C(F)(F)F)CCC1] |
| 318 | 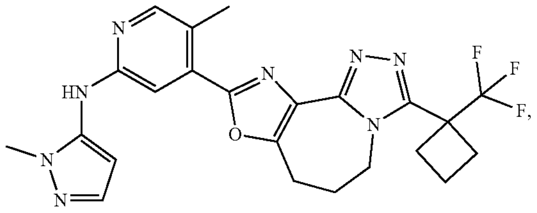 [SMILES: Cc1cnc(Nc2ccnn2C)cc1-c1nc2c(o1)CCCn1c-2nnc1C1(C(F)(F)F)CCC1] |
| 319 | 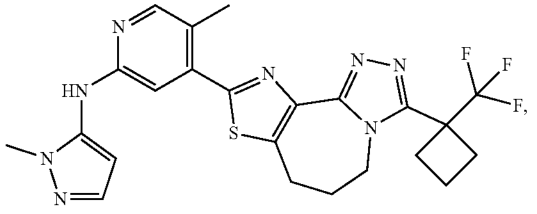 [SMILES: Cc1cnc(Nc2ccnn2C)cc1-c1nc2c(s1)CCCn1c-2nnc1C1(C(F)(F)F)CCC1] |
| 320 | 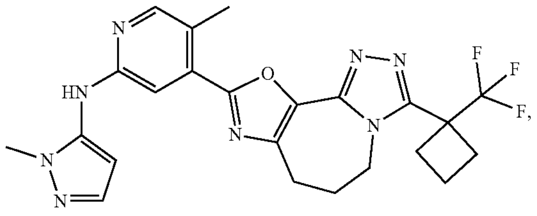 |

-continued

| Compound No. | Structure |
|---|---|
| 321 | 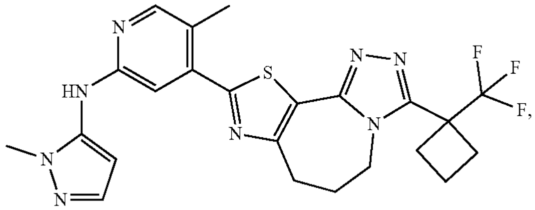 [SMILES: Cc1cnc(Nc2ccnn2C)cc1-c1nc2c(o1)-c1nnc(C3(C(F)(F)F)CCC3)n1CCC2] , and |
| | and |
| 322 | . 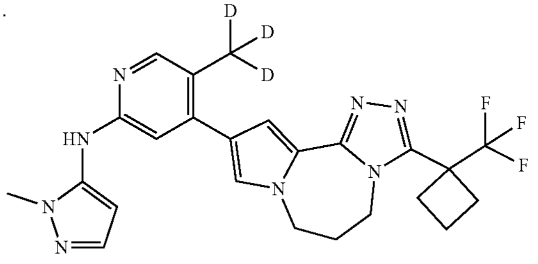 [SMILES: [2H]C([2H])([2H])c1cnc(Nc2ccnn2C)cc1-c1cc2n(c1)CCCn1c-2nnc1C1(C(F)(F)F)CCC1] |

19. The compound of formula (I) according to claim 1, or a pharmaceutically acceptable salt thereof, or a solvate, a racemic mixture, an enantiomer, a diastereomer, or a tautomer of the compound of formula (I) or a pharmaceutically acceptable salt thereof, wherein the compound of formula (I) is the compound of formula (I-1), (I-1)

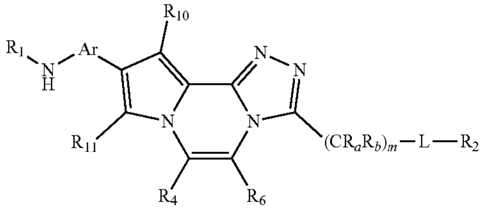

wherein $R_1$ is a heteroaryl optionally substituted with one or more substituents independently selected from $C_{1-6}$ alkyl optionally substituted with one or more deuterium, $C_{1-6}$ haloalkyl, $C_{1-6}$ alkoxyl, halo, —($C_{1-6}$ alkyl)-OH, —($C_{1-6}$ alkyl)-O—($C_{1-6}$ alkyl), and 3-6 membered heterocyclyl;

Ar is a heteroaryl optionally substituted with one or more substituents independently selected from halo, —CN, $C_{1-6}$ alkyl optionally substituted with one or more deuterium, $C_{1-6}$ alkoxyl, and $C_{1-6}$ haloalkyl;

$R_2$ is selected from halo, —CN, $C_{1-6}$ alkyl, $C_{1-6}$ haloalkyl, saturated monocyclic $C_{3-8}$ cycloalkyl, phenyl, and heteroaryl, wherein each of said saturated monocyclic $C_{3-8}$ cycloalkyl, phenyl, or heteroaryl is optionally substituted with one or more substituents independently selected from halo, —CN, $C_{1-6}$ alkyl, $C_{1-6}$ alkoxyl, $C_{1-6}$ haloalkyl, and oxo;

$R_4$ and $R_6$ are independently selected from hydrogen and $C_{1-6}$ alkyl;

$R_{10}$ and $R_{11}$ are independently selected from hydrogen, halo, $C_{1-6}$ alkyl, $C_{1-6}$ alkoxyl, $C_{1-6}$ haloalkyl, and —($C_{1-6}$ alkyl)-OH;

m is 0, 1, or 2;

$R_a$ and $R_b$ are independently selected from hydrogen, halo, hydroxy, or $C_{1-6}$ alkyl; or $R_a$ and $R_b$ together with the carbon atom they are attached to form a saturated monocyclic $C_{3-6}$ cycloalkyl or a 3-6 membered heterocyclyl, wherein said 3-6 membered heterocyclyl is a saturated monocyclic ring having 3-6 ring atoms with 1 or 2 of the ring atoms being ring heteroatoms independently selected from N, O and S, and the remaining ring atoms being carbon; wherein each of said saturated monocyclic $C_{3-6}$ cycloalkyl or 3-6 membered heterocyclyl is optionally substituted with one or more substituents selected from halo;

L is absent, or L is NH, O or S; and said heteroaryl for $R_1$, Ar and $R_2$ is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another.

20. The compound of formula (I) according to claim 19, or a pharmaceutically acceptable salt thereof, or a solvate, a racemic mixture, an enantiomer, a diastereomer, or a tautomer of the compound of formula (I) or a pharmaceutically acceptable salt thereof, wherein $R_1$ is pyrazolyl, which is optionally substituted with one or more substituents independently selected from $C_{1-6}$ alkyl;

Ar is pyrimidinyl, wich is optionally substituted with one or more substituents independently selected from $C_{1-6}$ alkyl optionally substituted with one or more deuterium, and halo;

$R_2$ is selected from $C_{1-6}$ haloalkyl or phenyl, wherein said phenyl is optionally substituted with one or more substituents independently selected from halo;

$R_{10}$ and $R_{11}$ are hydrogen;

m is 0 or 1;

$R_a$ and $R_b$ are independently selected from hydrogen or C1-6 alkyl; or $R_a$ and $R_b$ together with the carbon atom they are attached to form a saturated monocyclic $C_{3-6}$ cycloalkyl; and L is absent, or L is NH or O.

21. The compound of formula (I) according to claim 1, or a pharmaceutically acceptable salt thereof, or a solvate, a racemic mixture, an enantiomer, a diastereomer, or a tautomer of the compound of formula (I) or a pharmaceutically acceptable salt thereof, wherein the compound of formula (I) is the compound of formula (I-2), (I-2)

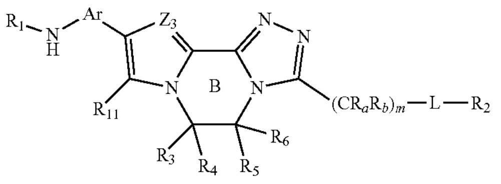

wherein $R_1$ is selected from $C_{1-6}$ alkyl, —($C_{1-6}$ alkyl)-OH, saturated monocyclic $C_{3-8}$ cycloalkyl, saturated 3-8 membered heterocyclyl containing 1 or 2 ring heteroatoms independently selected from N, O and S, and heteroaryl, wherein each of said $C_{3-8}$ cycloalkyl, 3-8 membered heterocyclyl, and heteroaryl is optionally substituted with one or more substituents independently selected from halo, —($C_{1-6}$ alkyl)-OH, —($C_{1-6}$ alkyl)-O—($C_{1-6}$ alkyl), saturated 3-6 membered heterocyclyl containing 1 or 2 ring heteroatoms independently selected from N, O and S, $C_{1-6}$ alkyl optionally substituted with one or more deuterium, $C_{1-6}$ alkoxyl, and $C_{1-6}$ haloalkyl;

Ar is a heteroaryl optionally substituted with one or more substituents independently selected from halo, —CN, $C_{1-6}$ alkyl optionally substituted with one or more deuterium, $C_{1-6}$ alkoxyl, and $C_{1-6}$ haloalkyl;

$R_2$ is selected from halo, —CN, $C_{1-6}$ alkyl, $C_{1-6}$ haloalkyl, saturated monocyclic $C_{3-8}$ cycloalkyl, phenyl, or heteroaryl, wherein each of said $C_{3-8}$ cycloalkyl, phenyl, or heteroaryl is optionally substituted with one or more substituents independently selected from halo, —CN, $C_{1-6}$ alkyl, $C_{1-6}$ alkoxyl, $C_{1-6}$ haloalkyl, and oxo;

$Z_3$ is $CR_{10}$ or N;

$R_3$, $R_4$, $R_5$, and $R_6$ are independently selected from hydrogen, $C_{1-6}$ alkyl, $C_{1-6}$ haloalkyl, —($C_{1-6}$ alkyl)-O—($C_{1-6}$ alkyl), and —($C_{1-6}$ alkyl)-phenyl; or any pair of $R_3$ and $R_4$, or $R_5$ and $R_6$, together with the carbon atom they are attached to form a saturated monocyclic $C_{3-6}$ cycloalkyl or a saturated monocyclic 3-6 membered heterocyclyl having 1 or 2 ring heteroatoms selected from N, O and S, thereby together with the B ring forming a spirocyclic ring;

$R_{10}$ and $R_{11}$ are independently selected from hydrogen, halo, $C_{1-6}$ alkyl, $C_{1-6}$ alkoxyl, $C_{1-6}$ haloalkyl, and —($C_{1-6}$ alkyl)-OH;

m is 0, 1, or 2;

$R_a$ and $R_b$ are independently selected from hydrogen, halo, hydroxy, or $C_{1-6}$ alkyl; or $R_a$ and $R_b$ together with the carbon atom they are attached to form a saturated monocyclic $C_{3-6}$ cycloalkyl or a 3-6 membered heterocyclyl, wherein said 3-6 membered heterocyclyl is a saturated monocyclic ring having 3-6 ring atoms with 1 or 2 of the ring atoms being ring heteroatoms independently selected from N, O and S, and the remaining ring atoms being carbon; wherein each of said saturated monocyclic $C_{3-6}$ cycloalkyl or 3-6 membered heterocyclyl is optionally substituted with one or more substituents selected from halo;

L is absent, or L is NH, O or S; and said heteroaryl for $R_1$, Ar and $R_2$ is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another.

22. The compound of formula (I) according to claim 21, or a pharmaceutically acceptable salt thereof, or a solvate, a racemic mixture, an enantiomer, a diastereomer, or a tautomer of the compound of formula (I) or a pharmaceutically acceptable salt thereof, wherein $R_1$ is selected from saturated monocyclic 3-8 membered heterocyclyl containing 1 or 2 ring heteroatoms independently selected from N, O and S, and heteroaryl, wherein said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another, and wherein each of said 3-8 membered heterocyclyl and heteroaryl is optionally substituted with one or more substituents independently selected from $C_{1-6}$ alkyl, $C_{1-6}$ haloalkyl, halo, —($C_{1-6}$ alkyl)-OH, $C_{1-6}$ alkoxyl, —($C_{1-6}$ alkyl)-O—($C_{1-6}$ alkyl), and saturated monocyclic 3-6 membered heterocyclyl containing 1 or 2 ring heteroatoms independently selected from N, O and S;

Ar is a heteroaryl, wherein said heteroaryl is monocyclic aromatic hydrocarbon radical having 5 or 6 ring atoms with 1, 2 or 3 of the ring atoms being heteroatoms independently selected from N, O, and S, and the remaining ring atoms being carbon, and when the total number of S and O atoms in the heteroaryl group exceeds 1, said S and O heteroatoms are not adjacent to one another, and wherein said heteroaryl is optionally substituted with one or more substituents independently selected from $C_{1-6}$ alkyl optionally substituted with one or more deuterium, and halo;

$R_2$ is selected from halo, $C_{1-6}$ alkyl, $C_{1-6}$ haloalkyl, phenyl, and heteroaryl, wherein said heteroaryl is a monocyclic aromatic hydrocarbon radical having 5 or 6 ring atoms with 1, 2 or 3 of the ring atoms being ring heteroatoms independently selected from N, O, and S, and the remaining ring atoms being carbon, or a bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another, and wherein each of said phenyl and heteroaryl is optionally substituted with one or more substituents independently selected from halo, $C_{1-6}$ alkyl, $C_{1-6}$ alkoxyl, and oxo;

$Z_3$ is $CR_{10}$ or N;

$R_3$, $R_4$, $R_5$, and $R_6$ are independently selected from hydrogen, $C_{1-6}$ alkyl, $C_{1-6}$ haloalkyl, —($C_{1-6}$ alkyl)-O—($C_{1-6}$ alkyl), and —($C_{1-6}$ alkyl)-phenyl; or any pair of $R_3$ and $R_4$, or $R_5$ and $R_6$, together with the carbon atom they are attached to form a saturated monocyclic $C_{3-6}$ cycloalkyl or a saturated monocyclic 3-6 membered heterocyclyl having 1 or 2 ring heteroatoms selected from N, O and S, thereby together with the B ring forming a spirocyclic ring;

m is 1 or 2;

$R_a$ and $R_b$ are independently selected from hydrogen and halo; or $R_a$ and $R_b$ together with the carbon atom they are attached to form a saturated monocyclic $C_{3-6}$ cycloalkyl;

$R_{10}$ and $R_{11}$ are hydrogen; and

L is absent, or L is O.

23. The compound of formula (I) according to claim 22, or a pharmaceutically acceptable salt thereof, or a solvate, a racemic mixture, an enantiomer, a diastereomer, or a tautomer of the compound of formula (I) or a pharmaceutically acceptable salt thereof, wherein said heteroaryl is selected from pyrazolyl, 2,4,5,6-tetrahydrocyclopentadieno[c]pyrazolyl, 1,2,4-triazolyl, 5,6,7,8-tetrahydro[1,2,4]triazolo[1,5-a]pyridyl, 1,3,4-thiadiazolyl, and pyridyl, and said heteroaryl is each optionally substituted with one or more substituents independently selected from $C_{1-6}$ alkyl, $C_{1-6}$ haloalkyl, halo, —($C_{1-6}$ alkyl)-OH, $C_{1-6}$ alkoxyl, —($C_{1-6}$ alkyl)-O—($C_{1-6}$ alkyl), and oxetanyl.

24. The compound of formula (I) according to claim 21, or a pharmaceutically acceptable salt thereof, or a solvate, a racemic mixture, an enantiomer, a diastereomer, or a tautomer of the compound of formula (I) or a pharmaceutically acceptable salt thereof, wherein Ar is a heteroaryl selected from pyridyl, pyrimidinyl, and 1,3,5-triazinyl; wherein said heteroaryl is each optionally substituted with one or more substituents selected from $C_{1-6}$ alkyl optionally substituted with one or more deuterium, and halo.

25. The compound of formula (I) according to claim 24, or a pharmaceutically acceptable salt thereof, or a solvate, a racemic mixture, an enantiomer, a diastereomer, or a tautomer of the compound of formula (I) or a pharmaceutically acceptable salt thereof, wherein Ar is (Ib-1)

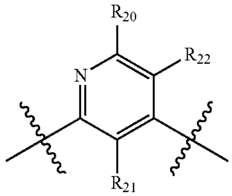

or

-continued (Ib-2)

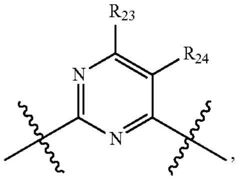

, wherein the wavy lines represent the attachment points of Ar, and wherein $R_{20}$, $R_{21}$, $R_{22}$, $R_{23}$, and $R_{24}$ are independently selected from hydrogen, halo, and $C_{1-6}$ alkyl optionally substituted with one or more deuterium.

26. The compound of formula (I) according to claim 21, or a pharmaceutically acceptable salt thereof, or a solvate, a racemic mixture, an enantiomer, a diastereomer, or a tautomer of the compound of formula (I) or a pharmaceutically acceptable salt thereof, wherein R2 is selected from halo, $C_{1-6}$ alkyl, $C_{1-6}$ haloalkyl, phenyl, and heteroaryl, wherein said heteroaryl is selected from isoxazolyl, 1,2,5-oxadiazolyl, pyrazolyl, oxazolyl, pyridyl, thiazolyl, isothiazolyl, thienyl, and benzo[d]isoxazolyl; wherein each of said phenyl and heteroaryl is optionally substituted with one or more substituents independently selected from halo, $C_{1-6}$ alkyl, $C_{1-6}$ haloalkyl, and oxo.

27. The compound of formula (I) according to claim 1, or a pharmaceutically acceptable salt thereof, or a solvate, a racemic mixture, an enantiomer, a diastereomer, or a tautomer of the compound of formula (I) or a pharmaceutically acceptable salt thereof, wherein the compound of formula (I) is the compound of formula (I-3), (I-3)

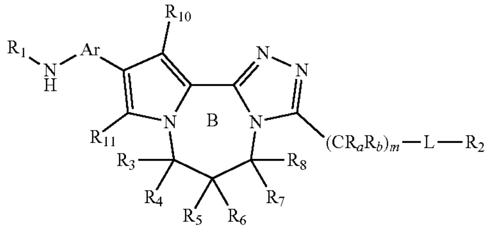

wherein $R_1$ is selected from $C_{1-6}$ alkyl, —($C_{1-6}$ alkyl)-OH, saturated monocyclic $C_{3-8}$ cycloalkyl, saturated monocyclic 3-8 membered heterocyclyl containing 1 or 2 ring heteroatoms independently selected from N, O and S, and heteroaryl; wherein each of said $C_{3-8}$ cycloalkyl, 3-8 membered heterocyclyl, and heteroaryl is optionally substituted with one or more substituents independently selected from halo, $C_{1-6}$ alkyl optionally substituted with one or more deuterium, $C_{1-6}$ alkoxyl, and $C_{1-6}$ haloalkyl;

Ar is a heteroaryl optionally substituted with one or more substituents independently selected from halo, —CN, $C_{1-6}$ alkyl optionally substituted with one or more deuterium, $C_{1-6}$ alkoxyl, and $C_{1-6}$ haloalkyl;

$R_2$ is selected from halo, —CN, $C_{1-6}$ alkyl, $C_{1-6}$ haloalkyl, saturated monocyclic $C_{3-8}$ cycloalkyl, phenyl, or heteroaryl, wherein each of said saturated monocyclic $C_{3-8}$ cycloalkyl, phenyl, or heteroaryl is optionally substituted with one or more substituents independently selected from halo, —CN, $C_{1-6}$ alkyl, $C_{1-6}$ alkoxyl, $C_{1-6}$ haloalkyl, and oxo;

$R_3$, $R_4$, $R_5$, $R_6$, $R_7$, and $R_8$ are independently selected from hydrogen, halo, hydroxy, $C_{1-6}$ alkyl, and $C_{1-6}$ alkoxyl; wherein said $C_{1-6}$ alkyl is optionally substituted with one or more substituents independently selected from hydroxy and $C_{1-6}$ alkoxyl; or any two of $R_3$, $R_4$, $R_5$, $R_6$, $R_7$, and $R_8$ together with the carbon atom they are attached to and the B ring form

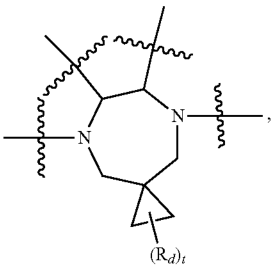
,
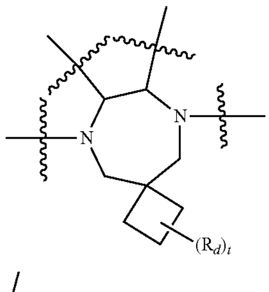
,
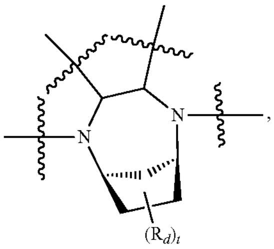
,
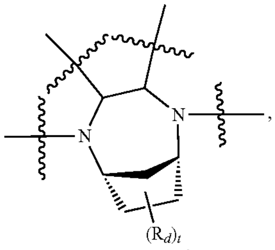
, or
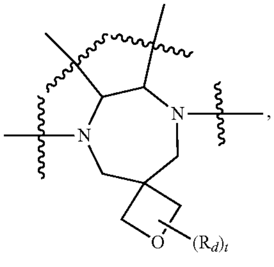
, wherein the wavy lines represent the attachment points of the ring, and $R_d$ is selected from hydrogen or halo, t is 0, 1, 2, or 3;

$R_{10}$ and $R_{11}$ are independently selected from hydrogen, halo, $C_{1-6}$ alkyl, $C_{1-6}$ alkoxyl, $C_{1-6}$ haloalkyl, and —($C_{1-6}$ alkyl)-OH;

m is 0, 1, or 2;

$R_a$ and $R_b$ are independently selected from hydrogen, halo, hydroxy, or $C_{1-6}$ alkyl; or $R_a$ and $R_b$ together with the carbon atom they are attached to form a saturated $C_{3-6}$ cycloalkyl or a 3-6 membered heterocyclyl, wherein said 3-6 membered heterocyclyl is a saturated monocyclic ring having 3-6 ring atoms with 1 or 2 of the ring atoms being ring heteroatoms independently selected from N, O and S, and the remaining ring atoms being carbon; wherein each of said saturated $C_{3-6}$ cycloalkyl or 3-6 membered heterocyclyl is optionally substituted with one or more substituents selected from halo;

L is absent, or L is NH, O or S; and said heteroaryl for $R_1$, Ar and $R_2$ is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another.

28. The compound of formula (I) according to claim 27, or a pharmaceutically acceptable salt thereof, or a solvate, a racemic mixture, an enantiomer, a diastereomer, or a tautomer of the compound of formula (I) or a pharmaceutically acceptable salt thereof, wherein $R_1$ is selected from $C_{1-6}$ alkyl, —($C_{1-6}$ alkyl)-OH, saturated monocyclic $C_{3-8}$ cycloalkyl, saturated monocyclic 3-8 membered heterocyclyl containing 1 or 2 ring heteroatoms independently selected from N, O and S, and heteroaryl; wherein each of said $C_{3-8}$ cycloalkyl, 3-8 membered heterocyclyl, and heteroaryl is optionally substituted with one or more substituents independently selected from halo, $C_{1-6}$ alkoxyl, $C_{1-6}$ haloalkyl, and $C_{1-6}$ alkyl optionally substituted with one or more deuterium;

Ar is a heteroaryl, wherein said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, and when the total number of S and O atoms in the heteroaryl group exceeds 1, said S and O heteroatoms are not adjacent to one another;

wherein said heteroaryl is optionally substituted with one or more substituents independently selected from halo, —CN, $C_{1-6}$ alkyl optionally substituted with one or more deuterium, $C_{1-6}$ alkoxyl, and $C_{1-6}$ haloalkyl;

$R_2$ is selected from —CN, $C_{1-6}$ haloalkyl, saturated monocyclic $C_{3-8}$ cycloalkyl, phenyl, or heteroaryl, wherein said heteroaryl is monocyclic aromatic hydrocarbon radical having 5 or 6 ring atoms with 1, 2 or 3 of the ring atoms being ring heteroatoms independently selected from N, O, and S, and the remaining ring atoms being carbon, or bicyclic aromatic hydrocarbon radical having 8, 9 or 10 ring atoms with 1, 2, 3 or 4 of the ring atoms being ring heteroatoms independently selected from N, O, and S, and the remaining ring atoms being carbon, wherein at least one of the rings is aromatic, and when the total number of S and O atoms in the heteroaryl group exceeds 1, said S and O heteroatoms are not adjacent to one another; wherein each of said saturated monocyclic $C_{3-8}$ cycloalkyl, phenyl, or heteroaryl is optionally substituted with one or more substituents independently selected from halo, —CN, $C_{1-6}$ alkyl, and $C_{1-6}$ haloalkyl;

$R_3$, $R_4$, $R_5$, $R_6$, $R_7$, and $R_8$ are independently selected from hydrogen, halo, hydroxy, $C_{1-6}$ alkyl, and $C_{1-6}$ alkoxyl; wherein said $C_{1-6}$ alkyl is optionally substituted with one or more substituents independently selected from hydroxy and $C_{1-6}$ alkoxyl; or any two of $R_3$, $R_4$, $R_5$, $R_6$, $R_7$, and $R_8$ together with the carbon atom they are attached to and the B ring form

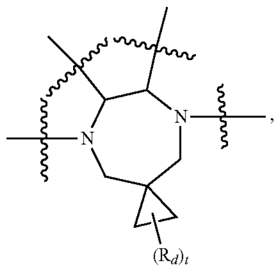,
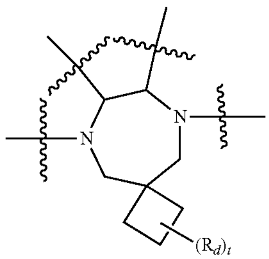,
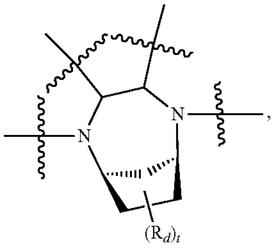,
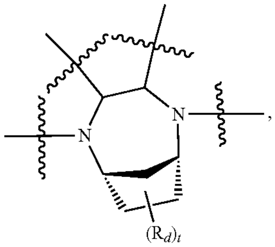, or
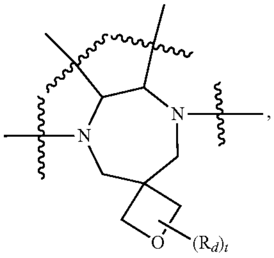, wherein the wavy lines represent the attachment points of the ring, and $R_d$ is selected from hydrogen and halo, t is 0, 1, 2, or 3;

$R_{10}$ and $R_{11}$ are independently selected from hydrogen, halo, and $C_{1-6}$ alkyl;

m is 0, 1, or 2;

$R_a$ and $R_b$ are independently selected from hydrogen, halo, hydroxy, and $C_{1-6}$ alkyl; or $R_a$ and $R_b$ together with the carbon atom they are attached to form a saturated monocyclic $C_{3-6}$ cycloalkyl or a 3-6 membered heterocyclyl, wherein said 3-6 membered heterocyclyl is a saturated monocyclic ring having 3-6 ring atoms with 1 or 2 of the ring atoms being ring heteroatoms independently selected from N, O and S, and the remaining ring atoms being carbon; wherein each of said saturated monocyclic $C_{3-6}$ cycloalkyl or 3-6 membered heterocyclyl is optionally substituted with one or more substituents selected from halo; and L is absent, or L is NH or O.

29. The compound of formula (I) according to claim 27, or a pharmaceutically acceptable salt thereof, or a solvate, a racemic mixture, an enantiomer, a diastereomer, or a tautomer of the compound of formula (I) or a pharmaceutically acceptable salt thereof, wherein $R_1$ is selected from: (1) $C_{1-6}$ alkyl, (2) —($C_{1-6}$ alkyl)-OH, (3) saturated monocyclic $C_{3-8}$ cycloalkyl, which is optionally substituted with one or more substituents independently selected from halo and $C_{1-6}$ alkoxyl, (4) saturated monocyclic 6 membered heterocyclyl containing 1 or 2 ring heteroatoms independently selected from N, O and S, and (5) heteroaryl selected from pyrazolyl, pyridyl, and isoxazolyl, wherein said heteroaryl is optionally substituted with one or more substituents independently selected from $C_{1-6}$ alkoxyl, $C_{1-6}$ haloalkyl, and $C_{1-6}$ alkyl optionally substituted with one or more deuterium.

30. The compound of formula (I) according to claim 27, or a pharmaceutically acceptable salt thereof, or a solvate, a racemic mixture, an enantiomer, a diastereomer, or a tautomer of the compound of formula (I) or a pharmaceutically acceptable salt thereof, wherein Ar is a heteroaryl selected from pyridyl and pyrimidinyl, wherein said heteroaryl is each optionally substituted with one or more substituents independently selected from halo, —CN, $C_{1-6}$ alkyl optionally substituted with one or more deuterium, $C_{1-6}$ alkoxyl, and $C_{1-6}$ haloalkyl.

31. The compound of formula (I) according to claim 30, or a pharmaceutically acceptable salt thereof, or a solvate, a racemic mixture, an enantiomer, a diastereomer, or a tautomer of the compound of formula (I) or a pharmaceutically acceptable salt thereof, wherein Ar is (Ib-1)

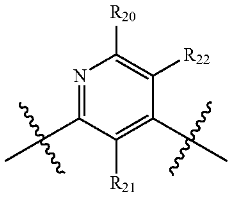 or (Ib-2)

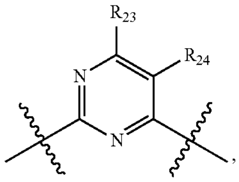, wherein the wavy lines represent the attachment points of Ar, and wherein $R_{20}$, $R_{21}$, $R_{22}$, $R_{23}$, and $R_{24}$ are independently selected from hydrogen, halo, —CN, $C_{1-6}$ alkyl optionally substituted with one or more deuterium, $C_{1-6}$ alkoxyl, and $C_{1-6}$ haloalkyl.

32. The compound of formula (I) according to claim 27, or a pharmaceutically acceptable salt thereof, or a solvate, a racemic mixture, an enantiomer, a diastereomer, or a tautomer of the compound of formula (I) or a pharmaceutically acceptable salt thereof, wherein $R_2$ is selected from: (1) —CN, (2) $C_{1-6}$ haloalkyl, (3) saturated monocyclic $C_{3-8}$ cycloalkyl, which is optionally substituted with one or more substituents selected from $C_{1-6}$ haloalkyl, (4) phenyl, which is optionally substituted with one or more substituents independently selected from halo and —CN, and (5) heteroaryl selected from 1,2,5-oxadiazolyl, indolinyl, 1,2,3,4-tetrahydroquinolinyl, pyrazolyl, indazolyl, and pyrrolyl, wherein said heteroaryl is each optionally substituted with one or more substituents independently selected from halo, —CN, and $C_{1-6}$ alkyl.

33. A pharmaceutical composition, comprising the compound of claim 1, or a pharmaceutically acceptable salt thereof, and optionally a pharmaceutically acceptable carrier.

34. A method of in vivo or in vitro inhibiting the activity of ERK, comprising contacting an effective amount of the compound of claim 1 or a pharmaceutically acceptable salt thereof with ERK.

35. A method of treating or preventing a disease responsive to inhibition of ERK, comprising administering to a subject in need thereof an effective amount of the compound of claim 1, or a pharmaceutically acceptable salt thereof, wherein the disease responsive to inhibition of ERK is cancer or an autoimmune disease.

36. The compound of claim 1, or a pharmaceutically acceptable salt thereof for use in the treatment or prevention of a disease responsive to inhibition of ERK, wherein the disease responsive to inhibition of ERK is cancer or an autoimmune disease.

37. A combination comprising the compound of claim 1, or a pharmaceutically acceptable salt thereof, and at least one additional therapeutic agent.

38. The combination according to claim 37, wherein said additional therapeutic agent is an anti-neoplastic agent, a radiotherapeutic agent, a chemotherapeutic agent, an immunotherapeutic agent, or a targeted therapeutic agent.

39. The compound according to claim 1, or a pharmaceutically acceptable salt thereof for use in the treatment or prevention of a disease responsive to inhibition of ERK, wherein the disease responsive to inhibition of ERK is leukemia, lymphoma, colorectal cancer, melanoma, glioma, pancreatic cancer, breast cancer, lung cancer, non-small cell lung cancer, thyroid cancer, papillary thyroid cancer, or ovarian cancer.

40. The method of claim 35, wherein the disease responsive to inhibition of ERK is leukemia, lymphoma, colorectal cancer, melanoma, glioma, pancreatic cancer, breast cancer, lung cancer, non-small cell lung cancer, thyroid cancer, papillary thyroid cancer, or ovarian cancer.

* * * * *